United States Patent
de Fallois et al.

(10) Patent No.: US 10,081,656 B2
(45) Date of Patent: Sep. 25, 2018

(54) ANTHELMINTIC DEPSIPEPTIDE COMPOUNDS

(71) Applicant: MERIAL INC., Duluth, GA (US)

(72) Inventors: Loic Le Hir de Fallois, Atlanta, GA (US); Greg Pacofsky, Raleigh, NC (US); Alan Long, Flowery Branch, GA (US); Charles Meng, Grayson, GA (US); Hyoung Ik Lee, Cary, NC (US); Cyprian O. Ogbu, Durham, NC (US)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 15/160,577

(22) Filed: May 20, 2016

(65) Prior Publication Data

US 2017/0022253 A1    Jan. 26, 2017

Related U.S. Application Data

(60) Provisional application No. 62/163,997, filed on May 20, 2015.

(51) Int. Cl.
| | |
|---|---|
| A61P 33/00 | (2006.01) |
| C07K 11/02 | (2006.01) |
| A01N 43/72 | (2006.01) |
| C07D 273/00 | (2006.01) |
| A61K 38/00 | (2006.01) |

(52) U.S. Cl.
CPC ............. *C07K 11/02* (2013.01); *A01N 43/72* (2013.01); *C07D 273/00* (2013.01); *A61K 38/00* (2013.01)

(58) Field of Classification Search
CPC ...... A61K 38/00; C07K 11/02; C07D 273/00; A01N 43/72
See application file for complete search history.

(56) References Cited

U.S. PATENT DOCUMENTS

| | | | |
|---|---|---|---|
| 5,116,815 A | 5/1992 | Takagi et al. | |
| 5,514,773 A | 5/1996 | Nishiyama et al. | |
| 5,589,503 A | 12/1996 | Mencke et al. | |
| 5,646,244 A | 7/1997 | Nishiyama et al. | |
| 5,717,063 A | 2/1998 | Scherkenbeck et al. | |
| 5,747,448 A | 5/1998 | Ohyama et al. | |
| 5,777,075 A | 7/1998 | Scherkenbeck et al. | |
| 5,856,346 A | 1/1999 | Nishiyama et al. | |
| 5,874,530 A | 2/1999 | Scherkenbeck et al. | |
| 6,159,932 A | 12/2000 | Mencke et al. | |
| 6,235,875 B1 | 5/2001 | Yamanishi et al. | |
| 6,265,537 B1 | 7/2001 | Jeschke et al. | |
| 6,329,338 B1 | 12/2001 | Sakanata et al. | |
| 6,355,615 B1 | 3/2002 | Dyker et al. | |
| 6,468,966 B1 | 10/2002 | Scherkenbeck et al. | |
| 6,630,569 B1 | 10/2003 | Jeschke et al. | |
| 6,828,300 B2 | 12/2004 | Dyker et al. | |
| 6,900,176 B2 | 5/2005 | Dyker et al. | |
| 7,763,583 B2 | 7/2010 | Kanikanti et al. | |
| 7,914,816 B2 | 3/2011 | Kalbe et al. | |
| 8,440,612 B2 | 5/2013 | Greif et al. | |
| 8,440,613 B2 | 5/2013 | Harder et al. | |
| 2003/0125244 A1 | 7/2003 | Kalbe et al. | |
| 2004/0115483 A1 | 6/2004 | Kalbe et al. | |
| 2009/0215678 A1 | 8/2009 | Bach | |
| 2011/0046072 A1 | 2/2011 | Kanikanti et al. | |
| 2011/0201550 A1 | 8/2011 | Harder et al. | |
| 2012/0302496 A1 | 11/2012 | Harder et al. | |
| 2014/0371139 A1 | 12/2014 | Kanikanti et al. | |
| 2015/0166608 A1 | 6/2015 | Mitomi et al. | |

FOREIGN PATENT DOCUMENTS

| | | |
|---|---|---|
| AU | 768910 B2 | 1/2004 |
| CA | 2876387 A1 | 12/2013 |
| EP | 0626375 A1 | 11/1994 |
| EP | 0634408 A1 | 1/1995 |
| EP | 0685469 A1 | 12/1995 |
| WO | 9947506 A1 | 9/1999 |
| WO | 2012028556 A1 | 3/2012 |
| WO | 2013092558 A1 | 6/2013 |

OTHER PUBLICATIONS

Krucken et al., "Anthelmintic cyclooctadepsipeptides: complex in structure and mode of action", Trends in Parasitology, 2012, vol. 28, No. 9, pp. 385-394.

Harder et al., "Cyclooctadepsipeptides—an anthelmintically active class of compounds exhibiting a novel mode of action", International Journal of Antimicrobial Agents, 2003, vol. 22, No. 3, pp. 318-331.

Scherkenbeck et al., "PF1022A—A Novel Anthelmintic Cyclooctadepsipeptide. Modification and Exchange of the N-Methyl Leucine Residues", Bioorganic and Medicinal Chemistry Letters, 1998, No. 8, pp. 1035-1040.

Ohyama et al., "Structure-activity relationship of anthelmintic cyclooctadepsipeptides", Biosci., Biotechnol., Biochem., 2011, vol. 75, No. 7, pp. 1354-1363.

Yanai et al., "Para-position derivatives of fungal anthelmintic cyclodepsipeptides engineered with Streptomyces venezuelae antibiotic biosynthetic genes", Nature Biotechnology, 2004, vol. 22, No. 7, pp. 848-855.

Scherkenbeck et al., "Chimeric cyclodepsipeptides as mimetics for the anthelmintic PF1022A", Bioorganic & Medicinal Chemistry Letters, 2004, vol. 14, pp. 6129-6132.

Jeschke et al., "Influence of the cyclooctadepsipeptides PF1022A and PF1022E as natural products on the design of semi-synthetic anthelmintics such as emodepside", Parasitology Research, 2005, 97, S11-S16.

(Continued)

*Primary Examiner* — Hasan Syed Ahmed
*Assistant Examiner* — Kaipeen E Yang
(74) *Attorney, Agent, or Firm* — Judy Jarecki-Black; John Ezcurra; Merial, Inc.

(57) ABSTRACT

The present invention provides cyclic depsipeptide compounds of formula (I) and compositions comprising the compounds that are effective against parasites that harm animals. The compounds and compositions may be used for combating parasites in or on mammals and birds. The invention also provides for an improved method for eradicating, controlling and preventing parasite infestation in birds and mammals.

39 Claims, No Drawings

(56) References Cited

OTHER PUBLICATIONS

Dutton and Lee, "Epsilon-lactam analogs of the anthelmintic cyclodepsipeptide PF1022A", Tetrahedron Letters, 1998, vol. 39, No.30, pp. 5313-5316.

Jeschke et al., "Synthesis of anthelmintically activeN-methylated amidoxime analogues of the cyclic octadepsipeptide PF1022A", Pest Management Science, 2002, vol. 58, No. 12, pp. 1205-1215.

B. Lee, "Generation of a small library of cyclodepsipeptide PF1022A analogues using a cyclization—Cleavage method with oxime resin", Bioorganic & Medicinal Chemistry Letters, 2002, vol. 12, No. 3, pp. 353-356.

Muller et al., "In vitro Synthesis of New Cyclodepsipeptides of the PF1022-Type: Probing the a-D-Hydroxy Acid Tolerance of PF1022 Synthetase", ChemBioChem, 2009, vol.10, No. 2, pp. 323-328.

Scherkenbeck et al., "Synthesis, conformational studies and anthelmintic activity of a constrained PF1022A analogue", Pesticide Science, 1999, vol. 55, pp. 457-461.

Dutton & Lee, "Restricted Conformation Analogues of an Anthelmintic Cyclodepsipeptide", Journal of Medicinal Chemistry, 2003, vol. 46, No. 11, pp. 2057-2073.

Biswas et al., "Oxyazapeptides: synthesis, structure determination, and conformational analysis", Journal of Organic Chemistry, 2013, vol. 78, No. 17, pp. 8502-8509.

Scherkenbeck et al., "PF1022A and Related Cyclodepsipeptides—A Novel Class of Anthelmintics", Current Topics in Medicinal Chemistry, 2002, vol. 2, No.7, pp. 759-777.

Jeschke et al., "Synthesis and anthelmintic activity of cyclohexadepsipeptides with cyclohexylmethyl side chains", Bioorganic & Medicinal Chemistry Letters, 2007, vol. 17, pp. 3690-3695.

Jeschke et al., "Synthesis and anthelmintic activity of thioamide analogues of cyclic octadepsipeptides such as PF1022A", Pest Management Science, 2001, vol. 57, pp. 1000-1006.

Scherkenbeck et al., "Azadepsipeptides: Synthesis and Evaluation of a Novel Class of Peptidomimetics", Journal of Organic Chemistry, 2001, vol. 66, pp. 3760-3766.

ANTHELMINTIC DEPSIPEPTIDE COMPOUNDS

CROSS REFERENCE TO RELATED APPLICATIONS

This application claims the benefit of U.S. Provisional Application No. 62/163,997 filed on May 20, 2015, which is herein incorporated by reference.

FIELD OF THE INVENTION

The present invention is directed to new anthelmintic depsipeptides compounds with improved activity against endoparasites and ectoparasites. The invention is also directed to compositions comprising the compounds, methods and uses of the compounds for eradicating, controlling, and preventing a parasite infestation and/or infection in animals. The compounds of the invention may be administered to animals, particularly mammals, fish and birds, to prevent or treat parasitic infections.

BACKGROUND OF THE INVENTION

Animals, such as mammals and birds, are often susceptible to parasite infestations. These parasites may be ectoparasites, such as fleas and ticks. Animals and humans also suffer from endoparasitic infections including, for example, helminthiasis which is most frequently caused by a group of parasitic worms described as nematodes or roundworms. These parasites cause severe economic losses in pigs, sheep, horses, and cattle as well as affecting companion animals (e.g. cats and dogs) and poultry. Other parasites include those which occur in the gastrointestinal tract of animals and humans include *Ancylostoma, Necator, Ascaris, Strongyloides, Trichinella, Capillaria, Toxocara, Toxascaris, Trichuris, Enterobius* and parasites which are found in the blood or other tissues and organs such as filarial worms and the extra intestinal stages of *Strongyloides, Toxocara* and *Trichinella*.

One type of endoparasite which seriously harms mammals is *Dirofilaria immitis*, also known as Heartworm. Other filarial endoparasites include *Dirofilaria repens* and *Dirofilaria honkongensis*, which can also infect humans. The most common hosts are dogs and cats but other mammals such as ferrets and raccoons may also be infected. Heartworms go through several life stages before they become adults infecting the pulmonary artery of the host mammal. The worms require the mosquito as an intermediate host to complete their life cycle. The period between the initial infection when the dog is bitten by a mosquito and the maturation of the worms into adults living in the heart and pulmonary arteries is six to seven months in dogs and is known as the "prepatent period". L3 larvae migrate during blood feeding of the mosquito to the tip of the mosquito's mouth parts (labium), leave the mosquito and are deposited on the skin of the dog where they then migrate through the bite wound into the host. Most L3 larvae molt to fourth-stage larvae (L4s) in canine subcutaneous tissues within 1-3 days after infection. Then, they migrate to the muscles of the chest and abdomen, and 45 to 60 days after infection, molt to the fifth stage (L5, immature adult). Between 75 and 120 days after infection, these immature heartworms then enter the bloodstream and are carried through the heart to reside in the pulmonary artery. Around seven months after infection, *Dirofilaria immitis* adults reach maturity and sexually reproduce in the pulmonary arteries and right ventricle. Adult males are around 15 cm in length, and females are around 25 cm in length and their normal life span as adults is calculated to be about 5 years.

Heartworm infection is a severe and life-threatening disease. Canine heartworm infection is preventable and prophylaxis treatment is a priority in heartworm endemic areas. Treatment of mature heartworm infection with an adulticide (e.g. melarsomine dihydrochloride) is costly and can cause serious adverse side effects, thus prevention by monthly administration of drugs that interrupt larvae development is widely used. The goal of marketed heartworm preventive therapies in dogs is to prevent the development of the parasite to adult heartworms by interrupting the *Dirofilaria immitis* life cycle post-infection.

The macrocyclic lactones (MLs, e.g. ivermectin, eprinomectin, milbemycin oxime, moxidectin, and selamectin) are the most commonly used chemoprophylaxis agents and are administered at monthly or six-month intervals. These drugs have been effective against *Dirofilaria immitis* infective third-stage larvae (L3) deposited by the mosquito as well as maturing fourth-stage larvae (L4). When administered monthly, MLs kill L3 and L4 larvae acquired within the previous 30 days, and thus prevent disease caused by adult worms. MLs can also be used monthly in infected dogs to suppress reproduction in adult worms and remove microfilariae, thereby reducing transmission and gradually causing the attrition of adult worms (*Vet. Parasitol.* 2005 Oct. 24 133(2-3) 197-206).

In recent years, an increased number of lack of efficacy (LOE) cases have been reported, in which dogs develop mature heartworm infections despite receiving monthly prophylactic doses of macrocyclic lactones drugs. For example, Atkins et al., (*Vet. Parasitol.* 206 (2014) 106-113) recently reported that an increasing number of cases of dogs that tested heartworm antigen positive while receiving heartworm preventive medication which suggests that some populations of *Dirofilaria immitis* have developed selectional resistance to heartworm preventives (American Heartworm Society, 2010. Heartworm Preventive Resistance. Is it Possible, vol. 37. Bulletin of the American Heartworm Society, pp. 5.). Thus, there is an ongoing need to develop new anthelmintic agents with improved activity against *Dirofilaria immitis* and other endoparasites.

Various parasiticides exist in the art for treating endoparasites infections in animals. In addition to the macrocyclic lactones, cyclic depsipeptides with antiparasitic activity are known. PF1022A, a 24-membered cyclooctadepsipeptide isolated from the fungus *Mycelia sterilia* by Sasaki et al. (see *J. Antibiotics* 45: 692-697 (1992)), has been found to exhibit broad anthelmintic activity against a variety of endoparasites in vivo with low toxicity. These compounds are described, for example, in U.S. Pat. Nos. 5,514,773; 5,747,448; 5,646,244; 5,874,530; among others, which are incorporated herein by reference. Emodepside is a semi synthetic analog of PF1022A containing a morpholine group at the para position of the aryl ring in the phenyl lactate groups. Emodepside is a potent anthelmintic used in combination with praziquantel in the product Profender® for the treatment of parasitic worms in cats and dogs. However, the antiparasitic activity of PF1022A and emodepside is not satisfactory for the treatment of certain parasites, especially for the control of *Dirofilaria immitis* in mammals to prevent the establishment of heartworm disease. Thus, there is a need in the art for more effective antiparasitic agents for treatment and protection of animals, e.g. mammals, fish and birds against parasites, in particular internal parasites including nematodes and filarial worms such as heartworm.

It is expressly noted that citation or identification of any document in this application is not an admission that such document is available as prior art to the present invention. Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SUMMARY OF THE INVENTION

The invention provides novel and inventive cyclic depsipeptide compounds with superior anthelmintic activity and also superior activity against ectoparasites. In addition the invention provides compositions comprising the novel depsipeptide compounds and methods and uses for the treatment and prevention of parasitic infection and possibly infestation of animals using the compounds.

In one embodiment, the present invention provides cyclic depsipeptide compounds of formula (I) shown below:

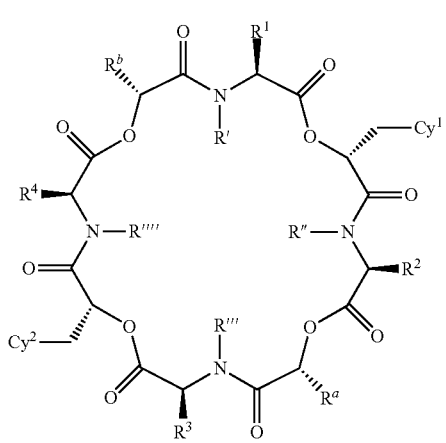

(I)

or a veterinarily acceptable salt thereof, wherein the meanings of variables $R^1$, $R^2$, $R^3$, $R^4$, $Cy^1$, $Cy^2$, $R^a$, $R^b$, R', R'', R''' and R'''' are as described below. The invention also provides veterinary compositions comprising the inventive compounds, or salts thereof, in combination with a pharmaceutically acceptable carrier or diluent.

The compounds of the invention are intended to encompass racemic mixtures, specific stereoisomers and tautomeric forms of the compound. Another aspect of the invention is a salt form of the compound of the invention.

The inventive compounds and compositions comprising the compounds are highly effective for the treatment and prophylaxis of internal parasites in mammals, fish and birds, and in particular, cats, dogs, horses, chickens, pigs, sheep and cattle with the aim of ridding these hosts of all the endoparasites commonly encountered by mammals, fish and birds.

In one embodiment, the compounds and compositions of the invention are highly effective against endoparasites, such as filariae (e.g. heartworm), hookworms, whipworms and roundworms of the digestive tract of animals and humans. In certain embodiments, the compounds and compositions of the invention are effective against *Dirofilaria immitis* (heartworm) isolates that are less sensitive to treatment with macrocyclic lactones. In another embodiment, the novel and inventive depsipeptides of the invention are effective for treating and preventing infections of animals with nematodes that are less sensitive to treatment with commercially available or known macrocyclic lactone active agents.

In certain embodiments, the invention provides compositions comprising a combination of a novel depsipeptide of the invention in combination with at least a second active agent, which broadens the scope of protection afforded to animals against endoparasites and possibly also ectoparasites.

The present invention is also directed to methods for the treatment and prevention of a parasitic infection or infestation in an animal comprising administering at least one of the compounds of formula (I) of the invention to the animal. Also included in the present invention are uses of the compounds for the treatment and/or prevention of a parasitic infections and infestations in animals and the use of the compounds in the preparation of a medicament for the treatment and/or prevention of a parasitic infection in an animal.

It is an object of the invention to not encompass within the invention any previously known product, process of making the product, or method of using the product such that the Applicants reserve the right to this invention and hereby disclose a disclaimer of any previously known product, process, or method.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law; e.g., they allow for elements not explicitly recited, but exclude elements that are found in the prior art or that affect a basic or novel characteristic of the invention.

These and other embodiments are disclosed or are obvious from, and encompassed by, the following Detailed Description.

DETAILED DESCRIPTION

The present invention provides novel and inventive cyclic depsipeptide compounds of formula (I) having parasiticidal activity against endoparasites and also against ectoparasites in certain embodiments, or veterinarily salts thereof, and compositions comprising the compounds or salts for the treatment or prevention of parasitic infections and/or infestations in an animal Also provided are methods for the treatment or prevention of parasitic infestations and/or infection in animals, comprising administering an effective amount of the depsipeptide compound of the invention, or a salt thereof, to the animal.

The novel and inventive cyclic depsipeptide of formula (I) described herein and their veterinarily acceptable salts are particularly effective for controlling endoparasites. Endoparasites include, but are not limited to, nematodes (such as roundworms, hookworms, and whipworms) and filarial worms such as *Dirofilaria immitis* (heartworm). In certain embodiments, the novel cyclic depsipeptides of the invention have been found to have significantly higher efficacy against endoparasites compared with known cyclic depsipeptides including PF1022A and emodepside. Furthermore, it has been discovered that the novel cyclic depsipeptides of the invention are significantly more resistant to metabolic modification in the body of animals so that they maintain at a higher concentration in the host animal's body and a higher level of activity against internal parasites for a longer duration of time.

In one embodiment, the cyclic depsipeptides of the invention have been found to be highly effective against filarial worms such as *Dirofilaria immitis* (microfilarial and larval stages), including isolates of the parasite that are resistant to macrocyclic lactones. In other embodiments, the compounds of the invention are effective against endoparasites that are not effectively controlled by the known cyclic depsipeptides such as PF1022A and emodepside.

In another embodiment, the cyclic depsipeptides of the invention have been found to have activity against ectoparasites such as fleas and ticks. Thus, in certain embodiments the cyclic depsipeptides may have endectocidal activity against both internal and external parasites.

The invention includes at least the following features:

(a) In one embodiment, the invention provides novel cyclic depsipeptide compounds of formula (I), or pharmaceutically or veterinarily acceptable salts thereof, which are active endoparasites and in some cases also active against ectoparasites;

(b) veterinary compositions comprising a parasiticidally effective amount of the cyclic depsipeptide compounds of formula (I), or a pharmaceutically or veterinarily acceptable salt thereof, in combination with a pharmaceutically or veterinarily acceptable carrier or diluent;

(c) veterinary compositions comprising a parasiticidally effective amount of the cyclic depsipeptide compounds of the invention, or pharmaceutically or veterinarily acceptable salts thereof, in combination with one more other active agents and a pharmaceutically or veterinarily acceptable carrier or diluent;

(d) methods for treating a parasitic infestation/infection in or on an animal are provided comprising administering a parasiticidally effective amount of a cyclic depsipeptide compound of formula (I), or a pharmaceutically or veterinarily acceptable salts thereof, optionally with one or more additional active agents, to the animal in need thereof;

(e) methods for the prevention of a parasitic infestation/infection of an animal, which comprise administering a parasiticidally effective amount of a cyclic depsipeptide compound of formula (I), or pharmaceutically or veterinarily acceptable salts thereof, optionally with one or more additional active agents, to the animal in need thereof;

(f) uses of the cyclic depsipeptide compounds of formula (I), or pharmaceutically or veterinarily acceptable salts thereof, for the treatment or prevention of a parasitic infection and possibly also a parasitic infestation in an animal;

(g) uses of the cyclic depsipeptide compounds of formula (I), or pharmaceutically or veterinarily acceptable salts thereof, in the manufacture of a veterinary medicament for the treatment or prevention of a parasitic infection in an animal; and (h) processes for the preparation of the compounds of formula (I).

Definitions

Terms used herein will have their customary meanings in the art unless specified. The organic moieties mentioned in the definitions of the variables of the cyclic depsipeptide formula (I) are like the term halogen—i.e., collective terms for individual listings of the individual group members—fluoro, chloro, bromo and iodo with respect to halogen. The prefix $C_n$-$C_m$ indicates in each case the possible number of carbon atoms in the group.

The term "alkyl" refers to saturated straight, branched, primary, secondary or tertiary hydrocarbons, including those having 1 to 12 atoms. In some embodiments, alkyl groups will include $C_1$-$C_{10}$, $C_1$-$C_8$, $C_1$-$C_6$, $C_1$-$C_4$ or $C_1$-$C_3$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

Carbocyclic groups are cyclic groups composed exclusively of carbon. The carbocyclic groups include both aromatic rings such as phenyl and non-aromatic rings such cyclohexyl and include those with 3 to 14 carbon atoms having single or multiple fused rings.

The alkyl and cycloalkyl and carbocyclic groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene and Wuts, *Protective Groups in Organic Synthesis*, John Wiley and Sons, Third Edition, 1999, hereby incorporated by reference.

The term "alkenyl" refers to both straight and branched carbon chains which have at least one carbon-carbon double bond. In some embodiments, alkenyl groups may include $C_2$-$C_{12}$ alkenyl groups. In other embodiments, alkenyl includes $C_2$-$C_{10}$, $C_2$-$C_8$, $C_2$-$C_6$ or $C_2$-$C_4$ alkenyl groups. In one embodiment of alkenyl, the number of double bonds is 1-3; in another embodiment of alkenyl, the number of double bonds is one. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Cycloalkenyl" refers to monovalent cyclic alkenyl groups of from 4 to 10 carbon atoms, preferably 5 to 8 carbon atoms, having single or multiple fused rings which fused rings may or may not be cycloalkenyl provided that the point of attachment is to a cycloalkenyl ring atom. Examples of cycloalkenyl groups include, by way of example, cyclopenten-4-yl, cyclooctene-5-yl and the like. Alkenyl and cycloalkenyl groups may be unsubstituted or substituted with one or more substituents as described for alkyl above.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one. In some embodiments, alkynyl groups include from 2 to 12 carbon atoms. In other embodiments, alkynyl groups may include $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "fluoroalkyl" as used herein refers to an alkyl in which one or more of the hydrogen atoms is replaced with fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

"Aryl" refers to a monovalent aromatic carbocyclic group of from 6 to 14 carbon atoms having a single ring or multiple fused rings. Aryl groups include, but are not limited to, phenyl, biphenyl, and naphthyl. In some embodiments aryl includes tetrahydronaphthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynylsulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, —$SF_5$, alkylamino, alkenylamino, alkynylamino, di(alkyl)amino, di(alkenyl)-amino, di(alkynyl)amino, or trialkylsilyl.

The term "aralkyl" refers to an aryl group that is bonded to the parent compound through a diradical alkylene bridge, (—$CH_2$—)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Examples of heteroaryls include pyridyl, pyridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, benzothiophenyl, imidazopyridyl, imidazopyrimidyl, or pyrrolopyrimidyl. Heteroaryl rings may be unsubstituted or substituted by one or more moieties as described for aryl above.

"Heterocyclyl," "heterocyclic" or "heterocyclo" refers to fully saturated or unsaturated, cyclic groups, for example, 3 to 7 membered monocyclic, 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, aziridinyl, azetidinyl, oxetanyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

The term "alkylthio" refers to alkyl-S—, where "alkyl" is as defined above. In some embodiments, the alkyl component of the alkylthio group will include $C_1$-$C_{10}$, $C_1$-$C_8$, $C_1$-$C_6$ $C_1$-$C_4$ or $C_1$-$C_3$ alkyl groups. For example, $C_1$-$C_4$-alkylthio include, but are not limited to, methylthio, ethylthio, propylthio, 1-methylethylthio, butylthio, 1-methylpropylthio, 2-methylpropylthio or 1,1-dimethylethylthio.

Similarly, the terms "haloalkylthio," "cycloalkylthio," "halocycloalkylthio" refer to the groups —S-haloalkyl, —S-cycloalkyl, and —S-halocycloalkyl, respectively, where the terms "haloalkyl," "cycloalkyl," and "halocycloalkyl" are as defined above.

The term "alkylsulfinyl" refers to the group alkyl-S(=O)—, where "alkyl" is as defined above. In some embodiments, the alkyl component in alkylsulfinyl groups will include $C_1$-$C_{12}$, $C_1$-$C_{10}$, $C_1$-$C_8$, $C_1$-$C_6$, $C_1$-$C_4$ or $C_1$-$C_3$ alkyl groups. Examples include, but are not limited to, —SO—$CH_3$, —SO—$C_2H_5$, n-propylsulfinyl, 1-methylethyl sulfinyl, n-butylsulfinyl, 1-methylpropylsulfinyl, 2-methylpropylsulfinyl, 1,1-dimethylethyl sulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentyl-sulfinyl, 3-methylpentylsulfinyl, 4-methylpentylsulfinyl, 1,1-dimethylbutyl sulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

Similarly, the terms "alkenylsulfinyl," "alkynylsulfinyl," "haloalkylsulfinyl," "haloalkenylsulfinyl," and "haloalkynylsulfinyl" refer to the groups alkenyl-S(=O)—, alkynyl-S(=O)—, and haloalkyl-S(=O)—, haloalkenyl-S(=O)—, and haloalkynyl-S(=O)—, where the terms "alkenyl," "alkynyl," "haloalkyl," "haloalkenyl," and "haloalkynyl" are as defined above.

The term "alkylsulfonyl" refers to the group alkyl-S(=O)$_2$—, where the term "alkyl" is as defined above. In some embodiments, the alkyl component in alkylsulfonyl groups will include $C_1$-$C_{12}$, $C_1$-$C_{10}$, $C_1$-$C_8$, $C_1$-$C_6$ or $C_1$-$C_4$ alkyl groups. Examples include, but are not limited to, —$SO_2$—$CH_3$, —$SO_2$—$C_2H_5$, n-propylsulfonyl, —$SO_2$—$CH(CH_3)_2$, n-butylsulfonyl, 1-methylpropylsulfonyl, 2-methylpropylsulfonyl, —$SO_2$—$C(CH_3)_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutyl sulfonyl, 1,2-dimethylbutylsulfonyl, 1,3-dimethylbutyl sulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropyl sulfonyl, 1-ethyl-1-methylpropyl sulfonyl or 1-ethyl-2-methylpropylsulfonyl and the like.

The terms "alkenylfulfonyl," "alkynylsulfonyl," "haloalkylsulfonyl," "haloalkenylsulfonyl," and "haloalkynylsulfonyl" refer to the groups alkenyl-S(=O)$_2$—, alkynyl-S(=O)$_2$—, and haloalkyl-S(=O)$_2$—, haloalkenyl-S(=O)$_2$—, and haloalkynyl-S(=O)$_2$—, where the terms "alkenyl," "alkynyl," "haloalkyl," "haloalkenyl," and "haloalkynyl" are as defined above.

The terms "alkylamino," "dialkylamino," "alkenylamino," "alkynylamino," "di(alkenyl)amino," and "di(alkynyl)amino" refer to the groups —NH(alkyl), —N(alkyl)$_2$, —NH(alkenyl), —NH(alkynyl), —N(alkenyl)$_2$ and —N(alkynyl)$_2$, where the terms "alkyl," "alkenyl," and "alkynyl" are as defined above. In some embodiments, the alkyl component in alkylamino or dialkylamino groups will include $C_1$-$C_{12}$, $C_1$-$C_{10}$, $C_1$-$C_8$, $C_1$-$C_6$ or $C_1$-$C_4$ alkyl groups.

Compounds of the Invention:

The compounds of the invention are 24-membered cyclic depsipeptide compounds which have potent activity against endoparasites such as nematodes and filarial worms (microfilarial and larval stages) and also in some cases against ectoparasites such as fleas and ticks. In one embodiment the invention provides cyclic depsipeptide compounds of formula (I), or a pharmaceutically or veterinarily acceptable salt thereof:

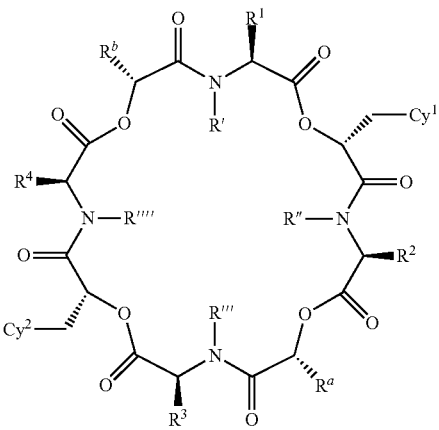

(I)

wherein:

Cy$^1$ and Cy$^2$ are independently aryl, carbocyclic, heteroaryl or heterocyclic optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN, —NO$_2$, cycloalkyl, heteroalkyl, heterocyclyl, aryl, heteroaryl, —O-heteroaryl, —S-heteroaryl, —O— heterocyclyl or —S-heterocyclyl, wherein each cycloalkyl, heteroalkyl, aryl or heteroaryl is optionally further substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$OC(O)—, R$^5$C(O)O—, R$^5$C(O)NR$^6$—, —CN and —NO$_2$;

R$^5$ and R$^6$ are independently hydrogen, alkyl, haloalkyl, thioalkyl, alkylthioalkyl, hydroxyalkyl, alkoxyalkyl, alkenyl, haloalkenyl, alkynyl, haloalkynyl, or the group —CH$_2$C(O)NHCH$_2$CF$_3$; or R$^5$ and R$^6$ together with the atom(s) to which they are bonded form a C$_3$-C$_6$ cyclic group;

R', R'', R''' and R'''' are each independently hydrogen or C$_1$-C$_3$alkyl;

R$^a$ and R$^b$ are independently hydrogen, C$_1$-C$_3$alkyl or C$_1$-C$_3$haloalkyl; and (a) R$^1$ is C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R$^2$, R$^3$ and R$^4$ are each independently C$_1$-C$_8$ alkyl; or (b) R$^2$ is C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R$^1$, R$^3$ and R$^4$ are each independently C$_1$-C$_8$ alkyl; or (c) R$^3$ is C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R$^1$, R$^2$ and R$^4$ are each independently C$_1$-C$_8$ alkyl; or (d) R$^4$ is C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R$^1$, R$^2$ and R$^3$ are each independently C$_1$-C$_8$ alkyl; or (e) R$^1$ and R$^2$ are each independently C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R$^3$ and R$^4$ are each independently C$_1$-C$_8$ alkyl; or (f) R$^1$ and R$^3$ are each independently C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R$^2$ and R$^4$ are each independently C$_1$-C$_8$ alkyl; or (g) R$^1$ and R$^4$ are each independently C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R$^2$ and R$^3$ are each independently C$_1$-C$_8$ alkyl; or (h) R$^2$ and R$^4$ are each independently C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R$^1$ and R$^3$ are each independently C$_1$-C$_8$ alkyl; or (i) R$^2$ and R$^3$ are each independently C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R$^1$ and R$^4$ are each independently C$_1$-C$_8$alkyl; or (j) R$^3$ and R$^4$ are each independently C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R$^1$ and R$^2$ are each independently C$_1$-C$_8$alkyl; or (k) R$^1$, R$^2$ and R$^3$ are each independently C$_1$-C$_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and R⁴ is $C_1$-$C_8$ alkyl; or (l) $R^2$, $R^3$ and $R^4$ are each independently $C_1$-$C_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and $R^1$ is $C_1$-$C_8$ alkyl; or (m) $R^1$, $R^3$ and $R^4$ are each independently $C_1$-$C_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino; and $R^2$ is $C_1$-$C_8$ alkyl; or (n) $R^1$, $R^2$ and $R^4$ are each independently $C_1$-$C_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino and alkylamino, dialkylamino; and $R^3$ is $C_1$-$C_8$ alkyl; or (o) $R^1$, $R^2$, $R^3$ and $R^4$ are each independently $C_1$-$C_8$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino.

$Cy^1$ and $Cy^2$ Groups

In one embodiment, $Cy^1$ and $Cy^2$ are independently phenyl optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl, heteroaryl, —O-heteroaryl, —S-heteroaryl, —O-heterocyclyl or —S— heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —$NO_2$, wherein $R^5$ and $R^6$ are as defined above for formula (I).

In another embodiment, $Cy^1$ and $Cy^2$ are independently phenyl, heteroaryl or heterocyclyl optionally independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —$NO_2$, wherein $R^5$ and $R^6$ are as defined above for formula (I).

In another embodiment, $Cy^1$ and $Cy^2$ are independently 6-12 membered bicyclic aryl or heteroaryl groups optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —$NO_2$, wherein $R^5$ and $R^6$ are as defined above for formula (I).

In another embodiment, $Cy^1$ and $Cy^2$ are independently bicyclic heterocyclic groups optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl, heteroaryl, —O-heteroaryl, —S-heteroaryl, —O— heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —$NO_2$, wherein $R^5$ and $R^6$ are as defined above for formula (I).

In another embodiment, $Cy^1$ and $Cy^2$ are independently phenyl, biphenyl, naphthyl, tetrahydronaphthyl, phenylcyclopropyl, biphenylene, fluorene, anthracene, acenaphthene, phenanthrene or indanyl optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —NO$_2$, wherein $R^5$ and $R^6$ are as defined above for formula (I).

In yet another embodiment, Cy$^1$ and Cy$^2$ are independently pyridyl, pyridazinyl, pyrimidinyl, pyrazinyl, triazinyl, pyrrolyl, indolyl, quinolinyl, isoquinolinyl, quinazolinyl, quinoxalinyl, furanyl, thiophenyl, pyrrolyl, imidazolyl, oxazolyl, isoxazolyl, isothiazolyl, pyrazolyl, benzofuranyl, dihydrobenzofuranyl, benzothiophenyl, imidazopyridyl, imidazopyrimidyl or pyrrolopyrimidyl optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —NO$_2$, cycloalkyl, heteroalkyl, heterocyclyl, aryl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —NO$_2$, wherein $R^5$ and $R^6$ are as defined above for formula (I).

In another embodiment, Cy$^1$ and Cy$^2$ are independently pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuranyl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl or triazinyl optionally independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —NO$_2$, cycloalkyl, heteroalkyl, heterocyclyl, aryl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —NO$_2$, wherein $R^5$ and $R^6$ are as defined above for formula (I).

In another embodiment, Cy$^1$ and Cy$^2$ are independently indolyl, isoindolyl, benzothiazolyl, benzoxazolyl, benz[d]isoxazolyl, benzotriazolyl, benzodioxolyl, benzothienyl, quinuclidinyl, quinazolinyl, quinoxalinyl, quinolinyl, isoquinolinyl, benzimidazolyl, benzopyranyl, indolizinyl, benzofuranyl, dihydrobenzofuranyl, chromonyl, coumarinyl, cinnolinyl, indazolyl, pyrrolopyridyl, phthalazinyl, 1,2,3-benzotriazinyl, 1,2,4-benzotriazinyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl or tetrahydroisoquinolinyl optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —NO$_2$, cycloalkyl, heteroalkyl, heterocyclyl, aryl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —NO$_2$, wherein $R^5$ and $R^6$ are as defined above for formula (I).

In one embodiment, Cy$^1$ and Cy$^2$ are independently phenyl substituted with heterocyclyl. In yet another embodiment, Cy$^1$ and Cy$^2$ are independently a 6-membered heteroaryl group substituted with heterocyclyl. In still another embodiment, Cy$^1$ and Cy$^2$ are independently heterocyclyl substituted with a heterocyclyl group. In yet another embodiment, Cy$^1$ and Cy$^2$ are independently phenyl, pyridinyl, pyridazinyl, pyrimidinyl, pyrazinyl or tetrazinyl substituted with heterocyclyl.

In one embodiment, Cy$^1$ and Cy$^2$ are independently phenyl, pyridinyl, pyridazinyl, pyrimidinyl, pyrazinyl or tetrazinyl substituted with morpholino, tetrahydropyran, tetrahydrofuran, pyrrolidino or piperidino.

In one embodiment, Cy$^1$ and Cy$^2$ are independently phenyl, a 5-membered or a 6-membered heteroaryl ring optionally substituted with halogen, hydroxy, alkoxy, haloalkoxy, alkylthio, haloalkylthio, thioamido, —SF$_5$, amino, alkylamino or dialkylamino.

In another embodiment, Cy$^1$ and Cy$^2$ are independently phenyl, a 5-membered or a 6-membered heteroaryl ring optionally substituted with alkyl, haloalkyl, alkenyl, haloalkenyl, alkynyl, haloalkynyl.

In another embodiment, Cy$^1$ and Cy$^2$ are independently phenyl, a 5-membered or a 6-membered heteroaryl ring optionally substituted with C$_1$-C$_3$alkyl, C$_1$-C$_3$haloalkyl, C$_2$-C$_4$alkenyl, C$_2$-C$_4$haloalkenyl, C$_2$-C$_4$alkynyl, C$_2$-C$_4$haloalkynyl, C$_1$-C$_3$alkoxy, C$_1$-C$_3$haloalkoxy, C$_1$-C$_3$alkylthio, C$_1$-C$_3$haloalkylthio, C$_1$-C$_3$alkylamino or C$_1$-C$_3$dialkylamino.

In another embodiment, Cy$^1$ and Cy$^2$ are independently phenyl, a 5-membered or a 6-membered heteroaryl ring optionally substituted with methyl, ethyl, propyl, isopropyl, butyl, isobutyl, tert-butyl, CF$_3$, —CH$_2$CF$_3$, —CHFCF$_3$ or —CF$_2$CF$_3$.

In another embodiment, Cy$^1$ and Cy$^2$ are independently phenyl, a 5-membered or a 6-membered heteroaryl ring optionally substituted with fluoro, chloro, bromo or iodo.

In another embodiment, Cy$^1$ and Cy$^2$ are independently phenyl, a 5-membered or a 6-membered heteroaryl ring optionally substituted with hydroxy, methoxy, trifluoromethoxy, —OCH$_2$CF$_3$, —OCHFCF$_3$, —OCF$_2$CF$_3$, —SCH$_3$, —SCF$_3$, —SCH$_2$CF$_3$, —SCHFCF$_3$, —SCF$_2$CF$_3$, —S(O)CH$_3$, —S(O)CF$_3$, —S(O)CH$_2$CF$_3$, —S(O)CHFCF$_3$, —S(O)CF$_2$CF$_3$, —S(O)$_2$CH$_3$, —S(O)$_2$CF$_3$, —S(O)$_2$CH$_2$CF$_3$, —S(O)$_2$CHFCF$_3$, —S(O)$_2$CF$_2$CF$_3$ or SF$_5$.

In yet another embodiment, Cy$^1$ and Cy$^2$ are independently phenyl, thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl or tetrazinyl optionally substituted with halogen, hydroxy, alkoxy, haloalkoxy, alkylthio, haloalkylthio, thioamido, amino, alkylamino or dialkylamino.

In yet another embodiment, Cy¹ and Cy² are independently phenyl, thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl or tetrazinyl optionally substituted with alkyl, haloalkyl, alkenyl, haloalkenyl, alkynyl or haloalkynyl.

In yet another embodiment, Cy¹ and Cy² are independently phenyl, thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl or tetrazinyl optionally substituted with $C_1$-$C_3$alkyl, $C_1$-$C_3$haloalkyl, $C_2$-$C_4$alkenyl, $C_2$-$C_4$haloalkenyl, $C_2$-$C_4$alkynyl, $C_2$-$C_4$haloalkynyl, $C_1$-$C_3$alkoxy, $C_1$-$C_3$haloalkoxy, $C_1$-$C_3$alkylthio, $C_1$-$C_3$haloalkylthio, $C_1$-$C_3$alkylamino or $C_1$-$C_3$dialkylamino.

In another embodiment, Cy¹ and Cy² are independently phenyl, a 5-membered or a 6-membered heteroaryl ring optionally substituted with methyl, ethyl, propyl, isopropyl, butyl, isobutyl, tert-butyl, $CF_3$, —$CH_2CF_3$, —$CHFCF_3$ or —$CF_2CF_3$.

In yet another embodiment, Cy¹ and Cy² are independently phenyl, thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl or tetrazinyl optionally substituted with fluoro, chloro, bromo or iodo.

In yet another embodiment, Cy¹ and Cy² are independently phenyl, thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl or tetrazinyl optionally substituted with hydroxy, methoxy, trifluoromethoxy, —$OCH_2CF_3$, —$OCHFCF_3$, —$OCF_2CF_3$, —$SCH_3$, —$SCF_3$, —$SCH_2CF_3$, —$SCHFCF_3$ or —$SCF_2CF_3$, —$S(O)CH_3$, —$S(O)CF_3$, —$S(O)CH_2CF_3$, —$S(O)CHFCF_3$, —$S(O)CF_2CF_3$, —$S(O)_2CH_3$, —$S(O)_2CF_3$, —$S(O)_2CH_2CF_3$, —$S(O)_2CHFCF_3$, —$S(O)_2CF_2CF_3$ or $SF_5$.

In another embodiment, Cy¹ and Cy² are independently one of R1 to R8 shown below:

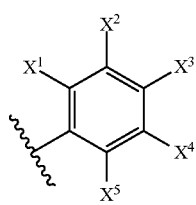

R1

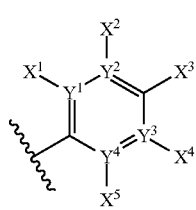

R2

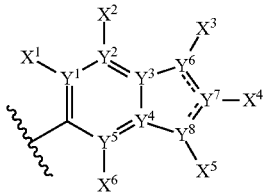

R3

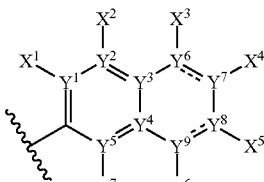

R4

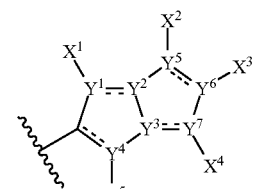

R5

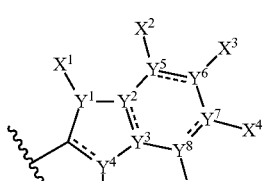

R6

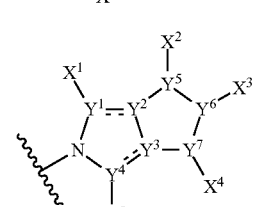

R7

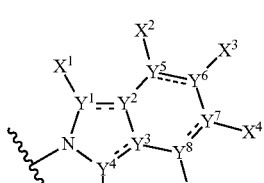

R8 wherein $Y^1$, $Y^2$, $Y^3$, $Y^4$, $Y^5$, $Y^6$, $Y^7$, $Y^8$ and $Y^9$ are each independently C, CH or N; and $X^1$, $X^2$, $X^3$, $X^4$, $X^5$, $X^6$ and $X^7$ are independently hydrogen, halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl, —O-heteroaryl, —S-heteroaryl, —O-heterocyclyl or —S-heterocyclyl, heteroaryl, wherein each cycloalkyl, heteroalkyl, aryl or heteroaryl is optionally further substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN and —NO$_2$, wherein R$^5$ and R$^6$ are as defined above for formula (I).

In one embodiment, Cy$^1$ and Cy$^2$ are independently R1 to R8 wherein Y$^1$, Y$^2$, Y$^3$, Y$^4$, Y$^5$, Y$^6$, Y$^7$, Y$^8$ and Y$^9$ are each independently C, CH or N; and X$^1$, X$^2$, X$^3$, X$^4$, X$^5$, X$^6$ and X$^7$ are independently hydrogen, halogen, hydroxy, alkoxy, haloalkoxy, alkylthio, haloalkylthio, R$^5$R$^6$NC(O)—, R$^5$R$^6$NC(O)NR$^5$—, thioamido, amino, alkylamino or dialkylamino.

In another embodiment, Cy$^1$ and Cy$^2$ are independently R1 to R8 wherein Y$^1$, Y$^2$, Y$^3$, Y$^4$, Y$^5$, Y$^6$, Y$^7$, Y$^8$ and Y$^9$ are each independently C, CH or N; and X$^1$, X$^2$, X$^3$, X$^4$, X$^5$, X$^6$ and X$^7$ are independently hydrogen, alkyl, haloalkyl, alkenyl, haloalkenyl, alkynyl, haloalkynyl.

In another embodiment, Cy$^1$ and Cy$^2$ are independently R1 to R8 wherein Y$^1$, Y$^2$, Y$^3$, Y$^4$, Y$^5$, Y$^6$, Y$^7$, Y$^8$ and Y$^9$ are each independently C, CH or N; and X$^1$, X$^2$, X$^3$, X$^4$, X$^5$, X$^6$ and X$^7$ are independently hydrogen, methyl, ethyl, propyl, isopropyl, butyl, isobutyl, tert-butyl, CF$_3$, —CH$_2$CF$_3$, —CHFCF$_3$ or CF$_2$CF$_3$.

In another embodiment, Cy$^1$ and Cy$^2$ are independently R1 to R8 wherein Y$^1$, Y$^2$, Y$^3$, Y$^4$, Y$^5$, Y$^6$, Y$^7$, Y$^8$ and Y$^9$ are each independently C, CH or N; and X$^1$, X$^2$, X$^3$, X$^4$, X$^5$, X$^6$ and X$^7$ are independently hydrogen, fluoro, chloro, bromo or iodo.

In another embodiment, Cy$^1$ and Cy$^2$ are independently R1 to R8, wherein Y$^1$, Y$^2$, Y$^3$, Y$^4$, Y$^5$, Y$^6$, Y$^7$, Y$^8$ and Y$^9$ are each independently C, CH or N; and X$^1$, X$^2$, X$^3$, X$^4$, X$^5$, X$^6$ and X$^7$ are independently hydrogen, hydroxy, methoxy, trifluoromethoxy, —OCH$_2$CF$_3$, —OCHFCF$_3$, —OCF$_2$CF$_3$, methylthio, trifluoromethylthio, —SCH$_2$CF$_3$, —SCHFCF$_3$, —SCF$_2$CF$_3$ or SF$_5$.

In another embodiment, Cy$^1$ and Cy$^2$ are independently R9 to R11 shown below:

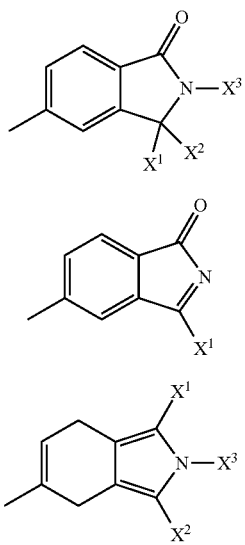

wherein X$^1$, X$^2$ and X$^3$ are independently hydrogen, halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN, —NO$_2$, cycloalkyl, heteroalkyl, heterocyclyl, aryl, —O-heteroaryl, —S-heteroaryl, —O-heterocyclyl or —S-heterocyclyl, heteroaryl, wherein each cycloalkyl, heteroalkyl, aryl or heteroaryl is optionally further substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN and —NO$_2$, wherein R$^5$ and R$^6$ are as defined above for formula (I).

In one embodiment, Cy$^1$ and Cy$^2$ are independently R9 to R11, wherein X$^1$, X$^2$ and X$^3$ are independently hydrogen, halogen, alkyl or haloalkyl. In another embodiment, Cy$^1$ and Cy$^2$ are independently R9 to R11, wherein X$^1$, X$^2$ and X$^3$ are independently hydrogen, fluoro, chloro, bromo or iodo. In another embodiment, Cy$^1$ and Cy$^2$ are independently R9 to R11, wherein X$^1$, X$^2$ and X$^3$ are independently hydrogen, methyl, ethyl, propyl, isopropyl, butyl, isobutyl, tert-butyl, CF$_3$, —CH$_2$CF$_3$, —CHFCF$_3$ or CF$_2$CF$_3$. In yet another embodiment, Cy$^1$ and Cy$^2$ are independently R9 to R11, wherein X$^1$, X$^2$ and X$^3$ are independently hydrogen, hydroxy, methoxy, trifluoromethoxy, —OCH$_2$CF$_3$, —OCHFCF$_3$, —OCF$_2$CF$_3$, methylthio, trifluoromethylthio, —SCH$_2$CF$_3$, —SCHFCF$_3$, —SCF$_2$CF$_3$ or SF$_5$.

In another embodiment, Cy$^1$ and/or Cy$^2$ are independently phenyl, p-morpholinophenyl, p-fluorophenyl, p-OCF$_3$-phenyl, p-CF$_3$-phenyl, 3,4,5-trifluoro-phenyl, p-tetrahydropyranyl-4-yl-phenyl, 2-(morpholin-4-yl)pyridine-5-yl, 5-(morpholin-4-yl)pyridin-2-yl, p-thiosulfonylmorpholin-4-yl-phenyl, p-NH$_2$-phenyl, p-(1-Me-1H-tetrazole-5-thiolyl) phenyl, p-NH$_2$— phenyl, 2,3-dihydrobenzofuran-5-yl, 4-(morpholin-4-yl)cyclylhexanyl, p-iodophenyl, p-bromophenyl, p-nitrophenyl and p-tert-butylphenyl.

In another embodiment, Cy$^1$ and Cy$^2$ are the groups shown in Table 1 below:

TABLE 1

| Cy$^1$ | Cy$^2$ |
|---|---|
| *p*-morpholinophenyl | Ph |
| p-F—Ph | p-F—Ph |
| p-OCF$_3$—Ph | p-OCF$_3$—Ph |
| Ph | Ph |
| p-CF$_3$—Ph | p-CF$_3$—Ph |
| 3,4,5-tri-F—Ph | 3,4,5-tri-F—Ph |
| *p*-morpholinophenyl | *p*-morpholinophenyl |
| *p*-tetrahydropyranyl-phenyl | *p*-tetrahydropyranyl-phenyl |
| 2-(morpholin-4-yl)pyridin-5-yl | 2-(morpholin-4-yl)pyridin-5-yl |

TABLE 1-continued

| Cy¹ | Cy² |
|---|---|
| (pyridine-morpholine) | (pyridine-morpholine) |
| (Ph-thiomorpholine dioxide) | (Ph-thiomorpholine dioxide) |
| p-NH₂—Ph | p-NH₂—Ph |
|  | p-I—Ph |
| (Ph-S-methyltetrazole) |  |
| (dihydrobenzofuran) | (dihydrobenzofuran) |
| (Ph-S-methyltetrazole) | (Ph-S-methyltetrazole) |
| (cyclohexyl-morpholine) | (cyclohexyl-morpholine) |
| p-I—Ph | p-I—Ph |
| p-Br—Ph | p-Br—Ph |
| p-NO₂—Ph | p-NO₂—Ph |
|  | Ph |
| (Ph-S-methyltetrazole) |  |
| p-tBu—Ph | p-tBu—Ph |
| p-SF₅—Ph | p-SF₅—Ph |
| (F-Ph-cyclohexyl) | (F-Ph-cyclohexyl) |
| (F-Ph-morpholine) | (F-Ph-morpholine) |
| (F-Ph-tetrahydropyran) | (F-Ph-tetrahydropyran) |
| (Ph-cyclohexyl-CF₂) | (Ph-cyclohexyl-CF₂) |
| (Ph-cyclohexyl-(CH₃)₂) | (Ph-cyclohexyl-(CH₃)₂) |
| (Ph-C(O)NH-CH₂CF₃) | (Ph-C(O)NH-CH₂CF₃) |
| (Ph-piperidine-CF₂) | (Ph-piperidine-CF₂) |
| (Ph-pyrrolidine-CF₂) | (Ph-pyrrolidine-CF₂) |
| (biphenyl-F) | (biphenyl-F) |
| (naphthyl-morpholine) | (naphthyl-morpholine) |

$R^a$ and $R^b$ $R^a$ and $R^b$ may independently be hydrogen, $C_1$-$C_3$alkyl or $C_1$-$C_3$haloalkyl. In one embodiment, $R^a$ and $R^b$ are independently hydrogen or methyl. In another embodiment, $R^a$ and $R^b$ are independently hydrogen, methyl, ethyl or propyl. In another embodiment, $R^a$ and $R^b$ are independently hydrogen, methyl or $CF_3$. In still another embodiment, $R^a$ and $R^b$ are both methyl. In yet another embodiment, $R^a$ and $R^b$ are both hydrogen.

R', R", R'" and R""

In one embodiment, each of R', R", R'" and R"" are independently hydrogen or $C_1$-$C_3$alkyl. In another embodiment, each of R', R", R'" and R"" are independently hydrogen or methyl. In another embodiment, each of R', R", R'" and R"" are independently hydrogen, methyl or ethyl.

$R^1$, $R^2$, $R^3$ and $R^4$

It will be understood that the invention includes compounds wherein the various groups Cy¹ and Cy² described in the above embodiments are combined with any combination of $R^1$, $R^2$, $R^3$ and $R^4$ described above for formula (I) and in the embodiments described below.

In one embodiment of the invention, one of $R^1$ to $R^4$ is a $C_1$-$C_8$ alkyl group substituted by one or more of the substituents for these variables described above for formula (I) while the others of $R^1$ to $R^4$ are unsubstituted $C_1$-$C_8$ alkyl.

In another embodiment, two of $R^1$ to $R^4$ are $C_1$-$C_8$alkyl independently substituted by one or more of the substituents for these variables described above for formula (I) while the other two of $R^1$ to $R^4$ are unsubstituted $C_1$-$C_8$ alkyl.

In yet another embodiment, three of $R^1$ to $R^4$ are $C_1$-$C_8$alkyl independently substituted by one or more of the substituents for these variables described above for formula (I) while the other of $R^1$ to $R^4$ is unsubstituted $C_1$-$C_8$ alkyl.

In still another embodiment, all four of $R^1$ to $R^4$ are $C_1$-$C_8$alkyl independently substituted by one or more of the substituents for these variables described above for formula (I).

In another embodiment of the invention, one of $R^1$ to $R^4$ is a $C_1$-$C_6$ alkyl group substituted by one or more of the substituents for these variables described above for formula (I) while the others of $R^1$ to $R^4$ are unsubstituted $C_1$-$C_6$ alkyl.

In another embodiment, two of $R^1$ to $R^4$ are $C_1$-$C_6$alkyl independently substituted by one or more of the substituents for these variables described above for formula (I) while the other two of $R^1$ to $R^4$ are unsubstituted $C_1$-$C_6$ alkyl.

In yet another embodiment, three of $R^1$ to $R^4$ are $C_1$-$C_6$alkyl independently substituted by one or more of the substituents for these variables described above for formula (I) while the other of $R^1$ to $R^4$ is unsubstituted $C_1$-$C_6$ alkyl.

In still another embodiment, all four of $R^1$ to $R^4$ are independently $C_1$-$C_6$alkyl substituted by one or more of the substituents for these variables described above for formula (I).

In another embodiment of the invention, one of $R^1$ to $R^4$ is a $C_1$-$C_6$ alkyl group substituted by one or more of the substituents for these variables described above for formula (I) while the others of $R^1$ to $R^4$ are unsubstituted 2-methylpropyl or 2,2-dimethylpropyl.

In another embodiment, two of $R^1$ to $R^4$ are $C_1$-$C_6$alkyl independently substituted by one or more of the substituents for these variables described above for formula (I) while the other two of $R^1$ to $R^4$ are unsubstituted 2-methylpropyl or 2,2-dimethylpropyl.

In yet another embodiment, three of $R^1$ to $R^4$ are $C_1$-$C_6$alkyl independently substituted by one or more of the substituents for these variables described above for formula (I) while the other of $R^1$ to $R^4$ is unsubstituted 2-methylpropyl or 2,2-dimethylpropyl.

In another embodiment of the invention, one of $R^1$ to $R^4$ is a $C_1$-$C_8$ alkyl group substituted by one or more halogen while the others of $R^1$ to $R^4$ are unsubstituted $C_1$-$C_8$ alkyl.

In another embodiment, two of $R^1$ to $R^4$ are $C_1$-$C_8$alkyl independently substituted by one or more halogen while the other two of $R^1$ to $R^4$ are unsubstituted $C_1$-$C_8$ alkyl.

In yet another embodiment, three of $R^1$ to $R^4$ are $C_1$-$C_8$alkyl independently substituted by one or more halogen while the other of $R^1$ to $R^4$ is unsubstituted $C_1$-$C_8$ alkyl.

In still another embodiment, all four of $R^1$ to $R^4$ are $C_1$-$C_8$alkyl independently substituted one or more halogen.

In another embodiment of the invention, one of $R^1$ to $R^4$ is a $C_1$-$C_6$ alkyl group substituted by one or more halogen while the others of $R^1$ to $R^4$ are unsubstituted $C_1$-$C_6$ alkyl.

In another embodiment, two of $R^1$ to $R^4$ are $C_1$-$C_6$alkyl independently substituted by one or more halogen while the other two of $R^1$ to $R^4$ are unsubstituted $C_1$-$C_6$ alkyl.

In yet another embodiment, three of $R^1$ to $R^4$ are $C_1$-$C_6$alkyl independently substituted by one or more halogen while the other of $R^1$ to $R^4$ is unsubstituted $C_1$-$C_6$ alkyl.

In still another embodiment, all four of $R^1$ to $R^4$ are $C_1$-$C_6$alkyl independently substituted one or more halogen.

In another embodiment of the invention, one of $R^1$ to $R^4$ is a $C_1$-$C_6$ alkyl group substituted by one or more halogen while the others of $R^1$ to $R^4$ are unsubstituted 2-methylpropyl or 2,2-dimethylpropyl.

In another embodiment, two of $R^1$ to $R^4$ are $C_1$-$C_6$alkyl independently substituted by one or more halogen while the other two of $R^1$ to $R^4$ are unsubstituted 2-methylpropyl or 2,2-dimethylpropyl.

In yet another embodiment, three of $R^1$ to $R^4$ are $C_1$-$C_6$alkyl independently substituted by one or more halogen while the other of $R^1$ to $R^4$ is unsubstituted 2-methylpropyl or 2,2-dimethylpropyl.

In another embodiment of the invention, one of $R^1$ to $R^4$ is a $C_1$-$C_8$ alkyl group substituted by one or more fluoro while the others of $R^1$ to $R^4$ are unsubstituted $C_1$-$C_8$ alkyl.

In another embodiment, two of $R^1$ to $R^4$ are $C_1$-$C_8$alkyl independently substituted by one or more fluoro while the other two of $R^1$ to $R^4$ are unsubstituted $C_1$-$C_8$ alkyl.

In yet another embodiment, three of $R^1$ to $R^4$ are $C_1$-$C_8$alkyl independently substituted by one or more fluoro while the other of $R^1$ to $R^4$ is unsubstituted $C_1$-$C_8$ alkyl.

In still another embodiment, all four of $R^1$ to $R^4$ are $C_1$-$C_8$alkyl independently substituted one or more fluoro.

In another embodiment of the invention, one of $R^1$ to $R^4$ is a $C_1$-$C_6$ alkyl group substituted by one or more fluoro while the others of $R^1$ to $R^4$ are unsubstituted $C_1$-$C_6$ alkyl.

In another embodiment, two of $R^1$ to $R^4$ are $C_1$-$C_6$alkyl independently substituted by one or more fluoro while the other two of $R^1$ to $R^4$ are unsubstituted $C_1$-$C_6$ alkyl.

In yet another embodiment, three of $R^1$ to $R^4$ are $C_1$-$C_6$alkyl independently substituted by one or more fluoro while the other of $R^1$ to $R^4$ is unsubstituted $C_1$-$C_6$ alkyl.

In still another embodiment, all four of $R^1$ to $R^4$ are $C_1$-$C_6$alkyl independently substituted one or more fluoro.

In another embodiment of the invention, one of $R^1$ to $R^4$ is a $C_1$-$C_6$ alkyl group substituted by one or more fluoro while the others of $R^1$ to $R^4$ are unsubstituted 2-methylpropyl or 2,2-dimethylpropyl.

In another embodiment, two of $R^1$ to $R^4$ are $C_1$-$C_6$alkyl independently substituted by one or more fluoro while the other two of $R^1$ to $R^4$ are unsubstituted 2-methylpropyl or 2,2-dimethylpropyl.

In yet another embodiment, three of $R^1$ to $R^4$ are $C_1$-$C_6$alkyl independently substituted by one or more fluoro while the other of $R^1$ to $R^4$ is unsubstituted 2-methylpropyl or 2,2-dimethylpropyl.

In one embodiment of the invention, one of $R^1$ to $R^4$ is $CH_2F$, $CHF_2$ or $CF_3$; and the others of $R^1$ to $R^4$ are unsubstituted 2-methylpropyl or 2,2-dimethylpropyl.

In another embodiment, two of $R^1$ to $R^4$ are $CH_2F$, $CHF_2$ or $CF_3$; and the other two of $R^1$ to $R^4$ are unsubstituted 2-methylpropyl or 2,2-dimethylpropyl.

In yet another embodiment, three of $R^1$ to $R^4$ are $CH_2F$, $CHF_2$ or $CF_3$; and the other of $R^1$ to $R^4$ is unsubstituted 2-methylpropyl or 2,2-dimethylpropyl.

In yet another embodiment, all four of $R^1$ to $R^4$ are $CH_2F$, $CHF_2$ or $CF_3$.

In one embodiment of the invention, one of $R^1$ to $R^4$ is —$CH_2CX(CH_3)_2$ wherein X is halogen; and the others of $R^1$ to $R^4$ are unsubstituted 2-methylpropyl or 2,2-dimethylpropyl.

In another embodiment, two of $R^1$ to $R^4$ are —$CH_2CX(CH_3)_2$ wherein X is halogen; and the other two of $R^1$ to $R^4$ are unsubstituted 2-methylpropyl or 2,2-dimethylpropyl.

In yet another embodiment, three of $R^1$ to $R^4$ are —$CH_2CX(CH_3)_2$ wherein X is halogen; and the other of $R^1$ to $R^4$ is unsubstituted 2-methylpropyl or 2,2-dimethylpropyl.

In yet another embodiment, all four of $R^1$ to $R^4$ are —$CH_2CX(CH_3)_2$ wherein X is halogen.

In one embodiment of the invention, one of $R^1$ to $R^4$ is —$CH_2CF(CH_3)_2$; and the others of $R^1$ to $R^4$ are unsubstituted 2-methylpropyl or 2,2-dimethylpropyl.

In another embodiment, two of $R^1$ to $R^4$ are —$CH_2CF(CH_3)_2$; and the other two of $R^1$ to $R^4$ are unsubstituted 2-methylpropyl or 2,2-dimethylpropyl.

In yet another embodiment, three of $R^1$ to $R^4$ are —$CH_2CF(CH_3)_2$; and the other of $R^1$ to $R^4$ is unsubstituted 2-methylpropyl or 2,2-dimethylpropyl.

In yet another embodiment, all four of $R^1$ to $R^4$ are —$CH_2CF(CH_3)_2$.

In another embodiment of the invention, one of $R^1$ to $R^4$ is —$CH_2CX(CH_3)_2$ wherein X is $CH_2F$, $CHF_2$ or $CF_3$; and the others of $R^1$ to $R^4$ are unsubstituted 2-methylpropyl or 2,2-dimethylpropyl.

In another embodiment, two of $R^1$ to $R^4$ are —$CH_2CX(CH_3)_2$ wherein X is $CH_2F$, $CHF_2$ or $CF_3$; and the other two of $R^1$ to $R^4$ are unsubstituted 2-methylpropyl or 2,2-dimethylpropyl.

In yet another embodiment, three of $R^1$ to $R^4$ are —$CH_2CX(CH_3)_2$ wherein X is $CH_2F$, $CHF_2$ or $CF_3$; and the other of $R^1$ to $R^4$ is unsubstituted 2-methylpropyl or 2,2-dimethylpropyl.

In yet another embodiment, all four of $R^1$ to $R^4$ are —$CH_2CX(CH_3)_2$ wherein X is $CH_2F$, $CHF_2$ or $CF_3$.

In one embodiment of the invention, one of $R^1$ to $R^4$ is a $C_1$-$C_8$ alkyl group substituted by one or more aryl or heteroaryl groups while the others of $R^1$ to $R^4$ are unsubstituted $C_1$-$C_8$ alkyl.

In another embodiment, two of $R^1$ to $R^4$ are $C_1$-$C_8$alkyl independently substituted by one or more aryl or heteroaryl groups while the other two of $R^1$ to $R^4$ are unsubstituted $C_1$-$C_8$ alkyl.

In yet another embodiment, three of $R^1$ to $R^4$ are $C_1$-$C_8$alkyl independently substituted by one or more aryl or heteroaryl groups while the other of $R^1$ to $R^4$ is unsubstituted $C_1$-$C_8$ alkyl.

In still another embodiment, all four of $R^1$ to $R^4$ are $C_1$-$C_8$alkyl independently substituted one or more aryl or heteroaryl groups.

In another embodiment of the invention, one of $R^1$ to $R^4$ is a $C_1$-$C_6$ alkyl group substituted by one or more aryl or heteroaryl groups while the others of $R^1$ to $R^4$ are unsubstituted $C_1$-$C_6$ alkyl.

In another embodiment, two of $R^1$ to $R^4$ are $C_1$-$C_6$alkyl independently substituted by one or more aryl or heteroaryl groups while the other two of $R^1$ to $R^4$ are unsubstituted $C_1$-$C_6$ alkyl.

In yet another embodiment, three of $R^1$ to $R^4$ are $C_1$-$C_6$alkyl independently substituted by one or more aryl or heteroaryl groups while the other of $R^1$ to $R^4$ is unsubstituted $C_1$-$C_6$ alkyl.

In still another embodiment, all four of $R^1$ to $R^4$ are $C_1$-$C_6$alkyl independently substituted one or more aryl or heteroaryl groups.

In another embodiment of the invention, one of $R^1$ to $R^4$ is a $C_1$-$C_6$ alkyl group substituted by one or more aryl or heteroaryl groups while the others of $R^1$ to $R^4$ are unsubstituted 2-methylpropyl or 2,2-dimethylpropyl.

In another embodiment, two of $R^1$ to $R^4$ are $C_1$-$C_6$alkyl independently substituted by one or more aryl or heteroaryl groups while the other two of $R^1$ to $R^4$ are unsubstituted 2-methylpropyl or 2,2-dimethylpropyl.

In yet another embodiment, three of $R^1$ to $R^4$ are $C_1$-$C_6$alkyl independently substituted by one or more aryl or heteroaryl groups while the other of $R^1$ to $R^4$ is unsubstituted 2-methylpropyl or 2,2-dimethylpropyl.

In another embodiment of the invention, one of $R^1$ to $R^4$ is a $C_1$-$C_6$ alkyl group substituted by an optionally substituted phenyl while the others of $R^1$ to $R^4$ are unsubstituted 2-methylpropyl or 2,2-dimethylpropyl.

In another embodiment, two of $R^1$ to $R^4$ are independently $C_1$-$C_6$alkyl substituted by an optionally substituted phenyl while the other two of $R^1$ to $R^4$ are unsubstituted 2-methylpropyl or 2,2-dimethylpropyl.

In yet another embodiment, three of $R^1$ to $R^4$ are independently $C_1$-$C_6$alkyl substituted by an optionally substituted phenyl while the other of $R^1$ to $R^4$ is unsubstituted 2-methylpropyl or 2,2-dimethylpropyl.

In yet another embodiment, all four of $R^1$ to $R^4$ are independently $C_1$-$C_6$alkyl substituted by an optionally substituted phenyl.

In another embodiment of the invention, one of $R^1$ to $R^4$ is a $C_1$-$C_6$ alkyl group substituted by an optionally substituted heteroaryl group selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl while the others of $R^1$ to $R^4$ are unsubstituted 2-methylpropyl or 2,2-dimethylpropyl.

In another embodiment, two of $R^1$ to $R^4$ are independently $C_1$-$C_6$alkyl substituted by an optionally substituted heteroaryl group selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl while the other two of $R^1$ to $R^4$ are unsubstituted 2-methylpropyl or 2,2-dimethylpropyl.

In yet another embodiment, three of $R^1$ to $R^4$ are independently $C_1$-$C_6$alkyl substituted by an optionally substituted heteroaryl group selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl while the other of $R^1$ to $R^4$ is unsubstituted 2-methylpropyl or 2,2-dimethylpropyl.

In yet another embodiment, all four of $R^1$ to $R^4$ are independently $C_1$-$C_6$alkyl substituted by an optionally substituted heteroaryl group selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl.

In another embodiment of the invention, one, two, three or all four of $R^1$ to $R^4$ is the group G-1:

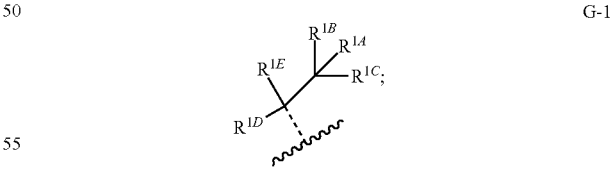

wherein $R^{1A}$, $R^{1B}$, $R^{1C}$, $R^{1D}$ and $R^{1E}$ are independently hydrogen, halogen, alkyl or haloalkyl; and the others of $R^1$ to $R^4$, if applicable, are unsubstituted $C_1$-$C_8$alkyl.

In one embodiment of the invention, one of $R^1$ to $R^4$ is G-1; and the others of $R^1$ to $R^4$ are unsubstituted 2-methylpropyl or 2,2-dimethylpropyl.

In another embodiment, two of $R^1$ to $R^4$ are G-1; and the other two of $R^1$ to $R^4$ are unsubstituted 2-methylpropyl or 2,2-dimethylpropyl.

In yet another embodiment, three of $R^1$ to $R^4$ are G-1; and the other of $R^1$ to $R^4$ is unsubstituted 2-methylpropyl or 2,2-dimethylpropyl.

In yet another embodiment, all four of $R^1$ to $R^4$ are G-1.

In one embodiment, one, two, three or all four of $R^1$ to $R^4$ are G-1, wherein $R^{1A}$, $R^{1B}$, $R^{1C}$, $R^{1D}$ and $R^{1E}$ are independently hydrogen, fluoro, $C_1$-$C_3$ alkyl or $C_1$-$C_3$ haloalkyl and the others of $R^1$ to $R^4$ are unsubstituted $C_1$-$C_6$alkyl. In another embodiment, one, two, three or all four of $R^1$ to $R^4$ are G-1, wherein $R^{1A}$, $R^{1B}$, $R^{1C}$, $R^{1D}$ and $R^{1E}$ are independently hydrogen, fluoro, $C_1$-$C_3$ alkyl or $C_1$-$C_3$ haloalkyl and the others of $R^1$ to $R^4$ are unsubstituted 2-methylpropyl or 2,2-dimethylpropyl.

In one embodiment, one, two, three or all four of $R^1$ to $R^4$ are G-1, wherein $R^{1D}$ and $R^{1E}$ are independently H or halogen. In another embodiment, one, two, three or all four of $R^1$ to $R^4$ are G-1, wherein $R^{1D}$ and $R^{1E}$ are independently $C_1$-$C_3$ alkyl or $C_1$-$C_3$ haloalkyl. In another embodiment, one, two, three or all four of $R^1$ to $R^4$ are G-1, wherein $R^{1A}$ is H or halogen. In another embodiment, one, two, three or all four of $R^1$ to $R^4$ are G-1, wherein $R^{1A}$ is $C_1$-$C_3$ alkyl or $C_1$-$C_3$ haloalkyl. In another embodiment, one, two or all four of $R^1$ to $R^4$ are G-1, wherein $R^{1A}$ is halogen, and $R^{1B}$ and $R^{1C}$ are independently $C_1$-$C_3$ alkyl or $C_1$-$C_3$ haloalkyl. In yet another embodiment, one, two, three or all four of $R^1$ to $R^4$ are G-1, wherein $R^{1D}$ and $R^{1E}$ are H, $R^{1A}$ is halogen, and $R^{1B}$ and $R^{1C}$ are independently $C_1$-$C_3$ alkyl or $C_1$-$C_3$ haloalkyl.

In one embodiment, one, two, three or all four of $R^1$ to $R^4$ are G-1, wherein $R^{1D}$ and $R^{1E}$ are independently H or F. In another embodiment, one, two, three or all four of $R^1$ to $R^4$ are G-1, wherein $R^{1D}$ and $R^{1E}$ are independently methyl or trifluoromethyl. In another embodiment, one, two, three or all four of $R^1$ to $R^4$ are G-1, wherein $R^{1A}$ is H or F. In another embodiment, one, two, three or all four of $R^1$ to $R^4$ are G-1, wherein $R^{1A}$ is methyl or trifluoromethyl. In another embodiment, one, two, three or all four of $R^1$ to $R^4$ are G-1, wherein $R^{1A}$ is F, and $R^{1B}$ and $R^{1C}$ are methyl or trifluoromethyl. In yet another embodiment, one, two, three or all four of $R^1$ to $R^4$ are G-1, wherein $R^{1D}$ and $R^{1E}$ are H, $R^{1A}$ is F, $R^{1B}$ and $R^c$ are methyl or trifluoromethyl.

In another embodiment, one, two, three or all four of $R^1$ to $R^4$ are G-1, wherein $R^{1A}$ is $C_1$-$C_3$ alkyl or $C_1$-$C_3$ haloalkyl; and the other of $R^1$ to $R^4$ are 2-methylpropyl or 2,2-dimethylpropyl. In another embodiment, one, two, three or all four of $R^1$ to $R^4$ are G-1, wherein $R^{1A}$ is halogen, and $R^{1B}$ and $R^{1C}$ are independently $C_1$-$C_3$ alkyl or $C_1$-$C_3$ haloalkyl; and the other of $R^1$ to $R^4$ are 2-methylpropyl or 2,2-dimethylpropyl. In yet another embodiment, one, two, three or all four of $R^1$ to $R^4$ are G-1, wherein $R^{1D}$ and $R^{1E}$ are H, $R^{1A}$ is halogen, and $R^{1B}$ and $R^{1C}$ are independently $C_1$-$C_3$ alkyl or $C_1$-$C_3$ haloalkyl; and the other of $R^1$ to $R^4$ are 2-methylpropyl or 2,2-dimethylpropyl.

In one embodiment, one, two, three or all four of $R^1$ to $R^4$ are G-1, wherein one of $R^{1D}$ and $R^{1E}$ is F; and the others of $R^1$ to $R^4$ are 2-methylpropyl or 2,2-dimethylpropyl. In another embodiment, one, two, three or all four of $R^1$ to $R^4$ are G-1, wherein one of $R^{1D}$ and $R^{1E}$ is methyl or trifluoromethyl; and the others of $R^1$ to $R^4$ are 2-methylpropyl or 2,2-dimethylpropyl. In another embodiment, one, two, three or all four of $R^1$ to $R^4$ are G-1, wherein $R^{1A}$ is F; and the others of $R^1$ to $R^4$ are 2-methylpropyl or 2,2-dimethylpropyl. In another embodiment, one, two, three or all four of $R^1$ to $R^4$ are G-1, wherein $R^{1A}$ is methyl or trifluoromethyl; and the others of $R^1$ to $R^4$ are 2-methylpropyl or 2,2-dimethylpropyl. In another embodiment, one, two, three or all four of $R^1$ to $R^4$ are G-1, wherein $R^{1A}$ is F, and $R^{1B}$ and $R^{1C}$ are methyl or trifluoromethyl; and the others of $R^1$ to $R^4$ are 2-methylpropyl or 2,2-dimethylpropyl. In yet another embodiment, one, two, three or all four of $R^1$ to $R^4$ are G-1, wherein $R^{1D}$ and $R^{1E}$ are H, $R^{1A}$ is F, $R^{1B}$ and $R^{1C}$ are methyl or trifluoromethyl; and the others of $R^1$ to $R^4$ are 2-methylpropyl or 2,2-dimethylpropyl.

In another embodiment, one of $R^1$ to $R^4$ are G-1, wherein $R^{1A}$ is F, and $R^{1B}$ and $R^{1C}$ are methyl or trifluoromethyl; and the others of $R^1$ to $R^4$ are 2-methylpropyl or 2,2-dimethylpropyl. In another embodiment, two of $R^1$ to $R^4$ are G-1, wherein $R^{1A}$ is F, and $R^{1B}$ and $R^{1C}$ are methyl or trifluoromethyl; and the others of $R^1$ to $R^4$ are 2-methylpropyl or 2,2-dimethylpropyl. In another embodiment, three of $R^1$ to $R^4$ are G-1, wherein $R^{1A}$ is F, and $R^{1B}$ and $R^{1C}$ are methyl or trifluoromethyl; and the others of $R^1$ to $R^4$ are 2-methylpropyl or 2,2-dimethylpropyl. In another embodiment, all four of $R^1$ to $R^4$ are G-1, wherein $R^{1A}$ is F, and $R^{1B}$ and $R^{1C}$ are methyl or trifluoromethyl. In one embodiment, $R^1$ is G-1, wherein $R^{1A}$ is F, and $R^{1B}$ and $R^{1C}$ are methyl or trifluoromethyl; and $R^2$, $R^3$ and $R^4$ are 2-methylpropyl or 2,2-dimethylpropyl. In another embodiment, $R^2$ is G-1, wherein $R^{1A}$ is F, and $R^{1B}$ and $R^{1C}$ are methyl or trifluoromethyl; and $R^2$, $R^3$ and $R^4$ are 2-methylpropyl or 2,2-dimethylpropyl. In yet another embodiment, $R^3$ is G-1, wherein $R^{1A}$ is F, and $R^{1B}$ and $R^{1C}$ are methyl or trifluoromethyl; and $R^1$, $R^2$ and $R^4$ are 2-methylpropyl or 2,2-dimethylpropyl. In another embodiment, $R^4$ is G-1, wherein $R^{1A}$ is F, and $R^{1B}$ and $R^{1C}$ are methyl or trifluoromethyl; and $R^1$, $R^2$ and $R^3$ are 2-methylpropyl or 2,2-dimethylpropyl.

In another embodiment, $R^1$ and $R^3$ are G-1, wherein $R^{1A}$ is F, and $R^{1B}$ and $R^{1C}$ are methyl or trifluoromethyl; and $R^2$ and $R^4$ are 2-methylpropyl or 2,2-dimethylpropyl. In another embodiment, $R^2$ and $R^4$ are G-1, wherein $R^{1A}$ is F, and $R^{1B}$ and $R^{1C}$ are methyl or trifluoromethyl; and $R^1$ and $R^3$ are 2-methylpropyl or 2,2-dimethylpropyl. In another embodiment, $R^1$ and $R^2$ are G-1, wherein $R^{1A}$ is F, and $R^{1B}$ and $R^{1C}$ are methyl or trifluoromethyl; and $R^3$ and $R^4$ are 2-methylpropyl or 2,2-dimethylpropyl. In yet another embodiment, $R^2$ and $R^3$ are G-1, wherein $R^{1A}$ is F, and $R^{1B}$ and $R^{1C}$ are methyl or trifluoromethyl; and $R^1$ and $R^4$ are 2-methylpropyl or 2,2-dimethylpropyl. In another embodiment, $R^1$ and $R^4$ are G-1, wherein $R^{1A}$ is F, and $R^{1B}$ and $R^{1C}$ are methyl or trifluoromethyl; and $R^2$ and $R^3$ are 2-methylpropyl or 2,2-dimethylpropyl.

In another embodiment, $R^1$, $R^2$ and $R^3$ are G-1, wherein $R^{1A}$ is F, and $R^{1B}$ and $R^{1C}$ are methyl or trifluoromethyl; and $R^4$ is 2-methylpropyl or 2,2-dimethylpropyl. In another embodiment, $R^1$, $R^2$ and $R^4$ are G-1, wherein $R^{1A}$ is F, and $R^{1B}$ and $R^{1C}$ are methyl or trifluoromethyl; and $R^3$ is 2-methylpropyl or 2,2-dimethylpropyl. In another embodiment, $R^1$, $R^3$ and $R^4$ are G-1, wherein $R^{1A}$ is F, and $R^{1B}$ and $R^{1C}$ are methyl or trifluoromethyl; and $R^2$ is 2-methylpropyl or 2,2-dimethylpropyl. In another embodiment, $R^2$, $R^3$ and $R^4$ are G-1, wherein $R^{1A}$ is F, and $R^{1B}$ and $R^{1C}$ are methyl or trifluoromethyl; and $R^1$ is 2-methylpropyl or 2,2-dimethylpropyl.

In one embodiment, the invention provides compounds of formula (I) wherein:

$Cy^1$ and $Cy^2$ are independently phenyl or naphthyl substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —$NO_2$;

$R^a$ and $R^b$ may independently be hydrogen, $C_1$-$C_3$alkyl or $C_1$-$C_3$haloalkyl;

R', R", R''' and R"" are each independently hydrogen or $C_1$-$C_3$alkyl;

$R^1$ and $R^3$ are independently $C_1$-$C_6$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino;

$R^2$ and $R^4$ are independently unsubstituted $C_1$-$C_6$ alkyl; and $R^5$ and $R^6$ are independently hydrogen, alkyl, haloalkyl, thioalkyl, alkylthioalkyl, hydroxyalkyl, alkoxyalkyl, alkenyl, haloalkenyl, alkynyl, haloalkynyl, or the group —$CH_2C(O)NHCH_2CF_3$; or $R^5$ and $R^6$ together with the atom(s) to which they are bonded form a $C_3$-$C_6$ cyclic group.

In another embodiment, the invention provides compounds of formula (I) wherein:

$Cy^1$ and $Cy^2$ are independently phenyl or naphthyl substituted with one or more substituents selected from the group consisting of halogen, alkoxy, haloalkoxy, alkylthio, haloalkylthio, amino, alkylamino, dialkylamino, alkyl, haloalkyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heterocyclyl, heteroaryl, —O-heteroaryl, —S-heteroaryl, —O-heterocyclyl or —S— heterocyclyl, wherein each cycloalkyl, heteroalkyl, aryl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R''' and R"" are each independently hydrogen or $C_1$-$C_3$alkyl; and $R^1$ and $R^3$ are independently $C_1$-$C_6$ alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^2$ and $R^4$ are independently unsubstituted $C_1$-$C_6$ alkyl; and $R^5$ and $R^6$ are independently hydrogen, alkyl, haloalkyl or the group —$CH_2C(O)NHCH_2CF_3$.

In another embodiment, the invention provides compounds of formula (I) wherein:

$Cy^1$ and $Cy^2$ are independently phenyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R''' and R"" are each independently hydrogen or methyl; and $R^1$ and $R^3$ are independently $C_1$-$C_6$alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^2$ and $R^4$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently phenyl substituted with one or more substituents selected from the group consisting of halogen, $C_1$-$C_3$alkyl, $C_1$-$C_3$haloalkyl, $R^5R^6NC(O)$—, phenyl, $C_3$-$C_6$cycloalkyl, $C_4$-$C_6$heterocyclyl, $C_5$-$C_6$heteroaryl, —O—$C_5$-$C_6$heteroaryl, —S—$C_5$-$C_6$heteroaryl, —O—$C_4$-$C_6$heterocyclyl or —S—$C_4$-$C_6$heterocyclyl, wherein each cycloalkyl, heterocyclyl, phenyl or heteroaryl is optionally further independently substituted with one or more substituents selected from the group consisting of halogen, CN, $NO_2$, $SF_5$, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, methyl or $CF_3$;

R', R", R''' and R"" are each independently hydrogen or methyl; and $R^1$ and $R^3$ are independently —$CH_2CX(CH_3)_2$ wherein X is halogen;

$R^2$ and $R^4$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently phenyl substituted with one or more substituents selected from the group consisting of halogen, CN, $NO_2$, $SF_5$, $C_1$-$C_3$alkyl, $C_1$-$C_3$haloalkyl, $C_3$-$C_6$cycloalkyl, morpholino, tetrahydropyran, tetrahydrofuran, piperidino or pyrrolidino, wherein each $C_3$-$C_6$cycloalkyl, morpholino, tetrahydropyran, tetrahydrofuran, piperidino or pyrrolidino is optionally further independently substituted with one or more substituents selected from the group consisting of halogen, alkoxy, haloalkoxy, alkylthio, haloalkylthio, alkylamino, dialkylamino, $C_1$-$C_3$alkyl or $C_1$-$C_3$haloalkyl;

$R^a$ and $R^b$ may independently be hydrogen, methyl or $CF_3$;

R', R", R''' and R"" are each independently hydrogen or methyl; and $R^1$ and $R^3$ are independently —$CH_2CX(CH_3)_2$ wherein X is halogen; and $R^2$ and $R^4$ are independently 2-methylpropyl or 2,2-dimethylpropyl.

In another embodiment, the invention provides compounds of formula (I) wherein:

Cy$^1$ and Cy$^2$ are independently phenyl substituted with one or more substituents selected from the group consisting of halogen, NO$_2$, SF$_5$, methyl, CF$_3$, OCF$_3$, cyclopropyl, cyclobutyl, cyclopentyl, cyclohexyl, morpholinyl, tetrahydropyranyl, tetrahydrofuryl, piperidinyl, —S— tetrazolyl or pyrrolidinyl, wherein each cyclopropyl, cyclobutyl, cyclopentyl, cyclohexyl, morpholino, tetrahydropyran, tetrahydrofuran, piperidino or pyrrolidino is optionally further independently substituted with one or more substituents selected from the group consisting of halogen, C$_1$-C$_3$alkoxy, C$_1$-C$_3$haloalkoxy, C$_1$-C$_3$alkylthio, C$_1$-C$_3$haloalkylthio, amino, C$_1$-C$_3$alkylamino, C$_1$-C$_3$dialkylamino, C$_1$-C$_3$alkyl or C$_1$-C$_3$haloalkyl;

R$^a$ and R$^b$ may independently be hydrogen, methyl or CF$_3$;

R', R'', R''' and R'''' are each independently hydrogen or methyl; and

R$^1$ and R$^3$ are independently —CH$_2$CX(CH$_3$)$_2$ wherein X is halogen; and R$^2$ and R$^4$ are independently 2-methylpropyl or 2,2-dimethylpropyl.

In yet another embodiment, the invention provides compounds of formula (I) wherein:

Cy$^1$ and Cy$^2$ are independently phenyl substituted with one or more substituents selected from the group consisting of halogen, NO$_2$, SF$_5$, methyl, CF$_3$, OCF$_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, C$_1$-C$_3$alkoxy, C$_1$-C$_3$haloalkoxy, C$_1$-C$_3$alkylthio, C$_1$-C$_3$haloalkylthio, amino, C$_1$-C$_3$alkylamino, C$_1$-C$_3$dialkylamino, C$_1$-C$_3$alkyl or C$_1$-C$_3$haloalkyl;

R$^a$ and R$^b$ may independently be hydrogen, methyl or CF$_3$;

R', R'', R''' and R'''' are each independently hydrogen or methyl; and

R$^1$ and R$^3$ are independently —CH$_2$CF(CH$_3$)$_2$; and

R$^2$ and R$^4$ are independently 2-methylpropyl or 2,2-dimethylpropyl.

In one embodiment, the invention provides compounds of formula (I) wherein:

Cy$^1$ and Cy$^2$ are independently phenyl or naphthyl substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN, —NO$_2$, cycloalkyl, heteroalkyl, heterocyclyl, aryl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN and —NO$_2$;

R$^a$ and R$^b$ may independently be hydrogen, C$_1$-C$_3$alkyl or C$_1$-C$_3$haloalkyl;

R', R'', R''' and R'''' are each independently hydrogen or C$_1$-C$_3$alkyl;

R$^2$ and R$^4$ are independently C$_1$-C$_6$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino;

R$^1$ and R$^3$ are independently unsubstituted C$_1$-C$_6$ alkyl; and

R$^5$ and R$^6$ are independently hydrogen, alkyl, haloalkyl, thioalkyl, alkylthioalkyl, hydroxyalkyl, alkoxyalkyl, alkenyl, haloalkenyl, alkynyl, haloalkynyl, or the group —CH$_2$C(O)NHCH$_2$CF$_3$; or R$^5$ and R$^6$ together with the atom(s) to which they are bonded form a C$_3$-C$_6$ cyclic group.

In another embodiment, the invention provides compounds of formula (I) wherein:

Cy$^1$ and Cy$^2$ are independently phenyl or naphthyl substituted with one or more substituents selected from the group consisting of halogen, alkoxy, haloalkoxy, alkylthio, haloalkylthio, amino, alkylamino, dialkylamino, alkyl, haloalkyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN, —NO$_2$, cycloalkyl, heterocyclyl, heteroaryl, —O-heteroaryl, —S-heteroaryl, —O-heterocyclyl or —S— heterocyclyl, wherein each cycloalkyl, heteroalkyl, aryl or heteroaryl is optionally further independently substituted with one or more substituents selected from the group consisting of halogen, alkoxy, haloalkoxy, alkylthio, haloalkylthio, amino, alkylamino, dialkylamino, C$_1$-C$_3$alkyl or C$_1$-C$_3$haloalkyl;

R$^a$ and R$^b$ may independently be hydrogen, C$_1$-C$_3$alkyl or C$_1$-C$_3$haloalkyl;

R', R'', R''' and R'''' are each independently hydrogen or C$_1$-C$_3$alkyl;

R$^2$ and R$^4$ are independently C$_1$-C$_6$ alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

R$^1$ and R$^3$ are independently unsubstituted C$_1$-C$_6$ alkyl; and

R$^5$ and R$^6$ are independently hydrogen, alkyl, haloalkyl or the group —CH$_2$C(O)NHCH$_2$CF$_3$.

In another embodiment, the invention provides compounds of formula (I) wherein:

Cy$^1$ and Cy$^2$ are independently phenyl substituted with one or more substituents selected from the group consisting of halogen, C$_1$-C$_3$alkoxy, C$_1$-C$_3$haloalkoxy, C$_1$-C$_3$alkylthio, C$_1$-C$_3$haloalkylthio, amino, C$_1$-C$_3$alkylamino, C$_1$-C$_3$dialkylamino, C$_1$-C$_3$alkyl, C$_1$-C$_3$haloalkyl, SF$_5$, R$^5$R$^6$NC(O)—, R$^5$R$^6$NC(O)NR$^5$—, R$^5$OC(O)—, R$^5$C(O)O—, R$^5$C(O)NR$^6$—, —CN, —NO$_2$, phenyl, C$_3$-C$_6$cycloalkyl, C$_4$-C$_7$heterocyclyl, C$_5$-C$_6$heteroaryl, —O—C$_5$-C$_6$heteroaryl, —S—C$_5$-C$_6$heteroaryl, —O—C$_4$-C$_7$heterocyclyl or —S—C$_4$-C$_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, C$_1$-C$_3$alkyl or C$_1$-C$_3$haloalkyl;

R$^a$ and R$^b$ may independently be hydrogen, C$_1$-C$_3$alkyl or C$_1$-C$_3$haloalkyl;

R', R'', R''' and R'''' are each independently hydrogen or methyl; and

R$^2$ and R$^4$ are independently C$_1$-C$_6$alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^1$ and $R^3$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently phenyl substituted with one or more substituents selected from the group consisting of halogen, $C_1$-$C_3$alkyl, $C_1$-$C_3$haloalkyl, $R^5R^6NC(O)$—, phenyl, $C_3$-$C_6$cycloalkyl, $C_4$-$C_6$heterocyclyl, $C_5$-$C_6$heteroaryl, —O—$C_5$-$C_6$heteroaryl, —S—$C_5$-$C_6$heteroaryl, —O—$C_4$-$C_6$heterocyclyl or —S—$C_4$-$C_6$heterocyclyl, wherein each cycloalkyl, heterocyclyl, phenyl or heteroaryl is optionally further independently substituted with one or more substituents selected from the group consisting of halogen, CN, $NO_2$, $SF_5$, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, methyl or $CF_3$;

R', R'', R''' and R'''' are each independently hydrogen or methyl; and $R^2$ and $R^4$ are independently —$CH_2CX(CH_3)_2$ wherein X is halogen;

$R^1$ and $R^3$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently phenyl substituted with one or more substituents selected from the group consisting of halogen, CN, $NO_2$, $SF_5$, $C_1$-$C_3$alkyl, $C_1$-$C_3$haloalkyl, $C_3$-$C_6$cycloalkyl, morpholino, tetrahydropyran, tetrahydrofuran, piperidino or pyrrolidino, wherein each $C_3$-$C_6$cycloalkyl, morpholino, tetrahydropyran, tetrahydrofuran, piperidino or pyrrolidino is optionally further independently substituted with one or more substituents selected from the group consisting of halogen, alkoxy, haloalkoxy, alkylthio, haloalkylthio, alkylamino, dialkylamino, $C_1$-$C_3$alkyl or $C_1$-$C_3$haloalkyl;

$R^a$ and $R^b$ may independently be hydrogen, methyl or $CF_3$;

R', R'', R''' and R'''' are each independently hydrogen or methyl; and $R^2$ and $R^4$ are independently —$CH_2CX(CH_3)_2$ wherein X is halogen;

$R^1$ and $R^3$ are independently 2-methylpropyl or 2,2-dimethylpropyl.

In another embodiment, the invention provides compounds of formula (I) wherein:

$Cy^1$ and $Cy^2$ are independently phenyl substituted with one or more substituents selected from the group consisting of halogen, $NO_2$, $SF_5$, methyl, $CF_3$, $OCF_3$, cyclopropyl, cyclobutyl, cyclopentyl, cyclohexyl, morpholinyl, tetrahydropyranyl, tetrahydrofuryl, piperidinyl, —S— tetrazolyl or pyrrolidinyl, wherein each cyclopropyl, cyclobutyl, cyclopentyl, cyclohexyl, morpholino, tetrahydropyran, tetrahydrofuran, piperidino or pyrrolidino is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R'', R''' and R'''' are each independently hydrogen or methyl;

$R^2$ and $R^4$ are independently —$CH_2CX(CH_3)_2$ wherein X is halogen; and $R^1$ and $R^3$ are independently 2-methylpropyl or 2,2-dimethylpropyl.

In yet another embodiment, the invention provides compounds of formula (I) wherein:

$Cy^1$ and $Cy^2$ are independently phenyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R'', R''' and R'''' are each independently hydrogen or methyl; and $R^2$ and $R^4$ are independently —$CH_2CF(CH_3)_2$; and $R^1$ and $R^3$ are independently 2-methylpropyl or 2,2-dimethylpropyl.

In one embodiment, the invention provides compounds of formula (I) wherein:

$Cy^1$ and $Cy^2$ are independently heteroaryl substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —$NO_2$;

$R^a$ and $R^b$ may independently be hydrogen, $C_1$-$C_3$alkyl or $C_1$-$C_3$haloalkyl;

R', R'', R''' and R'''' are each independently hydrogen or $C_1$-$C_3$alkyl; and $R^1$ and $R^3$ are independently $C_1$-$C_6$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino;

$R^2$ and $R^4$ are independently unsubstituted $C_1$-$C_6$ alkyl; and $R^5$ and $R^6$ are independently hydrogen, alkyl, haloalkyl, thioalkyl, alkylthioalkyl, hydroxyalkyl, alkoxyalkyl, alkenyl, haloalkenyl, alkynyl, haloalkynyl, or the group —$CH_2C(O)NHCH_2CF_3$; or $R^5$ and $R^6$ together with the atom(s) to which they are bonded form a $C_3$-$C_6$ cyclic group.

In another embodiment, the invention provides compounds of formula (I) wherein:

Cy$^1$ and Cy$^2$ are independently heteroaryl substituted with one or more substituents selected from the group consisting of halogen, alkoxy, haloalkoxy, alkylthio, haloalkylthio, amino, alkylamino, dialkylamino, alkyl, haloalkyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN, —NO$_2$, cycloalkyl, heterocyclyl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, alkoxy, haloalkoxy, alkylthio, haloalkylthio, amino, alkylamino, dialkylamino, C$_1$-C$_3$alkyl or C$_1$-C$_3$haloalkyl;

R$^a$ and R$^b$ may independently be hydrogen, C$_1$-C$_3$alkyl or C$_1$-C$_3$haloalkyl;

R', R'', R''' and R'''' are each independently hydrogen or C$_1$-C$_3$alkyl;

R$^1$ and R$^3$ are independently C$_1$-C$_6$ alkyl substituted by one or more aryl, heteroaryl, heterocyclyl or halogen;

R$^2$ and R$^4$ are independently unsubstituted C$_1$-C$_6$ alkyl; and

R$^5$ and R$^6$ are independently hydrogen, alkyl, haloalkyl or the group —CH$_2$C(O)NHCH$_2$CF$_3$.

In another embodiment, the invention provides compounds of formula (I) wherein:

Cy$^1$ and Cy$^2$ are independently thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl or tetrazinyl substituted with one or more substituents selected from the group consisting of halogen, C$_1$-C$_3$alkoxy, C$_1$-C$_3$haloalkoxy, C$_1$-C$_3$alkylthio, C$_1$-C$_3$haloalkylthio, amino, C$_1$-C$_3$alkylamino, C$_1$-C$_3$dialkylamino, C$_1$-C$_3$alkyl, C$_1$-C$_3$haloalkyl, SF$_5$, R$^5$R$^6$NC(O)—, R$^5$R$^6$NC(O)NR$^5$—, R$^5$OC(O)—, R$^5$C(O)O—, R$^5$C(O)NR$^6$—, —CN, —NO$_2$, phenyl, C$_3$-C$_6$cycloalkyl, C$_4$-C$_7$heterocyclyl, C$_5$-C$_6$heteroaryl, —O—C$_5$-C$_6$heteroaryl, —S—C$_5$-C$_6$heteroaryl, —O—C$_4$-C$_7$heterocyclyl or —S—C$_4$-C$_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, C$_1$-C$_3$alkyl or C$_1$-C$_3$haloalkyl;

R$^a$ and R$^b$ may independently be hydrogen, C$_1$-C$_3$alkyl or C$_1$-C$_3$haloalkyl;

R', R'', R''' and R'''' are each independently hydrogen or methyl;

R$^1$ and R$^3$ are independently C$_1$-C$_6$alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

R$^2$ and R$^4$ are independently 2-methylpropyl or 2,2-dimethylpropyl; and

R$^5$ and R$^6$ are independently hydrogen, C$_1$-C$_3$alkyl or C$_1$-C$_3$haloalkyl.

In another embodiment, the invention provides compounds of formula (I) wherein:

Cy$^1$ and Cy$^2$ are independently pyridinyl, pyrimidinyl, pyridazinyl, pyrazinyl, triazinyl or tetrazinyl substituted with one or more substituents selected from the group consisting of halogen, C$_1$-C$_3$alkyl, C$_1$-C$_3$haloalkyl, R$^5$R$^6$NC(O)—, phenyl, C$_3$-C$_6$cycloalkyl, C$_4$-C$_6$heterocyclyl, C$_5$-C$_6$heteroaryl, —O—C$_5$-C$_6$heteroaryl, —S—C$_5$-C$_6$heteroaryl, —O—C$_4$-C$_6$heterocyclyl or —S—C$_4$-C$_6$heterocyclyl, wherein each cycloalkyl, heterocyclyl, phenyl or heteroaryl is optionally further independently substituted with one or more substituents selected from the group consisting of halogen, CN, NO$_2$, SF$_5$, alkoxy, haloalkoxy, alkylthio, haloalkylthio, amino, alkylamino, dialkylamino, C$_1$-C$_3$alkyl or C$_1$-C$_3$haloalkyl;

R$^a$ and R$^b$ may independently be hydrogen, methyl or CF$_3$;

R', R'', R''' and R'''' are each independently hydrogen or methyl;

R$^1$ and R$^3$ are independently —CH$_2$CX(CH$_3$)$_2$ wherein X is halogen;

R$^2$ and R$^4$ are independently 2-methylpropyl or 2,2-dimethylpropyl; and

R$^5$ and R$^6$ are independently hydrogen, C$_1$-C$_3$alkyl or C$_1$-C$_3$haloalkyl.

In another embodiment, the invention provides compounds of formula (I) wherein:

Cy$^1$ and Cy$^2$ are independently pyridinyl, pyrimidinyl, pyridazinyl, or pyrazinyl substituted with one or more substituents selected from the group consisting of halogen, CN, NO$_2$, SF$_5$, C$_1$-C$_3$alkyl, C$_1$-C$_3$haloalkyl, C$_3$-C$_6$cycloalkyl, morpholino, tetrahydropyran, tetrahydrofuran, piperidino or pyrrolidino, wherein each C$_3$-C$_6$cycloalkyl, morpholino, tetrahydropyran, tetrahydrofuran, piperidino or pyrrolidino is optionally further independently substituted with one or more substituents selected from the group consisting of halogen, alkoxy, haloalkoxy, alkylthio, haloalkylthio, alkylamino, dialkylamino, C$_1$-C$_3$alkyl or C$_1$-C$_3$haloalkyl;

R$^a$ and R$^b$ may independently be hydrogen, methyl or CF$_3$;

R', R'', R''' and R'''' are each independently hydrogen or methyl; and

R$^1$ and R$^3$ are independently —CH$_2$CX(CH$_3$)$_2$ wherein X is halogen; and R$^2$ and R$^4$ are independently 2-methylpropyl or 2,2-dimethylpropyl.

In another embodiment, the invention provides compounds of formula (I) wherein:

Cy$^1$ and Cy$^2$ are independently pyridyl substituted with one or more substituents selected from the group consisting of halogen, NO$_2$, SF$_5$, methyl, CF$_3$, OCF$_3$, cyclopropyl, cyclobutyl, cyclopentyl, cyclohexyl, morpholinyl, tetrahydropyranyl, tetrahydrofuryl, piperidinyl, —S— tetrazolyl or pyrrolidinyl, wherein each cyclopropyl, cyclobutyl, cyclopentyl, cyclohexyl, morpholino, tetrahydropyran, tetrahydrofuran, piperidino or pyrrolidino is optionally further independently substituted with one or more substituents selected from the group consisting of halogen, C$_1$-C$_3$alkoxy, C$_1$-C$_3$haloalkoxy, C$_1$-C$_3$alkylthio, C$_1$-C$_3$haloalkylthio, amino, C$_1$-C$_3$alkylamino, C$_1$-C$_3$dialkylamino, C$_1$-C$_3$alkyl or C$_1$-C$_3$haloalkyl;

R$^a$ and R$^b$ may independently be hydrogen, methyl or CF$_3$;

R', R'', R''' and R'''' are each independently hydrogen or methyl;

R$^1$ and R$^3$ are independently —CH$_2$CX(CH$_3$)$_2$ wherein X is halogen; and R$^2$ and R$^4$ are independently 2-methylpropyl or 2,2-dimethylpropyl.

In yet another embodiment, the invention provides compounds of formula (I) wherein:

Cy$^1$ and Cy$^2$ are independently pyridyl substituted with one or more substituents selected from the group consisting of halogen, NO$_2$, SF$_5$, methyl, CF$_3$, OCF$_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl; and $R^1$ and $R^3$ are independently —$CH_2CF(CH_3)_2$; and $R^2$ and $R^4$ are independently 2-methylpropyl or 2,2-dimethylpropyl.

In one embodiment, the invention provides compounds of formula (I) wherein:

$Cy^1$ and $Cy^2$ are independently heteroaryl substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —$NO_2$;

$R^a$ and $R^b$ may independently be hydrogen, $C_1$-$C_3$alkyl or $C_1$-$C_3$haloalkyl;

R', R", R'" and R"" are each independently hydrogen or $C_1$-$C_3$alkyl;

$R^2$ and $R^4$ are independently $C_1$-$C_6$ alkyl substituted by one or more substituents selected from the group consisting of aryl, heteroaryl, heterocyclyl, halogen, hydroxy, alkoxy, haloalkoxy, alkylthio, haloalkylthio, alkylsulfinyl, haloalkylsulfinyl, alkylsulfonyl, haloalkylsulfonyl, alkoxyalkoxy, oxo, cyano, amino, alkylamino and dialkylamino;

$R^1$ and $R^3$ are independently unsubstituted $C_1$-$C_6$ alkyl; and $R^5$ and $R^6$ are independently hydrogen, alkyl, haloalkyl, thioalkyl, alkylthioalkyl, hydroxyalkyl, alkoxyalkyl, alkenyl, haloalkenyl, alkynyl, haloalkynyl, or the group —$CH_2C(O)NHCH_2CF_3$; or $R^5$ and $R^6$ together with the atom(s) to which they are bonded form a $C_3$-$C_6$ cyclic group.

In another embodiment, the invention provides compounds of formula (I) wherein:

$Cy^1$ and $Cy^2$ are independently heteroaryl substituted with one or more substituents selected from the group consisting of halogen, alkoxy, haloalkoxy, alkylthio, haloalkylthio, amino, alkylamino, dialkylamino, alkyl, haloalkyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heterocyclyl, heteroaryl, —O-heteroaryl, —S-heteroaryl, —O-heterocyclyl or —S-heterocyclyl, wherein each cycloalkyl, heteroalkyl, aryl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or $C_1$-$C_3$alkyl;

$R^2$ and $R^4$ are independently $C_1$-$C_6$ alkyl substituted by one or more aryl, heteroaryl, heterocyclyl or halogen;

$R^1$ and $R^3$ are independently unsubstituted $C_1$-$C_6$ alkyl; and $R^5$ and $R^6$ are independently hydrogen, alkyl, haloalkyl or the group —$CH_2C(O)NHCH_2CF_3$.

In another embodiment, the invention provides compounds of formula (I) wherein:

$Cy^1$ and $Cy^2$ are independently thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl or tetrazinyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl; and $R^2$ and $R^4$ are independently $C_1$-$C_6$alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^1$ and $R^3$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently pyridinyl, pyrimidinyl, pyridazinyl, pyrazinyl, triazinyl or tetrazinyl substituted with one or more substituents selected from the group consisting of halogen, $C_1$-$C_3$alkyl, $C_1$-$C_3$haloalkyl, $R^5R^6NC(O)$—, phenyl, $C_3$-$C_6$cycloalkyl, $C_4$-$C_6$heterocyclyl, $C_5$-$C_6$heteroaryl, —O—$C_5$-$C_6$heteroaryl, —S—$C_5$-$C_6$heteroaryl, —O—$C_4$-$C_6$heterocyclyl or —S—$C_4$-$C_6$heterocyclyl, wherein each cycloalkyl, heterocyclyl, phenyl or heteroaryl is optionally further independently substituted with one or more substituents selected from the group consisting of halogen, CN, $NO_2$, $SF_5$, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl;

$R^2$ and $R^4$ are independently —$CH_2CX(CH_3)_2$ wherein X is halogen;

$R^1$ and $R^3$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently pyridinyl, pyrimidinyl, pyridazinyl, or pyrazinyl substituted with one or more substituents selected from the group consisting of halogen, CN, $NO_2$, $SF_5$, $C_1$-$C_3$alkyl, $C_1$-$C_3$haloalkyl, $C_3$-$C_6$cycloalkyl, morpholino, tetrahydropyran, tetrahydrofuran, piperidino or pyrrolidino, wherein each $C_3$-$C_6$cycloalkyl, morpholino, tetrahydropyran, tetrahydrofuran, piperidino or pyrrolidino is optionally further independently substituted with one or more substituents selected from the group consisting of halogen, alkoxy, haloalkoxy, alkylthio, haloalkylthio, alkylamino, dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl;

$R^2$ and $R^4$ are independently —$CH_2CX(CH_3)_2$ wherein X is halogen; and $R^1$ and $R^3$ are independently 2-methylpropyl or 2,2-dimethylpropyl.

In another embodiment, the invention provides compounds of formula (I) wherein:

$Cy^1$ and $Cy^2$ are independently pyridyl substituted with one or more substituents selected from the group consisting of halogen, $NO_2$, $SF_5$, methyl, $CF_3$, $OCF_3$, cyclopropyl, cyclobutyl, cyclopentyl, cyclohexyl, morpholinyl, tetrahydropyranyl, tetrahydrofuryl, piperidinyl, —S— tetrazolyl or pyrrolidinyl, wherein each cyclopropyl, cyclobutyl, cyclopentyl, cyclohexyl, morpholino, tetrahydropyran, tetrahydrofuran, piperidino or pyrrolidino is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl; and $R^2$ and $R^4$ are independently —$CH_2CX(CH_3)_2$ wherein X is halogen; and $R^1$ and $R^3$ are independently 2-methylpropyl or 2,2-dimethylpropyl.

In yet another embodiment, the invention provides compounds of formula (I) wherein:

$Cy^1$ and $Cy^2$ are independently pyridyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl;

$R^2$ and $R^4$ are independently —$CH_2CF(CH_3)_2$; and $R^1$ and $R^3$ are independently 2-methylpropyl or 2,2-dimethylpropyl.

In another embodiment, the invention provides compounds of formula (I) wherein:

$Cy^1$ and $Cy^2$ are independently heteroaryl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl;

$R^1$ and $R^2$ are independently $C_1$-$C_6$alkyl substituted by one or more halogen, aryl, heteroaryl or heterocyclyl;

$R^3$ and $R^4$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently heteroaryl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl; and $R^3$ and $R^4$ are independently $C_1$-$C_6$alkyl substituted by one or more halogen, aryl, heteroaryl or heterocyclyl;

$R^1$ and $R^2$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently heteroaryl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R''' and R'''' are each independently hydrogen or methyl;

$R^2$ and $R^3$ are independently $C_1$-$C_6$alkyl substituted by one or more halogen, aryl, heteroaryl or heterocyclyl;

$R^1$ and $R^4$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently heteroaryl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R''' and R'''' are each independently hydrogen or methyl;

$R^1$ and $R^4$ are independently $C_1$-$C_6$alkyl substituted by one or more halogen, aryl, heteroaryl or heterocyclyl;

$R^2$ and $R^3$ are independently 2-methylpropyl or 2,2-dimethylpropyl; and $R^5$ and $R^6$ are independently hydrogen, $C_1$-$C_3$alkyl or $C_1$-$C_3$haloalkyl.

In yet another embodiment, the invention provides compounds of formula (I) wherein:

$Cy^1$ and $Cy^2$ are independently heteroaryl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R''' and R'''' are each independently hydrogen or methyl;

$R^1$ and $R^2$ are —$CH_2CF(CH_3)_2$; and $R^3$ and $R^4$ are independently 2-methylpropyl or 2,2-dimethylpropyl.

In yet another embodiment, the invention provides compounds of formula (I) wherein:

$Cy^1$ and $Cy^2$ are independently heteroaryl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R''' and R'''' are each independently hydrogen or methyl;

$R^3$ and $R^4$ are —$CH_2CF(CH_3)_2$; and $R^1$ and $R^2$ are independently 2-methylpropyl or 2,2-dimethylpropyl.

In yet another embodiment, the invention provides compounds of formula (I) wherein:

$Cy^1$ and $Cy^2$ are independently heteroaryl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R''' and R'''' are each independently hydrogen or methyl; and $R^2$ and $R^3$—$CH_2CF(CH_3)_2$; and $R^1$ and $R^4$ are independently 2-methylpropyl or 2,2-dimethylpropyl.

In yet another embodiment, the invention provides compounds of formula (I) wherein:

$Cy^1$ and $Cy^2$ are independently heteroaryl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R''' and R'''' are each independently hydrogen or methyl; and $R^1$ and $R^4$ are —$CH_2CF(CH_3)_2$; and $R^2$ and $R^3$ are independently 2-methylpropyl or 2,2-dimethylpropyl.

In another embodiment, the invention provides compounds of formula (I) wherein:

$Cy^1$ and $Cy^2$ are independently heteroaryl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R''' and R'''' are each independently hydrogen or methyl; and $R^1$, $R^2$ and $R^3$ are independently $C_1$-$C_6$alkyl substituted by one or more halogen, aryl, heteroaryl or heterocyclyl;

$R^4$ is 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently heteroaryl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R''' and R'''' are each independently hydrogen or methyl;

$R^1$, $R^2$ and $R^4$ are independently $C_1$-$C_6$alkyl substituted by one or more halogen, aryl, heteroaryl or heterocyclyl;

$R^3$ is 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently heteroaryl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R''' and R'''' are each independently hydrogen or methyl;

$R^1$, $R^3$ and $R^4$ are independently $C_1$-$C_6$alkyl substituted by one or more halogen, aryl, heteroaryl or heterocyclyl;

$R^2$ is 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently heteroaryl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R''' and R'''' are each independently hydrogen or methyl;

$R^2$, $R^3$ and $R^4$ are independently $C_1$-$C_6$alkyl substituted by one or more halogen, aryl, heteroaryl or heterocyclyl;

$R^1$ is 2-methylpropyl or 2,2-dimethylpropyl; and $R^5$ and $R^6$ are independently hydrogen, $C_1$-$C_3$alkyl or $C_1$-$C_3$haloalkyl.

In yet another embodiment, the invention provides compounds of formula (I) wherein:

$Cy^1$ and $Cy^2$ are independently heteroaryl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R''' and R'''' are each independently hydrogen or methyl;

$R^1$, $R^2$ and $R^3$ are —$CH_2CF(CH_3)_2$; and $R^4$ is 2-methylpropyl or 2,2-dimethylpropyl.

In yet another embodiment, the invention provides compounds of formula (I) wherein:

$Cy^1$ and $Cy^2$ are independently heteroaryl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R''' and R'''' are each independently hydrogen or methyl;

$R^1$, $R^2$ and $R^4$ are —$CH_2CF(CH_3)_2$; and $R^3$ is 2-methylpropyl or 2,2-dimethylpropyl.

In yet another embodiment, the invention provides compounds of formula (I) wherein:

$Cy^1$ and $Cy^2$ are independently heteroaryl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl;

$R^1$, $R^3$ and $R^4$ are —$CH_2CF(CH_3)_2$; and $R^2$ is 2-methylpropyl or 2,2-dimethylpropyl.

In yet another embodiment, the invention provides compounds of formula (I) wherein:

$Cy^1$ and $Cy^2$ are independently heteroaryl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl;

$R^2$, $R^3$ and $R^4$ are —$CH_2CF(CH_3)_2$; and $R^1$ is 2-methylpropyl or 2,2-dimethylpropyl.

In another embodiment, the invention provides compounds of formula (I) wherein:

$Cy^1$ and $Cy^2$ are independently heteroaryl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl; and $R^1$, $R^2$, $R^3$ and $R^4$ are each —$CH_2CF(CH_3)_2$.

In another embodiment, the invention provides compounds of formula (I) wherein:

$Cy^1$ and $Cy^2$ are independently phenyl or pyridyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl;

$R^1$ and $R^2$ are independently $C_1$-$C_6$alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^3$ and $R^4$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently phenyl or pyridyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl;

$R^3$ and $R^4$ are independently $C_1$-$C_6$alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^1$ and $R^2$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently phenyl or pyridyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R'', R''' and R'''' are each independently hydrogen or methyl;

$R^2$ and $R^3$ are independently $C_1$-$C_6$alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^1$ and $R^4$ are independently 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently phenyl or pyridyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R'', R''' and R'''' are each independently hydrogen or methyl;

$R^1$ and $R^4$ are independently $C_1$-$C_6$alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^2$ and $R^3$ are independently 2-methylpropyl or 2,2-dimethylpropyl; and $R^5$ and $R^6$ are independently hydrogen, $C_1$-$C_3$alkyl or $C_1$-$C_3$haloalkyl.

In yet another embodiment, the invention provides compounds of formula (I) wherein:

$Cy^1$ and $Cy^2$ are independently phenyl or pyridyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R'', R''' and R'''' are each independently hydrogen or methyl;

$R^1$ and $R^2$ are —$CH_2CF(CH_3)_2$; and $R^3$ and $R^4$ are independently 2-methylpropyl or 2,2-dimethylpropyl.

In yet another embodiment, the invention provides compounds of formula (I) wherein:

$Cy^1$ and $Cy^2$ are independently phenyl or pyridyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R'', R''' and R'''' are each independently hydrogen or methyl;

$R^3$ and $R^4$ are —$CH_2CF(CH_3)_2$; and $R^1$ and $R^2$ are independently 2-methylpropyl or 2,2-dimethylpropyl.

In yet another embodiment, the invention provides compounds of formula (I) wherein:

$Cy^1$ and $Cy^2$ are independently phenyl or pyridyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R'', R''' and R'''' are each independently hydrogen or methyl;

$R^2$ and $R^3$—$CH_2CF(CH_3)_2$; and $R^1$ and $R^4$ are independently 2-methylpropyl or 2,2-dimethylpropyl.

In yet another embodiment, the invention provides compounds of formula (I) wherein:

$Cy^1$ and $Cy^2$ are independently phenyl or pyridyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl;

$R^1$ and R4-$CH_2CF(CH_3)_2$; and $R^2$ and $R^3$ are independently 2-methylpropyl or 2,2-dimethylpropyl.

In another embodiment, the invention provides compounds of formula (I) wherein:

$Cy^1$ and $Cy^2$ are independently phenyl or pyridyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl;

$R^1$, $R^2$ and $R^3$ are independently $C_1$-$C_6$alkyl substituted by one or more halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^4$ is 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently phenyl or pyridyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl;

$R^1$, $R^2$ and $R^4$ are independently $C_1$-$C_6$alkyl substituted by halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^3$ is 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently phenyl or pyridyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl;

$R^1$, $R^3$ and $R^4$ are independently $C_1$-$C_6$alkyl substituted by halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^2$ is 2-methylpropyl or 2,2-dimethylpropyl; and $R^5$ and $R^6$ are independently hydrogen, $C_1$-$C_3$alkyl or $C_1$-$C_3$haloalkyl.

In another embodiment, the invention provides compounds of formula (I) wherein:

$Cy^1$ and $Cy^2$ are independently phenyl or pyridyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl;

$R^2$, $R^3$ and $R^4$ are independently $C_1$-$C_6$alkyl substituted by halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl;

$R^1$ is 2-methylpropyl or 2,2-dimethylpropyl; and $R^5$ and $R^6$ are independently hydrogen, $C_1$-$C_3$alkyl or $C_1$-$C_3$haloalkyl.

In yet another embodiment, the invention provides compounds of formula (I) wherein:

$Cy^1$ and $Cy^2$ are independently phenyl or pyridyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuryl, piperidinyl or pyrrolidinyl, wherein each cyclohexyl, morpholinyl, tetrahydropyranyl, tetrahydrofuryl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl;

$R^1$, $R^2$ and $R^3$ are —$CH_2CF(CH_3)_2$; and $R^4$ is 2-methylpropyl or 2,2-dimethylpropyl.

In yet another embodiment, the invention provides compounds of formula (I) wherein:

$Cy^1$ and $Cy^2$ are independently phenyl or pyridyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuranyl, piperidinyl or pyrrolidinyl, wherein each cyclohexyl, morpholinyl, tetrahydropyranyl, tetrahydrofuranyl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl;

$R^1$, $R^2$ and $R^4$ are —$CH_2CF(CH_3)_2$; and $R^3$ is 2-methylpropyl or 2,2-dimethylpropyl.

In yet another embodiment, the invention provides compounds of formula (I) wherein:

$Cy^1$ and $Cy^2$ are independently phenyl or pyridyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuranyl, piperidinyl or pyrrolidinyl, wherein each cyclohexyl, morpholinyl, tetrahydropyranyl, tetrahydrofuranyl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl;

$R^1$, $R^3$ and $R^4$ are —$CH_2CF(CH_3)_2$; and $R^2$ is 2-methylpropyl or 2,2-dimethylpropyl.

In yet another embodiment, the invention provides compounds of formula (I) wherein:

$Cy^1$ and $Cy^2$ are independently phenyl or pyridyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuranyl, piperidinyl or pyrrolidinyl, wherein each cyclohexyl, morpholinyl, tetrahydropyranyl, tetrahydrofuranyl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R", R'" and R"" are each independently hydrogen or methyl;

$R^2$, $R^3$ and $R^4$ are —$CH_2CF(CH_3)_2$; and $R^1$ is 2-methylpropyl or 2,2-dimethylpropyl.

In another embodiment, the invention provides compounds of formula (I) wherein:

$Cy^1$ and $Cy^2$ are independently phenyl or pyridyl substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl, $C_1$-$C_3$haloalkyl, $SF_5$, $R^5R^6NC(O)$—, $R^5R^6NC(O)NR^5$—, $R^5OC(O)$—, $R^5C(O)O$—, $R^5C(O)NR^6$—, —CN, —$NO_2$, phenyl, $C_3$-$C_6$cycloalkyl, $C_4$-$C_7$heterocyclyl, $C_5$-$C_6$heteroaryl, —O—$C_5$-$C_6$heteroaryl, —S—$C_5$-$C_6$heteroaryl, —O—$C_4$-$C_7$heterocyclyl or —S—$C_4$-$C_7$heterocyclyl, wherein each cycloalkyl, heterocyclyl, phenyl or heteroaryl is optionally further independently substituted with one or more substituents selected from the group consisting of halogen, alkoxy, haloalkoxy, alkylthio, haloalkylthio, amino, alkylamino, dialkylamino, $C_1$-$C_3$alkyl or $C_1$-$C_3$haloalkyl;

$R^a$ and $R^b$ may independently be hydrogen, $C_1$-$C_3$alkyl or $C_1$-$C_3$haloalkyl;

R', R", R'" and R"" are each independently hydrogen or methyl;

$R^1$, $R^2$, $R^3$ and $R^4$ are independently $C_1$-$C_6$alkyl substituted by halogen, optionally substituted phenyl or an optionally substituted heteroaryl selected from the group consisting of thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl, triazinyl and tetrazinyl; and $R^5$ and $R^6$ are independently hydrogen, $C_1$-$C_3$alkyl or $C_1$-$C_3$haloalkyl.

In yet another embodiment, the invention provides compounds of formula (I) wherein:

$Cy^1$ and $Cy^2$ are independently phenyl or pyridyl substituted with one or more substituents selected from the group consisting of halogen, $NO_2$, $SF_5$, methyl, $CF_3$, $OCF_3$, cyclohexyl, morpholinyl, tetrahydropyranyl, tetrahydrofuranyl, piperidinyl or pyrrolidinyl, wherein each cyclohexyl, morpholinyl, tetrahydropyranyl, tetrahydrofuranyl, piperidinyl or pyrrolidinyl is optionally further independently substituted with one or more substituents selected from the group consisting of halogen, $C_1$-$C_3$alkoxy, $C_1$-$C_3$haloalkoxy, $C_1$-$C_3$alkylthio, $C_1$-$C_3$haloalkylthio, amino, $C_1$-$C_3$alkylamino, $C_1$-$C_3$dialkylamino, $C_1$-$C_3$alkyl or $C_1$-$C_3$haloalkyl;

$R^a$ and $R^b$ may independently be hydrogen, methyl or $CF_3$;

R', R'', R''' and R'''' are each independently hydrogen or methyl; and $R^1$, $R^2$, $R^3$ and $R^4$ are each —$CH_2CF(CH_3)_2$.

In one embodiment, the invention provides compounds of formula (I) shown in Tables 2 to 39 below, wherein R', R'', R''' and R'''' are each independently hydrogen or $C_1$-$C_3$alkyl; and $Cy^1$, $Cy^2$, $R^a$, $R^b$, $R^1$, $R^2$, $R^3$ and $R^4$ are as shown in Tables 2 to 39 below. In the tables, Me indicates methyl.

TABLE 2

Compounds of formula (I), wherein $Cy^1$ and $Cy^2$ are unsubstituted phenyl and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 2-1 | $CH_3$ | $CH_2$—tBu | $CH_2$—tBu | $CH_2$—tBu | $CH_2$—tBu |
| 2-2 | $CH_3$ | $CH_2$—tBu | $CH_2$—iPr | $CH_2$—iPr | $CH_2$—iPr |
| 2-3 | $CH_3$ | $CH_2$—iPr | $CH_2$—tBu | $CH_2$—iPr | $CH_2$—iPr |
| 2-4 | $CH_3$ | $CH_2$—iPr | $CH_2$—iPr | $CH_2$—tBu | $CH_2$—iPr |
| 2-5 | $CH_3$ | $CH_2$—iPr | $CH_2$—iPr | $CH_2$—iPr | $CH_2$—tBu |
| 2-6 | $CH_3$ | $CH_2$—iPr | $CH_2$—tBu | $CH_2$—iPr | $CH_2$—tBu |
| 2-7 | $CH_3$ | $CH_2$—tBu | $CH_2$—iPr | $CH_2$—tBu | $CH_2$—iPr |
| 2-8 | $CH_3$ | $CH_2$—iPr | $CH_2$—tBu | $CH_2$—tBu | $CH_2$—iPr |
| 2-9 | $CH_3$ | $CH_2$—tBu | $CH_2$—iPr | $CH_2$—iPr | $CH_2$—tBu |
| 2-10 | $CH_3$ | $CH_2$—iPr | $CH_2$—tBu | $CH_2$—tBu | $CH_2$—tBu |
| 2-11 | $CH_3$ | $CH_2$—tBu | $CH_2$—iPr | $CH_2$—tBu | $CH_2$—tBu |
| 2-12 | $CH_3$ | $CH_2$—tBu | $CH_2$—tBu | $CH_2$—iPr | $CH_2$—tBu |
| 2-13 | $CH_3$ | $CH_2$—tBu | $CH_2$—tBu | $CH_2$—tBu | $CH_2$—iPr |
| 2-14 | $CH_3$ | $CH_2CMe_2F$ | $CH_2$—iPr | $CH_2$—iPr | $CH_2$—iPr |
| 2-15 | $CH_3$ | $CH_2$—iPr | $CH_2CMe_2F$ | $CH_2$—iPr | $CH_2$—iPr |
| 2-16 | $CH_3$ | $CH_2$—iPr | $CH_2$—iPr | $CH_2CMe_2F$ | $CH_2$—iPr |
| 2-17 | $CH_3$ | $CH_2$—iPr | $CH_2$—iPr | $CH_2$—iPr | $CH_2CMe_2F$ |
| 2-18 | $CH_3$ | $CH_2CMe_2F$ | $CH_2$—iPr | $CH_2CMe_2F$ | $CH_2$—iPr |
| 2-19 | $CH_3$ | $CH_2$—iPr | $CH_2CMe_2F$ | $CH_2$—iPr | $CH_2CMe_2F$ |
| 2-20 | $CH_3$ | $CH_2$—iPr | $CH_2CMe_2F$ | $CH_2CMe_2F$ | $CH_2$—iPr |
| 2-21 | $CH_3$ | $CH_2CMe_2F$ | $CH_2$—iPr | $CH_2$—iPr | $CH_2CMe_2F$ |
| 2-22 | $CH_3$ | $CH_2$—iPr | $CH_2CMe_2F$ | $CH_2CMe_2F$ | $CH_2CMe_2F$ |
| 2-23 | $CH_3$ | $CH_2CMe_2F$ | $CH_2$—iPr | $CH_2CMe_2F$ | $CH_2CMe_2F$ |
| 2-24 | $CH_3$ | $CH_2CMe_2F$ | $CH_2CMe_2F$ | $CH_2$—iPr | $CH_2CMe_2F$ |
| 2-25 | $CH_3$ | $CH_2CMe_2F$ | $CH_2CMe_2F$ | $CH_2CMe_2F$ | $CH_2$—iPr |
| 2-26 | $CH_3$ | $CH_2CMe_2F$ | $CH_2CMe_2F$ | $CH_2CMe_2F$ | $CH_2CMe_2F$ |
| 2-27 | $CH_3$ | $CH_2$—iPr | $CH_2$—iPr | $CH_2$—iPr | $CH_2$—iPr |
| 2-28 | $CH_3$ | $CH_2$—tBu | $CH_2$—tBu | $CH_2$—iPr | $CH_2$—iPr |
| 2-29 | $CH_3$ | $CH_2$—iPr | $CH_2$—iPr | $CH_2$—tBu | $CH_2$—tBu |
| 2-30 | $CH_3$ | $CH_2CMe_2F$ | $CH_2CMe_2F$ | $CH_2$—iPr | $CH_2$—iPr |
| 2-31 | $CH_3$ | $CH_2$—iPr | $CH_2$—iPr | $CH_2CMe_2F$ | $CH_2CMe_2F$ |
| 2-32 | $CH_3$ | $CH_2CMe_2F$ | $CH_2$—tBu | $CH_2CMe_2F$ | $CH_2$—tBu |
| 2-33 | $CH_3$ | $CH_2CF_2Me$ | $CH_2$—iPr | $CH_2CF_2Me$ | $CH_2$—iPr |
| 2-34 | $CH_3$ | $CH_2CF_3$ | $CH_2$—iPr | $CH_2CF_3$ | $CH_2$—iPr |
| 2-35 | $CH_3$ | $CH_2CH(CF_3)_2$ | $CH_2$—iPr | $CH_2CH(CF_3)_2$ | $CH_2$—iPr |
| 2-36 | $CH_2F$ | $CH_2CMe_2F$ | $CH_2$—iPr | $CH_2CMe_2F$ | $CH_2$—iPr |
| 2-37 | H | $CH_2CMe_2F$ | $CH_2$—iPr | $CH_2CMe_2F$ | $CH_2$—iPr |
| 2-38 | Et | $CH_2CMe_2F$ | $CH_2$—iPr | $CH_2CMe_2F$ | $CH_2$—iPr |
| 2-39 | $CH_2F$ | $CH_2$—iPr | $CH_2$—iPr | $CH_2$—iPr | $CH_2$—iPr |
| 2-40 | H | $CH_2$—iPr | $CH_2$—iPr | $CH_2$—iPr | $CH_2$—iPr |
| 2-41 | Et | $CH_2$—iPr | $CH_2$—iPr | $CH_2$—iPr | $CH_2$—iPr |
| 2-42 | H | $CH_2CMe_2F$ | $CH_2$—tBu | $CH_2CMe_2F$ | $CH_2$—tBu |
| 2-43 | $CH_3$ | $CH_2CMe_2F$ | iPr | $CH_2CMe_2F$ | iPr |
| 2-44 | $CH_3$ | $CH_2CMe_2F$ | nPr | $CH_2CMe_2F$ | nPr |
| 2-45 | $CH_3$ | $CH_2CMe_2F$ | sBu | $CH_2CMe_2F$ | sBu |
| 2-46 | $CH_3$ | $CH_2CMe_2F$ | tBu | $CH_2CMe_2F$ | tBu |
| 2-47 | $CH_3$ | $CH_2CMe_2F$ | $CH_2$-p-biphenyl | $CH_2CMe_2F$ | $CH_2$-p-biphenyl |
| 2-48 | $CH_3$ | $CH_2CMe_2F$ | $CH_2$—p-tBuPh | $CH_2CMe_2F$ | $CH_2$—p-tBuPh |
| 2-49 | $CH_3$ | $CH_2CMe_2F$ | $CH_3$ | $CH_2CMe_2F$ | $CH_3$ |
| 2-50 | H | $CH_2CMe_2F$ | iPr | $CH_2CMe_2F$ | iPr |
| 2-51 | $CH_3$ | $CH_2CMe_2F$ | $CH_2CH_2CMe_3$ | $CH_2CMe_2F$ | $CH_2CH_2CMe_3$ |
| 2-52 | $CH_3$ | $CH_2CMe_2F$ | $CH_2CH_2$—iPr | $CH_2CMe_2F$ | $CH_2CH_2$—iPr |
| 2-53 | $CH_3$ | $CH_2$-p-pyridyl | $CH_2$—iPr | $CH_2$-p-pyridyl | $CH_2$—iPr |
| 2-54 | $CH_3$ | $CH_2$-p-pyridyl | $CH_2$—tBu | $CH_2$-p-pyridyl | $CH_2$—tBu |

TABLE 3

Compounds of formula (I), wherein $Cy^1$ and $Cy^2$ are p-fluorophenyl and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 3-1 | $CH_3$ | $CH_2$—tBu | $CH_2$—tBu | $CH_2$—tBu | $CH_2$—tBu |
| 3-2 | $CH_3$ | $CH_2$—tBu | $CH_2$—iPr | $CH_2$—iPr | $CH_2$—iPr |
| 3-3 | $CH_3$ | $CH_2$—iPr | $CH_2$—tBu | $CH_2$—iPr | $CH_2$—iPr |
| 3-4 | $CH_3$ | $CH_2$—iPr | $CH_2$—iPr | $CH_2$—tBu | $CH_2$—iPr |

TABLE 3-continued

Compounds of formula (I), wherein $Cy^1$ and $Cy^2$ are p-fluorophenyl and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 3-5 | $CH_3$ | $CH_2$—iPr | $CH_2$—iPr | $CH_2$—iPr | $CH_2$—tBu |
| 3-6 | $CH_3$ | $CH_2$—iPr | $CH_2$—tBu | $CH_2$—iPr | $CH_2$—tBu |
| 3-7 | $CH_3$ | $CH_2$—tBu | $CH_2$—iPr | $CH_2$—tBu | $CH_2$—iPr |
| 3-8 | $CH_3$ | $CH_2$—iPr | $CH_2$—tBu | $CH_2$—tBu | $CH_2$—iPr |
| 3-9 | $CH_3$ | $CH_2$—tBu | $CH_2$—iPr | $CH_2$—iPr | $CH_2$—tBu |
| 3-10 | $CH_3$ | $CH_2$—iPr | $CH_2$—tBu | $CH_2$—tBu | $CH_2$—tBu |
| 3-11 | $CH_3$ | $CH_2$—tBu | $CH_2$—iPr | $CH_2$—tBu | $CH_2$—tBu |
| 3-12 | $CH_3$ | $CH_2$—tBu | $CH_2$—tBu | $CH_2$—iPr | $CH_2$—tBu |
| 3-13 | $CH_3$ | $CH_2$—tBu | $CH_2$—tBu | $CH_2$—tBu | $CH_2$—iPr |
| 3-14 | $CH_3$ | $CH_2CMe_2F$ | $CH_2$—iPr | $CH_2$—iPr | $CH_2$—iPr |
| 3-15 | $CH_3$ | $CH_2$—iPr | $CH_2CMe_2F$ | $CH_2$—iPr | $CH_2$—iPr |
| 3-16 | $CH_3$ | $CH_2$—iPr | $CH_2$—iPr | $CH_2CMe_2F$ | $CH_2$—iPr |
| 3-17 | $CH_3$ | $CH_2$—iPr | $CH_2$—iPr | $CH_2$—iPr | $CH_2CMe_2F$ |
| 3-18 | $CH_3$ | $CH_2CMe_2F$ | $CH_2$—iPr | $CH_2CMe_2F$ | $CH_2$—iPr |
| 3-19 | $CH_3$ | $CH_2$—iPr | $CH_2CMe_2F$ | $CH_2$—iPr | $CH_2CMe_2F$ |
| 3-20 | $CH_3$ | $CH_2$—iPr | $CH_2CMe_2F$ | $CH_2CMe_2F$ | $CH_2$—iPr |
| 3-21 | $CH_3$ | $CH_2CMe_2F$ | $CH_2$—iPr | $CH_2$—iPr | $CH_2CMe_2F$ |
| 3-22 | $CH_3$ | $CH_2$—iPr | $CH_2CMe_2F$ | $CH_2CMe_2F$ | $CH_2CMe_2F$ |
| 3-23 | $CH_3$ | $CH_2CMe_2F$ | $CH_2$—iPr | $CH_2CMe_2F$ | $CH_2CMe_2F$ |
| 3-24 | $CH_3$ | $CH_2CMe_2F$ | $CH_2CMe_2F$ | $CH_2$—iPr | $CH_2CMe_2F$ |
| 3-25 | $CH_3$ | $CH_2CMe_2F$ | $CH_2CMe_2F$ | $CH_2CMe_2F$ | $CH_2$—iPr |
| 3-26 | $CH_3$ | $CH_2CMe_2F$ | $CH_2CMe_2F$ | $CH_2CMe_2F$ | $CH_2CMe_2F$ |
| 3-27 | $CH_3$ | $CH_2$—iPr | $CH_2$—iPr | $CH_2$—iPr | $CH_2$—iPr |
| 3-28 | $CH_3$ | $CH_2$—tBu | $CH_2$—tBu | $CH_2$—iPr | $CH_2$—iPr |
| 3-29 | $CH_3$ | $CH_2$—iPr | $CH_2$—iPr | $CH_2$—tBu | $CH_2$—tBu |
| 3-30 | $CH_3$ | $CH_2CMe_2F$ | $CH_2CMe_2F$ | $CH_2$—iPr | $CH_2$—iPr |
| 3-31 | $CH_3$ | $CH_2$—iPr | $CH_2$—iPr | $CH_2CMe_2F$ | $CH_2CMe_2F$ |
| 3-32 | $CH_3$ | $CH_2CMe_2F$ | $CH_2$—tBu | $CH_2CMe_2F$ | $CH_2$—tBu |
| 3-33 | $CH_3$ | $CH_2CF_2Me$ | $CH_2$—iPr | $CH_2CF_2Me$ | $CH_2$—iPr |
| 3-34 | $CH_3$ | $CH_2CF_3$ | $CH_2$—iPr | $CH_2CF_3$ | $CH_2$—iPr |
| 3-35 | $CH_3$ | $CH_2CH(CF_3)_2$ | $CH_2$—iPr | $CH_2CH(CF_3)_2$ | $CH_2$—iPr |
| 3-36 | $CH_2F$ | $CH_2CMe_2F$ | $CH_2$—iPr | $CH_2CMe_2F$ | $CH_2$—iPr |
| 3-37 | H | $CH_2CMe_2F$ | $CH_2$—iPr | $CH_2CMe_2F$ | $CH_2$—iPr |
| 3-38 | Et | $CH_2CMe_2F$ | $CH_2$—iPr | $CH_2CMe_2F$ | $CH_2$—iPr |
| 3-39 | $CH_2F$ | $CH_2$—iPr | $CH_2$—iPr | $CH_2$—iPr | $CH_2$—iPr |
| 3-40 | H | $CH_2$—iPr | $CH_2$—iPr | $CH_2$—iPr | $CH_2$—iPr |
| 3-41 | Et | $CH_2$—iPr | $CH_2$—iPr | $CH_2$—iPr | $CH_2$—iPr |
| 3-42 | H | $CH_2CMe_2F$ | $CH_2$—tBu | $CH_2CMe_2F$ | $CH_2$—tBu |
| 3-43 | $CH_3$ | $CH_2CMe_2F$ | iPr | $CH_2CMe_2F$ | iPr |
| 3-44 | $CH_3$ | $CH_2CMe_2F$ | nPr | $CH_2CMe_2F$ | nPr |
| 3-45 | $CH_3$ | $CH_2CMe_2F$ | sBu | $CH_2CMe_2F$ | sBu |
| 3-46 | $CH_3$ | $CH_2CMe_2F$ | tBu | $CH_2CMe_2F$ | tBu |
| 3-47 | $CH_3$ | $CH_2CMe_2F$ | $CH_2$-p-biphenyl | $CH_2CMe_2F$ | $CH_2$-p-biphenyl |
| 3-48 | $CH_3$ | $CH_2CMe_2F$ | $CH_2$—p-tBuPh | $CH_2CMe_2F$ | $CH_2$—p-tBuPh |
| 3-49 | $CH_3$ | $CH_2CMe_2F$ | $CH_3$ | $CH_2CMe_2F$ | $CH_3$ |
| 3-50 | H | $CH_2CMe_2F$ | iPr | $CH_2CMe_2F$ | iPr |
| 3-51 | $CH_3$ | $CH_2CMe_2F$ | $CH_2CH_2CMe_3$ | $CH_2CMe_2F$ | $CH_2CH_2CMe_3$ |
| 3-52 | $CH_3$ | $CH_2CMe_2F$ | $CH_2CH_2$—iPr | $CH_2CMe_2F$ | $CH_2CH_2$—iPr |
| 3-53 | $CH_3$ | $CH_2$-p-pyridyl | $CH_2$—iPr | $CH_2$-p-pyridyl | $CH_2$—iPr |
| 3-54 | $CH_3$ | $CH_2$-p-pyridyl | $CH_2$—tBu | $CH_2$-p-pyridyl | $CH_2$—tBu |

TABLE 4

Compounds of formula (I), wherein $Cy^1$ and $Cy^2$ are p-trifluoromethylphenyl and $R^a$, $R^b$, $R^1$ to $R^4$ are as shown in Table 2.

| Compound # | $R^a/R^b$ | $R^1$ | $R^2$ | $R^3$ | $R^4$ |
|---|---|---|---|---|---|
| 4-1 | $CH_3$ | $CH_2$—tBu | $CH_2$—tBu | $CH_2$—tBu | $CH_2$—tBu |
| 4-2 | $CH_3$ | $CH_2$—tBu | $CH_2$—iPr | $CH_2$—iPr | $CH_2$—iPr |
| 4-3 | $CH_3$ | $CH_2$—iPr | $CH_2$—tBu | $CH_2$—iPr | $CH_2$—iPr |
| 4-4 | $CH_3$ | $CH_2$—iPr | $CH_2$—iPr | $CH_2$—tBu | $CH_2$—iPr |
| 4-5 | $CH_3$ | $CH_2$—iPr | $CH_2$—iPr | $CH_2$—iPr | $CH_2$—tBu |
| 4-6 | $CH_3$ | $CH_2$—iPr | $CH_2$—tBu | $CH_2$—iPr | $CH_2$—tBu |
| 4-7 | $CH_3$ | $CH_2$—tBu | $CH_2$—iPr | $CH_2$—tBu | $CH_2$—iPr |
| 4-8 | $CH_3$ | $CH_2$—iPr | $CH_2$—tBu | $CH_2$—tBu | $CH_2$—iPr |
| 4-9 | $CH_3$ | $CH_2$—tBu | $CH_2$—iPr | $CH_2$—iPr | $CH_2$—tBu |
| 4-10 | $CH_3$ | $CH_2$—iPr | $CH_2$—tBu | $CH_2$—tBu | $CH_2$—tBu |
| 4-11 | $CH_3$ | $CH_2$—tBu | $CH_2$—iPr | $CH_2$—tBu | $CH_2$—tBu |
| 4-12 | $CH_3$ | $CH_2$—tBu | $CH_2$—tBu | $CH_2$—iPr | $CH_2$—tBu |
| 4-13 | $CH_3$ | $CH_2$—tBu | $CH_2$—tBu | $CH_2$—tBu | $CH_2$—iPr |
| 4-14 | $CH_3$ | $CH_2CMe_2F$ | $CH_2$—iPr | $CH_2$—iPr | $CH_2$—iPr |

TABLE 4-continued

Compounds of formula (I), wherein Cy$^1$ and Cy$^2$ are p-trifluoromethylphenyl and R$^a$, R$^b$, R$^1$ to R$^4$ are as shown in Table 2.

| Compound # | R$^a$/R$^b$ | R$^1$ | R$^2$ | R$^3$ | R$^4$ |
|---|---|---|---|---|---|
| 4-15 | CH$_3$ | CH$_2$—iPr | CH$_2$CMe$_2$F | CH$_2$—iPr | CH$_2$—iPr |
| 4-16 | CH$_3$ | CH$_2$—iPr | CH$_2$—iPr | CH$_2$CMe$_2$F | CH$_2$—iPr |
| 4-17 | CH$_3$ | CH$_2$—iPr | CH$_2$—iPr | CH$_2$—iPr | CH$_2$CMe$_2$F |
| 4-18 | CH$_3$ | CH$_2$CMe$_2$F | CH$_2$—iPr | CH$_2$CMe$_2$F | CH$_2$—iPr |
| 4-19 | CH$_3$ | CH$_2$—iPr | CH$_2$CMe$_2$F | CH$_2$—iPr | CH$_2$CMe$_2$F |
| 4-20 | CH$_3$ | CH$_2$—iPr | CH$_2$CMe$_2$F | CH$_2$CMe$_2$F | CH$_2$—iPr |
| 4-21 | CH$_3$ | CH$_2$CMe$_2$F | CH$_2$—iPr | CH$_2$—iPr | CH$_2$CMe$_2$F |
| 4-22 | CH$_3$ | CH$_2$—iPr | CH$_2$CMe$_2$F | CH$_2$CMe$_2$F | CH$_2$CMe$_2$F |
| 4-23 | CH$_3$ | CH$_2$CMe$_2$F | CH$_2$—iPr | CH$_2$CMe$_2$F | CH$_2$CMe$_2$F |
| 4-24 | CH$_3$ | CH$_2$CMe$_2$F | CH$_2$CMe$_2$F | CH$_2$—iPr | CH$_2$CMe$_2$F |
| 4-25 | CH$_3$ | CH$_2$CMe$_2$F | CH$_2$CMe$_2$F | CH$_2$CMe$_2$F | CH$_2$—iPr |
| 4-26 | CH$_3$ | CH$_2$CMe$_2$F | CH$_2$CMe$_2$F | CH$_2$CMe$_2$F | CH$_2$CMe$_2$F |
| 4-27 | CH$_3$ | CH$_2$—iPr | CH$_2$—iPr | CH$_2$—iPr | CH$_2$—iPr |
| 4-28 | CH$_3$ | CH$_2$—tBu | CH$_2$—tBu | CH$_2$—iPr | CH$_2$—iPr |
| 4-29 | CH$_3$ | CH$_2$—iPr | CH$_2$—iPr | CH$_2$—tBu | CH$_2$—tBu |
| 4-30 | CH$_3$ | CH$_2$CMe$_2$F | CH$_2$CMe$_2$F | CH$_2$—iPr | CH$_2$—iPr |
| 4-31 | CH$_3$ | CH$_2$—iPr | CH$_2$—iPr | CH$_2$CMe$_2$F | CH$_2$CMe$_2$F |
| 4-32 | CH$_3$ | CH$_2$CMe$_2$F | CH$_2$—tBu | CH$_2$CMe$_2$F | CH$_2$—tBu |
| 4-33 | CH$_3$ | CH$_2$CF$_2$Me | CH$_2$—iPr | CH$_2$CF$_2$Me | CH$_2$—iPr |
| 4-34 | CH$_3$ | CH$_2$CF$_3$ | CH$_2$—iPr | CH$_2$CF$_3$ | CH$_2$—iPr |
| 4-35 | CH$_3$ | CH$_2$CH(CF$_3$)$_2$ | CH$_2$—iPr | CH$_2$CH(CF$_3$)$_2$ | CH$_2$—iPr |
| 4-36 | CH$_2$F | CH$_2$CMe$_2$F | CH$_2$—iPr | CH$_2$CMe$_2$F | CH$_2$—iPr |
| 4-37 | H | CH$_2$CMe$_2$F | CH$_2$—iPr | CH$_2$CMe$_2$F | CH$_2$—iPr |
| 4-38 | Et | CH$_2$CMe$_2$F | CH$_2$—iPr | CH$_2$CMe$_2$F | CH$_2$—iPr |
| 4-39 | CH$_2$F | CH$_2$—iPr | CH$_2$—iPr | CH$_2$—iPr | CH$_2$—iPr |
| 4-40 | H | CH$_2$—iPr | CH$_2$—iPr | CH$_2$—iPr | CH$_2$—iPr |
| 4-41 | Et | CH$_2$—iPr | CH$_2$—iPr | CH$_2$—iPr | CH$_2$—iPr |
| 4-42 | H | CH$_2$CMe$_2$F | CH$_2$—tBu | CH$_2$CMe$_2$F | CH$_2$—tBu |
| 4-43 | CH$_3$ | CH$_2$CMe$_2$F | iPr | CH$_2$CMe$_2$F | iPr |
| 4-44 | CH$_3$ | CH$_2$CMe$_2$F | nPr | CH$_2$CMe$_2$F | nPr |
| 4-45 | CH$_3$ | CH$_2$CMe$_2$F | sBu | CH$_2$CMe$_2$F | sBu |
| 4-46 | CH$_3$ | CH$_2$CMe$_2$F | tBu | CH$_2$CMe$_2$F | tBu |
| 4-47 | CH$_3$ | CH$_2$CMe$_2$F | CH$_2$-p-biphenyl | CH$_2$CMe$_2$F | CH$_2$-p-biphenyl |
| 4-48 | CH$_3$ | CH$_2$CMe$_2$F | CH$_2$—p-tBuPh | CH$_2$CMe$_2$F | CH$_2$—p-tBuPh |
| 4-49 | CH$_3$ | CH$_2$CMe$_2$F | CH$_3$ | CH$_2$CMe$_2$F | CH$_3$ |
| 4-50 | H | CH$_2$CMe$_2$F | iPr | CH$_2$CMe$_2$F | iPr |
| 4-51 | CH$_3$ | CH$_2$CMe$_2$F | CH$_2$CH$_2$CMe$_3$ | CH$_2$CMe$_2$F | CH$_2$CH$_2$CMe$_3$ |
| 4-52 | CH$_3$ | CH$_2$CMe$_2$F | CH$_2$CH$_2$—iPr | CH$_2$CMe$_2$F | CH$_2$CH$_2$—iPr |
| 4-53 | CH$_3$ | CH$_2$-p-pyridyl | CH$_2$—iPr | CH$_2$-p-pyridyl | CH$_2$—iPr |
| 4-54 | CH$_3$ | CH$_2$-p-pyridyl | CH$_2$—tBu | CH$_2$-p-pyridyl | CH$_2$—tBu |

TABLE 5

Compounds of formula (I), wherein Cy$^1$ and Cy$^2$ are p-trifluoromethoxyphenyl and R$^a$, R$^b$, R$^1$ to R$^4$ are as shown.

| Compound # | R$^a$/R$^b$ | R$^1$ | R$^2$ | R$^3$ | R$^4$ |
|---|---|---|---|---|---|
| 5-1 | CH$_3$ | CH$_2$—tBu | CH$_2$—tBu | CH$_2$—tBu | CH$_2$—tBu |
| 5-2 | CH$_3$ | CH$_2$—tBu | CH$_2$—iPr | CH$_2$—iPr | CH$_2$—iPr |
| 5-3 | CH$_3$ | CH$_2$—iPr | CH$_2$—tBu | CH$_2$—iPr | CH$_2$—iPr |
| 5-4 | CH$_3$ | CH$_2$—iPr | CH$_2$—iPr | CH$_2$—tBu | CH$_2$—iPr |
| 5-5 | CH$_3$ | CH$_2$—iPr | CH$_2$—iPr | CH$_2$—iPr | CH$_2$—tBu |
| 5-6 | CH$_3$ | CH$_2$—iPr | CH$_2$—tBu | CH$_2$—iPr | CH$_2$—tBu |
| 5-7 | CH$_3$ | CH$_2$—tBu | CH$_2$—iPr | CH$_2$—tBu | CH$_2$—iPr |
| 5-8 | CH$_3$ | CH$_2$—iPr | CH$_2$—tBu | CH$_2$—tBu | CH$_2$—iPr |
| 5-9 | CH$_3$ | CH$_2$—tBu | CH$_2$—iPr | CH$_2$—iPr | CH$_2$—tBu |
| 5-10 | CH$_3$ | CH$_2$—iPr | CH$_2$—tBu | CH$_2$—tBu | CH$_2$—tBu |
| 5-11 | CH$_3$ | CH$_2$—tBu | CH$_2$—iPr | CH$_2$—tBu | CH$_2$—tBu |
| 5-12 | CH$_3$ | CH$_2$—tBu | CH$_2$—tBu | CH$_2$—iPr | CH$_2$—tBu |
| 5-13 | CH$_3$ | CH$_2$—tBu | CH$_2$—tBu | CH$_2$—tBu | CH$_2$—iPr |
| 5-14 | CH$_3$ | CH$_2$CMe$_2$F | CH$_2$—iPr | CH$_2$—iPr | CH$_2$—iPr |
| 5-15 | CH$_3$ | CH$_2$—iPr | CH$_2$CMe$_2$F | CH$_2$—iPr | CH$_2$—iPr |
| 5-16 | CH$_3$ | CH$_2$—iPr | CH$_2$—iPr | CH$_2$CMe$_2$F | CH$_2$—iPr |
| 5-17 | CH$_3$ | CH$_2$—iPr | CH$_2$—iPr | CH$_2$—iPr | CH$_2$CMe$_2$F |
| 5-18 | CH$_3$ | CH$_2$CMe$_2$F | CH$_2$—iPr | CH$_2$CMe$_2$F | CH$_2$—iPr |
| 5-19 | CH$_3$ | CH$_2$—iPr | CH$_2$CMe$_2$F | CH$_2$—iPr | CH$_2$CMe$_2$F |
| 5-20 | CH$_3$ | CH$_2$—iPr | CH$_2$CMe$_2$F | CH$_2$CMe$_2$F | CH$_2$—iPr |
| 5-21 | CH$_3$ | CH$_2$CMe$_2$F | CH$_2$—iPr | CH$_2$—iPr | CH$_2$CMe$_2$F |
| 5-22 | CH$_3$ | CH$_2$—iPr | CH$_2$CMe$_2$F | CH$_2$CMe$_2$F | CH$_2$CMe$_2$F |
| 5-23 | CH$_3$ | CH$_2$CMe$_2$F | CH$_2$—iPr | CH$_2$CMe$_2$F | CH$_2$CMe$_2$F |
| 5-24 | CH$_3$ | CH$_2$CMe$_2$F | CH$_2$CMe$_2$F | CH$_2$—iPr | CH$_2$CMe$_2$F |

TABLE 5-continued

Compounds of formula (I), wherein Cy¹ and Cy² are p-trifluoromethoxyphenyl and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 5-25 | CH₃ | CH₂CMe₂F | CH₂CMe₂F | CH₂CMe₂F | CH₂—iPr |
| 5-26 | CH₃ | CH₂CMe₂F | CH₂CMe₂F | CH₂CMe₂F | CH₂CMe₂F |
| 5-27 | CH₃ | CH₂—iPr | CH₂—iPr | CH₂—iPr | CH₂—iPr |
| 5-28 | CH₃ | CH₂—tBu | CH₂—tBu | CH₂—iPr | CH₂—iPr |
| 5-29 | CH₃ | CH₂—iPr | CH₂—iPr | CH₂—tBu | CH₂—tBu |
| 5-30 | CH₃ | CH₂CMe₂F | CH₂CMe₂F | CH₂—iPr | CH₂—iPr |
| 5-31 | CH₃ | CH₂—iPr | CH₂—iPr | CH₂CMe₂F | CH₂CMe₂F |
| 5-32 | CH₃ | CH₂CMe₂F | CH₂—tBu | CH₂CMe₂F | CH₂—tBu |
| 5-33 | CH₃ | CH₂CF₂Me | CH₂—iPr | CH₂CF₂Me | CH₂—iPr |
| 5-34 | CH₃ | CH₂CF₃ | CH₂—iPr | CH₂CF₃ | CH₂—iPr |
| 5-35 | CH₃ | CH₂CH(CF₃)₂ | CH₂—iPr | CH₂CH(CF₃)₂ | CH₂—iPr |
| 5-36 | CH₂F | CH₂CMe₂F | CH₂—iPr | CH₂CMe₂F | CH₂—iPr |
| 5-37 | H | CH₂CMe₂F | CH₂—iPr | CH₂CMe₂F | CH₂—iPr |
| 5-38 | Et | CH₂CMe₂F | CH₂—iPr | CH₂CMe₂F | CH₂—iPr |
| 5-39 | CH₂F | CH₂—iPr | CH₂—iPr | CH₂—iPr | CH₂—iPr |
| 5-40 | H | CH₂—iPr | CH₂—iPr | CH₂—iPr | CH₂—iPr |
| 5-41 | Et | CH₂—iPr | CH₂—iPr | CH₂—iPr | CH₂—iPr |
| 5-42 | H | CH₂CMe₂F | CH₂—tBu | CH₂CMe₂F | CH₂—tBu |
| 5-43 | CH₃ | CH₂CMe₂F | iPr | CH₂CMe₂F | iPr |
| 5-44 | CH₃ | CH₂CMe₂F | nPr | CH₂CMe₂F | nPr |
| 5-45 | CH₃ | CH₂CMe₂F | sBu | CH₂CMe₂F | sBu |
| 5-46 | CH₃ | CH₂CMe₂F | tBu | CH₂CMe₂F | tBu |
| 5-47 | CH₃ | CH₂CMe₂F | CH₂-p-biphenyl | CH₂CMe₂F | CH₂-p-biphenyl |
| 5-48 | CH₃ | CH₂CMe₂F | CH₂—p-tBuPh | CH₂CMe₂F | CH₂—p-tBuPh |
| 5-49 | CH₃ | CH₂CMe₂F | CH₃ | CH₂CMe₂F | CH₃ |
| 5-50 | H | CH₂CMe₂F | iPr | CH₂CMe₂F | iPr |
| 5-51 | CH₃ | CH₂CMe₂F | CH₂CH₂CMe₃ | CH₂CMe₂F | CH₂CH₂CMe₃ |
| 5-52 | CH₃ | CH₂CMe₂F | CH₂CH₂—iPr | CH₂CMe₂F | CH₂CH₂—iPr |
| 5-53 | CH₃ | CH₂-p-pyridyl | CH₂—iPr | CH₂-p-pyridyl | CH₂—iPr |
| 5-54 | CH₃ | CH₂-p-pyridyl | CH₂—tBu | CH₂-p-pyridyl | CH₂—tBu |

TABLE 6

Compounds of formula (I), wherein Cy¹ and Cy² are

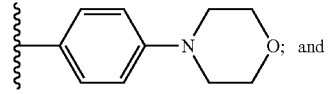

; and $R^a$, $R^b$, $R^1$ to $R^4$ are as shown.

| # | $R^a/R^b$ | $R^1$ | $R^2$ | $R^3$ | $R^4$ |
|---|---|---|---|---|---|
| 6-1 | CH₃ | CH₂—tBu | CH₂—tBu | CH₂—tBu | CH₂—tBu |
| 6-2 | CH₃ | CH₂—tBu | CH₂—iPr | CH₂—iPr | CH₂—iPr |
| 6-3 | CH₃ | CH₂—iPr | CH₂—tBu | CH₂—iPr | CH₂—iPr |
| 6-4 | CH₃ | CH₂—iPr | CH₂—iPr | CH₂—tBu | CH₂—iPr |
| 6-5 | CH₃ | CH₂—iPr | CH₂—iPr | CH₂—iPr | CH₂—tBu |
| 6-6 | CH₃ | CH₂—iPr | CH₂—tBu | CH₂—tBu | CH₂—tBu |
| 6-7 | CH₃ | CH₂—tBu | CH₂—iPr | CH₂—tBu | CH₂—iPr |
| 6-8 | CH₃ | CH₂—iPr | CH₂—tBu | CH₂—tBu | CH₂—iPr |
| 6-9 | CH₃ | CH₂—tBu | CH₂—iPr | CH₂—iPr | CH₂—tBu |
| 6-10 | CH₃ | CH₂—iPr | CH₂—tBu | CH₂—tBu | CH₂—iPr |
| 6-11 | CH₃ | CH₂—tBu | CH₂—iPr | CH₂—tBu | CH₂—tBu |
| 6-12 | CH₃ | CH₂—tBu | CH₂—tBu | CH₂—iPr | CH₂—tBu |
| 6-13 | CH₃ | CH₂—tBu | CH₂—tBu | CH₂—tBu | CH₂—iPr |
| 6-14 | CH₃ | CH₂CMe₂F | CH₂—iPr | CH₂—iPr | CH₂—iPr |
| 6-15 | CH₃ | CH₂—iPr | CH₂CMe₂F | CH₂—iPr | CH₂—iPr |
| 6-16 | CH₃ | CH₂—iPr | CH₂—iPr | CH₂CMe₂F | CH₂—iPr |
| 6-17 | CH₃ | CH₂—iPr | CH₂—iPr | CH₂—iPr | CH₂CMe₂F |
| 6-18 | CH₃ | CH₂CMe₂F | CH₂—iPr | CH₂CMe₂F | CH₂—iPr |
| 6-19 | CH₃ | CH₂—iPr | CH₂CMe₂F | CH₂—iPr | CH₂CMe₂F |
| 6-20 | CH₃ | CH₂—iPr | CH₂CMe₂F | CH₂CMe₂F | CH₂—iPr |
| 6-21 | CH₃ | CH₂CMe₂F | CH₂—iPr | CH₂—iPr | CH₂CMe₂F |
| 6-22 | CH₃ | CH₂—iPr | CH₂CMe₂F | CH₂CMe₂F | CH₂CMe₂F |
| 6-23 | CH₃ | CH₂CMe₂F | CH₂—iPr | CH₂CMe₂F | CH₂CMe₂F |
| 6-24 | CH₃ | CH₂CMe₂F | CH₂CMe₂F | CH₂—iPr | CH₂CMe₂F |
| 6-25 | CH₃ | CH₂CMe₂F | CH₂CMe₂F | CH₂CMe₂F | CH₂—iPr |
| 6-26 | CH₃ | CH₂CMe₂F | CH₂CMe₂F | CH₂CMe₂F | CH₂CMe₂F |
| 6-27 | CH₃ | CH₂—iPr | CH₂—iPr | CH₂—iPr | CH₂—iPr |
| 6-28 | CH₃ | CH₂—tBu | CH₂—tBu | CH₂—iPr | CH₂—iPr |
| 6-29 | CH₃ | CH₂—iPr | CH₂—iPr | CH₂—tBu | CH₂—tBu |
| 6-30 | CH₃ | CH₂CMe₂F | CH₂CMe₂F | CH₂—iPr | CH₂—iPr |
| 6-31 | CH₃ | CH₂—iPr | CH₂—iPr | CH₂CMe₂F | CH₂CMe₂F |
| 6-32 | CH₃ | CH₂CMe₂F | CH₂—tBu | CH₂CMe₂F | CH₂—tBu |
| 6-33 | CH₃ | CH₂CF₂Me | CH₂—iPr | CH₂CF₂Me | CH₂—iPr |
| 6-34 | CH₃ | CH₂CF₃ | CH₂—iPr | CH₂CF₃ | CH₂—iPr |
| 6-35 | CH₃ | CH₂CH(CF₃)₂ | CH₂—iPr | CH₂CH(CF₃)₂ | CH₂—iPr |
| 6-36 | CH₂F | CH₂CMe₂F | CH₂—iPr | CH₂CMe₂F | CH₂—iPr |
| 6-37 | H | CH₂CMe₂F | CH₂—iPr | CH₂CMe₂F | CH₂—iPr |
| 6-38 | Et | CH₂CMe₂F | CH₂—iPr | CH₂CMe₂F | CH₂—iPr |
| 6-39 | CH₂F | CH₂—iPr | CH₂—iPr | CH₂—iPr | CH₂—iPr |
| 6-40 | H | CH₂—iPr | CH₂—iPr | CH₂—iPr | CH₂—iPr |
| 6-41 | Et | CH₂—iPr | CH₂—iPr | CH₂—iPr | CH₂—iPr |
| 6-42 | H | CH₂CMe₂F | CH₂—tBu | CH₂CMe₂F | CH₂—tBu |
| 6-43 | CH₃ | CH₂CMe₂F | iPr | CH₂CMe₂F | iPr |
| 6-44 | CH₃ | CH₂CMe₂F | nPr | CH₂CMe₂F | nPr |
| 6-45 | CH₃ | CH₂CMe₂F | sBu | CH₂CMe₂F | sBu |
| 6-46 | CH₃ | CH₂CMe₂F | tBu | CH₂CMe₂F | tBu |
| 6-47 | CH₃ | CH₂CMe₂F | CH₂-p-biphenyl | CH₂CMe₂F | CH₂-p-biphenyl |
| 6-48 | CH₃ | CH₂CMe₂F | CH₂-p-tBuPh | CH₂CMe₂F | CH₂-p-tBuPh |
| 6-49 | CH₃ | CH₂CMe₂F | CH₃ | CH₂CMe₂F | CH₃ |
| 6-50 | H | CH₂CMe₂F | iPr | CH₂CMe₂F | iPr |
| 6-51 | CH₃ | CH₂CMe₂F | CH₂CH₂CMe₃ | CH₂CMe₂F | CH₂CH₂CMe₃ |
| 6-52 | CH₃ | CH₂CMe₂F | CH₂CH₂—Pr | CH₂CMe₂F | CH₂CH₂—iPr |

TABLE 6-continued

Compounds of formula (I), wherein Cy¹ and Cy² are

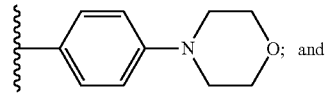; and $R^a$, $R^b$, $R^1$ to $R^4$ are as shown.

| # | $R^a/R^b$ | $R^1$ | $R^2$ | $R^3$ | $R^4$ |
|---|---|---|---|---|---|
| 6-53 | CH₃ | CH₂-p-pyridyl | CH₂—iPr | CH₂-p-pyridyl | CH₂—iPr |
| 6-54 | CH₃ | CH₂-p-pyridyl | CH₂—tBu | CH₂-p-pyridyl | CH₂—tBu |

TABLE 7

Compounds of formula (I), wherein Cy¹ and Cy² are

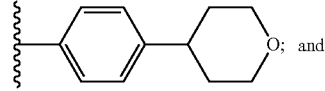 [SMILES: *c1ccc(C2CCOCC2)cc1 ; "and"]; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 7-1 | CH₃ | CH₂—tBu | CH₂—tBu | CH₂—tBu | CH₂—tBu |
| 7-2 | CH₃ | CH₂—tBu | CH₂—iPr | CH₂—iPr | CH₂—iPr |
| 7-3 | CH₃ | CH₂—iPr | CH₂—tBu | CH₂—iPr | CH₂—iPr |
| 7-4 | CH₃ | CH₂—iPr | CH₂—iPr | CH₂—tBu | CH₂—iPr |
| 7-5 | CH₃ | CH₂—iPr | CH₂—iPr | CH₂—iPr | CH₂—tBu |
| 7-6 | CH₃ | CH₂—iPr | CH₂—tBu | CH₂—iPr | CH₂—tBu |
| 7-7 | CH₃ | CH₂—tBu | CH₂—iPr | CH₂—tBu | CH₂—iPr |
| 7-8 | CH₃ | CH₂—iPr | CH₂—tBu | CH₂—tBu | CH₂—iPr |
| 7-9 | CH₃ | CH₂—tBu | CH₂—iPr | CH₂—iPr | CH₂—tBu |
| 7-10 | CH₃ | CH₂—iPr | CH₂—tBu | CH₂—tBu | CH₂—tBu |
| 7-11 | CH₃ | CH₂—tBu | CH₂—iPr | CH₂—tBu | CH₂—tBu |
| 7-12 | CH₃ | CH₂—tBu | CH₂—tBu | CH₂—iPr | CH₂—tBu |
| 7-13 | CH₃ | CH₂—tBu | CH₂—tBu | CH₂—tBu | CH₂—iPr |
| 7-14 | CH₃ | CH₂CMe₂F | CH₂—iPr | CH₂—iPr | CH₂—iPr |
| 7-15 | CH₃ | CH₂—iPr | CH₂CMe₂F | CH₂—iPr | CH₂—iPr |
| 7-16 | CH₃ | CH₂—iPr | CH₂—iPr | CH₂CMe₂F | CH₂—iPr |
| 7-17 | CH₃ | CH₂—iPr | CH₂—iPr | CH₂—iPr | CH₂CMe₂F |
| 7-18 | CH₃ | CH₂CMe₂F | CH₂—iPr | CH₂CMe₂F | CH₂—iPr |
| 7-19 | CH₃ | CH₂—iPr | CH₂CMe₂F | CH₂—iPr | CH₂CMe₂F |
| 7-20 | CH₃ | CH₂—iPr | CH₂CMe₂F | CH₂CMe₂F | CH₂—iPr |
| 7-21 | CH₃ | CH₂CMe₂F | CH₂—iPr | CH₂—iPr | CH₂CMe₂F |
| 7-22 | CH₃ | CH₂—iPr | CH₂CMe₂F | CH₂CMe₂F | CH₂CMe₂F |
| 7-23 | CH₃ | CH₂CMe₂F | CH₂—iPr | CH₂CMe₂F | CH₂CMe₂F |
| 7-24 | CH₃ | CH₂CMe₂F | CH₂CMe₂F | CH₂—iPr | CH₂CMe₂F |
| 7-25 | CH₃ | CH₂CMe₂F | CH₂CMe₂F | CH₂CMe₂F | CH₂—iPr |
| 7-26 | CH₃ | CH₂CMe₂F | CH₂CMe₂F | CH₂CMe₂F | CH₂CMe₂F |
| 7-27 | CH₃ | CH₂—iPr | CH₂—iPr | CH₂—iPr | CH₂—iPr |
| 7-28 | CH₃ | CH₂—tBu | CH₂—tBu | CH₂—iPr | CH₂—iPr |
| 7-29 | CH₃ | CH₂—iPr | CH₂—iPr | CH₂—tBu | CH₂—tBu |
| 7-30 | CH₃ | CH₂CMe₂F | CH₂CMe₂F | CH₂—iPr | CH₂—iPr |
| 7-31 | CH₃ | CH₂—iPr | CH₂—iPr | CH₂CMe₂F | CH₂CMe₂F |
| 7-32 | CH₃ | CH₂—tBu | CH₂—tBu | CH₂CMe₂F | CH₂—tBu |
| 7-33 | CH₃ | CH₂CF₂Me | CH₂—iPr | CH₂CF₂Me | CH₂—iPr |
| 7-34 | CH₃ | CH₂CF₃ | CH₂—iPr | CH₂CF₃ | CH₂—iPr |
| 7-35 | CH₃ | CH₂CH(CF₃)₂ | CH₂—iPr | CH₂CH(CF₃)₂ | CH₂—iPr |
| 7-36 | CH₂F | CH₂CMe₂F | CH₂—iPr | CH₂CMe₂F | CH₂—iPr |
| 7-37 | H | CH₂CMe₂F | CH₂—iPr | CH₂CMe₂F | CH₂—iPr |
| 7-38 | Et | CH₂CMe₂F | CH₂—iPr | CH₂CMe₂F | CH₂—iPr |
| 7-39 | CH₂F | CH₂—iPr | CH₂—iPr | CH₂—iPr | CH₂—iPr |
| 7-40 | H | CH₂—iPr | CH₂—iPr | CH₂—iPr | CH₂—iPr |
| 7-41 | Et | CH₂—iPr | CH₂—iPr | CH₂—iPr | CH₂—iPr |
| 7-42 | H | CH₂CMe₂F | CH₂—tBu | CH₂CMe₂F | CH₂—tBu |
| 7-43 | CH₃ | CH₂CMe₂F | iPr | CH₂CMe₂F | iPr |
| 7-44 | CH₃ | CH₂CMe₂F | nPr | CH₂CMe₂F | nPr |
| 7-45 | CH₃ | CH₂CMe₂F | sBu | CH₂CMe₂F | sBu |

TABLE 7-continued

Compounds of formula (I), wherein Cy¹ and Cy² are

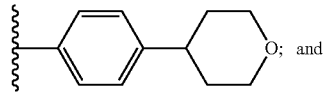; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 7-46 | CH₃ | CH₂CMe₂F | tBu | CH₂CMe₂F | tBu |
| 7-47 | CH₃ | CH₂CMe₂F | CH₂-p-biphenyl | CH₂CMe₂F | CH₂-p-biphenyl |
| 7-48 | CH₃ | CH₂CMe₂F | CH₂-p-tBuPh | CH₂CMe₂F | CH₂-p-tBuPh |
| 7-49 | CH₃ | CH₂CMe₂F | CH₃ | CH₂CMe₂F | CH₃ |
| 7-50 | H | CH₂CMe₂F | iPr | CH₂CMe₂F | iPr |
| 7-51 | CH₃ | CH₂CMe₂F | CH₂CH₂CMe₃ | CH₂CMe₂F | CH₂CH₂CMe₃ |
| 7-52 | CH₃ | CH₂CMe₂F | CH₂CH₂—iPr | CH₂CMe₂F | CH₂CH₂—iPr |
| 7-53 | CH₃ | CH₂-p-pyridyl | CH₂—iPr | CH₂-p-pyridyl | CH₂—iPr |
| 7-54 | CH₃ | CH₂-p-pyridyl | CH₂—tBu | CH₂-p-pyridyl | CH₂—tBu |

TABLE 8

Compounds of formula (I), wherein Cy¹ and Cy² are

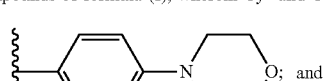; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 8-1 | CH₃ | CH₂—tBu | CH₂—tBu | CH₂—tBu | CH₂—tBu |
| 8-2 | CH₃ | CH₂—tBu | CH₂—iPr | CH₂—iPr | CH₂—iPr |
| 8-3 | CH₃ | CH₂—iPr | CH₂—tBu | CH₂—iPr | CH₂—iPr |
| 8-4 | CH₃ | CH₂—iPr | CH₂—iPr | CH₂—tBu | CH₂—iPr |
| 8-5 | CH₃ | CH₂—iPr | CH₂—iPr | CH₂—iPr | CH₂—tBu |
| 8-6 | CH₃ | CH₂—iPr | CH₂—tBu | CH₂—iPr | CH₂—tBu |
| 8-7 | CH₃ | CH₂—tBu | CH₂—iPr | CH₂—tBu | CH₂—iPr |
| 8-8 | CH₃ | CH₂—iPr | CH₂—tBu | CH₂—tBu | CH₂—iPr |
| 8-9 | CH₃ | CH₂—tBu | CH₂—iPr | CH₂—iPr | CH₂—tBu |
| 8-10 | CH₃ | CH₂—iPr | CH₂—tBu | CH₂—tBu | CH₂—tBu |
| 8-11 | CH₃ | CH₂—tBu | CH₂—iPr | CH₂—tBu | CH₂—tBu |
| 8-12 | CH₃ | CH₂—tBu | CH₂—tBu | CH₂—iPr | CH₂—tBu |
| 8-13 | CH₃ | CH₂—tBu | CH₂—tBu | CH₂—tBu | CH₂—iPr |
| 8-14 | CH₃ | CH₂CMe₂F | CH₂—iPr | CH₂—iPr | CH₂—iPr |
| 8-15 | CH₃ | CH₂—iPr | CH₂CMe₂F | CH₂—iPr | CH₂—iPr |
| 8-16 | CH₃ | CH₂—iPr | CH₂—iPr | CH₂CMe₂F | CH₂—iPr |
| 8-17 | CH₃ | CH₂—iPr | CH₂—iPr | CH₂—iPr | CH₂CMe₂F |
| 8-18 | CH₃ | CH₂CMe₂F | CH₂—iPr | CH₂CMe₂F | CH₂—iPr |
| 8-19 | CH₃ | CH₂—iPr | CH₂CMe₂F | CH₂—iPr | CH₂CMe₂F |
| 8-20 | CH₃ | CH₂—iPr | CH₂CMe₂F | CH₂CMe₂F | CH₂—iPr |
| 8-21 | CH₃ | CH₂CMe₂F | CH₂—iPr | CH₂—iPr | CH₂CMe₂F |
| 8-22 | CH₃ | CH₂—iPr | CH₂CMe₂F | CH₂CMe₂F | CH₂CMe₂F |
| 8-23 | CH₃ | CH₂CMe₂F | CH₂—iPr | CH₂CMe₂F | CH₂CMe₂F |
| 8-24 | CH₃ | CH₂CMe₂F | CH₂CMe₂F | CH₂—iPr | CH₂CMe₂F |
| 8-25 | CH₃ | CH₂CMe₂F | CH₂CMe₂F | CH₂CMe₂F | CH₂—iPr |
| 8-26 | CH₃ | CH₂CMe₂F | CH₂CMe₂F | CH₂CMe₂F | CH₂CMe₂F |
| 8-27 | CH₃ | CH₂—iPr | CH₂—iPr | CH₂—iPr | CH₂—iPr |
| 8-28 | CH₃ | CH₂—tBu | CH₂—tBu | CH₂—iPr | CH₂—iPr |
| 8-29 | CH₃ | CH₂—iPr | CH₂—iPr | CH₂—tBu | CH₂—tBu |
| 8-30 | CH₃ | CH₂CMe₂F | CH₂CMe₂F | CH₂—iPr | CH₂—iPr |
| 8-31 | CH₃ | CH₂—iPr | CH₂—iPr | CH₂CMe₂F | CH₂CMe₂F |
| 8-32 | CH₃ | CH₂CMe₂F | CH₂—tBu | CH₂CMe₂F | CH₂—tBu |
| 8-33 | CH₃ | CH₂CF₂Me | CH₂—iPr | CH₂CF₂Me | CH₂—iPr |
| 8-34 | CH₃ | CH₂CF₃ | CH₂—iPr | CH₂CF₃ | CH₂—iPr |

TABLE 8-continued

Compounds of formula (I), wherein $Cy^1$ and $Cy^2$ are


and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 8-35 | $CH_3$ | $CH_2CH(CF_3)_2$ | $CH_2$—iPr | $CH_2CH(CF_3)_2$ | $CH_2$—iPr |
| 8-36 | $CH_2F$ | $CH_2CMe_2F$ | $CH_2$—iPr | $CH_2CMe_2F$ | $CH_2$—iPr |
| 8-37 | H | $CH_2CMe_2F$ | $CH_2$—iPr | $CH_2CMe_2F$ | $CH_2$—iPr |
| 8-38 | Et | $CH_2CMe_2F$ | $CH_2$—iPr | $CH_2CMe_2F$ | $CH_2$—iPr |
| 8-39 | $CH_2F$ | $CH_2$—iPr | $CH_2$—iPr | $CH_2$—iPr | $CH_2$—iPr |
| 8-40 | H | $CH_2$—iPr | $CH_2$—iPr | $CH_2$—iPr | $CH_2$—iPr |
| 8-41 | Et | $CH_2$—iPr | $CH_2$—iPr | $CH_2$—iPr | $CH_2$—iPr |
| 8-42 | H | $CH_2CMe_2F$ | $CH_2$—tBu | $CH_2CMe_2F$ | $CH_2$—tBu |
| 8-43 | $CH_3$ | $CH_2CMe_2F$ | iPr | $CH_2CMe_2F$ | iPr |
| 8-44 | $CH_3$ | $CH_2CMe_2F$ | nPr | $CH_2CMe_2F$ | nPr |
| 8-45 | $CH_3$ | $CH_2CMe_2F$ | sBu | $CH_2CMe_2F$ | sBu |
| 8-46 | $CH_3$ | $CH_2CMe_2F$ | tBu | $CH_2CMe_2F$ | tBu |
| 8-47 | $CH_3$ | $CH_2CMe_2F$ | $CH_2$-p-biphenyl | $CH_2CMe_2F$ | $CH_2$-p-biphenyl |
| 8-48 | $CH_3$ | $CH_2CMe_2F$ | $CH_2$-p-tBuPh | $CH_2CMe_2F$ | $CH_2$-p-tBuPh |
| 8-49 | $CH_3$ | $CH_2CMe_2F$ | $CH_3$ | $CH_2CMe_2F$ | $CH_3$ |
| 8-50 | H | $CH_2CMe_2F$ | iPr | $CH_2CMe_2F$ | iPr |
| 8-51 | $CH_3$ | $CH_2CMe_2F$ | $CH_2CH_2CMe_3$ | $CH_2CMe_2F$ | $CH_2CH_2CMe_3$ |
| 8-52 | $CH_3$ | $CH_2CMe_2F$ | $CH_2CH_2$—iPr | $CH_2CMe_2F$ | $CH_2CH_2$—iPr |
| 8-53 | $CH_3$ | $CH_2$-p-pyridyl | $CH_2$—iPr | $CH_2$-p-pyridyl | $CH_2$—iPr |
| 8-54 | $CH_3$ | $CH_2$-p-pyridyl | $CH_2$—tBu | $CH_2$-p-pyridyl | $CH_2$—tBu |

TABLE 9

Compounds of formula (I), wherein $Cy^1$ and $Cy^2$ are

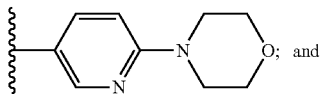

and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 9-1 | $CH_3$ | $CH_2$—tBu | $CH_2$—tBu | $CH_2$—tBu | $CH_2$—tBu |
| 9-2 | $CH_3$ | $CH_2$—tBu | $CH_2$—iPr | $CH_2$—iPr | $CH_2$—iPr |
| 9-3 | $CH_3$ | $CH_2$—tBu | $CH_2$—iPr | $CH_2$—iPr | $CH_2$—iPr |
| 9-4 | $CH_3$ | $CH_2$—iPr | $CH_2$—iPr | $CH_2$—tBu | $CH_2$—iPr |
| 9-5 | $CH_3$ | $CH_2$—iPr | $CH_2$—iPr | $CH_2$—iPr | $CH_2$—tBu |
| 9-6 | $CH_3$ | $CH_2$—iPr | $CH_2$—tBu | $CH_2$—iPr | $CH_2$—tBu |
| 9-7 | $CH_3$ | $CH_2$—tBu | $CH_2$—iPr | $CH_2$—tBu | $CH_2$—iPr |
| 9-8 | $CH_3$ | $CH_2$—iPr | $CH_2$—tBu | $CH_2$—tBu | $CH_2$—iPr |
| 9-9 | $CH_3$ | $CH_2$—tBu | $CH_2$—iPr | $CH_2$—iPr | $CH_2$—tBu |
| 9-10 | $CH_3$ | $CH_2$—iPr | $CH_2$—tBu | $CH_2$—tBu | $CH_2$—tBu |
| 9-11 | $CH_3$ | $CH_2$—tBu | $CH_2$—iPr | $CH_2$—tBu | $CH_2$—tBu |
| 9-12 | $CH_3$ | $CH_2$—tBu | $CH_2$—tBu | $CH_2$—iPr | $CH_2$—tBu |
| 9-13 | $CH_3$ | $CH_2$—tBu | $CH_2$—tBu | $CH_2$—tBu | $CH_2$—iPr |
| 9-14 | $CH_3$ | $CH_2CMe_2F$ | $CH_2$—iPr | $CH_2$—iPr | $CH_2$—iPr |
| 9-15 | $CH_3$ | $CH_2$—iPr | $CH_2CMe_2F$ | $CH_2$—iPr | $CH_2$—iPr |
| 9-16 | $CH_3$ | $CH_2$—iPr | $CH_2$—iPr | $CH_2CMe_2F$ | $CH_2$—iPr |
| 9-17 | $CH_3$ | $CH_2$—iPr | $CH_2$—iPr | $CH_2$—iPr | $CH_2CMe_2F$ |
| 9-18 | $CH_3$ | $CH_2CMe_2F$ | $CH_2$—iPr | $CH_2CMe_2F$ | $CH_2$—iPr |
| 9-19 | $CH_3$ | $CH_2$—iPr | $CH_2CMe_2F$ | $CH_2$—iPr | $CH_2CMe_2F$ |
| 9-20 | $CH_3$ | $CH_2$—iPr | $CH_2CMe_2F$ | $CH_2CMe_2F$ | $CH_2$—iPr |
| 9-21 | $CH_3$ | $CH_2CMe_2F$ | $CH_2$—iPr | $CH_2$—iPr | $CH_2CMe_2F$ |
| 9-22 | $CH_3$ | $CH_2$—iPr | $CH_2CMe_2F$ | $CH_2CMe_2F$ | $CH_2CMe_2F$ |
| 9-23 | $CH_3$ | $CH_2CMe_2F$ | $CH_2$—iPr | $CH_2CMe_2F$ | $CH_2CMe_2F$ |
| 9-24 | $CH_3$ | $CH_2CMe_2F$ | $CH_2CMe_2F$ | $CH_2$—iPr | $CH_2CMe_2F$ |

TABLE 9-continued

Compounds of formula (I), wherein $Cy^1$ and $Cy^2$ are

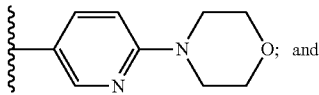

and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 9-25 | $CH_3$ | $CH_2CMe_2F$ | $CH_2CMe_2F$ | $CH_2CMe_2F$ | $CH_2$—iPr |
| 9-26 | $CH_3$ | $CH_2CMe_2F$ | $CH_2CMe_2F$ | $CH_2CMe_2F$ | $CH_2CMe_2F$ |
| 9-27 | $CH_3$ | $CH_2$—iPr | $CH_2$—iPr | $CH_2$—iPr | $CH_2$—iPr |
| 9-28 | $CH_3$ | $CH_2$—tBu | $CH_2$—tBu | $CH_2$—iPr | $CH_2$—iPr |
| 9-29 | $CH_3$ | $CH_2$—tBu | $CH_2$—iPr | $CH_2$—tBu | $CH_2$—tBu |
| 9-30 | $CH_3$ | $CH_2CMe_2F$ | $CH_2CMe_2F$ | $CH_2$—iPr | $CH_2$—iPr |
| 9-31 | $CH_3$ | $CH_2$—iPr | $CH_2$—iPr | $CH_2CMe_2F$ | $CH_2CMe_2F$ |
| 9-32 | $CH_3$ | $CH_2CMe_2F$ | $CH_2$—tBu | $CH_2CMe_2F$ | $CH_2$—tBu |
| 9-33 | $CH_3$ | $CH_2CF_2Me$ | $CH_2$—iPr | $CH_2CF_2Me$ | $CH_2$—iPr |
| 9-34 | $CH_3$ | $CH_2CF_3$ | $CH_2$—iPr | $CH_2CF_3$ | $CH_2$—iPr |
| 9-35 | $CH_3$ | $CH_2CH(CF_3)_2$ | $CH_2$—iPr | $CH_2CH(CF_3)_2$ | $CH_2$—iPr |
| 9-36 | $CH_2F$ | $CH_2CMe_2F$ | $CH_2$—iPr | $CH_2CMe_2F$ | $CH_2$—iPr |
| 9-37 | H | $CH_2CMe_2F$ | $CH_2$—iPr | $CH_2CMe_2F$ | $CH_2$—iPr |
| 9-38 | Et | $CH_2CMe_2F$ | $CH_2$—iPr | $CH_2CMe_2F$ | $CH_2$—iPr |
| 9-39 | $CH_2F$ | $CH_2$—iPr | $CH_2$—iPr | $CH_2$—iPr | $CH_2$—iPr |
| 9-40 | H | $CH_2$—iPr | $CH_2$—iPr | $CH_2$—iPr | $CH_2$—iPr |
| 9-41 | Et | $CH_2$—iPr | $CH_2$—iPr | $CH_2$—iPr | $CH_2$—iPr |
| 9-42 | H | $CH_2CMe_2F$ | $CH_2$—tBu | $CH_2CMe_2F$ | $CH_2$—tBu |
| 9-43 | $CH_3$ | $CH_2CMe_2F$ | iPr | $CH_2CMe_2F$ | iPr |
| 9-44 | $CH_3$ | $CH_2CMe_2F$ | nPr | $CH_2CMe_2F$ | nPr |
| 9-45 | $CH_3$ | $CH_2CMe_2F$ | sBu | $CH_2CMe_2F$ | sBu |
| 9-46 | $CH_3$ | $CH_2CMe_2F$ | tBu | $CH_2CMe_2F$ | tBu |
| 9-47 | $CH_3$ | $CH_2CMe_2F$ | $CH_2$-p-biphenyl | $CH_2CMe_2F$ | $CH_2$-p-biphenyl |
| 9-48 | $CH_3$ | $CH_2CMe_2F$ | $CH_2$-p-tBuPh | $CH_2CMe_2F$ | $CH_2$-p-tBuPh |
| 9-49 | $CH_3$ | $CH_2CMe_2F$ | $CH_3$ | $CH_2CMe_2F$ | $CH_3$ |
| 9-50 | H | $CH_2CMe_2F$ | iPr | $CH_2CMe_2F$ | iPr |
| 9-51 | $CH_3$ | $CH_2CMe_2F$ | $CH_2CH_2CMe_3$ | $CH_2CMe_2F$ | $CH_2CH_2CMe_3$ |
| 9-52 | $CH_3$ | $CH_2CMe_2F$ | $CH_2CH_2$—iPr | $CH_2CMe_2F$ | $CH_2CH_2$—iPr |
| 9-53 | $CH_3$ | $CH_2$-p-pyridyl | $CH_2$—iPr | $CH_2$-p-pyridyl | $CH_2$—iPr |
| 9-54 | $CH_3$ | $CH_2$-p-pyridyl | $CH_2$—tBu | $CH_2$-p-pyridyl | $CH_2$—tBu |

TABLE 10

Compounds of formula (I), wherein $Cy^1$ and $Cy^2$ are

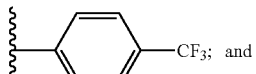

and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 10-1 | $CH_3$ | $CH_2$—tBu | $CH_2$—tBu | $CH_2$—tBu | $CH_2$—tBu |
| 10-2 | $CH_3$ | $CH_2$—tBu | $CH_2$—iPr | $CH_2$—iPr | $CH_2$—iPr |
| 10-3 | $CH_3$ | $CH_2$—iPr | $CH_2$—tBu | $CH_2$—iPr | $CH_2$—iPr |
| 10-4 | $CH_3$ | $CH_2$—iPr | $CH_2$—iPr | $CH_2$—tBu | $CH_2$—iPr |
| 10-5 | $CH_3$ | $CH_2$—iPr | $CH_2$—iPr | $CH_2$—iPr | $CH_2$—tBu |
| 10-6 | $CH_3$ | $CH_2$—iPr | $CH_2$—tBu | $CH_2$—iPr | $CH_2$—tBu |
| 10-7 | $CH_3$ | $CH_2$—tBu | $CH_2$—iPr | $CH_2$—tBu | $CH_2$—iPr |
| 10-8 | $CH_3$ | $CH_2$—iPr | $CH_2$—tBu | $CH_2$—tBu | $CH_2$—iPr |
| 10-9 | $CH_3$ | $CH_2$—tBu | $CH_2$—iPr | $CH_2$—iPr | $CH_2$—tBu |
| 10-10 | $CH_3$ | $CH_2$—iPr | $CH_2$—tBu | $CH_2$—tBu | $CH_2$—tBu |
| 10-11 | $CH_3$ | $CH_2$—tBu | $CH_2$—iPr | $CH_2$—tBu | $CH_2$—tBu |
| 10-12 | $CH_3$ | $CH_2$—tBu | $CH_2$—tBu | $CH_2$—iPr | $CH_2$—tBu |
| 10-13 | $CH_3$ | $CH_2$—tBu | $CH_2$—tBu | $CH_2$—tBu | $CH_2$—iPr |
| 10-14 | $CH_3$ | $CH_2CMe_2F$ | $CH_2$—iPr | $CH_2$—iPr | $CH_2$—iPr |

TABLE 10-continued

Compounds of formula (I), wherein $Cy^1$ and $Cy^2$ are

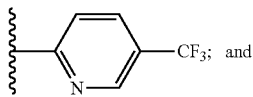

; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 10-15 | $CH_3$ | $CH_2$—iPr | $CH_2CMe_2F$ | $CH_2$—iPr | $CH_2$—iPr |
| 10-16 | $CH_3$ | $CH_2$—iPr | $CH_2$—iPr | $CH_2CMe_2F$ | $CH_2$—iPr |
| 10-17 | $CH_3$ | $CH_2$—iPr | $CH_2$—iPr | $CH_2$—iPr | $CH_2CMe_2F$ |
| 10-18 | $CH_3$ | $CH_2CMe_2F$ | $CH_2$—iPr | $CH_2CMe_2F$ | $CH_2$—iPr |
| 10-19 | $CH_3$ | $CH_2$—iPr | $CH_2CMe_2F$ | $CH_2$—iPr | $CH_2CMe_2F$ |
| 10-20 | $CH_3$ | $CH_2$—iPr | $CH_2CMe_2F$ | $CH_2CMe_2F$ | $CH_2$—iPr |
| 10-21 | $CH_3$ | $CH_2CMe_2F$ | $CH_2$—iPr | $CH_2$—iPr | $CH_2CMe_2F$ |
| 10-22 | $CH_3$ | $CH_2$—iPr | $CH_2CMe_2F$ | $CH_2CMe_2F$ | $CH_2CMe_2F$ |
| 10-23 | $CH_3$ | $CH_2CMe_2F$ | $CH_2$—iPr | $CH_2CMe_2F$ | $CH_2CMe_2F$ |
| 10-24 | $CH_3$ | $CH_2CMe_2F$ | $CH_2CMe_2F$ | $CH_2$—iPr | $CH_2CMe_2F$ |
| 10-25 | $CH_3$ | $CH_2CMe_2F$ | $CH_2CMe_2F$ | $CH_2CMe_2F$ | $CH_2$—iPr |
| 10-26 | $CH_3$ | $CH_2CMe_2F$ | $CH_2CMe_2F$ | $CH_2CMe_2F$ | $CH_2CMe_2F$ |
| 10-27 | $CH_3$ | $CH_2$—iPr | $CH_2$—iPr | $CH_2$—iPr | $CH_2$—iPr |
| 10-28 | $CH_3$ | $CH_2$—tBu | $CH_2$—iPr | $CH_2$—iPr | $CH_2$—iPr |
| 10-29 | $CH_3$ | $CH_2$—iPr | $CH_2$—iPr | $CH_2$—tBu | $CH_2$—tBu |
| 10-30 | $CH_3$ | $CH_2CMe_2F$ | $CH_2CMe_2F$ | $CH_2$—iPr | $CH_2$—iPr |
| 10-31 | $CH_3$ | $CH_2$—iPr | $CH_2$—iPr | $CH_2CMe_2F$ | $CH_2CMe_2F$ |
| 10-32 | $CH_3$ | $CH_2CMe_2F$ | $CH_2$—tBu | $CH_2CMe_2F$ | $CH_2$—tBu |
| 10-33 | $CH_3$ | $CH_2CF_2Me$ | $CH_2$—iPr | $CH_2CF_2Me$ | $CH_2$—iPr |
| 10-34 | $CH_3$ | $CH_2CF_3$ | $CH_2$—iPr | $CH_2CF_3$ | $CH_2$—iPr |
| 10-35 | $CH_3$ | $CH_2CH(CF_3)_2$ | $CH_2$—iPr | $CH_2CH(CF_3)_2$ | $CH_2$—iPr |
| 10-36 | $CH_2F$ | $CH_2CMe_2F$ | $CH_2$—iPr | $CH_2CMe_2F$ | $CH_2$—iPr |
| 10-37 | H | $CH_2CMe_2F$ | $CH_2CMe_2F$ | $CH_2CMe_2F$ | $CH_2CMe_2F$ |
| 10-38 | Et | $CH_2CMe_2F$ | $CH_2CMe_2F$ | $CH_2CMe_2F$ | $CH_2CMe_2F$ |
| 10-39 | $CH_2F$ | $CH_2$—iPr | $CH_2$—iPr | $CH_2$—iPr | $CH_2$—iPr |
| 10-40 | H | $CH_2$—iPr | $CH_2$—iPr | $CH_2$—iPr | $CH_2$—iPr |
| 10-41 | Et | $CH_2$—iPr | $CH_2$—iPr | $CH_2$—iPr | $CH_2$—iPr |
| 10-42 | H | $CH_2CMe_2F$ | $CH_2$—tBu | $CH_2CMe_2F$ | $CH_2$—tBu |
| 10-43 | $CH_3$ | $CH_2CMe_2F$ | iPr | $CH_2CMe_2F$ | iPr |
| 10-44 | $CH_3$ | $CH_2CMe_2F$ | nPr | $CH_2CMe_2F$ | nPr |
| 10-45 | $CH_3$ | $CH_2CMe_2F$ | sBu | $CH_2CMe_2F$ | sBu |
| 10-46 | $CH_3$ | $CH_2CMe_2F$ | tBu | $CH_2CMe_2F$ | tBu |
| 10-47 | $CH_3$ | $CH_2CMe_2F$ | $CH_2$-p-biphenyl | $CH_2CMe_2F$ | $CH_2$-p-biphenyl |
| 10-48 | $CH_3$ | $CH_2CMe_2F$ | $CH_2$-p-tBuPh | $CH_2CMe_2F$ | $CH_2$-p-tBuPh |
| 10-49 | $CH_3$ | $CH_2CMe_2F$ | $CH_3$ | $CH_2CMe_2F$ | $CH_3$ |
| 10-50 | H | $CH_2CMe_2F$ | iPr | $CH_2CMe_2F$ | iPr |
| 10-51 | $CH_3$ | $CH_2CMe_2F$ | $CH_2CH_2CMe_3$ | $CH_2CMe_2F$ | $CH_2CH_2CMe_3$ |
| 10-52 | $CH_3$ | $CH_2CMe_2F$ | $CH_2CH_2$—iPr | $CH_2CMe_2F$ | $CH_2CH_2$—iPr |
| 10-53 | $CH_3$ | $CH_2$-p-pyridyl | $CH_2$—iPr | $CH_2$-p-pyridyl | $CH_2$—iPr |
| 10-54 | $CH_3$ | $CH_2$-p-pyridyl | $CH_2$—tBu | $CH_2$-p-pyridyl | $CH_2$—tBu |

TABLE 11

Compounds of formula (I), wherein $Cy^1$ and $Cy^2$ are

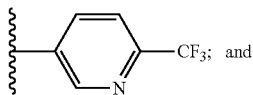

; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 11-1 | $CH_3$ | $CH_2$—tBu | $CH_2$—tBu | $CH_2$—tBu | $CH_2$—tBu |
| 11-2 | $CH_3$ | $CH_2$—tBu | $CH_2$—iPr | $CH_2$—iPr | $CH_2$—iPr |
| 11-3 | $CH_3$ | $CH_2$—iPr | $CH_2$—tBu | $CH_2$—iPr | $CH_2$—iPr |
| 11-4 | $CH_3$ | $CH_2$—iPr | $CH_2$—iPr | $CH_2$—tBu | $CH_2$—iPr |
| 11-5 | $CH_3$ | $CH_2$—iPr | $CH_2$—iPr | $CH_2$—iPr | $CH_2$—tBu |
| 11-6 | $CH_3$ | $CH_2$—iPr | $CH_2$—tBu | $CH_2$—iPr | $CH_2$—tBu |
| 11-7 | $CH_3$ | $CH_2$—tBu | $CH_2$—iPr | $CH_2$—tBu | $CH_2$—iPr |
| 11-8 | $CH_3$ | $CH_2$—iPr | $CH_2$—tBu | $CH_2$—tBu | $CH_2$—iPr |
| 11-9 | $CH_3$ | $CH_2$—tBu | $CH_2$—iPr | $CH_2$—iPr | $CH_2$—tBu |
| 11-10 | $CH_3$ | $CH_2$—iPr | $CH_2$—tBu | $CH_2$—tBu | $CH_2$—tBu |
| 11-11 | $CH_3$ | $CH_2$—tBu | $CH_2$—iPr | $CH_2$—tBu | $CH_2$—tBu |
| 11-12 | $CH_3$ | $CH_2$—tBu | $CH_2$—tBu | $CH_2$—iPr | $CH_2$—tBu |
| 11-13 | $CH_3$ | $CH_2$—tBu | $CH_2$—tBu | $CH_2$—tBu | $CH_2$—iPr |
| 11-14 | $CH_3$ | $CH_2CMe_2F$ | $CH_2$—iPr | $CH_2$—iPr | $CH_2$—iPr |
| 11-15 | $CH_3$ | $CH_2$—iPr | $CH_2CMe_2F$ | $CH_2$—iPr | $CH_2$—iPr |
| 11-16 | $CH_3$ | $CH_2$—iPr | $CH_2$—iPr | $CH_2CMe_2F$ | $CH_2$—iPr |
| 11-17 | $CH_3$ | $CH_2$—iPr | $CH_2$—iPr | $CH_2$—iPr | $CH_2CMe_2F$ |
| 11-18 | $CH_3$ | $CH_2CMe_2F$ | $CH_2$—iPr | $CH_2CMe_2F$ | $CH_2$—iPr |
| 11-19 | $CH_3$ | $CH_2$—iPr | $CH_2CMe_2F$ | $CH_2$—iPr | $CH_2CMe_2F$ |
| 11-20 | $CH_3$ | $CH_2$—iPr | $CH_2CMe_2F$ | $CH_2CMe_2F$ | $CH_2$—iPr |
| 11-21 | $CH_3$ | $CH_2CMe_2F$ | $CH_2$—iPr | $CH_2$—iPr | $CH_2CMe_2F$ |
| 11-22 | $CH_3$ | $CH_2$—iPr | $CH_2CMe_2F$ | $CH_2CMe_2F$ | $CH_2CMe_2F$ |
| 11-23 | $CH_3$ | $CH_2CMe_2F$ | $CH_2$—iPr | $CH_2CMe_2F$ | $CH_2CMe_2F$ |
| 11-24 | $CH_3$ | $CH_2CMe_2F$ | $CH_2CMe_2F$ | $CH_2$—iPr | $CH_2CMe_2F$ |
| 11-25 | $CH_3$ | $CH_2CMe_2F$ | $CH_2CMe_2F$ | $CH_2CMe_2F$ | $CH_2$—iPr |
| 11-26 | $CH_3$ | $CH_2CMe_2F$ | $CH_2CMe_2F$ | $CH_2CMe_2F$ | $CH_2CMe_2F$ |
| 11-27 | $CH_3$ | $CH_2$—iPr | $CH_2$—iPr | $CH_2$—iPr | $CH_2$—iPr |
| 11-28 | $CH_3$ | $CH_2$—tBu | $CH_2$—tBu | $CH_2$—iPr | $CH_2$—iPr |
| 11-29 | $CH_3$ | $CH_2$—iPr | $CH_2$—iPr | $CH_2$—tBu | $CH_2$—tBu |
| 11-30 | $CH_3$ | $CH_2CMe_2F$ | $CH_2CMe_2F$ | $CH_2$—iPr | $CH_2$—iPr |
| 11-31 | $CH_3$ | $CH_2$—iPr | $CH_2$—iPr | $CH_2CMe_2F$ | $CH_2CMe_2F$ |
| 11-32 | $CH_3$ | $CH_2CMe_2F$ | $CH_2$—tBu | $CH_2CMe_2F$ | $CH_2$—tBu |
| 11-33 | $CH_3$ | $CH_2CF_2Me$ | $CH_2$—iPr | $CH_2CF_2Me$ | $CH_2$—iPr |
| 11-34 | $CH_3$ | $CH_2CF_3$ | $CH_2$—iPr | $CH_2CF_3$ | $CH_2$—iPr |
| 11-35 | $CH_3$ | $CH_2CH(CF_3)_2$ | $CH_2$—iPr | $CH_2CH(CF_3)_2$ | $CH_2$—iPr |
| 11-36 | $CH_2F$ | $CH_2CMe_2F$ | $CH_2$—iPr | $CH_2CMe_2F$ | $CH_2$—iPr |
| 11-37 | H | $CH_2CMe_2F$ | $CH_2CMe_2F$ | $CH_2CMe_2F$ | $CH_2CMe_2F$ |
| 11-38 | Et | $CH_2CMe_2F$ | $CH_2CMe_2F$ | $CH_2CMe_2F$ | $CH_2CMe_2F$ |
| 11-39 | $CH_2F$ | $CH_2$—iPr | $CH_2$—iPr | $CH_2$—iPr | $CH_2$—iPr |
| 11-40 | H | $CH_2$—iPr | $CH_2$—iPr | $CH_2$—iPr | $CH_2$—iPr |
| 11-41 | Et | $CH_2$—iPr | $CH_2$—iPr | $CH_2$—iPr | $CH_2$—iPr |
| 11-42 | H | $CH_2CMe_2F$ | $CH_2$—tBu | $CH_2CMe_2F$ | $CH_2$—tBu |
| 11-43 | $CH_3$ | $CH_2CMe_2F$ | iPr | $CH_2CMe_2F$ | iPr |
| 11-44 | $CH_3$ | $CH_2CMe_2F$ | nPr | $CH_2CMe_2F$ | nPr |
| 11-45 | $CH_3$ | $CH_2CMe_2F$ | sBu | $CH_2CMe_2F$ | sBu |
| 11-46 | $CH_3$ | $CH_2CMe_2F$ | tBu | $CH_2CMe_2F$ | tBu |
| 11-47 | $CH_3$ | $CH_2CMe_2F$ | $CH_2$-p-biphenyl | $CH_2CMe_2F$ | $CH_2$-p-biphenyl |
| 11-48 | $CH_3$ | $CH_2CMe_2F$ | $CH_2$-p-tBuPh | $CH_2CMe_2F$ | $CH_2$-p-tBuPh |
| 11-49 | $CH_3$ | $CH_2CMe_2F$ | $CH_3$ | $CH_2CMe_2F$ | $CH_3$ |
| 11-50 | H | $CH_2CMe_2F$ | iPr | $CH_2CMe_2F$ | iPr |
| 11-51 | $CH_3$ | $CH_2CMe_2F$ | $CH_2CH_2CMe_3$ | $CH_2CMe_2F$ | $CH_2CH_2CMe_3$ |
| 11-52 | $CH_3$ | $CH_2CMe_2F$ | $CH_2CH_2$—iPr | $CH_2CMe_2F$ | $CH_2CH_2$—iPr |
| 11-53 | $CH_3$ | $CH_2$-p-pyridyl | $CH_2$—iPr | $CH_2$-p-pyridyl | $CH_2$—iPr |
| 11-54 | $CH_3$ | $CH_2$-p-pyridyl | $CH_2$—tBu | $CH_2$-p-pyridyl | $CH_2$—tBu |

TABLE 12

Compounds of formula (I), wherein Cy¹ and Cy² are

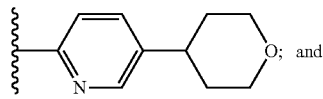; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 12-1 | CH₃ | CH₂—tBu | CH₂—tBu | CH₂—tBu | CH₂—tBu |
| 12-2 | CH₃ | CH₂—tBu | CH₂—iPr | CH₂—iPr | CH₂—iPr |
| 12-3 | CH₃ | CH₂—iPr | CH₂—tBu | CH₂—iPr | CH₂—iPr |
| 12-4 | CH₃ | CH₂—iPr | CH₂—iPr | CH₂—tBu | CH₂—iPr |
| 12-5 | CH₃ | CH₂—iPr | CH₂—iPr | CH₂—iPr | CH₂—tBu |
| 12-6 | CH₃ | CH₂—iPr | CH₂—tBu | CH₂—iPr | CH₂—tBu |
| 12-7 | CH₃ | CH₂—tBu | CH₂—iPr | CH₂—tBu | CH₂—iPr |
| 12-8 | CH₃ | CH₂—iPr | CH₂—tBu | CH₂—tBu | CH₂—iPr |
| 12-9 | CH₃ | CH₂—tBu | CH₂—iPr | CH₂—iPr | CH₂—tBu |
| 12-10 | CH₃ | CH₂—iPr | CH₂—iPr | CH₂—tBu | CH₂—tBu |
| 12-11 | CH₃ | CH₂—tBu | CH₂—iPr | CH₂—tBu | CH₂—tBu |
| 12-12 | CH₃ | CH₂—tBu | CH₂—tBu | CH₂—iPr | CH₂—tBu |
| 12-13 | CH₃ | CH₂—tBu | CH₂—tBu | CH₂—tBu | CH₂—iPr |
| 12-14 | CH₃ | CH₂CMe₂F | CH₂—iPr | CH₂—iPr | CH₂—iPr |
| 12-15 | CH₃ | CH₂—iPr | CH₂CMe₂F | CH₂—iPr | CH₂—iPr |
| 12-16 | CH₃ | CH₂—iPr | CH₂—iPr | CH₂CMe₂F | CH₂—iPr |
| 12-17 | CH₃ | CH₂—iPr | CH₂—iPr | CH₂—iPr | CH₂CMe₂F |
| 12-18 | CH₃ | CH₂CMe₂F | CH₂—iPr | CH₂CMe₂F | CH₂—iPr |
| 12-19 | CH₃ | CH₂—iPr | CH₂CMe₂F | CH₂—iPr | CH₂CMe₂F |
| 12-20 | CH₃ | CH₂—iPr | CH₂CMe₂F | CH₂CMe₂F | CH₂—iPr |
| 12-21 | CH₃ | CH₂CMe₂F | CH₂—iPr | CH₂—iPr | CH₂CMe₂F |
| 12-22 | CH₃ | CH₂—iPr | CH₂CMe₂F | CH₂CMe₂F | CH₂CMe₂F |
| 12-23 | CH₃ | CH₂CMe₂F | CH₂CMe₂F | CH₂—iPr | CH₂CMe₂F |
| 12-24 | CH₃ | CH₂CMe₂F | CH₂CMe₂F | CH₂—iPr | CH₂CMe₂F |
| 12-25 | CH₃ | CH₂CMe₂F | CH₂CMe₂F | CH₂CMe₂F | CH₂—iPr |
| 12-26 | CH₃ | CH₂CMe₂F | CH₂CMe₂F | CH₂CMe₂F | CH₂CMe₂F |
| 12-27 | CH₃ | CH₂—iPr | CH₂—iPr | CH₂—iPr | CH₂—iPr |
| 12-28 | CH₃ | CH₂—tBu | CH₂—tBu | CH₂—iPr | CH₂—iPr |
| 12-29 | CH₃ | CH₂—iPr | CH₂—iPr | CH₂—tBu | CH₂—tBu |
| 12-30 | CH₃ | CH₂CMe₂F | CH₂CMe₂F | CH₂—iPr | CH₂—iPr |
| 12-31 | CH₃ | CH₂—iPr | CH₂—iPr | CH₂CMe₂F | CH₂CMe₂F |
| 12-32 | CH₃ | CH₂CMe₂F | CH₂—tBu | CH₂CMe₂F | CH₂—tBu |
| 12-33 | CH₃ | CH₂CF₂Me | CH₂—iPr | CH₂CF₂Me | CH₂—iPr |
| 12-34 | CH₃ | CH₂CF₃ | CH₂—iPr | CH₂CF₃ | CH₂—iPr |
| 12-35 | CH₃ | CH₂CH(CF₃)₂ | CH₂—iPr | CH₂CH(CF₃)₂ | CH₂—iPr |
| 12-36 | CH₂F | CH₂CMe₂F | CH₂—iPr | CH₂CMe₂F | CH₂—iPr |
| 12-37 | H | CH₂CMe₂F | CH₂—iPr | CH₂CMe₂F | CH₂—iPr |
| 12-38 | Et | CH₂CMe₂F | CH₂—iPr | CH₂CMe₂F | CH₂—iPr |
| 12-39 | CH₂F | CH₂—iPr | CH₂—iPr | CH₂—iPr | CH₂—iPr |
| 12-40 | H | CH₂—iPr | CH₂—iPr | CH₂—iPr | CH₂—iPr |
| 12-41 | Et | CH₂—iPr | CH₂—iPr | CH₂—iPr | CH₂—iPr |
| 12-42 | H | CH₂CMe₂F | CH₂—tBu | CH₂CMe₂F | CH₂—tBu |
| 12-43 | CH₃ | CH₂CMe₂F | iPr | CH₂CMe₂F | iPr |
| 12-44 | CH₃ | CH₂CMe₂F | nPr | CH₂CMe₂F | nPr |
| 12-45 | CH₃ | CH₂CMe₂F | sBu | CH₂CMe₂F | sBu |
| 12-46 | CH₃ | CH₂CMe₂F | tBu | CH₂CMe₂F | tBu |
| 12-47 | CH₃ | CH₂CMe₂F | CH₂-p-biphenyl | CH₂CMe₂F | CH₂-p-biphenyl |
| 12-48 | CH₃ | CH₂CMe₂F | CH₂-p-tBuPh | CH₂CMe₂F | CH₂-p-tBuPh |
| 12-49 | CH₃ | CH₂CMe₂F | CH₃ | CH₂CMe₂F | CH₃ |
| 12-50 | H | CH₂CMe₂F | iPr | CH₂CMe₂F | iPr |
| 12-51 | CH₃ | CH₂CMe₂F | CH₂CH₂CMe₃ | CH₂CMe₂F | CH₂CH₂CMe₃ |
| 12-52 | CH₃ | CH₂CMe₂F | CH₂CH₂—iPr | CH₂CMe₂F | CH₂CH₂—iPr |
| 12-53 | CH₃ | CH₂-p-pyridyl | CH₂—iPr | CH₂-p-pyridyl | CH₂—iPr |
| 12-54 | CH₃ | CH₂-p-pyridyl | CH₂—tBu | CH₂-p-pyridyl | CH₂—tBu |

TABLE 13

Compounds of formula (I), wherein Cy¹ and Cy² are

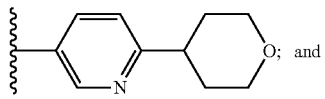; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 13-1 | CH₃ | CH₂—tBu | CH₂—tBu | CH₂—tBu | CH₂—tBu |
| 13-2 | CH₃ | CH₂—tBu | CH₂—iPr | CH₂—iPr | CH₂—iPr |
| 13-3 | CH₃ | CH₂—iPr | CH₂—tBu | CH₂—iPr | CH₂—iPr |
| 13-4 | CH₃ | CH₂—iPr | CH₂—iPr | CH₂—tBu | CH₂—iPr |
| 13-5 | CH₃ | CH₂—iPr | CH₂—iPr | CH₂—iPr | CH₂—tBu |
| 13-6 | CH₃ | CH₂—iPr | CH₂—tBu | CH₂—iPr | CH₂—tBu |
| 13-7 | CH₃ | CH₂—tBu | CH₂—iPr | CH₂—tBu | CH₂—iPr |
| 13-8 | CH₃ | CH₂—iPr | CH₂—tBu | CH₂—tBu | CH₂—iPr |
| 13-9 | CH₃ | CH₂—tBu | CH₂—iPr | CH₂—iPr | CH₂—tBu |
| 13-10 | CH₃ | CH₂—iPr | CH₂—iPr | CH₂—tBu | CH₂—tBu |
| 13-11 | CH₃ | CH₂—tBu | CH₂—iPr | CH₂—tBu | CH₂—tBu |
| 13-12 | CH₃ | CH₂—tBu | CH₂—tBu | CH₂—iPr | CH₂—tBu |
| 13-13 | CH₃ | CH₂—tBu | CH₂—tBu | CH₂—tBu | CH₂—iPr |
| 13-14 | CH₃ | CH₂CMe₂F | CH₂—iPr | CH₂—iPr | CH₂—iPr |
| 13-15 | CH₃ | CH₂—iPr | CH₂CMe₂F | CH₂—iPr | CH₂—iPr |
| 13-16 | CH₃ | CH₂—iPr | CH₂—iPr | CH₂CMe₂F | CH₂—iPr |
| 13-17 | CH₃ | CH₂—iPr | CH₂—iPr | CH₂—iPr | CH₂CMe₂F |
| 13-18 | CH₃ | CH₂CMe₂F | CH₂—iPr | CH₂CMe₂F | CH₂—iPr |
| 13-19 | CH₃ | CH₂—iPr | CH₂CMe₂F | CH₂—iPr | CH₂CMe₂F |
| 13-20 | CH₃ | CH₂—iPr | CH₂CMe₂F | CH₂CMe₂F | CH₂—iPr |
| 13-21 | CH₃ | CH₂CMe₂F | CH₂—iPr | CH₂—iPr | CH₂CMe₂F |
| 13-22 | CH₃ | CH₂—iPr | CH₂CMe₂F | CH₂CMe₂F | CH₂CMe₂F |
| 13-23 | CH₃ | CH₂CMe₂F | CH₂CMe₂F | CH₂—iPr | CH₂CMe₂F |
| 13-24 | CH₃ | CH₂CMe₂F | CH₂CMe₂F | CH₂—iPr | CH₂CMe₂F |
| 13-25 | CH₃ | CH₂CMe₂F | CH₂CMe₂F | CH₂CMe₂F | CH₂—iPr |
| 13-26 | CH₃ | CH₂CMe₂F | CH₂CMe₂F | CH₂CMe₂F | CH₂CMe₂F |
| 13-27 | CH₃ | CH₂—iPr | CH₂—iPr | CH₂—iPr | CH₂—iPr |
| 13-28 | CH₃ | CH₂—tBu | CH₂—tBu | CH₂—iPr | CH₂—iPr |
| 13-29 | CH₃ | CH₂—iPr | CH₂—iPr | CH₂—tBu | CH₂—tBu |
| 13-30 | CH₃ | CH₂CMe₂F | CH₂CMe₂F | CH₂—iPr | CH₂—iPr |
| 13-31 | CH₃ | CH₂—iPr | CH₂—iPr | CH₂CMe₂F | CH₂CMe₂F |
| 13-32 | CH₃ | CH₂CMe₂F | CH₂—tBu | CH₂CMe₂F | CH₂—tBu |
| 13-33 | CH₃ | CH₂CF₂Me | CH₂—iPr | CH₂CF₂Me | CH₂—iPr |
| 13-34 | CH₃ | CH₂CF₃ | CH₂—iPr | CH₂CF₃ | CH₂—iPr |
| 13-35 | CH₃ | CH₂CH(CF₃)₂ | CH₂—iPr | CH₂CH(CF₃)₂ | CH₂—iPr |
| 13-36 | CH₂F | CH₂CMe₂F | CH₂—iPr | CH₂CMe₂F | CH₂—iPr |
| 13-37 | H | CH₂CMe₂F | CH₂—iPr | CH₂CMe₂F | CH₂—iPr |
| 13-38 | Et | CH₂CMe₂F | CH₂—iPr | CH₂CMe₂F | CH₂—iPr |
| 13-39 | CH₂F | CH₂—iPr | CH₂—iPr | CH₂—iPr | CH₂—iPr |
| 13-40 | H | CH₂—iPr | CH₂—iPr | CH₂—iPr | CH₂—iPr |
| 13-41 | Et | CH₂—iPr | CH₂—iPr | CH₂—iPr | CH₂—iPr |
| 13-42 | H | CH₂CMe₂F | CH₂—tBu | CH₂CMe₂F | CH₂—tBu |
| 13-43 | CH₃ | CH₂CMe₂F | iPr | CH₂CMe₂F | iPr |
| 13-44 | CH₃ | CH₂CMe₂F | nPr | CH₂CMe₂F | nPr |
| 13-45 | CH₃ | CH₂CMe₂F | sBu | CH₂CMe₂F | sBu |
| 13-46 | CH₃ | CH₂CMe₂F | tBu | CH₂CMe₂F | tBu |
| 13-47 | CH₃ | CH₂CMe₂F | CH₂-p-biphenyl | CH₂CMe₂F | CH₂-p-biphenyl |
| 13-48 | CH₃ | CH₂CMe₂F | CH₂-p-tBuPh | CH₂CMe₂F | CH₂-p-tBuPh |
| 13-49 | CH₃ | CH₂CMe₂F | CH₃ | CH₂CMe₂F | CH₃ |
| 13-50 | H | CH₂CMe₂F | iPr | CH₂CMe₂F | iPr |
| 13-51 | CH₃ | CH₂CMe₂F | CH₂CH₂CMe₃ | CH₂CMe₂F | CH₂CH₂CMe₃ |
| 13-52 | CH₃ | CH₂CMe₂F | CH₂CH₂—iPr | CH₂CMe₂F | CH₂CH₂—iPr |
| 13-53 | CH₃ | CH₂-p-pyridyl | CH₂—iPr | CH₂-p-pyridyl | CH₂—iPr |
| 13-54 | CH₃ | CH₂-p-pyridyl | CH₂—tBu | CH₂-p-pyridyl | CH₂—tBu |

TABLE 14

Compounds of formula (I), wherein Cy¹ and Cy² are

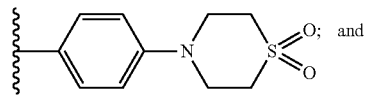

; and

R$^a$, R$^b$, R$^1$ to R$^4$ are as shown.

| Compound # | R$^a$/R$^b$ | R$^1$ | R$^2$ | R$^3$ | R$^4$ |
|---|---|---|---|---|---|
| 14-1 | CH$_3$ | CH$_2$—tBu | CH$_2$—tBu | CH$_2$—tBu | CH$_2$—tBu |
| 14-2 | CH$_3$ | CH$_2$—tBu | CH$_2$—iPr | CH$_2$—iPr | CH$_2$—iPr |
| 14-3 | CH$_3$ | CH$_2$—iPr | CH$_2$—tBu | CH$_2$—iPr | CH$_2$—iPr |
| 14-4 | CH$_3$ | CH$_2$—iPr | CH$_2$—iPr | CH$_2$—tBu | CH$_2$—iPr |
| 14-5 | CH$_3$ | CH$_2$—iPr | CH$_2$—iPr | CH$_2$—iPr | CH$_2$—tBu |
| 14-6 | CH$_3$ | CH$_2$—iPr | CH$_2$—tBu | CH$_2$—iPr | CH$_2$—tBu |
| 14-7 | CH$_3$ | CH$_2$—tBu | CH$_2$—iPr | CH$_2$—tBu | CH$_2$—iPr |
| 14-8 | CH$_3$ | CH$_2$—iPr | CH$_2$—tBu | CH$_2$—tBu | CH$_2$—iPr |
| 14-9 | CH$_3$ | CH$_2$—tBu | CH$_2$—iPr | CH$_2$—iPr | CH$_2$—tBu |
| 14-10 | CH$_3$ | CH$_2$—iPr | CH$_2$—iPr | CH$_2$—tBu | CH$_2$—tBu |
| 14-11 | CH$_3$ | CH$_2$—tBu | CH$_2$—iPr | CH$_2$—tBu | CH$_2$—tBu |
| 14-12 | CH$_3$ | CH$_2$—tBu | CH$_2$—tBu | CH$_2$—iPr | CH$_2$—tBu |
| 14-13 | CH$_3$ | CH$_2$—tBu | CH$_2$—tBu | CH$_2$—tBu | CH$_2$—iPr |
| 14-14 | CH$_3$ | CH$_2$CMe$_2$F | CH$_2$—iPr | CH$_2$—iPr | CH$_2$—iPr |
| 14-15 | CH$_3$ | CH$_2$—iPr | CH$_2$CMe$_2$F | CH$_2$—iPr | CH$_2$—iPr |
| 14-16 | CH$_3$ | CH$_2$—iPr | CH$_2$—iPr | CH$_2$CMe$_2$F | CH$_2$—iPr |
| 14-17 | CH$_3$ | CH$_2$—iPr | CH$_2$—iPr | CH$_2$—iPr | CH$_2$CMe$_2$F |
| 14-18 | CH$_3$ | CH$_2$CMe$_2$F | CH$_2$CMe$_2$F | CH$_2$—iPr | CH$_2$—iPr |
| 14-19 | CH$_3$ | CH$_2$—iPr | CH$_2$CMe$_2$F | CH$_2$—iPr | CH$_2$CMe$_2$F |
| 14-20 | CH$_3$ | CH$_2$—iPr | CH$_2$CMe$_2$F | CH$_2$CMe$_2$F | CH$_2$—iPr |
| 14-21 | CH$_3$ | CH$_2$CMe$_2$F | CH$_2$—iPr | CH$_2$—iPr | CH$_2$CMe$_2$F |
| 14-22 | CH$_3$ | CH$_2$—iPr | CH$_2$CMe$_2$F | CH$_2$CMe$_2$F | CH$_2$CMe$_2$F |
| 14-23 | CH$_3$ | CH$_2$CMe$_2$F | CH$_2$—iPr | CH$_2$CMe$_2$F | CH$_2$CMe$_2$F |
| 14-24 | CH$_3$ | CH$_2$CMe$_2$F | CH$_2$CMe$_2$F | CH$_2$—iPr | CH$_2$CMe$_2$F |
| 14-25 | CH$_3$ | CH$_2$CMe$_2$F | CH$_2$CMe$_2$F | CH$_2$CMe$_2$F | CH$_2$—iPr |
| 14-26 | CH$_3$ | CH$_2$CMe$_2$F | CH$_2$CMe$_2$F | CH$_2$CMe$_2$F | CH$_2$CMe$_2$F |
| 14-27 | CH$_3$ | CH$_2$—iPr | CH$_2$—iPr | CH$_2$—iPr | CH$_2$—iPr |
| 14-28 | CH$_3$ | CH$_2$—tBu | CH$_2$—tBu | CH$_2$—iPr | CH$_2$—iPr |
| 14-29 | CH$_3$ | CH$_2$—iPr | CH$_2$—iPr | CH$_2$—tBu | CH$_2$—tBu |
| 14-30 | CH$_3$ | CH$_2$CMe$_2$F | CH$_2$CMe$_2$F | CH$_2$—iPr | CH$_2$—iPr |
| 14-31 | CH$_3$ | CH$_2$—iPr | CH$_2$—iPr | CH$_2$CMe$_2$F | CH$_2$CMe$_2$F |
| 14-32 | CH$_3$ | CH$_2$CMe$_2$F | CH$_2$—tBu | CH$_2$CMe$_2$F | CH$_2$—tBu |
| 14-33 | CH$_3$ | CH$_2$CF$_2$Me | CH$_2$—iPr | CH$_2$CF$_2$Me | CH$_2$—iPr |
| 14-34 | CH$_3$ | CH$_2$CF$_3$ | CH$_2$—iPr | CH$_2$CF$_3$ | CH$_2$—iPr |
| 14-35 | CH$_3$ | CH$_2$CH(CF$_3$)$_2$ | CH$_2$—iPr | CH$_2$CH(CF$_3$)$_2$ | CH$_2$—iPr |
| 14-36 | CH$_2$F | CH$_2$CMe$_2$F | CH$_2$—iPr | CH$_2$CMe$_2$F | CH$_2$—iPr |
| 14-37 | H | CH$_2$CMe$_2$F | CH$_2$—iPr | CH$_2$CMe$_2$F | CH$_2$—iPr |
| 14-38 | Et | CH$_2$CMe$_2$F | CH$_2$—iPr | CH$_2$CMe$_2$F | CH$_2$—iPr |
| 14-39 | CH$_2$F | CH$_2$—iPr | CH$_2$—iPr | CH$_2$—iPr | CH$_2$—iPr |
| 14-40 | H | CH$_2$—iPr | CH$_2$—iPr | CH$_2$—iPr | CH$_2$—iPr |
| 14-41 | Et | CH$_2$—iPr | CH$_2$—iPr | CH$_2$—iPr | CH$_2$—iPr |
| 14-42 | H | CH$_2$CMe$_2$F | CH$_2$—tBu | CH$_2$CMe$_2$F | CH$_2$—tBu |
| 14-43 | CH$_3$ | CH$_2$CMe$_2$F | iPr | CH$_2$CMe$_2$F | iPr |
| 14-44 | CH$_3$ | CH$_2$CMe$_2$F | nPr | CH$_2$CMe$_2$F | nPr |
| 14-45 | CH$_3$ | CH$_2$CMe$_2$F | sBu | CH$_2$CMe$_2$F | sBu |
| 14-46 | CH$_3$ | CH$_2$CMe$_2$F | tBu | CH$_2$CMe$_2$F | tBu |
| 14-47 | CH$_3$ | CH$_2$CMe$_2$F | CH$_2$-p-biphenyl | CH$_2$CMe$_2$F | CH$_2$-p-biphenyl |
| 14-48 | CH$_3$ | CH$_2$CMe$_2$F | CH$_2$-p-tBuPh | CH$_2$CMe$_2$F | CH$_2$-p-tBuPh |
| 14-49 | CH$_3$ | CH$_2$CMe$_2$F | CH$_3$ | CH$_2$CMe$_2$F | CH$_3$ |
| 14-50 | H | CH$_2$CMe$_2$F | iPr | CH$_2$CMe$_2$F | iPr |
| 14-51 | CH$_3$ | CH$_2$CMe$_2$F | CH$_2$CH$_2$CMe$_3$ | CH$_2$CMe$_2$F | CH$_2$CH$_2$CMe$_3$ |
| 14-52 | CH$_3$ | CH$_2$CMe$_2$F | CH$_2$CH$_2$—iPr | CH$_2$CMe$_2$F | CH$_2$CH$_2$—iPr |
| 14-53 | CH$_3$ | CH$_2$-p-pyridyl | CH$_2$—iPr | CH$_2$-p-pyridyl | CH$_2$—iPr |
| 14-54 | CH$_3$ | CH$_2$-p-pyridyl | CH$_2$—tBu | CH$_2$-p-pyridyl | CH$_2$—tBu |

TABLE 15

Compounds of formula (I), wherein Cy¹ and Cy² are

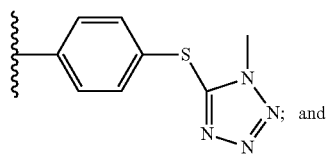

; and

R$^a$, R$^b$, R$^1$ to R$^4$ are as shown.

| Compound # | R$^a$/R$^b$ | R$^1$ | R | R$^3$ | R$^4$ |
|---|---|---|---|---|---|
| 15-1 | CH$_3$ | CH$_2$—tBu | CH$_2$—tBu | CH$_2$—tBu | CH$_2$—tBu |
| 15-2 | CH$_3$ | CH$_2$—tBu | CH$_2$—iPr | CH$_2$—iPr | CH$_2$—iPr |
| 15-3 | CH$_3$ | CH$_2$—iPr | CH$_2$—tBu | CH$_2$—iPr | CH$_2$—iPr |
| 15-4 | CH$_3$ | CH$_2$—iPr | CH$_2$—iPr | CH$_2$—tBu | CH$_2$—iPr |
| 15-5 | CH$_3$ | CH$_2$—iPr | CH$_2$—iPr | CH$_2$—iPr | CH$_2$—tBu |
| 15-6 | CH$_3$ | CH$_2$—iPr | CH$_2$—tBu | CH$_2$—iPr | CH$_2$—tBu |
| 15-7 | CH$_3$ | CH$_2$—tBu | CH$_2$—iPr | CH$_2$—tBu | CH$_2$—iPr |
| 15-8 | CH$_3$ | CH$_2$—iPr | CH$_2$—tBu | CH$_2$—tBu | CH$_2$—iPr |
| 15-9 | CH$_3$ | CH$_2$—tBu | CH$_2$—iPr | CH$_2$—iPr | CH$_2$—tBu |
| 15-10 | CH$_3$ | CH$_2$—iPr | CH$_2$—tBu | CH$_2$—tBu | CH$_2$—tBu |
| 15-11 | CH$_3$ | CH$_2$—tBu | CH$_2$—iPr | CH$_2$—tBu | CH$_2$—tBu |
| 15-12 | CH$_3$ | CH$_2$—tBu | CH$_2$—tBu | CH$_2$—iPr | CH$_2$—tBu |
| 15-13 | CH$_3$ | CH$_2$—tBu | CH$_2$—tBu | CH$_2$—tBu | CH$_2$—iPr |
| 15-14 | CH$_3$ | CH$_2$CMe$_2$F | CH$_2$—iPr | CH$_2$—iPr | CH$_2$—iPr |
| 15-15 | CH$_3$ | CH$_2$—iPr | CH$_2$CMe$_2$F | CH$_2$—iPr | CH$_2$—iPr |
| 15-16 | CH$_3$ | CH$_2$—iPr | CH$_2$—iPr | CH$_2$CMe$_2$F | CH$_2$—iPr |
| 15-17 | CH$_3$ | CH$_2$—iPr | CH$_2$—iPr | CH$_2$—iPr | CH$_2$CMe$_2$F |
| 15-18 | CH$_3$ | CH$_2$CMe$_2$F | CH$_2$—iPr | CH$_2$CMe$_2$F | CH$_2$—iPr |

TABLE 15-continued

Compounds of formula (I), wherein $Cy^1$ and $Cy^2$ are

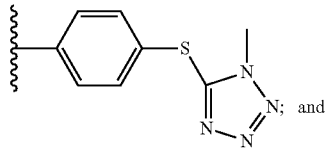

$R^a$, $R^b$, $R^1$ to $R^4$ are as shown.

| Compound # | $R^a/R^b$ | $R^1$ | R | $R^3$ | $R^4$ |
|---|---|---|---|---|---|
| 15-19 | CH₃ | CH₂—iPr | CH₂CMe₂F | CH₂—iPr | CH₂CMe₂F |
| 15-20 | CH₃ | CH₂—iPr | CH₂CMe₂F | CH₂CMe₂F | CH₂—iPr |
| 15-21 | CH₃ | CH₂CMe₂F | CH₂—iPr | CH₂—iPr | CH₂CMe₂F |
| 15-22 | CH₃ | CH₂—iPr | CH₂CMe₂F | CH₂CMe₂F | CH₂CMe₂F |
| 15-23 | CH₃ | CH₂CMe₂F | CH₂—iPr | CH₂CMe₂F | CH₂CMe₂F |
| 15-24 | CH₃ | CH₂CMe₂F | CH₂CMe₂F | CH₂—iPr | CH₂CMe₂F |
| 15-25 | CH₃ | CH₂CMe₂F | CH₂CMe₂F | CH₂CMe₂F | CH₂—iPr |
| 15-26 | CH₃ | CH₂CMe₂F | CH₂CMe₂F | CH₂CMe₂F | CH₂CMe₂F |
| 15-27 | CH₃ | CH₂—iPr | CH₂—iPr | CH₂—iPr | CH₂—iPr |
| 15-28 | CH₃ | CH₂—tBu | CH₂—tBu | CH₂—iPr | CH₂—iPr |
| 15-29 | CH₃ | CH₂—iPr | CH₂-iPr | CH₂—tBu | CH₂—tBu |
| 15-30 | CH₃ | CH₂CMe₂F | CH₂CMe₂F | CH₂—iPr | CH₂-iPr |
| 15-31 | CH₃ | CH₂—iPr | CH₂—iPr | CH₂CMe₂F | CH₂CMe₂F |
| 15-32 | CH₃ | CH₂CMe₂F | CH₂—tBu | CH₂CMe₂F | CH₂—tBu |
| 15-33 | CH₃ | CH₂CF₂Me | CH₂—iPr | CH₂CF₂Me | CH₂—iPr |
| 15-34 | CH₃ | CH₂CF₃ | CH₂—iPr | CH₂CF₃ | CH₂—iPr |
| 15-35 | CH₃ | CH₂CH(CF₃)₂ | CH₂—iPr | CH₂CH(CF₃)₂ | CH₂—iPr |
| 15-36 | CH₂F | CH₂CMe₂F | CH₂—iPr | CH₂CMe₂F | CH₂—iPr |
| 15-37 | H | CH₂CMe₂F | CH₂—iPr | CH₂CMe₂F | CH₂—iPr |
| 15-38 | Et | CH₂CMe₂F | CH₂—iPr | CH₂CMe₂F | CH₂—iPr |
| 15-39 | CH₂F | CH₂—iPr | CH₂—iPr | CH₂—iPr | CH₂—iPr |
| 15-40 | H | CH₂—iPr | CH₂—iPr | CH₂-iPr | CH₂—iPr |
| 15-41 | Et | CH₂—iPr | CH₂—iPr | CH₂—iPr | CH₂—iPr |
| 15-42 | H | CH₂CMe₂F | CH₂—tBu | CH₂CMe₂F | CH₂—tBu |
| 15-43 | CH₃ | CH₂CMe₂F | iPr | CH₂CMe₂F | iPr |
| 15-44 | CH₃ | CH₂CMe₂F | nPr | CH₂CMe₂F | nPr |
| 15-45 | CH₃ | CH₂CMe₂F | sBu | CH₂CMe₂F | sBu |
| 15-46 | CH₃ | CH₂CMe₂F | tBu | CH₂CMe₂F | tBu |
| 15-47 | CH₃ | CH₂CMe₂F | CH₂-p-biphenyl | CH₂CMe₂F | CH₂-p-biphenyl |
| 15-48 | CH₃ | CH₂CMe₂F | CH₂-p-tBuPh | CH₂CMe₂F | CH₂-p-tBuPh |
| 15-49 | CH₃ | CH₂CMe₂F | CH₃ | CH₂CMe₂F | CH₃ |
| 15-50 | H | CH₂CMe₂F | iPr | CH₂CMe₂F | iPr |
| 15-51 | CH₃ | CH₂CMe₂F | CH₂CH₂CMe₃ | CH₂CMe₂F | CH₂CH₂CMe₃ |
| 15-52 | CH₃ | CH₂CMe₂F | CH₂CH₂—iPr | CH₂CMe₂F | CH₂CH₂—iPr |
| 15-53 | CH₃ | CH₂-p-pyriyl | CH₂—iPr | CH₂-p-pyridyl | CH₂—iPr |
| 15-54 | CH₃ | CH₂-p-pyridyl | CH₂—tBu | CH₂-p-pyridyl | CH₂—tBu |

TABLE 16

Compounds of formula (I), wherein $Cy^1$ and $Cy^2$ are

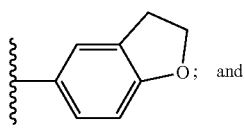

$R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 16-1 | CH₃ | CH₂—tBu | CH₂—tBu | CH₂—tBu | CH₂—tBu |
| 16-2 | CH₃ | CH₂—tBu | CH₂—iPr | CH₂—iPr | CH₂—iPr |
| 16-3 | CH₃ | CH₂—iPr | CH₂—tBu | CH₂—iPr | CH₂—iPr |
| 16-4 | CH₃ | CH₂—iPr | CH₂—iPr | CH₂—tBu | CH₂—iPr |
| 16-5 | CH₃ | CH₂—iPr | CH₂—iPr | CH₂—iPr | CH₂—tBu |
| 16-6 | CH₃ | CH₂—iPr | CH₂—tBu | CH₂—iPr | CH₂—tBu |
| 16-7 | CH₃ | CH₂—tBu | CH₂—iPr | CH₂—tBu | CH₂—iPr |
| 16-8 | CH₃ | CH₂—iPr | CH₂—tBu | CH₂—tBu | CH₂—iPr |
| 16-9 | CH₃ | CH₂—tBu | CH₂—iPr | CH₂—iPr | CH₂—tBu |
| 16-10 | CH₃ | CH₂—iPr | CH₂—tBu | CH₂—tBu | CH₂—tBu |

TABLE 16-continued

Compounds of formula (I), wherein $Cy^1$ and $Cy^2$ are

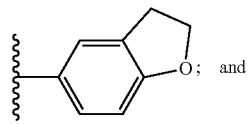

; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 16-11 | $CH_3$ | $CH_2$—tBu | $CH_2$—iPr | $CH_2$—tBu | $CH_2$—tBu |
| 16-12 | $CH_3$ | $CH_2$—tBu | $CH_2$—tBu | $CH_2$—iPr | $CH_2$—tBu |
| 16-13 | $CH_3$ | $CH_2$—tBu | $CH_2$—tBu | $CH_2$—tBu | $CH_2$—iPr |
| 16-14 | $CH_3$ | $CH_2CMe_2F$ | $CH_2$—iPr | $CH_2$—iPr | $CH_2$—iPr |
| 16-15 | $CH_3$ | $CH_2$—iPr | $CH_2CMe_2F$ | $CH_2$—iPr | $CH_2$—iPr |
| 16-16 | $CH_3$ | $CH_2$—iPr | $CH_2$—iPr | $CH_2CMe_2F$ | $CH_2$—iPr |
| 16-17 | $CH_3$ | $CH_2$—iPr | $CH_2$—iPr | $CH_2$—iPr | $CH_2CMe_2F$ |
| 16-18 | $CH_3$ | $CH_2CMe_2F$ | $CH_2$—iPr | $CH_2CMe_2F$ | $CH_2$—iPr |
| 16-19 | $CH_3$ | $CH_2$—iPr | $CH_2CMe_2F$ | $CH_2$—iPr | $CH_2CMe_2F$ |
| 16-20 | $CH_3$ | $CH_2$—iPr | $CH_2CMe_2F$ | $CH_2CMe_2F$ | $CH_2$—iPr |
| 16-21 | $CH_3$ | $CH_2CMe_2F$ | $CH_2$—iPr | $CH_2$—iPr | $CH_2CMe_2F$ |
| 16-22 | $CH_3$ | $CH_2$—iPr | $CH_2CMe_2F$ | $CH_2CMe_2F$ | $CH_2CMe_2F$ |
| 16-23 | $CH_3$ | $CH_2CMe_2F$ | $CH_2$—iPr | $CH_2CMe_2F$ | $CH_2CMe_2F$ |
| 16-24 | $CH_3$ | $CH_2CMe_2F$ | $CH_2CMe_2F$ | $CH_2$—iPr | $CH_2CMe_2F$ |
| 16-25 | $CH_3$ | $CH_2CMe_2F$ | $CH_2CMe_2F$ | $CH_2CMe_2F$ | $CH_2$—iPr |
| 16-26 | $CH_3$ | $CH_2CMe_2F$ | $CH_2CMe_2F$ | $CH_2CMe_2F$ | $CH_2CMe_2F$ |
| 16-27 | $CH_3$ | $CH_2$—iPr | $CH_2$—iPr | $CH_2$—iPr | $CH_2$—iPr |
| 16-28 | $CH_3$ | $CH_2$—tBu | $CH_2$—tBu | $CH_2$—iPr | $CH_2$—iPr |
| 16-29 | $CH_3$ | $CH_2$—iPr | $CH_2$—iPr | $CH_2$—tBu | $CH_2$—tBu |
| 16-30 | $CH_3$ | $CH_2CMe_2F$ | $CH_2CMe_2F$ | $CH_2$—iPr | $CH_2$—iPr |
| 16-31 | $CH_3$ | $CH_2$—iPr | $CH_2$—iPr | $CH_2CMe_2F$ | $CH_2CMe_2F$ |
| 16-32 | $CH_3$ | $CH_2CMe_2F$ | $CH_2$—tBu | $CH_2CMe_2F$ | $CH_2$—tBu |
| 16-33 | $CH_3$ | $CH_2CF_2Me$ | $CH_2$—iPr | $CH_2CF_2Me$ | $CH_2$—iPr |
| 16-34 | $CH_3$ | $CH_2CF_3$ | $CH_2$—iPr | $CH_2CF_3$ | $CH_2$—iPr |
| 16-35 | $CH_3$ | $CH_2CH(CF_3)_2$ | $CH_2$—iPr | $CH_2CH(CF_3)_2$ | $CH_2$—iPr |
| 16-36 | $CH_2F$ | $CH_2CMe_2F$ | $CH_2$—iPr | $CH_2CMe_2F$ | $CH_2$—iPr |
| 16-37 | H | $CH_2CMe_2F$ | $CH_2$—iPr | $CH_2CMe_2F$ | $CH_2$—iPr |
| 16-38 | Et | $CH_2CMe_2F$ | $CH_2$—iPr | $CH_2CMe_2F$ | $CH_2$—iPr |
| 16-39 | $CH_2F$ | $CH_2$—iPr | $CH_2$—iPr | $CH_2$—iPr | $CH_2$—iPr |
| 16-40 | H | $CH_2$—iPr | $CH_2$—iPr | $CH_2$—iPr | $CH_2$—iPr |
| 16-41 | Et | $CH_2$—iPr | $CH_2$—iPr | $CH_2$—iPr | $CH_2$—iPr |
| 16-42 | H | $CH_2CMe_2F$ | $CH_2$—tBu | $CH_2CMe_2F$ | $CH_2$—tBu |
| 16-43 | $CH_3$ | $CH_2CMe_2F$ | iPr | $CH_2CMe_2F$ | iPr |
| 16-44 | $CH_3$ | $CH_2CMe_2F$ | nPr | $CH_2CMe_2F$ | nPr |
| 16-45 | $CH_3$ | $CH_2CMe_2F$ | sBu | $CH_2CMe_2F$ | sBu |
| 16-46 | $CH_3$ | $CH_2CMe_2F$ | tBu | $CH_2CMe_2F$ | tBu |
| 16-47 | $CH_3$ | $CH_2CMe_2F$ | $CH_2$-p-biphenyl | $CH_2CMe_2F$ | $CH_2$-p-biphenyl |
| 16-48 | $CH_3$ | $CH_2CMe_2F$ | $CH_2$-p-tBuPh | $CH_2CMe_2F$ | $CH_2$-p-tBuPh |
| 16-49 | $CH_3$ | $CH_2CMe_2F$ | $CH_3$ | $CH_2CMe_2F$ | $CH_3$ |
| 16-50 | H | $CH_2CMe_2F$ | iPr | $CH_2CMe_2F$ | iPr |
| 16-51 | $CH_3$ | $CH_2CMe_2F$ | $CH_2CH_2CMe_3$ | $CH_2CMe_2F$ | $CH_2CH_2CMe_3$ |
| 16-52 | $CH_3$ | $CH_2CMe_2F$ | $CH_2CH_2$—iPr | $CH_2CMe_2F$ | $CH_2CH_2$—iPr |
| 16-53 | $CH_3$ | $CH_2$-p-pyridyl | $CH_2$—iPr | $CH_2$-p-pyridyl | $CH_2$—iPr |
| 16-54 | $CH_3$ | $CH_2$-p-pyridyl | $CH_2$—tBu | $CH_2$-p-pyridyl | $CH_2$—tBu |

TABLE 17

Compounds of formula (I), wherein $Cy^1$ and $Cy^2$ are

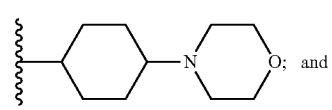

; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 17-1 | $CH_3$ | $CH_2$—tBu | $CH_2$—tBu | $CH_2$—tBu | $CH_2$—tBu |
| 17-2 | $CH_3$ | $CH_2$—tBu | $CH_2$—iPr | $CH_2$—iPr | $CH_2$—iPr |
| 17-3 | $CH_3$ | $CH_2$—iPr | $CH_2$—tBu | $CH_2$—iPr | $CH_2$—iPr |
| 17-4 | $CH_3$ | $CH_2$—iPr | $CH_2$—iPr | $CH_2$—tBu | $CH_2$—iPr |

TABLE 17-continued

Compounds of formula (I), wherein $Cy^1$ and $Cy^2$ are

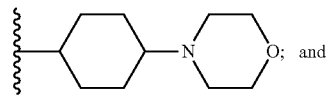 ; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 17-5 | CH$_3$ | CH$_2$—iPr | CH$_2$—iPr | CH$_2$—iPr | CH$_2$—tBu |
| 17-6 | CH$_3$ | CH$_2$—iPr | CH$_2$—tBu | CH$_2$—iPr | CH$_2$—tBu |
| 17-7 | CH$_3$ | CH$_2$—tBu | CH$_2$—iPr | CH$_2$—tBu | CH$_2$—iPr |
| 17-8 | CH$_3$ | CH$_2$—iPr | CH$_2$—tBu | CH$_2$—tBu | CH$_2$—iPr |
| 17-9 | CH$_3$ | CH$_2$—tBu | CH$_2$—iPr | CH$_2$—iPr | CH$_2$—tBu |
| 17-10 | CH$_3$ | CH$_2$—iPr | CH$_2$—tBu | CH$_2$—tBu | CH$_2$—tBu |
| 17-11 | CH$_3$ | CH$_2$—tBu | CH$_2$—iPr | CH$_2$—tBu | CH$_2$—tBu |
| 17-12 | CH$_3$ | CH$_2$—tBu | CH$_2$—tBu | CH$_2$—iPr | CH$_2$—tBu |
| 17-13 | CH$_3$ | CH$_2$—tBu | CH$_2$—tBu | CH$_2$—tBu | CH$_2$—iPr |
| 17-14 | CH$_3$ | CH$_2$CMe$_2$F | CH$_2$—iPr | CH$_2$—iPr | CH$_2$—iPr |
| 17-15 | CH$_3$ | CH$_2$—iPr | CH$_2$CMe$_2$F | CH$_2$—iPr | CH$_2$—iPr |
| 17-16 | CH$_3$ | CH$_2$—iPr | CH$_2$—iPr | CH$_2$CMe$_2$F | CH$_2$—iPr |
| 17-17 | CH$_3$ | CH$_2$—iPr | CH$_2$—iPr | CH$_2$—iPr | CH$_2$CMe$_2$F |
| 17-18 | CH$_3$ | CH$_2$CMe$_2$F | CH$_2$—iPr | CH$_2$CMe$_2$F | CH$_2$—iPr |
| 17-19 | CH$_3$ | CH$_2$—iPr | CH$_2$CMe$_2$F | CH$_2$—iPr | CH$_2$CMe$_2$F |
| 17-20 | CH$_3$ | CH$_2$—iPr | CH$_2$CMe$_2$F | CH$_2$CMe$_2$F | CH$_2$—iPr |
| 17-21 | CH$_3$ | CH$_2$CMe$_2$F | CH$_2$—iPr | CH$_2$—iPr | CH$_2$CMe$_2$F |
| 17-22 | CH$_3$ | CH$_2$—iPr | CH$_2$CMe$_2$F | CH$_2$CMe$_2$F | CH$_2$CMe$_2$F |
| 17-23 | CH$_3$ | CH$_2$CMe$_2$F | CH$_2$—iPr | CH$_2$CMe$_2$F | CH$_2$CMe$_2$F |
| 17-24 | CH$_3$ | CH$_2$CMe$_2$F | CH$_2$CMe$_2$F | CH$_2$—iPr | CH$_2$CMe$_2$F |
| 17-25 | CH$_3$ | CH$_2$CMe$_2$F | CH$_2$CMe$_2$F | CH$_2$CMe$_2$F | CH$_2$—iPr |
| 17-26 | CH$_3$ | CH$_2$CMe$_2$F | CH$_2$CMe$_2$F | CH$_2$CMe$_2$F | CH$_2$CMe$_2$F |
| 17-27 | CH$_3$ | CH$_2$—iPr | CH$_2$—iPr | CH$_2$—iPr | CH$_2$—iPr |
| 17-28 | CH$_3$ | CH$_2$—tBu | CH$_2$—tBu | CH$_2$—iPr | CH$_2$—iPr |
| 17-29 | CH$_3$ | CH$_2$—iPr | CH$_2$—iPr | CH$_2$—tBu | CH$_2$—tBu |
| 17-30 | CH$_3$ | CH$_2$CMe$_2$F | CH$_2$CMe$_2$F | CH$_2$—iPr | CH$_2$—iPr |
| 17-31 | CH$_3$ | CH$_2$—iPr | CH$_2$—iPr | CH$_2$CMe$_2$F | CH$_2$CMe$_2$F |
| 17-32 | CH$_3$ | CH$_2$CMe$_2$F | CH$_2$—tBu | CH$_2$CMe$_2$F | CH$_2$—tBu |
| 17-33 | CH$_3$ | CH$_2$CF$_2$Me | CH$_2$—iPr | CH$_2$CF$_2$Me | CH$_2$—iPr |
| 17-34 | CH$_3$ | CH$_2$CF$_3$ | CH$_2$—iPr | CH$_2$CF$_3$ | CH$_2$—iPr |
| 17-35 | CH$_3$ | CH$_2$CH(CF$_3$)$_2$ | CH$_2$—iPr | CH$_2$CH(CF$_3$)$_2$ | CH$_2$—iPr |
| 17-36 | CH$_2$F | CH$_2$CMe$_2$F | CH$_2$—iPr | CH$_2$CMe$_2$F | CH$_2$—iPr |
| 17-37 | H | CH$_2$CMe$_2$F | CH$_2$—iPr | CH$_2$CMe$_2$F | CH$_2$—iPr |
| 17-38 | Et | CH$_2$CMe$_2$F | CH$_2$—iPr | CH$_2$CMe$_2$F | CH$_2$—iPr |
| 17-39 | CH$_2$F | CH$_2$—iPr | CH$_2$—iPr | CH$_2$—iPr | CH$_2$—iPr |
| 17-40 | H | CH$_2$—iPr | CH$_2$—iPr | CH$_2$—iPr | CH$_2$—iPr |
| 17-41 | Et | CH$_2$—iPr | CH$_2$—iPr | CH$_2$—iPr | CH$_2$—iPr |
| 17-42 | H | CH$_2$CMe$_2$F | CH$_2$—tBu | CH$_2$CMe$_2$F | CH$_2$—tBu |
| 17-43 | CH$_3$ | CH$_2$CMe$_2$F | iPr | CH$_2$CMe$_2$F | iPr |
| 17-44 | CH$_3$ | CH$_2$CMe$_2$F | nPr | CH$_2$CMe$_2$F | nPr |
| 17-45 | CH$_3$ | CH$_2$CMe$_2$F | sBu | CH$_2$CMe$_2$F | sBu |
| 17-46 | CH$_3$ | CH$_2$CMe$_2$F | tBu | CH$_2$CMe$_2$F | tBu |
| 17-47 | CH$_3$ | CH$_2$CMe$_2$F | CH$_2$-p-biphenyl | CH$_2$CMe$_2$F | CH$_2$-p-biphenyl |
| 17-48 | CH$_3$ | CH$_2$CMe$_2$F | CH$_2$-p-tBuPh | CH$_2$CMe$_2$F | CH$_2$-p-tBuPh |
| 17-49 | CH$_3$ | CH$_2$CMe$_2$F | CH$_3$ | CH$_2$CMe$_2$F | CH$_3$ |
| 17-50 | H | CH$_2$CMe$_2$F | iPr | CH$_2$CMe$_2$F | iPr |
| 17-51 | CH$_3$ | CH$_2$CMe$_2$F | CH$_2$CH$_2$CMe$_3$ | CH$_2$CMe$_2$F | CH$_2$CH$_2$CMe$_3$ |
| 17-52 | CH$_3$ | CH$_2$CMe$_2$F | CH$_2$CH$_2$—iPr | CH$_2$CMe$_2$F | CH$_2$CH$_2$—iPr |
| 17-53 | CH$_3$ | CH$_2$-p-pyridyl | CH$_2$—iPr | CH$_2$-p-pyridyl | CH$_2$—iPr |
| 17-54 | CH$_3$ | CH$_2$-p-pyridyl | CH$_2$—tBu | CH$_2$-p-pyridyl | CH$_2$—tBu |

TABLE 18

Compounds of formula (I), wherein Cy¹ and Cy² are

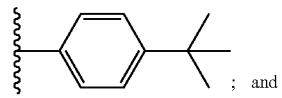 ; and

Rᵃ, Rᵇ, R¹ to R⁴ are as shown.

| Compound # | Rᵃ/Rᵇ | R¹ | R² | R³ | R⁴ |
|---|---|---|---|---|---|
| 18-1 | CH₃ | CH₂—tBu | CH₂—tBu | CH₂—tBu | CH₂—tBu |
| 18-2 | CH₃ | CH₂—tBu | CH₂—iPr | CH₂—iPr | CH₂—iPr |
| 18-3 | CH₃ | CH₂—iPr | CH₂—tBu | CH₂—iPr | CH₂—iPr |
| 18-4 | CH₃ | CH₂—iPr | CH₂—iPr | CH₂—tBu | CH₂—iPr |
| 18-5 | CH₃ | CH₂—iPr | CH₂—iPr | CH₂—iPr | CH₂—tBu |
| 18-6 | CH₃ | CH₂—iPr | CH₂—tBu | CH₂—iPr | CH₂—tBu |
| 18-7 | CH₃ | CH₂—tBu | CH₂—iPr | CH₂—tBu | CH₂—iPr |
| 18-8 | CH₃ | CH₂—iPr | CH₂—tBu | CH₂—tBu | CH₂—iPr |
| 18-9 | CH₃ | CH₂—tBu | CH₂—iPr | CH₂—iPr | CH₂—tBu |
| 18-10 | CH₃ | CH₂—iPr | CH₂—tBu | CH₂—tBu | CH₂—tBu |
| 18-11 | CH₃ | CH₂—tBu | CH₂—iPr | CH₂—tBu | CH₂—tBu |
| 18-12 | CH₃ | CH₂—tBu | CH₂—tBu | CH₂—iPr | CH₂—tBu |
| 18-13 | CH₃ | CH₂—tBu | CH₂—tBu | CH₂—tBu | CH₂—tBu |
| 18-14 | CH₃ | CH₂CMe₂F | CH₂—iPr | CH₂—iPr | CH₂—iPr |
| 18-15 | CH₃ | CH₂—iPr | CH₂CMe₂F | CH₂—iPr | CH₂—iPr |
| 18-16 | CH₃ | CH₂—iPr | CH₂—iPr | CH₂CMe₂F | CH₂—iPr |
| 18-17 | CH₃ | CH₂—iPr | CH₂—iPr | CH₂—iPr | CH₂CMe₂F |
| 18-18 | CH₃ | CH₂CMe₂F | CH₂—iPr | CH₂CMe₂F | CH₂—iPr |
| 18-19 | CH₃ | CH₂—iPr | CH₂CMe₂F | CH₂—iPr | CH₂CMe₂F |
| 18-20 | CH₃ | CH₂—iPr | CH₂CMe₂F | CH₂CMe₂F | CH₂—iPr |
| 18-21 | CH₃ | CH₂CMe₂F | CH₂—iPr | CH₂—iPr | CH₂CMe₂F |
| 18-22 | CH₃ | CH₂—iPr | CH₂CMe₂F | CH₂CMe₂F | CH₂CMe₂F |
| 18-23 | CH₃ | CH₂CMe₂F | CH₂—iPr | CH₂CMe₂F | CH₂CMe₂F |
| 18-24 | CH₃ | CH₂CMe₂F | CH₂CMe₂F | CH₂—iPr | CH₂CMe₂F |
| 18-25 | CH₃ | CH₂CMe₂F | CH₂CMe₂F | CH₂CMe₂F | CH₂—iPr |
| 18-26 | CH₃ | CH₂CMe₂F | CH₂CMe₂F | CH₂CMe₂F | CH₂CMe₂F |
| 18-27 | CH₃ | CH₂—iPr | CH₂—iPr | CH₂—iPr | CH₂—iPr |
| 18-28 | CH₃ | CH₂—tBu | CH₂—tBu | CH₂—iPr | CH₂—iPr |
| 18-29 | CH₃ | CH₂—iPr | CH₂—iPr | CH₂—tBu | CH₂—tBu |
| 18-30 | CH₃ | CH₂CMe₂F | CH₂CMe₂F | CH₂—iPr | CH₂—iPr |
| 18-31 | CH₃ | CH₂—iPr | CH₂—iPr | CH₂CMe₂F | CH₂CMe₂F |
| 18-32 | CH₃ | CH₂CMe₂F | CH₂—tBu | CH₂CMe₂F | CH₂—tBu |
| 18-33 | CH₃ | CH₂CF₂Me | CH₂—iPr | CH₂CF₂Me | CH₂—iPr |
| 18-34 | CH₃ | CH₂CF₃ | CH₂—iPr | CH₂CF₃ | CH₂—iPr |
| 18-35 | CH₃ | CH₂CH(CF₃)₂ | CH₂—iPr | CH₂CH(CF₃)₂ | CH₂—iPr |
| 18-36 | CH₂F | CH₂CMe₂F | CH₂—iPr | CH₂CMe₂F | CH₂—iPr |
| 18-37 | H | CH₂CMe₂F | CH₂—iPr | CH₂CMe₂F | CH₂—iPr |
| 18-38 | Et | CH₂CMe₂F | CH₂—iPr | CH₂CMe₂F | CH₂—iPr |
| 18-39 | CH₂F | CH₂—iPr | CH₂—iPr | CH₂—iPr | CH₂—iPr |
| 18-40 | H | CH₂—iPr | CH₂—iPr | CH₂—iPr | CH₂—iPr |
| 18-41 | Et | CH₂—iPr | CH₂—iPr | CH₂—iPr | CH₂—iPr |
| 18-42 | H | CH₂CMe₂F | CH₂—tBu | CH₂CMe₂F | CH₂—tBu |
| 18-43 | CH₃ | CH₂CMe₂F | iPr | CH₂CMe₂F | iPr |
| 18-44 | CH₃ | CH₂CMe₂F | nPr | CH₂CMe₂F | nPr |
| 18-45 | CH₃ | CH₂CMe₂F | sBu | CH₂CMe₂F | sBu |
| 18-46 | CH₃ | CH₂CMe₂F | tBu | CH₂CMe₂F | tBu |
| 18-47 | CH₃ | CH₂CMe₂F | CH₂-p-biphenyl | CH₂CMe₂F | CH₂-p-biphenyl |
| 18-48 | CH₃ | CH₂CMe₂F | CH₂-p-tBuPh | CH₂CMe₂F | CH₂-p-tBuPh |
| 18-49 | CH₃ | CH₂CMe₂F | CH₃ | CH₂CMe₂F | CH₃ |
| 18-50 | H | CH₂CMe₂F | iPr | CH₂CMe₂F | iPr |
| 18-51 | CH₃ | CH₂CMe₂F | CH₂CH₂CMe₃ | CH₂CMe₂F | CH₂CH₂CMe₃ |
| 18-52 | CH₃ | CH₂CMe₂F | CH₂CH₂—iPr | CH₂CMe₂F | CH₂CH₂—iPr |
| 18-53 | CH₃ | CH₃-p-pyridyl | CH₂—iPr | CH₂-p-pyridyl | CH₂—iPr |
| 18-54 | CH₃ | CH₂-p-pyridyl | CH₂—tBu | CH₂-p-pyridyl | CH₂—tBu |

TABLE 19

Compounds of formula (I), wherein Cy¹ and Cy² are

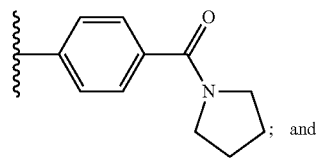; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 19-1 | CH₃ | CH₂—tBu | CH₂—tBu | CH₂—tBu | CH₂—tBu |
| 19-2 | CH₃ | CH₂—tBu | CH₂—iPr | CH₂—iPr | CH₂—iPr |
| 19-3 | CH₃ | CH₂—iPr | CH₂—tBu | CH₂—iPr | CH₂—iPr |
| 19-4 | CH₃ | CH₂—iPr | CH₂—iPr | CH₂—tBu | CH₂—iPr |
| 19-5 | CH₃ | CH₂—iPr | CH₂—iPr | CH₂—iPr | CH₂—tBu |
| 19-6 | CH₃ | CH₂—iPr | CH₂—tBu | CH₂—iPr | CH₂—tBu |
| 19-7 | CH₃ | CH₂—tBu | CH₂—iPr | CH₂—tBu | CH₂—iPr |
| 19-8 | CH₃ | CH₂—iPr | CH₂—tBu | CH₂—tBu | CH₂—iPr |
| 19-9 | CH₃ | CH₂—tBu | CH₂—iPr | CH₂—iPr | CH₂—tBu |
| 19-10 | CH₃ | CH₂—iPr | CH₂—tBu | CH₂—tBu | CH₂—tBu |
| 19-11 | CH₃ | CH₂—tBu | CH₂—iPr | CH₂—tBu | CH₂—tBu |
| 19-12 | CH₃ | CH₂—tBu | CH₂—tBu | CH₂—iPr | CH₂—tBu |
| 19-13 | CH₃ | CH₂—tBu | CH₂—tBu | CH₂—tBu | CH₂—iPr |
| 19-14 | CH₃ | CH₂CMe₂F | CH₂—iPr | CH₂—iPr | CH₂—iPr |
| 19-15 | CH₃ | CH₂—iPr | CH₂CMe₂F | CH₂—iPr | CH₂—iPr |
| 19-16 | CH₃ | CH₂—iPr | CH₂—iPr | CH₂CMe₂F | CH₂—iPr |
| 19-17 | CH₃ | CH₂—iPr | CH₂—iPr | CH₂—iPr | CH₂CMe₂F |
| 19-18 | CH₃ | CH₂CMe₂F | CH₂—iPr | CH₂CMe₂F | CH₂—iPr |
| 19-19 | CH₃ | CH₂—iPr | CH₂CMe₂F | CH₂—iPr | CH₂CMe₂F |
| 19-20 | CH₃ | CH₂—iPr | CH₂CMe₂F | CH₂CMe₂F | CH₂—iPr |
| 19-21 | CH₃ | CH₂CMe₂F | CH₂—iPr | CH₂—iPr | CH₂CMe₂F |
| 19-22 | CH₃ | CH₂—iPr | CH₂CMe₂F | CH₂CMe₂F | CH₂CMe₂F |
| 19-23 | CH₃ | CH₂CMe₂F | CH₂—iPr | CH₂CMe₂F | CH₂CMe₂F |
| 19-24 | CH₃ | CH₂CMe₂F | CH₂CMe₂F | CH₂—iPr | CH₂CMe₂F |
| 19-25 | CH₃ | CH₂CMe₂F | CH₂CMe₂F | CH₂CMe₂F | CH₂—iPr |
| 19-26 | CH₃ | CH₂CMe₂F | CH₂CMe₂F | CH₂CMe₂F | CH₂CMe₂F |
| 19-27 | CH₃ | CH₂—iPr | CH₂—iPr | CH₂—iPr | CH₂—iPr |
| 19-28 | CH₃ | CH₂—tBu | CH₂—tBu | CH₂—iPr | CH₂—iPr |
| 19-29 | CH₃ | CH₂—iPr | CH₂—iPr | CH₂—tBu | CH₂—tBu |
| 19-30 | CH₃ | CH₂CMe₂F | CH₂CMe₂F | CH₂—iPr | CH₂—iPr |
| 19-31 | CH₃ | CH₂—iPr | CH₂—iPr | CH₂CMe₂F | CH₂CMe₂F |
| 19-32 | CH₃ | CH₂CMe₂F | CH₂—tBu | CH₂CMe₂F | CH₂—tBu |
| 19-33 | CH₃ | CH₂CF₂Me | CH₂—iPr | CH₂CF₂Me | CH₂—iPr |
| 19-34 | CH₃ | CH₂CF₃ | CH₂—iPr | CH₂CF₃ | CH₂—iPr |
| 19-35 | CH₃ | CH₂CH(CF₃)₂ | CH₂—iPr | CH₂CH(CF₃)₂ | CH₂—iPr |
| 19-36 | CH₂F | CH₂CMe₂F | CH₂—iPr | CH₂CMe₂F | CH₂—iPr |
| 19-37 | H | CH₂CMe₂F | CH₂—iPr | CH₂CMe₂F | CH₂—iPr |
| 19-38 | Et | CH₂CMe₂F | CH₂—iPr | CH₂CMe₂F | CH₂—iPr |
| 19-39 | CH₂F | CH₂—iPr | CH₂—iPr | CH₂—iPr | CH₂—iPr |
| 19-40 | H | CH₂—iPr | CH₂—iPr | CH₂—iPr | CH₂—iPr |
| 19-41 | Et | CH₂—iPr | CH₂—iPr | CH₂—iPr | CH₂—iPr |
| 19-42 | H | CH₂CMe₂F | CH₂—tBu | CH₂CMe₂F | CH₂—tBu |
| 19-43 | CH₃ | CH₂CMe₂F | iPr | CH₂CMe₂F | iPr |
| 19-44 | CH₃ | CH₂CMe₂F | nPr | CH₂CMe₂F | nPr |
| 19-45 | CH₃ | CH₂CMe₂F | sBu | CH₂CMe₂F | sBu |
| 19-46 | CH₃ | CH₂CMe₂F | tBu | CH₂CMe₂F | tBu |
| 19-47 | CH₃ | CH₂CMe₂F | CH₂-p-biphenyl | CH₂CMe₂F | CH₂-p-biphenyl |
| 19-48 | CH₃ | CH₂CMe₂F | CH₂-p-tBuPh | CH₂CMe₂F | CH₂-p-tBuPh |
| 19-49 | CH₃ | CH₂CMe₂F | CH₃ | CH₂CMe₂F | CH₃ |
| 19-50 | H | CH₂CMe₂F | iPr | CH₂CMe₂F | iPr |
| 19-51 | CH₃ | CH₂CMe₂F | CH₂CH₂CMe₃ | CH₂Me₂F | CH₂CH₂CMe₃ |
| 19-52 | CH₃ | CH₂CMe₂F | CH₂CH₂—iPr | CH₂CMe₂F | CH₂CH₂—iPr |
| 19-53 | CH₃ | CH₂-p-pyridyl | CH₂—iPr | CH₂-p-pyridyl | CH₂—iPr |
| 19-54 | CH₃ | CH₂-p-pyridyl | CH₂—tBu | CH₂-p-pyridyl | CH₂—tBu |

TABLE 20

Compounds of formula (I), wherein $Cy^1$ and $Cy^2$ are 3,4,5-trifluorophenyl; and $R^a$, $R^b$, $R^1$ to $R^4$ are as shown.

| Compound # | $R^a/R^b$ | $R^1$ | $R^2$ | $R^3$ | $R^4$ |
| --- | --- | --- | --- | --- | --- |
| 20-1 | CH₃ | CH₂—tBu | CH₂—tBu | CH₂—tBu | CH₂—tBu |
| 20-2 | CH₃ | CH₂—tBu | CH₂—iPr | CH₂—iPr | CH₂—iPr |
| 20-3 | CH₃ | CH₂—tBu | CH₂—tBu | CH₂—iPr | CH₂—iPr |
| 20-4 | CH₃ | CH₂—iPr | CH₂—iPr | CH₂—tBu | CH₂—iPr |
| 20-5 | CH₃ | CH₂—iPr | CH₂—iPr | CH₂—iPr | CH₂—tBu |
| 20-6 | CH₃ | CH₂—iPr | CH₂—tBu | CH₂—iPr | CH₂—tBu |
| 20-7 | CH₃ | CH₂—tBu | CH₂—iPr | CH₂—tBu | CH₂—iPr |
| 20-8 | CH₃ | CH₂—iPr | CH₂—tBu | CH₂—tBu | CH₂—iPr |
| 20-9 | CH₃ | CH₂—tBu | CH₂—iPr | CH₂—iPr | CH₂—tBu |
| 20-10 | CH₃ | CH₂—iPr | CH₂—tBu | CH₂—tBu | CH₂—tBu |
| 20-11 | CH₃ | CH₂—tBu | CH₂—iPr | CH₂—tBu | CH₂—tBu |
| 20-12 | CH₃ | CH₂—tBu | CH₂—tBu | CH₂—iPr | CH₂—tBu |
| 20-13 | CH₃ | CH₂—tBu | CH₂—tBu | CH₂—tBu | CH₂—iPr |
| 20-14 | CH₃ | CH₂CMe₂F | CH₂—iPr | CH₂—iPr | CH₂—iPr |
| 20-15 | CH₃ | CH₂—iPr | CH₂CMe₂F | CH₂—iPr | CH₂—iPr |
| 20-16 | CH₃ | CH₂—iPr | CH₂—iPr | CH₂CMe₂F | CH₂—iPr |
| 20-17 | CH₃ | CH₂—iPr | CH₂—iPr | CH₂—iPr | CH₂CMe₂F |
| 20-18 | CH₃ | CH₂CMe₂F | CH₂—iPr | CH₂CMe₂F | CH₂—iPr |
| 20-19 | CH₃ | CH₂—iPr | CH₂CMe₂F | CH₂—iPr | CH₂CMe₂F |
| 20-20 | CH₃ | CH₂—iPr | CH₂CMe₂F | CH₂CMe₂F | CH₂—iPr |
| 20-21 | CH₃ | CH₂CMe₂F | CH₂—iPr | CH₂—iPr | CH₂CMe₂F |
| 20-22 | CH₃ | CH₂—iPr | CH₂CMe₂F | CH₂CMe₂F | CH₂CMe₂F |
| 20-23 | CH₃ | CH₂CMe₂F | CH₂—iPr | CH₂CMe₂F | CH₂CMe₂F |
| 20-24 | CH₃ | CH₂CMe₂F | CH₂CMe₂F | CH₂—iPr | CH₂CMe₂F |
| 20-25 | CH₃ | CH₂CMe₂F | CH₂CMe₂F | CH₂CMe₂F | CH₂—iPr |
| 20-26 | CH₃ | CH₂CMe₂F | CH₂CMe₂F | CH₂CMe₂F | CH₂CMe₂F |
| 20-27 | CH₃ | CH₂—iPr | CH₂—iPr | CH₂—iPr | CH₂—iPr |
| 20-28 | CH₃ | CH₂—tBu | CH₂—tBu | CH₂—iPr | CH₂—iPr |
| 20-29 | CH₃ | CH₂—iPr | CH₂—iPr | CH₂—tBu | CH₂—tBu |
| 20-30 | CH₃ | CH₂CMe₂F | CH₂CMe₂F | CH₂—iPr | CH₂—iPr |
| 20-31 | CH₃ | CH₂—iPr | CH₂—iPr | CH₂CMe₂F | CH₂CMe₂F |
| 20-32 | CH₃ | CH₂CMe₂F | CH₂—tBu | CH₂CMe₂F | CH₂—tBu |
| 20-33 | CH₃ | CH₂CF₂Me | CH₂—iPr | CH₂CF₂Me | CH₂—iPr |
| 20-34 | CH₃ | CH₂CF₃ | CH₂—iPr | CH₂CF₃ | CH₂—iPr |
| 20-35 | CH₃ | CH₂CH(CF₃)₂ | CH₂—iPr | CH₂CH(CF₃)₂ | CH₂—iPr |
| 20-36 | CH₂F | CH₂CMe₂F | CH₂—iPr | CH₂CMe₂F | CH₂—iPr |
| 20-37 | H | CH₂CMe₂F | CH₂—iPr | CH₂CMe₂F | CH₂—iPr |
| 20-38 | Et | CH₂CMe₂F | CH₂—iPr | CH₂CMe₂F | CH₂—iPr |
| 20-39 | CH₂F | CH₂—iPr | CH₂—iPr | CH₂—iPr | CH₂—iPr |
| 20-40 | H | CH₂—iPr | CH₂—iPr | CH₂—iPr | CH₂—iPr |
| 20-41 | Et | CH₂—iPr | CH₂—iPr | CH₂—iPr | CH₂—iPr |
| 20-42 | H | CH₂CMe₂F | CH₂—tBu | CH₂CMe₂F | CH₂—tBu |
| 20-43 | CH₃ | CH₂CMe₂F | iPr | CH₂CMe₂F | iPr |
| 20-44 | CH₃ | CH₂CMe₂F | nPr | CH₂CMe₂F | nPr |
| 20-45 | CH₃ | CH₂CMe₂F | sBu | CH₂CMe₂F | sBu |
| 20-46 | CH₃ | CH₂CMe₂F | tBu | CH₂CMe₂F | tBu |
| 20-47 | CH₃ | CH₂CMe₂F | CH₂-p-biphenyl | CH₂CMe₂F | CH₂-p-biphenyl |
| 20-48 | CH₃ | CH₂CMe₂F | CH₂—p-tBuPh | CH₂CMe₂F | CH₂—p-tBuPh |
| 20-49 | CH₃ | CH₂CMe₂F | CH₃ | CH₂CMe₂F | CH₃ |
| 20-50 | H | CH₂CMe₂F | iPr | CH₂CMe₂F | iPr |
| 20-51 | CH₃ | CH₂CMe₂F | CH₂CH₂CMe₃ | CH₂CMe₂F | CH₂CH₂CMe₃ |
| 20-52 | CH₃ | CH₂CMe₂F | CH₂CH₂—iPr | CH₂CMe₂F | CH₂CH₂—iPr |
| 20-53 | CH₃ | CH₂-p-pyridyl | CH₂—iPr | CH₂-p-pyridyl | CH₂—iPr |
| 20-54 | CH₃ | CH₂-p-pyridyl | CH₂—tBu | CH₂-p-pyridyl | CH₂—tBu |

TABLE 21

Compounds of formula (I), wherein $Cy^1$ and $Cy^2$ are p-aminophenyl; and $R^a$, $R^b$, $R^1$ to $R^4$ are as shown.

| Compound # | $R^a/R^b$ | $R^1$ | $R^2$ | $R^3$ | $R^4$ |
| --- | --- | --- | --- | --- | --- |
| 21-1 | CH₃ | CH₂—tBu | CH₂—tBu | CH₂—tBu | CH₂—tBu |
| 21-2 | CH₃ | CH₂—tBu | CH₂—iPr | CH₂—iPr | CH₂—iPr |
| 21-3 | CH₃ | CH₂—iPr | CH₂—tBu | CH₂—iPr | CH₂—iPr |
| 21-4 | CH₃ | CH₂—iPr | CH₂—iPr | CH₂—tBu | CH₂—iPr |
| 21-5 | CH₃ | CH₂—iPr | CH₂—iPr | CH₂—iPr | CH₂—tBu |
| 21-6 | CH₃ | CH₂—iPr | CH₂—tBu | CH₂—iPr | CH₂—tBu |
| 21-7 | CH₃ | CH₂—tBu | CH₂—iPr | CH₂—tBu | CH₂—iPr |
| 21-8 | CH₃ | CH₂—iPr | CH₂—tBu | CH₂—tBu | CH₂—iPr |
| 21-9 | CH₃ | CH₂—tBu | CH₂—iPr | CH₂—iPr | CH₂—tBu |
| 21-10 | CH₃ | CH₂—iPr | CH₂—tBu | CH₂—tBu | CH₂—tBu |

TABLE 21-continued

Compounds of formula (I), wherein $Cy^1$ and $Cy^2$ are p-aminophenyl; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 21-11 | CH₃ | CH₂—tBu | CH₂—iPr | CH₂—tBu | CH₂—tBu |
| 21-12 | CH₃ | CH₂—tBu | CH₂—tBu | CH₂—iPr | CH₂—tBu |
| 21-13 | CH₃ | CH₂—tBu | CH₂—tBu | CH₂—tBu | CH₂—iPr |
| 21-14 | CH₃ | CH₂CMe₂F | CH₂—iPr | CH₂—iPr | CH₂—iPr |
| 21-15 | CH₃ | CH₂—iPr | CH₂CMe₂F | CH₂—iPr | CH₂—iPr |
| 21-16 | CH₃ | CH₂—iPr | CH₂—iPr | CH₂CMe₂F | CH₂—iPr |
| 21-17 | CH₃ | CH₂—iPr | CH₂—iPr | CH₂—iPr | CH₂CMe₂F |
| 21-18 | CH₃ | CH₂CMe₂F | CH₂—iPr | CH₂CMe₂F | CH₂—iPr |
| 21-19 | CH₃ | CH₂—iPr | CH₂CMe₂F | CH₂—iPr | CH₂CMe₂F |
| 21-20 | CH₃ | CH₂—iPr | CH₂CMe₂F | CH₂CMe₂F | CH₂—iPr |
| 21-21 | CH₃ | CH₂CMe₂F | CH₂—iPr | CH₂—iPr | CH₂CMe₂F |
| 21-22 | CH₃ | CH₂—iPr | CH₂CMe₂F | CH₂CMe₂F | CH₂CMe₂F |
| 21-23 | CH₃ | CH₂CMe₂F | CH₂—iPr | CH₂CMe₂F | CH₂CMe₂F |
| 21-24 | CH₃ | CH₂CMe₂F | CH₂CMe₂F | CH₂—iPr | CH₂CMe₂F |
| 21-25 | CH₃ | CH₂CMe₂F | CH₂CMe₂F | CH₂CMe₂F | CH₂—iPr |
| 21-26 | CH₃ | CH₂CMe₂F | CH₂CMe₂F | CH₂CMe₂F | CH₂CMe₂F |
| 21-27 | CH₃ | CH₂—iPr | CH₂—iPr | CH₂—iPr | CH₂—iPr |
| 21-28 | CH₃ | CH₂—tBu | CH₂—tBu | CH₂—iPr | CH₂—iPr |
| 21-29 | CH₃ | CH₂—iPr | CH₂—iPr | CH₂—tBu | CH₂—tBu |
| 21-30 | CH₃ | CH₂CMe₂F | CH₂CMe₂F | CH₂—iPr | CH₂—iPr |
| 21-31 | CH₃ | CH₂—iPr | CH₂—iPr | CH₂CMe₂F | CH₂CMe₂F |
| 21-32 | CH₃ | CH₂CMe₂F | CH₂—tBu | CH₂CMe₂F | CH₂—tBu |
| 21-33 | CH₃ | CH₂CF₂Me | CH₂—iPr | CH₂CF₂Me | CH₂—iPr |
| 21-34 | CH₃ | CH₂CF₃ | CH₂—iPr | CH₂CF₃ | CH₂—iPr |
| 21-35 | CH₃ | CH₂CH(CF₃)₂ | CH₂—iPr | CH₂CH(CF₃)₂ | CH₂—iPr |
| 21-36 | CH₂F | CH₂CMe₂F | CH₂—iPr | CH₂CMe₂F | CH₂—iPr |
| 21-37 | H | CH₂CMe₂F | CH₂—iPr | CH₂CMe₂F | CH₂—iPr |
| 21-38 | Et | CH₂CMe₂F | CH₂—iPr | CH₂CMe₂F | CH₂—iPr |
| 21-39 | CH₂F | CH₂—iPr | CH₂—iPr | CH₂—iPr | CH₂—iPr |
| 21-40 | H | CH₂—iPr | CH₂—iPr | CH₂—iPr | CH₂—iPr |
| 21-41 | Et | CH₂—iPr | CH₂—iPr | CH₂—iPr | CH₂—iPr |
| 21-42 | H | CH₂CMe₂F | CH₂—tBu | CH₂CMe₂F | CH₂—tBu |
| 21-43 | CH₃ | CH₂CMe₂F | iPr | CH₂CMe₂F | iPr |
| 21-44 | CH₃ | CH₂CMe₂F | nPr | CH₂CMe₂F | nPr |
| 21-45 | CH₃ | CH₂CMe₂F | sBu | CH₂CMe₂F | sBu |
| 21-46 | CH₃ | CH₂CMe₂F | tBu | CH₂CMe₂F | tBu |
| 21-47 | CH₃ | CH₂CMe₂F | CH₂-p-biphenyl | CH₂CMe₂F | CH₂-p-biphenyl |
| 21-48 | CH₃ | CH₂CMe₂F | CH₂—p-tBuPh | CH₂CMe₂F | CH₂—p-tBuPh |
| 21-49 | CH₃ | CH₂CMe₂F | CH₃ | CH₂CMe₂F | CH₃ |
| 21-50 | H | CH₂CMe₂F | iPr | CH₂CMe₂F | iPr |
| 21-51 | CH₃ | CH₂CMe₂F | CH₂CH₂CMe₃ | CH₂CMe₂F | CH₂CH₂CMe₃ |
| 21-52 | CH₃ | CH₂CMe₂F | CH₂CH₂—iPr | CH₂CMe₂F | CH₂CH₂—iPr |
| 21-53 | CH₃ | CH₂-p-pyridyl | CH₂—iPr | CH₂-p-pyridyl | CH₂—iPr |
| 21-54 | CH₃ | CH₂-p-pyridyl | CH₂—tBu | CH₂-p-pyridyl | CH₂—tBu |

TABLE 22

Compounds of formula (I), wherein $Cy^1$ and $Cy^2$ are p-iodophenyl; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 22-1 | CH₃ | CH₂—tBu | CH₂—tBu | CH₂—tBu | CH₂—tBu |
| 22-2 | CH₃ | CH₂—tBu | CH₂—iPr | CH₂—iPr | CH₂—iPr |
| 22-3 | CH₃ | CH₂—iPr | CH₂—tBu | CH₂—iPr | CH₂—iPr |
| 22-4 | CH₃ | CH₂—iPr | CH₂—iPr | CH₂—tBu | CH₂—iPr |
| 22-5 | CH₃ | CH₂—iPr | CH₂—iPr | CH₂—iPr | CH₂—tBu |
| 22-6 | CH₃ | CH₂—iPr | CH₂—tBu | CH₂—iPr | CH₂—tBu |
| 22-7 | CH₃ | CH₂—tBu | CH₂—iPr | CH₂—tBu | CH₂—iPr |
| 22-8 | CH₃ | CH₂—iPr | CH₂—tBu | CH₂—tBu | CH₂—iPr |
| 22-9 | CH₃ | CH₂—tBu | CH₂—iPr | CH₂—iPr | CH₂—tBu |
| 22-10 | CH₃ | CH₂—iPr | CH₂—tBu | CH₂—tBu | CH₂—tBu |
| 22-11 | CH₃ | CH₂—tBu | CH₂—iPr | CH₂—tBu | CH₂—tBu |
| 22-12 | CH₃ | CH₂—tBu | CH₂—tBu | CH₂—iPr | CH₂—tBu |
| 22-13 | CH₃ | CH₂—tBu | CH₂—tBu | CH₂—tBu | CH₂—iPr |
| 22-14 | CH₃ | CH₂CMe₂F | CH₂—iPr | CH₂—iPr | CH₂—iPr |
| 22-15 | CH₃ | CH₂—iPr | CH₂CMe₂F | CH₂—iPr | CH₂—iPr |
| 22-16 | CH₃ | CH₂—iPr | CH₂—iPr | CH₂CMe₂F | CH₂—iPr |
| 22-17 | CH₃ | CH₂—iPr | CH₂—iPr | CH₂—iPr | CH₂CMe₂F |
| 22-18 | CH₃ | CH₂CMe₂F | CH₂—iPr | CH₂CMe₂F | CH₂—iPr |
| 22-19 | CH₃ | CH₂—iPr | CH₂CMe₂F | CH₂—iPr | CH₂CMe₂F |
| 22-20 | CH₃ | CH₂—iPr | CH₂CMe₂F | CH₂CMe₂F | CH₂—iPr |

TABLE 22-continued

Compounds of formula (I), wherein Cy¹ and Cy² are p-iodophenyl; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 22-21 | CH₃ | CH₂CMe₂F | CH₂—iPr | CH₂—iPr | CH₂CMe₂F |
| 22-22 | CH₃ | CH₂—iPr | CH₂CMe₂F | CH₂CMe₂F | CH₂CMe₂F |
| 22-23 | CH₃ | CH₂CMe₂F | CH₂—iPr | CH₂CMe₂F | CH₂CMe₂F |
| 22-24 | CH₃ | CH₂CMe₂F | CH₂CMe₂F | CH₂—iPr | CH₂CMe₂F |
| 22-25 | CH₃ | CH₂CMe₂F | CH₂CMe₂F | CH₂CMe₂F | CH₂—iPr |
| 22-26 | CH₃ | CH₂CMe₂F | CH₂CMe₂F | CH₂CMe₂F | CH₂CMe₂F |
| 22-27 | CH₃ | CH₂—iPr | CH₂—iPr | CH₂—iPr | CH₂—iPr |
| 22-28 | CH₃ | CH₂—tBu | CH₂—tBu | CH₂—tBu | CH₂—iPr |
| 22-29 | CH₃ | CH₂—iPr | CH₂—iPr | CH₂—tBu | CH₂—tBu |
| 22-30 | CH₃ | CH₂CMe₂F | CH₂CMe₂F | CH₂—iPr | CH₂—iPr |
| 22-31 | CH₃ | CH₂—iPr | CH₂—iPr | CH₂CMe₂F | CH₂CMe₂F |
| 22-32 | CH₃ | CH₂CMe₂F | CH₂—tBu | CH₂CMe₂F | CH₂—tBu |
| 22-33 | CH₃ | CH₂CF₂Me | CH₂—iPr | CH₂CF₂Me | CH₂—iPr |
| 22-34 | CH₃ | CH₂CF₃ | CH₂—iPr | CH₂CF₃ | CH₂—iPr |
| 22-35 | CH₃ | CH₂CH(CF₃)₂ | CH₂—iPr | CH₂CH(CF₃)₂ | CH₂—iPr |
| 22-36 | CH₂F | CH₂CMe₂F | CH₂—iPr | CH₂CMe₂F | CH₂—iPr |
| 22-37 | H | CH₂CMe₂F | CH₂—iPr | CH₂CMe₂F | CH₂—iPr |
| 22-38 | Et | CH₂CMe₂F | CH₂—iPr | CH₂CMe₂F | CH₂—iPr |
| 22-39 | CH₂F | CH₂—iPr | CH₂—iPr | CH₂—iPr | CH₂—iPr |
| 22-40 | H | CH₂—iPr | CH₂—iPr | CH₂—iPr | CH₂—iPr |
| 22-41 | Et | CH₂—iPr | CH₂—iPr | CH₂—iPr | CH₂—iPr |
| 22-42 | H | CH₂CMe₂F | CH₂—tBu | CH₂CMe₂F | CH₂—tBu |
| 22-43 | CH₃ | CH₂CMe₂F | iPr | CH₂CMe₂F | iPr |
| 22-44 | CH₃ | CH₂CMe₂F | nPr | CH₂CMe₂F | nPr |
| 22-45 | CH₃ | CH₂CMe₂F | sBu | CH₂CMe₂F | sBu |
| 22-46 | CH₃ | CH₂CMe₂F | tBu | CH₂CMe₂F | tBu |
| 22-47 | CH₃ | CH₂CMe₂F | CH₂-p-biphenyl | CH₂CMe₂F | CH₂-p-biphenyl |
| 22-48 | CH₃ | CH₂CMe₂F | CH₂—p-tBuPh | CH₂CMe₂F | CH₂—p-tBuPh |
| 22-49 | CH₃ | CH₂CMe₂F | CH₃ | CH₂CMe₂F | CH₃ |
| 22-50 | H | CH₂CMe₂F | iPr | CH₂CMe₂F | iPr |
| 22-51 | CH₃ | CH₂CMe₂F | CH₂CH₂CMe₃ | CH₂CMe₂F | CH₂CH₂CMe₃ |
| 22-52 | CH₃ | CH₂CMe₂F | CH₂CH₂—iPr | CH₂CMe₂F | CH₂CH₂—iPr |
| 22-53 | CH₃ | CH₂-p-pyridyl | CH₂—iPr | CH₂-p-pyridyl | CH₂—iPr |
| 22-54 | CH₃ | CH₂-p-pyridyl | CH₂—tBu | CH₂-p-pyridyl | CH₂—tBu |

TABLE 23

Compounds of formula (I), wherein Cy¹ and Cy² are p-bromophenyl; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 23-1 | CH₃ | CH₂—tBu | CH₂—tBu | CH₂—tBu | CH₂—tBu |
| 23-2 | CH₃ | CH₂—tBu | CH₂—iPr | CH₂—iPr | CH₂—iPr |
| 23-3 | CH₃ | CH₂—iPr | CH₂—tBu | CH₂—iPr | CH₂—iPr |
| 23-4 | CH₃ | CH₂—iPr | CH₂—iPr | CH₂—tBu | CH₂—iPr |
| 23-5 | CH₃ | CH₂—iPr | CH₂—iPr | CH₂—iPr | CH₂—tBu |
| 23-6 | CH₃ | CH₂—iPr | CH₂—tBu | CH₂—iPr | CH₂—tBu |
| 23-7 | CH₃ | CH₂—tBu | CH₂—iPr | CH₂—tBu | CH₂—iPr |
| 23-8 | CH₃ | CH₂—iPr | CH₂—tBu | CH₂—tBu | CH₂—iPr |
| 23-9 | CH₃ | CH₂—tBu | CH₂—iPr | CH₂—iPr | CH₂—tBu |
| 23-10 | CH₃ | CH₂—iPr | CH₂—tBu | CH₂—tBu | CH₂—tBu |
| 23-11 | CH₃ | CH₂—tBu | CH₂—iPr | CH₂—tBu | CH₂—tBu |
| 23-12 | CH₃ | CH₂—tBu | CH₂—tBu | CH₂—iPr | CH₂—tBu |
| 23-13 | CH₃ | CH₂—tBu | CH₂—tBu | CH₂—tBu | CH₂—iPr |
| 23-14 | CH₃ | CH₂CMe₂F | CH₂—iPr | CH₂—iPr | CH₂—iPr |
| 23-15 | CH₃ | CH₂—iPr | CH₂CMe₂F | CH₂—iPr | CH₂—iPr |
| 23-16 | CH₃ | CH₂—iPr | CH₂—iPr | CH₂CMe₂F | CH₂—iPr |
| 23-17 | CH₃ | CH₂—iPr | CH₂—iPr | CH₂—iPr | CH₂CMe₂F |
| 23-18 | CH₃ | CH₂CMe₂F | CH₂—iPr | CH₂CMe₂F | CH₂—iPr |
| 23-19 | CH₃ | CH₂—iPr | CH₂CMe₂F | CH₂—iPr | CH₂CMe₂F |
| 23-20 | CH₃ | CH₂—iPr | CH₂CMe₂F | CH₂CMe₂F | CH₂—iPr |
| 23-21 | CH₃ | CH₂CMe₂F | CH₂—iPr | CH₂—iPr | CH₂CMe₂F |
| 23-22 | CH₃ | CH₂—iPr | CH₂CMe₂F | CH₂CMe₂F | CH₂CMe₂F |
| 23-23 | CH₃ | CH₂CMe₂F | CH₂—iPr | CH₂CMe₂F | CH₂CMe₂F |
| 23-24 | CH₃ | CH₂CMe₂F | CH₂CMe₂F | CH₂—iPr | CH₂CMe₂F |
| 23-25 | CH₃ | CH₂CMe₂F | CH₂CMe₂F | CH₂CMe₂F | CH₂—iPr |
| 23-26 | CH₃ | CH₂CMe₂F | CH₂CMe₂F | CH₂CMe₂F | CH₂CMe₂F |
| 23-27 | CH₃ | CH₂—iPr | CH₂—iPr | CH₂—iPr | CH₂—iPr |
| 23-28 | CH₃ | CH₂—tBu | CH₂—tBu | CH₂—iPr | CH₂—iPr |
| 23-29 | CH₃ | CH₂—iPr | CH₂—iPr | CH₂—tBu | CH₂—tBu |
| 23-30 | CH₃ | CH₂CMe₂F | CH₂CMe₂F | CH₂—iPr | CH₂—iPr |

TABLE 23-continued

Compounds of formula (I), wherein Cy$^1$ and Cy$^2$ are p-bromophenyl; and R$^a$, R$^b$, R$^1$ to R$^4$ are as shown.

| Compound # | R$^a$/R$^b$ | R$^1$ | R$^2$ | R$^3$ | R$^4$ |
|---|---|---|---|---|---|
| 23-31 | CH$_3$ | CH$_2$—iPr | CH$_2$—iPr | CH$_2$CMe$_2$F | CH$_2$CMe$_2$F |
| 23-32 | CH$_3$ | CH$_2$CMe$_2$F | CH$_2$—tBu | CH$_2$CMe$_2$F | CH$_2$—tBu |
| 23-33 | CH$_3$ | CH$_2$CF$_2$Me | CH$_2$—iPr | CH$_2$CF$_2$Me | CH$_2$—iPr |
| 23-34 | CH$_3$ | CH$_2$CF$_3$ | CH$_2$—iPr | CH$_2$CF$_3$ | CH$_2$—iPr |
| 23-35 | CH$_3$ | CH$_2$CH(CF$_3$)$_2$ | CH$_2$—iPr | CH$_2$CH(CF$_3$)$_2$ | CH$_2$—iPr |
| 23-36 | CH$_2$F | CH$_2$CMe$_2$F | CH$_2$—iPr | CH$_2$CMe$_2$F | CH$_2$—iPr |
| 23-37 | H | CH$_2$CMe$_2$F | CH$_2$—iPr | CH$_2$CMe$_2$F | CH$_2$—iPr |
| 23-38 | Et | CH$_2$CMe$_2$F | CH$_2$—iPr | CH$_2$CMe$_2$F | CH$_2$—iPr |
| 23-39 | CH$_2$F | CH$_2$—iPr | CH$_2$—iPr | CH$_2$—iPr | CH$_2$—iPr |
| 23-40 | H | CH$_2$—iPr | CH$_2$—iPr | CH$_2$—iPr | CH$_2$—iPr |
| 23-41 | Et | CH$_2$—iPr | CH$_2$—iPr | CH$_2$—iPr | CH$_2$—iPr |
| 23-42 | H | CH$_2$CMe$_2$F | CH$_2$—tBu | CH$_2$CMe$_2$F | CH$_2$—tBu |
| 23-43 | CH$_3$ | CH$_2$CMe$_2$F | iPr | CH$_2$CMe$_2$F | iPr |
| 23-44 | CH$_3$ | CH$_2$CMe$_2$F | nPr | CH$_2$CMe$_2$F | nPr |
| 23-45 | CH$_3$ | CH$_2$CMe$_2$F | sBu | CH$_2$CMe$_2$F | sBu |
| 23-46 | CH$_3$ | CH$_2$CMe$_2$F | tBu | CH$_2$CMe$_2$F | tBu |
| 23-47 | CH$_3$ | CH$_2$CMe$_2$F | CH$_2$-p-biphenyl | CH$_2$CMe$_2$F | CH$_2$-p-biphenyl |
| 23-48 | CH$_3$ | CH$_2$CMe$_2$F | CH$_2$—p-tBuPh | CH$_2$CMe$_2$F | CH$_2$—p-tBuPh |
| 23-49 | CH$_3$ | CH$_2$CMe$_2$F | CH$_3$ | CH$_2$CMe$_2$F | CH$_3$ |
| 23-50 | H | CH$_2$CMe$_2$F | iPr | CH$_2$CMe$_2$F | iPr |
| 23-51 | CH$_3$ | CH$_2$CMe$_2$F | CH$_2$CH$_2$CMe$_3$ | CH$_2$CMe$_2$F | CH$_2$CH$_2$CMe$_3$ |
| 23-52 | CH$_3$ | CH$_2$CMe$_2$F | CH$_2$CH$_2$—iPr | CH$_2$CMe$_2$F | CH$_2$CH$_2$—iPr |
| 23-53 | CH$_3$ | CH$_2$-p-pyridyl | CH$_2$—iPr | CH$_2$-p-pyridyl | CH$_2$—iPr |
| 23-54 | CH$_3$ | CH$_2$-p-pyridyl | CH$_2$—tBu | CH$_2$-p-pyridyl | CH$_2$—tBu |

TABLE 24

Compounds of formula (I), wherein Cy$^1$ and Cy$^2$ are p-cyanophenyl; and R$^a$, R$^b$, R$^1$ to R$^4$ are as shown.

| Compound # | R$^a$/R$^b$ | R$^1$ | R$^2$ | R$^3$ | R$^4$ |
|---|---|---|---|---|---|
| 24-1 | CH$_3$ | CH$_2$—tBu | CH$_2$—tBu | CH$_2$—tBu | CH$_2$—tBu |
| 24-2 | CH$_3$ | CH$_2$—tBu | CH$_2$—iPr | CH$_2$—iPr | CH$_2$—iPr |
| 24-3 | CH$_3$ | CH$_2$—iPr | CH$_2$—tBu | CH$_2$—iPr | CH$_2$—iPr |
| 24-4 | CH$_3$ | CH$_2$—iPr | CH$_2$—iPr | CH$_2$—tBu | CH$_2$—iPr |
| 24-5 | CH$_3$ | CH$_2$—iPr | CH$_2$—iPr | CH$_2$—iPr | CH$_2$—tBu |
| 24-6 | CH$_3$ | CH$_2$—iPr | CH$_2$—tBu | CH$_2$—iPr | CH$_2$—tBu |
| 24-7 | CH$_3$ | CH$_2$—tBu | CH$_2$—iPr | CH$_2$—tBu | CH$_2$—iPr |
| 24-8 | CH$_3$ | CH$_2$—iPr | CH$_2$—tBu | CH$_2$—tBu | CH$_2$—iPr |
| 24-9 | CH$_3$ | CH$_2$—tBu | CH$_2$—iPr | CH$_2$—iPr | CH$_2$—tBu |
| 24-10 | CH$_3$ | CH$_2$—iPr | CH$_2$—tBu | CH$_2$—tBu | CH$_2$—tBu |
| 24-11 | CH$_3$ | CH$_2$—tBu | CH$_2$—iPr | CH$_2$—tBu | CH$_2$—tBu |
| 24-12 | CH$_3$ | CH$_2$—tBu | CH$_2$—tBu | CH$_2$—iPr | CH$_2$—tBu |
| 24-13 | CH$_3$ | CH$_2$—tBu | CH$_2$—tBu | CH$_2$—tBu | CH$_2$—iPr |
| 24-14 | CH$_3$ | CH$_2$CMe$_2$F | CH$_2$—iPr | CH$_2$—iPr | CH$_2$—iPr |
| 24-15 | CH$_3$ | CH$_2$—iPr | CH$_2$CMe$_2$F | CH$_2$—iPr | CH$_2$—iPr |
| 24-16 | CH$_3$ | CH$_2$—iPr | CH$_2$—iPr | CH$_2$CMe$_2$F | CH$_2$—iPr |
| 24-17 | CH$_3$ | CH$_2$—iPr | CH$_2$—iPr | CH$_2$—iPr | CH$_2$CMe$_2$F |
| 24-18 | CH$_3$ | CH$_2$CMe$_2$F | CH$_2$—iPr | CH$_2$CMe$_2$F | CH$_2$—iPr |
| 24-19 | CH$_3$ | CH$_2$—iPr | CH$_2$CMe$_2$F | CH$_2$—iPr | CH$_2$CMe$_2$F |
| 24-20 | CH$_3$ | CH$_2$—iPr | CH$_2$CMe$_2$F | CH$_2$CMe$_2$F | CH$_2$—iPr |
| 24-21 | CH$_3$ | CH$_2$CMe$_2$F | CH$_2$—iPr | CH$_2$—iPr | CH$_2$CMe$_2$F |
| 24-22 | CH$_3$ | CH$_2$—iPr | CH$_2$CMe$_2$F | CH$_2$CMe$_2$F | CH$_2$CMe$_2$F |
| 24-23 | CH$_3$ | CH$_2$CMe$_2$F | CH$_2$—iPr | CH$_2$CMe$_2$F | CH$_2$CMe$_2$F |
| 24-24 | CH$_3$ | CH$_2$CMe$_2$F | CH$_2$CMe$_2$F | CH$_2$—iPr | CH$_2$CMe$_2$F |
| 24-25 | CH$_3$ | CH$_2$CMe$_2$F | CH$_2$CMe$_2$F | CH$_2$CMe$_2$F | CH$_2$—iPr |
| 24-26 | CH$_3$ | CH$_2$CMe$_2$F | CH$_2$CMe$_2$F | CH$_2$CMe$_2$F | CH$_2$CMe$_2$F |
| 24-27 | CH$_3$ | CH$_2$—iPr | CH$_2$—iPr | CH$_2$—iPr | CH$_2$—iPr |
| 24-28 | CH$_3$ | CH$_2$—tBu | CH$_2$—tBu | CH$_2$—iPr | CH$_2$—iPr |
| 24-29 | CH$_3$ | CH$_2$—iPr | CH$_2$—iPr | CH$_2$—tBu | CH$_2$—tBu |
| 24-30 | CH$_3$ | CH$_2$CMe$_2$F | CH$_2$CMe$_2$F | CH$_2$—iPr | CH$_2$—iPr |
| 24-31 | CH$_3$ | CH$_2$—iPr | CH$_2$—iPr | CH$_2$CMe$_2$F | CH$_2$CMe$_2$F |
| 24-32 | CH$_3$ | CH$_2$CMe$_2$F | CH$_2$—tBu | CH$_2$CMe$_2$F | CH$_2$—tBu |
| 24-33 | CH$_3$ | CH$_2$CF$_2$Me | CH$_2$—iPr | CH$_2$CF$_2$Me | CH$_2$—iPr |
| 24-34 | CH$_3$ | CH$_2$CF$_3$ | CH$_2$—iPr | CH$_2$CF$_3$ | CH$_2$—iPr |
| 24-35 | CH$_3$ | CH$_2$CH(CF$_3$)$_2$ | CH$_2$—iPr | CH$_2$CH(CF$_3$)$_2$ | CH$_2$—iPr |
| 24-36 | CH$_2$F | CH$_2$CMe$_2$F | CH$_2$—iPr | CH$_2$CMe$_2$F | CH$_2$—iPr |
| 24-37 | H | CH$_2$CMe$_2$F | CH$_2$—iPr | CH$_2$CMe$_2$F | CH$_2$—iPr |
| 24-38 | Et | CH$_2$CMe$_2$F | CH$_2$—iPr | CH$_2$CMe$_2$F | CH$_2$—iPr |
| 24-39 | CH$_2$F | CH$_2$—iPr | CH$_2$—iPr | CH$_2$—iPr | CH$_2$—iPr |
| 24-40 | H | CH$_2$—iPr | CH$_2$—iPr | CH$_2$—iPr | CH$_2$—iPr |

TABLE 24-continued

Compounds of formula (I), wherein Cy¹ and Cy² are p-cyanophenyl; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 24-41 | Et | CH$_2$—iPr | CH$_2$—iPr | CH$_2$—iPr | CH$_2$—iPr |
| 24-42 | H | CH$_2$CMe$_2$F | CH$_2$—tBu | CH$_2$CMe$_2$F | CH$_2$—tBu |
| 24-43 | CH$_3$ | CH$_2$CMe$_2$F | iPr | CH$_2$CMe$_2$F | iPr |
| 24-44 | CH$_3$ | CH$_2$CMe$_2$F | nPr | CH$_2$CMe$_2$F | nPr |
| 24-45 | CH$_3$ | CH$_2$CMe$_2$F | sBu | CH$_2$CMe$_2$F | sBu |
| 24-46 | CH$_3$ | CH$_2$CMe$_2$F | tBu | CH$_2$CMe$_2$F | tBu |
| 24-47 | CH$_3$ | CH$_2$CMe$_2$F | CH$_2$-p-biphenyl | CH$_2$CMe$_2$F | CH$_2$-p-biphenyl |
| 24-48 | CH$_3$ | CH$_2$CMe$_2$F | CH$_2$—p-tBuPh | CH$_2$CMe$_2$F | CH$_2$—p-tBuPh |
| 24-49 | CH$_3$ | CH$_2$CMe$_2$F | CH$_3$ | CH$_2$CMe$_2$F | CH$_3$ |
| 24-50 | H | CH$_2$CMe$_2$F | iPr | CH$_2$CMe$_2$F | iPr |
| 24-51 | CH$_3$ | CH$_2$CMe$_2$F | CH$_2$CH$_2$CMe$_3$ | CH$_2$CMe$_2$F | CH$_2$CH$_2$CMe$_3$ |
| 24-52 | CH$_3$ | CH$_2$CMe$_2$F | CH$_2$CH$_2$—iPr | CH$_2$CMe$_2$F | CH$_2$CH$_2$—iPr |
| 24-53 | CH$_3$ | CH$_2$-p-pyridyl | CH$_2$—iPr | CH$_2$-p-pyridyl | CH$_2$—iPr |
| 24-54 | CH$_3$ | CH$_2$-p-pyridyl | CH$_2$—tBu | CH$_2$-p-pyridyl | CH$_2$—tBu |

TABLE 25

Compounds of formula (I), wherein Cy¹ and Cy² are

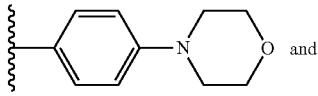

and unsubstituted phenyl, respectively; and $R^a$, $R^b$, $R^1$ to $R^4$ are as shown.

| $R^a$, $R^b$, # | $R^a/R^b$ | $R^1$ | $R^2$ | $R^3$ | $R^4$ |
|---|---|---|---|---|---|
| 25-1 | CH$_3$ | CH$_2$—tBu | CH$_2$—tBu | CH$_2$—tBu | CH$_2$—tBu |
| 25-2 | CH$_3$ | CH$_2$—tBu | CH$_2$—iPr | CH$_2$—iPr | CH$_2$—iPr |
| 25-3 | CH$_3$ | CH$_2$—iPr | CH$_2$—tBu | CH$_2$—iPr | CH$_2$—iPr |
| 25-4 | CH$_3$ | CH$_2$—iPr | CH$_2$—iPr | CH$_2$—tBu | CH$_2$—iPr |
| 25-5 | CH$_3$ | CH$_2$—iPr | CH$_2$—iPr | CH$_2$—iPr | CH$_2$—tBu |
| 25-6 | CH$_3$ | CH$_2$—iPr | CH$_2$—tBu | CH$_2$—iPr | CH$_2$—tBu |
| 25-7 | CH$_3$ | CH$_2$—tBu | CH$_2$—iPr | CH$_2$—tBu | CH$_2$—iPr |
| 25-8 | CH$_3$ | CH$_2$—iPr | CH$_2$—tBu | CH$_2$—tBu | CH$_2$—iPr |
| 25-9 | CH$_3$ | CH$_2$—tBu | CH$_2$—iPr | CH$_2$—iPr | CH$_2$—tBu |
| 25-10 | CH$_3$ | CH$_2$—iPr | CH$_2$—tBu | CH$_2$—tBu | CH$_2$—tBu |
| 25-11 | CH$_3$ | CH$_2$—tBu | CH$_2$—iPr | CH$_2$—tBu | CH$_2$—tBu |
| 25-12 | CH$_3$ | CH$_2$—tBu | CH$_2$—tBu | CH$_2$—iPr | CH$_2$—tBu |
| 25-13 | CH$_3$ | CH$_2$—tBu | CH$_2$—tBu | CH$_2$—tBu | CH$_2$—iPr |
| 25-14 | CH$_3$ | CH$_2$CMe$_2$F | CH$_2$—iPr | CH$_2$—iPr | CH$_2$—iPr |
| 25-15 | CH$_3$ | CH$_2$—iPr | CH$_2$CMe$_2$F | CH$_2$—iPr | CH$_2$—iPr |
| 25-16 | CH$_3$ | CH$_2$—iPr | CH$_2$—iPr | CH$_2$CMe$_2$F | CH$_2$—iPr |
| 25-17 | CH$_3$ | CH$_2$—iPr | CH$_2$—iPr | CH$_2$—iPr | CH$_2$CMe$_2$F |
| 25-18 | CH$_3$ | CH$_2$CMe$_2$F | CH$_2$—iPr | CH$_2$CMe$_2$F | CH$_2$—iPr |
| 25-19 | CH$_3$ | CH$_2$—iPr | CH$_2$CMe$_2$F | CH$_2$—iPr | CH$_2$CMe$_2$F |
| 25-20 | CH$_3$ | CH$_2$—iPr | CH$_2$CMe$_2$F | CH$_2$CMe$_2$F | CH$_2$—iPr |
| 25-21 | CH$_3$ | CH$_2$CMe$_2$F | CH$_2$—iPr | CH$_2$—iPr | CH$_2$CMe$_2$F |
| 25-22 | CH$_3$ | CH$_2$—iPr | CH$_2$CMe$_2$F | CH$_2$CMe$_2$F | CH$_2$CMe$_2$F |
| 25-23 | CH$_3$ | CH$_2$CMe$_2$F | CH$_2$—iPr | CH$_2$CMe$_2$F | CH$_2$CMe$_2$F |
| 25-24 | CH$_3$ | CH$_2$CMe$_2$F | CH$_2$CMe$_2$F | CH$_2$—iPr | CH$_2$CMe$_2$F |
| 25-25 | CH$_3$ | CH$_2$CMe$_2$F | CH$_2$CMe$_2$F | CH$_2$CMe$_2$F | CH$_2$—iPr |
| 25-26 | CH$_3$ | CH$_2$CMe$_2$F | CH$_2$CMe$_2$F | CH$_2$CMe$_2$F | CH$_2$CMe$_2$F |
| 25-27 | CH$_3$ | CH$_2$—iPr | CH$_2$—iPr | CH$_2$—iPr | CH$_2$—iPr |
| 25-28 | CH$_3$ | CH$_2$—tBu | CH$_2$—tBu | CH$_2$—iPr | CH$_2$—iPr |
| 25-29 | CH$_3$ | CH$_2$—iPr | CH$_2$—iPr | CH$_2$—tBu | CH$_2$—tBu |
| 25-30 | CH$_3$ | CH$_2$CMe$_2$F | CH$_2$CMe$_2$F | CH$_2$—iPr | CH$_2$—iPr |
| 25-31 | CH$_3$ | CH$_2$—iPr | CH$_2$—iPr | CH$_2$CMe$_2$F | CH$_2$CMe$_2$F |
| 25-32 | CH$_3$ | CH$_2$CMe$_2$F | CH$_2$—tBu | CH$_2$CMe$_2$F | CH$_2$—tBu |
| 25-33 | CH$_3$ | CH$_2$CF$_2$Me | CH$_2$—iPr | CH$_2$CF$_2$Me | CH$_2$—iPr |
| 25-34 | CH$_3$ | CH$_2$CF$_3$ | CH$_2$—iPr | CH$_2$CF$_3$ | CH$_2$—iPr |
| 25-35 | CH$_3$ | CH$_2$CH(CF$_3$)$_2$ | CH$_2$—iPr | CH$_2$CH(CF$_3$)$_2$ | CH$_2$—iPr |
| 25-36 | CH$_2$F | CH$_2$CMe$_2$F | CH$_2$—iPr | CH$_2$CMe$_2$F | CH$_2$—iPr |
| 25-37 | H | CH$_2$CMe$_2$F | CH$_2$—iPr | CH$_2$CMe$_2$F | CH$_2$—iPr |
| 25-38 | Et | CH$_2$CMe$_2$F | CH$_2$—iPr | CH$_2$CMe$_2$F | CH$_2$—iPr |
| 25-39 | CH$_2$F | CH$_2$—iPr | CH$_2$—iPr | CH$_2$—iPr | CH$_2$—iPr |
| 25-40 | H | CH$_2$—iPr | CH$_2$—iPr | CH$_2$—iPr | CH$_2$—iPr |
| 25-41 | Et | CH$_2$—iPr | CH$_2$—iPr | CH$_2$—iPr | CH$_2$—iPr |
| 25-42 | H | CH$_2$CMe$_2$F | CH$_2$—tBu | CH$_2$CMe$_2$F | CH$_2$—tBu |

TABLE 25-continued

Compounds of formula (I), wherein $Cy^1$ and $Cy^2$ are

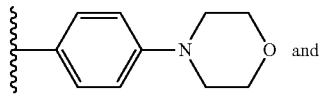 and unsubstituted phenyl, respectively; and $R^a$, $R^b$, $R^1$ to $R^4$ are as shown.

| $R^a$, $R^b$, # | $R^a/R^b$ | $R^1$ | $R^2$ | $R^3$ | $R^4$ |
|---|---|---|---|---|---|
| 25-43 | $CH_3$ | $CH_2CMe_2F$ | iPr | $CH_2CMe_2F$ | iPr |
| 25-44 | $CH_3$ | $CH_2CMe_2F$ | nPr | $CH_2CMe_2F$ | nPr |
| 25-45 | $CH_3$ | $CH_2CMe_2F$ | sBu | $CH_2CMe_2F$ | sBu |
| 25-46 | $CH_3$ | $CH_2CMe_2F$ | tBu | $CH_2CMe_2F$ | tBu |
| 25-47 | $CH_3$ | $CH_2CMe_2F$ | $CH_2$-p-biphenyl | $CH_2CMe_2F$ | $CH_2$-p-biphenyl |
| 25-48 | $CH_3$ | $CH_2CMe_2F$ | $CH_2$-p-tBuPh | $CH_2CMe_2F$ | $CH_2$-p-tBuPh |
| 25-49 | $CH_3$ | $CH_2CMe_2F$ | $CH_3$ | $CH_2CMe_2F$ | $CH_3$ |
| 25-50 | H | $CH_2CMe_2F$ | iPr | $CH_2CMe_2F$ | iPr |
| 25-51 | $CH_3$ | $CH_2CMe_2F$ | $CH_2CH_2CMe_3$ | $CH_2CMe_2F$ | $CH_2CH_2CMe_3$ |
| 25-52 | $CH_3$ | $CH_2CMe_2F$ | $CH_2CH_2$—iPr | $CH_2CMe_2F$ | $CH_2CH_2$—iPr |
| 25-53 | $CH_3$ | $CH_2$-p-pyridyl | $CH_2$—iPr | $CH_2$-p-pyridyl | $CH_2$—iPr |
| 25-54 | $CH_3$ | $CH_2$-p-pyridyl | $CH_2$—tBu | $CH_2$-p-pyridyl | $CH_2$—tBu |

TABLE 26

Compounds of formula (I), wherein $Cy^1$ and $Cy^2$ are

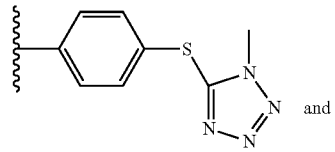 and p-iodophenyl, respectively; and $R^a$, $R^b$, $R^1$ to $R^4$ are as shown.

| Compound # | $R^1/R^b$ | $R^1$ | $R^2$ | $R^3$ | $R^4$ |
|---|---|---|---|---|---|
| 26-1 | $CH_3$ | $CH_2$—tBu | $CH_2$—tBu | $CH_2$—tBu | $CH_2$—tBu |
| 26-2 | $CH_3$ | $CH_2$—tBu | $CH_2$—iPr | $CH_2$—iPr | $CH_2$—iPr |
| 26-3 | $CH_3$ | $CH_2$—iPr | $CH_2$—tBu | $CH_2$—iPr | $CH_2$—iPr |
| 26-4 | $CH_3$ | $CH_2$—iPr | $CH_2$—iPr | $CH_2$—tBu | $CH_2$—iPr |
| 26-5 | $CH_3$ | $CH_2$—iPr | $CH_2$—iPr | $CH_2$—iPr | $CH_2$—tBu |
| 26-6 | $CH_3$ | $CH_2$—iPr | $CH_2$—tBu | $CH_2$—iPr | $CH_2$—tBu |
| 26-7 | $CH_3$ | $CH_2$—tBu | $CH_2$—iPr | $CH_2$—tBu | $CH_2$—iPr |
| 26-8 | $CH_3$ | $CH_2$—iPr | $CH_2$—tBu | $CH_2$—tBu | $CH_2$—iPr |
| 26-9 | $CH_3$ | $CH_2$—tBu | $CH_2$—iPr | $CH_2$—iPr | $CH_2$—tBu |
| 26-10 | $CH_3$ | $CH_2$—iPr | $CH_2$—tBu | $CH_2$—tBu | $CH_2$—tBu |
| 26-11 | $CH_3$ | $CH_2$—tBu | $CH_2$—iPr | $CH_2$—tBu | $CH_2$—tBu |
| 26-12 | $CH_3$ | $CH_2$—tBu | $CH_2$—tBu | $CH_2$—iPr | $CH_2$—tBu |
| 26-13 | $CH_3$ | $CH_2$—tBu | $CH_2$—tBu | $CH_2$—tBu | $CH_2$—iPr |
| 26-14 | $CH_3$ | $CH_2CMe_2F$ | $CH_2$—iPr | $CH_2$—iPr | $CH_2$—iPr |
| 26-15 | $CH_3$ | $CH_2$—iPr | $CH_2CMe_2F$ | $CH_2$—iPr | $CH_2$—iPr |
| 26-16 | $CH_3$ | $CH_2$—iPr | $CH_2$—iPr | $CH_2CMe_2F$ | $CH_2$—iPr |
| 26-17 | $CH_3$ | $CH_2$—iPr | $CH_2$—iPr | $CH_2$—iPr | $CH_2CMe_2F$ |
| 26-18 | $CH_3$ | $CH_2CMe_2F$ | $CH_2$—iPr | $CH_2CMe_2F$ | $CH_2$—iPr |
| 26-19 | $CH_3$ | $CH_2$—iPr | $CH_2CMe_2F$ | $CH_2$—iPr | $CH_2CMe_2F$ |
| 26-20 | $CH_3$ | $CH_2$—iPr | $CH_2CMe_2F$ | $CH_2CMe_2F$ | $CH_2$—iPr |
| 26-21 | $CH_3$ | $CH_2CMe_2F$ | $CH_2$—iPr | $CH_2$—iPr | $CH_2CMe_2F$ |
| 26-22 | $CH_3$ | $CH_2$—iPr | $CH_2CMe_2F$ | $CH_2CMe_2F$ | $CH_2CMe_2F$ |
| 26-23 | $CH_3$ | $CH_2CMe_2F$ | $CH_2$—iPr | $CH_2CMe_2F$ | $CH_2CMe_2F$ |
| 26-24 | $CH_3$ | $CH_2CMe_2F$ | $CH_2CMe_2F$ | $CH_2$—iPr | $CH_2CMe_2F$ |
| 26-25 | $CH_3$ | $CH_2CMe_2F$ | $CH_2CMe_2F$ | $CH_2CMe_2F$ | $CH_2$—iPr |
| 26-26 | $CH_3$ | $CH_2CMe_2F$ | $CH_2CMe_2F$ | $CH_2CMe_2F$ | $CH_2CMe_2F$ |
| 26-27 | $CH_3$ | $CH_2$—iPr | $CH_2$—iPr | $CH_2$—iPr | $CH_2$—iPr |
| 26-28 | $CH_3$ | $CH_2$—tBu | $CH_2$—tBu | $CH_2$—iPr | $CH_2$—iPr |
| 26-29 | $CH_3$ | $CH_2$—iPr | $CH_2$—iPr | $CH_2$—tBu | $CH_2$—tBu |
| 26-30 | $CH_3$ | $CH_2CMe_2F$ | $CH_2CMe_2F$ | $CH_2$—iPr | $CH_2$—iPr |
| 26-31 | $CH_3$ | $CH_2$—iPr | $CH_2$—iPr | $CH_2CMe_2F$ | $CH_2CMe_2F$ |
| 26-32 | $CH_3$ | $CH_2CMe_2F$ | $CH_2$—tBu | $CH_2CMe_2F$ | $CH_2$—tBu |

TABLE 26-continued

Compounds of formula (I), wherein $Cy^1$ and $Cy^2$ are

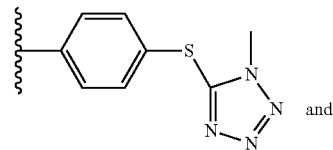 and p-iodophenyl, respectively; and
$R^a$, $R^b$, $R^1$ to $R^4$ are as shown.

| Compound # | $R^1/R^b$ | $R^1$ | $R^2$ | $R^3$ | $R^4$ |
|---|---|---|---|---|---|
| 26-33 | $CH_3$ | $CH_2CF_2Me$ | $CH_2$—iPr | $CH_2CF_2Me$ | $CH_2$—iPr |
| 26-34 | $CH_3$ | $CH_2CF_3$ | $CH_2$—iPr | $CH_2CF_3$ | $CH_2$—iPr |
| 26-35 | $CH_3$ | $CH_2CH(CF_3)_2$ | $CH_2$—iPr | $CH_2CH(CF_3)_2$ | $CH_2$—iPr |
| 26-36 | $CH_2F$ | $CH_2CMe_2F$ | $CH_2$—iPr | $CH_2CMe_2F$ | $CH_2$—iPr |
| 26-37 | H | $CH_2CMe_2F$ | $CH_2$—iPr | $CH_2CMe_2F$ | $CH_2$—iPr |
| 26-38 | Et | $CH_2CMe_2F$ | $CH_2$—iPr | $CH_2CMe_2F$ | $CH_2$—iPr |
| 26-39 | $CH_2F$ | $CH_2$—iPr | $CH_2$—iPr | $CH_2$—iPr | $CH_2$—iPr |
| 26-40 | H | $CH_2$—iPr | $CH_2$—iPr | $CH_2$—iPr | $CH_2$—iPr |
| 26-41 | Et | $CH_2$—iPr | $CH_2$—iPr | $CH_2$—iPr | $CH_2$—iPr |
| 26-42 | H | $CH_2CMe_2F$ | $CH_2$—tBu | $CH_2CMe_2F$ | $CH_2$—tBu |
| 25-43 | $CH_3$ | $CH_2CMe_2F$ | iPr | $CH_2CMe_2F$ | iPr |
| 26-44 | $CH_3$ | $CH_2CMe_2F$ | nPr | $CH_2CMe_2F$ | nPr |
| 26-45 | $CH_3$ | $CH_2CMe_2F$ | sBu | $CH_2CMe_2F$ | sBu |
| 26-46 | $CH_3$ | $CH_2CMe_2F$ | tBu | $CH_2CMe_2F$ | tBu |
| 26-47 | $CH_3$ | $CH_2CMe_2F$ | $CH_2$-p-biphenyl | $CH_2CMe_2F$ | $CH_2$-p-biphenyl |
| 26-48 | $CH_3$ | $CH_2CMe_2F$ | $CH_2$-p-tBuPh | $CH_2CMe_2F$ | $CH_2$-p-tBuPh |
| 26-49 | $CH_3$ | $CH_2CMe_2F$ | $CH_3$ | $CH_2CMe_2F$ | $CH_3$ |
| 26-50 | H | $CH_2CMe_2F$ | iPr | $CH_2CMe_2F$ | iPr |
| 26-51 | $CH_3$ | $CH_2CMe_2F$ | $CH_2CH_2CMe_3$ | $CH_2CMe_2F$ | $CH_2CH_2OMe_3$ |
| 26-52 | $CH_3$ | $CH_2CMe_2F$ | $CH_2CH_2$—iPr | $CH_2CMe_2F$ | $CH_2CH_2$—iPr |
| 26-53 | $CH_3$ | $CH_2$-p-pyridyl | $CH_2$—iPr | $CH_2$-p-pyridyl | $CH_2$—iPr |
| 26-54 | $CH_3$ | $CH_2$-p-pyridyl | $CH_2$—tBu | $CH_2$-p-pyridyl | $CH_2$—tBu |

TABLE 27

Compounds of formula (I), wherein $Cy^1$ and $Cy^2$ are

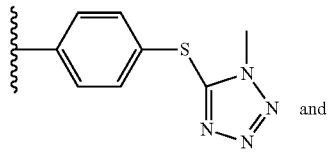 and unsubstituted phenyl, respectively; and
$R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 27-1 | $CH_3$ | $CH_2$—tBu | $CH_2$—tBu | $CH_2$—tBu | $CH_2$—tBu |
| 27-2 | $CH_3$ | $CH_2$—tBu | $CH_2$—iPr | $CH_2$—iPr | $CH_2$—iPr |
| 27-3 | $CH_3$ | $CH_2$—iPr | $CH_2$—tBu | $CH_2$—iPr | $CH_2$—iPr |
| 27-4 | $CH_3$ | $CH_2$—iPr | $CH_2$—iPr | $CH_2$—tBu | $CH_2$—iPr |
| 27-5 | $CH_3$ | $CH_2$—iPr | $CH_2$—iPr | $CH_2$—iPr | $CH_2$—tBu |
| 27-6 | $CH_3$ | $CH_2$—iPr | $CH_2$—tBu | $CH_2$—iPr | $CH_2$—tBu |
| 27-7 | $CH_3$ | $CH_2$—tBu | $CH_2$—iPr | $CH_2$—tBu | $CH_2$—iPr |
| 27-8 | $CH_3$ | $CH_2$—iPr | $CH_2$—tBu | $CH_2$—tBu | $CH_2$—iPr |
| 27-9 | $CH_3$ | $CH_2$—tBu | $CH_2$—iPr | $CH_2$—iPr | $CH_2$—tBu |
| 27-10 | $CH_3$ | $CH_2$—iPr | $CH_2$—tBu | $CH_2$—tBu | $CH_2$—tBu |
| 27-11 | $CH_3$ | $CH_2$—tBu | $CH_2$—iPr | $CH_2$—tBu | $CH_2$—tBu |
| 27-12 | $CH_3$ | $CH_2$—tBu | $CH_2$—tBu | $CH_2$—iPr | $CH_2$—tBu |
| 27-13 | $CH_3$ | $CH_2$—tBu | $CH_2$—tBu | $CH_2$—tBu | $CH_2$—iPr |
| 27-14 | $CH_3$ | $CH_2CMe_2F$ | $CH_2$—iPr | $CH_2$—iPr | $CH_2$—iPr |
| 27-15 | $CH_3$ | $CH_2$—iPr | $CH_2CMe_2F$ | $CH_2$—iPr | $CH_2$—iPr |
| 27-16 | $CH_3$ | $CH_2$—iPr | $CH_2$—iPr | $CH_2CMe_2F$ | $CH_2$—iPr |
| 27-17 | $CH_3$ | $CH_2$—iPr | $CH_2$—iPr | $CH_2$—iPr | $CH_2CMe_2F$ |
| 27-18 | $CH_3$ | $CH_2CMe_2F$ | $CH_2$—iPr | $CH_2CMe_2F$ | $CH_2$—iPr |
| 27-19 | $CH_3$ | $CH_2$—iPr | $CH_2CMe_2F$ | $CH_2$—iPr | $CH_2CMe_2F$ |
| 27-20 | $CH_3$ | $CH_2$—iPr | $CH_2CMe_2F$ | $CH_2CMe_2F$ | $CH_2$—iPr |

TABLE 27-continued

Compounds of formula (I), wherein $Cy^1$ and $Cy^2$ are

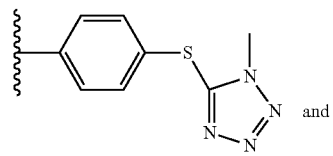

and unsubstituted phenyl, respectively; and
$R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 27-21 | CH₃ | CH₂CMe₂F | CH₂—iPr | CH₂—iPr | CH₂CMe₂F |
| 27-22 | CH₃ | CH₂—iPr | CH₂CMe₂F | CH₂CMe₂F | CH₂CMe₂F |
| 27-23 | CH₃ | CH₂CMe₂F | CH₂—iPr | CH₂CMe₂F | CH₂CMe₂F |
| 27-24 | CH₃ | CH₂CMe₂F | CH₂CMe₂F | CH₂—iPr | CH₂CMe₂F |
| 27-25 | CH₃ | CH₂CMe₂F | CH₂CMe₂F | CH₂CMe₂F | CH₂—iPr |
| 27-26 | CH₃ | CH₂CMe₂F | CH₂CMe₂F | CH₂CMe₂F | CH₂CMe₂F |
| 27-27 | CH₃ | CH₂—iPr | CH₂—iPr | CH₂—iPr | CH₂—iPr |
| 27-28 | CH₃ | CH₂—tBu | CH₂—tBu | CH₂—iPr | CH₂—iPr |
| 27-29 | CH₃ | CH₂—iPr | CH₂—iPr | CH₂—tBu | CH₂—tBu |
| 27-30 | CH₃ | CH₂CMe₂F | CH₂CMe₂F | CH₂—iPr | CH₂—iPr |
| 27-31 | CH₃ | CH₂—iPr | CH₂—iPr | CH₂CMe₂F | CH₂CMe₂F |
| 27-32 | CH₃ | CH₂CMe₂F | CH₂—tBu | CH₂CMe₂F | CH₂—tBu |
| 27-33 | CH₃ | CH₂CF₂Me | CH₂—iPr | CH₂CF₂Me | CH₂—iPr |
| 27-34 | CH₃ | CH₂CF₃ | CH₂—iPr | CH₂CF₃ | CH₂—iPr |
| 27-35 | CH₃ | CH₂CH(CF₃)₂ | CH₂—iPr | CH₂CH(CF₃)₂ | CH₂—iPr |
| 27-36 | CH₂F | CH₂CMe₂F | CH₂—iPr | CH₂CMe₂F | CH₂—iPr |
| 27-37 | H | CH₂CMe₂F | CH₂—iPr | CH₂CMe₂F | CH₂—iPr |
| 27-38 | Et | CH₂CMe₂F | CH₂—iPr | CH₂CMe₂F | CH₂—iPr |
| 27-39 | CH₂F | CH₂—iPr | CH₂—iPr | CH₂—iPr | CH₂—iPr |
| 27-40 | H | CH₂—iPr | CH₂—iPr | CH₂—iPr | CH₂—iPr |
| 27-41 | Et | CH₂—iPr | CH₂—iPr | CH₂—iPr | CH₂—iPr |
| 27-42 | H | CH₂CMe₂F | CH₂—tBu | CH₂CMe₂F | CH₂—tBu |
| 27-43 | CH₃ | CH₂CMe₂F | iPr | CH₂CMe₂F | iPr |
| 27-44 | CH₃ | CH₂CMe₂F | nPr | CH₂CMe₂F | nPr |
| 27-45 | CH₃ | CH₂CMe₂F | sBu | CH₂CMe₂F | sBu |
| 27-46 | CH₃ | CH₂CMe₂F | tBu | CH₂CMe₂F | tBu |
| 27-47 | CH₃ | CH₂CMe₂F | CH₂-p-biphenyl | CH₂CMe₂F | CH₂-p-biphenyl |
| 27-48 | CH₃ | CH₂CMe₂F | CH₂-p-tBuPh | CH₂CMe₂F | CH₂-p-tBuPh |
| 27-49 | CH₃ | CH₂CMe₂F | CH₃ | CH₂CMe₂F | CH₃ |
| 27-50 | H | CH₂CMe₂F | iPr | CH₂CMe₂F | iPr |
| 27-51 | CH₃ | CH₂CMe₂F | CH₂CH₂CMe₃ | CH₂CMe₂F | CH₂CH₂CMe₃ |
| 27-52 | CH₃ | CH₂CMe₂F | CH₂CH₂—iPr | CH₂CMe₂F | CH₂CH₂—iPr |
| 27-53 | CH₃ | CH₂-p-pyridyl | CH₂—iPr | CH₂-p-pyridyl | CH₂—iPr |
| 27-54 | CH₃ | CH₂-p-pyridyl | CH₂—tBu | CH₂-p-pyridyl | CH₂—tBu |

TABLE 28

Compounds of formula (I), wherein $Cy^1$ and $Cy^2$ are
p-nitrophenyl; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 28-1 | CH₃ | CH₂—tBu | CH₂—tBu | CH₂—tBu | CH₂—tBu |
| 28-2 | CH₃ | CH₂—tBu | CH₂—tBu | CH₂—iPr | CH₂—iPr |
| 28-3 | CH₃ | CH₂—iPr | CH₂—tBu | CH₂—iPr | CH₂—iPr |
| 28-4 | CH₃ | CH₂—iPr | CH₂—iPr | CH₂—tBu | CH₂—iPr |
| 28-5 | CH₃ | CH₂—iPr | CH₂—iPr | CH₂—iPr | CH₂—tBu |
| 28-6 | CH₃ | CH₂—iPr | CH₂—tBu | CH₂—iPr | CH₂—tBu |
| 28-7 | CH₃ | CH₂—tBu | CH₂—iPr | CH₂—tBu | CH₂—iPr |
| 28-8 | CH₃ | CH₂—iPr | CH₂—tBu | CH₂—tBu | CH₂—iPr |
| 28-9 | CH₃ | CH₂—tBu | CH₂—iPr | CH₂—iPr | CH₂—tBu |
| 28-10 | CH₃ | CH₂—iPr | CH₂—tBu | CH₂—tBu | CH₂—tBu |
| 28-11 | CH₃ | CH₂—tBu | CH₂—iPr | CH₂—tBu | CH₂—tBu |
| 28-12 | CH₃ | CH₂—tBu | CH₂—tBu | CH₂—iPr | CH₂—tBu |
| 28-13 | CH₃ | CH₂—tBu | CH₂—tBu | CH₂—tBu | CH₂—iPr |
| 28-14 | CH₃ | CH₂CMe₂F | CH₂—iPr | CH₂—iPr | CH₂—iPr |
| 28-15 | CH₃ | CH₂—iPr | CH₂CMe₂F | CH₂—iPr | CH₂—iPr |
| 28-16 | CH₃ | CH₂—iPr | CH₂—iPr | CH₂CMe₂F | CH₂—iPr |
| 28-17 | CH₃ | CH₂—iPr | CH₂—iPr | CH₂—iPr | CH₂CMe₂F |
| 28-18 | CH₃ | CH₂CMe₂F | CH₂—iPr | CH₂CMe₂F | CH₂—iPr |

TABLE 28-continued

Compounds of formula (I), wherein $Cy^1$ and $Cy^2$ are p-nitrophenyl; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 28-19 | $CH_3$ | $CH_2$—iPr | $CH_2CMe_2F$ | $CH_2$—iPr | $CH_2CMe_2F$ |
| 28-20 | $CH_3$ | $CH_2$—iPr | $CH_2CMe_2F$ | $CH_2CMe_2F$ | $CH_2$—iPr |
| 28-21 | $CH_3$ | $CH_2CMe_2F$ | $CH_2$—iPr | $CH_2$—iPr | $CH_2CMe_2F$ |
| 28-22 | $CH_3$ | $CH_2$—iPr | $CH_2CMe_2F$ | $CH_2CMe_2F$ | $CH_2CMe_2F$ |
| 28-23 | $CH_3$ | $CH_2CMe_2F$ | $CH_2$—iPr | $CH_2CMe_2F$ | $CH_2CMe_2F$ |
| 28-24 | $CH_3$ | $CH_2CMe_2F$ | $CH_2CMe_2F$ | $CH_2$—iPr | $CH_2CMe_2F$ |
| 28-25 | $CH_3$ | $CH_2CMe_2F$ | $CH_2CMe_2F$ | $CH_2CMe_2F$ | $CH_2$—iPr |
| 28-26 | $CH_3$ | $CH_2CMe_2F$ | $CH_2CMe_2F$ | $CH_2CMe_2F$ | $CH_2CMe_2F$ |
| 28-27 | $CH_3$ | $CH_2$—iPr | $CH_2$—iPr | $CH_2$—iPr | $CH_2$—iPr |
| 28-28 | $CH_3$ | $CH_2$—tBu | $CH_2$—tBu | $CH_2$—iPr | $CH_2$—iPr |
| 28-29 | $CH_3$ | $CH_2$—iPr | $CH_2$—iPr | $CH_2$—tBu | $CH_2$—tBu |
| 28-30 | $CH_3$ | $CH_2CMe_2F$ | $CH_2CMe_2F$ | $CH_2$—iPr | $CH_2$—iPr |
| 28-31 | $CH_3$ | $CH_2$—iPr | $CH_2$—iPr | $CH_2CMe_2F$ | $CH_2CMe_2F$ |
| 28-32 | $CH_3$ | $CH_2CMe_2F$ | $CH_2$—tBu | $CH_2CMe_2F$ | $CH_2$—tBu |
| 28-33 | $CH_3$ | $CH_2CF_2Me$ | $CH_2$—iPr | $CH_2CF_2Me$ | $CH_2$—iPr |
| 28-34 | $CH_3$ | $CH_2CF_3$ | $CH_2$—iPr | $CH_2CF_3$ | $CH_2$—iPr |
| 28-35 | $CH_3$ | $CH_2CH(CF_3)_2$ | $CH_2$—iPr | $CH_2CH(CF_3)_2$ | $CH_2$—iPr |
| 28-36 | $CH_2F$ | $CH_2CMe_2F$ | $CH_2$—iPr | $CH_2CMe_2F$ | $CH_2$—iPr |
| 28-37 | H | $CH_2CMe_2F$ | $CH_2$—iPr | $CH_2CMe_2F$ | $CH_2$—iPr |
| 28-38 | Et | $CH_2CMe_2F$ | $CH_2$—iPr | $CH_2CMe_2F$ | $CH_2$—iPr |
| 28-39 | $CH_2F$ | $CH_2$—iPr | $CH_2$—iPr | $CH_2$—iPr | $CH_2$—iPr |
| 28-40 | H | $CH_2$—iPr | $CH_2$—iPr | $CH_2$—iPr | $CH_2$—iPr |
| 28-41 | Et | $CH_2$—iPr | $CH_2$—iPr | $CH_2$—iPr | $CH_2$—iPr |
| 28-42 | H | $CH_2CMe_2F$ | $CH_2$—tBu | $CH_2CMe_2F$ | $CH_2$—tBu |
| 28-43 | $CH_3$ | $CH_2CMe_2F$ | iPr | $CH_2CMe_2F$ | iPr |
| 28-44 | $CH_3$ | $CH_2CMe_2F$ | nPr | $CH_2CMe_2F$ | nPr |
| 28-45 | $CH_3$ | $CH_2CMe_2F$ | sBu | $CH_2CMe_2F$ | sBu |
| 28-46 | $CH_3$ | $CH_2CMe_2F$ | tBu | $CH_2CMe_2F$ | tBu |
| 28-47 | $CH_3$ | $CH_2CMe_2F$ | $CH_2$-p-biphenyl | $CH_2CMe_2F$ | $CH_2$-p-biphenyl |
| 28-48 | $CH_3$ | $CH_2CMe_2F$ | $CH_2$—p-tBuPh | $CH_2CMe_2F$ | $CH_2$—p-tBuPh |
| 28-49 | $CH_3$ | $CH_2CMe_2F$ | $CH_3$ | $CH_2CMe_2F$ | $CH_3$ |
| 28-50 | H | $CH_2CMe_2F$ | iPr | $CH_2CMe_2F$ | iPr |
| 28-51 | $CH_3$ | $CH_2CMe_2F$ | $CH_2CH_2CMe_3$ | $CH_2CMe_2F$ | $CH_2CH_2CMe_3$ |
| 28-52 | $CH_3$ | $CH_2CMe_2F$ | $CH_2CH_2$—iPr | $CH_2CMe_2F$ | $CH_2CH_2$—iPr |
| 28-53 | $CH_3$ | $CH_2$-p-pyridyl | $CH_2$—iPr | $CH_2$-p-pyridyl | $CH_2$—iPr |
| 28-54 | $CH_3$ | $CH_2$-p-pyridyl | $CH_2$—tBu | $CH_2$-p-pyridyl | $CH_2$—tBu |

TABLE 29

Compounds of formula (I), wherein $Cy^1$ and $Cy^2$ are

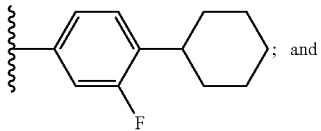

; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 29-1 | $CH_3$ | $CH_2$—tBu | $CH_2$—tBu | $CH_2$—tBu | $CH_2$—tBu |
| 29-2 | $CH_3$ | $CH_2$—tBu | $CH_2$—iPr | $CH_2$—iPr | $CH_2$—iPr |
| 29-3 | $CH_3$ | $CH_2$—iPr | $CH_2$—tBu | $CH_2$—iPr | $CH_2$—iPr |
| 29-4 | $CH_3$ | $CH_2$—iPr | $CH_2$—iPr | $CH_2$—tBu | $CH_2$—iPr |
| 29-5 | $CH_3$ | $CH_2$—iPr | $CH_2$—iPr | $CH_2$—iPr | $CH_2$—tBu |
| 29-6 | $CH_3$ | $CH_2$—iPr | $CH_2$—tBu | $CH_2$—iPr | $CH_2$—tBu |
| 29-7 | $CH_3$ | $CH_2$—tBu | $CH_2$—iPr | $CH_2$—tBu | $CH_2$—iPr |
| 29-8 | $CH_3$ | $CH_2$—iPr | $CH_2$—tBu | $CH_2$—tBu | $CH_2$—iPr |
| 29-9 | $CH_3$ | $CH_2$—tBu | $CH_2$—iPr | $CH_2$—iPr | $CH_2$—tBu |
| 29-10 | $CH_3$ | $CH_2$—iPr | $CH_2$—tBu | $CH_2$—tBu | $CH_2$—tBu |
| 29-11 | $CH_3$ | $CH_2$—tBu | $CH_2$—iPr | $CH_2$—tBu | $CH_2$—tBu |
| 29-12 | $CH_3$ | $CH_2$—tBu | $CH_2$—tBu | $CH_2$—iPr | $CH_2$—tBu |
| 29-13 | $CH_3$ | $CH_2$—tBu | $CH_2$—tBu | $CH_2$—tBu | $CH_2$—iPr |
| 29-14 | $CH_3$ | $CH_2CMe_2F$ | $CH_2$—iPr | $CH_2$—iPr | $CH_2$—iPr |
| 29-15 | $CH_3$ | $CH_2$—iPr | $CH_2CMe_2F$ | $CH_2$—iPr | $CH_2$—iPr |
| 29-16 | $CH_3$ | $CH_2$—iPr | $CH_2$—iPr | $CH_2CMe_2F$ | $CH_2$—iPr |
| 29-17 | $CH_3$ | $CH_2$—iPr | $CH_2$—iPr | $CH_2$—iPr | $CH_2CMe_2F$ |
| 29-18 | $CH_3$ | $CH_2CMe_2F$ | $CH_2$—iPr | $CH_2CMe_2F$ | $CH_2$—iPr |
| 29-19 | $CH_3$ | $CH_2$—iPr | $CH_2CMe_2F$ | $CH_2$—iPr | $CH_2CMe_2F$ |
| 29-20 | $CH_3$ | $CH_2$—iPr | $CH_2CMe_2F$ | $CH_2CMe_2F$ | $CH_2$—iPr |

TABLE 29-continued

Compounds of formula (I), wherein Cy¹ and Cy² are

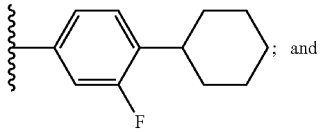

; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 29-21 | CH₃ | CH₂CMe₂F | CH₂—iPr | CH₂—iPr | CH₂CMe₂F |
| 29-22 | CH₃ | CH₂—iPr | CH₂CMe₂F | CH₂CMe₂F | CH₂CMe₂F |
| 29-23 | CH₃ | CH₂CMe₂F | CH₂—iPr | CH₂CMe₂F | CH₂CMe₂F |
| 29-24 | CH₃ | CH₂CMe₂F | CH₂CMe₂F | CH₂—iPr | CH₂CMe₂F |
| 29-25 | CH₃ | CH₂CMe₂F | CH₂CMe₂F | CH₂CMe₂F | CH₂—iPr |
| 29-26 | CH₃ | CH₂CMe₂F | CH₂CMe₂F | CH₂CMe₂F | CH₂CMe₂F |
| 29-27 | CH₃ | CH₂—iPr | CH₂—iPr | CH₂—iPr | CH₂—iPr |
| 29-28 | CH₃ | CH₂—tBu | CH₂—tBu | CH₂—iPr | CH₂—iPr |
| 29-29 | CH₃ | CH₂—iPr | CH₂—iPr | CH₂—tBu | CH₂—tBu |
| 29-30 | CH₃ | CH₂CMe₂F | CH₂CMe₂F | CH₂—iPr | CH₂—iPr |
| 29-31 | CH₃ | CH₂—iPr | CH₂—iPr | CH₂CMe₂F | CH₂CMe₂F |
| 29-32 | CH₃ | CH₂CMe₂F | CH₂—tBu | CH₂CMe₂F | CH₂—tBu |
| 29-33 | CH₃ | CH₂CF₂Me | CH₂—iPr | CH₂CF₂Me | CH₂—iPr |
| 29-34 | CH₃ | CH₂CF₃ | CH₂—iPr | CH₂CF₃ | CH₂—iPr |
| 29-35 | CH₃ | CH₂CH(CF₃)₂ | CH₂—iPr | CH₂CH(CF₃)₂ | CH₂—iPr |
| 29-36 | CH₂F | CH₂CMe₂F | CH₂—iPr | CH₂CMe₂F | CH₂—iPr |
| 29-37 | H | CH₂CMe₂F | CH₂—iPr | CH₂CMe₂F | CH₂—iPr |
| 29-38 | Et | CH₂CMe₂F | CH₂—iPr | CH₂CMe₂F | CH₂—iPr |
| 29-39 | CH₂F | CH₂—iPr | CH₂—iPr | CH₂—iPr | CH₂—iPr |
| 29-40 | H | CH₂—iPr | CH₂—iPr | CH₂—iPr | CH₂—iPr |
| 29-41 | Et | CH₂—iPr | CH₂—iPr | CH₂—iPr | CH₂—iPr |
| 29-42 | H | CH₂CMe₂F | CH₂—tBu | CH₂CMe₂F | CH₂—tBu |
| 29-43 | CH₃ | CH₂CMe₂F | iPr | CH₂CMe₂F | iPr |
| 29-44 | CH₃ | CH₂CMe₂F | nPr | CH₂CMe₂F | nPr |
| 29-45 | CH₃ | CH₂CMe₂F | sBu | CH₂CMe₂F | sBu |
| 29-46 | CH₃ | CH₂CMe₂F | tBu | CH₂CMe₂F | tBu |
| 29-47 | CH₃ | CH₂CMe₂F | CH₂-p-biphenyl | CH₂CMe₂F | CH₂-p-biphenyl |
| 29-48 | CH₃ | CH₂CMe₂F | CH₂-p-tBuPh | CH₂CMe₂F | CH₂-p-tBuPh |
| 29-49 | CH₃ | CH₂CMe₂F | CH₃ | CH₂CMe₂F | CH₃ |
| 29-50 | H | CH₂CMe₂F | iPr | CH₂CMe₂F | iPr |
| 29-51 | CH₃ | CH₂CMe₂F | CH₂CH₂CMe₃ | CH₂CMe₂F | CH₂CH₂CMe₃ |
| 29-52 | CH₃ | CH₂CMe₂F | CH₂CH₂—iPr | CH₂CMe₂F | CH₂CH₂—iPr |
| 29-53 | CH₃ | CH₂-p-pyridyl | CH₂—iPr | CH₂-p-pyridyl | CH₂—iPr |
| 29-54 | CH₃ | CH₂-p-pyridyl | CH₂—tBu | CH₂-p-pyridyl | CH₂—tBu |

TABLE 30

Compounds of formula (I), wherein Cy¹ and Cy² are

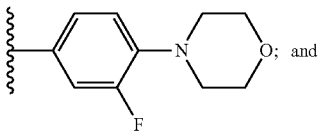

; and

Ra, Rb, R1 to R4 are as shown.

| Compound # | $R^a/R^b$ | $R^1$ | $R^2$ | $R^3$ | $R^4$ |
|---|---|---|---|---|---|
| 30-1 | CH₃ | CH₂—tBu | CH₂—tBu | CH₂—tBu | CH₂—tBu |
| 30-2 | CH₃ | CH₂—tBu | CH₂—iPr | CH₂—iPr | CH₂—iPr |
| 30-3 | CH₃ | CH₂—iPr | CH₂—tBu | CH₂—iPr | CH₂—iPr |
| 30-4 | CH₃ | CH₂—iPr | CH₂—iPr | CH₂—tBu | CH₂—iPr |
| 30-5 | CH₃ | CH₂—iPr | CH₂—iPr | CH₂—iPr | CH₂—tBu |
| 30-6 | CH₃ | CH₂—iPr | CH₂—tBu | CH₂—iPr | CH₂—tBu |
| 30-7 | CH₃ | CH₂—tBu | CH₂—iPr | CH₂—tBu | CH₂—iPr |
| 30-8 | CH₃ | CH₂—iPr | CH₂—tBu | CH₂—iPr | CH₂—iPr |
| 30-9 | CH₃ | CH₂—iPr | CH₂—iPr | CH₂—iPr | CH₂—tBu |
| 30-10 | CH₃ | CH₂—iPr | CH₂—tBu | CH₂—tBu | CH₂—tBu |
| 30-11 | CH₃ | CH₂—tBu | CH₂—tBu | CH₂—iPr | CH₂—tBu |
| 30-12 | CH₃ | CH₂—tBu | CH₂—tBu | CH₂—iPr | CH₂—tBu |
| 30-13 | CH₃ | CH₂—tBu | CH₂—tBu | CH₂—tBu | CH₂—iPr |

TABLE 30-continued

Compounds of formula (I), wherein $Cy^1$ and $Cy^2$ are

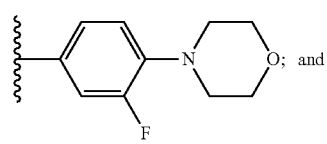; and $R^a$, $R^b$, R1 to R4 are as shown.

| Compound # | $R^a/R^b$ | $R^1$ | $R^2$ | $R^3$ | $R^4$ |
|---|---|---|---|---|---|
| 30-14 | $CH_3$ | $CH_2CMe_2F$ | $CH_2$—iPr | $CH_2$—iPr | $CH_2$—iPr |
| 30-15 | $CH_3$ | $CH_2$—iPr | $CH_2CMe_2F$ | $CH_2$—iPr | $CH_2$—iPr |
| 30-16 | $CH_3$ | $CH_2$—iPr | $CH_2$—iPr | $CH_2CMe_2F$ | $CH_2$—iPr |
| 30-17 | $CH_3$ | $CH_2$—iPr | $CH_2$—iPr | $CH_2$—iPr | $CH_2CMe_2F$ |
| 30-18 | $CH_3$ | $CH_2CMe_2F$ | $CH_2$—iPr | $CH_2CMe_2F$ | $CH_2$—iPr |
| 30-19 | $CH_3$ | $CH_2$—iPr | $CH_2CMe_2F$ | $CH_2$—iPr | $CH_2CMe_2F$ |
| 30-20 | $CH_3$ | $CH_2$—iPr | $CH_2CMe_2F$ | $CH_2CMe_2F$ | $CH_2$—iPr |
| 30-21 | $CH_3$ | $CH_2CMe_2F$ | $CH_2$—iPr | $CH_2$—iPr | $CH_2CMe_2F$ |
| 30-22 | $CH_3$ | $CH_2$—iPr | $CH_2CMe_2F$ | $CH_2CMe_2F$ | $CH_2CMe_2F$ |
| 30-23 | $CH_3$ | $CH_2CMe_2F$ | $CH_2$—iPr | $CH_2CMe_2F$ | $CH_2CMe_2F$ |
| 30-24 | $CH_3$ | $CH_2CMe_2F$ | $CH_2CMe_2F$ | $CH_2$—iPr | $CH_2CMe_2F$ |
| 30-25 | $CH_3$ | $CH_2CMe_2F$ | $CH_2CMe_2F$ | $CH_2CMe_2F$ | $CH_2$—iPr |
| 30-26 | $CH_3$ | $CH_2CMe_2F$ | $CH_2CMe_2F$ | $CH_2CMe_2F$ | $CH_2CMe_2F$ |
| 30-27 | $CH_3$ | $CH_2$—iPr | $CH_2$—iPr | $CH_2$—iPr | $CH_2$—iPr |
| 30-28 | $CH_3$ | $CH_2$—tBu | $CH_2$—tBu | $CH_2$—iPr | $CH_2$—iPr |
| 30-29 | $CH_3$ | $CH_2$—iPr | $CH_2$—iPr | $CH_2$—tBu | $CH_2$—tBu |
| 30-30 | $CH_3$ | $CH_2CMe_2F$ | $CH_2CMe_2F$ | $CH_2$—iPr | $CH_2$—iPr |
| 30-31 | $CH_3$ | $CH_2$—iPr | $CH_2$—iPr | $CH_2CMe_2F$ | $CH_2CMe_2F$ |
| 30-32 | $CH_3$ | $CH_2CMe_2F$ | $CH_2$—tBu | $CH_2CMe_2F$ | $CH_2$—tBu |
| 30-33 | $CH_3$ | $CH_2CF_2Me$ | $CH_2$—iPr | $CH_2CF_2Me$ | $CH_2$—iPr |
| 30-34 | $CH_3$ | $CH_2CF_3$ | $CH_2$—iPr | $CH_2CF_2Me$ | $CH_2$—iPr |
| 30-35 | $CH_3$ | $CH_2CH(CF_3)_2$ | $CH_2$—iPr | $CH_2CH(CF_3)_2$ | $CH_2$—iPr |
| 30-36 | $CH_2F$ | $CH_2CMe_2F$ | $CH_2$—iPr | $CH_2CMe_2F$ | $CH_2$—iPr |
| 30-37 | H | $CH_2CMe_2F$ | $CH_2$—iPr | $CH_2CMe_2F$ | $CH_2$—iPr |
| 30-38 | Et | $CH_2CMe_2F$ | $CH_2$—iPr | $CH_2CMe_2F$ | $CH_2$—iPr |
| 30-39 | $CH_2F$ | $CH_2$—iPr | $CH_2$—iPr | $CH_2$—iPr | $CH_2$—iPr |
| 30-40 | H | $CH_2$—iPr | $CH_2$—iPr | $CH_2$-iPr | $CH_2$—iPr |
| 30-41 | Et | $CH_2$—iPr | $CH_2$—iPr | $CH_2$—iPr | $CH_2$—iPr |
| 30-42 | H | $CH_2CMe_2F$ | $CH_2$—tBu | $CH_2CMe_2F$ | $CH_2$—tBu |
| 30-43 | $CH_3$ | $CH_2CMe_2F$ | iPr | $CH_2CMe_2F$ | iPr |
| 30-44 | $CH_3$ | $CH_2CMe_2F$ | nPr | $CH_2CMe_2F$ | nPr |
| 30-45 | $CH_3$ | $CH_2CMe_2F$ | sBu | $CH_2CMe_2F$ | sBu |
| 30-46 | $CH_3$ | $CH_2CMe_2F$ | tBu | $CH_2CMe_2F$ | tBu |
| 30-47 | $CH_3$ | $CH_2CMe_2F$ | $CH_2$-p-biphenyl | $CH_2CMe_2F$ | $CH_2$-p-biphenyl |
| 30-48 | $CH_3$ | $CH_2CMe_2F$ | $CH_2$-p-tBuPh | $CH_2CMe_2F$ | $CH_2$-p-tBuPh |
| 30-49 | $CH_3$ | $CH_2CMe_2F$ | $CH_3$ | $CH_2CMe_2F$ | $CH_3$ |
| 30-50 | H | $CH_2CMe_2F$ | iPr | $CH_2CMe_2F$ | iPr |
| 30-51 | $CH_3$ | $CH_2CMe_2F$ | $CH_2CH_2CMe_3$ | $CH_2CMe_2F$ | $CH_2CH_2CMe_3$ |
| 30-52 | $CH_3$ | $CH_2CMe_2F$ | $CH_2CH_2$—iPr | $CH_2CMe_2F$ | $CH_2CH_2$—iPr |
| 30-53 | $CH_3$ | $CH_2$-p-pyridyl | $CH_2$—iPr | $CH_2$-p-pyridyl | $CH_2$—iPr |
| 30-54 | $CH_3$ | $CH_2$-p-pyridyl | $CH_2$—tBu | $CH_2$-p-pyridyl | $CH_2$—tBu |

TABLE 31

Compounds of formula (I), wherein $Cy^1$ and $Cy^2$ are

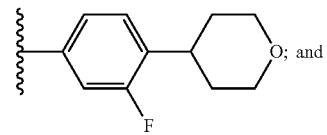 [SMILES: *c1ccc(C2CCOCC2)c(F)c1 ; "and"]; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 31-1 | $CH_3$ | $CH_2$-tBu | $CH_2$-tBu | $CH_2$-tBu | $CH_2$-tBu |
| 31-2 | $CH_3$ | $CH_2$-tBu | $CH_2$-iPr | $CH_2$-iPr | $CH_2$-iPr |
| 31-3 | $CH_3$ | $CH_2$-iPr | $CH_2$-tBu | $CH_2$-iPr | $CH_2$-iPr |
| 31-4 | $CH_3$ | $CH_2$-iPr | $CH_2$-iPr | $CH_2$-tBu | $CH_2$-iPr |
| 31-5 | $CH_3$ | $CH_2$-iPr | $CH_2$-iPr | $CH_2$-iPr | $CH_2$-tBu |
| 31-6 | $CH_3$ | $CH_2$-iPr | $CH_2$-tBu | $CH_2$-iPr | $CH_2$-tBu |

TABLE 31-continued

Compounds of formula (I), wherein Cy¹ and Cy² are

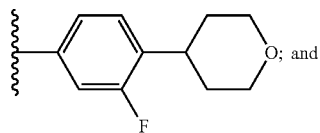

O; and

R$^a$, R$^b$, R$^1$ to R$^4$ are as shown.

| Compound # | R$^a$/R$^b$ | R$^1$ | R$^2$ | R$^3$ | R$^4$ |
| --- | --- | --- | --- | --- | --- |
| 31-7 | CH$_3$ | CH$_2$-tBu | CH$_2$-iPr | CH$_2$-tBu | CH$_2$-iPr |
| 31-8 | CH$_3$ | CH$_2$-iPr | CH$_2$-tBu | CH$_2$-tBu | CH$_2$-iPr |
| 31-9 | CH$_3$ | CH$_2$-tBu | CH$_2$-iPr | CH$_2$-iPr | CH$_2$-tBu |
| 31-10 | CH$_3$ | CH$_2$-iPr | CH$_2$-tBu | CH$_2$-tBu | CH$_2$-tBu |
| 31-11 | CH$_3$ | CH$_2$-tBu | CH$_2$-iPr | CH$_2$-tBu | CH$_2$-tBu |
| 31-12 | CH$_3$ | CH$_2$-tBu | CH$_2$-tBu | CH$_2$-iPr | CH$_2$-tBu |
| 31-13 | CH$_3$ | CH$_2$-tBu | CH$_2$-tBu | CH$_2$-tBu | CH$_2$-iPr |
| 31-14 | CH$_3$ | CH$_2$CMe$_2$F | CH$_2$-iPr | CH$_2$-iPr | CH$_2$-iPr |
| 31-15 | CH$_3$ | CH$_2$-iPr | CH$_2$CMe$_2$F | CH$_2$-iPr | CH$_2$-iPr |
| 31-16 | CH$_3$ | CH$_2$-iPr | CH$_2$-iPr | CH$_2$CMe$_2$F | CH$_2$-iPr |
| 31-17 | CH$_3$ | CH$_2$-iPr | CH$_2$-iPr | CH$_2$-iPr | CH$_2$CMe$_2$F |
| 31-18 | CH$_3$ | CH$_2$CMe$_2$F | CH$_2$-iPr | CH$_2$CMe$_2$F | CH$_2$-iPr |
| 31-19 | CH$_3$ | CH$_2$-iPr | CH$_2$CMe$_2$F | CH$_2$-iPr | CH$_2$CMe$_2$F |
| 31-20 | CH$_3$ | CH$_2$-iPr | CH$_2$CMe$_2$F | CH$_2$CMe$_2$F | CH$_2$-iPr |
| 31-21 | CH$_3$ | CH$_2$CMe$_2$F | CH$_2$-iPr | CH$_2$-iPr | CH$_2$CMe$_2$F |
| 31-22 | CH$_3$ | CH$_2$-iPr | CH$_2$CMe$_2$F | CH$_2$CMe$_2$F | CH$_2$CMe$_2$F |
| 31-23 | CH$_3$ | CH$_2$CMe$_2$F | CH$_2$-iPr | CH$_2$CMe$_2$F | CH$_2$CMe$_2$F |
| 31-24 | CH$_3$ | CH$_2$CMe$_2$F | CH$_2$CMe$_2$F | CH$_2$-iPr | CH$_2$CMe$_2$F |
| 31-25 | CH$_3$ | CH$_2$CMe$_2$F | CH$_2$CMe$_2$F | CH$_2$CMe$_2$F | CH$_2$-iPr |
| 31-26 | CH$_3$ | CH$_2$CMe$_2$F | CH$_2$CMe$_2$F | CH$_2$CMe$_2$F | CH$_2$CMe$_2$F |
| 31-27 | CH$_3$ | CH$_2$-iPr | CH$_2$-iPr | CH$_2$-iPr | CH$_2$-iPr |
| 31-28 | CH$_3$ | CH$_2$-tBu | CH$_2$-tBu | CH$_2$-iPr | CH$_2$-iPr |
| 31-29 | CH$_3$ | CH$_2$-iPr | CH$_2$-iPr | CH$_2$-tBu | CH$_2$-tBu |
| 31-30 | CH$_3$ | CH$_2$CMe$_2$F | CH$_2$CMe$_2$F | CH$_2$-iPr | CH$_2$-iPr |
| 31-31 | CH$_3$ | CH$_2$-iPr | CH$_2$-iPr | CH$_2$CMe$_2$F | CH$_2$CMe$_2$F |
| 31-32 | CH$_3$ | CH$_2$CMe$_2$F | CH$_2$-tBu | CH$_2$CMe$_2$F | CH$_2$-tBu |
| 31-33 | CH$_3$ | CH$_2$CF$_2$Me | CH$_2$-iPr | CH$_2$CF$_2$Me | CH$_2$-iPr |
| 31-34 | CH$_3$ | CH$_2$CF$_3$ | CH$_2$-iPr | CH$_2$CF$_3$ | CH$_2$-iPr |
| 31-35 | CH$_3$ | CH$_2$CH(CF$_3$)$_2$ | CH$_2$-iPr | CH$_2$CH(CF$_3$)$_2$ | CH$_2$-iPr |
| 31-36 | CH$_2$F | CH$_2$CMe$_2$F | CH$_2$-iPr | CH$_2$CMe$_2$F | CH$_2$-iPr |
| 31-37 | H | CH$_2$CMe$_2$F | CH$_2$-iPr | CH$_2$CMe$_2$F | CH$_2$-iPr |
| 31-38 | Et | CH$_2$CMe$_2$F | CH$_2$-iPr | CH$_2$CMe$_2$F | CH$_2$-iPr |
| 31-39 | CH$_2$F | CH$_2$-iPr | CH$_2$-iPr | CH$_2$-iPr | CH$_2$-iPr |
| 31-40 | H | CH$_2$-iPr | CH$_2$-iPr | CH$_2$-iPr | CH$_2$-iPr |
| 31-41 | Et | CH$_2$-iPr | CH$_2$-iPr | CH$_2$-iPr | CH$_2$-iPr |
| 31-42 | H | CH$_2$CMe$_2$F | CH$_2$-tBu | CH$_2$CMe$_2$F | CH$_2$-tBu |
| 31-43 | CH$_3$ | CH$_2$CMe$_2$F | iPr | CH$_2$CMe$_2$F | iPr |
| 31-44 | CH$_3$ | CH$_2$CMe$_2$F | nPr | CH$_2$CMe$_2$F | nPr |
| 31-45 | CH$_3$ | CH$_2$CMe$_2$F | sBu | CH$_2$CMe$_2$F | sBu |
| 31-46 | CH$_3$ | CH$_2$CMe$_2$F | tBu | CH$_2$CMe$_2$F | tBu |
| 31-47 | CH$_3$ | CH$_2$CMe$_2$F | CH$_2$-p-biphenyl | CH$_2$CMe$_2$F | CH$_2$-p-biphenyl |
| 31-48 | CH$_3$ | CH$_2$CMe$_2$F | CH$_2$-p-tBuPh | CH$_2$CMe$_2$F | CH$_2$-p-tBuPh |
| 31-49 | CH$_3$ | CH$_2$CMe$_2$F | CH$_3$ | CH$_2$CMe$_2$F | CH$_3$ |
| 31-50 | H | CH$_2$CMe$_2$F | iPr | CH$_2$CMe$_2$F | iPr |
| 31-51 | CH$_3$ | CH$_2$CMe$_2$F | CH$_2$CH$_2$CMe$_3$ | CH$_2$CMe$_2$F | CH$_2$CH$_2$CMe$_3$ |
| 31-52 | CH$_3$ | CH$_2$CMe$_2$F | CH$_2$CH$_2$-iPr | CH$_2$CMe$_2$F | CH$_2$CH$_2$-iPr |
| 31-53 | CH$_3$ | CH$_2$-p-pyridyl | CH$_2$-iPr | CH$_2$-p-pyridyl | CH$_2$-iPr |
| 31-54 | CH$_3$ | CH$_2$-p-pyridyl | CH$_2$-tBu | CH$_2$-p-pyridyl | CH$_2$-tBu |

TABLE 32

Compounds of formula (I), wherein $Cy^1$ and $Cy^2$ are

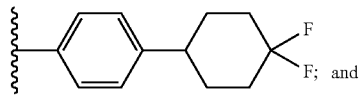 [SMILES: *c1ccc(C2CCC(F)(F)CC2)cc1 ; "and"]

F; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 32-1 | $CH_3$ | $CH_2$-tBu | $CH_2$-tBu | $CH_2$-tBu | $CH_2$-tBu |
| 32-2 | $CH_3$ | $CH_2$-tBu | $CH_2$-iPr | $CH_2$-iPr | $CH_2$-iPr |
| 32-3 | $CH_3$ | $CH_2$-iPr | $CH_2$-tBu | $CH_2$-iPr | $CH_2$-iPr |
| 32-4 | $CH_3$ | $CH_2$-iPr | $CH_2$-iPr | $CH_2$-tBu | $CH_2$-iPr |
| 32-5 | $CH_3$ | $CH_2$-iPr | $CH_2$-iPr | $CH_2$-iPr | $CH_2$-tBu |
| 32-6 | $CH_3$ | $CH_2$-iPr | $CH_2$-tBu | $CH_2$-iPr | $CH_2$-tBu |
| 32-7 | $CH_3$ | $CH_2$-tBu | $CH_2$-iPr | $CH_2$-tBu | $CH_2$-iPr |
| 32-8 | $CH_3$ | $CH_2$-iPr | $CH_2$-tBu | $CH_2$-tBu | $CH_2$-iPr |
| 32-9 | $CH_3$ | $CH_2$-tBu | $CH_2$-iPr | $CH_2$-iPr | $CH_2$-tBu |
| 32-10 | $CH_3$ | $CH_2$-iPr | $CH_2$-tBu | $CH_2$-tBu | $CH_2$-tBu |
| 32-11 | $CH_3$ | $CH_2$-tBu | $CH_2$-iPr | $CH_2$-tBu | $CH_2$-tBu |
| 32-12 | $CH_3$ | $CH_2$-tBu | $CH_2$-tBu | $CH_2$-iPr | $CH_2$-tBu |
| 32-13 | $CH_3$ | $CH_2$-tBu | $CH_2$-tBu | $CH_2$-tBu | $CH_2$-iPr |
| 32-14 | $CH_3$ | $CH_2CMe_2F$ | $CH_2$-iPr | $CH_2$-iPr | $CH_2$-iPr |
| 32-15 | $CH_3$ | $CH_2$-iPr | $CH_2CMe_2F$ | $CH_2$-iPr | $CH_2$-iPr |
| 32-16 | $CH_3$ | $CH_2$-iPr | $CH_2$-iPr | $CH_2CMe_2F$ | $CH_2$-iPr |
| 32-17 | $CH_3$ | $CH_2$-iPr | $CH_2$-iPr | $CH_2$-iPr | $CH_2CMe_2F$ |
| 32-18 | $CH_3$ | $CH_2CMe_2F$ | $CH_2$-iPr | $CH_2CMe_2F$ | $CH_2$-iPr |
| 32-19 | $CH_3$ | $C_2$-iPr | $CH_2CMe_2F$ | $CH_2$-iPr | $CH_2CMe_2F$ |
| 32-20 | $CH_3$ | $CH_2$-iPr | $CH_2CMe_2F$ | $CH_2CMe_2F$ | $CH_2$-iPr |
| 32-21 | $CH_3$ | $CH_2CMe_2F$ | $CH_2$-iPr | $CH_2$-iPr | $CH_2CMe_2F$ |
| 32-22 | $CH_3$ | $CH_2$-iPr | $CH_2CMe_2F$ | $CH_2CMe_2F$ | $CH_2CMe_2F$ |
| 32-23 | $CH_3$ | $CH_2CMe_2F$ | $CH_2$-iPr | $CH_2CMe_2F$ | $CH_2CMe_2F$ |
| 32-24 | $CH_3$ | $CH_2CMe_2F$ | $CH_2CMe_2F$ | $CH_2$-iPr | $CH_2CMe_2F$ |
| 32-25 | $CH_3$ | $CH_2CMe_2F$ | $CH_2CMe_2F$ | $CH_2CMe_2F$ | $CH_2$-iPr |
| 32-26 | $CH_3$ | $CH_2CMe_2F$ | $CH_2CMe_2F$ | $CH_2CMe_2F$ | $CH_2CMe_2F$ |
| 32-27 | $CH_3$ | $CH_2$-iPr | $CH_2$-iPr | $CH_2$-iPr | $CH_2$-iPr |
| 32-28 | $CH_3$ | $CH_2$-tBu | $CH_2$-tBu | $CH_2$-iPr | $CH_2$-iPr |
| 32-29 | $CH_3$ | $CH_2$-iPr | $CH_2$-iPr | $CH_2$-tBu | $CH_2$-tBu |
| 32-30 | $CH_3$ | $CH_2CMe_2F$ | $CH_2CMe_2F$ | $CH_2$-iPr | $CH_2$-iPr |
| 32-31 | $CH_3$ | $CH_2$-iPr | $CH_2$-iPr | $CH_2CMe_2F$ | $CH_2CMe_2F$ |
| 32-32 | $CH_3$ | $CH_2CMe_2F$ | $CH_2$-tBu | $CH_2CMe_2F$ | $CH_2$-tBu |
| 32-33 | $CH_3$ | $CH_2CF_2Me$ | $CH_2$-iPr | $CH_2CF_2Me$ | $CH_2$-iPr |
| 32-34 | $CH_3$ | $CH_2CF_3$ | $CH_2$-iPr | $CH_2CF_3$ | $CH_2$-iPr |
| 32-35 | $CH_3$ | $CH_2CH(CF_3)_2$ | $CH_2$-iPr | $CH_2CH(CF_3)_2$ | $CH_2$-iPr |
| 32-36 | $CH_2F$ | $CH_2CMe_2F$ | $CH_2$-iPr | $CH_2CMe_2F$ | $CH_2$-iPr |
| 32-37 | H | $CH_2CMe_2F$ | $CH_2$-iPr | $CH_2CMe_2F$ | $CH_2$-iPr |
| 32-38 | Et | $CH_2CMe_2F$ | $CH_2$-iPr | $CH_2CMe_2F$ | $CH_2$-iPr |
| 32-39 | $CH_2F$ | $CH_2$-iPr | $CH_2$-iPr | $CH_2$-iPr | $CH_2$-iPr |
| 32-40 | H | $CH_2$-iPr | $CH_2$-iPr | $CH_2$-iPr | $CH_2$-iPr |
| 32-41 | Et | $CH_2$-iPr | $CH_2$-iPr | $CH_2$-iPr | $CH_2$-iPr |
| 32-42 | H | $CH_2CMe_2F$ | $CH_2$-tBu | $CH_2CMe_2F$ | $CH_2$-tBu |
| 32-43 | $CH_3$ | $CH_2CMe_2F$ | iPr | $CH_2CMe_2F$ | iPr |
| 32-44 | $CH_3$ | $CH_2CMe_2F$ | nPr | $CH_2CMe_2F$ | nPr |
| 32-45 | $CH_3$ | $CH_2CMe_2F$ | sBu | $CH_2CMe_2F$ | sBu |
| 32-46 | $CH_3$ | $CH_2CMe_2F$ | tBu | $CH_2CMe_2F$ | tBu |
| 32-47 | $CH_3$ | $CH_2CMe_2F$ | $CH_2$-p-biphenyl | $CH_2CMe_2F$ | $CH_2$-p-biphenyl |
| 32-48 | $CH_3$ | $CH_2CMe_2F$ | $CH_2$-p-tBuPh | $CH_2CMe_2F$ | $CH_2$-p-tBuPh |
| 32-49 | $CH_3$ | $CH_2CMe_2F$ | $CH_3$ | $CH_2CMe_2F$ | $CH_3$ |
| 32-50 | H | $CH_2CMe_2F$ | iPr | $CH_2CMe_2F$ | iPr |
| 32-51 | $CH_3$ | $CH_2CMe_2F$ | $CH_2CH_2CMe_3$ | $CH_2CMe_2F$ | $CH_2CH_2CMe_3$ |
| 32-52 | $CH_3$ | $CH_2CMe_2F$ | $CH_2CH_2$-iPr | $CH_2CMe_2F$ | $CH_2CH_2$-iPr |
| 32-53 | $CH_3$ | $CH_2$-p-pyridyl | $CH_2$-iPr | $CH_2$-p-pyridyl | $CH_2$-iPr |
| 32-54 | $CH_3$ | $CH_2$-p-pyridyl | $CH_2$-tBu | $CH_2$-p-pyridyl | $CH_2$-tBu |

TABLE 33

Compounds of formula (I), wherein $Cy^1$ and $Cy^2$ are

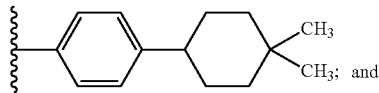; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 33-1 | CH₃ | CH₂-tBu | CH₂-tBu | CH₂-tBu | CH₂-tBu |
| 33-2 | CH₃ | CH₂-tBu | CH₂-iPr | CH₂-iPr | CH₂-iPr |
| 33-3 | CH₃ | CH₂-iPr | CH₂-tBu | CH₂-iPr | CH₂-iPr |
| 33-4 | CH₃ | CH₂-iPr | CH₂-iPr | CH₂-tBu | CH₂-iPr |
| 33-5 | CH₃ | CH₂-iPr | CH₂-iPr | CH₂-iPr | CH₂-tBu |
| 33-6 | CH₃ | CH₂-iPr | CH₂-tBu | CH₂-iPr | CH₂-tBu |
| 33-7 | CH₃ | CH₂-tBu | CH₂-iPr | CH₂-tBu | CH₂-iPr |
| 33-8 | CH₃ | CH₂-iPr | CH₂-tBu | CH₂-tBu | CH₂-iPr |
| 33-9 | CH₃ | CH₂-tBu | CH₂-iPr | CH₂-iPr | CH₂-tBu |
| 33-10 | CH₃ | CH₂-iPr | CH₂-tBu | CH₂-tBu | CH₂-tBu |
| 33-11 | CH₃ | CH₂-tBu | CH₂-iPr | CH₂-tBu | CH₂-tBu |
| 33-12 | CH₃ | CH₂-tBu | CH₂-tBu | CH₂-iPr | CH₂-tBu |
| 33-13 | CH₃ | CH₂-tBu | CH₂-tBu | CH₂-tBu | CH₂-iPr |
| 33-14 | CH₃ | CH₂CMe₂F | CH₂-iPr | CH₂-iPr | CH₂-iPr |
| 33-15 | CH₃ | CH₂-iPr | CH₂CMe₂F | CH₂-iPr | CH₂-iPr |
| 33-16 | CH₃ | CH₂-iPr | CH₂-iPr | CH₂CMe₂F | CH₂-iPr |
| 33-17 | CH₃ | CH₂-iPr | CH₂-iPr | CH₂-iPr | CH₂CMe₂F |
| 33-18 | CH₃ | CH₂CMe₂F | CH₂-iPr | CH₂CMe₂F | CH₂-iPr |
| 33-19 | CH₃ | CH₂-iPr | CH₂CMe₂F | CH₂-iPr | CH₂CMe₂F |
| 33-20 | CH₃ | CH₂-iPr | CH₂CMe₂F | CH₂CMe₂F | CH₂-iPr |
| 33-21 | CH₃ | CH₂CMe₂F | CH₂-iPr | CH₂-iPr | CH₂CMe₂F |
| 33-22 | CH₃ | CH₂-iPr | CH₂CMe₂F | CH₂CMe₂F | CH₂CMe₂F |
| 33-23 | CH₃ | CH₂CMe₂F | CH₂-iPr | CH₂CMe₂F | CH₂CMe₂F |
| 33-24 | CH₃ | CH₂CMe₂F | CH₂CMe₂F | CH₂-iPr | CH₂CMe₂F |
| 33-25 | CH₃ | CH₂CMe₂F | CH₂CMe₂F | CH₂CMe₂F | CH₂-iPr |
| 33-26 | CH₃ | CH₂CMe₂F | CH₂CMe₂F | CH₂CMe₂F | CH₂CMe₂F |
| 33-27 | CH₃ | CH₂-iPr | CH₂-iPr | CH₂-iPr | CH₂-iPr |
| 33-28 | CH₃ | CH₂-tBu | CH₂-tBu | CH₂-iPr | CH₂-iPr |
| 33-29 | CH₃ | CH₂-iPr | CH₂-iPr | CH₂-tBu | CH₂-tBu |
| 33-30 | CH₃ | CH₂CMe₂F | CH₂CMe₂F | CH₂-iPr | CH₂-iPr |
| 33-31 | CH₃ | CH₂-iPr | CH₂-iPr | CH₂CMe₂F | CH₂CMe₂F |
| 33-32 | CH₃ | CH₂CMe₂F | CH₂-tBu | CH₂CMe₂F | CH₂-tBu |
| 33-33 | CH₃ | CH₂CF₂Me | CH₂-iPr | CH₂CF₂Me | CH₂-iPr |
| 33-34 | CH₃ | CH₂CF₃ | CH₂-iPr | CH₂CF₃ | CH₂-iPr |
| 33-35 | CH₃ | CH₂CH(CF₃)₂ | CH₂-iPr | CH₂CH(CF₃)₂ | CH₂-iPr |
| 33-36 | CH₂F | CH₂CMe₂F | CH₂-iPr | CH₂CMe₂F | CH₂-iPr |
| 33-37 | H | CH₂CMe₂F | CH₂-iPr | CH₂CMe₂F | CH₂-iPr |
| 33-38 | Et | CH₂CMe₂F | CH₂-iPr | CH₂CMe₂F | CH₂-iPr |
| 33-39 | CH₂F | CH₂-iPr | CH₂-iPr | CH₂-iPr | CH₂-iPr |
| 33-40 | H | CH₂-iPr | CH₂-iPr | CH₂-iPr | CH₂-iPr |
| 33-41 | Et | CH₂-iPr | CH₂-iPr | CH₂-iPr | CH₂-iPr |
| 33-42 | H | CH₂CMe₂F | CH₂-tBu | CH₂CMe₂F | CH₂-tBu |
| 33-43 | CH₃ | CH₂CMe₂F | iPr | CH₂CMe₂F | iPr |
| 33-44 | CH₃ | CH₂CMe₂F | nPr | CH₂CMe₂F | nPr |
| 33-45 | CH₃ | CH₂CMe₂F | sBu | CH₂CMe₂F | sBu |
| 33-46 | CH₃ | CH₂CMe₂F | tBu | CH₂CMe₂F | tBu |
| 33-47 | CH₃ | CH₂CMe₂F | CH₂-p-biphenyl | CH₂CMe₂F | CH₂-p-biphenyl |
| 33-48 | CH₃ | CH₂CMe₂F | CH₂-p-tBuPh | CH₂CMe₂F | CH₂-p-tBuPh |
| 33-49 | CH₃ | CH₂CMe₂F | CH₃ | CH₂CMe₂F | CH₃ |
| 33-50 | H | CH₂CMe₂F | iPr | CH₂CMe₂F | iPr |
| 33-51 | CH₃ | CH₂CMe₂F | CH₂CH₂CMe₃ | CH₂CMe₂F | CH₂CH₂CMe₃ |
| 33-52 | CH₃ | CH₂CMe₂F | CH₂CH₂-iPr | CH₂CMe₂F | CH₂CH₂-iPr |
| 33-53 | CH₃ | CH₂-p-pyridyl | CH₂-iPr | CH₂-p-pyridyl | CH₂-iPr |
| 33-54 | CH₃ | CH₂-p-pyridyl | CH₂-tBu | CH₂-p-pyridyl | CH₂-tBu |

TABLE 34

Compounds of formula (I), wherein $Cy^1$ and $Cy^2$ are

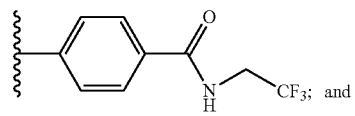; and $R^a$, $R^b$, $R^1$ to $R^4$ are as shown.

| Compound # | $R^a/R^b$ | $R^1$ | $R^2$ | $R^3$ | $R^4$ |
|---|---|---|---|---|---|
| 34-1 | $CH_3$ | $CH_2$-tBu | $CH_2$-tBu | $CH_2$-tBu | $CH_2$-tBu |
| 34-2 | $CH_3$ | $CH_2$-tBu | $CH_2$-iPr | $CH_2$-iPr | $CH_2$-iPr |
| 34-3 | $CH_3$ | $CH_2$-iPr | $CH_2$-tBu | $CH_2$-iPr | $CH_2$-iPr |
| 34-4 | $CH_3$ | $CH_2$-iPr | $CH_2$-iPr | $CH_2$-tBu | $CH_2$-iPr |
| 34-5 | $CH_3$ | $CH_2$-iPr | $CH_2$-iPr | $CH_2$-iPr | $CH_2$-tBu |
| 34-6 | $CH_3$ | $CH_2$-iPr | $CH_2$-tBu | $CH_2$-iPr | $CH_2$-tBu |
| 34-7 | $CH_3$ | $CH_2$-tBu | $CH_2$-iPr | $CH_2$-tBu | $CH_2$-iPr |
| 34-8 | $CH_3$ | $CH_2$-iPr | $CH_2$-tBu | $CH_2$-tBu | $CH_2$-iPr |
| 34-9 | $CH_3$ | $CH_2$-tBu | $CH_2$-iPr | $CH_2$-iPr | $CH_2$-tBu |
| 34-10 | $CH_3$ | $CH_2$-iPr | $CH_2$-tBu | $CH_2$-tBu | $CH_2$-tBu |
| 34-11 | $CH_3$ | $CH_2$-tBu | $CH_2$-iPr | $CH_2$-tBu | $CH_2$-tBu |
| 34-12 | $CH_3$ | $CH_2$-tBu | $CH_2$-tBu | $CH_2$-iPr | $CH_2$-tBu |
| 34-13 | $CH_3$ | $CH_2$-tBu | $CH_2$-tBu | $CH_2$-tBu | $CH_2$-iPr |
| 34-14 | $CH_3$ | $CH_2CMe_2F$ | $CH_2$-iPr | $CH_2$-iPr | $CH_2$-iPr |
| 34-15 | $CH_3$ | $CH_2$-iPr | $CH_2CMe_2F$ | $CH_2$-iPr | $CH_2$-iPr |
| 34-16 | $CH_3$ | $CH_2$-iPr | $CH_2$-iPr | $CH_2CMe_2F$ | $CH_2$-iPr |
| 34-17 | $CH_3$ | $CH_2$-iPr | $CH_2$-iPr | $CH_2$-iPr | $CH_2CMe_2F$ |
| 34-18 | $CH_3$ | $CH_2CMe_2F$ | $CH_2$-iPr | $CH_2CMe_2F$ | $CH_2$-iPr |
| 34-19 | $CH_3$ | $CH_2$-iPr | $CH_2CMe_2F$ | $CH_2$-iPr | $CH_2CMe_2F$ |
| 34-20 | $CH_3$ | $CH_2$-iPr | $CH_2CMe_2F$ | $CH_2CMe_2F$ | $CH_2$-iPr |
| 34-21 | $CH_3$ | $CH_2CMe_2F$ | $CH_2$-iPr | $CH_2$-iPr | $CH_2CMe_2F$ |
| 34-22 | $CH_3$ | $CH_2$-iPr | $CH_2CMe_2F$ | $CH_2CMe_2F$ | $CH_2CMe_2F$ |
| 34-23 | $CH_3$ | $CH_2CMe_2F$ | $CH_2$-iPr | $CH_2CMe_2F$ | $CH_2CMe_2F$ |
| 34-24 | $CH_3$ | $CH_2CMe_2F$ | $CH_2CMe_2F$ | $CH_2$-iPr | $CH_2CMe_2F$ |
| 34-25 | $CH_3$ | $CH_2CMe_2F$ | $CH_2CMe_2F$ | $CH_2CMe_2F$ | $CH_2$-iPr |
| 34-26 | $CH_3$ | $CH_2CMe_2F$ | $CH_2CMe_2F$ | $CH_2CMe_2F$ | $CH_2CMe_2F$ |
| 34-27 | $CH_3$ | $CH_2$-iPr | $CH_2$-iPr | $CH_2$-iPr | $CH_2$-iPr |
| 34-28 | $CH_3$ | $CH_2$-tBu | $CH_2$-tBu | $CH_2$-iPr | $CH_2$-iPr |
| 34-29 | $CH_3$ | $CH_2$-iPr | $CH_2$-iPr | $CH_2$-tBu | $CH_2$-tBu |
| 34-30 | $CH_3$ | $CH_2CMe_2F$ | $CH_2CMe_2F$ | $CH_2$-iPr | $CH_2$-iPr |
| 34-31 | $CH_3$ | $CH_2$-iPr | $CH_2$-iPr | $CH_2CMe_2F$ | $CH_2CMe_2F$ |
| 34-32 | $CH_3$ | $CH_2CMe_2F$ | $CH_2$-tBu | $CH_2CMe_2F$ | $CH_2$-tBu |
| 34-33 | $CH_3$ | $CH_2CF_2Me$ | $CH_2$-iPr | $CH_2CF_2Me$ | $CH_2$-iPr |
| 34-34 | $CH_3$ | $CH_2CF_3$ | $CH_2$-iPr | $CH_2CF_3$ | $CH_2$-iPr |
| 34-35 | $CH_3$ | $CH_2CH(CF_3)_2$ | $CH_2$-iPr | $CH_2CH(CF_3)_2$ | $CH_2$-iPr |
| 34-36 | $CH_2F$ | $CH_2CMe_2F$ | $CH_2$-iPr | $CH_2CMe_2F$ | $CH_2$-iPr |
| 34-37 | H | $CH_2CMe_2F$ | $CH_2$-iPr | $CH_2CMe_2F$ | $CH_2$-iPr |
| 34-38 | Et | $CH_2CMe_2F$ | $CH_2$-iPr | $CH_2CMe_2F$ | $CH_2$-iPr |
| 34-39 | $CH_2F$ | $CH_2$-iPr | $CH_2$-iPr | $CH_2$-iPr | $CH_2$-iPr |
| 34-40 | H | $CH_2$-iPr | $CH_2$-iPr | $CH_2$-iPr | $CH_2$-iPr |
| 34-41 | Et | $CH_2$-iPr | $CH_2$-iPr | $CH_2$-iPr | $CH_2$-iPr |
| 34-42 | H | $CH_2CMe_2F$ | $CH_2$-tBu | $CH_2CMe_2F$ | $CH_2$-tBu |
| 34-43 | $CH_3$ | $CH_2CMe_2F$ | iPr | $CH_2CMe_2F$ | iPr |
| 34-44 | $CH_3$ | $CH_2CMe_2F$ | nPr | $CH_2CMe_2F$ | nPr |
| 34-45 | $CH_3$ | $CH_2CMe_2F$ | sBu | $CH_2CMe_2F$ | sBu |
| 34-46 | $CH_3$ | $CH_2CMe_2F$ | tBu | $CH_2CMe_2F$ | tBu |
| 34-47 | $CH_3$ | $CH_2CMe_2F$ | $CH_2$-p-biphenyl | $CH_2CMe_2F$ | $CH_2$-p-biphenyl |
| 34-48 | $CH_3$ | $CH_2CMe_2F$ | $CH_2$-p-tBuPh | $CH_2CMe_2F$ | $CH_2$-p-tBuPh |
| 34-49 | $CH_3$ | $CH_2CMe_2F$ | $CH_3$ | $CH_2CMe_2F$ | $CH_3$ |
| 34-50 | H | $CH_2CMe_2F$ | iPr | $CH_2CMe_2F$ | iPr |
| 34-51 | $CH_3$ | $CH_2CMe_2F$ | $CH_2CH_2CMe_3$ | $CH_2CMe_2F$ | $CH_2CH_2CMe_3$ |
| 34-52 | $CH_3$ | $CH_2CMe_2F$ | $CH_2CH_2$-iPr | $CH_2CMe_2F$ | $CH_2CH_2$-iPr |
| 34-53 | $CH_3$ | $CH_2$-p-pyridyl | $CH_2$-iPr | $CH_2$-p-pyridyl | $CH_2$-iPr |
| 34-54 | $CH_3$ | $CH_2$-p-pyridyl | $CH_2$-tBu | $CH_2$-p-pyridyl | $CH_2$-tBu |

TABLE 35

Compounds of formula (I), wherein Cy¹ and Cy² are

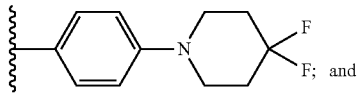

and

Rᵃ, Rᵇ, R¹ to R⁴ are as shown.

| Compound # | Rᵃ/Rᵇ | R¹ | R² | R³ | R⁴ |
|---|---|---|---|---|---|
| 35-1 | CH₃ | CH₂-tBu | CH₂-tBu | CH₂-tBu | CH₂-tBu |
| 35-2 | CH₃ | CH₂-tBu | CH₂-iPr | CH₂-iPr | CH₂-iPr |
| 35-3 | CH₃ | CH₂-iPr | CH₂-tBu | CH₂-iPr | CH₂-iPr |
| 35-4 | CH₃ | CH₂-iPr | CH₂-iPr | CH₂-tBu | CH₂-iPr |
| 35-5 | CH₃ | CH₂-iPr | CH₂-iPr | CH₂-iPr | CH₂-tBu |
| 35-6 | CH₃ | CH₂-iPr | CH₂-tBu | CH₂-iPr | CH₂-tBu |
| 35-7 | CH₃ | CH₂-tBu | CH₂-iPr | CH₂-tBu | CH₂-iPr |
| 35-8 | CH₃ | CH₂-iPr | CH₂-tBu | CH₂-tBu | CH₂-iPr |
| 35-9 | CH₃ | CH₂-tBu | CH₂-iPr | CH₂-iPr | CH₂-tBu |
| 35-10 | CH₃ | CH₂-iPr | CH₂-tBu | CH₂-tBu | CH₂-tBu |
| 35-11 | CH₃ | CH₂-tBu | CH₂-iPr | CH₂-tBu | CH₂-tBu |
| 35-12 | CH₃ | CH₂-tBu | CH₂-tBu | CH₂-iPr | CH₂-tBu |
| 35-13 | CH₃ | CH₂-tBu | CH₂-tBu | CH₂-tBu | CH₂-iPr |
| 35-14 | CH₃ | CH₂CMe₂F | CH₂-iPr | CH₂-iPr | CH₂-iPr |
| 35-15 | CH₃ | CH₂-iPr | CH₂CMe₂F | CH₂-iPr | CH₂-iPr |
| 35-16 | CH₃ | CH₂-iPr | CH₂-iPr | CH₂CMe₂F | CH₂-iPr |
| 35-17 | CH₃ | CH₂-iPr | CH₂-iPr | CH₂-iPr | CH₂CMe₂F |
| 35-18 | CH₃ | CH₂CMe₂F | CH₂-iPr | CH₂CMe₂F | CH₂-iPr |
| 35-19 | CH₃ | CH₂-iPr | CH₂CMe₂F | CH₂-iPr | CH₂CMe₂F |
| 35-20 | CH₃ | CH₂-iPr | CH₂CMe₂F | CH₂CMe₂F | CH₂-iPr |
| 35-21 | CH₃ | CH₂CMe₂F | CH₂-iPr | CH₂-iPr | CH₂CMe₂F |
| 35-22 | CH₃ | CH₂-iPr | CH₂CMe₂F | CH₂CMe₂F | CH₂CMe₂F |
| 35-23 | CH₃ | CH₂CMe₂F | CH₂-iPr | CH₂CMe₂F | CH₂CMe₂F |
| 35-24 | CH₃ | CH₂CMe₂F | CH₂CMe₂F | CH₂-iPr | CH₂CMe₂F |
| 35-25 | CH₃ | CH₂CMe₂F | CH₂CMe₂F | CH₂CMe₂F | CH₂-iPr |
| 35-26 | CH₃ | CH₂CMe₂F | CH₂CMe₂F | CH₂CMe₂F | CH₂CMe₂F |
| 35-27 | CH₃ | CH₂-iPr | CH₂-iPr | CH₂-iPr | CH₂-iPr |
| 35-28 | CH₃ | CH₂-tBu | CH₂-tBu | CH₂-iPr | CH₂-iPr |
| 35-29 | CH₃ | CH₂-iPr | CH₂-iPr | CH₂-tBu | CH₂-tBu |
| 35-30 | CH₃ | CH₂CMe₂F | CH₂CMe₂F | CH₂-iPr | CH₂-iPr |
| 35-31 | CH₃ | CH₂-iPr | CH₂-iPr | CH₂CMe₂F | CH₂CMe₂F |
| 35-32 | CH₃ | CH₂CMe₂F | CH₂-tBu | CH₂CMe₂F | CH₂-tBu |
| 35-33 | CH₃ | CH₂CF₂Me | CH₂-iPr | CH₂CF₂Me | CH₂-iPr |
| 35-34 | CH₃ | CH₂CF₃ | CH₂-iPr | CH₂CF₃ | CH₂-iPr |
| 35-35 | CH₃ | CH₂CH(CF₃)₂ | CH₂-iPr | CH₂CH(CF₃)₂ | CH₂-iPr |
| 35-36 | CH₂F | CH₂CMe₂F | CH₂-iPr | CH₂CMe₂F | CH₂-iPr |
| 35-37 | H | CH₂CMe₂F | CH₂-iPr | CH₂CMe₂F | CH₂-iPr |
| 35-38 | Et | CH₂CMe₂F | CH₂-iPr | CH₂CMe₂F | CH₂-iPr |
| 35-39 | CH₂F | CH₂-iPr | CH₂-iPr | CH₂-iPr | CH₂-iPr |
| 35-40 | H | CH₂-iPr | CH₂-iPr | CH₂-iPr | CH₂-iPr |
| 35-41 | Et | CH₂-iPr | CH₂-iPr | CH₂-iPr | CH₂-iPr |
| 35-42 | H | CH₂CMe₂F | CH₂-tBu | CH₂CMe₂F | CH₂-tBu |
| 35-43 | CH₃ | CH₂CMe₂F | iPr | CH₂CMe₂F | iPr |
| 35-44 | CH₃ | CH₂CMe₂F | nPr | CH₂CMe₂F | nPr |
| 35-45 | CH₃ | CH₂CMe₂F | sBu | CH₂CMe₂F | sBu |
| 35-46 | CH₃ | CH₂CMe₂F | tBu | CH₂CMe₂F | tBu |
| 35-47 | CH₃ | CH₂CMe₂F | CH₂-p-biphenyl | CH₂CMe₂F | CH₂-p-biphenyl |
| 35-48 | CH₃ | CH₂CMe₂F | CH₂-p-tBuPh | CH₂CMe₂F | CH₂-p-tBuPh |
| 35-49 | CH₃ | CH₂CMe₂F | CH₃ | CH₂CMe₂F | CH₃ |
| 35-50 | H | CH₂CMe₂F | iPr | CH₂CMe₂F | iPr |
| 35-51 | CH₃ | CH₂CMe₂F | CH₂CH₂CMe₃ | CH₂CMe₂F | CH₂CH₂CMe₃ |
| 35-52 | CH₃ | CH₂CMe₂F | CH₂CH₂-iPr | CH₂CMe₂F | CH₂CH₂-iPr |
| 35-53 | CH₃ | CH₂-p-pyridyl | CH₂-iPr | CH₂-p-pyridyl | CH₂-iPr |
| 35-54 | CH₃ | CH₂-p-pyridyl | CH₂-tBu | CH₂-p-pyridyl | CH₂-tBu |

TABLE 36

Compounds of formula (I), wherein Cy¹ and Cy² are

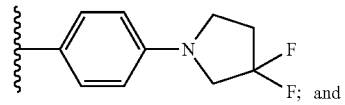 [SMILES: *c1ccc(N2CCC(F)(F)C2)cc1 ; "and"]; and

Rᵃ, Rᵇ, R¹ to R⁴ are as shown.

| Compound # | Rᵃ/Rᵇ | R¹ | R² | R³ | R⁴ |
|---|---|---|---|---|---|
| 36-1 | CH₃ | CH₂-tBu | CH₂-tBu | CH₂-tBu | CH₂-tBu |
| 36-2 | CH₃ | CH₂-tBu | CH₂-iPr | CH₂-iPr | CH₂-iPr |
| 36-3 | CH₃ | CH₂-iPr | CH₂-tBu | CH₂-iPr | CH₂-iPr |
| 36-4 | CH₃ | CH₂-iPr | CH₂-iPr | CH₂-tBu | CH₂-iPr |
| 36-5 | CH₃ | CH₂-iPr | CH₂-iPr | CH₂-iPr | CH₂-tBu |
| 36-6 | CH₃ | CH₂-iPr | CH₂-tBu | CH₂-iPr | CH₂-tBu |
| 36-7 | CH₃ | CH₂-tBu | CH₂-iPr | CH₂-tBu | CH₂-iPr |
| 36-8 | CH₃ | CH₂-iPr | CH₂-tBu | CH₂-tBu | CH₂-iPr |
| 36-9 | CH₃ | CH₂-tBu | CH₂-iPr | CH₂-iPr | CH₂-tBu |
| 36-10 | CH₃ | CH₂-iPr | CH₂-tBu | CH₂-tBu | CH₂-tBu |
| 36-11 | CH₃ | CH₂-tBu | CH₂-iPr | CH₂-tBu | CH₂-tBu |
| 36-12 | CH₃ | CH₂-tBu | CH₂-tBu | CH₂-iPr | CH₂-tBu |
| 36-13 | CH₃ | CH₂-tBu | CH₂-tBu | CH₂-tBu | CH₂-iPr |
| 36-14 | CH₃ | CH₂CMe₂F | CH₂-iPr | CH₂-iPr | CH₂-iPr |
| 36-15 | CH₃ | CH₂-iPr | CH₂CMe₂F | CH₂-iPr | CH₂-iPr |
| 36-16 | CH₃ | CH₂-iPr | CH₂-iPr | CH₂CMe₂F | CH₂-iPr |
| 36-17 | CH₃ | CH₂-iPr | CH₂-iPr | CH₂-iPr | CH₂CMe₂F |
| 36-18 | CH₃ | CH₂CMe₂F | CH₂-iPr | CH₂CMe₂F | CH₂-iPr |
| 36-19 | CH₃ | CH₂-iPr | CH₂CMe₂F | CH₂-iPr | CH₂CMe₂F |
| 36-20 | CH₃ | CH₂-iPr | CH₂CMe₂F | CH₂CMe₂F | CH₂-iPr |
| 36-21 | CH₃ | CH₂CMe₂F | CH₂-iPr | CH₂-iPr | CH₂CMe₂F |
| 36-22 | CH₃ | CH₂-iPr | CH₂CMe₂F | CH₂CMe₂F | CH₂CMe₂F |
| 36-23 | CH₃ | CH₂CMe₂F | CH₂-iPr | CH₂CMe₂F | CH₂CMe₂F |
| 36-24 | CH₃ | CH₂CMe₂F | CH₂CMe₂F | CH₂-iPr | CH₂CMe₂F |
| 36-25 | CH₃ | CH₂CMe₂F | CH₂CMe₂F | CH₂CMe₂F | CH₂-iPr |
| 36-26 | CH₃ | CH₂CMe₂F | CH₂CMe₂F | CH₂CMe₂F | CH₂CMe₂F |
| 36-27 | CH₃ | CH₂-iPr | CH₂-iPr | CH₂-iPr | CH₂-iPr |
| 36-28 | CH₃ | CH₂-tBu | CH₂-tBu | CH₂-iPr | CH₂-iPr |
| 36-29 | CH₃ | CH₂-iPr | CH₂-iPr | CH₂-tBu | CH₂-tBu |
| 36-30 | CH₃ | CH₂CMe₂F | CH₂CMe₂F | CH₂-iPr | CH₂-iPr |
| 36-31 | CH₃ | CH₂-iPr | CH₂-iPr | CH₂CMe₂F | CH₂CMe₂F |
| 36-32 | CH₃ | CH₂CMe₂F | CH₂-tBu | CH₂CMe₂F | CH₂-tBu |
| 36-33 | CH₃ | CH₂CF₂Me | CH₂-iPr | CH₂CF₂Me | CH₂-iPr |
| 36-34 | CH₃ | CH₂CF₃ | CH₂-iPr | CH₂CF₃ | CH₂-iPr |
| 36-35 | CH₃ | CH₂CH(CF₃)₂ | CH₂-iPr | CH₂CH(CF₃)₂ | CH₂-iPr |
| 36-36 | CH₂F | CH₂CMe₂F | CH₂-iPr | CH₂CMe₂F | CH₂-iPr |
| 36-37 | H | CH₂CMe₂F | CH₂-iPr | CH₂CMe₂F | CH₂-iPr |
| 36-38 | Et | CH₂CMe₂F | CH₂-iPr | CH₂CMe₂F | CH₂-iPr |
| 36-39 | CH₂F | CH₂-iPr | CH₂-iPr | CH₂-iPr | CH₂-iPr |
| 36-40 | H | CH₂-iPr | CH₂-iPr | CH₂-iPr | CH₂-iPr |
| 36-41 | Et | CH₂-iPr | CH₂-iPr | CH₂-iPr | CH₂-iPr |
| 36-42 | H | CH₂CMe₂F | CH₂-tBu | CH₂CMe₂F | CH₂-tBu |
| 36-43 | CH₃ | CH₂CMe₂F | iPr | CH₂CMe₂F | iPr |
| 36-44 | CH₃ | CH₂CMe₂F | nPr | CH₂CMe₂F | nPr |
| 36-45 | CH₃ | CH₂CMe₂F | sBu | CH₂CMe₂F | sBu |
| 36-46 | CH₃ | CH₂CMe₂F | tBu | CH₂CMe₂F | tBu |
| 36-47 | CH₃ | CH₂CMe₂F | CH₂-p-biphenyl | CH₂CMe₂F | CH₂-p-biphenyl |
| 36-48 | CH₃ | CH₂CMe₂F | CH₂-p-tBuPh | CH₂CMe₂F | CH₂-p-tBuPh |
| 36-49 | CH₃ | CH₂CMe₂F | CH₃ | CH₂CMe₂F | CH₃ |
| 36-50 | H | CH₂CMe₂F | iPr | CH₂CMe₂F | iPr |
| 36-51 | CH₃ | CH₂CMe₂F | CH₂CH₂CMe₃ | CH₂CMe₂F | CH₂CH₂CMe₃ |
| 36-52 | CH₃ | CH₂CMe₂F | CH₂CH₂-iPr | CH₂CMe₂F | CH₂CH₂-iPr |
| 36-53 | CH₃ | CH₂-p-pyridyl | CH₂-iPr | CH₂-p-pyridyl | CH₂-iPr |
| 36-54 | CH₃ | CH₂-p-pyridyl | CH₂-tBu | CH₂-p-pyridyl | CH₂-tBu |

TABLE 37

Compounds of formula (I), wherein $Cy^1$ and $Cy^2$ are

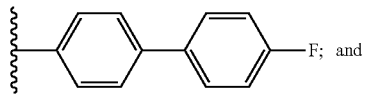—F; and $R^a$, $R^b$, $R^1$ to $R^4$ are as shown.

| Compound # | $R^a/R^b$ | $R^1$ | $R^2$ | $R^3$ | $R^4$ |
| --- | --- | --- | --- | --- | --- |
| 37-1 | CH₃ | CH₂-tBu | CH₂-tBu | CH₂-tBu | CH₂-tBu |
| 37-2 | CH₃ | CH₂-tBu | CH₂-iPr | CH₂-iPr | CH₂-iPr |
| 37-3 | CH₃ | CH₂-iPr | CH₂-tBu | CH₂-iPr | CH₂-iPr |
| 37-4 | CH₃ | CH₂-iPr | CH₂-iPr | CH₂-tBu | CH₂-iPr |
| 37-5 | CH₃ | CH₂-iPr | CH₂-iPr | CH₂-iPr | CH₂-tBu |
| 37-6 | CH₃ | CH₂-iPr | CH₂-tBu | CH₂-iPr | CH₂-tBu |
| 37-7 | CH₃ | CH₂-tBu | CH₂-iPr | CH₂-tBu | CH₂-iPr |
| 37-8 | CH₃ | CH₂-iPr | CH₂-tBu | CH₂-tBu | CH₂-iPr |
| 37-9 | CH₃ | CH₂-tBu | CH₂-iPr | CH₂-iPr | CH₂-tBu |
| 37-10 | CH₃ | CH₂-iPr | CH₂-tBu | CH₂-tBu | CH₂-tBu |
| 37-11 | CH₃ | CH₂-tBu | CH₂-iPr | CH₂-tBu | CH₂-tBu |
| 37-12 | CH₃ | CH₂-tBu | CH₂-tBu | CH₂-iPr | CH₂-tBu |
| 37-13 | CH₃ | CH₂-tBu | CH₂-tBu | CH₂-tBu | CH₂-iPr |
| 37-14 | CH₃ | CH₂CMe₂F | CH₂-iPr | CH₂-iPr | CH₂-iPr |
| 37-15 | CH₃ | CH₂-iPr | CH₂CMe₂F | CH₂-iPr | CH₂-iPr |
| 37-16 | CH₃ | CH₂-iPr | CH₂-iPr | CH₂CMe₂F | CH₂-iPr |
| 37-17 | CH₃ | CH₂-iPr | CH₂-iPr | CH₂-iPr | CH₂CMe₂F |
| 37-18 | CH₃ | CH₂CMe₂F | CH₂-iPr | CH₂CMe₂F | CH₂-iPr |
| 37-19 | CH₃ | CH₂-iPr | CH₂CMe₂F | CH₂-iPr | CH₂CMe₂F |
| 37-20 | CH₃ | CH₂-iPr | CH₂CMe₂F | CH₂CMe₂F | CH₂-iPr |
| 37-21 | CH₃ | CH₂CMe₂F | CH₂-iPr | CH₂-iPr | CH₂CMe₂F |
| 37-22 | CH₃ | CH₂-iPr | CH₂CMe₂F | CH₂CMe₂F | CH₂CMe₂F |
| 37-23 | CH₃ | CH₂CMe₂F | CH₂-iPr | CH₂CMe₂F | CH₂CMe₂F |
| 37-24 | CH₃ | CH₂CMe₂F | CH₂CMe₂F | CH₂-iPr | CH₂CMe₂F |
| 37-25 | CH₃ | CH₂CMe₂F | CH₂CMe₂F | CH₂CMe₂F | CH₂-iPr |
| 37-26 | CH₃ | CH₂CMe₂F | CH₂CMe₂F | CH₂CMe₂F | CH₂CMe₂F |
| 37-27 | CH₃ | CH₂-iPr | CH₂-iPr | CH₂-iPr | CH₂-iPr |
| 37-28 | CH₃ | CH₂-tBu | CH₂-tBu | CH₂-iPr | CH₂-iPr |
| 37-29 | CH₃ | CH₂-iPr | CH₂-iPr | CH₂-tBu | CH₂-tBu |
| 37-30 | CH₃ | CH₂CMe₂F | CH₂CMe₂F | CH₂-iPr | CH₂-iPr |
| 37-31 | CH₃ | CH₂-iPr | CH₂-iPr | CH₂CMe₂F | CH₂CMe₂F |
| 37-32 | CH₃ | CH₂CMe₂F | CH₂-tBu | CH₂CMe₂F | CH₂-tBu |
| 37-33 | CH₃ | CH₂CF₂Me | CH₂-iPr | CH₂CF₂Me | CH₂-iPr |
| 37-34 | CH₃ | CH₂CF₃ | CH₂-iPr | CH₂CF₃ | CH₂-iPr |
| 37-35 | CH₃ | CH₂CH(CF₃)₂ | CH₂-iPr | CH₂CH(CF₃)₂ | CH₂-iPr |
| 37-36 | CH₂F | CH₂CMe₂F | CH₂-iPr | CH₂CMe₂F | CH₂-iPr |
| 37-37 | H | CH₂CMe₂F | CH₂-iPr | CH₂CMe₂F | CH₂-iPr |
| 37-38 | Et | CH₂CMe₂F | CH₂-iPr | CH₂CMe₂F | CH₂-iPr |
| 37-39 | CH₂F | CH₂-iPr | CH₂-iPr | CH₂-iPr | CH₂-iPr |
| 37-40 | H | CH₂-iPr | CH₂-iPr | CH₂-iPr | CH₂-iPr |
| 37-41 | Et | CH₂-iPr | CH₂-iPr | CH₂-iPr | CH₂-iPr |
| 37-42 | H | CH₂CMe₂F | CH₂-tBu | CH₂CMe₂F | CH₂-tBu |
| 37-43 | CH₃ | CH₂CMe₂F | iPr | CH₂CMe₂F | iPr |
| 37-44 | CH₃ | CH₂CMe₂F | nPr | CH₂CMe₂F | nPr |
| 37-45 | CH₃ | CH₂CMe₂F | sBu | CH₂CMe₂F | sBu |
| 37-46 | CH₃ | CH₂CMe₂F | tBu | CH₂CMe₂F | tBu |
| 37-47 | CH₃ | CH₂CMe₂F | CH₂-p-biphenyl | CH₂CMe₂F | CH₂-p-biphenyl |
| 37-48 | CH₃ | CH₂CMe₂F | CH₂-p-tBuPh | CH₂CMe₂F | CH₂-p-tBuPh |
| 37-49 | CH₃ | CH₂CMe₂F | CH₃ | CH₂CMe₂F | CH₃ |
| 37-50 | H | CH₂CMe₂F | iPr | CH₂CMe₂F | iPr |
| 37-51 | CH₃ | CH₂CMe₂F | CH₂CH₂CMe₃ | CH₂CMe₂F | CH₂CH₂CMe₃ |
| 37-52 | CH₃ | CH₂CMe₂F | CH₂CH₂-iPr | CH₂CMe₂F | CH₂CH₂-iPr |
| 37-53 | CH₃ | CH₂-p-pyridyl | CH₂-iPr | CH₂-p-pyridyl | CH₂-iPr |
| 37-54 | CH₃ | CH₂-p-pyridyl | CH₂-tBu | CH₂-p-pyridyl | CH₂-tBu |

TABLE 38

Compounds of formula (I), wherein Cy$^1$ and Cy$^2$ are

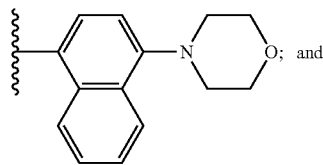 [SMILES: *c1ccc(N2CCOCC2)c2ccccc12 ; "and"]; and

R$^a$, R$^b$, R$^1$ to R$^4$ are as shown.

| Compound # | R$^a$/R$^b$ | R$^1$ | R$^2$ | R$^3$ | R$^4$ |
|---|---|---|---|---|---|
| 38-1 | CH$_3$ | CH$_2$-tBu | CH$_2$-tBu | CH$_2$-tBu | CH$_2$-tBu |
| 38-2 | CH$_3$ | CH$_2$-tBu | CH$_2$-iPr | CH$_2$-iPr | CH$_2$-iPr |
| 38-3 | CH$_3$ | CH$_2$-iPr | CH$_2$-tBu | CH$_2$-iPr | CH$_2$-iPr |
| 38-4 | CH$_3$ | CH$_2$-iPr | CH$_2$-iPr | CH$_2$-tBu | CH$_2$-iPr |
| 38-5 | CH$_3$ | CH$_2$-iPr | CH$_2$-iPr | CH$_2$-iPr | CH$_2$-tBu |
| 38-6 | CH$_3$ | CH$_2$-iPr | CH$_2$-tBu | CH$_2$-iPr | CH$_2$-tBu |
| 38-7 | CH$_3$ | CH$_2$-tBu | CH$_2$-iPr | CH$_2$-tBu | CH$_2$-iPr |
| 38-8 | CH$_3$ | CH$_2$-iPr | CH$_2$-tBu | CH$_2$-tBu | CH$_2$-iPr |
| 38-9 | CH$_3$ | CH$_2$-tBu | CH$_2$-iPr | CH$_2$-iPr | CH$_2$-tBu |
| 38-10 | CH$_3$ | CH$_2$-iPr | CH$_2$-tBu | CH$_2$-tBu | CH$_2$-tBu |
| 38-11 | CH$_3$ | CH$_2$-tBu | CH$_2$-iPr | CH$_2$-tBu | CH$_2$-tBu |
| 38-12 | CH$_3$ | CH$_2$-tBu | CH$_2$-tBu | CH$_2$-iPr | CH$_2$-tBu |
| 38-13 | CH$_3$ | CH$_2$-tBu | CH$_2$-tBu | CH$_2$-tBu | CH$_2$-iPr |
| 38-14 | CH$_3$ | CH$_2$CMe$_2$F | CH$_2$-iPr | CH$_2$-iPr | CH$_2$-iPr |
| 38-15 | CH$_3$ | CH$_2$-iPr | CH$_2$CMe$_2$F | CH$_2$-iPr | CH$_2$-iPr |
| 38-16 | CH$_3$ | CH$_2$-iPr | CH$_2$-iPr | CH$_2$CMe$_2$F | CH$_2$-iPr |
| 38-17 | CH$_3$ | CH$_2$-iPr | CH$_2$-iPr | CH$_2$-iPr | CH$_2$CMe$_2$F |
| 38-18 | CH$_3$ | CH$_2$CMe$_2$F | CH$_2$-iPr | CH$_2$CMe$_2$F | CH$_2$-iPr |
| 38-19 | CH$_3$ | CH$_2$-iPr | CH$_2$CMe$_2$F | CH$_2$-iPr | CH$_2$CMe$_2$F |
| 38-20 | CH$_3$ | CH$_2$-iPr | CH$_2$CMe$_2$F | CH$_2$CMe$_2$F | CH$_2$-iPr |
| 38-21 | CH$_3$ | CH$_2$CMe$_2$F | CH$_2$-iPr | CH$_2$-iPr | CH$_2$CMe$_2$F |
| 38-22 | CH$_3$ | CH$_2$-iPr | CH$_2$CMe$_2$F | CH$_2$CMe$_2$F | CH$_2$CMe$_2$F |
| 38-23 | CH$_3$ | CH$_2$CMe$_2$F | CH$_2$-iPr | CH$_2$CMe$_2$F | CH$_2$CMe$_2$F |
| 38-24 | CH$_3$ | CH$_2$CMe$_2$F | CH$_2$CMe$_2$F | CH$_2$-iPr | CH$_2$CMe$_2$F |
| 38-25 | CH$_3$ | CH$_2$CMe$_2$F | CH$_2$CMe$_2$F | CH$_2$CMe$_2$F | CH$_2$-iPr |
| 38-26 | CH$_3$ | CH$_2$CMe$_2$F | CH$_2$CMe$_2$F | CH$_2$CMe$_2$F | CH$_2$CMe$_2$F |
| 38-27 | CH$_3$ | CH$_2$-iPr | CH$_2$-iPr | CH$_2$-iPr | CH$_2$-iPr |
| 38-28 | CH$_3$ | CH$_2$-tBu | CH$_2$-tBu | CH$_2$-iPr | CH$_2$-iPr |
| 38-29 | CH$_3$ | CH$_2$-iPr | CH$_2$-iPr | CH$_2$-tBu | CH$_2$-tBu |
| 38-30 | CH$_3$ | CH$_2$CMe$_2$F | CH$_2$CMe$_2$F | CH$_2$-iPr | CH$_2$-iPr |
| 38-31 | CH$_3$ | CH$_2$-iPr | CH$_2$-iPr | CH$_2$CMe$_2$F | CH$_2$CMe$_2$F |
| 38-32 | CH$_3$ | CH$_2$CMe$_2$F | CH$_2$-tBu | CH$_2$CMe$_2$F | CH$_2$-tBu |
| 38-33 | CH$_3$ | CH$_2$CF$_2$Me | CH$_2$-iPr | CH$_2$CF$_2$Me | CH$_2$-iPr |
| 38-34 | CH$_3$ | CH$_2$CF$_3$ | CH$_2$-iPr | CH$_2$CF$_3$ | CH$_2$-iPr |
| 38-35 | CH$_3$ | CH$_2$CH(CF$_3$)$_2$ | CH$_2$-iPr | CH$_2$CH(CF$_3$)$_2$ | CH$_2$-iPr |
| 38-36 | CH$_2$F | CH$_2$CMe$_2$F | CH$_2$-iPr | CH$_2$CMe$_2$F | CH$_2$-iPr |
| 38-37 | H | CH$_2$CMe$_2$F | CH$_2$-iPr | CH$_2$CMe$_2$F | CH$_2$-iPr |
| 38-38 | Et | CH$_2$CMe$_2$F | CH$_2$-iPr | CH$_2$CMe$_2$F | CH$_2$-iPr |
| 38-39 | CH$_2$F | CH$_2$-iPr | CH$_2$-iPr | CH$_2$-iPr | CH$_2$-iPr |
| 38-40 | H | CH$_2$-iPr | CH$_2$-iPr | CH$_2$-iPr | CH$_2$-iPr |
| 38-41 | Et | CH$_2$-iPr | CH$_2$-iPr | CH$_2$-iPr | CH$_2$-iPr |
| 38-42 | H | CH$_2$CMe$_2$F | CH$_2$-tBu | CH$_2$CMe$_2$F | CH$_2$-tBu |
| 38-43 | CH$_3$ | CH$_2$CMe$_2$F | iPr | CH$_2$CMe$_2$F | iPr |
| 38-44 | CH$_3$ | CH$_2$CMe$_2$F | nPr | CH$_2$CMe$_2$F | nPr |
| 38-45 | CH$_3$ | CH$_2$CMe$_2$F | sBu | CH$_2$CMe$_2$F | sBu |
| 38-46 | CH$_3$ | CH$_2$CMe$_2$F | tBu | CH$_2$CMe$_2$F | tBu |
| 38-47 | CH$_3$ | CH$_2$CMe$_2$F | CH$_2$-p-biphenyl | CH$_2$CMe$_2$F | CH$_2$-p-biphenyl |
| 38-48 | CH$_3$ | CH$_2$CMe$_2$F | CH$_2$-p-tBuPh | CH$_2$CMe$_2$F | CH$_2$-p-tBuPh |
| 38-49 | CH$_3$ | CH$_2$CMe$_2$F | CH$_3$ | CH$_2$CMe$_2$F | CH$_3$ |
| 38-50 | H | CH$_2$CMe$_2$F | iPr | CH$_2$CMe$_2$F | iPr |
| 38-51 | CH$_3$ | CH$_2$CMe$_2$F | CH$_2$CH$_2$CMe$_3$ | CH$_2$CMe$_2$F | CH$_2$CH$_2$CMe$_3$ |
| 38-52 | CH$_3$ | CH$_2$CMe$_2$F | CH$_2$CH$_2$-iPr | CH$_2$CMe$_2$F | CH$_2$CH$_2$-iPr |
| 38-53 | CH$_3$ | CH$_2$-p-pyridyl | CH$_2$-iPr | CH$_2$-p-pyridyl | CH$_2$-iPr |
| 38-54 | CH$_3$ | CH$_2$-p-pyridyl | CH$_2$-tBu | CH$_2$-p-pyridyl | CH$_2$-tBu |

Particular embodiments of the compounds of the invention are further described in Tables 39-112 wherein the meaning of the variables $Cy^1$, $Cy^2$, $R^a$, $R^b$, $R^1$, $R^2$, $R^3$ and $R^4$ are as described for Tables 2-38, respectively, with the exception that R', R", R'" and R"" are each specifically defined below.

Table 39: Compounds of formula (I), wherein $Cy^1$, $Cy^2$, $R^a$, $R^b$, $R^1$, $R^2$, $R^3$ and $R^4$ are as shown in Table 2, and R', R", R'" and R"" are each methyl.

Table 40: Compounds of formula (I), wherein $Cy^1$, $Cy^2$, $R^a$, $R^b$, $R^1$, $R^2$, $R^3$ and $R^4$ are as shown in Table 3, and R', R", R'" and R"" are each methyl.

Table 41: Compounds of formula (I), wherein $Cy^1$, $Cy^2$, $R^a$, $R^b$, $R^1$, $R^2$, $R^3$ and $R^4$ are as shown in Table 4, and R', R", R'" and R"" are each methyl.

Table 42: Compounds of formula (I), wherein $Cy^1$, $Cy^2$, $R^a$, $R^b$, $R^1$, $R^2$, $R^3$ and $R^4$ are as shown in Table 5, and R', R", R'" and R"" are each methyl.

Table 43: Compounds of formula (I), wherein $Cy^1$, $Cy^2$, $R^a$, $R^b$, $R^1$, $R^2$, $R^3$ and $R^4$ are as shown in Table 6, and R', R", R'" and R"" are each methyl.

Table 44: Compounds of formula (I), wherein $Cy^1$, $Cy^2$, $R^a$, $R^b$, $R^1$, $R^2$, $R^3$ and $R^4$ are as shown in Table 7, and R', R", R'" and R"" are each methyl.

Table 45: Compounds of formula (I), wherein $Cy^1$, $Cy^2$, $R^a$, $R^b$, $R^1$, $R^2$, $R^3$ and $R^4$ are as shown in Table 8, and R', R", R'" and R"" are each methyl.

Table 46: Compounds of formula (I), wherein $Cy^1$, $Cy^2$, $R^a$, $R^b$, $R^1$, $R^2$, $R^3$ and $R^4$ are as shown in Table 9, and R', R", R'" and R"" are each methyl.

Table 47: Compounds of formula (I), wherein $Cy^1$, $Cy^2$, $R^a$, $R^b$, $R^1$, $R^2$, $R^3$ and $R^4$ are as shown in Table 10, and R', R", R'" and R"" are each methyl.

Table 48: Compounds of formula (I), wherein $Cy^1$, $Cy^2$, $R^a$, $R^b$, $R^1$, $R^2$, $R^3$ and $R^4$ are as shown in Table 11, and R', R", R'" and R"" are each methyl.

Table 49: Compounds of formula (I), wherein $Cy^1$, $Cy^2$, $R^a$, $R^b$, $R^1$, $R^2$, $R^3$ and $R^4$ are as shown in Table 12, and R', R", R'" and R"" are each methyl.

Table 50: Compounds of formula (I), wherein $Cy^1$, $Cy^2$, $R^a$, $R^b$, $R^1$, $R^2$, $R^3$ and $R^4$ are as shown in Table 13, and R', R", R'" and R"" are each methyl.

Table 51: Compounds of formula (I), wherein $Cy^1$, $Cy^2$, $R^a$, $R^b$, $R^1$, $R^2$, $R^3$ and $R^4$ are as shown in Table 14, and R', R", R'" and R"" are each methyl.

Table 52: Compounds of formula (I), wherein $Cy^1$, $Cy^2$, $R^a$, $R^b$, $R^1$, $R^2$, $R^3$ and $R^4$ are as shown in Table 15, and R', R", R'" and R"" are each methyl.

Table 53: Compounds of formula (I), wherein $Cy^1$, $Cy^2$, $R^a$, $R^b$, $R^1$, $R^2$, $R^3$ and $R^4$ are as shown in Table 16, and R', R", R'" and R"" are each methyl.

Table 54: Compounds of formula (I), wherein $Cy^1$, $Cy^2$, $R^a$, $R^b$, $R^1$, $R^2$, $R^3$ and $R^4$ are as shown in Table 17, and R', R", R'" and R"" are each methyl.

Table 55: Compounds of formula (I), wherein $Cy^1$, $Cy^2$, $R^a$, $R^b$, $R^1$, $R^2$, $R^3$ and $R^4$ are as shown in Table 18, and R', R", R'" and R"" are each methyl.

Table 56: Compounds of formula (I), wherein $Cy^1$, $Cy^2$, $R^a$, $R^b$, $R^1$, $R^2$, $R^3$ and $R^4$ are as shown in Table 19, and R', R", R'" and R"" are each methyl.

Table 57: Compounds of formula (I), wherein $Cy^1$, $Cy^2$, $R^a$, $R^b$, $R^1$, $R^2$, $R^3$ and $R^4$ are as shown in Table 20, and R', R", R'" and R"" are each methyl.

Table 58: Compounds of formula (I), wherein $Cy^1$, $Cy^2$, $R^a$, $R^b$, $R^1$, $R^2$, $R^3$ and $R^4$ are as shown in Table 21, and R', R", R'" and R"" are each methyl.

Table 59: Compounds of formula (I), wherein $Cy^1$, $Cy^2$, $R^a$, $R^b$, $R^1$, $R^2$, $R^3$ and $R^4$ are as shown in Table 22, and R', R", R'" and R"" are each methyl.

Table 60: Compounds of formula (I), wherein $Cy^1$, $Cy^2$, $R^a$, $R^b$, $R^1$, $R^2$, $R^3$ and $R^4$ are as shown in Table 23, and R', R", R'" and R"" are each methyl.

Table 61: Compounds of formula (I), wherein $Cy^1$, $Cy^2$, $R^a$, $R^b$, $R^1$, $R^2$, $R^3$ and $R^4$ are as shown in Table 24, and R', R", R'" and R"" are each methyl.

Table 62: Compounds of formula (I), wherein $Cy^1$, $Cy^2$, $R^a$, $R^b$, $R^1$, $R^2$, $R^3$ and $R^4$ are as shown in Table 25, and R', R", R'" and R"" are each methyl.

Table 63: Compounds of formula (I), wherein $Cy^1$, $Cy^2$, $R^a$, $R^b$, $R^1$, $R^2$, $R^3$ and $R^4$ are as shown in Table 26, and R', R", R'" and R"" are each methyl.

Table 64: Compounds of formula (I), wherein $Cy^1$, $Cy^2$, $R^a$, $R^b$, $R^1$, $R^2$, $R^3$ and $R^4$ are as shown in Table 27, and R', R", R'" and R"" are each methyl.

Table 65: Compounds of formula (I), wherein $Cy^1$, $Cy^2$, $R^a$, $R^b$, $R^1$, $R^2$, $R^3$ and $R^4$ are as shown in Table 28, and R', R", R'" and R"" are each methyl.

Table 66: Compounds of formula (I), wherein $Cy^1$, $Cy^2$, $R^a$, $R^b$, $R^1$, $R^2$, $R^3$ and $R^4$ are as shown in Table 29, and R', R", R'" and R"" are each methyl.

Table 67: Compounds of formula (I), wherein $Cy^1$, $Cy^2$, $R^a$, $R^b$, $R^1$, $R^2$, $R^3$ and $R^4$ are as shown in Table 30, and R', R", R'" and R"" are each methyl.

Table 68: Compounds of formula (I), wherein $Cy^1$, $Cy^2$, $R^a$, $R^b$, $R^1$, $R^2$, $R^3$ and $R^4$ are as shown in Table 31, and R', R", R'" and R"" are each methyl.

Table 69: Compounds of formula (I), wherein $Cy^1$, $Cy^2$, $R^a$, $R^b$, $R^1$, $R^2$, $R^3$ and $R^4$ are as shown in Table 32, and R', R", R'" and R"" are each methyl.

Table 70: Compounds of formula (I), wherein $Cy^1$, $Cy^2$, $R^a$, $R^b$, $R^1$, $R^2$, $R^3$ and $R^4$ are as shown in Table 33, and R', R", R'" and R"" are each methyl.

Table 71: Compounds of formula (I), wherein $Cy^1$, $Cy^2$, $R^a$, $R^b$, $R^1$, $R^2$, $R^3$ and $R^4$ are as shown in Table 34, and R', R", R'" and R"" are each methyl.

Table 72: Compounds of formula (I), wherein $Cy^1$, $Cy^2$, $R^a$, $R^b$, $R^1$, $R^2$, $R^3$ and $R^4$ are as shown in Table 35, and R', R", R'" and R"" are each methyl.

Table 73: Compounds of formula (I), wherein $Cy^1$, $Cy^2$, $R^a$, $R^b$, $R^1$, $R^2$, $R^3$ and $R^4$ are as shown in Table 36, and R', R", R'" and R"" are each methyl.

Table 74: Compounds of formula (I), wherein $Cy^1$, $Cy^2$, $R^a$, $R^b$, $R^1$, $R^2$, $R^3$ and $R^4$ are as shown in Table 37, and R', R", R'" and R"" are each methyl.

Table 75: Compounds of formula (I), wherein $Cy^1$, $Cy^2$, $R^a$, $R^b$, $R^1$, $R^2$, $R^3$ and $R^4$ are as shown in Table 38, and R', R", R'" and R"" are each methyl.

Table 76: Compounds of formula (I), wherein $Cy^1$, $Cy^2$, $R^a$, $R^b$, $R^1$, $R^2$, $R^3$ and $R^4$ are as shown in Table 2, and R', R", R'" and R"" are each hydrogen.

Table 77: Compounds of formula (I), wherein $Cy^1$, $Cy^2$, $R^a$, $R^b$, $R^1$, $R^2$, $R^3$ and $R^4$ are as shown in Table 3, and R', R", R'" and R"" are each hydrogen.

Table 78: Compounds of formula (I), wherein $Cy^1$, $Cy^2$, $R^a$, $R^b$, $R^1$, $R^2$, $R^3$ and $R^4$ are as shown in Table 4, and R', R", R'" and R"" are each hydrogen.

Table 79: Compounds of formula (I), wherein $Cy^1$, $Cy^2$, $R^a$, $R^b$, $R^1$, $R^2$, $R^3$ and $R^4$ are as shown in Table 5, and R', R", R'" and R"" are each hydrogen.

Table 80: Compounds of formula (I), wherein $Cy^1$, $Cy^2$, $R^a$, $R^b$, $R^1$, $R^2$, $R^3$ and $R^4$ are as shown in Table 6, and R', R", R'" and R"" are each hydrogen.

Table 81: Compounds of formula (I), wherein $Cy^1$, $Cy^2$, $R^a$, $R^b$, $R^1$, $R^2$, $R^3$ and $R^4$ are as shown in Table 7, and R', R", R'" and R"" are each hydrogen.

Table 82: Compounds of formula (I), wherein $Cy^1$, $Cy^2$, $R^a$, $R^b$, $R^1$, $R^2$, $R^3$ and $R^4$ are as shown in Table 8, and R', R", R'" and R"" are each hydrogen.

Table 83: Compounds of formula (I), wherein $Cy^1$, $Cy^2$, $R^a$, $R^b$, $R^1$, $R^2$, $R^3$ and $R^4$ are as shown in Table 9, and R', R", R'" and R"" are each hydrogen.

Table 84: Compounds of formula (I), wherein $Cy^1$, $Cy^2$, $R^a$, $R^b$, $R^1$, $R^2$, $R^3$ and $R^4$ are as shown in Table 10, and R', R", R'" and R"" are each hydrogen.

Table 85: Compounds of formula (I), wherein $Cy^1$, $Cy^2$, $R^a$, $R^b$, $R^1$, $R^2$, $R^3$ and $R^4$ are as shown in Table 11, and R', R", R'" and R"" are each hydrogen.

Table 86: Compounds of formula (I), wherein $Cy^1$, $Cy^2$, $R^a$, $R^b$, $R^1$, $R^2$, $R^3$ and $R^4$ are as shown in Table 12, and R', R", R'" and R"" are each hydrogen.

Table 87: Compounds of formula (I), wherein $Cy^1$, $Cy^2$, $R^a$, $R^b$, $R^1$, $R^2$, $R^3$ and $R^4$ are as shown in Table 13, and R', R", R'" and R"" are each hydrogen.

Table 88: Compounds of formula (I), wherein $Cy^1$, $Cy^2$, $R^a$, $R^b$, $R^1$, $R^2$, $R^3$ and $R^4$ are as shown in Table 14, and R', R", R'" and R"" are each hydrogen.

Table 89: Compounds of formula (I), wherein $Cy^1$, $Cy^2$, $R^a$, $R^b$, $R^1$, $R^2$, $R^3$ and $R^4$ are as shown in Table 15, and R', R", R'" and R"" are each hydrogen.

Table 90: Compounds of formula (I), wherein $Cy^1$, $Cy^2$, $R^a$, $R^b$, $R^1$, $R^2$, $R^3$ and $R^4$ are as shown in Table 16, and R', R", R'" and R"" are each hydrogen.

Table 91: Compounds of formula (I), wherein $Cy^1$, $Cy^2$, $R^a$, $R^b$, $R^1$, $R^2$, $R^3$ and $R^4$ are as shown in Table 17, and R', R", R'" and R"" are each hydrogen.

Table 92: Compounds of formula (I), wherein $Cy^1$, $Cy^2$, $R^a$, $R^b$, $R^1$, $R^2$, $R^3$ and $R^4$ are as shown in Table 18, and R', R", R'" and R"" are each hydrogen.

Table 93: Compounds of formula (I), wherein $Cy^1$, $Cy^2$, $R^a$, $R^b$, $R^1$, $R^2$, $R^3$ and $R^4$ are as shown in Table 19, and R', R", R'" and R"" are each hydrogen.

Table 94: Compounds of formula (I), wherein $Cy^1$, $Cy^2$, $R^a$, $R^b$, $R^1$, $R^2$, $R^3$ and $R^4$ are as shown in Table 20, and R', R", R'" and R"" are each hydrogen.

Table 95: Compounds of formula (I), wherein $Cy^1$, $Cy^2$, $R^a$, $R^b$, $R^1$, $R^2$, $R^3$ and $R^4$ are as shown in Table 21, and R', R", R'" and R"" are each hydrogen.

Table 96: Compounds of formula (I), wherein $Cy^1$, $Cy^2$, $R^a$, $R^b$, $R^1$, $R^2$, $R^3$ and $R^4$ are as shown in Table 22, and R', R", R'" and R"" are each hydrogen.

Table 97: Compounds of formula (I), wherein $Cy^1$, $Cy^2$, $R^a$, $R^b$, $R^1$, $R^2$, $R^3$ and $R^4$ are as shown in Table 23, and R', R", R'" and R"" are each hydrogen.

Table 98: Compounds of formula (I), wherein $Cy^1$, $Cy^2$, $R^a$, $R^b$, $R^1$, $R^2$, $R^3$ and $R^4$ are as shown in Table 24, and R', R", R'" and R"" are each hydrogen.

Table 99: Compounds of formula (I), wherein $Cy^1$, $Cy^2$, $R^a$, $R^b$, $R^1$, $R^2$, $R^3$ and $R^4$ are as shown in Table 25, and R', R", R'" and R"" are each hydrogen.

Table 100: Compounds of formula (I), wherein $Cy^1$, $Cy^2$, $R^a$, $R^b$, $R^1$, $R^2$, $R^3$ and $R^4$ are as shown in Table 26, and R', R", R'" and R"" are each hydrogen.

Table 101: Compounds of formula (I), wherein $Cy^1$, $Cy^2$, $R^a$, $R^b$, $R^1$, $R^2$, $R^3$ and $R^4$ are as shown in Table 27, and R', R", R'" and R"" are each hydrogen.

Table 102: Compounds of formula (I), wherein $Cy^1$, $Cy^2$, $R^a$, $R^b$, $R^1$, $R^2$, $R^3$ and $R^4$ are as shown in Table 28, and R', R", R'" and R"" are each hydrogen.

Table 103: Compounds of formula (I), wherein $Cy^1$, $Cy^2$, $R^a$, $R^b$, $R^1$, $R^2$, $R^3$ and $R^4$ are as shown in Table 29, and R', R", R'" and R"" are each hydrogen.

Table 104: Compounds of formula (I), wherein $Cy^1$, $Cy^2$, $R^a$, $R^b$, $R^1$, $R^2$, $R^3$ and $R^4$ are as shown in Table 30, and R', R", R'" and R"" are each hydrogen.

Table 105: Compounds of formula (I), wherein $Cy^1$, $Cy^2$, $R^a$, $R^b$, $R^1$, $R^2$, $R^3$ and $R^4$ are as shown in Table 31, and R', R", R'" and R"" are each hydrogen.

Table 106: Compounds of formula (I), wherein $Cy^1$, $Cy^2$, $R^a$, $R^b$, $R^1$, $R^2$, $R^3$ and $R^4$ are as shown in Table 32, and R', R", R'" and R"" are each hydrogen.

Table 107: Compounds of formula (I), wherein $Cy^1$, $Cy^2$, $R^a$, $R^b$, $R^1$, $R^2$, $R^3$ and $R^4$ are as shown in Table 33, and R', R", R'" and R"" are each hydrogen.

Table 108: Compounds of formula (I), wherein $Cy^1$, $Cy^2$, $R^a$, $R^b$, $R^1$, $R^2$, $R^3$ and $R^4$ are as shown in Table 34, and R', R", R'" and R"" are each hydrogen.

Table 109: Compounds of formula (I), wherein $Cy^1$, $Cy^2$, $R^a$, $R^b$, $R^1$, $R^2$, $R^3$ and $R^4$ are as shown in Table 35, and R', R", R'" and R"" are each hydrogen.

Table 110: Compounds of formula (I), wherein $Cy^1$, $Cy^2$, $R^a$, $R^b$, $R^1$, $R^2$, $R^3$ and $R^4$ are as shown in Table 36, and R', R", R'" and R"" are each hydrogen.

Table 111: Compounds of formula (I), wherein $Cy^1$, $Cy^2$, $R^a$, $R^b$, $R^1$, $R^2$, $R^3$ and $R^4$ are as shown in Table 37, and R', R", R'" and R"" are each hydrogen.

Table 112: Compounds of formula (I), wherein $Cy^1$, $Cy^2$, $R^a$, $R^b$, $R^1$, $R^2$, $R^3$ and $R^4$ are as shown in Table 38, and R', R", R'" and R"" are each hydrogen.

Surprisingly, it has been found that substitution of the alkyl groups $R^1$, $R^2$, $R^3$ and $R^4$, which are 2-methylpropyl groups in the parent cyclic depsipeptide PF1022 and also in emodepside, with certain groups improve the in vitro metabolic stability of the compounds and may also improve the activity of the compounds against endoparasites and ectoparasites. Furthermore, it has been surprisingly found that substitution of the compounds of formula (I) with certain $Cy^1$ and/or $Cy^2$ groups also significantly improves the in vitro metabolic stability of the compounds of the invention compared with PF1022 and emodepside. Thus, the compounds of the invention where the groups $Cy^1$ and/or $Cy^2$ and at least one of $R^1$, $R^2$, $R^3$ and $R^4$ are substituted with certain substituents have been found to have significantly improved metabolic stability and equal or significantly improved efficacy against endoparasites including *Dirofilaria immitis* microfilaria and/or L3 and L4 larvae and/or *Haemonchus contortus* larvae. In embodiments, the compounds of formula (I) with certain substituents will also exhibit improved activity against ectoparasites.

It has also been surprisingly found that the spatial order of substitution of $R^1$ to $R^4$ also has a significant impact on the activity of the compounds. For example it has been found that when the naturally-occurring 2-methylpropyl groups of PF1022A and emodepside represented by positions identified as $R^1$ and $R^3$ in the compound of formula (I) are modified the activity of the compounds is significantly improved over compounds where the 2-methylpropyl groups at the positions $R^2$ and $R^4$ are substituted.

The influence of certain substituents on one or more of $R^1$, $R^2$, $R^3$ and $R^4$ is also surprising. Thus, substitution of one or more of $R^1$, $R^2$, $R^3$ and $R^4$ with fluoro has been found to significantly improve the in vitro activity of the compounds of formula (I) on the motility of *Haemonchus contortus* larvae and *Dirofilaria immitis* microfilaria compared with unsubstituted compounds (e.g. PF1022 or analogs where $Cy^1$ and/or $Cy^2$ are substituted phenyl but $R^1$ to $R^4$ are 2-methylpropyl) or compounds in which the naturally-occurring 2-methylpropyl groups of PF1022A and emodepside, represented by positions identified as $R^1$ and $R^3$ in the compound of formula (I), are substituted with a methyl group. In addition, the substitution of $R^1$ and $R^3$ groups with fluoro has been found to result in significantly improved in vitro activity against *H. contortus* larvae and *D. immitis* microfilaria compared with compounds substituted with fluoro at $R^2$ or other combinations. It is apparent that the type of substitution in groups $R^1$, $R^2$, $R^3$ and $R^4$ as well as which of $R^1$, $R^2$, $R^3$ and $R^4$ are substituted have a significant influence on the activity of the compounds.

Scherkenbeck et al. (*Bioorg. Med. Chem. Lett.* 8 (1998), 1035-1040) described that the replacement of the N-methyl leucine residues for a series of related N-methylated amino acids such as isoleucine, valine, norvaline, alanine and phenylalanine resulted in nearly complete loss of anthelmintic efficacy following oral administration in sheep. Furthermore, the publication reported that modification of half of the N-methyl leucine residues with either methyl or n-propyl side chains also surprisingly resulted in significantly reduced activity. It was concluded that the (L)-N-methyl leucine residues in the cyclic depsipeptide PF1022A were a critical part of the pharmacophore and essential for in vivo activity.

Thus, it is surprising and unexpected that modification of the groups $R^1$ to $R^4$ in the compound of formula (I), which correspond to the N-methyl leucine residues in PF1022A or emodepside, result in enhanced in vitro metabolic stability and/or improved activity compared with the compounds containing unmodified N-methyl leucine residues. It is also very surprising and unexpected that the compounds of formula (I) in which the alkyl groups represented by $R^1$ and $R^3$ are substituted with certain groups exhibit significantly improved efficacy against endoparasites compared to compounds that are substituted with the same groups at $R^2$ and $R^4$ or in other combinations. In addition, the inclusion of certain substituents in groups $R^1$ to $R^4$ and $Cy^1$ and $Cy^2$ result in improved in vitro metabolic stability compared with unsubstituted compounds. It follows that an appropriate combination of the substitution at $Cy^1$ and $Cy^2$ and $R^1$ to $R^4$ in the compounds of formula (I) results in significantly improved activity against endoparasites and improved metabolic stability in animals.

Furthermore, the substitution of the naturally-occurring 2-methylpropyl groups of PF1022A and emodepside, represented by positions $R^1$ and $R^3$ in the compound of formula (I), with certain substituents, including fluoro and methyl, has been found to improve the in vitro permeability of the compounds. For example, compounds of formula (I) wherein $Cy^1$ and $Cy^2$ are either both unsubstituted phenyl or p-fluorophenyl groups and $R^2$ and $R^4$, respectively, are 2-methylpropyl fluoro-substituted were found to have significantly improved permeability compared with the compounds where $R^2$ and $R^4$ are unsubstituted 2-methylpropyl. Further, compounds where $Cy^1$ and $Cy^2$ are p-morpholino phenyl and $R^2$ and $R^4$ are methyl-substituted 2-methylpropyl were found to have significantly improved permeability compared with emodepside ($R^2$ and $R^4$=2-methylpropyl).

The characteristics described above for the compounds of formula (I) are expected to result in compounds with superior antiparasitic efficacy against endoparasites and ectoparasites in or on animals.

Stereoisomers and Polymorphic Forms

It will be appreciated by those of skill in the art that the compounds of the invention may exist and be isolated as optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the invention may include one or more chiral centers, which results in a theoretical number of optically active isomers. Where compounds of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds of present invention may also be present in different solid forms such as different crystalline forms or in the form of an amorphous solid. The present invention encompasses different crystalline forms as well as amorphous forms of the inventive compounds.

In addition, the compounds of the invention may exist as hydrates or solvates, in which a certain stoichiometric amount of water or a solvent is associated with the molecule in the crystalline form. The hydrates and solvates of the compounds of formula (I) are also the subject of the invention.

Salts

In addition to the neutral compounds of formula (I), salt forms of the compounds are also active against endoparasites. The term "veterinarily acceptable salt" is used throughout the specification to describe any salts of the compounds that are acceptable for administration for veterinary applications, and which provides the active compound upon administration.

In cases where compounds are sufficiently basic or acidic to form stable non-toxic acid or base salts, the compounds may be in the form of a veterinarily or agriculturally acceptable salt. Veterinarily acceptable salts include those derived from veterinarily or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the invention.

Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartarate, succinate, benzoate, ascorbate, $\alpha$-ketoglutarate, and $\alpha$-glycerophosphate. Of course, other acceptable organic acids may be used.

Alkali metal (for example, sodium, potassium or lithium) or alkaline earth metal (for example calcium) salts of the compounds can also be made by reacting a sufficiently acidic residue on the compounds with a hydroxide of the alkali metal or alkaline earth metal.

Veterinarily acceptable salts may be obtained using standard procedures well known in the art, for example by reacting a sufficiently basic compound such as an amine with a suitably acid functional group present in the compound, or by reacting a suitable acid with a suitably basic functional group on the compound of the invention.

Processes for the Preparation of Compounds of Formula (I):

The compounds of formula (I) may be prepared by processes adapted from those described in U.S. Pat. Nos. 5,514,773; 5,747,448; 5,874,530; 5,856,436; 6,033,879; 5,763,221; 6,329,338, 5,116,815; 6,468,966; 6,369,028; 5,777,075; and 5,646,244, all which are hereby incorporated by reference in their entirety. In addition, various synthetic methods for cyclic depsipeptides have been reported in the chemical literature (see Luttenberg et al., *Tetrahedron* 68 (2012), 2068-2073; Byung H. Lee, *Tetrahedron Letters*, 1997, 38 (5), 757-760; Scherkenbeck et al., *Eur. J. Org. Chem.*, 2012, 1546-1553; *Biosci. Biotech. Biochem.*, 1994, 58(6), 1193-1194; and Scherkenbeck et al., *Tetrahedron*, 1995, 51(31), 8459-8470) It will be understood by those skilled in the art that certain functional groups in the compounds and intermediates may be unprotected or protected by suitable protecting groups, as taught by Greene and Wuts, *Protective Groups in Organic Synthesis*, John Wiley and Sons, Inc., 4th edition 2006. Further, it will be apparent to those skilled in the art that the compounds and intermediates may be isolated by standard aqueous work-up conditions and optionally purified. For example, the compounds or intermediates may be purified by chromatographic methods or crystallized to yield the desired product in suitable purity.

In one embodiment, the compounds of formula (I) where $R^1$, $R^2$, $R^3$, $R^4$, $Cy^1$ and $Cy^2$ are as defined above and R', R", R'" and R"" are methyl are prepared according to the general process described in Scheme 1 below:

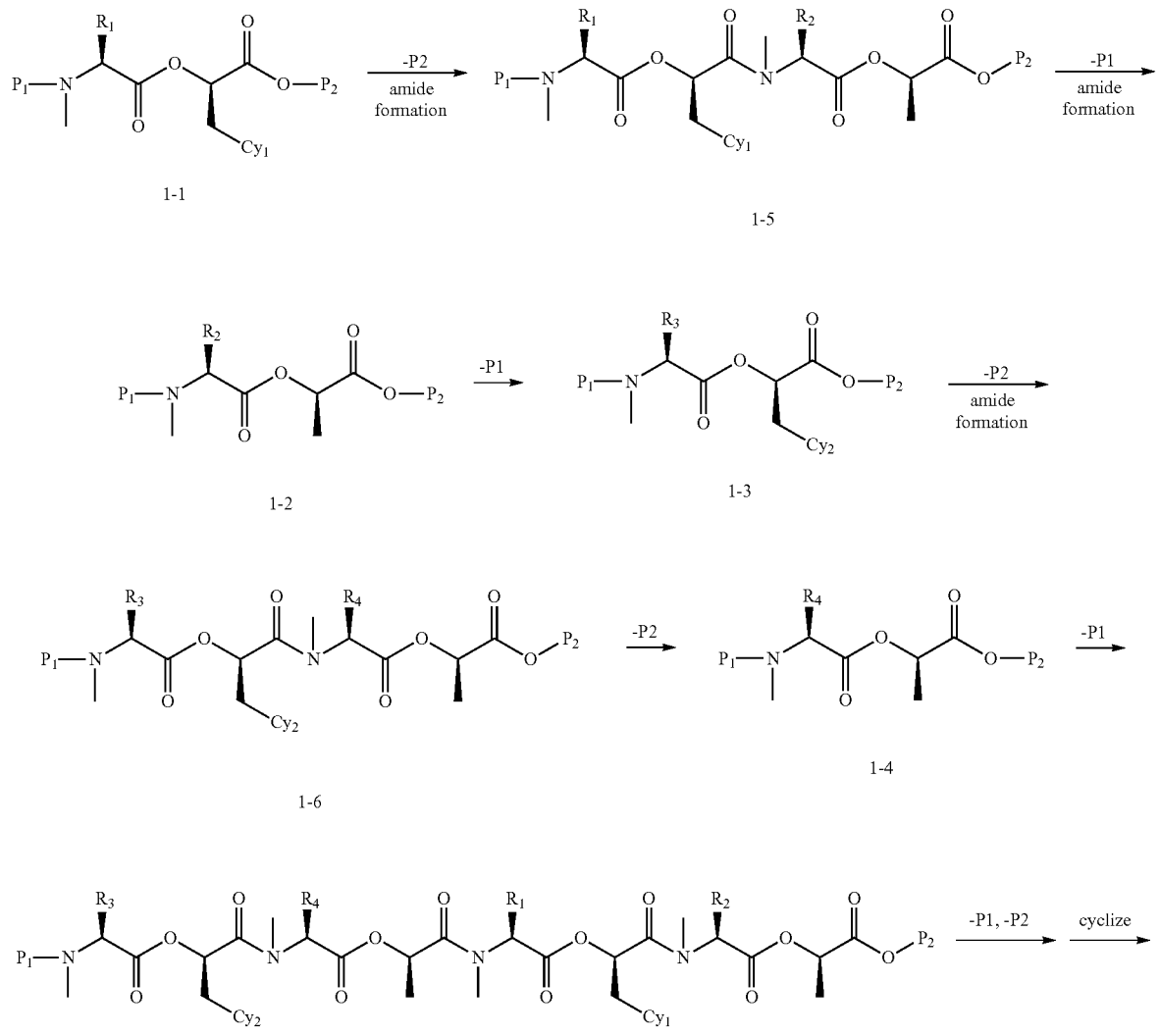

-continued

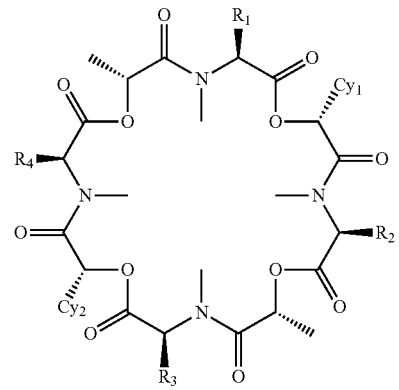

1-8

P$_1$ and P$_2$ are amine and carboxylic acid protecting groups, respectively, commonly used in the art (see, for example, Greene and Wuts, *Protective Groups in Organic Synthesis*, John Wiley and Sons, Inc., 4th edition 2006) and R$^1$, R$^2$, R$^3$, R$^4$, Cy$^1$ and Cy$^2$ are as defined above.

Furthermore, the coupling of amines with carboxylic acids to form amides is well known in the art and standard reagents may be used in the coupling of a fragment with an unprotected amine with a second fragment having a free carboxylic acid group (see for example, Peptide Synthesis by Miklos Bodanszky and Miguel Ondetti, Interscience Publishers, 1966; Amino Acid and Peptide Synthesis, 2$^{nd}$ Ed. By John Jones, Oxford University Press, 2002). The compounds may be prepared by solution phase synthesis or using solid-phase synthesis with polymeric supports. For example, the formation of amide bonds may be mediated by activating reagents such as carbodiimide reagents (e.g. dicyclohexyldiimide, diisopropyldiimide and (N-(3-Dimethylaminopropyl)-N'-ethylcarbodiimide.HCl) in combination with additives such as N-hydroxybenzotriazole (HOBt) and the like. In addition, the formation of amide bonds in the synthesis may be accomplished by using phosphonium reagents such as BOP (Benzotriazol-1-yloxy-tris (dimethylamino)-phosphonium hexafluorophosphate), PyBOP (Benzotriazol-1-yloxy-tripyrrolidino-phosphonium hexafluorophosphate), PyBrOP (Bromo-tripyrrolidino-phosphonium hexa-fluorophosphate) and the like. Other useful reagents for forming the amide bonds of the compounds of the invention are the so called aminium/uronium-imonium reagents such as TBTU/HBTU (2-(1H-Benzotriazol-1-yl)-N,N,N',N'-tetramethylaminium tetrafluoroborate/hexafluorophosphate), HATU (2-(7-Aza-1H-benzotriazol-1-yl)-N,N,N',N'-tetramethylaminium hexafluorophosphate) and the like. These reagents and the methods employing these reagents for the preparation of amide bonds are well known in the art.

Veterinary Compositions:

The compounds of formula (I) and compositions comprising the compounds are useful for the prevention and treatment of parasitic infestations/infections in animals. The compositions of the invention comprise an effective amount of at least one cyclic depsipeptide compound of formula (I), or a veterinarily acceptable salt thereof, in combination with a veterinarily acceptable carrier or diluent and optionally other non-active excipients. The compositions may be in a variety of solid and liquid forms which are suitable for various forms of application or administration to an animal. For example, the veterinary compositions comprising the inventive compounds may be in formulations suitable for oral administration, injectable administration, including subcutaneous and parenteral administration, and topical administration (e.g. spot-on or pour-on), dermal or subdermal administration. The formulations are intended to be administered to an animal including, but not limited to, mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds. The use of the compounds of formula (I) to protect companion animals such as dogs and cats from endoparasites is particularly useful.

As discussed above, the compositions of the invention may be in a form suitable for oral use (see, e.g., U.S. Pat. No. 4,564,631, which is hereby incorporated by reference in its entirety), dietary supplements, troches, lozenges, chewables, tablets, hard or soft capsules, bolus, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (all incorporated herein by reference in their entirety) to form osmotic therapeutic tablets for controlled release.

Oral formulations include hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

In one embodiment, the compounds of formula (I) may be administered in chewable tablet compositions or soft chewable compositions such as those described in US 2013/0203692 A1, US 2010/0087492, US 2006/0222684, US 2004/0151759, U.S. Pat. No. 7,955,632, all incorporated herein by reference. The veterinary compositions may be in the form of a soft chewable formulation ("soft chew") which is palatable and acceptable to the animal. In addition to the active ingredient(s), the soft chews of the invention may include one or more of the following components: a solvent or mixture of solvents, one or more fillers, one or more binders, one or more surfactants, one or more humectants, one or more lubricants, one or more disintegrants, one or more colorants, one or more antimicrobial agents, one or more antioxidants, one or more pH modifiers and one or more flavoring agents.

Solvents that may be used in the compositions of the invention include, but are not limited to, various grades of liquid polyethylene glycol (PEG) including PEG 200, PEG 300, PEG 400 and PEG 540; propylene carbonate; propylene glycol; triglycerides including, but not limited to caprylic/capric triglyceride, caprylic/capric/linoleic triglyceride (e.g. MIGLYOL® 810 and 812, caprylic/capric/succinic triglyceride, propylene glycol dicaprylate/dicaprate, and the like; water, sorbitol solution, glycerol caprylate/caprate and polyglycolized glycerides (GELUCIRE®), or a combination thereof.

Various fillers known in the art may be used in the soft chewable compositions of the invention. Fillers include, but are not limited to, corn starch, pre-gelatinized corn starch, soy protein fines, corn cob, and corn gluten meal, and the like. In some embodiments, a combination of two or more fillers may be used in the compositions.

Binders that may be used in the compositions of the invention include, but are not limited to, polyvinylpyrrolidone (e.g. Povidone), cross-linked polyvinylpyrrolidone (Crospovidone), polyethylene glycols of various grades including PEG 3350, PEG 4000, PEG 6000, PEG 8000 and even PEG 20,000, and the like; co-polymers of vinylpyrrolidone and vinyl acetate (e.g. Copovidone) such as the product sold by BASF by the tradename Kollidon® VA 64 and the like; starch such as potato starch, tapioca starch or corn starch; molasses, corn syrup, honey, maple syrup and sugars of various types; or a combination of two or more binders.

Humectants that may be used in the compositions include, but are not limited to, glycerol (also referred to herein as glycerin), propylene glycol, cetyl alcohol and glycerol monostearate, and the like. Polyethylene glycols of various grades may also be used as humectants.

Surfactants may be present in the composition to improve their solubility and absorption after ingestion. Surfactants are typically present in a concentration of about 1 to 10% (w/w), more typically about 1 to about 5% (w/w). Examples of surfactants that may be used in the compositions include, but are not limited to, glyceryl monooleate, polyoxyethylene sorbitan fatty acid esters, sorbitan esters including sorbitan monooleate (Span® 20), polyvinyl alcohol, polysorbates including polysorbate 20 and polysorbate 80, d-α-tocopheryl polyethylene glycol 1000 succinate (TPGS), sodium lauryl sulfate, co-polymers of ethylene oxide and propylene oxide (e.g. poloxamers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (LAUROGLYCOL®); glyceride esters including glycerol caprylate/caprate (CAPMUL® MCM), polyglycolized glycerides (GELUCIRE®), PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate, and the like.

The inventive formulations may contain other inert ingredients such as antioxidants, preservatives, or pH stabilizers. These compounds are well known in the formulation art. Antioxidants may be added to the compositions of the invention to inhibit degradation of the active agents. Suitable antioxidants include, but are not limited to, alpha tocopherol, ascorbic acid, ascrobyl palmitate, fumaric acid, malic acid, sodium ascorbate, sodium metabisulfate, n-propyl gallate, BHA (butylated hydroxy anisole), BHT (butylated hydroxy toluene) monothioglycerol and the like.

The compositions of the invention may also include one or more lubricants and/or processing aids. In some cases, the lubricant/processing aid may also behave as a solvent, and accordingly, there some of the components of the inventive compositions may have dual functions. Lubricants/processing aids include, but are not limited to polyethylene glycols of various molecular weight ranges including PEG 3350 (Dow Chemical) and PEG 4000, corn oil, mineral oil, hydrogenated vegetable oils (STEROTEX or LUBRITAB), peanut oil and/or castor oil.

Many flavoring agents may be used in the compositions of the invention to improve the palatability of the oral veterinary formulations. Preferred flavoring agents are those that are not derived from animal sources. In various embodiments, flavoring components derived from fruit, meat (including, but not limited to pork, beef, chicken, fish, poultry, and the like), vegetable, cheese, bacon, cheese-bacon and/or artificial flavorings may be used. A flavoring component is typically chosen based upon consideration related to the organism that will be ingesting the soft chew. For example, a horse may prefer an apple flavoring component, while a dog may prefer a meat flavoring component. Although flavoring components derived from non-animal sources are preferred, in some embodiments, natural flavors containing beef or liver extracts, etc., may be used such as braised beef flavor artificial powdered beef flavor, roast beef flavor and corned beef flavor among others.

In another embodiment of the invention, the active composition may be administered via a drench, and may be administered either topically or orally. Drench formulations are those in which the liquid-containing compositions of the invention are administered to the mouth or throat of the animal, or poured onto the skin or coat of the animal.

The compositions of the invention may also be in the form of oil-in-water or water-in-oil emulsions. The oily phase maybe a vegetable oil, for example, olive oil or *arachis* oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment, the composition of the invention may be in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets may be less than 200 nm (1000 to 100,000 nm for emulsions). The interfacial film may be composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment, the glycol may be propylene glycol, diethylene glycol monoethyl ether, dipropylene glycol monoethyl ether or mixtures thereof. Generally, the aqueous phase will represent a proportion from about 1 to about 4% v/v in the microemulsion.

Surfactants for the microemulsion may include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants may include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients include suspending agents, for example, sodium carboxymethylcellulose, methylcellulose, hydroxy-propylmethylcellulose, sodium alginate, polvinylpyrrolidone, gum tragacanth and gum acacia; dispersing or wetting agents include naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water may provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition may be in paste form. Examples of embodiments in a paste form include, but are not limited to, those described in U.S. Pat. Nos. 6,787,342 and 7,001,889 (each of which are incorporated herein by reference). In addition to the compounds of the invention, the paste may further contain fumed silica; a viscosity modifier; a carrier; optionally, an absorbent; and optionally, a colorant, stabilizer, surfactant, or preservative.

In one embodiment of the formulation, the formulation may be a paste containing the compounds of the invention, fumed silica, a viscosity modifier, an absorbent, a colorant; and a hydrophilic carrier which is triacetin, a monoglyceride, a diglyceride, or a triglyceride.

The paste may also include a viscosity modifier. Suitable viscosity modifiers include, but are not limited to, polyethylene glycols (PEG) including, but not limited to, PEG 200, PEG 300, PEG 400, PEG 600; monoethanolamine, triethanolamine, glycerol, propylene glycol, polyoxyethylene (20) sorbitan mono-oleate (polysorbate 80 or Tween 80), or poloxamers (e.g., Pluronic L 81); an absorbent such as magnesium carbonate, calcium carbonate, starch, and cellulose and its derivatives; and a colorant including, but not limited to, titanium dioxide iron oxide, or FD&C Blue #1 Aluminum Lake.

In some embodiments, the compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol, glycerol formal or polyethylene glycols may also be used. Preservatives, such as phenol or benzyl alcohol, may be used.

In addition, sterile, fixed oils may be conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations may include, by way of non-limiting example, emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, in the form of a spot-on, spray-on or pour-on composition, may allow for the inventive composition to be absorbed through the skin to achieve systemic levels, distributed through the sebaceous glands or on the surface of the skin achieving levels throughout the coat. When the compound is distributed through the sebaceous glands, they may act as a reservoir, whereby there may be a long-lasting effect (up to several months) effect. Spot-on formulations are typically applied in a localized region which refers to an area other than the entire animal. In one embodiment, the location may be between the shoulders. In another embodiment it may be a stripe, e.g. a stripe from head to tail of the animal.

Pour-on formulations are described in U.S. Pat. No. 6,010,710, also incorporated herein by reference. Pour-on formulations may be advantageously oily, and generally comprise a diluent or vehicle and also a solvent (e.g. an organic solvent) for the active ingredient if the latter is not soluble in the diluent.

Organic solvents that can be used in the invention include, but are not limited to, acetyltributyl citrate, fatty acid esters such as the dimethyl ester, diisobutyl adipate, acetone, acetonitrile, benzyl alcohol, ethyl alcohol, butyl diglycol, dimethylacetamide, dimethylformamide, dimethyl sulfoxide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, triacetin, $C_1$-$C_{10}$ esters of carboxylic acids such as butyl or octyl acetate, and diethyl phthalate, or a mixture of at least two of these solvents.

The solvent will be used in proportion with the concentration of the active agent compound and its solubility in this solvent. It will be sought to have the lowest possible volume. The vehicle makes up the difference to 100%.

A vehicle or diluent for the formulations may include dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the invention, an emollient and/or spreading and/or film-forming agent may be added. In one embodiment, the emollient and/or spreading and/or film-forming agent may be:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants include water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (d) amine salts of formula $N^+HR'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the invention, the composition may be in ready-to-use solution form as is described in U.S. Pat. No. 6,395,765, incorporated herein by reference. In addition to the compounds of the invention, the ready-to-use solution may contain a crystallization inhibitor and an organic solvent or a mixture of organic solvents. In some embodiments, water may be included with the organic solvent.

In various embodiments of the invention, the compositions may include a crystallization inhibitor in an amount of about 1 to about 50% (w/v) or about 5 to about 40% (w/v) based on the total weight of the formulation. In other embodiments, the amount of crystallization inhibitor in the inventive formulations may be about 1% to about 30%, about 5% to about 20%, about 1% to about 15%, or about 1% to about 10% (w/w). The type of crystallization inhibitor used in the inventive formulations is not limited as long as it functions to inhibit crystallization of the active or inactive agents from the formulation. For example, in certain embodiments of the invention, a solvent or co-solvent of the formulation may also function as a crystallization inhibitor if it sufficiently inhibits the formation of crystals from forming over time when the formulation is administered.

Crystallization inhibitors which are useful for the invention include, but are not limited to:

(a) polyvinylpyrrolidone, polyvinyl alcohols, copolymers of vinyl acetate and vinylpyrrolidone, polyethylene glycols, benzyl alcohol, dimethylformamide, dimethylacetamide, dimethylsulfoxide, 2-pyrrolidone, N-methylpyrrolidone, mannitol, glycerol, sorbitol or polyoxyethylenated esters of sorbitan; lecithin or sodium carboxymethylcellulose; or acrylic derivatives, such as acrylates or methacrylates or polymers or copolymers thereof, polyethyleneglycols (PEG) or polymers containing polyethyleneglycols, such as glycofurol and the like, and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula N+R'R"R'"R""Y$^-$, in which the R radicals are identical or different optionally hydroxylated hydrocarbon radicals and Y$^-$ is an anion of a strong acid, such as halide, sulphate and sulphonate anions; cetyltrimethylammonium bromide is one of the cationic surfactants which can be used;

(d) amine salts of formula N+HR'R"R'", in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine;

(g) a mixture of at least two of the compounds listed in (a)-(f) above; or (h) an organic solvent or mixture of solvents which inhibit the formation of crystals or amorphous solid after the formulation is administered.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In some embodiments, the organic solvent(s) may have a dielectric constant of between about 10 and about 35 or between about 20 and about 30. In other embodiments, the organic solvent may have a dielectric constant of between about 10 and about 40 or between about 20 and about 30. The content of this organic solvent or mixture of solvents in the overall composition is not limited and will be present in an amount sufficient to dissolve the desired components to a desired concentration. As discussed above, the organic solvent may also function as a crystallization inhibitor in the formulation.

In some embodiments, one or more of the organic solvent(s) may have a boiling point of below about 100° C., or below about 80° C. In other embodiments, the organic solvent(s) may have a boiling point of below about 300° C., below about 250° C., below about 230° C., below about 210° C. or below about 200° C.

In some embodiments where there is a mixture of solvents, i.e. a solvent and a co-solvent, the solvents may be present in the composition in a weight/weight (W/W) ratio of about 1/50 to about 1/1. Typically the solvents will be in a ratio of about 1/30 to about 1/1, about 1/20 to about 1/1, or about 1/15 to about 1/1 by weight. Preferably, the two solvents will be present in a weight/weight ratio of about 1/15 to about 1/2. In some embodiments, at least one of the solvents present may act as to improve solubility of the active agent or as a drying promoter. In particular embodiments, at least one of the solvents will be miscible with water.

The formulation may also comprise an antioxidizing agent intended to inhibit oxidation in air, this agent may be present in a proportion of about 0.005 to about 1% (w/v), about 0.01 to about 0.1%, or about 0.01 to about 0.05%.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent may be incorporated in similar or identical amounts within the limit of the total amounts of crystallization inhibitor mentioned elsewhere.

The crystallization inhibitor inhibits the formation of crystals on the coat, and improves the maintenance of the cosmetic appearance of the skin or fur; that is to say without a tendency towards sticking or towards a sticky appearance, despite the high concentration of active material. Substances other than those mentioned herein may be used as crystallization inhibitors in the present invention. In one embodiment, the effectiveness of the crystallization inhibitor may be demonstrated by a test according to which 0.3 mL of a solution comprising 10% (w/v) of the active agent in an appropriate solvent as defined above, and 10% (w/v) of the compound acting as a crystallization inhibitor are placed on a glass slide at 20° C. for 24 hours, after which fewer than 10 crystals, preferably 0 crystals, are seen with the naked eye on the glass slide.

In one embodiment of the antioxidizing agents, the agents are those conventional in the art and include but are not limited to butylated hydroxyanisole, butylated hydroxytoluene, ascorbic acid, sodium metabisulphite, propyl gallate, sodium thiosulphate or a mixture of at least two compounds with antioxidant properties.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume of the formulation applied will depend on the type of animal and the size of the animal as well as the strength of the formulation and the potency of the active agents. In one embodiment, an amount of about 0.1 to about 20 ml of the formulation may be applied to the animal. In other embodiment for the volume, the volume may be about 0.1 to about 10 ml, about 0.1 to about 5 ml, about 0.5 ml to about 10 ml, or about 0.3 to about 3 ml.

In another embodiment of the invention, application of a spot-on formulation according to the present invention may also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier may be a liquid carrier vehicle as described in U.S. Pat. No. 6,426,333 (incorporated herein by reference), which in one embodiment of the spot-on formulation may comprise a solvent or mixture of solvents including, but not limited to, acetone, an aliphatic alcohol such as methanol, ethanol, propanol, butanol, isopropanol, pentanol, hexanol, heptanol, octanol, nonanol, cyclopentanol, cyclohexanol, ethylene glycol, propylene glycol and the like; an aromatic alcohol such as phenol, cresol, naphthol, benzyl alcohol and the like; acetonitrile, butyl diglycol, an organic amide such as dimethylacetamide, dimethylformamide, monomethylacetamide, 2-pyrrolidone, N-methylpyrrolidone, vinylpyrrolidone and the like; propylene or ethylene carbonate, dimethylsulfoxide (DMSO), a glycol polymer or an ether thereof, such as polyethylene glycol (PEG) of various grades, polypropylene glycols of various grades, dipropylene glycol n-butyl ether, ethylene glycol monoethyl ether, ethylene glycol monomethyl ether, dipropylene glycol monomethyl ether, diethylene glycol monoethyl ether, ethylene glycol, diethyl phthalate fatty acid esters, such as the diethyl ester or diisobutyl adipate, or a mixture of at least two of these solvents.

The liquid carrier vehicle may optionally contain a crystallization inhibitor including, but not limited to, those described in (a) to (h) above, or a compound that may act both as a solvent and a crystallization inhibitor (as defined above), or a mixture of these crystallization inhibitors.

Spot-on formulations may be prepared by dissolving the active ingredients into the pharmaceutically or veterinary acceptable vehicle. Alternatively, the spot-on formulation may be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may typically contain from about 0.1 mg to about 5 g. In other embodiments, the dosage form may contain about 0.5 mg to about 5 g of an active agent. In one embodiment of the dosage form, the dosage may contain from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent may be present in the formulation at a concentration of about 0.05 to about 10% weight/volume. In another embodiment of the invention, the active agent may be present in the formulation as a concentration from about 0.1 to about 2% weight/volume. In yet another embodiment of the invention, the active agent may be present in the formulation as a concentration from about 0.25 to about 1.5% weight/volume. In still another embodiment of the invention, the active agent may be present in the formulation as a concentration about 1% weight/volume.

II. Methods of Treatment:

As discussed above, the compounds of formula (I) are effective against endoparasites and may be used to treat and prevent parasitic infections in or on animals. In one embodiment, the present invention provides a method of treating or preventing an endoparasite infection in or on an animal (e.g. a mammal or bird) comprising administering an endoparasiticidally effective amount of a compound of formula (I), or veterinarily acceptable salts thereof, or a composition of the invention, to the animal.

The compounds of formula (I) may also effective against ectoparasites and may be used to treat and prevent ectoparasitic infestations on animals. In another embodiment, the present invention provides a method of treating or preventing an ectoparasitic infestation on an animal (e.g. a mammal or bird) comprising administering an ectoparasiticidally effective amount of a compound of formula (I), or veterinarily acceptable salts thereof, or a composition of the invention, to the animal.

In another embodiment, the invention provides a method for treating or preventing an endoparasitic infection and an ectoparasitic infestation in and on an animal, comprising administering a composition comprising an effective amount of a compound of formula (I) in combination with an effective amount of at least a second active agent, or veterinarily acceptable salts thereof, to the animal.

In still another embodiment of the invention, a method is provided for the treatment or prevention of a parasitic infestation at a locus, which comprises administering or applying a parasiticidally effective amount of a compound of formula (I), or veterinarily acceptable salts thereof, to the locus. With respect to animal health applications, "locus" is intended to mean a habitat, breeding ground, area, material or environment in which a parasite is growing or may grow, excluding in or on an animal.

In another embodiment, the invention provides methods and uses of the compounds of formula (I) for controlling pests in plants and crops or for protecting wood-containing structures.

Mammals which can be treated include but are not limited to humans, cats, dogs, cattle, chickens, cows, bison, deer, goats, horses, llamas, camels, pigs, sheep and yaks. In one embodiment of the invention, the mammals treated are humans, cats or dogs.

In one embodiment of the invention, the compounds of formula (I) have been superior efficacy against endoparasites, and in particular against endoparasites that are resistant to active agents of the macrocyclic lactone class. In one embodiment, the compounds and compositions of the invention are effective for controlling *Haemonchus contortus*, *Ostertagia circumcincta* and *Trichostrongylus colubriformis* in mammals or birds.

In another embodiment, the invention provides a method for treating an parasitic infestation or infection in an animal, comprising administering an effective amount of an anthelmintic compound of the invention in combination with an effective amount of activators of invertebrate GABA receptors including an avermectin or milbemycin to the animal in need thereof. Avermectins that may be used in combination with the compounds of the invention include, but are not limited to abamectin, dimadectin, doramectin, emamectin, eprinomectin, ivermectin, latidectin, lepimectin, and selamectin Milbemycins compounds that may be used in combination with the compounds of the invention include, but are not limited to, milbemectin, milbemycin D, moxidectin and nemadectin. Also included are the 5-oxo and 5-oxime derivatives of said avermectins and milbemycins.

In one embodiment, the compounds and compositions of the invention may be used for treating or preventing an endoparasitic infection of the following parasite: *Anaplocephala* (*Anoplocephala*), *Ancylostoma, Necator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostomum, Onchocerca, Ostertagia, Oxyuris, Parascaris, Schistosoma, Strongylus, Taenia, Toxocara, Strongyloides, Toxascaris, Trichinella, Trichuris, Trichostrongylus, Triodontophorus, Uncinaria, Wuchereria,* and combinations thereof.

In a particularly preferred embodiment of the invention, the compounds and compositions of the invention are used to treat or prevent an infection by *Dirofilaria immitis*. The compounds of formula (I) have been found to be highly effective against *D. immitis* microfilaria and L4 larvae. Thus, the compounds of formula (I) may be used to protect animals from developing heartworm disease by killing the immature stages of *D. immitis* before they can develop into adult worms. In one embodiment, the compounds of formula (I) and compositions comprising the compounds may be used to prevent the development of heartworm disease by killing immature stages of *D. immitis* that are resistant to macrocyclic lactones. In another embodiment the compounds and compositions of the invention are used to treat or prevent an infection by *Dirofilaria repens* or *Dirofilaria hongkongensis*.

In another embodiment of the invention, the parasite is *Haemonchus contortus, Ostertagia circumcincta, Trichostrongylus axei, Trichostrongylus colubriformis, Cooperia curticei, Nematodirus battus* and combinations thereof.

In another embodiment for treatment against both endoparasites and ectoparasites when combined with ectoparasiticidal agents, the ectoparasite is one or more insect or arachnid including those of the genera *Ctenocephalides, Rhipicephalus, Dermacentor, Ixodes, Boophilus, Amblyomma, Haemaphysalis, Hyalomma, Sarcoptes, Psoroptes, Otodectes, Chorioptes, Hypoderma, Damalinia, Linognathus, Haematopinus, Solenoptes, Trichodectes,* and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis, Ctenocephalides* spp. and the like), ticks (*Rhipicephalus* spp., *Ixodes* spp., *Dermacentor* spp., *Amblyomma* spp. and the like), and mites (*Demodex* spp., *Sarcoptes* spp., *Otodectes* spp. and the like), lice (*Trichodectes* spp., *Cheyletiella* spp., *Linognathus* spp., and the like), mosquitoes (*Aedes* spp., *Culex* spp., *Anopheles* spp., and the like) and flies (*Haematobia* spp., *Musca* spp., *Stomoxys* spp., *Dermatobia* spp., *Cochliomyia* spp., and the like). In yet another embodiment for the treatment against ectoparasites, the ectoparasite is a flea and/or tick.

Additional examples of ectoparasites include but are not limited to the tick genus *Boophilus*, especially those of the species *microplus* (cattle tick), *decoloratus* and *annulatus*; myiasis such as *Dermatobia hominis* (known as Berne in Brazil) and *Cochliomyia hominivorax* (greenbottle); sheep myiasis such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In another embodiment of the invention, the compounds and compositions of the invention are suitable for controlling pests such as insects selected from the group consisting of *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the invention can also be used to treat other pests which include but are not limited to pests:

(1) from the order of Isopoda, for example *Oniscus asellus, Armadillidium vulgare* and *Porcellio scaber;*

(2) from the order of Diplopoda, for example *Blaniulus guttulatus;*

(3) from the order of Chilopoda, for example *Geophilus carpophagus* and *Scutigera* spp.;

(4) from the order of Symphyla, for example *Scutigerella immaculata;*

(5) from the order of Thysanura, for example *Lepisma saccharina;*

(6) from the order of Collembola, for example *Onychiurus armatus;*

(7) from the order of Blattaria, for example *Blatta orientalis, Periplaneta americana, Leucophaea maderae* and *Blattella germanica;*

(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*

(12) from the class of Bivalva, for example, *Dreissena* spp.;

(13) *from the order of Coleoptera, for example, Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipulapaludosa, Wohlfahrtia* spp.;

(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Ancylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloidesfuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;*

(17) from the order of Heteroptera, for example, *Anasa tristis, Antestiopsis* spp., *Blissus* spp., *Calocoris* spp., *Camnpylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(18) from the order of Homoptera, for example, *Acyrthosipon* spp., *Aeneolanmia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;*

(19) from the order of Isoptera, for example, *Reticulitermes* spp., *Odontotermes* spp.;

(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;*

(22) from the order of Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

In each aspect of the invention, the compounds and compositions of the invention can be applied against a single pest or combinations thereof.

III. Mixtures with Other Active Agents

In another embodiment, the compositions comprising the cyclic depsipeptides of formula (I) may also include other veterinary therapeutic agents. Veterinary pharmaceutical agents that may be included in the compositions of the invention are well-known in the art (see e.g. *Plumb' Veteri-*

*nary Drug Handbook*, 5th Edition, ed. Donald C. Plumb, Blackwell Publishing, (2005) or *The Merck Veterinary Manual*, 9th Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *propionibacterium acnes* injection, propofol, propranolol, protamine sulfate, pseudoephedrine, *psyllium* hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodium thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles may be included in the veterinary compositions of the invention. Arylpyrazoles are known in the art and are suitable for combination with the cyclic depsipeptides of formula (I) in the compositions of the invention. Examples of such arylpyrazole compounds include but are not limited to those described in U.S. Pat. Nos. 6,001,384; 6,010,710; 6,083,519; 6,096,329; 6,174,540; 6,685,954, 6,998,131 and 7,759,381 (all of which are incorporated herein by reference). A particularly preferred arylpyrazole active agent is fipronil.

In another embodiment of the invention, one or more macrocyclic lactones, which act as an acaricide, an anthelmintic agent and/or an insecticide, can be included in the compositions of the invention in combination with the compounds of formula (I). For the avoidance of doubt, the term "macrocyclic lactone" as used herein includes both naturally occurring and synthetic or semi-synthetic avermectin and milbemycin compounds.

The macrocyclic lactones that may be used in the compositions of the invention include, but are not limited to, the naturally produced avermectins (e.g. including the components designated as $A_1a$, $A_1b$, $A_2a$, $A_2b$, $B_1a$, $B_1b$, $B_2a$ and $B_2b$) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin $A_3$, milbemycin $A_4$, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" $12^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information, vol.* 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

In one embodiment, the veterinary compositions of the invention comprise an effective amount of at least one of abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof. In another embodiment, the invention provides a veterinary composition comprising an effective amount of at least one of abamectin, emamectin, eprinomectin, ivermectin, doramectin or selamectin, or a combination thereof. In still another embodiment, the veterinary compositions of the invention comprise an effective amount of at least one of ivermectin, milbemectin, milbemycin oxime or moxidectin, or a combination thereof.

In another embodiment of the invention, a composition comprising a compound of formula (I) in combination with a class of acaricide or insecticides known as insect growth regulators (IGRs) are provided. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the compositions of the invention may include an IGR compound that mimics juvenile hormone or that modulates levels of juvenile hormones in insects. Examples of juvenile hormone mimics include azadirachtin, diofenolan, fenoxycarb, hydroprene, kinoprene, methoprene, pyriproxyfen, tetrahydroazadirachtin and 4-chloro-2 (2-chloro-2-methyl-propyl)-5-(6-iodo-3-pyridylmethoxy) pyridazine-3(2H)-one. In another embodiment, the compositions of the invention comprise a compound of formula (I) in combination with methoprene or pyriproxyfen and a pharmaceutically acceptable carrier.

In another embodiment, the compositions of the invention include an IGR compound that is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In some embodiments, the compositions of the invention may include one or more antinematodal agents including, but not limited to, active agents in the benzimidazoles, imidazothiazoles, tetrahydropyrimidines and the organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions of the invention may include an imidazothiazole compounds including, but not limited to, tetramisole, levamisole and butamisole.

In still other embodiments, the compositions of the invention may include tetrahydropyrimidine active agents including, but not limited to, pyrantel, oxantel, and morantel.

Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, nitroxynil, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin, paromomycin II, praziquantel and epsiprantel.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a (4H)-dibenzofurancarboxaldehyde (MGK-11), 2-(2-ethylhexyl)-3a,4,7,7a-tetrahydro-4,7-methano-1H-isoindole-1,3 (2H)dione (MGK-264), dipropyl-2,5-pyridinedicarboxylate (MGK-326) and 2-(octylthio)ethanol (MGK-874).

In another embodiment, an antiparasitic agent that can be included in the veterinary composition containing a compound of formula (I) can be a biologically active peptide or protein including, but not limited to, depsipeptides other than the compounds of formula (I). These include PF1022A or analogs thereof and emodepside. These compounds act at the neuromuscular junction by stimulating presynaptic receptors belonging to the secretin receptor family resulting in the paralysis and death of parasites. In one embodiment of the depsipeptide, the depsipeptide is emodepside (see Wilson et al., *Parasitology*, January 2003, 126(Pt 1):79-86).

In another embodiment, the compositions of the invention may comprise an active agent from the neonicotinoid class of parasiticides. The neonicotinoids bind and inhibit insect specific nicotinic acetylcholine receptors. In one embodiment, the neonicotinoid insecticidal agent that can be combined with a compound of formula (I) in a composition of the invention is imidacloprid. Agents of this class are described, for example, in U.S. Pat. No. 4,742,060 or in EP 0 892 060 (both incorporated herein by reference). In another embodiment, the compositions of the invention may comprise nitenpyram, another active agent of the neonicotinoid class of pesticides. The use of nitenpyram for controlling fleas is described in U.S. Pat. No. 5,750,548, which is incorporated herein by reference in its entirety.

In certain other embodiments of the invention, the cyclic depsipeptides of formula (I) can be combined with the compositions of the invention is a semicarbazone, such as metaflumizone.

In another embodiment, the compositions of the invention may advantageously include a mixture of one or more other isoxazoline compounds known in the art, in addition to or in place of the isoxazoline active agents described above. Isoxazoline active agents are highly effective against a variety of ectoparasites and combination with the cyclic depsipeptides of formula (I) would expand the scope of efficacy against these parasites. Particularly useful isoxazoline active agents that can be combined with the compounds of formula (I) include afoxolaner (including substantially pure active enantiomer), sarolaner, fluralaner (including substantially pure active enantiomer) and lotilaner. These active agents are described in U.S. Pat. No. 7,964,204, US 2010/0254960 A1, US2011/0159107, US2012/0309620, US2012/0030841, US2010/0069247, WO 2007/125984, WO 2012/086462, U.S. Pat. No. 8,318,757, U.S. Pat. No. 8,466,115, U.S. Pat. No. 8,618,126, U.S. Pat. No. 8,822,466, U.S. Pat. No. 8,383,659, U.S. Pat. No. 8,853,186, U.S. Pat. No. 9,221,835, US 2011/0144349, U.S. Pat. No. 8,053,452; US 2010/0137612, U.S. Pat. No. 8,410,153, US 2011/152081, WO 2012/089623, WO 2012/089622, U.S. Pat. No. 8,119,671; U.S. Pat. No. 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1, US 2015/0126523, WO 2010/003923, WO 2010/003877, WO 2010/072602, WO 2014/134236, U.S. Pat. No. 7,897,630, and U.S. Pat. No. 7,951,828, all of which are incorporated herein by reference in their entirety.

In another embodiment of the invention, nodulisporic acid and its derivatives may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in U.S. Pat. No. 7,084,280 to Ducray et al. (incorporated herein by reference); Sager et al., Veterinary Parasitology, 2009, 159, 49-54; Kaminsky et al., Nature vol. 452, 13 Mar. 2008, 176-181.

The compositions of the invention may also include aryloazol-2-yl cyanoethylamino compounds such as those described in U.S. Pat. No. 8,088,801 to Soll et al., which is incorporated herein by reference, and thioamide derivatives of these compounds, as described in U.S. Pat. No. 7,964,621 to Le Hir de Fallois, which is also incorporated herein by reference. Aryloazol-2-yl cyanoethylamino active agents, which are systemically-acting against endoparasites, may be used in combination with the compounds of formula (I) in veterinary compositions of the invention.

The compositions of the invention may also include paraherquamide compounds and derivatives of these compounds, including derquantel (see Ostlind et al., Research in Veterinary Science, 1990, 48, 260-61; and Ostlind et al., Medical and Veterinary Entomology, 1997, 11, 407-408). The paraherquamide family of compounds is a known class of compounds that include a spirodioxepino indole core with activity against certain parasites (see Tett. Lett. 1981, 22, 135; J. Antibiotics 1990, 43, 1380, and J. Antibiotics 1991, 44, 492). In addition, the structurally related marcfortine family of compounds, such as marcfortines A-C, are also known and may be combined with the formulations of the invention (see J. Chem. Soc.—Chem. Comm. 1980, 601 and Tet. Lett. 1981, 22, 1977). Further references to the paraherquamide derivatives can be found, for example, in WO 91/09961, WO 92/22555, WO 97/03988, WO 01/076370, WO 09/004432 and US 2010/0197624, U.S. Pat. No. 5,703,078 and U.S. Pat. No. 5,750,695, all of which are hereby incorporated by reference in their entirety.

In another embodiment of the invention, the compositions may include a spinosyn active agent produced by the soil actinomycete Saccharopolyspora spinosa (see, for example Salgado V. L. and Sparks T. C., "The Spinosyns: Chemistry, Biochemistry, Mode of Action, and Resistance," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by Saccharopolyspora pagona, which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In general, additional active agents (other than the compound of formula (I) described above) is included in the dosage units of the invention in an amount of between about 0.1 µg and about 1000 mg. Typically, the active agent may be included in an amount of about 10 µg to about 500 mg, about 10 µg to about 400 mg, about 1 mg to about 300 mg, about 10 mg to about 200 mg or about 10 mg to about 100 mg. More typically the additional active agent will be present in an amount of about 5 mg to about 50 mg in the compositions of the invention.

The concentration of the additional active agent in the compositions of the invention will typically be from about 0.01% to about 30% (w/w) depending on the potency of the active agent. In certain embodiments for very potent active agents including, but not limited to a macrocyclic lactone active agent, the concentration of the active agent will typically be from about 0.01% to about 10% (w/w), from about 0.01 to about 1% (w/w), from about 0.01% to about 0.5% (w/w), from about 0.1% to about 0.5% (w/w) or from about 0.01% to about 0.1% (w/w). In other embodiments, the concentration of the active agent will typically be from about 0.1% to about 2% (w/w) or about 0.1% to about 1% (w/w).

In other embodiments, the additional active agent will typically be present at higher concentrations to achieve the desired efficacy. In some embodiments, the active agent will be present in a concentration of about 1% to about 30% (w/w), about 1% to about 20% (w/w) or about 1% to about 15% (w/w). In still other embodiments, the active agent will be present in a concentration of about 5% to about 20% (w/w) or about 5% to about 15% (w/w) in the composition.

In various embodiments of the invention, an additional active agent may be included in the composition to deliver a dose of about 0.001 mg/kg to about 50 mg/kg or about 0.5 mg/kg to about 50 mg/kg of body weight of the animal. In other embodiments, the active agent will typically be present in an amount sufficient to deliver a dose of about 0.05 mg/kg to about 30 mg/kg, about 0.1 mg/kg to about 20 mg/kg. In other embodiments, the active agent will be present in an amount sufficient to deliver a dose of about 0.1 mg/kg to about 10 mg/kg, about 0.1 mg/kg to about 1 mg/kg or about 0.5 mg/kg to about 50 mg/kg per body weight of the animal.

In certain embodiments of the invention where the additional active agent is a very potent compound such as a macrocyclic lactone or other potent compounds, the active agent will be present in a concentration to provide a dose of about 0.001 mg/kg to about 5 mg/kg, about 0.001 mg/kg to about 0.1 mg/kg or about 0.001 mg/kg to about 0.01 mg/kg. In still other embodiments, the active agent is present in an amount sufficient to deliver a dose of about 0.01 mg/kg to about 2 mg/kg or about 0.1 mg/kg to about 1 mg/kg per body weight of the animal. In still other embodiments, the additional active agent may be present in an amount to deliver a dose of about 1 µg/kg to about 200 µg/kg or about 0.1 mg/kg to about 1 mg/kg of weight of animal.

In addition to the other active agents mentioned above, combinations of two or more active agents may be used with the compounds of the invention in a composition to treat a desired spectrum of pests and parasites. It would be well within the skill level of the practitioner to decide which individual compound can be used in the inventive formulation to treat a particular infection of an insect.

The invention will now be further described by way of the following non-limiting examples.

EXAMPLES

List of Abbreviations

ACN acetonitrile
AIBN azobisisobutyronitrile

BSA bovine serum albumin
BOC tert-butoxycarbonyl
BOP-Cl Bis(2-oxo-3-oxazolidinyl)phosphinic chloride
DCC N,N'-Dicyclohexylcarbodiimide solution
DCM dichloromethane
DEAD Diethyl azodicarboxylate
DIEA diisopropylethylamine
DMF N,N-dimethylformamide
DMAP 4-(Dimethylamino)pyridine
DMSO dimethylsulfoxide
EDAC  N-(3-Dimethylaminopropyl)-N'-ethylcarbodiimide hydrochloride
ES electrospray
EtOAc or EA ethyl acetate
HATU 1-[bis(dimethylamino)methylene]-1H-1,2,3-triazolo[4,5 b]pyridinium 3-oxide hexafluorophosphate
HOBt or HOBT 1-hydroxybenzotriazole
KHMDS potassium hexamethyldisilazide, more precisely potassium bis(trimethylsilyl)amide
MeOH methanol
PE petroleum ether
TBAF tert-butyl ammonium fluoride
THF tetrahydrofuran
TLC thin-layer chromatography Preparation Examples The preparation examples below are non-limiting examples of methods used to prepare the examples of the invention. The 4-fluoro-N-methyl leucine reagent protected with the tert-butyloxycarbonyl group (BOC) shown below is used in the preparation of the starting material shown in schemes 1 and 2.

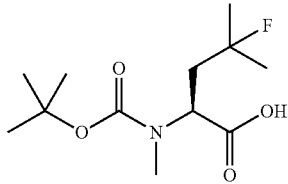 [SMILES: CN(C(=O)OC(C)(C)C)[C@@H](CC(C)(C)F)C(=O)O]

This compound is prepared according to standard procedures from commercially-available 4-fluoroleucine (Chemical Abstracts Registry Number 857026-04-1). It will be appreciated that other groups $R^1$ to $R^4$ may also be prepared with different leucine analogs in a similar manner. For example, 3-fluoroleucine (Chemical Abstracts Registry No. 171077-98-8, for example see Kaneko et al., *Chem. Pharm Bul.*, 1995, 43(5), 760-765) and 5-fluoroleucine (Chemical Abstracts Registry No. 159415-71-1, see Moody et al., *Tett. Lett.*, 1994, 35(30), 5485-8) are also known and could be used to prepare compounds where $R^1$ to $R^4$ are differently substituted fluoro leucine residues. In addition, it will be appreciated that alternative amino acids with different side chains may also used to prepare alternative compounds of the invention.

As shown in Scheme 1 above, the preparation of the compounds of the invention is conducted by cyclization of the precursor 1-7 after deprotection of the terminal amine and carboxylic acid groups. It will be appreciated by skilled persons in the art that using the general process outlined in Scheme 1 a wide variety of compounds of the invention may be prepared by selecting the appropriate monomer starting materials with the desired groups $R^1$, $R^2$, $R^3$, $R^4$, $Cy^1$ and $Cy^2$ in place and preparing the dimers of general formulae 1-1, 1-2, 1-3 and 1-4 by deprotection of the appropriate carboxylic acid and amino groups and amide formation.

Preparation Examples 1-28 shown below provide processes for the preparation of various monomer compounds M1 to M49 substituted with a wide variety of groups $R^1$, $R^2$, $R^3$, $R^4$, $Cy^1$ and $Cy^2$ that enable the preparation of a diverse set of dimer compounds used for the preparation of the compounds of the invention.

Preparation Example 1: Preparation of Monomer M1

Monomer M1 was prepared by the process shown in Scheme 2 below.

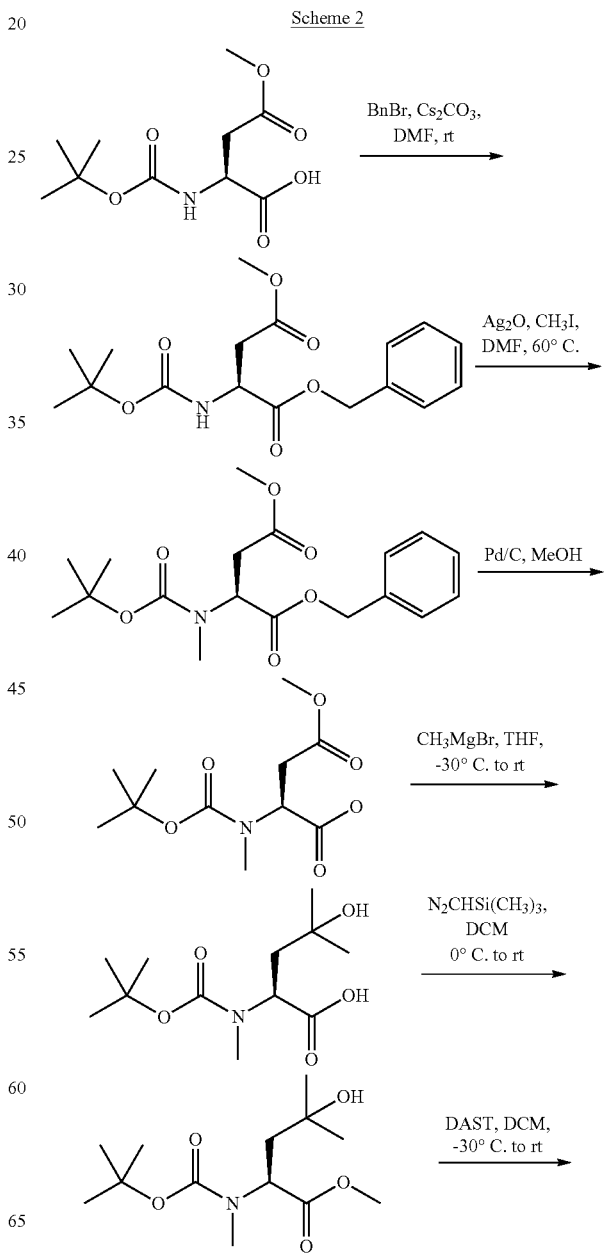

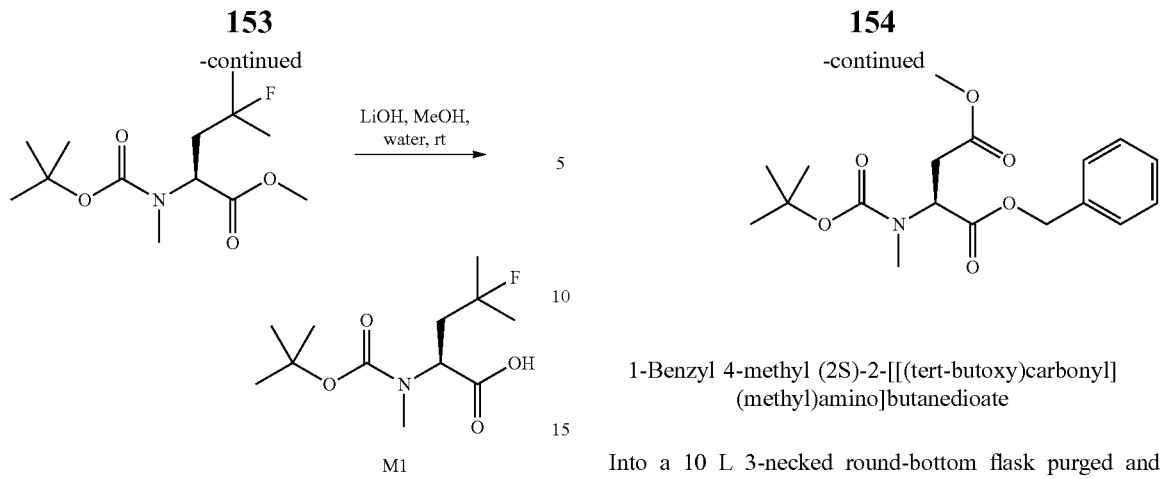

Experimental Details

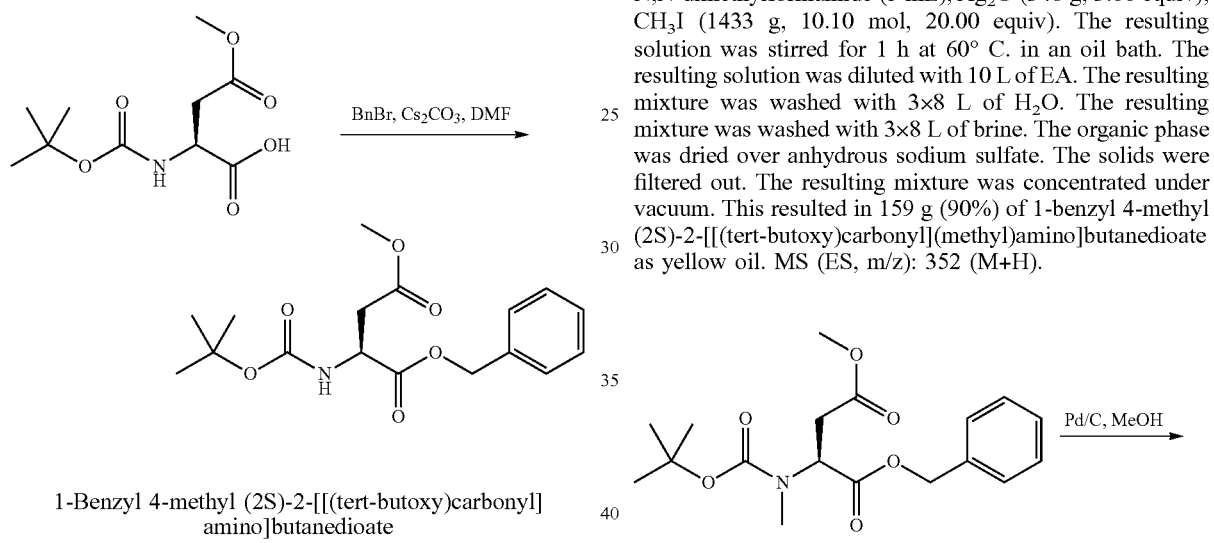

1-Benzyl 4-methyl (2S)-2-[[(tert-butoxy)carbonyl]amino]butanedioate

Into a 20-L 3-necked round-bottom flask purged and maintained with an inert atmosphere of nitrogen, was placed a solution of (2S)-2-[[(tert-butoxy)carbonyl]amino]-4-methoxy-4-oxobutanoic acid (150 g, 606.69 mmol, 1.00 equiv) in N,N-dimethylformamide (5 L), $Cs_2CO_3$ (396 g, 1.22 mol, 2.00 equiv), BnBr (124 g, 725.02 mmol, 1.20 equiv). The resulting solution was stirred for 2 h at room temperature. The resulting solution was diluted with 10 L of EA. The resulting mixture was washed with 3×5 L of $H_2O$. The resulting mixture was washed with 3×5 L of brine. The mixture was dried over anhydrous sodium sulfate. The solids were filtered out. The resulting mixture was concentrated under vacuum. This resulted in 170 g (83%) of 1-benzyl 4-methyl (2S)-2-[[(tert-butoxy)carbonyl]amino]butanedioate as a white solid. MS (ES, m/z): 338 (M+H).

1-Benzyl 4-methyl (2S)-2-[[(tert-butoxy)carbonyl](methyl)amino]butanedioate

Into a 10 L 3-necked round-bottom flask purged and maintained with an inert atmosphere of nitrogen, was placed a solution of 1-benzyl 4-methyl (2S)-2-[[(tert-butoxy)carbonyl]amino]butanedioate (170 g, 503.90 mmol, 1.00 equiv) in N,N-dimethylformamide (5 mL), $Ag_2O$ (348 g, 3.00 equiv), $CH_3I$ (1433 g, 10.10 mol, 20.00 equiv). The resulting solution was stirred for 1 h at 60° C. in an oil bath. The resulting solution was diluted with 10 L of EA. The resulting mixture was washed with 3×8 L of $H_2O$. The resulting mixture was washed with 3×8 L of brine. The organic phase was dried over anhydrous sodium sulfate. The solids were filtered out. The resulting mixture was concentrated under vacuum. This resulted in 159 g (90%) of 1-benzyl 4-methyl (2S)-2-[[(tert-butoxy)carbonyl](methyl)amino]butanedioate as yellow oil. MS (ES, m/z): 352 (M+H).

(2S)-2-[[(tert-butoxy)carbonyl](methyl)amino]-4-methoxy-4-oxobutanoic acid

Into a 10-L 3-necked round-bottom flask, was placed a solution of 1-benzyl 4-methyl (2S)-2-[[(tert-butoxy)carbonyl](methyl)amino]butanedioate (159 g) in methanol (3 L), Palladium on carbon (15.9 g, 0.10 equiv), $H_2$ (gas) (enough). The resulting solution was stirred for 2 h at room temperature. The solids were filtered out. The resulting mixture was concentrated under vacuum. This resulted in 115 g (97%) of (2S)-2-[[(tert-butoxy)carbonyl](methyl)amino]-4-methoxy-4-oxobutanoic acid as yellow oil. MS (ES, m/z): 262 (M+H).

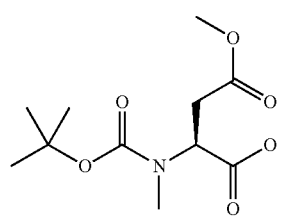

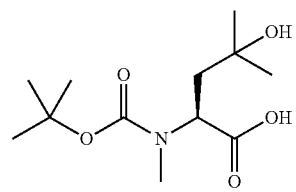

(2S)-2-[[(tert-butoxy)carbonyl](methyl)amino]-4-hydroxy-4-methylpentanoic acid

Into a 3-L 3-necked round-bottom flask purged and maintained with an inert atmosphere of nitrogen, was placed a solution of (2S)-2-[[(tert-butoxy)carbonyl](methyl)amino]-4-methoxy-4-oxobutanoic acid (114 g) in tetrahydrofuran (4 L), CH₃MgBr (874 mL, 6.00 equiv). The resulting solution was stirred for 3 h at −30° C. in a cold bath. The reaction was then quenched by the addition of 1000 mL of NH₄Cl/H₂O. The pH value of the solution was adjusted to 3~4 with hydrogen chloride/H₂O. The resulting solution was diluted with 6 L of H₂O. The resulting solution was extracted with 3×4 L of ethyl acetate and the organic layers combined. The resulting mixture was washed with 2×5 L of brine. The organic phase was dried over anhydrous sodium sulfate. The solids were filtered out. The resulting mixture was concentrated under vacuum. This resulted in 90 g (crude) of (2S)-2-[[(tert-butoxy)carbonyl](methyl)amino]-4-hydroxy-4-methylpentanoic acid as yellow oil. MS (ES, m/z): 262 (M+H).

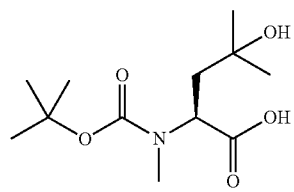

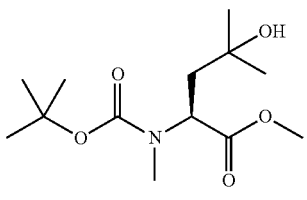

Methyl (2S)-2-[[(tert-butoxy)carbonyl](methyl)amino]-4-hydroxy-4-methylpentanoate Into a 3-L 3-necked round-bottom flask purged and maintained with an inert atmosphere of nitrogen, was placed a solution of (2S)-2-[[(tert-butoxy)carbonyl](methyl)amino]-4-hydroxy-4-methylpentanoic acid (90 g) in dichloromethane (4 L), (diazomethyl)trimethylsilane (340 mL, 2.00 equiv, 2M). The resulting solution was stirred for 2 h at room temperature in an ice/salt bath. The resulting mixture was washed with 2×3 L of H₂O. The resulting mixture was washed with 2×3 L of brine. The organic phase was dried over anhydrous sodium sulfate. The solids were filtered out. The resulting mixture was concentrated under vacuum. This resulted in 92 g (crude) of methyl (2S)-2-[[(tert-butoxy)carbonyl](methyl)amino]-4-hydroxy-4-methylpentanoate as yellow oil. MS (ES, m/z): 276 (M+H).

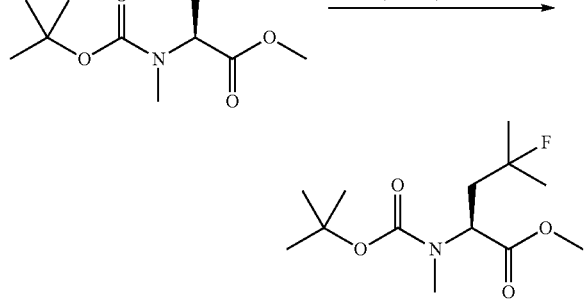

Methyl (2S)-2-[[(tert-butoxy)carbonyl](methyl)amino]-4-fluoro-4-methylpentanoate Into a 3-L 3-necked round-bottom flask purged and maintained with an inert atmosphere of nitrogen, was placed a solution of methyl (2S)-2-[[(tert-butoxy)carbonyl](methyl)amino]-4-hydroxy-4-methylpentanoate (90 g) in dichloromethane (3.0 L), DAST (106 g, 2.00 equiv). The resulting solution was stirred for 2 h at −30° C. in a cold bath. The reaction was then quenched by the addition of 1 L of NaHCO₃ at 0° C. The resulting mixture was washed with 2×1 L of H₂O. The resulting mixture was washed with 2×1 L of brine. The organic phase was dried over anhydrous sodium sulfate. The solids were filtered out. The resulting mixture was concentrated under vacuum. The residue was applied onto a silica gel column with ethyl acetate/petroleum ether (1:100~1:20). This resulted in 15 g (16%) of methyl (2S)-2-[[(tert-butoxy)carbonyl](methyl)amino]-4-fluoro-4-methylpentanoate as yellow oil. MS (ES, m/z): 278 (M+H).

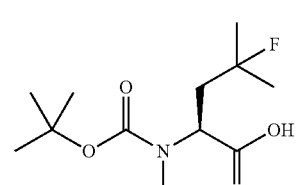

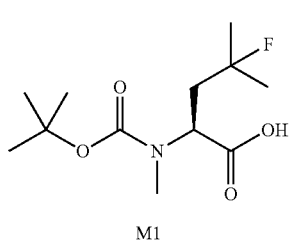

M1

(S)-2-(tert-butoxycarbonyl(methyl)amino)-4-fluoro-4-methylpentanoic acid (M1)

Into a 500 mL 3-necked round-bottom flask, was placed a solution of (S)-methyl 2-(tert-butoxycarbonyl(methyl)amino)-4-fluoro-4-methylpentanoate (15 g) in MeOH (80 mL), LiOH (11.4 g, 5.00 equiv) in H₂O (150 mL). The resulting solution was stirred for 2 h at room temperature. The resulting solution was extracted with 3×100 mL of ethyl acetate. The pH value of the water layers was adjusted to 3~4 with hydrogen chloride/H₂O. The resulting solution was extracted with 3×100 mL of ethyl acetate and the organic layers combined. The resulting mixture was washed with 2×5 L of brine. The organic phase was dried over anhydrous sodium sulfate. The solids were filtered out. The resulting mixture was concentrated under vacuum. This resulted in 12.6 g (89%) of (S)-2-(tert-butoxycarbonyl(methyl)amino)-4-fluoro-4-methylpentanoic acid as yellow oil. MS (ES, m/z): 264 (M+H).

Preparation Example 2: Preparation of Monomer M2

Monomer M2 was prepared by the process shown in Scheme 3 below.

Scheme 3

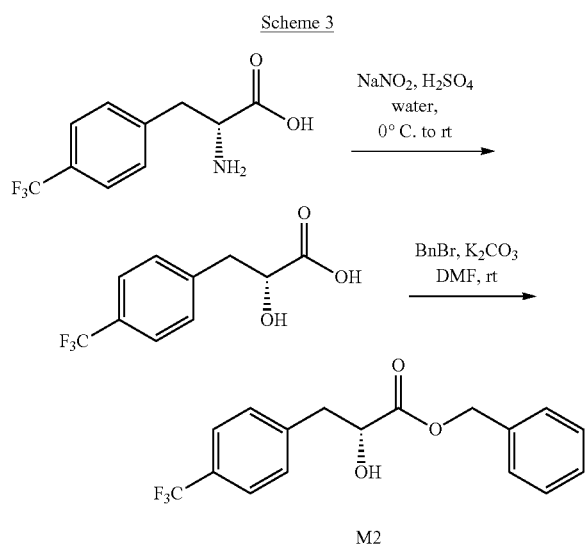

Experimental Details

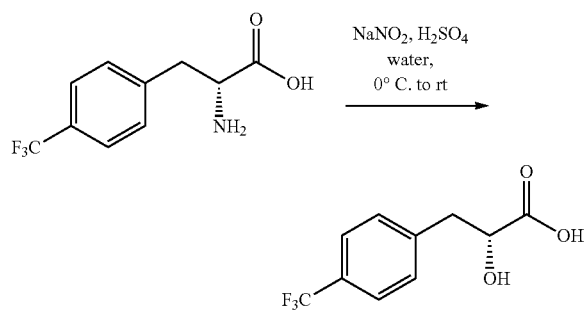

(R)-2-Hydroxy-3-[4-(trifluoromethyl)phenyl]propanoic acid

Into a 500-mL 3-necked round-bottom flask, was placed (R)-2-amino-3-[4-(trifluoromethyl)phenyl]propanoic acid (20 g, 85.77 mmol, 1.00 equiv), sulfuric acid (0.5 M) (340 mL). This was followed by the addition of a solution of NaNO₂ (35.5 g, 514.49 mmol, 6.00 equiv) in water (80 mL) dropwise with stirring at 0° C. The resulting solution was stirred for 1 h at 0° C. The resulting solution was allowed to react, with stirring, overnight at room temperature. The solids were collected by filtration. This resulted in 17.5 g (87%) of (R)-2-hydroxy-3-[4-(trifluoromethyl)phenyl]propanoic acid as a white solid. MS (ES, m/z): 233 (M−H); ¹H NMR (DMSO, 300 MHz) δ: 7.63 (d, J=3.9 Hz, 2H), 7.46 (d, J=4.0 Hz, 2H), 4.21-4.17 (m, 1H), 3.09-3.03 (m, 1H), 2.91-2.84 (m, 1H).

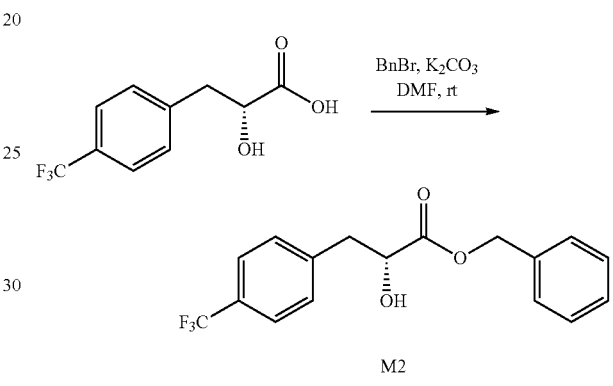

Benzyl (2R)-2-hydroxy-3-[4-(trifluoromethyl)phenyl]propanoate (M2)

Into a 500-mL 3-necked round-bottom flask, was placed (2R)-2-hydroxy-3-[4-(trifluoromethyl)phenyl]propanoic acid (17.5 g, 74.73 mmol, 1.00 equiv), (bromomethyl)benzene (15.3 g, 89.46 mmol, 1.20 equiv), potassium carbonate (31 g, 224.30 mmol, 3.00 equiv), N,N-dimethylformamide (100 mL). The resulting solution was stirred for 30 min at 0° C. and allowed to reach room temperature with stirring overnight. The reaction was then quenched by the addition of 250 mL of water. The resulting solution was extracted with 3×150 mL of ethyl acetate and the organic layers were combined. The resulting mixture was washed with 3×250 mL of brine. The organic phase was dried over anhydrous sodium sulfate and concentrated under vacuum. The residue was purified on a silica gel column with ethyl acetate/petroleum ether (1:6) to give 10.6 g (44%) of benzyl (2R)-2-hydroxy-3-[4-(trifluoromethyl)phenyl]propanoate as a white solid. ¹H NMR (DMSO, 300 MHz) δ: 7.60 (d, J=4.0 Hz, 2H), 7.42 (d, J=4.0 Hz, 2H), 7.39-7.27 (m, 5H), 5.72 (d, J=3 Hz, 1H), 5.10 (s, 2H), 4.40-4.33 (m, 1H), 3.10-3.04 (m, 1H), 2.99-2.91 (m, 1H).

Preparation Example 3: Preparation of Monomer M3

Monomer M3 was prepared by the process shown in Scheme 4 below.

Scheme 4

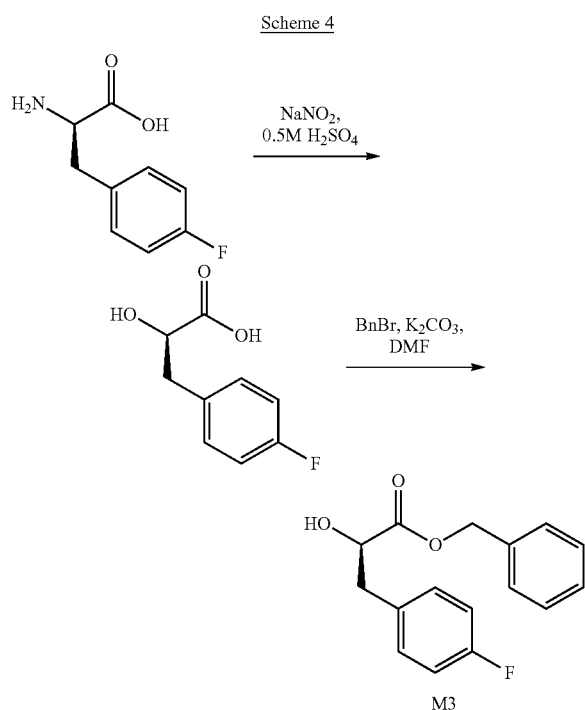

Experimental Details

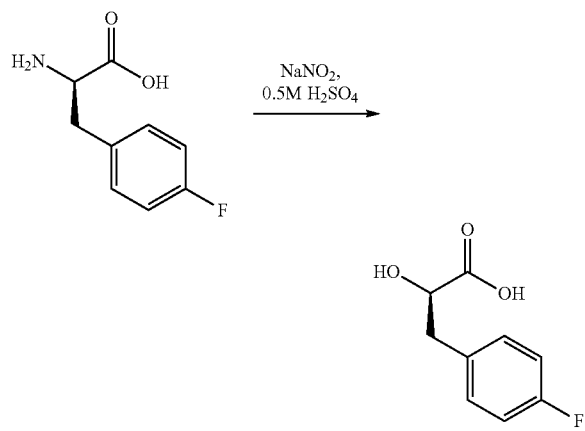

(2R)-3-(4-fluorophenyl)-2-hydroxypropanoic acid

Into a 500-mL 4-necked round-bottom flask, was placed (2R)-2-amino-3-(4-fluorophenyl)propanoic acid (10 g, 54.59 mmol, 1.00 equiv), sulfuric acid (218.6 mL, 2.00 equiv). This was followed by the addition of a solution of NaNO$_2$ (23 g, 333.33 mmol, 6.00 equiv) in water (15 mL) dropwise with stirring at 0° C. The resulting solution was stirred for 3 h at 5° C. The resulting solution was extracted with 3×30 mL of ethyl acetate and the organic layers combined. The resulting mixture was washed with 5×40 mL of sodium chloride. The mixture was dried over anhydrous sodium sulfate and concentrated under vacuum. This resulted in 12 g (crude) of (2R)-3-(4-fluorophenyl)-2-hydroxypropanoic acid as a white solid. MS (ES, m/z): 183 (M−H).

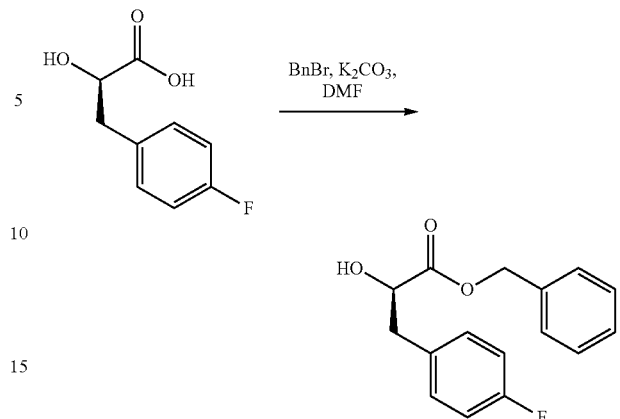

Benzyl (2R)-3-(4-fluorophenyl)-2-hydroxypropanoate (M3)

benzyl (2R)-3-(4-fluorophenyl)-2-hydroxypropanoate (M3): Into a 50-mL 3-necked round-bottom flask, was placed (2R)-3-(4-fluorophenyl)-2-hydroxypropanoic acid (7 g, 38.01 mmol, 1.00 equiv), N,N-dimethylformamide (30 mL), potassium carbonate (16 g, 115.77 mmol, 3.00 equiv). This was followed by the addition of BnBr (7.8 g, 45.61 mmol, 1.20 equiv) dropwise with stirring at 0° C. The resulting solution was stirred for 30 min at 0° C. The resulting solution was allowed to react, with stirring, for an additional 14 h at room temperature. The solids were filtered out. The residue was applied onto a silica gel column with ethyl acetate/petroleum ether (1:30). The collected fractions were combined and concentrated under vacuum. This resulted in 6 g (58%) of benzyl (2R)-3-(4-fluorophenyl)-2-hydroxypropanoate as a white solid. $^1$H NMR (DMSO, 300 MHz) δ: 7.41-7.22 (m, 7H), 7.09-7.03 (m, 2H), 5.10 (s, 2H), 4.31-4.27 (m, 1H), 2.99-2.93 (m, 1H), 2.88-2.81 (m, 1H).

Preparation Example 4: Preparation of Monomer M4

Monomer M4 was prepared by the process shown in Scheme 5 below.

Scheme 5

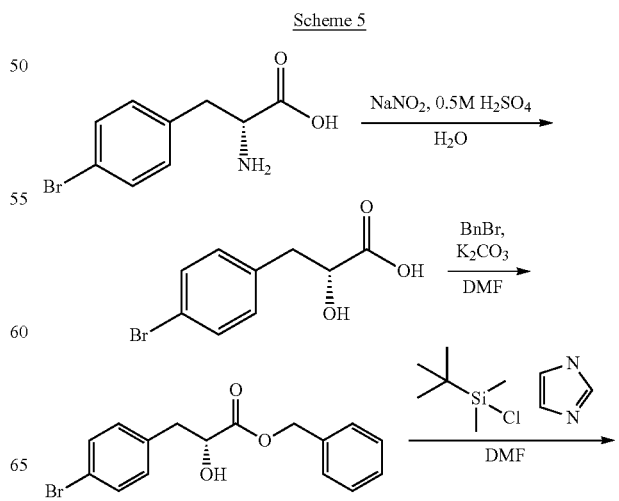

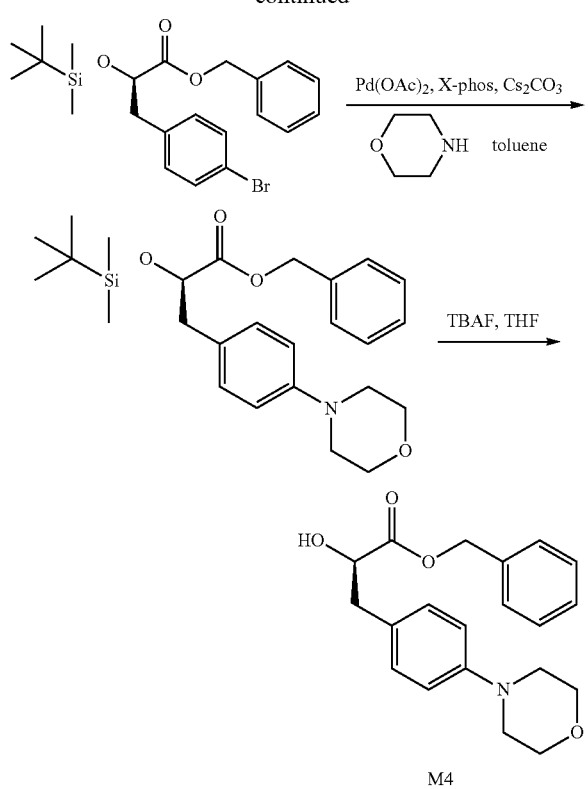

M4

Experimental Details

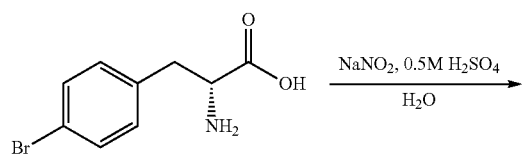

(2R)-3-(4-bromophenyl)-2-hydroxypropanoic acid

Into a 2000-mL 4-necked round-bottom flask, was placed (2R)-2-amino-3-(4-bromophenyl)propanoic acid (150 g, 614.54 mmol, 1.00 equiv), sulfuric acid (0.5M/L) (2500 mL). This was followed by the addition of a solution of $NaNO_2$ (256 g, 3.71 mol, 6.00 equiv) in water (900 mL) dropwise with stirring. The resulting solution was stirred for 48 h at room temperature. The solids were collected by filtration. The solid was dried in an oven under reduced pressure. This resulted in 240 g (80%) of (2R)3-(4-bromophenyl)-2-hydroxypropanoic acid as a white solid. MS (ES, m/z): 243 (M−H); $^1$H NMR (DMSO, 300 MHz) δ: 12.59 (br s, 1H), 7.51-7.44 (m, 2H), 7.27-7.14 (m, 2H), 5.34 (br s, 1H), 4.16-4.12 (m, 1H), 2.97-2.91 (m, 1H), 2.80-2.70 (m, 1H).

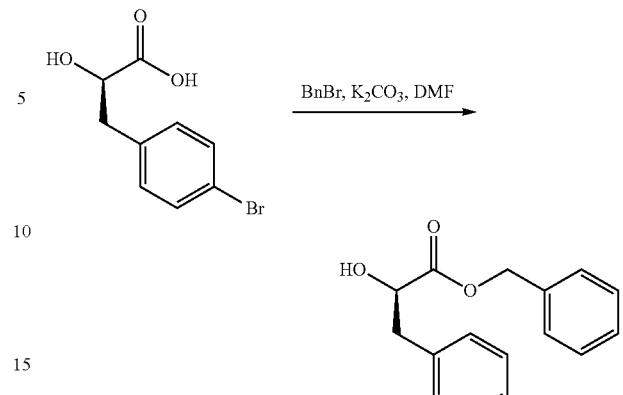

Benzyl (2R)-3-(4-bromophenyl)-2-hydroxypropanoate

Into a 2000-mL 4-necked round-bottom flask, was placed (2R)-3-(4-bromophenyl)-2-hydroxypropanoic acid (60 g, 244.83 mmol, 1.00 equiv), potassium carbonate (67.6 g, 489.11 mmol, 2.00 equiv), N,N-dimethylformamide (1000 mL). This was followed by the addition of BnBr (50.3 g, 294.10 mmol, 1.20 equiv) dropwise with stirring. The resulting solution was stirred for 1 overnight at room temperature. The resulting solution was diluted with 2000 mL of $H_2O$. The resulting solution was extracted with 3×500 mL of ethyl acetate and the organic layers combined. The organic layers were washed with 3×500 mL of water and 1×500 mL of brine. The organic layers were dried over anhydrous sodium sulfate and concentrated under vacuum. The residue was applied onto a silica gel column with ethyl acetate/petroleum ether (1:5). This resulted in 62 g (76%) of benzyl (2R)-3-(4-bromophenyl)-2-hydroxypropanoate as a white solid. $^1$H NMR (DMSO, 300 MHz) δ: 7.49 (d, J=3.9 Hz, 2H), 741-7.34 (m, 5H), 7.15 (d, J=4.4 Hz, 2H), 5.28-5.15 (m, 2H), 4.55-4.51 (m, 1H), 3.23-3.16 (m, 1H), 3.07-3.01 (m, 1H).

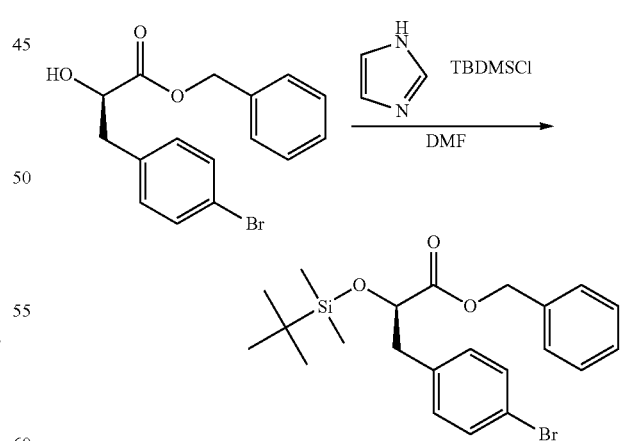

Benzyl (2R)-3-(4-bromophenyl)-2-[(tert-butyldimethylsilyl)oxy]propanoate

Into a 2-L 4-necked round-bottom flask, was placed benzyl (2R)-3-(4-bromophenyl)-2-hydroxypropanoate (60 g, 179.00 mmol, 1.00 equiv), N,N-dimethylformamide (1000 mL), 1H-imidazole (24.5 g, 359.89 mmol, 2.00 equiv). This was followed by the addition of TBDMSCl (32.4 g, 1.20 equiv) dropwise with stirring. The resulting solution was stirred for 16 h at room temperature. The resulting solution was diluted with 2 L of $H_2O$. The resulting solution was extracted with 3×500 mL of ethyl acetate and the organic layers combined. The organic layers were washed with 3×500 mL of brine. The organic layers were dried over anhydrous sodium sulfate and concentrated under vacuum. The residue was applied onto a silica gel column with ethyl acetate/petroleum ether (1:50). This resulted in 78 g (97%) of benzyl (2R)-3-(4-bromophenyl)-2-[(tert-butyldimethylsilyl)oxy]propanoate as yellow oil. MS (ES, m/z): 449 (M+H); $^1$H NMR (DMSO, 300 MHz) δ: 7.44 (d, J=4.2 Hz, 2H), 7.40-7.31 (m, 5H), 7.16 (d, J=4.0 Hz, 2H), 5.13 (s, 2H), 4.50-4.46 (m, 1H), 3.03-2.98 (m, 1H), 2.86-2.79 (m, 1H), 0.73 (s, 9H), −0.15 (s, 3H), −0.25 (s, 3H).

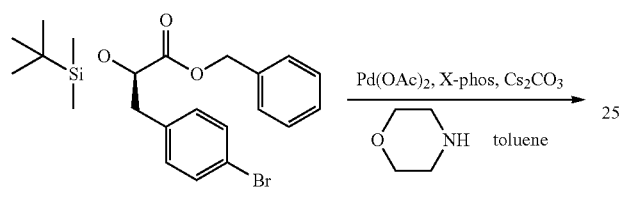

Benzyl (2R)-2-[(tert-butyldimethylsilyl)oxy]-3-[4-(morpholin-4-yl)phenyl]propanoate Into a 2-L 4-necked round-bottom flask purged and maintained with an inert atmosphere of nitrogen, was placed benzyl (2R)-3-(4-bromophenyl)-2-[(tert-butyldimethylsilyl)oxy]propanoate (78 g, 173.54 mmol, 1.00 equiv), X-phos (8.27 g, 0.10 equiv), Pd(OAc)$_2$ (1.95 g, 8.69 mmol, 0.05 equiv), toluene (1500 mL), morpholine (45.3 g, 519.97 mmol, 3.00 equiv), Cs$_2$CO$_3$ (170 g, 3.00 equiv). The resulting solution was stirred for 16 h at 90° C. The solids were filtered out. The residue was applied onto a silica gel column with ethyl acetate/petroleum ether (1:5). This resulted in 64 g (81%) of benzyl (2R)-2-[(tert-butyldimethylsilyl)oxy]-3-[4-(morpholin-4-yl)phenyl]propanoate as yellow oil. MS (ES, m/z): 456 (M+H); $^1$H NMR (CDCl$_3$, 300 MHz) δ: 7.34-7.31 (m, 5H), 7.12 (d, J=4.2 Hz, 2H), 6.90-6.80 (m, 2H), 5.20-5.10 (m, 2H), 4.36-4.32 (m, 1H), 3.90-3.80 (m, 4H), 3.13-3.05 (m, 4H), 3.04-2.95 (m, 1H), 2.89-2.82 (m, 1H), 0.79 (s, 9H), −0.15 (s, 3H), −0.20 (s, 3H).

Benzyl (2R)-2-hydroxy-3-[4-(morpholin-4-yl)phenyl]propanoate (M4)

Into a 2000-mL 4-necked round-bottom flask, was placed benzyl (2R)-2-[(tert-butyldimethylsilyl)oxy]-3-[4-(morpholin-4-yl)phenyl]propanoate (60 g, 131.68 mmol, 1.00 equiv), tetrahydrofuran (1200 mL). This was followed by the addition of TBAF (51.7 g, 197.74 mmol, 1.20 equiv), in portions at 0° C. The resulting solution was stirred for 20 min at room temperature. The resulting solution was diluted with 2000 mL of H$_2$O. The resulting solution was extracted with 3×500 mL of ethyl acetate and the organic layers combined. The organic layers were washed with 3×500 mL of water and 1×500 mL of brine. The organic layers were dried over anhydrous sodium sulfate and concentrated under vacuum. The residue was applied onto a silica gel column with ethyl acetate/petroleum ether (1:3). This resulted in 42 g (93%) of benzyl (2R)-2-hydroxy-3-[4-(morpholin-4-yl)phenyl]propanoate as a yellow solid. MS (ES, m/z): 342 (M+H); $^1$H NMR (DMSO, 300 MHz) δ: 7.40-7.27 (m, 5H), 7.06 (d, J=8.4 Hz, 2H), 6.82 (d, J=8.7 Hz, 2H), 5.57 (d, J=6.3 Hz, 1H), 5.08 (s, 2H), 4.27-4.21 (m, 1H), 3.75-3.71 (m, 4H), 3.06-3.03 (m, 4H), 2.91-2.74 (m, 2H).

Preparation Example 5: Preparation of Monomer M5

Monomer M5 was prepared by the process shown below.

165
-continued

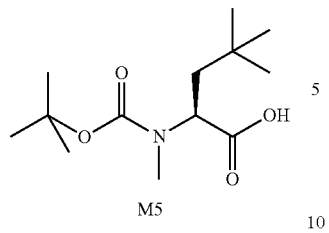

M5

(2S)-2-[[(tert-butoxy)carbonyl](methyl)amino]-4,4-dimethylpentanoic acid (M5)

Into a 3000-mL round-bottom flask, was placed tetrahydrofuran (2 L), (2S)-2-[[(tert-butoxy)carbonyl]amino]-4,4-dimethylpentanoic acid (30 g, 122.29 mmol, 1.00 equiv), sodium hydride (48 g, 2.00 mol, 16.35 equiv), CH$_3$I (348 g, 2.45 mol, 20.05 equiv). The resulting solution was stirred overnight at 35° C. The reaction was then quenched by the addition of 2000 mL of water/ice. The pH value of the solution was adjusted to 4 with hydrogen chloride (2 mol/L). The resulting solution was extracted with 3×2 L of ethyl acetate and the organic layers combined and dried over anhydrous sodium sulfate and concentrated under vacuum. This resulted in 23 g (73%) of (2S)-2-[[(tert-butoxy)carbonyl](methyl)amino]-4,4-dimethylpentanoic acid as a yellow solid. MS (ES, m/z): 260 (M+H); $^1$H NMR (300 MHz, CDCl$_3$): δ 4.92-4.88 (m, 0.5H), 4.68-4.64 (m, 0.5H), 2.83-2.80 (m, 3H), 1.91-1.64 (m, 2H), 1.51 (s, 9H), 0.96 (s, 9H).

Preparation Example 6: Preparation of Monomer M8

Monomer M8 was prepared by the process shown in Scheme 6 below.

Scheme 6

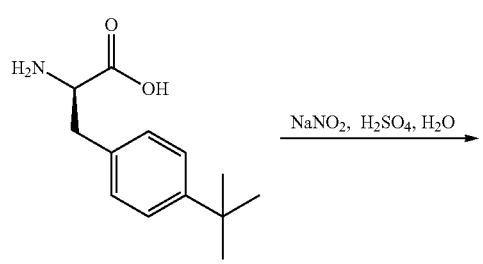

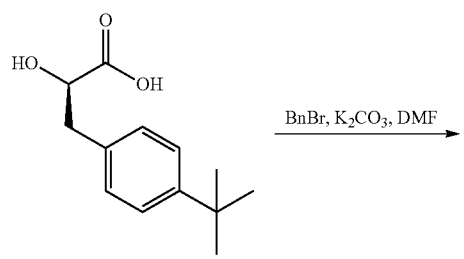

BnBr, K$_2$CO$_3$, DMF

166
-continued

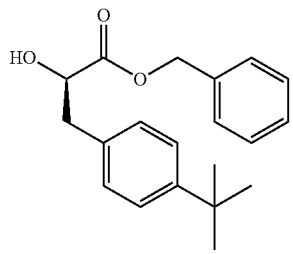

M8

Experimental Details

NaNO$_2$, H$_2$SO$_4$, H$_2$O (2R)-3-(4-tert-butylphenyl)-2-hydroxypropanoic acid Into a 2000-mL 3-necked round-bottom flask, was placed a solution of (2R)-2-amino-3-(4-tert-butylphenyl)propanoic acid (30 g, 135.57 mmol, 1.00 equiv) in sulfuric acid (0.5M) (480 mL), a solution of NaNO$_2$ (94 g, 1.36 mol, 10.00 equiv) in water (180 mL). The resulting solution was stirred overnight at room temperature in an ice/salt bath. The solids were collected by filtration. This resulted in 20.0 g (66%) of (2R)-3-(4-tert-butylphenyl)-2-hydroxypropanoic acid as a white solid. MS (ES, m/z): 221 (M−H).

BnBr, K$_2$CO$_3$, DMF

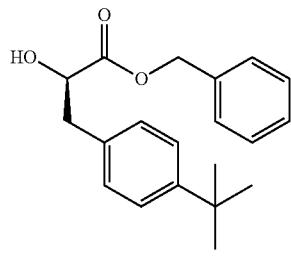

M8

(2R)-3-(4-tert-butylphenyl)-2-hydroxypropanoate (M8)

Into a 2000-mL 3-necked round-bottom flask, was placed a solution of (2R)3-(4-tert-butylphenyl)-2-hydroxypropanoic acid (40 g, 179.95 mmol, 1.00 equiv) in N,N-dimethylformamide (1000 mL), potassium carbonate (50 g, 361.77 mmol, 2.00 equiv), BnBr (61 g, 356.66 mmol, 2.00 equiv). The resulting solution was stirred for 2 h at room temperature. The resulting solution was diluted with 2000 mL of EA. The resulting mixture was washed with 3×2000 mL of water. The resulting mixture was washed with 2×2000 mL of brine. The mixture was dried over anhydrous sodium sulfate. The solids were filtered out. The resulting mixture was concentrated under vacuum. The residue was applied onto a silica gel column with ethyl acetate/petroleum ether (1:50~1:10). This resulted in 42 g (75%) of benzyl (2R)-3-(4-tert-butylphenyl)-2-hydroxypropanoate as yellow oil. $^1$H NMR (300 MHz, CDCl$_3$): δ 7.40-7.27 (m, 7H), 7.10 (d, J=8.1 Hz, 2H), 5.20 (s, 2H), 4.49 (t, J=5.4 Hz, 1H), 3.14-2.93 (m, 2H), 1.31 (s, 9H).

Preparation Example 7: Preparation of Monomer M9

Monomer M9 was prepared by the process shown in Scheme 7 below.

Scheme 7

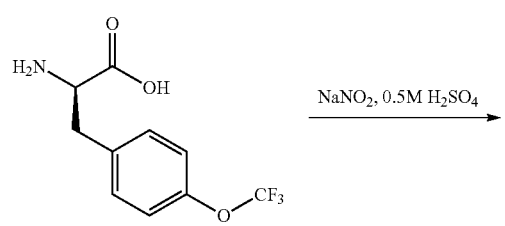

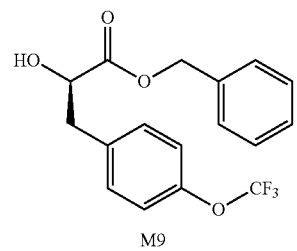

M9

Experimental Details

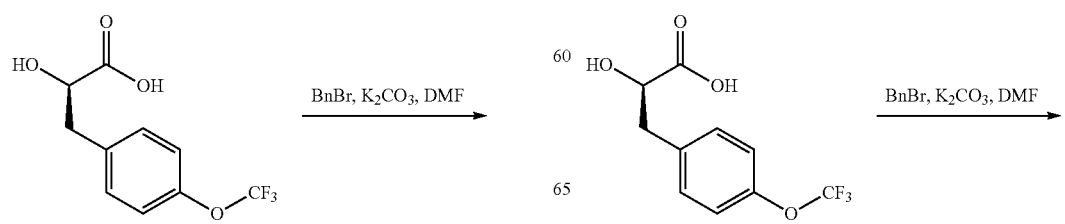

(2R)-2-hydroxy-3-[4-(trifluoromethoxy)phenyl]propanoic acid

Into a 1000-mL 3-necked round-bottom flask, was placed (2R)2-amino-3-[4-(trifluoromethoxy)phenyl]propanoic acid hydrochloride (10 g, 35.01 mmol, 1.00 equiv). This was followed by the addition of a solution of NaNO$_2$ (29 g, 420.29 mmol, 12.00 equiv) in water (150 mL) dropwise with stirring at 0° C. To this was added sulfuric acid (0.5M/L) (300 mL). The resulting solution was stirred overnight at room temperature. The resulting solution was extracted with 3×200 mL of ethyl acetate and the organic layers combined. The resulting mixture was washed with 3×200 mL of brine. The mixture was dried over anhydrous sodium sulfate and concentrated under vacuum. This resulted in 11 g (crude) of (2R)-2-hydroxy-3-[4-(trifluoromethoxy)phenyl]propanoic acid as yellow oil. MS (ES, m/z): 249 (M−H).

-continued

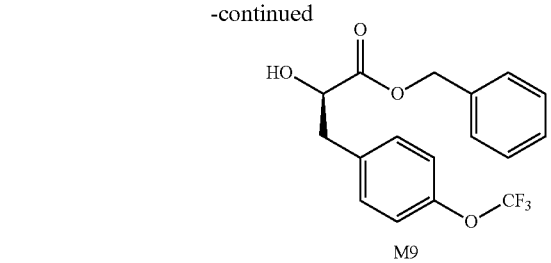

Benzyl (2R)-2-hydroxy-3-[4-(trifluoromethoxy)phenyl]propanoate (M9)

Into a 1000-mL 3-necked round-bottom flask, was placed (2R)2-hydroxy-3-[4-(trifluoromethoxy)phenyl]propanoic acid (11 g, 43.97 mmol, 1.00 equiv), N,N-dimethylformamide (300 mL), potassium carbonate (12 g, 86.82 mmol, 2.00 equiv). This was followed by the addition of (bromomethyl)benzene (9 g, 52.62 mmol, 1.20 equiv) dropwise with stirring at 0° C. The resulting solution was stirred overnight at room temperature. The reaction was then quenched by the addition of 100 mL of water. The resulting solution was extracted with 3×150 mL of ethyl acetate and the organic layers combined. The resulting mixture was washed with 3×200 mL of brine. The mixture was dried over anhydrous sodium sulfate and concentrated under vacuum. This resulted in 7.6 g (51%) of benzyl (2R)-2-hydroxy-3-[4-(trifluoromethoxy)phenyl]propanoate as yellow oil. $^1$H NMR (DMSO, 300 MHz) δ: 7.45-7.30 (m, 7H), 7.25-7.17 (m, 2H), 5.70 (d, J=2.7 Hz, 1H), 5.10 (s, 2H), 4.34-4.32 (m, 1H), 3.04-2.98 (m, 1H), 2.92-2.85 (m, 1H).

Preparation Example 8: Preparation of Monomer M10

Monomer M10 was prepared by the process shown in Scheme 8 below.

Scheme 8

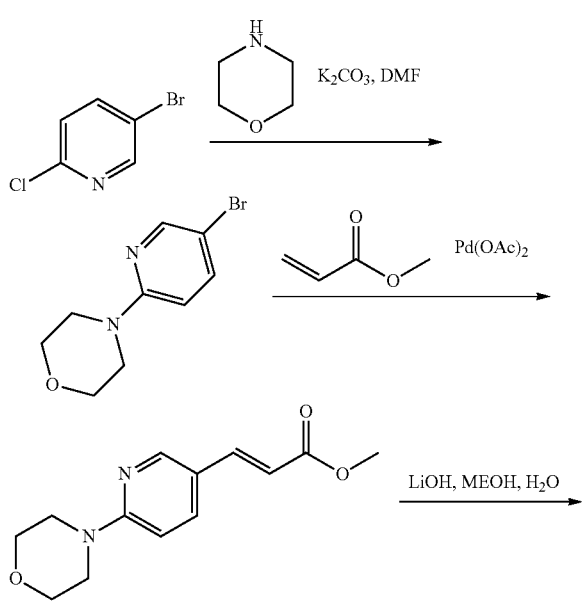

-continued

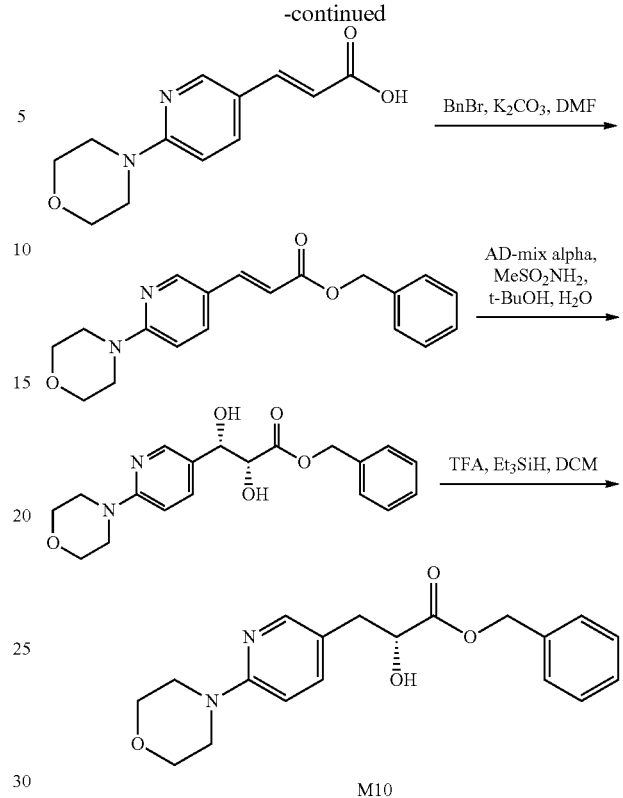

Experimental Details

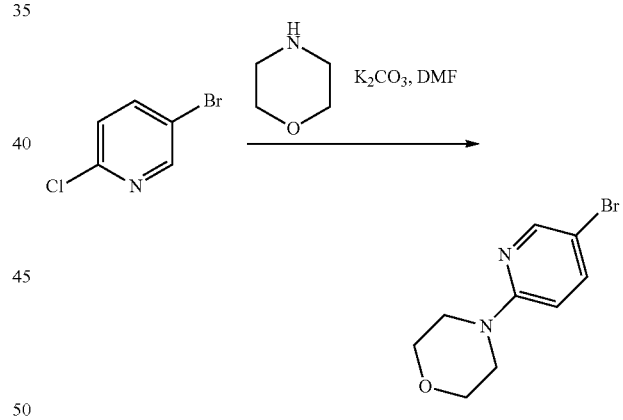

4-(5-bromopyridin-2-yl)morpholine

Into a 1-L round-bottom flask, was placed a solution of 5-bromo-2-chloropyridine (50 g, 259.82 mmol, 1.00 equiv) in N,N-dimethylformamide (300 mL), morpholine (91 g, 1.04 mol, 4.00 equiv), potassium carbonate (108 g, 781.42 mmol, 3.00 equiv). The resulting solution was stirred overnight at 120° C. The resulting solution was extracted with 5×150 mL of ethyl acetate and the organic layers were combined. The resulting mixture was washed with 3×100 mL of brine. The mixture was dried over anhydrous sodium sulfate and concentrated under vacuum. The resulting mixture was washed with PE:EA=1:5. This resulted in 80 g (63%) of 4-(5-bromopyridin-2-yl)morpholine as a white solid. MS (ES, m/z): 243 (M+H); $^1$HNMR (CDCl$_3$, 300

MHz) δ: 8.22 (s, 1H), 7.57 (d, J=4.5 Hz, 1H), 6.54 (d, J=2.4 Hz, 1H), 3.82 (t, J=5.1 Hz, 4H), 3.48 (t, J=5.1 Hz, 4H).

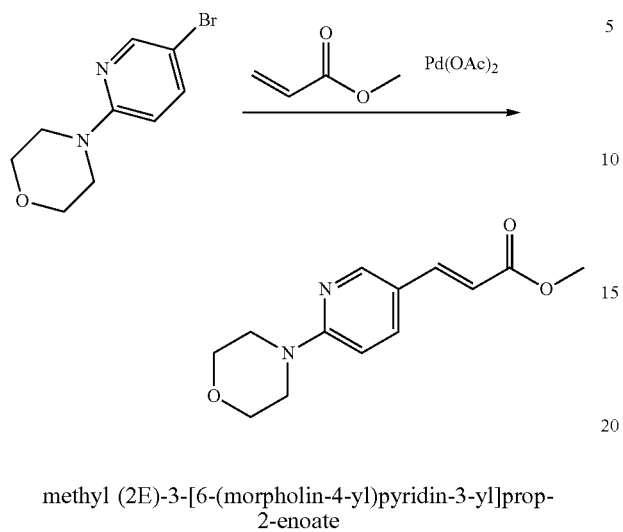

methyl (2E)-3-[6-(morpholin-4-yl)pyridin-3-yl]prop-2-enoate

Into a 250-mL round-bottom flask and maintained with an inert atmosphere of nitrogen, was placed a solution of 4-(5-bromopyridin-2-yl)morpholine (5 g, 20.57 mmol, 1.00 equiv) in N,N-dimethylformamide (120 mL), methyl prop-2-enoate (3.54 g, 41.12 mmol, 2.00 equiv), Pd(OAc)$_2$ (92 mg, 0.41 mmol, 0.02 equiv), sodium bicarbonate (3.46 g, 41.19 mmol, 2.00 equiv), Bu$_4$NCl (11.4 g, 41.02 mmol, 2.00 equiv). The resulting solution was stirred for 3 days at 100° C. The resulting solution was extracted with 5×150 mL of ethyl acetate and the organic layers combined. The resulting mixture was washed with 3×100 mL of brine. The mixture was dried over anhydrous sodium sulfate and concentrated under vacuum. The solids were filtered out. This resulted in 11.5 g (56%) of methyl (2E)-3-[6-(morpholin-4-yl)pyridin-3-yl]prop-2-enoate as a light brown solid. MS (ES, m/z): 249 (M+H); $^1$H NMR (CDCl$_3$, 300 MHz) δ: 8.30 (s, 1H), 7.72-7.58 (m, 2H), 6.64 (d, J=4.5 Hz, 1H), 6.27 (d, J=8.0 Hz, 1H), 3.84-3.80 (m, 7H), 3.62 (t, J=4.8 Hz, 4H).

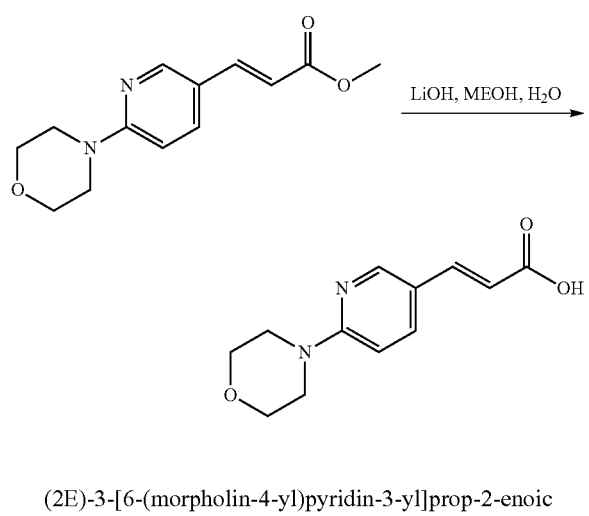

(2E)-3-[6-(morpholin-4-yl)pyridin-3-yl]prop-2-enoic acid

Into a 500-mL round-bottom flask, was placed a solution of methyl (2E)-3-[6-(morpholin-4-yl)pyridin-3-yl]prop-2-enoate (11 g, 44.31 mmol, 1.00 equiv) in methanol/H$_2$O (60:60 mL), LiOH (10.6 g, 442.59 mmol, 10.00 equiv). The resulting solution was stirred for 1 h at 80° C. The resulting solution was diluted with 150 ml of water. The pH value of the solution was adjusted to 6-7 with NaHCO$_3$(Sat.). The resulting solution was extracted with 5×150 mL of ethyl acetate and the organic layers combined. The organic phase was washed with 3×150 mL of brine. The organic phase was dried over anhydrous sodium sulfate and concentrated under vacuum. This resulted in 10.4 g (crude) of (2E)-3-[6-(morpholin-4-yl)pyridin-3-yl]prop-2-enoic acid as a light brown solid. MS (ES, m/z): 245 (M+H).

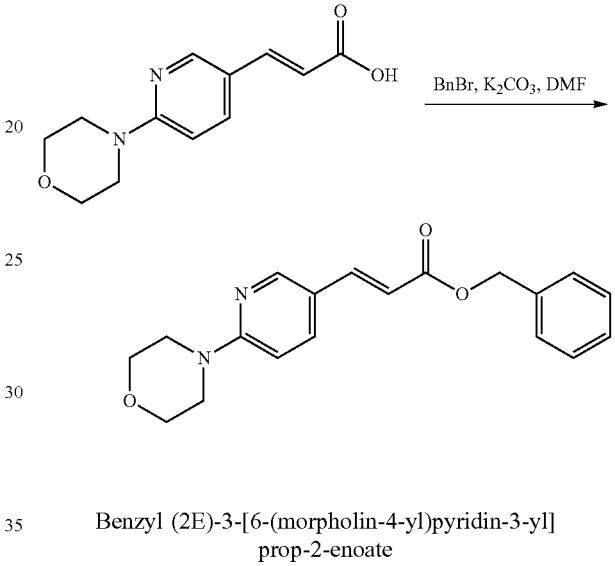

Benzyl (2E)-3-[6-(morpholin-4-yl)pyridin-3-yl]prop-2-enoate

Into a 250-mL round-bottom flask, was placed a solution of (2E)-3-[6-(morpholin-4-yl)pyridin-3-yl]prop-2-enoic acid (4 g, 17.08 mmol, 1.00 equiv) in N,N-dimethylformamide (70 mL), potassium carbonate (7.1 g, 51.37 mmol, 3.00 equiv), (bromomethyl)benzene (4.4 g, 25.73 mmol, 1.50 equiv). The resulting solution was stirred overnight at room temperature. The resulting solution was extracted with 5×150 mL of ethyl acetate and the organic layers were combined. The resulting mixture was washed with 3×150 mL of brine. The mixture was dried over anhydrous sodium sulfate and concentrated under vacuum. The resulting mixture was washed with 1×70 mL of PE. The solids were collected by filtration. This resulted in 10 g (72%) of benzyl (2E)-3-[6-(morpholin-4-yl)pyridin-3-yl]prop-2-enoate as a yellow solid. MS (ES, m/z): 325 (M+H); $^1$H NMR (CDCl$_3$, 300 MHz) δ: 8.30 (s, 1H), 7.70-7.62 (m, 2H), 7.45-7.32 (m, 5H), 6.63 (d, J=4.5 Hz, 1H), 6.32 (d, J=8.0 Hz, 1H), 5.25 (s, 2H), 3.82 (t, J=4.5 Hz, 4H), 3.63-3.60 (m, 4H).

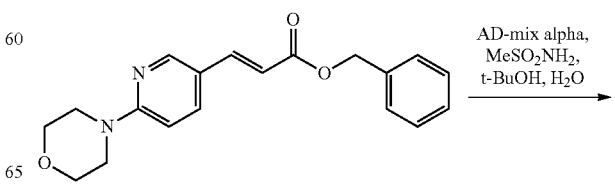

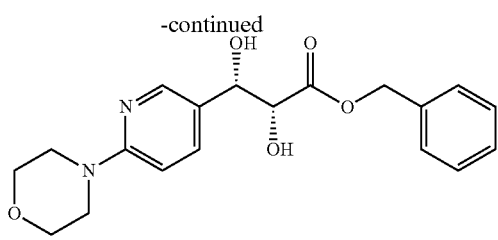

(2R, 3S)-2,3-dihydroxy-3-[6-(morpholin-4-yl)pyridin-3-yl]propanoate

Into a 100-mL 3-necked round-bottom flask, was placed tert-Butanol:H$_2$O (20:20 mL), AD-mix-α (8.6 g), This was followed by addition of benzyl (2E)-3-[6-(morpholin-4-yl)pyridin-3-yl]prop-2-enoate (2 g, 6.17 mmol, 1.00 equiv) and MeSO$_2$NH$_2$ (586 g, 6.17 mol, 1.00 equiv) with stirring at 0° C. The resulting solution was stirred for 3 days at room temperature. The reaction was then quenched by the addition of Na$_2$SO$_3$. The resulting solution was extracted with 3×150 mL of ethyl acetate and the organic layers combined and dried over anhydrous sodium sulfate and concentrated under vacuum. The residue was applied onto a silica gel column with ethyl acetate/petroleum ether (1:1). This resulted in 5.4 g (49%) of benzyl (2R, 3S)-2,3-dihydroxy-3-[6-(morpholin-4-yl)pyridin-3-yl]propanoate as a light yellow solid. MS (ES, m/z): 359 (M+H).

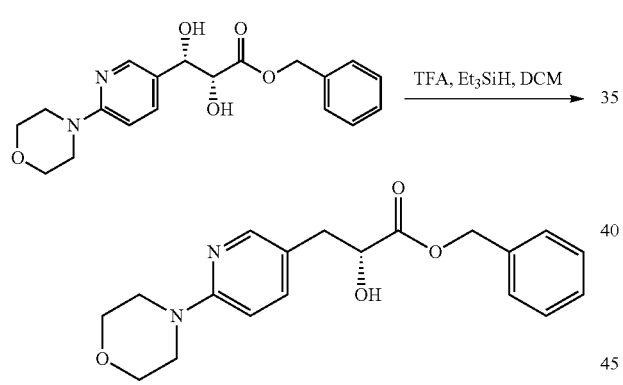

M10

Benzyl (2R)-2-hydroxy-3-[6-(morpholin-4-yl)pyridin-3-yl]propanoate (M10)

Into a 100-mL round-bottom flask, was placed a solution of benzyl (2R, 3S)-2,3-dihydroxy-3-[6-(morpholin-4-yl)pyridin-3-yl]propanoate (1.5 g, 4.19 mmol, 1.00 equiv) in dichloromethane (15 mL), trifluoroacetic acid (5 mL), Et$_3$SiH (10 mL). The resulting solution was stirred for 3 days at 50° C. The resulting mixture was concentrated under vacuum. The reaction was then quenched by the addition of water/ice. The pH value of the solution was adjusted to 9 with sodium bicarbonate aq. The resulting solution was extracted with 3×40 mL of dichloromethane and the organic layers were combined and dried over anhydrous sodium sulfate and concentrated under vacuum. The residue was applied onto a silica gel column with ethyl acetate/petroleum ether (1:2). This resulted in 2.3 g (27%) of benzyl (2R)-2-hydroxy-3-[6-(morpholin-4-yl)pyridin-3-yl]propanoate as yellow oil. MS (ES, m/z): 343 (M+H); $^1$H NMR (CDCl$_3$, 300 MHz) δ: 8.02 (s, 1H), 7.43-7.32 (m, 6H), 6.54 (d, J=4.4 Hz, 1H), 5.21 (s, 2H), 4.52-4.46 (m, 1H), 3.84 (t, J=7.8 Hz, 4H), 3.48 (t, J=4.8 Hz, 4H) 3.05-3.01 (m, 1H), 2.91-2.85 (m, 1H).

Preparation Example 9: Preparation of Monomer M11

Monomer M11 was prepared by the process shown in Scheme 9 below.

Scheme 9

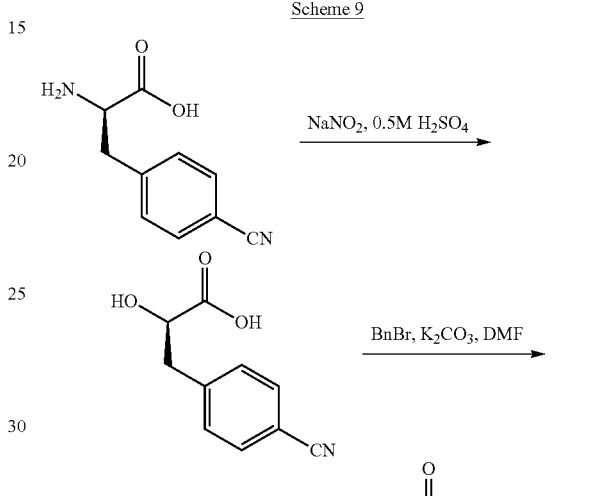

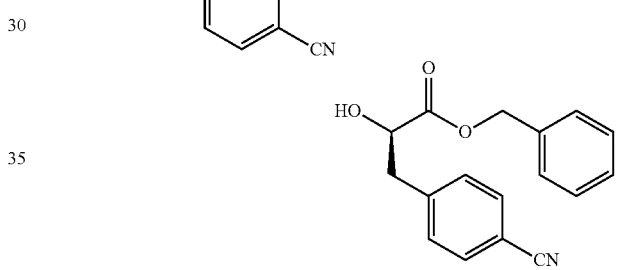

M11

Experimental Details

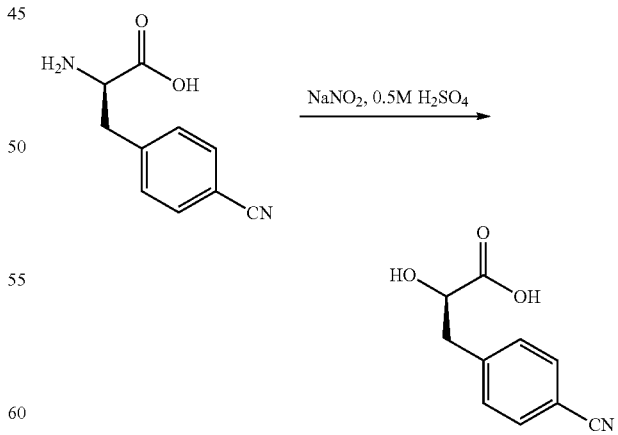

(2R)-3-(4-cyanophenyl)-2-hydroxypropanoic acid

Into a 500-mL 3-necked round-bottom flask, was placed (2R)2-amino-3-(4-cyanophenyl)propanoic acid (10 g, 52.58 mmol, 1.00 equiv), 0.5M sulfuric acid (100 mL). This was followed by the addition of a solution of NaNO$_2$ (21.8 g, 315.94 mmol, 5.98 equiv) in water (20 mL) dropwise with stirring at 0° C. The resulting solution was stirred for 18 h at room temperature. The resulting solution was extracted with 2×500 mL of ethyl acetate and the organic layers combined. The organic mixture was washed with 2×500 mL of brine and dried over anhydrous sodium sulfate. The solids were filtered out. The filtrate was concentrated under vacuum. This resulted in 9 g (crude) of (2R)-3-(4-cyanophenyl)-2-hydroxypropanoic acid as a light yellow liquid. MS (ES, m/z): 190 (M–H).

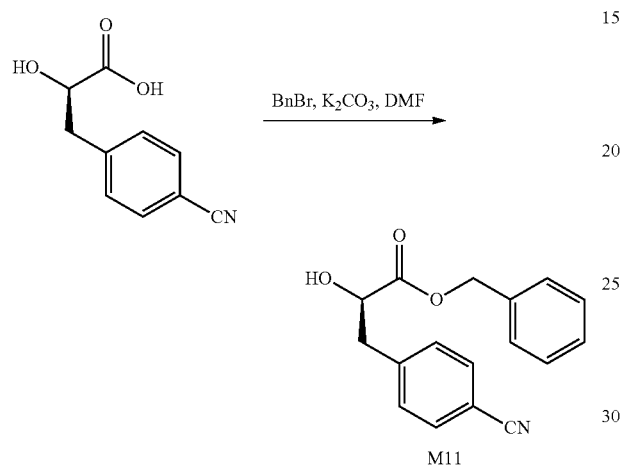

Benzyl (2R)-3-(4-cyanophenyl)-2-hydroxypropanoate (M11)

Into a 250-mL round-bottom flask, was placed (2R)3-(4-cyanophenyl)-2-hydroxypropanoic acid (9 g, 47.08 mmol, 1.00 equiv), N,N-dimethylformamide (150 mL). This was followed by the addition of potassium carbonate (20.6 g, 149.05 mmol, 3.17 equiv), in portions at 0° C. To this was added BnBr (16.9 g, 98.81 mmol, 2.10 equiv) dropwise with stirring at 0° C. The resulting solution was stirred for 16 h at room temperature. The resulting solution was diluted with 50 mL of water and extracted with 2×200 mL of ethyl acetate. The organic layers combined. The combined mixture was washed with 3×150 mL of aq.NaCl and dried over anhydrous sodium sulfate. The solids were filtered out. The filtrate was concentrated under vacuum. The residue was applied onto a silica gel column with ethyl acetate/petroleum ether (1/10-1/5). This resulted in 2.5 g (19%) of benzyl (2R)-3-(4-cyanophenyl)-2-hydroxypropanoate as a light yellow liquid. $^1$H NMR (CDCl$_3$, 300 MHz) δ: 7.50 (d, J=4.0 Hz, 2H), 7.43-7.32 (m, 5H), 7.23 (d, J=4.0 Hz, 2H), 5.31-5.13 (m, 2H), 4.53-4.49 (m, 1H), 3.21-3.15 (m, 1H), 3.06-2.99 (m, 1H).

Preparation Example 10: Preparation of Monomer M16

Monomer M16 was prepared by the process shown in Scheme 10 below.

Scheme 10

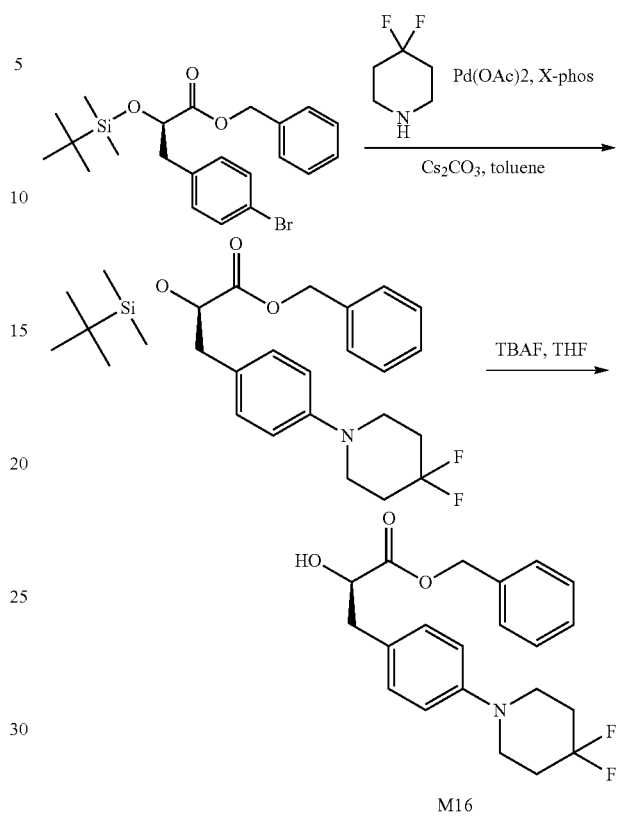

M16

Experimental Details

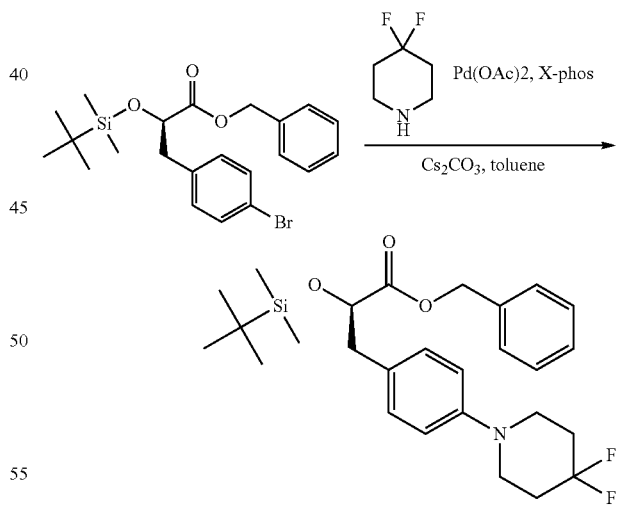

Benzyl (2R)-2-[(tert-butyldimethylsilyl)oxy]-3-[4-(4,4-difluoropiperidin-1-yl)phenyl]propanoate Into a 250-mL round-bottom flask purged and maintained with an inert atmosphere of nitrogen, was placed benzyl (2R)-3-(4-bromophenyl)-2-[(tert-butyldimethylsilyl)oxy] propanoate (14.53 g, 32.33 mmol, 1.00 equiv), 4,4-difluoropiperidine (6.2 g, 51.19 mmol, 1.20 equiv), Cs$_2$CO$_3$ (19 g, 3.00 equiv), X-PhOS (309 mg, 0.02 equiv), Toluene (50 mL), Pd(OAc)$_2$ (145 mg, 0.65 mmol, 0.02 equiv). The resulting solution was stirred for 16 h at 90° C. The resulting mixture was concentrated under vacuum. The residue was applied onto a silica gel column with ethyl acetate/petroleum ether (1:6). This resulted in 12.28 g (78%) of benzyl (2R)-2-[(tert-butyldimethylsilyl)oxy]-3-[4-(4,4-difluoropiperidin-1-yl)phenyl] propanoate as colorless oil.

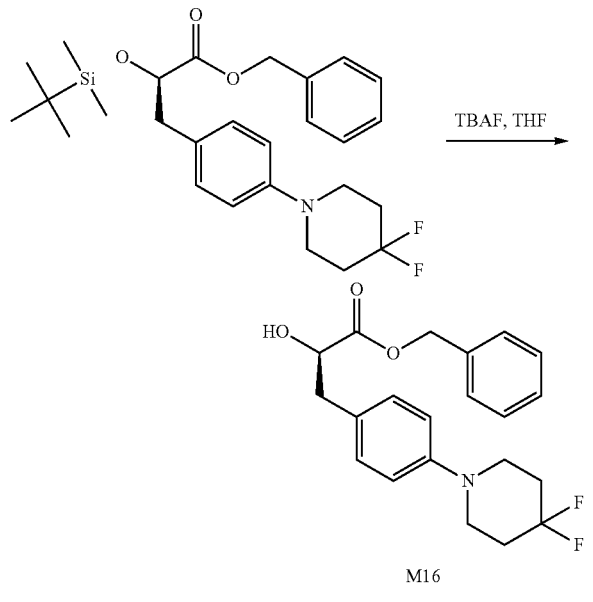

M16

Benzyl (2R)-3-[4-(4,4-difluoropiperidin-1-yl)phenyl]-2-hydroxypropanoate (M16)

Into a 100-mL 3-necked round-bottom flask, was placed benzyl (2R)-2-[(tert-butyldimethylsilyl)oxy]-3-[4-(4,4-difluoropiperidin-1-yl)phenyl]propanoate (12.28 g, 25.08 mmol, 1.00 equiv), tetrahydrofuran (30 mL), TBAF (8.4 g, 32.13 mmol, 1.20 equiv). The resulting solution was stirred for 20 min at room temperature. The resulting mixture was concentrated under vacuum. The resulting solution was diluted with 100 mL of ethyl acetate. The residue was applied onto a silica gel column with ethyl acetate/petroleum ether (1:10). This resulted in 6.8 g (72%) of benzyl (2R)-3-[4-(4,4-difluoropiperidin-1-yl)phenyl]-2-hydroxypropanoate as a white solid. MS (ES, m/z): 376 (M+H).

Preparation Example 11: Preparation of Monomer M17

Monomer M17 was prepared by the process shown in Scheme 11 below.

Scheme 11

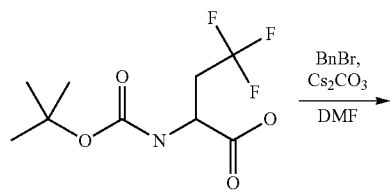

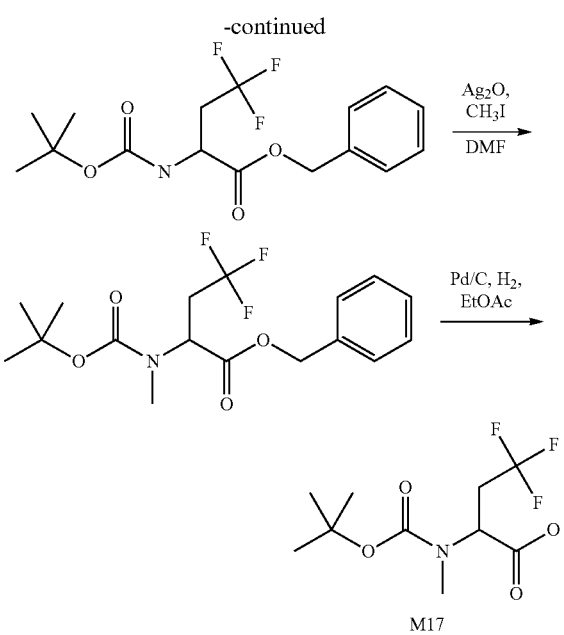

M17

Experimental Details

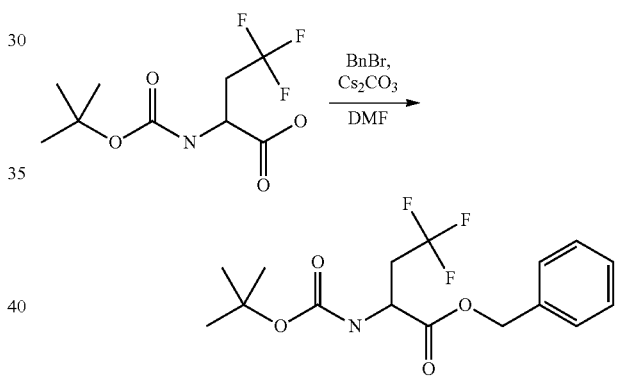

Benzyl (2S)-2-[[(tert-butoxy)carbonyl]amino]-4,4,4-trifluorobutanoate

Into a 100-mL round-bottom flask, was placed N,N-dimethylformamide (15 mL), 2-[[(tert-butoxy)carbonyl]amino]-4,4,4-trifluorobutanoic acid (1.5 g, 5.83 mmol, 1.00 equiv), Cs$_2$CO$_3$ (5.7 g, 17.49 mmol, 3.00 equiv), BnBr (1.1 g, 6.43 mmol, 1.10 equiv). The resulting solution was stirred for 4 h at room temperature. The resulting solution was diluted with 20 mL of water, extracted with 3×30 mL of ethyl acetate and the organic layers combined. The organic layers were washed with 1×40 mL of brine. The organic layers were dried over anhydrous sodium sulfate and concentrated under vacuum. The residue was applied onto a silica gel column with ethyl acetate/petroleum ether (1:20). This resulted in 1.3 g (64%) of benzyl (2S)-2-[[(tert-butoxy)carbonyl]amino]-4,4,4-trifluorobutanoate as a white solid. $^1$H NMR (300 MHz, CDCl$_3$): δ 7.40-7.34 (m, 5H), 5.25 (s, 2H), 4.60-4.59 (m, 1H), 2.78-2.71 (m, 2H), 1.45 (s, 9H).

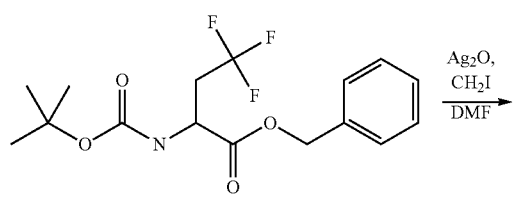

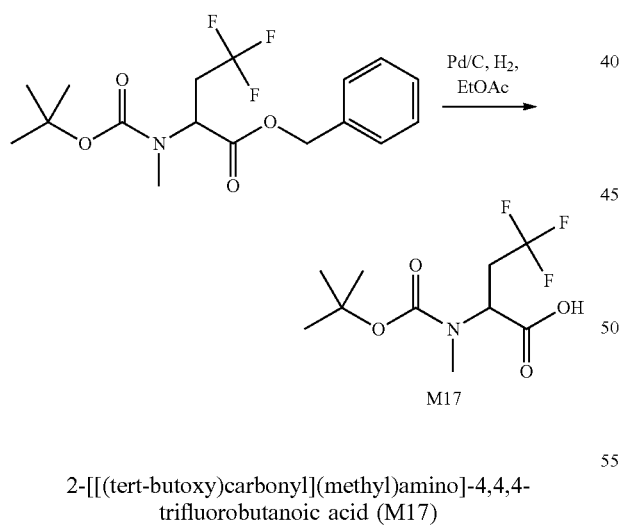

Benzyl-2-[[(tert-butoxy)carbonyl](methyl)amino]-4,4,4-trifluorobutanoate

Into a 250-mL round-bottom flask, was placed N,N-dimethylformamide (25 mL), benzyl-2-[[(tert-butoxy)carbonyl]amino]-4,4,4-trifluorobutanoate (3.1 g, 8.93 mmol, 1.00 equiv), Ag$_2$O (5.4 g), CH$_3$I (17 g, 119.77 mmol, 13.42 equiv). The resulting solution was stirred for 2 h at 60° C. The solids were filtered out. The filtrate was diluted with 80 mL of water, extracted with 3×50 mL of ethyl acetate and the organic layers combined. The organic layers were washed with 1×20 mL of brine. The organic layers were dried over anhydrous sodium sulfate and concentrated under vacuum. This resulted in 2.8 g (87%) of benzyl-2-[[(tert-butoxy)carbonyl](methyl)amino]-4,4,4-trifluorobutanoate as yellow oil. $^1$H NMR (300 MHz, CDCl$_3$): δ 7.38-7.35 (m, 5H), 5.26-5.20 (m, 2H), 4.47-4.44 (m, 1H), 2.96-2.89 (m, 3H), 2.79-2.63 (m, 2H), 1.47-1.41 (m 9H).

2-[[(tert-butoxy)carbonyl](methyl)amino]-4,4,4-trifluorobutanoic acid (M17)

Into a 100-mL round-bottom flask, was placed ethyl acetate (20 mL), benzyl-2-[[(tert-butoxy)carbonyl](methyl)amino]-4,4,4-trifluorobutanoate (3.1 g, 8.58 mmol, 1.00 equiv), Palladium on carbon (300 mg), to the above hydrogen was introduced. The resulting solution was stirred for 1 h at room temperature. The solids were filtered out. The filtrate was concentrated under vacuum. This resulted in 2.1 g (90%) of 2-[[(tert-butoxy)carbonyl](methyl)amino]-4,4,4-trifluorobutanoic acid as yellow oil.

Preparation Example 12: Preparation of Monomer M19

Monomer M19 was prepared by the process shown in Scheme 12 below.

Scheme 12

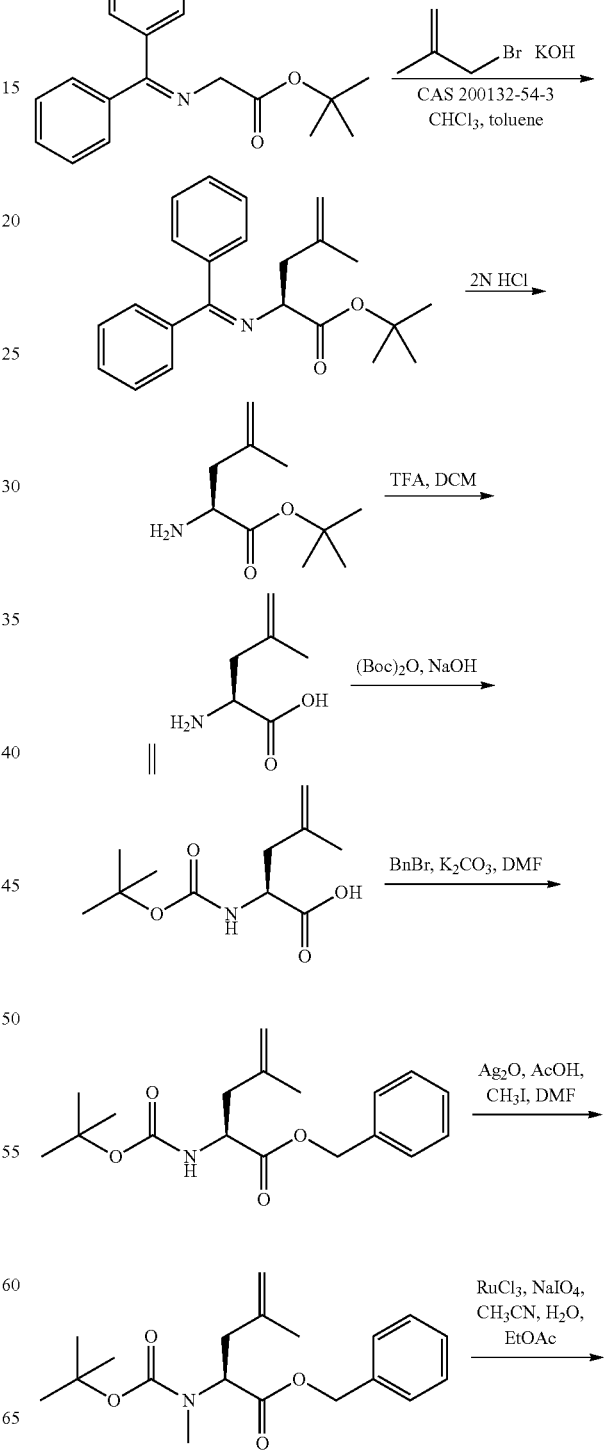

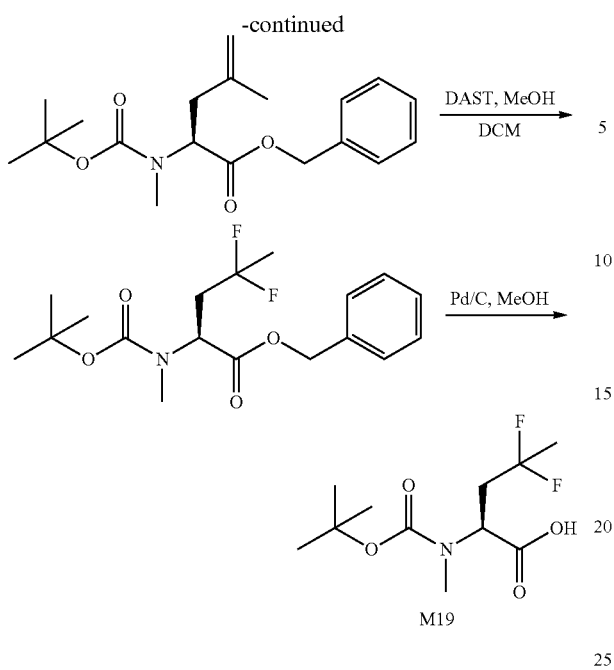

Experimental Details

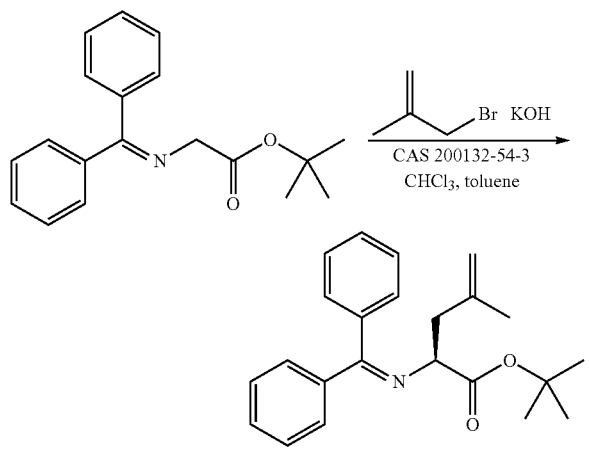

tert-butyl (2S)-2-[(diphenylmethylidene)amino]-4-methylpent-4-enoate

Into a 500-mL 3-necked round-bottom flask, was placed tert-butyl 2-[(diphenylmethylidene)amino]acetate (15 g, 50.78 mmol, 1.00 equiv), 1-bromopropan-2-one (8.2 g, 59.86 mmol, 1.20 equiv), toluene (150 mL), chloromethane (65 mL). This was followed by the addition of CAS:200132-54-3 (1.57 g, 2.59 mmol, 0.05 equiv), in portions at −20° C. To this was added a solution of potassium hydroxide (28.6 g, 510.71 mmol, 10.00 equiv) in water (30 mL) dropwise with stirring at −20° C. The resulting solution was stirred for 48 h at −20° C. The solids were filtered out. The filtrate was washed by water (50 mL×3) and brine (50 mL×1). The organic phase was dried over anhydrous sodium sulfate and concentrated under vacuum. The crude product was purified by chromatography with the following conditions (Intel-Flash-1): Column, C18 silica gel; mobile phase, CH$_3$CN/H$_2$O (0.5% NH$_3$H$_2$O); Detector, UV 254 nm. This resulted in 12.0 g (68%) of tert-butyl (2S)-2-[(diphenylmethylidene) amino]-4-methylpent-4-enoate as a white solid. MS (ES, m/z): 350 (M+H); $^1$H NMR (CDCl$_3$, 300 MHz) δ: 7.64-7.61 (m, 2H), 7.45-7.28 (m, 6H), 7.19-7.16 (m, 2H), 4.74-4.72 (m, 2H), 4.10-4.06 (m, 1H), 2.62-2.57 (m, 2H), 1.52 (s, 3H), 1.45 (s, 9H).

tert-butyl (2S)-2-amino-4-methylpent-4-enoate

Into a 250-mL round-bottom flask, was placed a solution of tert-butyl (2S)-2-[(diphenylmethylidene)amino]-4-methylpent-4-enoate (10 g, 28.62 mmol, 1.00 equiv) in 2N HCl (100 mL). The resulting solution was stirred for 1 h at room temperature. The resulting solution was extracted with 3×30 mL of n-hexane and the aqueous layer combined. The pH value of the aqueous phase was adjusted to 9 with NaHCO3 (Sat.). The resulting solution was extracted with 4×30 mL of ethyl acetate and the organic layers combined. The organic phase was washed with 3×30 mL of brine. The organic phase was dried over anhydrous sodium sulfate and concentrated under vacuum. This resulted in 4.2 g (79%) of tert-butyl (2S)-2-amino-4-methylpent-4-enoate as light yellow oil. MS (ES, m/z): 186 (M+H).

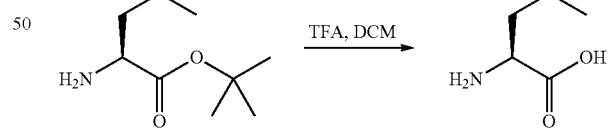

(2S)-2-amino-4-methylpent-4-enoic acid

Into a 250-mL round-bottom flask, was placed a solution of tert-butyl (2S)-2-amino-4-methylpent-4-enoate (4.2 g, 22.67 mmol, 1.00 equiv) in dichloromethane (20 mL), trifluoroacetic acid (10 mL). The resulting solution was stirred for 2 h at room temperature. The resulting mixture was concentrated under vacuum. This resulted in 3 g (crude) of (2S)-2-amino-4-methylpent-4-enoic acid as brown oil. MS (ES, m/z): 128 (M−H).

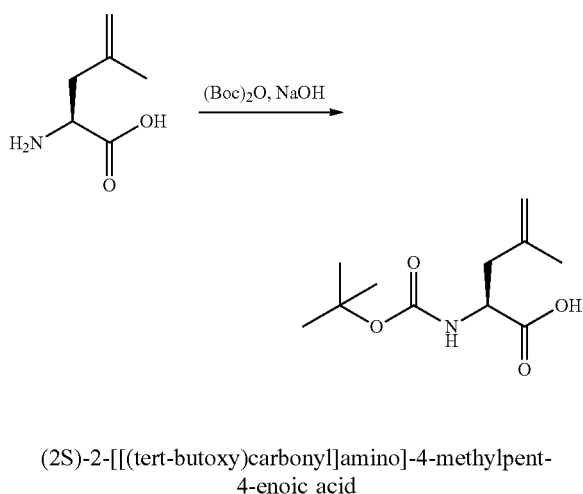

(2S)-2-[[(tert-butoxy)carbonyl]amino]-4-methylpent-4-enoic acid

Into a 250-mL round-bottom flask, was placed a solution of (2S)-2-amino-4-methylpent-4-enoic acid (3 g, 23.23 mmol, 1.00 equiv) in dioxane (100 mL), (Boc)₂O (7.5 g, 34.36 mmol, 1.50 equiv), a solution of sodium hydroxide (3 g, 75.00 mmol, 3.00 equiv) in water (5 mL). The resulting solution was stirred for 1 h at room temperature. The resulting solution was extracted with 2×20 mL of n-hexane and the aqueous phase combined. The pH value of the aqueous phase was adjusted to 6-5 with HCl (2N.). The resulting solution was extracted with 3×30 mL of ethyl acetate and the organic layers combined. The organic phase was washed with 3×30 mL of brine. The organic phase was dried over anhydrous sodium sulfate and concentrated under vacuum. This resulted in 3.5 g (66%) of (2S)-2-[[(tert-butoxy)carbonyl]amino]-4-methylpent-4-enoic acid as light yellow oil. MS (ES, m/z): 228 (M−H).

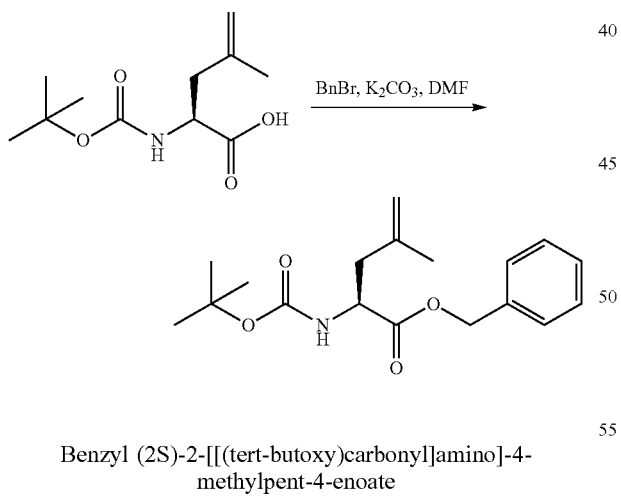

Benzyl (2S)-2-[[(tert-butoxy)carbonyl]amino]-4-methylpent-4-enoate

Into a 250-mL round-bottom flask, was placed a solution of (2S)-2-[[(tert-butoxy)carbonyl]amino]-4-methylpent-4-enoic acid (3.5 g, 15.27 mmol, 1.00 equiv) in N,N-dimethylformamide (80 mL), BnBr (3.2 g, 18.71 mmol, 1.20 equiv), potassium carbonate (6.3 g, 45.58 mmol, 3.00 equiv). The resulting solution was stirred overnight at room temperature. The reaction was then quenched by the addition of water (100 ml). The resulting solution was extracted with 3×40 mL of ethyl acetate and the organic layers combined. The organic phase was washed with 3×30 mL of brine. The organic phase was dried over anhydrous sodium sulfate and concentrated under vacuum. The residue was applied onto a silica gel column with ethyl acetate/petroleum ether (1:10). This resulted in 4 g (82%) of benzyl (2S)-2-[[(tert-butoxy)carbonyl]amino]-4-methylpent-4-enoate as light yellow oil. MS (ES, m/z): 320 (M+H); ¹H NMR (CDCl₃, 300 MHz) δ: 7.39-7.33 (m, 5H), 5.23-5.12 (m, 2H), 4.96-4.94 (m, 1H), 4.80 (d, J=14.0 Hz, 2H), 4.47-4.46 (m, 1H), 2.58-2.51 (m, 1H), 2.42-2.35 (m, 1H), 1.73 (s, 3H), 1.27 (s, 9H).

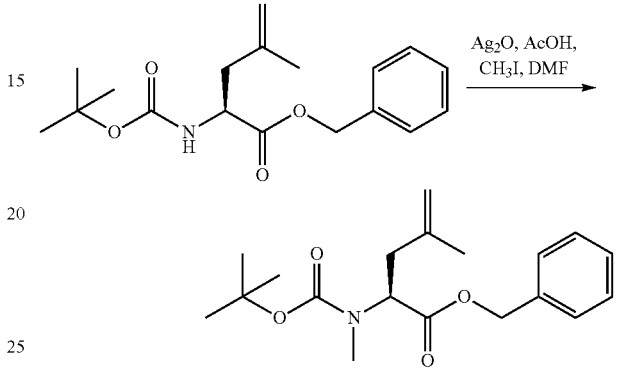

Benzyl (2S)-2-[[(tert-butoxy)carbonyl](methyl)amino]-4-methylpent-4-enoate

Into a 250-mL round-bottom flask, was placed a solution of benzyl (2S)-2-[[(tert-butoxy)carbonyl]amino]-4-methylpent-4-enoate (5.2 g, 16.28 mmol, 1.00 equiv) in N,N-dimethylformamide (100 mL), Ag₂O (11.2 g, 3.00 equiv), AcOH (1 g, 16.65 mmol, 1.00 equiv)., CH₃I (23 g, 162.04 mmol, 10.00 equiv). The resulting solution was stirred overnight at room temperature. The solids were filtered out. The filtrate was diluted with water (200 mL) and extracted with 3×70 mL of ethyl acetate and the organic layers combined. The organic phase was washed with 2×50 mL of brine. The organic phase was dried over anhydrous sodium sulfate and concentrated under vacuum. The residue was applied onto a silica gel column with ethyl acetate/petroleum ether (1:10). This resulted in 4 g (74%) of benzyl (2S)-2-[[(tert-butoxy)carbonyl](methyl)amino]-4-methylpent-4-enoate as light yellow oil. MS (ES, m/z): 334 (M+H); 1H NMR (CDCl₃, 300 MHz) δ: 7.36 (s, 5H), 5.23 (s, 2H), 5.13-5.06 (m, 0.5H), 4.83-4.73 (m, 2.5H), 2.83-2.77 (m, 3H), 2.66-2.46 (m, 2H), 1.78 (s, 3H), 1.47-1.33 (m, 9H).

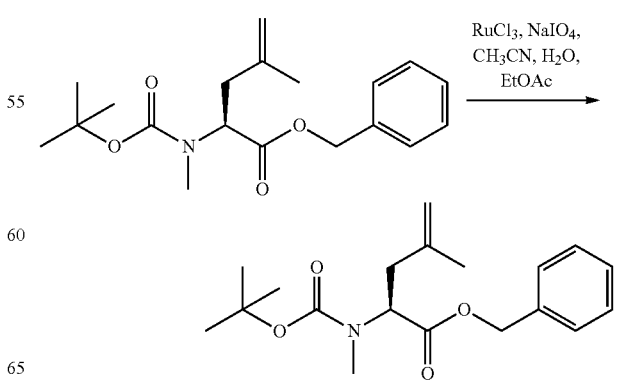

Benzyl (2S)-2-[[(tert-butoxy)carbonyl](methyl)
amino]-4-oxopentanoate

Into a 100-mL round-bottom flask, was placed a solution of benzyl (2S)-2-[[(tert-butoxy)carbonyl](methyl)amino]-4-methylpent-4-enoate (4 g, 12.00 mmol, 1.00 equiv) in CH$_3$CN:H$_2$O:EA (mL), RuCl$_3$ (124 mg, 0.05 equiv), NaIO$_4$ (10.3 g, 4.00 equiv). The resulting solution was stirred for 1 h at room temperature. The resulting solution was extracted with 3×60 mL of ethyl acetate and the organic layers combined. The organic phase was washed with 3×30 mL of brine. The organic phase was dried over anhydrous sodium sulfate and concentrated under vacuum. The residue was applied onto a silica gel column with ethyl acetate/petroleum ether (1:10). This resulted in 3 g (75%) of benzyl (2S)-2-[[(tert-butoxy)carbonyl](methyl)amino]-4-oxopentanoate as light brown oil. MS (ES, m/z): 336 (M+H); $^1$H NMR (CDCl$_3$, 300 MHz) δ: 7.35 (s, 5H), 5.20-5.10 (m, 2H), 4.70-4.66 (m, 1H), 2.94-2.74 (m, 5H), 2.24-2.22 (m, 3H), 1.49-1.31 (m, 9H).

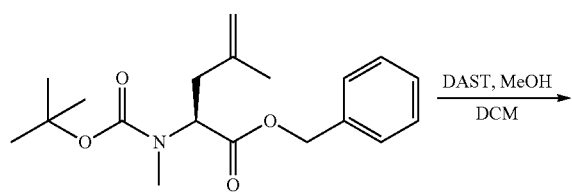

Benzyl (2S)-2-[[(tert-butoxy)carbonyl](methyl)
amino]-4,4-difluoropentanoate

Into a 30-mL vial, was placed a solution of benzyl (2S)-2-[[(tert-butoxy)carbonyl](methyl)amino]-4-oxopentanoate (500 mg, 1.49 mmol, 1.00 equiv), dichloromethane (3 mL), methanol (0.01 mL). This was followed by the addition of DAST (1.5 mL) dropwise with stirring at 0° C. The resulting solution was stirred overnight at room temperature. The reaction was then quenched by the addition of water/ice. The pH value of the solution was adjusted to 9 with NaHCO$_3$(sat.). The resulting solution was extracted with 3×50 mL of dichloromethane and the organic layers combined The organic phase was washed with 3×30 mL of brine. The organic phase was dried over anhydrous sodium sulfate and concentrated under vacuum. This resulted in 1.8 g (42%) of benzyl (2S)-2-[[(tert-butoxy)carbonyl](methyl)amino]-4,4-difluoropentanoate as yellow oil. MS (ES, m/z): 338 (M+H); $^1$H NMR (DMSO, 300 MHz) δ: 7.37-7.33 (m, 5H), 5.20-5.09 (m, 2H), 4.82-4.59 (m, 1H), 2.77-2.76 (m, 3H), 2.57-2.47 (m, 2H), 1.72-1.57 (m, 3H), 1.41-1.30 (m, 9H).

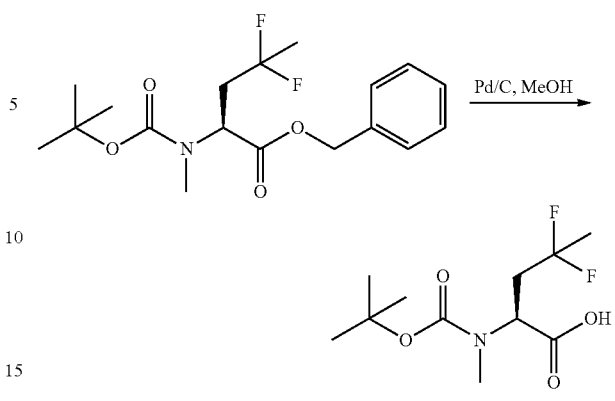

(2S)-2-[[(tert-butoxy)carbonyl](methyl)amino]-4,4-
difluoropentanoic acid (M19)

Into a 100-mL round-bottom flask, was placed a solution of benzyl (2S)-2-[[(tert-butoxy)carbonyl](methyl)amino]-4,4-difluoropentanoate (900 mg, 2.52 mmol, 1.00 equiv) in methanol (20 mL), Palladium on carbon (50 mg). To the above hydrogen was introduced. The resulting solution was stirred for 30 min at room temperature. The solids were filtered out. The filtrate was concentrated under vacuum. This resulted in 700 mg (crude) of (2S)-2-[[(tert-butoxy)carbonyl](methyl)amino]-4,4-difluoropentanoic acid as a white solid. MS (ES, m/z): 268 (M+H).

Preparation Example 13: Preparation of Monomer
M20

Monomer M20 was prepared by the process shown in Scheme 13 below.

Scheme 13

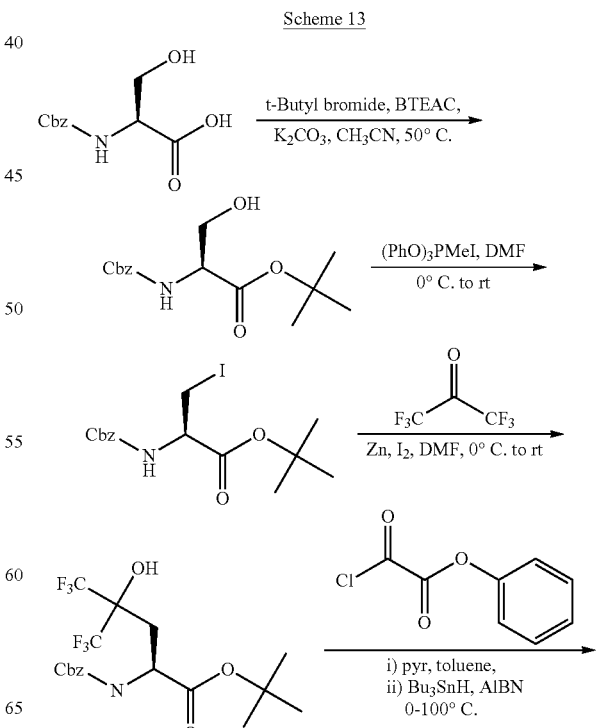

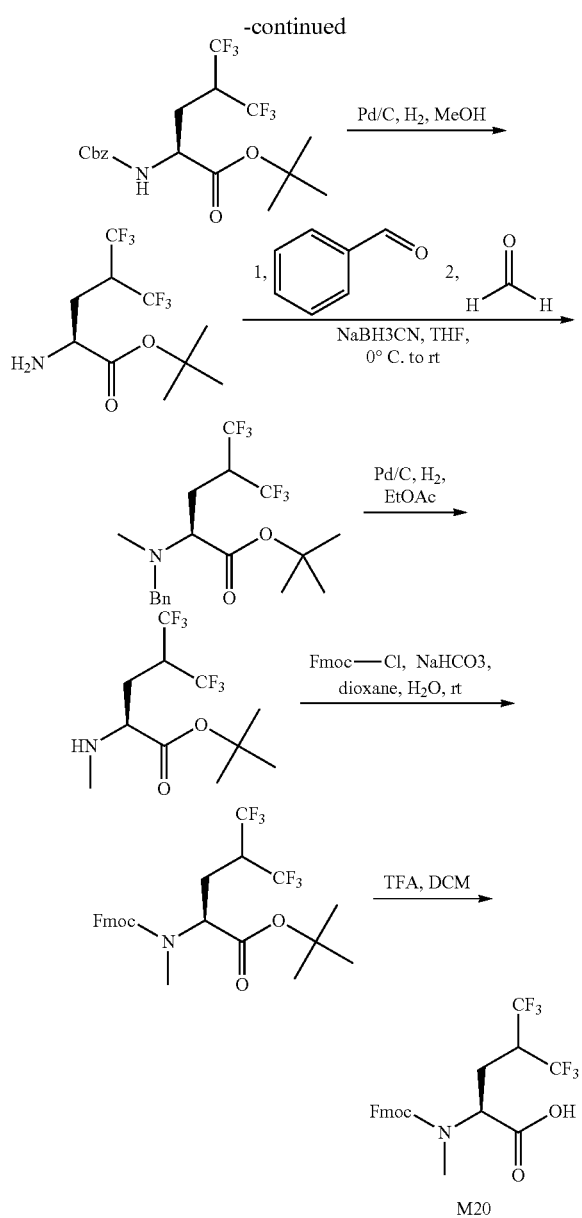

Experimental Details tert-butyl (2S)-2-[[(benzyloxy)carbonyl]amino]-3-hydroxypropanoate

Into a 2-L round-bottom flask, was placed (2S)-2-[[(benzyloxy)carbonyl]amino]-3-hydroxypropanoic acid (50 g, 209.01 mmol, 1.00 equiv), acetonitrile (400 mL), potassium potassium methaneperoxate (180 g, 1.29 mol, 6.50 equiv), benzyltriethylazanium chloride (47 g, 206.35 mmol, 1.00 equiv). The resulting solution was stirred for 5 h at r.t. Then 2-bromo-2-methylpropane (250 mL, 10.20 equiv) was added. The resulting solution was stirred overnight at 50° C. in an oil bath. The reaction mixture was cooled. The resulting mixture was concentrated under vacuum. The residue was dissolved in 1.5 L of ethyl acetate. The resulting mixture was washed with 1×500 mL of H₂O. The organic layer was washed with 2×400 mL of brine. The organic layer was dried over anhydrous sodium sulfate and concentrated under vacuum. This resulted in 39 g (63%) of tert-butyl (2S)-2-[[(benzyloxy)carbonyl]amino]-3-hydroxypropanoate as a white solid. MS (ES, m/z): 296 (M+H).

tert-butyl (2R)-2-[[(benzyloxy)carbonyl]amino]-3-iodopropanoate

Into a 250-mL round-bottom flask, was placed N,N-dimethylformamide (150 mL), tert-butyl (2S)-2-[[(benzyloxy)carbonyl]amino]-3-hydroxypropanoate (20 g, 67.72 mmol, 1.00 equiv). This was followed by the addition of methyltriphenoxyphosphonium iodide (43 g, 95.09 mmol, 1.30 equiv) in portions with stirring at 0° C. The resulting solution was stirred for 2 h at room temperature. The reaction mixture was cooled to 0° C. with a water/ice bath. The reaction was then quenched by the addition of 30 g of sodium bicarbonate. The resulting solution was diluted with 260 mL of H₂O. The resulting solution was extracted with 3×300 mL of ethyl acetate and the organic layers combined. The organic layers were washed with 2×200 mL of aqueous sodium hydroxide (0.05 mol/L). The organic layers were washed with 1×200 mL of brine. The organic layers were dried over anhydrous sodium sulfate and concentrated under vacuum. The residue was applied onto a silica gel column with ethyl acetate/petroleum ether (1:100-1:30). This resulted in 20 g (73%) of tert-butyl (2R)2-[[(benzyloxy)carbonyl]amino]-3-iodopropanoate as colorless oil. MS (ES, m/z): 406 (M+H).

tert-butyl (2S)-2-[[(benzyloxy)carbonyl]amino]-5,5,5-trifluoro-4-hydroxy-4-(trifluoromethyl)pentanoate Into a 250-mL round-bottom flask purged and maintained with an inert atmosphere of nitrogen, was placed N,N-dimethylformamide (50 mL), zinc (16 g, 244.61 mmol, 5.00 equiv), diiodane (1.25 g, 4.92 mmol, 0.10 equiv), the mixture was stirred then the reaction mixture turned colorless, tert-butyl (2R)2-[[(benzyloxy)carbonyl]amino]-3-iodopropanoate (20 g, 49.35 mmol, 1.00 equiv) and I2 (1.25 g, 4.92 mmol, 0.10 equiv) was added to reaction mixture. This was followed by the addition of a solution of hexafluoropropan-2-one (100 mL, 3.00 equiv) in N,N-dimethylformamide (50 mL) at −30° C. The resulting solution was stirred for 4 h at room temperature. The resulting solution was diluted with 500 mL of ice-water. The resulting solution was extracted with 3×200 mL of ethyl acetate and the organic layers combined. The organic layers were washed with 3×100 mL of brine. The organic layers were dried over anhydrous sodium sulfate and concentrated under vacuum. The crude product was purified by Flash-Prep-HPLC with the following conditions (IntelFlash-1): Column, C18 silica gel; mobile phase, CH3CN/H$_2$O=30% increasing to CH$_3$CN/H$_2$O=65% within 20 min; Detector, UV 220 nm. This resulted in 17 g (77%) of tert-butyl (2S)-2-[[(benzyloxy)carbonyl]amino]-5,5,5-trifluoro-4-hydroxy-4-(trifluoromethyl)pentanoate as a white solid. MS (ES, m/z): 446 (M+H); $^1$HNMR (300 MHz, CDCl$_3$): δ 7.52-7.3 (m, 5H), 6.15-5.80 (br, 1H), 5.16 (s, 2H), 4.52-4.40 (m, 1H), 2.80-2.70 (m, 1H), 2.40-2.25 (m, 1H), 1.50 (s, 9H).

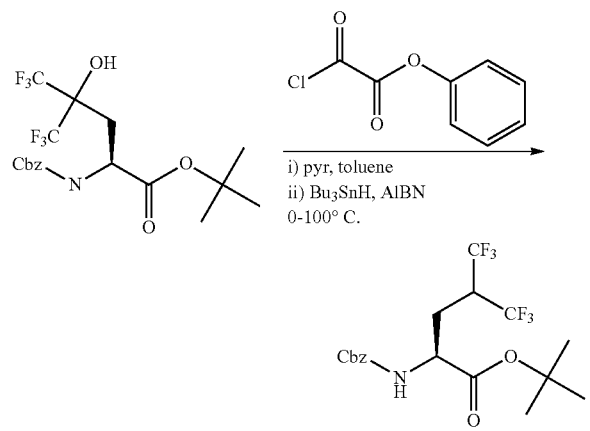

Of tert-butyl (2S)-2-[[(benzyloxy)carbonyl]amino]-5,5,5-trifluoro-4-(trifluoromethyl)pentanoate Into a 250-mL round-bottom flask purged and maintained with an inert atmosphere of nitrogen, was placed Tol (50 mL), tert-butyl (2S)-2-[[(benzyloxy)carbonyl]amino]-5,5,5-trifluoro-4-hydroxy-4-(trifluoromethyl)pentanoate (12.34 g, 27.71 mmol, 1.00 equiv), phenyl 2-chloro-2-oxoacetate (7.4 g, 40.09 mmol, 1.45 equiv). This was followed by the addition of pyridine (3 g, 37.93 mmol, 1.40 equiv) dropwise with stirring at 0° C. for 1 hour. The solids were filtered out. The resulting mixture was concentrated under vacuum. To this was added AIBN (1.8 g, 10.96 mmol, 0.40 equiv) and the crude product to Tributyltin hydride (14.4 g, 49.65 mmol, 1.80 equiv) and toluene at 100° C. in an oil bath. The resulting solution was stirred for 1 h at 100° C. in an oil bath. The reaction mixture was cooled. The resulting solution was diluted with 100 mL of ether. The reaction was then quenched by the addition of 30 g of KF/Al2O3. the reaction mixture was stirred at roomtemperature for 1 hour. The solids were filtered out. The resulting mixture was concentrated under vacuum. The residue was applied onto a silica gel column with ethyl acetate/petroleum ether (1:100-1:30). The crude product was purified by Flash-Prep-HPLC with the following conditions (IntelFlash-1): Column, C18 silica gel; mobile phase, CH3CN/H$_2$O=40% increasing to CH3CN/H$_2$O=78% within 20 min; Detector, UV 254 nm. This resulted in 1.2 g (10%) of tert-butyl (2S)-2-[[(benzyloxy)carbonyl]amino]-5,5,5-trifluoro-4-(trifluoromethyl)pentanoate as a white solid. MS (ES, m/z): 430 (M+H); $^1$H NMR: (300 MHz, CDCl$_3$, ppm): 7.46-7.31 (m, 5H), 5.46-5.30 (br, 1H), 5.15 (s, 2H), 4.50-4.30 (m, 1H), 3.40-3.20 (m, 1H), 2.45-2.00 (m, 2H), 1.49 (s, 9H).

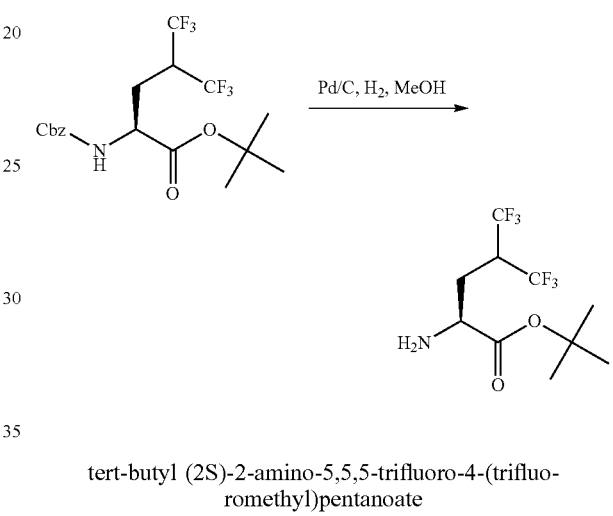

tert-butyl (2S)-2-amino-5,5,5-trifluoro-4-(trifluoromethyl)pentanoate

Into a 100-mL round-bottom flask, was placed Palladium on carbon (400 mg), methanol (40 mL), tert-butyl (2S)-2-[[(benzyloxy)carbonyl]amino]-5,5,5-trifluo-4-(trifluoromethyl)pentanoate (2.1 g, 4.89 mmol, 1.00 equiv), to the above hydrogen was introduced. The resulting solution was stirred overnight at room temperature. The solids were filtered out. The resulting mixture was concentrated under vacuum. This resulted in 1.4 g (97%) of tert-butyl (2S)-2-amino-5,5,5-trifluoro-4-(trifluoromethyl)pentanoate as colorless oil. MS (ES, m/z): 296 (M+H).

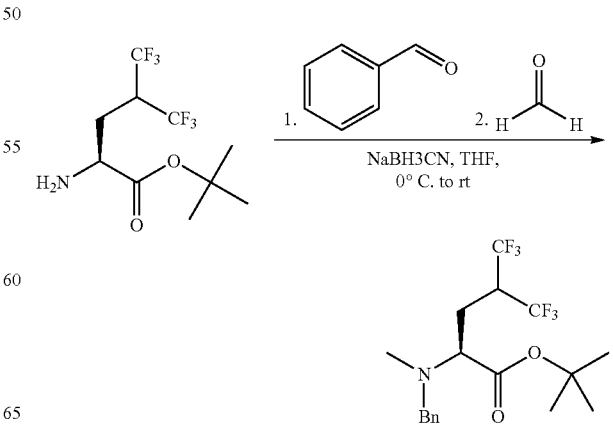

tert-butyl (2S)-2-[benzyl(methyl)amino]-5,5,5-trifluoro-4-(trifluoromethyl)pentanoate Into a 250-mL round-bottom flask, was placed tetrahydrofuran (40 mL), tert-butyl (2S)-2-amino-5,5,5-trifluoro-4-(trifluoromethyl)pentanoate (1.35 g, 4.57 mmol, 1.00 equiv). This was followed by the addition of benzaldehyde (1.17 g, 11.03 mmol, 2.50 equiv) dropwise at 0° C. The resulting solution was stirred for 2 hour at room temperature. To this was added NaBH3CN (820 mg, 13.23 mmol, 3.00 equiv) in portions at 0° C. The resulting solution was stirred for 2 hour at room temperature. To the mixture was added formaldehyde (330 mg, 10.99 mmol, 2.50 equiv) in portions at 0° C. To this was added NaBH$_3$CN (820 mg, 13.23 mmol, 3.00 equiv) in portions at 0° C. The resulting solution was stirred overnight at room temperature. The solids were filtered out. The resulting mixture was concentrated under vacuum. The residue was purified by preparative TLC (ether:n-hexane=1:1). This resulted in 800 mg (44%) of tert-butyl (2S)-2-[benzyl(methyl)amino]-5,5,5-trifluoro-4-(trifluoromethyl)pentanoate as colorless oil. MS (ES, m/z): 400 (M+H).

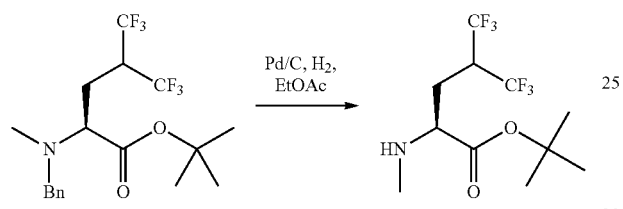

tert-butyl (2S)-5,5,5-trifluoro-2-(methylamino)-4-(trifluoromethyl)pentanoate Into a 50-mL round-bottom flask, was placed tert-butyl (2S)-2-[benzyl(methyl)amino]-5,5,5-trifluoro-4-(trifluoromethyl)pentanoate (240 mg, 0.60 mmol, 1.00 equiv), ethyl acetate (10 mL), Palladium on carbon (50 mg). To the above H2 (gas) was introduced. The resulting solution was stirred for 3 h at room temperature. This resulted in 130 mg (70%) of tert-butyl (2S)-5,5,5-trifluoro-2-(methylamino)-4-(trifluoromethyl)pentanoate as colorless oil. MS (ES, m/z): 310 (M+H).

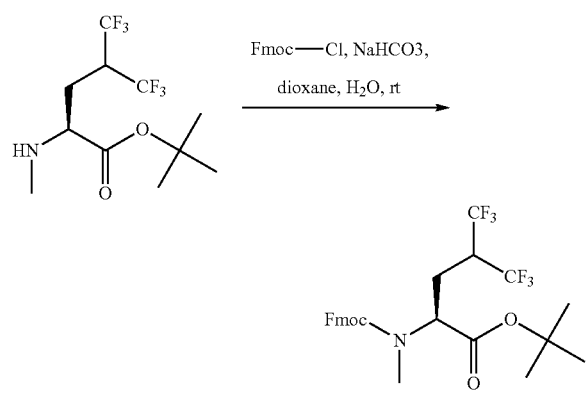

tert-butyl (2S)-2-[[(9H-fluoren-9-ylmethoxy)carbonyl](methyl)amino]-5,5,5-trifluoro-4-(trifluoromethyl)pentanoate Into a 8-mL round-bottom flask, was placed dioxane (2 mL), water (1 drop), tert-butyl (2S)-5,5,5-trifluoro-2-(methylamino)-4-(trifluoromethyl)pentanoate (130 mg, 0.42 mmol, 1.00 equiv), NaHCO3 (43 mg, 0.51 mmol, 1.20 equiv), 9H-fluoren-9-ylmethyl chloroformate (120 mg, 0.46 mmol, 1.10 equiv). The resulting solution was stirred for 3 h at room temperature. The resulting mixture was concentrated under vacuum. The residue was purified by preparative TLC (EtOAc:PE=1:5). This resulted in 150 mg (67%) of tert-butyl (2S)-2-[[(9H-fluoren-9-ylmethoxy)carbonyl](methyl)amino]-5,5,5-trifluoro-4-(trifluoromethyl) pentanoate as colorless oil. MS (ES, m/z): 554 (M+Na).

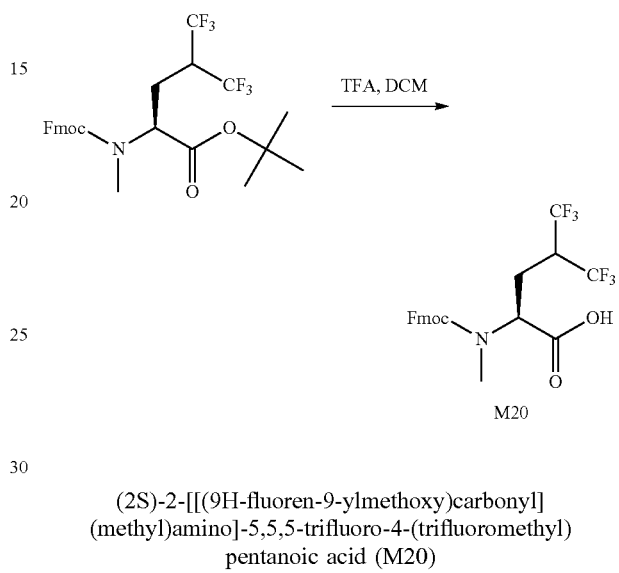

(2S)-2-[[(9H-fluoren-9-ylmethoxy)carbonyl](methyl)amino]-5,5,5-trifluoro-4-(trifluoromethyl) pentanoic acid (M20)

Into a 50-mL round-bottom flask, was placed dichloromethane (10 mL), tert-butyl (2S)-2-[[(9H-fluoren-9-ylmethoxy)carbonyl](methyl) amino]-5,5,5-trifluoro-4-(trifluoromethyl)pentanoate (150 mg, 0.28 mmol, 1.00 equiv). This was followed by the addition of trifluoroacetic acid (3 mL) dropwise with stirring. The resulting solution was stirred for 4 h at room temperature. The resulting mixture was concentrated under vacuum. This resulted in 210 mg of (2S)-2-[[(9H-fluoren-9-ylmethoxy)carbonyl](methyl) amino]-5,5,5-trifluoro-4-(trifluoromethyl)pentanoic acid as colorless oil. MS (ES, m/z): 476 (M+H); $^1$H NMR: (300 MHz, CDCl$_3$, ppm): 7.82-7.78 (m, 2H), 7.63-7.50 (m, 2H), 7.47-7.30 (m, 4H), 4.82-4.30 (m, 5H), 2.90-2.78 (m, 3H), 2.60-2.20 (m, 2H).

Preparation Example 14: Preparation of Monomer M21

Monomer M21 was prepared by the process shown in Scheme 14 below.

Scheme 14

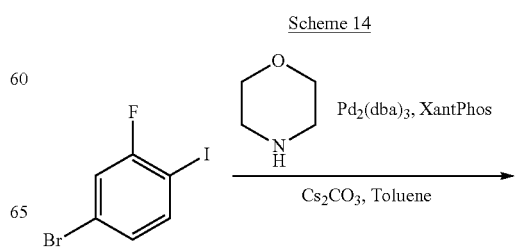

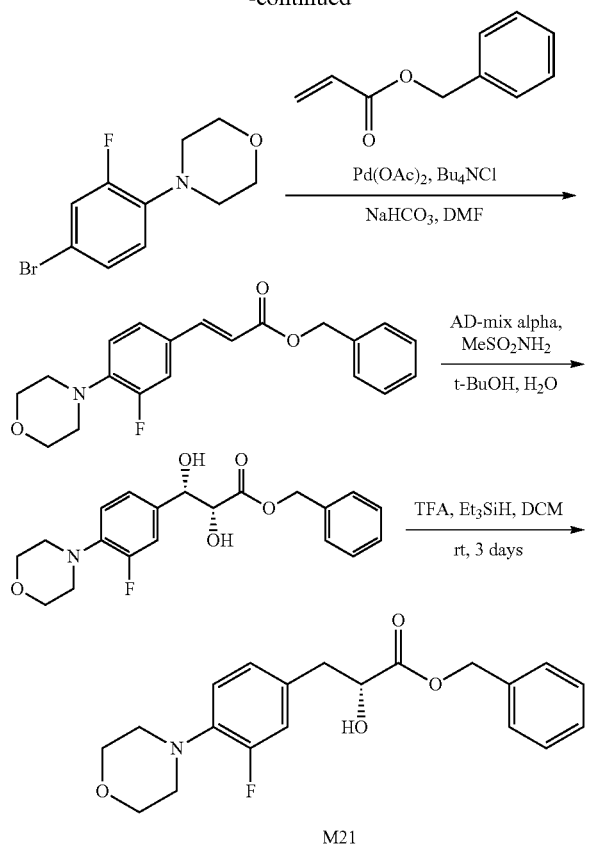

M21

Experimental Details

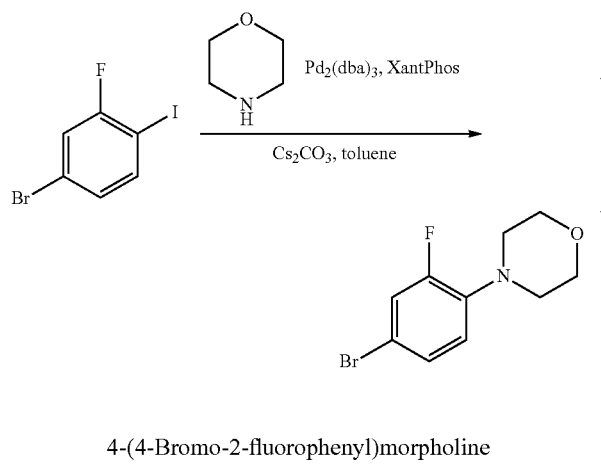

4-(4-Bromo-2-fluorophenyl)morpholine

Into a 1-L round-bottom flask purged and maintained with an inert atmosphere of nitrogen, was placed a solution of 4-bromo-2-fluoro-1-iodobenzene (15 g, 49.85 mmol, 1.00 equiv) in toluene (300 mL). Pd$_2$(dba)$_3$ (1.3 g, 1.42 mmol, 0.03 equiv). Cs$_2$CO$_3$ (41 g, 125.45 mmol, 2.50 equiv). XantPhos (2.9 g, 5.01 mmol, 0.10 equiv). morpholine (4.3 g, 49.36 mmol, 1.00 equiv). The resulting solution was stirred overnight at 100° C. The reaction was then quenched by the addition of 150 mL of water. The resulting solution was extracted with 3×100 mL of ethyl acetate and the organic layers combined and dried over anhydrous sodium sulfate and concentrated under vacuum. The residue was applied onto a silica gel column with ethyl acetate/petroleum ether (1:15). This resulted in 10.5 g (81%) of 4-(4-bromo-2-fluorophenyl)morpholine as a yellow solid. MS (ES, m/z): 260 (M+H).

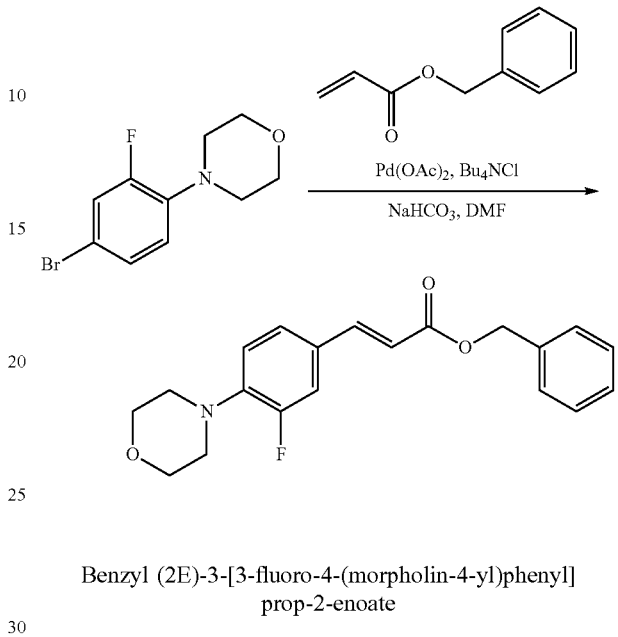

Benzyl (2E)-3-[3-fluoro-4-(morpholin-4-yl)phenyl]
prop-2-enoate

Into a 100-mL round-bottom flask purged and maintained with an inert atmosphere of nitrogen, was placed 4-(4-bromo-2-fluorophenyl)morpholine (1.25 g, 4.81 mmol, 1.00 equiv). Pd(OAc)$_2$ (50 mg, 0.22 mmol, 0.05 equiv). a solution of sodium bicarbonate (810 mg, 9.64 mmol, 2.00 equiv) in N,N-dimethylformamide (30 mL). Bu$_4$NCl (2.7 g, 9.72 mmol, 2.00 equiv). benzyl prop-2-enoate (1.6 g, 9.87 mmol, 2.00 equiv). The resulting solution was stirred for 36 h at 100° C. The reaction was then quenched by the addition of water. The resulting solution was extracted with 4×100 mL of ethyl acetate and the organic layers combined. The organic phase was washed with 3×60 mL of brine. The organic phase was dried over anhydrous sodium sulfate and concentrated under vacuum. The residue was applied onto a silica gel column with ethyl acetate/petroleum ether (1:5). This resulted in 10.5 g (80%) of benzyl (2E)-3-[3-fluoro-4-(morpholin-4-yl)phenyl]prop-2-enoate as a yellow solid. MS (ES, m/z): 342 (M+H).

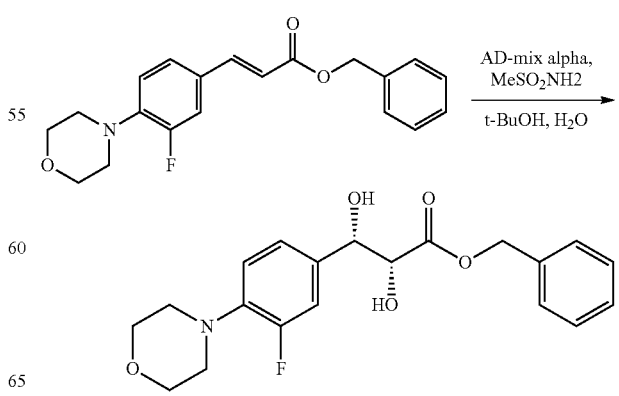

Benzyl (2R, 3S)-3-[3-fluoro-4-(morpholin-4-yl) phenyl]-2,3-dihydroxypropanoate Into a 250-mL 3-necked round-bottom flask, was placed a solution of AD-mix-α (12.3 g) in tert-Butanol/H$_2$O (60:60 mL). This was followed by the addition of benzyl (2E)-3-[3-fluoro-4-(morpholin-4-yl)phenyl]prop-2-enoate (3 g, 8.79 mmol, 1.00 equiv), in portions at 0° C. To this was added MeSO$_2$NH$_2$ (1.23 g, 1.00 equiv), in portions at 0° C. The resulting solution was stirred for 3 days at room temperature. The reaction was then quenched by the addition of Na$_2$SO$_3$. The resulting solution was extracted with 3×100 mL of ethyl acetate and the organic layers combined. The organic phase was washed with 3×60 mL of brine. The organic phase was dried over anhydrous sodium sulfate and concentrated under vacuum. The residue was applied onto a silica gel column with ethyl acetate/petroleum ether (1:1). This resulted in 9.5 g (72%) of benzyl (2R, 3S)-3-[3-fluoro-4-(morpholin-4-yl)phenyl]-2,3-dihydroxypropanoate as yellow oil. MS (ES, m/z): 376 (M+H).

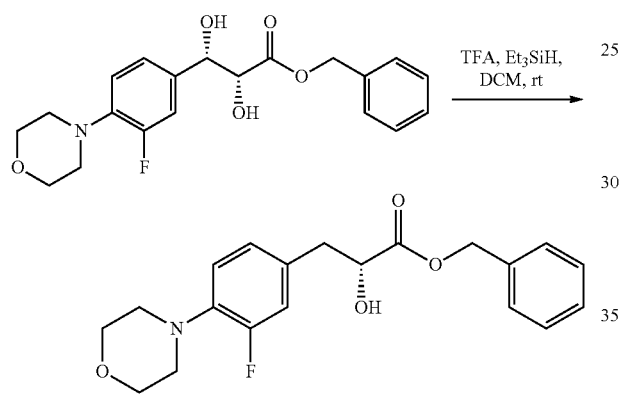

M21

Benzyl (2R)-3-[3-fluoro-4-(morpholin-4-yl)phenyl]-2-hydroxypropanoate (M21)

Into a 40-mL vial, was placed a solution of benzyl (2R, 3S)-3-[3-fluoro-4-(morpholin-4-yl)phenyl]-2,3-dihydroxypropanoate (900 mg, 2.40 mmol, 1.00 equiv) in dichloromethane (2 mL), Et$_3$SiH (4 mL), trifluoroacetic acid (2 mL). The resulting solution was stirred for 3 days at room temperature. The reaction was then quenched by the addition of water/ice. The resulting solution was extracted with 3×80 mL of ethyl acetate and the organic layers combined. The organic phase was washed with 3×60 mL of brine. The organic phase was dried over anhydrous sodium sulfate and concentrated under vacuum. The residue was applied onto a silica gel column with ethyl acetate/petroleum ether (1:3). This resulted in 4.1 g (48%) of benzyl (2R)-3-[3-fluoro-4-(morpholin-4-yl)phenyl]-2-hydroxypropanoate as reddish oil. MS (ES, m/z): 360 (M+H).

Preparation Example 15: Preparation of Monomer M24

Monomer M24 was prepared by the process shown in Scheme 15 below.

Scheme 15

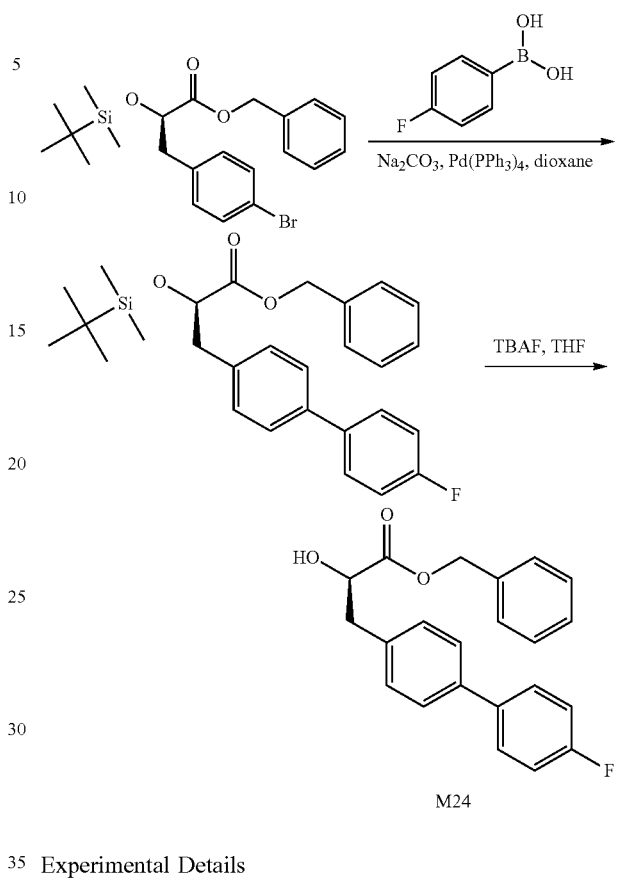

M24

Experimental Details

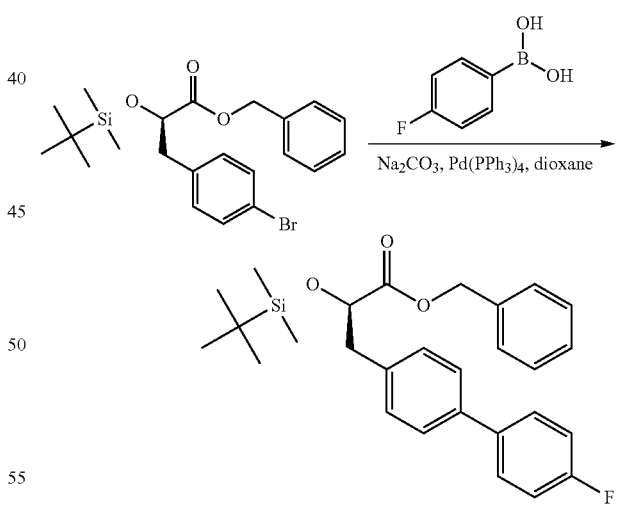

Benzyl (2R)-2-[(tert-butyldimethylsilyl)oxy]-3-[4-(4-fluorophenyl)phenyl]propanoate Into a 100-mL round-bottom flask purged and maintained with an inert atmosphere of nitrogen, was placed (4-fluorophenyl)boronic acid (1 g, 7.15 mmol, 1.50 equiv), dioxane (20 mL), water (2 mL), benzyl (2R)3-(4-bromophenyl)-2-[(tert-butyldimethylsilyl)oxy]propanoate (2 g, 4.45 mmol, 1.00 equiv), sodium carbonate (1.2 g, 11.32 mmol, 2.50 equiv), Pd(PPh3)4 (250 mg, 0.22 mmol, 0.05 equiv). The resulting solution was stirred for 3 h at 70° C. The resulting mixture was concentrated under vacuum. The residue was applied onto a silica gel column with petroleum ether. This resulted in 2.1 g (crude) of benzyl (2R)2-[(tert-butyldimethylsilyl)oxy]-3-[4-(4-fluorophenyl)phenyl]propanoate as colorless oil. $^1$H NMR (DMSO, 300 MHz) δ: 7.70-7.54 (m, 4H), 7.45 (d, J=4.2 Hz, 1H), 7.39-7.25 (m, 8H), 7.16 (d, J=4.2 Hz, 1H), 5.14 (s, 2H), 4.53-4.47 (m, 1H), 3.06-2.86 (m, 2H), 0.73 (s, 9H), −0.13 (s, 3H), −0.23 (s, 3H).

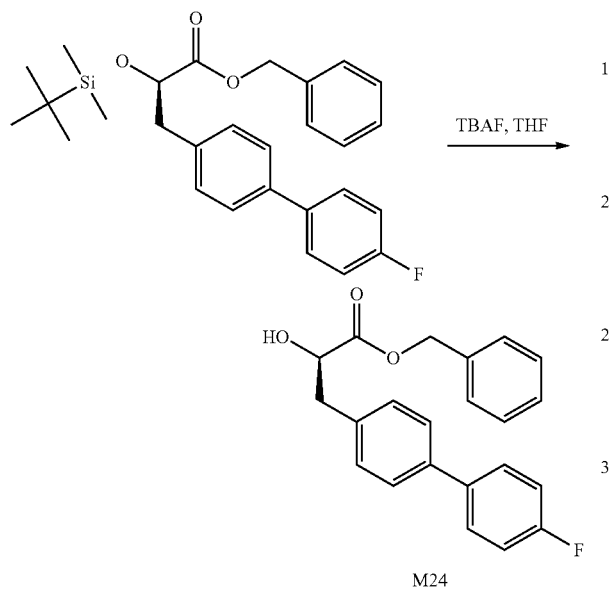

M24

Benzyl (2R)-3-[4-(4-fluorophenyl)phenyl]-2-hydroxypropanoate (M24)

(2R)2-[(tert-butyldimethylsilyl)oxy]-3-[4-(4-fluorophenyl)phenyl]propanoate (2.1 g, 4.52 mmol, 1.00 equiv), tetrahydrofuran (50 mL). This was followed by the addition of TBAF (1.5 g, 5.74 mmol, 1.30 equiv) in portions at 0° C. The resulting solution was stirred for 40 min at room temperature. The reaction was then quenched by the addition of water/ice. The resulting solution was extracted with 3×60 mL of ethyl acetate and the organic layers combined. The organic phase was washed with 3×50 mL of brine. The organic phase was dried over anhydrous sodium sulfate and concentrated under vacuum. The residue was applied onto a silica gel column with ethyl acetate/petroleum ether (1:10). This resulted in 1.2 g (76%) of benzyl (2R)3-[4-(4-fluorophenyl)phenyl]-2-hydroxypropanoate as a white crude solid. $^1$H NMR (CDCl$_3$, 300 MHz) δ: 7.56-7.51 (m, 2H), 7.46-7.32 (m, 7H), 7.25-7.22 (m, 2H), 7.17-7.11 (m, 2H), 5.27-5.15 (m, 2H), 4.53-4.47 (m, 1H), 3.12-2.92 (m, 2H).

Preparation Example 16: Preparation of Monomer M25

Monomer M25 was prepared by the process shown in Scheme 16 below.

Scheme 16

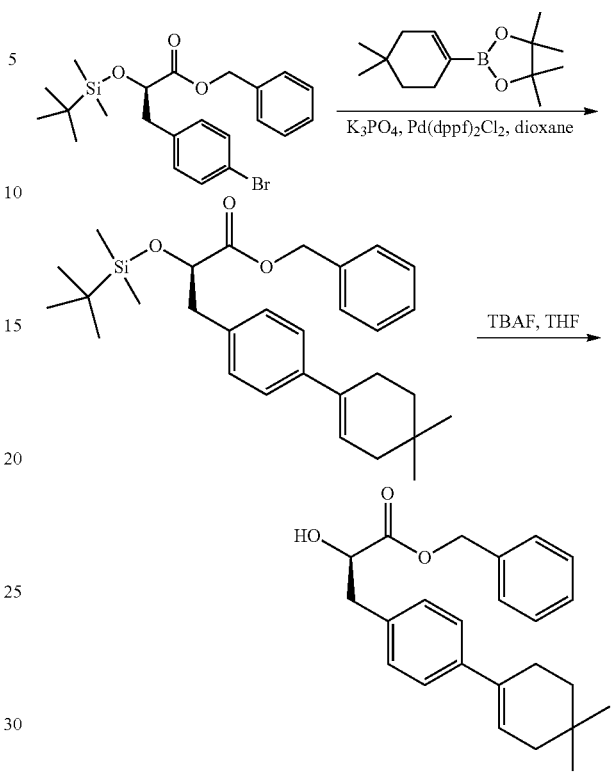

M25

Experimental Details

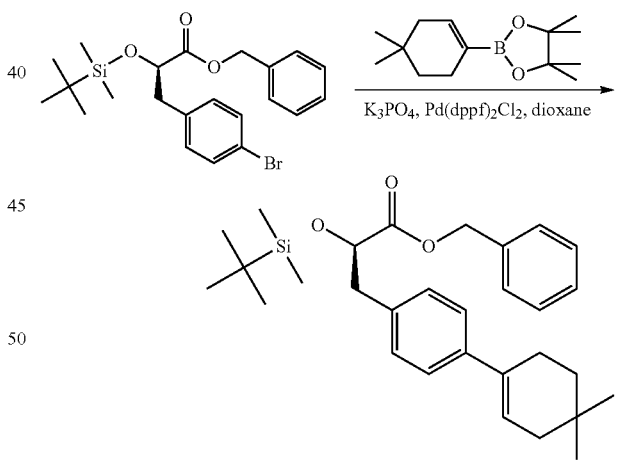

Benzyl (2R)-2-[(tert-butyldimethylsilyl)oxy]-3-[4-(4,4-dimethylcyclohex-1-en-1-yl)phenyl]propanoate Into a 250-mL round-bottom flask purged and maintained with an inert atmosphere of nitrogen, was placed benzyl (2R)3-(4-bromophenyl)-2-[(tert-butyldimethylsilyl)oxy] propanoate (1.58 g, 3.52 mmol, 1.00 equiv), 2-(4,4-dimethylcyclohex-1-en-1-yl)-4,4,5,5-tetramethyl-1,3,2-dioxaborolane (1 g, 4.23 mmol, 1.20 equiv), K$_3$PO$_4$ (1.86 g, 8.76 mmol, 2.50 equiv), Pd(dppf)2Cl2 (130 mg, 0.18 mmol, 0.05 equiv), dioxane (25 mL), water (2.5 mL). The resulting solution was stirred for 2 h at 75° C. The solids were filtered out. The resulting mixture was concentrated under vacuum. The residue was applied onto a silica gel column with ethyl acetate/petroleum ether (1:50). This resulted in 1.5 g (89%) of benzyl (2R)-2-[(tert-butyldimethylsilyl)oxy]-3-[4-(4,4-dimethylcyclohex-1-en-1-yl)phenyl]propanoate as yellow oil. $^1$H NMR (DMSO, 300 MHz) δ: 7.40-7.28 (m, 7H), 7.17 (d, J=4.0 Hz, 2H), 6.07 (t, J=3.9 Hz, 1H), 5.23-5.13 (m, 2H), 4.44-4.40 (m, 1H), 3.13-3.08 (m, 1H), 2.98-2.91 (m, 1H), 2.47-2.42 (m, 2H), 2.04-2.03 (m, 2H), 1.57 (t, J=6.1 Hz, 2H), 1.01 (s, 6H), 0.85 (s, 9H), −0.07 (s, 3H), −0.15 (s, 3H).

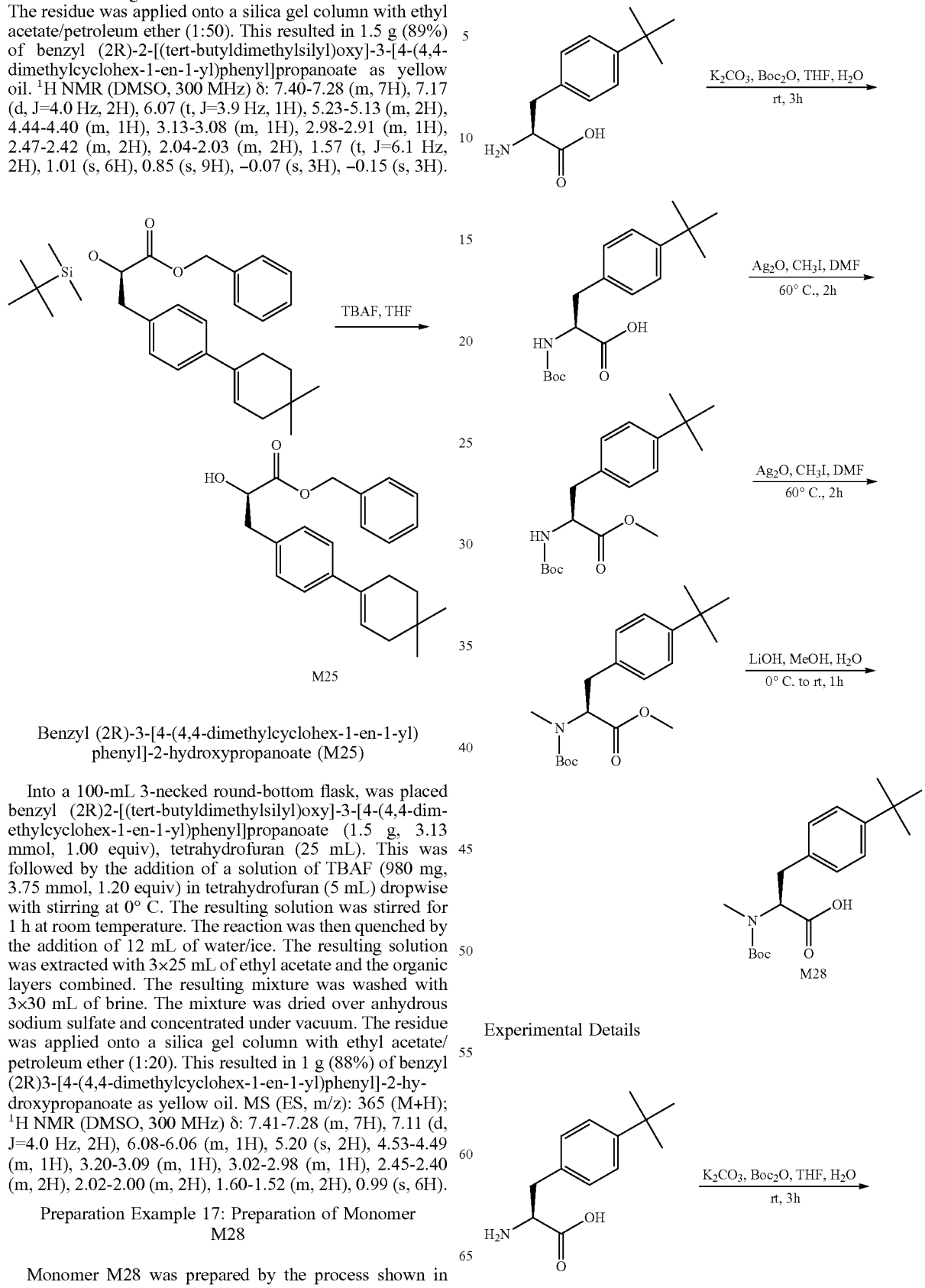

Scheme 17

M25

Benzyl (2R)-3-[4-(4,4-dimethylcyclohex-1-en-1-yl)phenyl]-2-hydroxypropanoate (M25)

Into a 100-mL 3-necked round-bottom flask, was placed benzyl (2R)2-[(tert-butyldimethylsilyl)oxy]-3-[4-(4,4-dimethylcyclohex-1-en-1-yl)phenyl]propanoate (1.5 g, 3.13 mmol, 1.00 equiv), tetrahydrofuran (25 mL). This was followed by the addition of a solution of TBAF (980 mg, 3.75 mmol, 1.20 equiv) in tetrahydrofuran (5 mL) dropwise with stirring at 0° C. The resulting solution was stirred for 1 h at room temperature. The reaction was then quenched by the addition of 12 mL of water/ice. The resulting solution was extracted with 3×25 mL of ethyl acetate and the organic layers combined. The resulting mixture was washed with 3×30 mL of brine. The mixture was dried over anhydrous sodium sulfate and concentrated under vacuum. The residue was applied onto a silica gel column with ethyl acetate/petroleum ether (1:20). This resulted in 1 g (88%) of benzyl (2R)3-[4-(4,4-dimethylcyclohex-1-en-1-yl)phenyl]-2-hydroxypropanoate as yellow oil. MS (ES, m/z): 365 (M+H); $^1$H NMR (DMSO, 300 MHz) δ: 7.41-7.28 (m, 7H), 7.11 (d, J=4.0 Hz, 2H), 6.08-6.06 (m, 1H), 5.20 (s, 2H), 4.53-4.49 (m, 1H), 3.20-3.09 (m, 1H), 3.02-2.98 (m, 1H), 2.45-2.40 (m, 2H), 2.02-2.00 (m, 2H), 1.60-1.52 (m, 2H), 0.99 (s, 6H).

Preparation Example 17: Preparation of Monomer M28

Monomer M28 was prepared by the process shown in Scheme 17 below.

Experimental Details

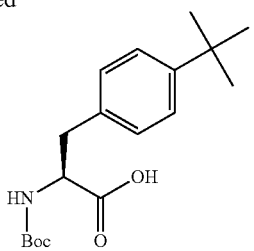

(2S)-2-[[(tert-butoxy)carbonyl]amino]-3-(4-tert-butylphenyl)propanoic acid

Into a 250-mL round-bottom flask, was placed tetrahydrofuran (140 mL), (2S)-2-amino-3-(4-tert-butylphenyl)propanoic acid (7 g, 31.63 mmol, 1.00 equiv). This was followed by the addition of a solution of potassium carbonate (10.9 g, 78.87 mmol, 2.50 equiv) in H₂O (25 mL) dropwise with stirring at 0° C. To this was added a solution of Boc₂O (10.2 g, 46.74 mmol, 1.50 equiv) in tetrahydrofuran (5 mL) dropwise with stirring at 0° C. The resulting solution was stirred for 3 h at room temperature. The pH value of the solution was adjusted to 6 with hydrogen chloride (3 mol/L). The resulting solution was extracted with 3×100 mL of ethyl acetate and the organic layers combined. The organic layers were washed with 3×50 mL of brine. The layers were dried over anhydrous sodium sulfate and concentrated under vacuum. This resulted in 14 g of (2S)-2-[[(tert-butoxy)carbonyl]amino]-3-(4-tert-butylphenyl)propanoic acid as a white solid. MS (ES, m/z): 322 (M+H).

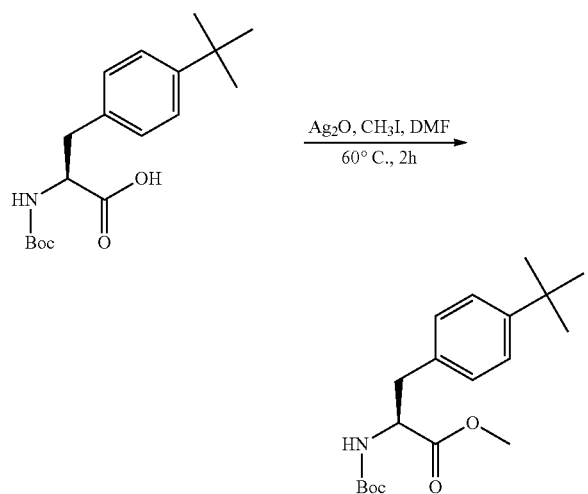

Methyl (2S)-2-[[(tert-butoxy)carbonyl]amino]-3-(4-tert-butylphenyl)propanoate Into a 100-mL round-bottom flask, was placed N,N-dimethylformamide (80 mL), (2S)-2-[[(tert-butoxy)carbonyl]amino]-3-(4-tert-butylphenyl)propanoic acid (10.1 g, 31.42 mmol, 1.00 equiv), Ag₂O (14.6 g, 2.00 equiv), CH₃I (5.4 g, 38.04 mmol, 1.10 equiv). The resulting solution was stirred for 2 h at 60° C. in an oil bath. The reaction mixture was cooled. The resulting solution was diluted with 200 mL of ice-water. The resulting solution was extracted with 3×100 mL of ethyl acetate and the organic layers combined. The organic layers were washed with 3×50 mL of brine. The organic layers were dried over anhydrous sodium sulfate and concentrated under vacuum. This resulted in 11.7 g (crude) of methyl (2S)-2-[[(tert-butoxy)carbonyl]amino]-3-(4-tert-butylphenyl)propanoate as light yellow oil. MS (ES, m/z): 336 (M+H).

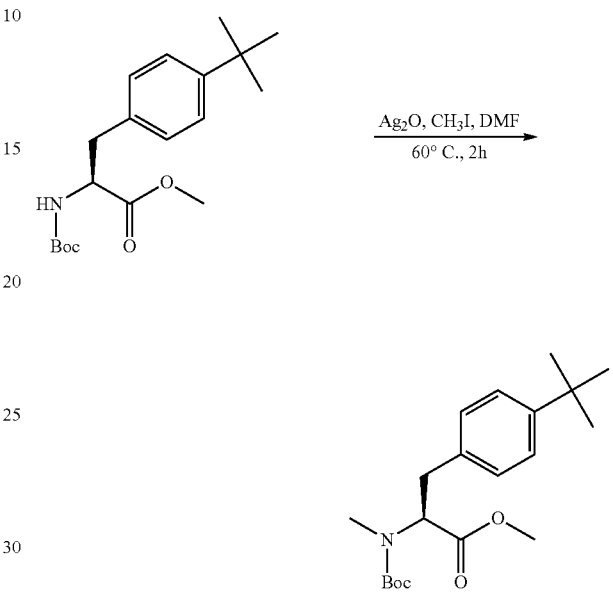

Methyl (2S)-2-[[(tert-butoxy)carbonyl](methyl)amino]-3-(4-tert-butylphenyl)propanoate Into a 250-mL 3-necked round-bottom flask, was placed N,N-dimethylformamide (150 mL), methyl (2S)-2-[[(tert-butoxy)carbonyl]amino]-3-(4-tert-butylphenyl)propanoate (11.7 g, 34.88 mmol, 1.00 equiv), Ag₂O (16 g, 3.00 equiv), CH₃I (14.7 g, 103.56 mmol, 2.00 equiv). The resulting solution was stirred for 2 h at 60° C. The reaction mixture was cooled. The resulting solution was diluted with 400 mL of ice-water. The resulting solution was extracted with 3×300 mL of ethyl acetate and the organic layers combined. The organic layers were washed with 3×100 mL of brine. The organic layers were dried over anhydrous sodium sulfate and concentrated under vacuum. This resulted in 13.7 g (crude) of methyl (2S)-2-[[(tert-butoxy)carbonyl](methyl)amino]-3-(4-tert-butylphenyl)propanoate as light yellow oil.

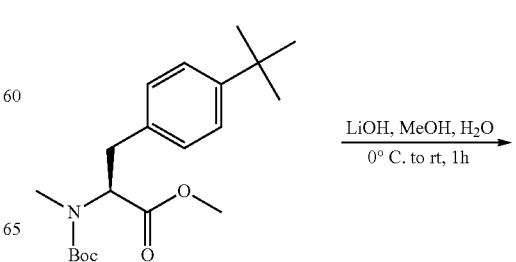

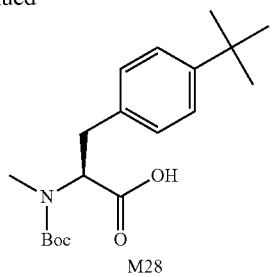

M28

(2S)-2-[[(tert-butoxy)carbonyl](methyl)amino]-3-(4-tert-butylphenyl)propanoic acid (M28)

Into a 500-mL round-bottom flask, was placed methanol (200 mL), methyl (2S)-2-[[(tert-butoxy)carbonyl](methyl)amino]-3-(4-tert-butylphenyl)propanoate (13.7 g, 39.20 mmol, 1.00 equiv). This was followed by the addition of a solution of LiOH (9.4 g, 392.48 mmol, 10.00 equiv) in H₂O (40 mL) dropwise with stirring at 0° C. The resulting solution was stirred for 1 h at room temperature. The resulting mixture was concentrated under vacuum. The pH value of the solution was adjusted to 7 with hydrogen chloride (12 mol/L). The resulting solution was extracted with 3×100 mL of dichloromethane and the organic layers combined and dried over anhydrous sodium sulfate and concentrated under vacuum. This resulted in 10 g (76%) of (2S)-2-[[(tert-butoxy)carbonyl](methyl)amino]-3-(4-tert-butylphenyl)propanoic acid as colorless oil. MS (ES, m/z): 336 (Ms+H); ¹HNMR (300 MHz, CDCl₃): δ 7.33-7.27 (m, 2H), 7.17-7.11 (m, 2H), 4.90-4.63 (m, 1H), 3.35-3.23 (m, 1H), 3.15-2.89 (m, 1H), 2.75 (d, J=22.8 Hz, 3H), 1.47-1.23 (m, 18H).

Preparation Example 18: Preparation of Monomer M29

Monomer M29 was prepared by the process shown in Scheme 18 below.
Scheme 18

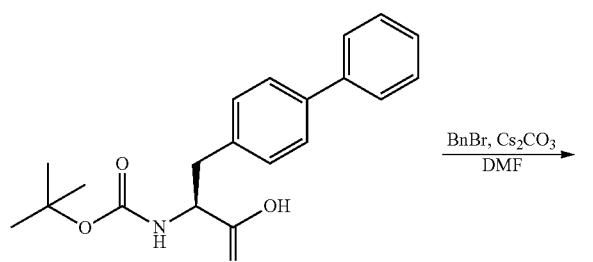

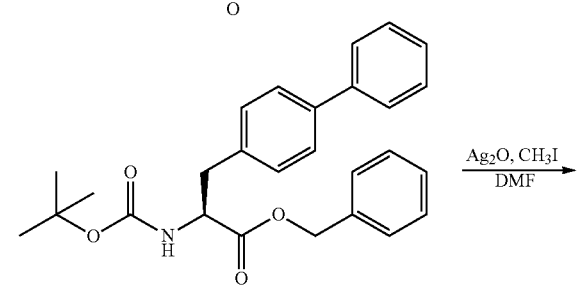

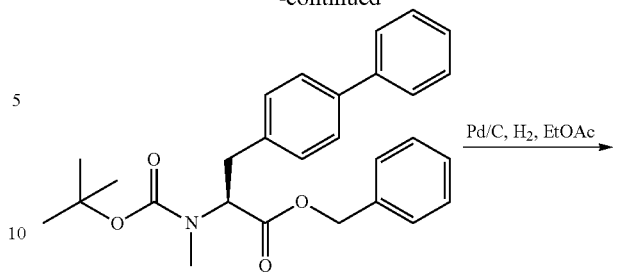

M29

Experimental Details

Benzyl (2S)-2-[[(tert-butoxy)carbonyl]amino]-3-(4-phenylphenyl)propanoate

Into a 100-mL round-bottom flask, was placed N,N-dimethylformamide (20 mL), (2S)-2-[[(tert-butoxy)carbonyl]amino]-3-(4-phenylphenyl)propanoic acid (3 g, 8.79 mmol, 1.00 equiv), Cs₂CO₃ (9 g, 27.62 mmol, 3.14 equiv), BnBr (1.6 g, 9.36 mmol, 1.06 equiv). The resulting solution was stirred for 3 h at room temperature. The solids were filtered out. The resulting solution was extracted with 3×30 mL of ethyl acetate and the organic layers combined and concentrated under vacuum. The residue was applied onto a silica gel column with ethyl acetate/petroleum ether (1:4). This resulted in 4.5 g of benzyl (2S)-2-[[(tert-butoxy)carbonyl]amino]-3-(4-phenylphenyl)propanoate as a white solid. MS (ES, m/z): 432 (M+H); ¹HNMR (300 MHz, CDCl₃): δ 7.59-7.11 (m, 14H), 5.23-5.19 (m, 2H), 5.05-5.04 (m, 0.5H), 4.72-4.65 (m, 0.5H), 3.15-3.14 (m, 2H), 1.44 (s, 9H).

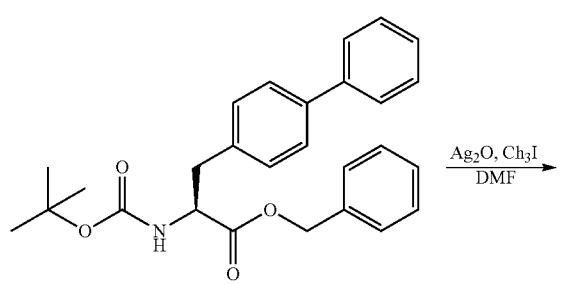

Benzyl (2S)-2-[[(tert-butoxy)carbonyl](methyl)amino]-3-(4-phenylphenyl)propanoate Benzyl (2S)-2-[[(tert-butoxy)carbonyl]amino]-3-(4-phenylphenyl)propanoate (4.5 g, 10.43 mmol, 1.00 equiv), Ag₂O (4.8 g), CH₃I (7.4 g, 52.13 mmol, 5.00 equiv). The resulting solution was stirred for 3 h at 60° C. The solids were filtered out. The resulting solution was extracted with 3×30 mL of ethyl acetate and the organic layers combined and dried over anhydrous sodium sulfate and concentrated under vacuum. The residue was applied onto a silica gel column with ethyl acetate/petroleum ether (1:5). This resulted in 2.4 g (52%) of benzyl (2S)-2-[[(tert-butoxy)carbonyl](methyl)amino]-3-(4-phenylphenyl)propanoate as colorless oil. MS (ES, m/z): 446 (M+H); ¹HNMR (300 MHz, CD₃OD): δ7.59-7.28 (m, 14H), 5.22 (s, 2H), 4.80-4.71 (m, 1H), 3.37-3.11 (m, 2H), 2.71 (s, 3H), 1.48-1.45 (m, 9H)

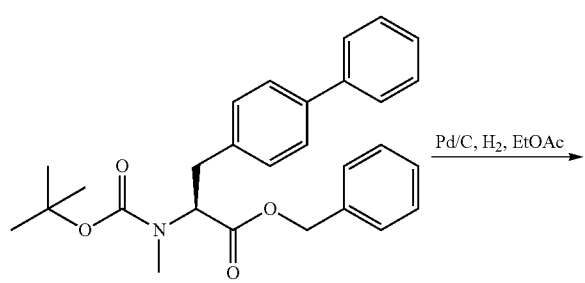

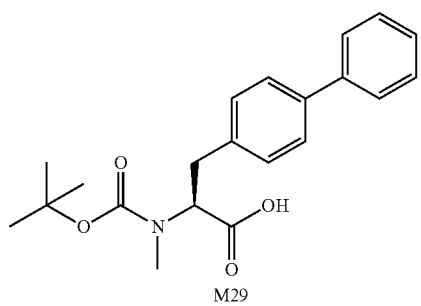

M29

(2S)-2-[[(tert-butoxy)carbonyl](methyl)amino]-3-(4-phenylphenyl)propanoic acid (M29)

Into a 100-mL round-bottom flask, was placed ethyl acetate (10 mL), benzyl (2S)-2-[[(tert-butoxy)carbonyl](methyl)amino]-3-(4-phenylphenyl)propanoate (2.4 g, 5.39 mmol, 1.00 equiv), Palladium on carbon (0.4 g), hydrogen (enough g). The resulting solution was stirred for 1 h at room temperature. The solids were filtered out. The filtrate was concentrated under vacuum. This resulted in 1.4 g (73%) of (2S)-2-[[(tert-butoxy)carbonyl](methyl)amino]-3-(4-phenylphenyl)propanoic acid as colorless oil.

Preparation Example 19: Preparation of Monomer M30

Monomer M30 was prepared by the process shown in Scheme 19 below.

Scheme 19

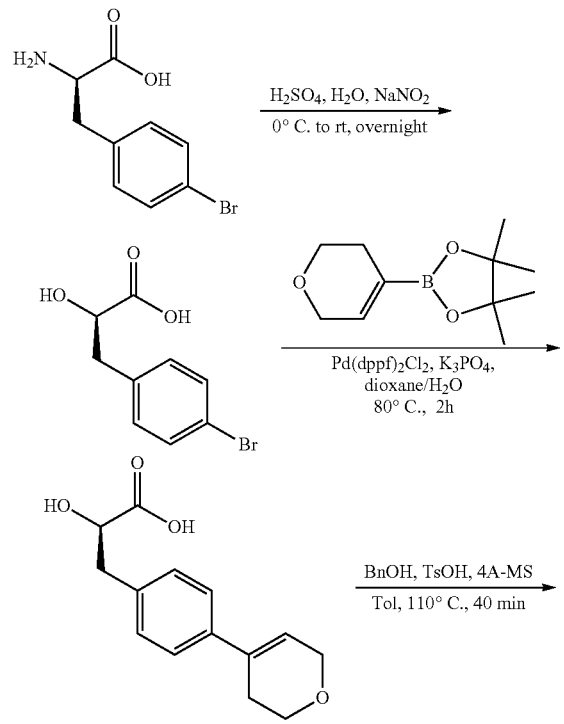

-continued

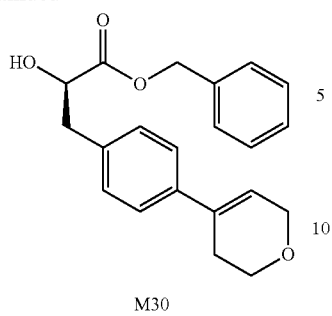

M30

Experimental Details

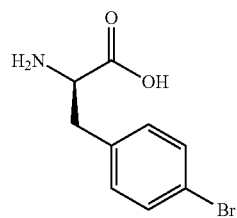

(2R)-3-(4-bromophenyl)-2-hydroxypropanoic acid

Into a 5-L 4-necked round-bottom flask, was placed sulfuric acid/H₂O (0.5 mol/L)(3.2 L), (2R)2-amino-3-(4-bromophenyl)propanoic acid (100 g, 409.69 mmol, 1.00 equiv). This was followed by the addition of a solution of NaNO₂ (350 g, 5.07 mol, 12.38 equiv) in H₂O (500 mL) dropwise with stirring at 0° C. The resulting solution was stirred overnight at room temperature. The solids were collected by filtration. The solid was dried in an oven under reduced pressure. This resulted in 146 g (73%) of (2R)3-(4-bromophenyl)-2-hydroxypropanoic acid as a white solid. MS (ES, m/z): 243 (M–H).

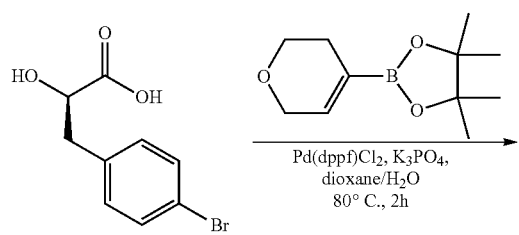

-continued

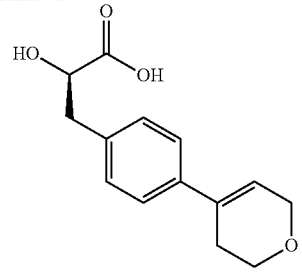

(2R)-3-[4-(3,6-dihydro-2H-pyran-4-yl)phenyl]-2-hydroxypropanoic acid

Into a 1-L round-bottom flask purged and maintained with an inert atmosphere of nitrogen, was placed dioxane (500 mL), H₂O (50 mL), (2R)-3-(4-bromophenyl)-2-hydroxypropanoic acid (30 g, 122.41 mmol, 1.00 equiv), 2-(3,6-dihydro-2H-pyran-4-yl)-4,4,5,5-tetramethyl-1,3,2-dioxaborolane (40 g, 190.41 mmol, 1.60 equiv), K₃PO₄ (65 g, 306.21 mmol, 2.50 equiv), Pd(dppf)Cl₂ (4.5 g, 6.15 mmol, 0.05 equiv). The resulting solution was stirred for 2 h at 75° C. in an oil bath. The reaction mixture was cooled. The resulting mixture was concentrated under vacuum. The residue was dissolved in 100 mL of ether. The solids were filtered out. The solids were dissolved in 10 mL of H₂O and 500 mL of THF. The pH value of the solution was adjusted to 4-5 with hydrogen chloride (12 mol/L). The solids were filtered out. The filtrate was dried over anhydrous sodium sulfate and concentrated under vacuum. This resulted in 28 g (92%) of (2R)-3-[4-(3,6-dihydro-2H-pyran-4-yl)phenyl]-2-hydroxypropanoic acid as a light brown solid. MS (ES, m/z): 249 (M+H).

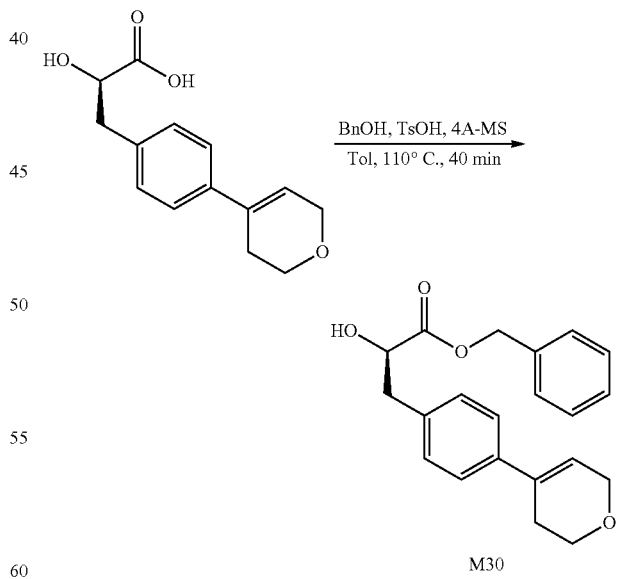

Benzyl (2R)-3-[4-(3,6-dihydro-2H-pyran-4-yl)phenyl]-2-hydroxypropanoate (M30)

Into a 500-mL round-bottom flask, was placed toluene (300 mL), (2R)3-[4-(3,6-dihydro-2H-pyran-4-yl)phenyl]-2- hydroxypropanoic acid (9 g, 36.25 mmol, 1.00 equiv), phenylmethanol (10.3 g, 95.25 mmol, 2.50 equiv), TsOH (2 g, 11.61 mmol, 0.30 equiv), 4A-MS (5.4 g). The resulting solution was stirred for 40 min at 110° C. in an oil bath. The reaction mixture was cooled. The solids were filtered out. The filtrate was concentrated under vacuum. The residue was applied onto a silica gel column with ethyl acetate/petroleum ether (1:10-1:3). This resulted in 24 g (98%) of benzyl (2R)-3-[4-(3,6-dihydro-2H-pyran-4-yl)phenyl]-2-hydroxypropanoate as a white solid. MS (ES, m/z): 339 (M+H); $^1$HNMR (300 MHz, CDCl$_3$): δ 7.62-7.30 (m, 7H), 7.13 (d, J=8.4 Hz, 2H), 6.12-6.10 (m, 1H), 5.24 (s, 2H), 4.52-4.48 (m, 1H), 4.35-4.32 (m, 2H), 3.96-3.92 (m, 2H), 3.16-2.95 (m, 2H), 2.67-2.49 (m, 2H).

Preparation Example 20: Preparation of Monomer M33

Monomer M33 was prepared by the process shown in Scheme 20 below.

Scheme 20

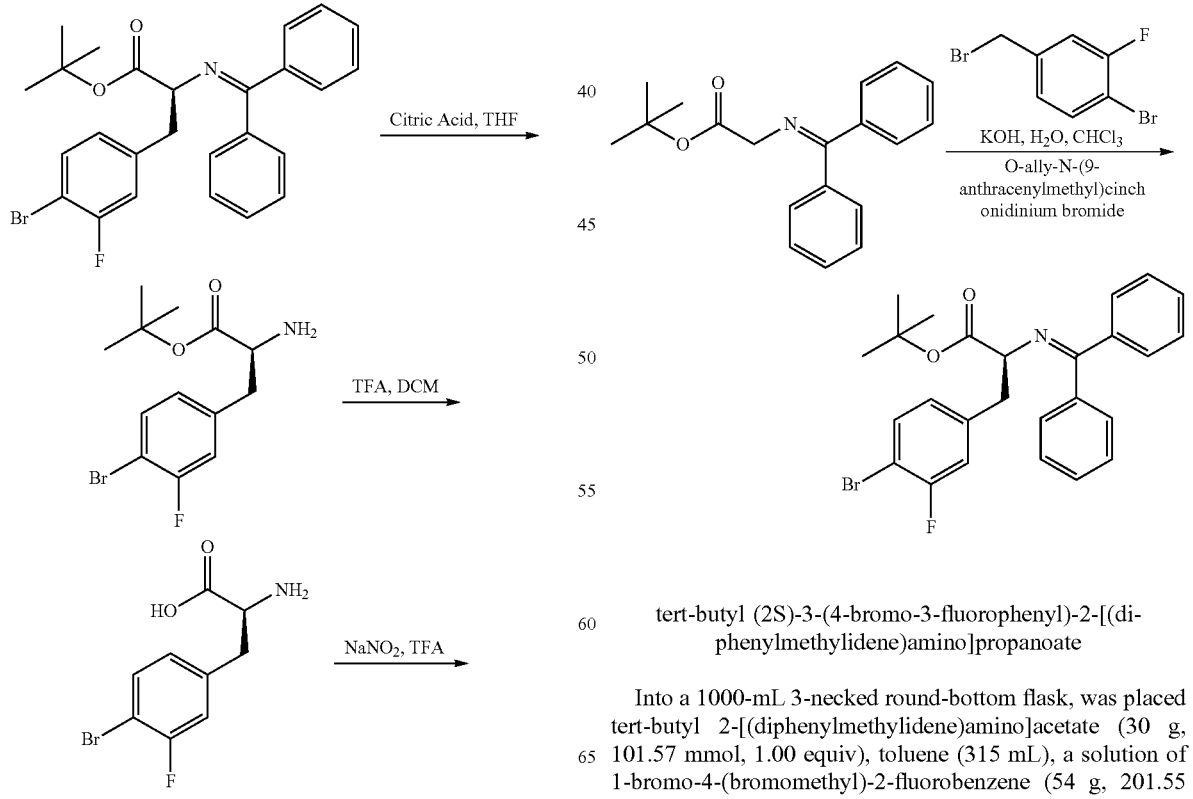

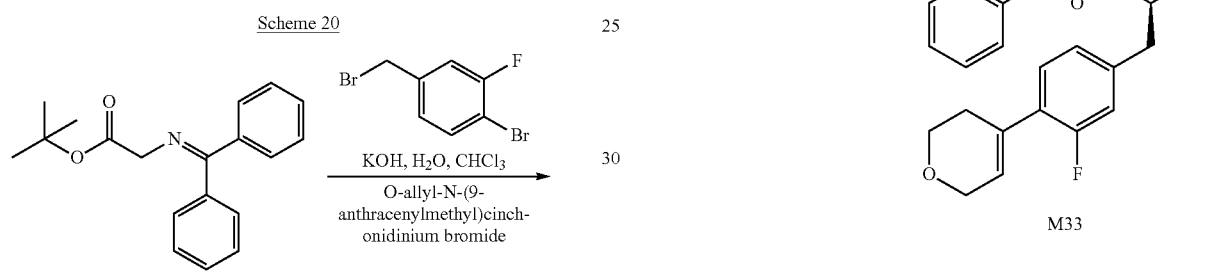

Experimental Details tert-butyl (2S)-3-(4-bromo-3-fluorophenyl)-2-[(diphenylmethylidene)amino]propanoate Into a 1000-mL 3-necked round-bottom flask, was placed tert-butyl 2-[(diphenylmethylidene)amino]acetate (30 g, 101.57 mmol, 1.00 equiv), toluene (315 mL), a solution of 1-bromo-4-(bromomethyl)-2-fluorobenzene (54 g, 201.55 mmol, 1.98 equiv) in chloroform (135 mL), O-allyl-N-(9- anthracenylmethyl)cinchonidinium bromide (1.1 g, 2.09 mmol, 0.02 equiv), potassium hydroxide (56 g, 998.04 mmol, 9.83 equiv). The resulting solution was stirred for 3 days at −20° C. The resulting solution was diluted with 1000 mL of EA. The resulting mixture was washed with 3×1000 mL of H₂O. The organic layer was dried over sodium sulfate. The solids were filtered out. The filtrate was concentrated under vacuum. The residue was applied onto a C18 reversed phase column with H₂O/ACN (1/9). This resulted in 28 g (57%) of tert-butyl (2S)-3-(4-bromo-3-fluorophenyl)-2-[(diphenylmethylidene)amino]propanoate as light yellow oil. MS (ES, m/z): 482 (M+H).

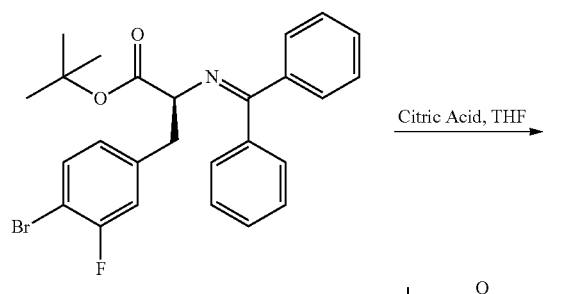

tert-butyl (2S)-2-amino-3-(4-bromo-3-fluorophenyl) propanoate

Into a 2-L 3-necked round-bottom flask, was placed tert-butyl (2S)-3-(4-bromo-3-fluorophenyl)-2-[(diphenylmethylidene)amino]propanoate (28 g, 58.04 mmol, 1.00 equiv), tetrahydrofuran (580 mL), citric acid (580 mL). The resulting solution was stirred for 4 h at room temperature. The resulting mixture was concentrated under vacuum. The resulting solution was diluted with 1000 mL of water. The resulting solution was extracted with 3×200 mL of ether and the aqueous layers combined. The pH value of the aqueous layer was adjusted to 8 with sodium bicarbonate and extracted with 3×300 mL of ethyl acetate. The organic layers combined and dried over sodium sulfate and concentrated under vacuum. This resulted in 14.8 g (80%) of tert-butyl (2S)-2-amino-3-(4-bromo-3-fluorophenyl)propanoate as light yellow oil. MS (ES, m/z): 318 (M+H).

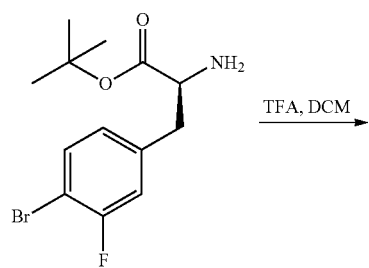

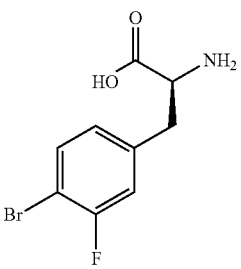

(2S)-2-amino-3-(4-bromo-3-fluorophenyl)propanoic acid

Into a 500-mL round-bottom flask, was placed tert-butyl (2S)-2-amino-3-(4-bromo-3-fluorophenyl)propanoate (5.9 g, 18.54 mmol, 1.00 equiv), dichloromethane (200 mL), trifluoroacetic acid (21 g, 185.77 mmol, 10.02 equiv). The resulting solution was stirred for 3 days at room temperature. The resulting mixture was concentrated under vacuum. The residue was applied onto a C18 reversed phase column with H₂O/ACN (1/3). This resulted in 5.4 g (crude) of (2S)-2-amino-3-(4-bromo-3-fluorophenyl)propanoic acid as a white solid. MS (ES, m/z): 262 (M+H).

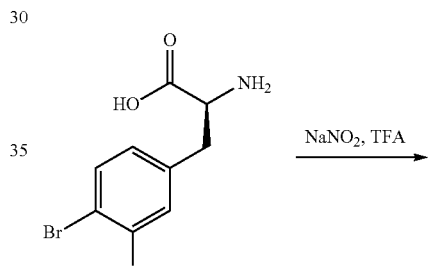

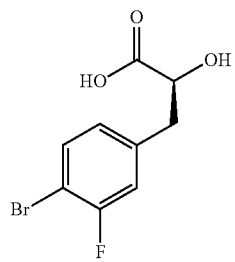

(2S)-3-(4-bromo-3-fluorophenyl)-2-hydroxypropanoic acid

Into a 500-mL 3-necked round-bottom flask, was placed (2S)-2-amino-3-(4-bromo-3-fluorophenyl)propanoic acid (5.4 g, 20.60 mmol, 1.00 equiv), trifluoroacetic acid (28.3 g, 250.35 mmol, 12.15 equiv), water (180 mL), to the above was added a solution of NaNO₂ (17.1 g, 247.83 mmol, 12.03 equiv) in water (180 mL) slowly. The resulting solution was stirred for 16 h at room temperature. The solids were collected by filtration. This resulted in 3.1 g (57%) of (2S)-3-(4-bromo-3-fluorophenyl)-2-hydroxypropanoic acid as a light yellow solid.

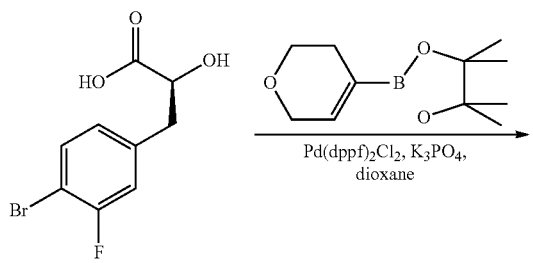

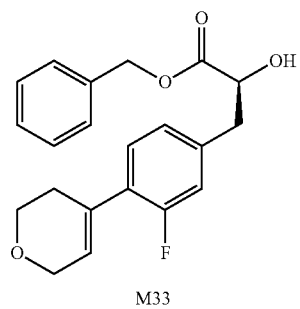

Benzyl(2S)-3-[4-(3,6-dihydro-2H-pyran-4-yl)-3-fluorophenyl]-2-hydroxypropanoate (M33)

Into a 100-mL round-bottom flask, was placed (2S)-3-[4-(3,6-dihydro-2H-pyran-4-yl)-3-fluorophenyl]-2-hydroxypropanoic acid (1 g, 3.76 mmol, 1.00 equiv), BnOH (1.1 g), TsOH (160 mg, 0.93 mmol, 0.25 equiv), 4A-Ms (1 g), toluene (20 mL). The resulting solution was stirred for 4 h at 110° C. The resulting mixture was concentrated under vacuum. The residue was applied onto a silica gel column with ethyl acetate/petroleum ether (1/4). This resulted in 350 mg (26%) of benzyl (2S)-3-[4-(3,6-dihydro-2H-pyran-4-yl)-3-fluorophenyl]-2-hydroxypropanoate as brown oil. ¹HNMR (300 MHz, CD₃OD): δ 7.37-7.29 (m, 5H), 7.20-7.15 (m, 1H), 6.97-6.92 (m, 2H), 6.02 (br, 1H), 5.19 (s, 2H), 4.44-4.40 (m, 1H), 4.30-4.27 (m, 2H), 3.92-3.885 (m, 2H), 3.33-2.90 (m, 2H), 2.47-2.46 (m, 2H).

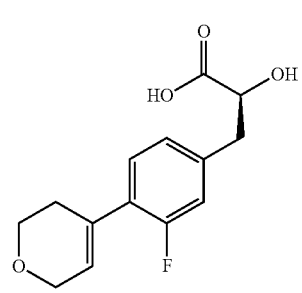

(2S)-3-[4-(3,6-dihydro-2H-pyran-4-yl)-3-fluorophenyl]-2-hydroxypropanoic acid

Into a 500-mL 3-necked round-bottom flask purged and maintained with an inert atmosphere of nitrogen, was placed (2S)-3-(4-bromo-3-fluorophenyl)-2-hydroxypropanoic acid (3 g, 11.40 mmol, 1.00 equiv), 2-(3,6-dihydro-2H-pyran-4-yl)-4,4,5,5-tetramethyl-1,3,2-dioxaborolane (4.8 g, 22.85 mmol, 2.00 equiv), K₃PO₄ (7.28 g, 34.30 mmol, 3.01 equiv), dioxane (180 mL), water (18 mL), Pd(dppf)Cl₂ (1.67 g, 2.28 mmol, 0.20 equiv). The resulting solution was stirred for 5 h at 80° C. The resulting mixture was concentrated under vacuum. The resulting mixture was diluted with 900 mL of ether. The solids were collected by filtration. The solids were dissolved in 200 mL of tetrahydrofuran. The pH value of the solution was adjusted to 3-4 with hydrogen chloride. The solid was filtered out. The filtrate was concentrated under vacuum. The residue was applied onto a silica gel column with ethyl acetate/petroleum ether (1/10). This resulted in 2.63 g (87%) of (2S)-3-[4-(3,6-dihydro-2H-pyran-4-yl)-3-fluorophenyl]-2-hydroxypropanoic acid as brown solid. MS (ES, m/z): 265 (M−H).

Preparation Example 21: Preparation of Monomer M34

Monomer M34 was prepared by the process shown in Scheme 21 below.

Scheme 21

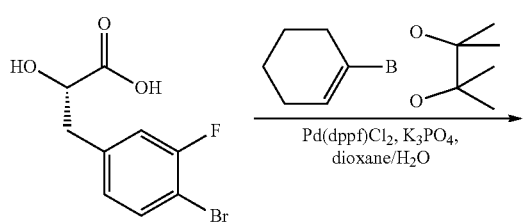

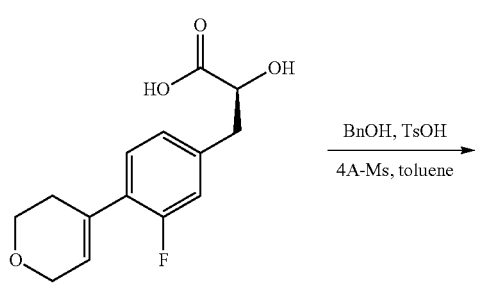

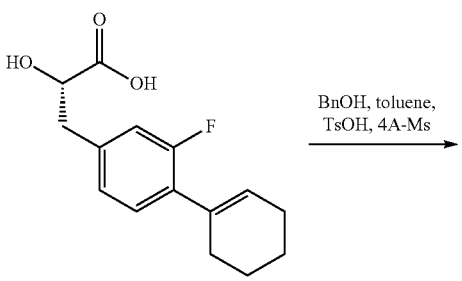

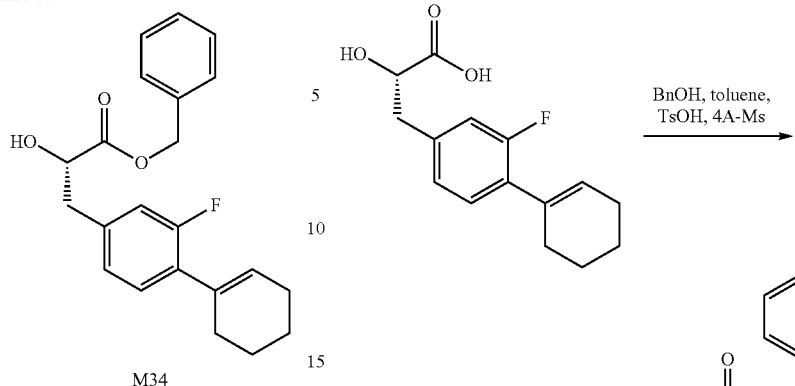

Experimental Details

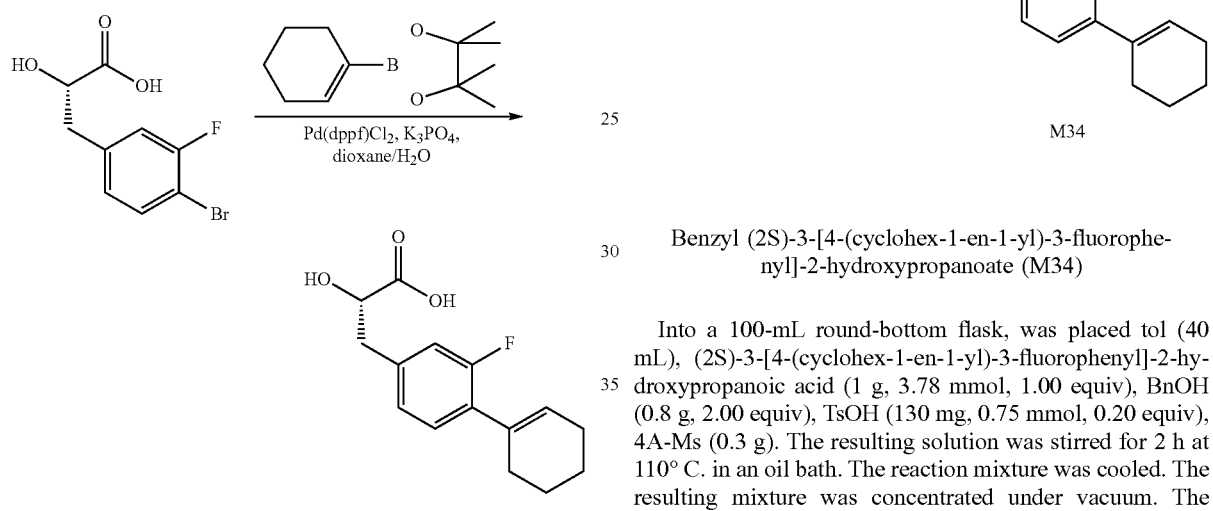

(2S)-3-[4-(cyclohex-1-en-1-yl)-3-fluorophenyl]-2-hydroxypropanoic acid

Into a 50-mL round-bottom flask purged and maintained with an inert atmosphere of nitrogen, was placed dioxane/H₂O (20/2 mL), (2S)-3-(4-bromo-3-fluorophenyl)-2-hydroxypropanoic acid (830 mg, 3.16 mmol, 1.00 equiv), 2-(cyclohex-1-en-1-yl)-4,4,5,5-tetramethyl-1,3,2-dioxaborolane (790 mg, 3.80 mmol, 1.20 equiv), Pd(dppf)Cl₂ (115 mg, 0.16 mmol, 0.05 equiv), K₃PO₄ (2 g, 9.42 mmol, 3.00 equiv). The resulting solution was stirred for 1 h at 80° C. in an oil bath. The reaction mixture was cooled. The resulting mixture was concentrated under vacuum. The residue was dissolved in 20 mL of ether. The solids were filtered out. The filtrate was concentrated under vacuum. The residue was dissolved in 20 mL of THF. The pH value of the solution was adjusted to 4 with hydrogen chloride (12 mol/L). The solids were filtered out. The filtrate was dried over anhydrous sodium sulfate and concentrated under vacuum. This resulted in 1 g of (2S)-3-[4-(cyclohex-1-en-1-yl)-3-fluorophenyl]-2-hydroxypropanoic acid as a brown solid. MS (ES, m/z): 263 (M−H).

Benzyl (2S)-3-[4-(cyclohex-1-en-1-yl)-3-fluorophenyl]-2-hydroxypropanoate (M34)

Into a 100-mL round-bottom flask, was placed tol (40 mL), (2S)-3-[4-(cyclohex-1-en-1-yl)-3-fluorophenyl]-2-hydroxypropanoic acid (1 g, 3.78 mmol, 1.00 equiv), BnOH (0.8 g, 2.00 equiv), TsOH (130 mg, 0.75 mmol, 0.20 equiv), 4A-Ms (0.3 g). The resulting solution was stirred for 2 h at 110° C. in an oil bath. The reaction mixture was cooled. The resulting mixture was concentrated under vacuum. The residue was applied onto a silica gel column with ethyl acetate/petroleum ether (1:20-1:10). This resulted in 730 g (crude) of benzyl (2S)-3-[4-(cyclohex-1-en-1-yl)-3-fluorophenyl]-2-hydroxypropanoate as colorless oil. MS (ES, m/z): 355 (M+H); ¹HNMR (300 MHz, CDCl₃): δ 7.41-7.33 (m, 5H), 7.14-7.08 (m, 1H), 6.88-6.83 (m, 2H), 5.92 (m, 1H), 5.25 (s, 2H), 4.45-4.47 (m, 1H), 3.13-2.91 (m, 2H), 2.35 (br, 2H), 2.22 (br, 2H), 1.87-1.58 (m, 4H).

Preparation Example 22: Preparation of Monomer M35

Monomer M35 was prepared by the process shown in Scheme 22 below.

Scheme 22

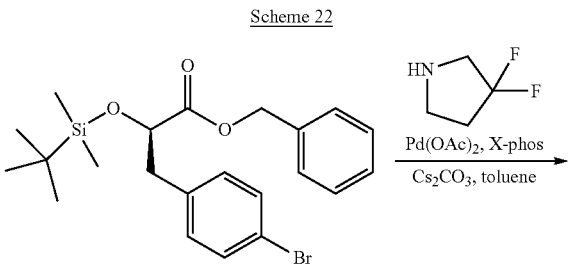

217
-continued

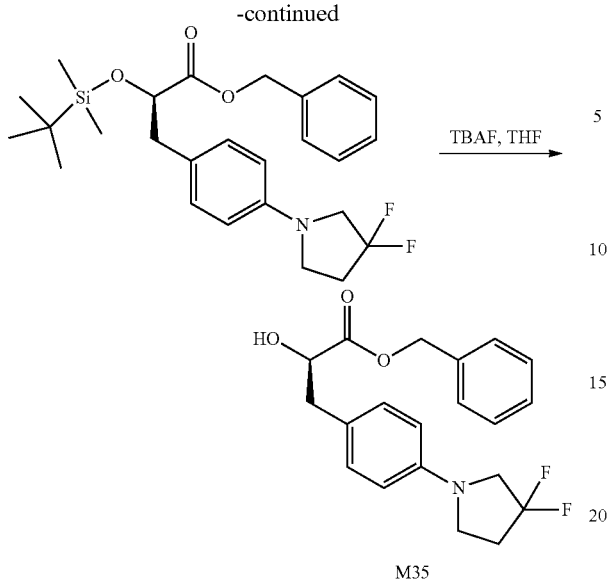

M35

Experimental Details

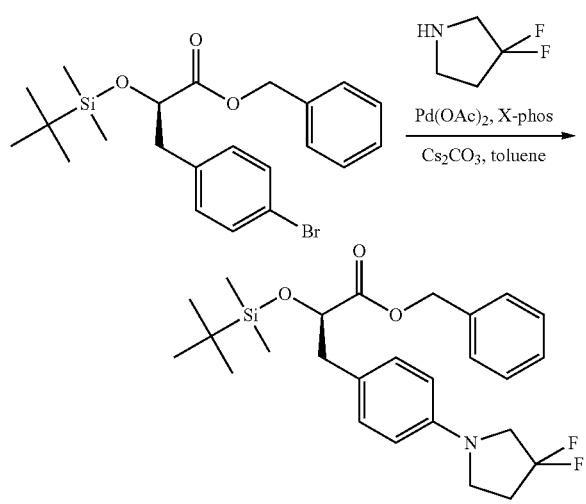

Benzyl (2R)-2-[(tert-butyldimethylsilyl)oxy]-3-[4-(3,3-difluoropyrrolidin-1-yl)phenyl]propanoate Into a 250-mL round-bottom flask purged and maintained with an inert atmosphere of nitrogen, was placed benzyl (2R)-3-(4-bromophenyl)-2-[(tert-butyldimethylsilyl)oxy]propanoate (5 g, 11.12 mmol, 1.00 equiv), toluene (100 mL), 3,3-difluoropyrrolidine hydrochloride (4.7 g, 32.74 mmol, 3.00 equiv), X-Phos (2.1 g, 0.40 equiv), Pd(OAc)$_2$ (500 mg, 2.23 mmol, 0.20 equiv), Cs$_2$CO$_3$ (14.3 g, 43.89 mmol, 4.00 equiv). The resulting solution was stirred overnight at 90° C. The solids were filtered out. The resulting mixture was concentrated under vacuum. The residue was applied onto a silica gel column with ethyl acetate/petroleum ether (1:30). This resulted in 4.2 g (79%) of benzyl (2R)-2-[(tert-butyldimethylsilyl)oxy]-3-[4-(3,3-difluoropyrrolidin-1-yl)phenyl]propanoate as yellow oil. MS (ES, m/z): 476 (M+H); $^1$H NMR (CDCl$_3$, 300 MHz) δ: 7.37-7.30 (m, 5H), 7.10 (d, J=4.4 Hz, 2H), 6.50 (d, J=4.2 Hz, 2H), 5.20-5.10 (m, 2H), 218
4.38-4.33 (m, 1H), 3.66 (t, J=13.2 Hz, 2H), 3.51 (t, J=6.9 Hz, 2H), 3.04-2.98 (m, 1H), 2.90-2.83 (m, 1H), 2.58-2.46 (m, 2H), 0.79 (s, 9H), −0.10 (s, 3H), −0.15 (s, 3H).

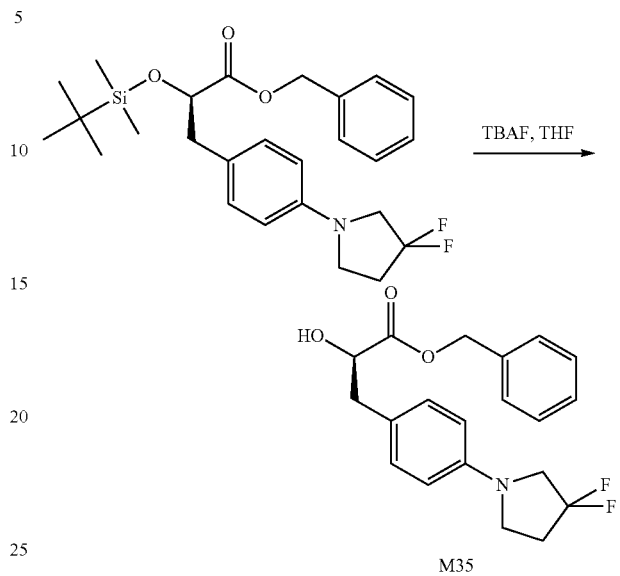

M35

Benzyl (2R)-3-[4-(3,3-difluoropyrrolidin-1-yl)phenyl]-2-hydroxypropanoate (M35)

Into a 250-mL 3-necked round-bottom flask, was placed benzyl (2R)-2-[(tert-butyldimethylsilyl)oxy]-3-[4-(3,3-difluoropyrrolidin-1-yl)phenyl]propanoate (4.2 g, 8.83 mmol, 1.00 equiv), tetrahydrofuran (80 mL). This was followed by the addition of TBAF (4.6 g, 17.59 mmol, 2.00 equiv) dropwise with stirring at 0° C. The resulting solution was stirred for 30 min at room temperature. The reaction was then quenched by the addition of 100 mL of water/ice. The resulting solution was extracted with 3×100 mL of ethyl acetate and the organic layers combined. The organic phase was washed with 3×50 mL of brine. The organic phase was dried over anhydrous sodium sulfate and concentrated under vacuum. The residue was applied onto a silica gel column with ethyl acetate/petroleum ether (1:15). This resulted in 2.5 g (78%) of benzyl (2R)-3-[4-(3,3-difluoropyrrolidin-1-yl)phenyl]-2-hydroxypropanoate as yellow oil. MS (ES, m/z): 362 (M+H); $^1$H NMR (DMSO, 300 MHz) δ: 7.38-7.24 (m, 5H), 7.04 (d, J=4.0 Hz, 2H), 6.51 (d, J=4.4 Hz, 2H), 5.54-5.52 (m, 1H), 5.08 (s, 2H), 4.25-4.19 (m, 1H), 3.64 (t, J=13.5 Hz, 2H), 3.42 (t, J=6.9 Hz, 2H), 2.90-2.74 (m, 2H), 2.58-2.44 (m, 2H).

Preparation Example 23: Preparation of Monomer M45

Monomer M45 was prepared by the process shown in Scheme 23 below.

Scheme 23

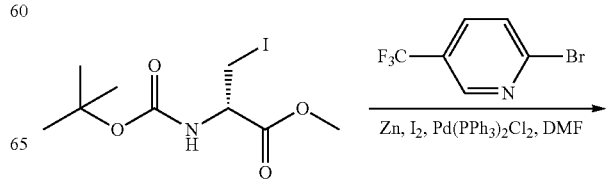

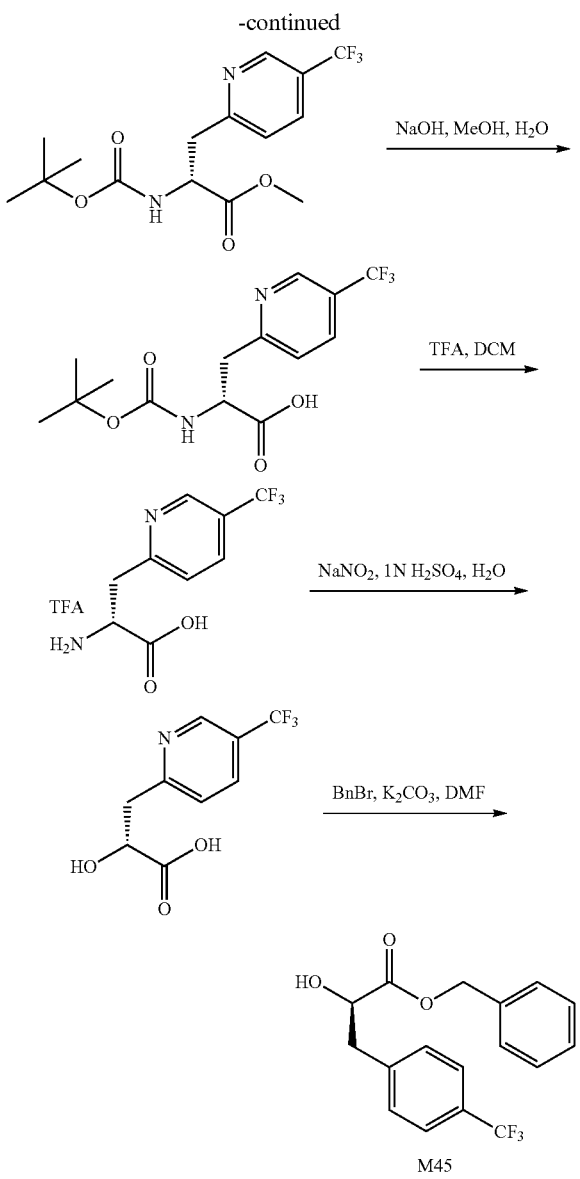

Experimental Details

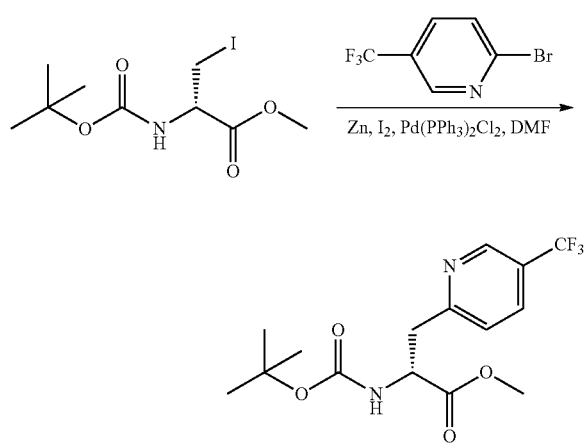 [SMILES: COC(=O)[C@@H](CI)NC(=O)OC(C)(C)C ; FC(F)(F)c1ccc(Br)nc1 ; COC(=O)[C@@H](Cc1ccc(C(F)(F)F)cn1)NC(=O)OC(C)(C)C]

Methyl (2R)-2-[[(tert-butoxy)carbonyl]amino]-3-[5-(trifluoromethyl)pyridin-2-yl]propanoate Into a 500-mL 3-necked round-bottom flask purged and maintained with an inert atmosphere of nitrogen, was placed Zn (1.35 g), N,N-dimethylformamide (100 mL). This was followed by the addition of $I_2$ (188.1 mg) in several batches at 50° C. in 10 min. To this was added methyl (2S)-2-[[(tert-butoxy)carbonyl]amino]-3-iodopropanoate (6 g, 18.23 mmol, 1.00 equiv) in several batches at 0° C. in 30 min. To the mixture was added 2-bromo-5-(trifluoromethyl)pyridine (3.3 g, 14.60 mmol, 0.80 equiv) in several batches at 0° C. To the mixture was added $Pd(PPh_3)_2Cl_2$ (1.04 g, 1.48 mmol, 0.08 equiv) in several batches at 0° C. The resulting solution was stirred for 5 h at 50° C. The reaction mixture was cooled. The solids were filtered out. The resulting solution was diluted with 50 mL of $H_2O$. The resulting solution was extracted with 3×100 mL of ethyl acetate and the organic layers combined. The organic phase was washed with 6×100 mL of brine. The organic phase was dried over anhydrous sodium sulfate and concentrated under vacuum. The residue was applied onto a silica gel column with ethyl acetate/petroleum ether (1:4). The collected fractions were combined and concentrated under vacuum. This resulted in 5 g (79%) of methyl (2R)-2-[[(tert-butoxy)carbonyl]amino]-3-[5-(trifluoromethyl)pyridin-2-yl]propanoate as yellow oil. MS (ES, m/z): 349 (M+H); $^1$H NMR (CDCl$_3$, 300 MHz) δ: 8.80 (s, 1H), 7.89-7.86 (m, 1H), 7.32 (d, J=4.5 Hz, 1H), 5.80-5.60 (m, 1H), 4.77-4.75 (m, 1H), 3.73 (s, 3H), 3.42-3.41 (m, 2H), 1.43 (s, 9H).

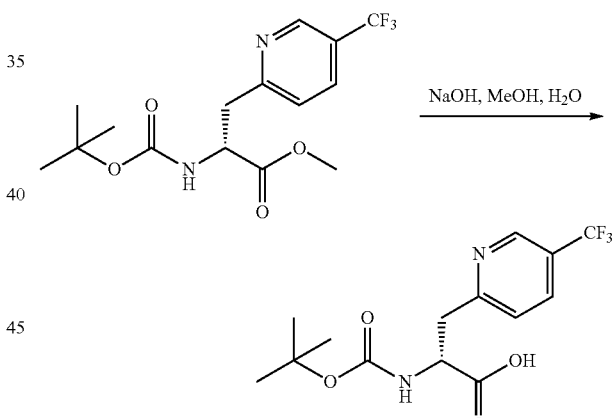

(2R)-2-[[(tert-butoxy)carbonyl]amino]-3-[5-(trifluoromethyl)pyridin-2-yl]propanoic acid Into a 250-mL round-bottom flask, was placed methyl (2R)-2-[[(tert-butoxy)carbonyl]amino]-3-[5-(trifluoromethyl)pyridin-2-yl]propanoate (5 g, 14.35 mmol, 1.00 equiv), methanol (60 mL), to the above was added a solution of sodium hydroxide (1.7 g, 42.50 mmol, 2.96 equiv) in water (15 mL). The resulting solution was stirred for 12 h at 25° C. The resulting mixture was concentrated under vacuum. The resulting solution was diluted with 10 mL of $H_2O$. The pH value of the solution was adjusted to 6 with sulfuric acid (1 mol/L). The resulting solution was extracted with 3×50 mL of ethyl acetate and the organic layers combined. The organic phase was washed with 3×100 mL of brine. The organic phase was dried over anhydrous sodium sulfate and concentrated under vacuum. This resulted in 4.2 g (88%) of (2R)-2-[[(tert-butoxy)carbonyl]amino]-3-[5-(trifluoromethyl)pyridin-2-yl]propanoic acid as yellow oil. MS (ES, m/z): 335 (M+H).

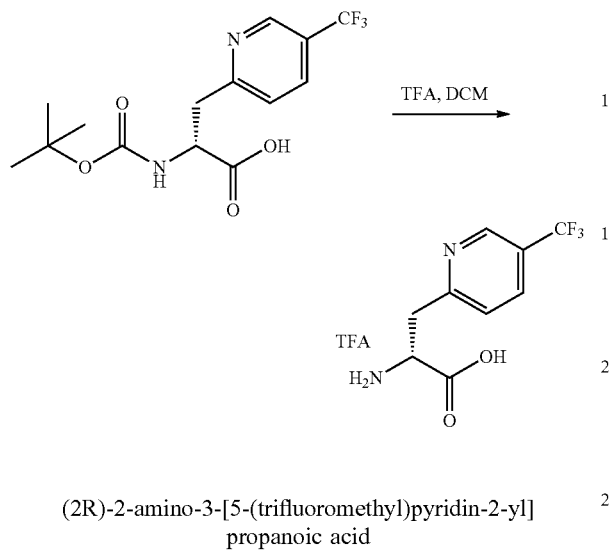

(2R)-2-amino-3-[5-(trifluoromethyl)pyridin-2-yl]propanoic acid

Into a 100-mL round-bottom flask, was placed (2R)-2-[[(tert-butoxy)carbonyl]amino]-3-[5-(trifluoromethyl)pyridin-2-yl]propanoic acid (3 g, 8.97 mmol, 1.00 equiv), dichloromethane (30 mL), trifluoroacetic acid (6 mL). The resulting solution was stirred for 2 h at 25° C. The resulting mixture was concentrated under vacuum. This resulted in 4 g (crude) of (2R)-2-amino-3-[5-(trifluoromethyl)pyridin-2-yl]propanoic acid; trifluoroacetic acid as brown oil. MS: (ES, m/z): 235 (M+H); $^1$H NMR (DMSO, 300 MHz) δ: 8.89 (s, 1H), 8.22-8.21 (br s 3H), 8.19-8.18 (m, 1H), 7.65-7.54 (m, 1H), 4.46 (br s, 1H), 3.50-3.35 (m, 2H).

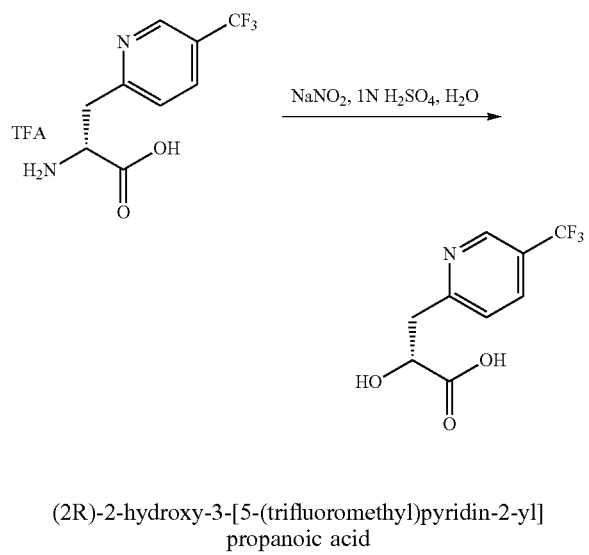

(2R)-2-hydroxy-3-[5-(trifluoromethyl)pyridin-2-yl]propanoic acid

Into a 250-mL round-bottom flask, was placed water (76 mL). This was followed by the addition of sulfuric acid (7.5 g, 76.47 mmol, 6.34 equiv) dropwise with stirring at 0° C. To this was added (2R)-2-amino-3-[5-(trifluoromethyl)pyridin-2-yl]propanoic acid; trifluoroacetic acid (4.2 g, 12.06 mmol, 1.00 equiv), NaNO$_2$ (1.75 g, 25.36 mmol, 2.10 equiv). The resulting solution was stirred for 12 h at 25° C. The resulting solution was extracted with 5×100 mL of ethyl acetate and the organic layers combined. The organic phase was washed with 3×100 mL of brine. The organic phase was dried over anhydrous sodium sulfate and concentrated under vacuum. This resulted in 2.5 g (88%) of (2R)-2-hydroxy-3-[5-(trifluoromethyl)pyridin-2-yl]propanoic acid as yellow oil. MS (ES, m/z): 236 (M+H).

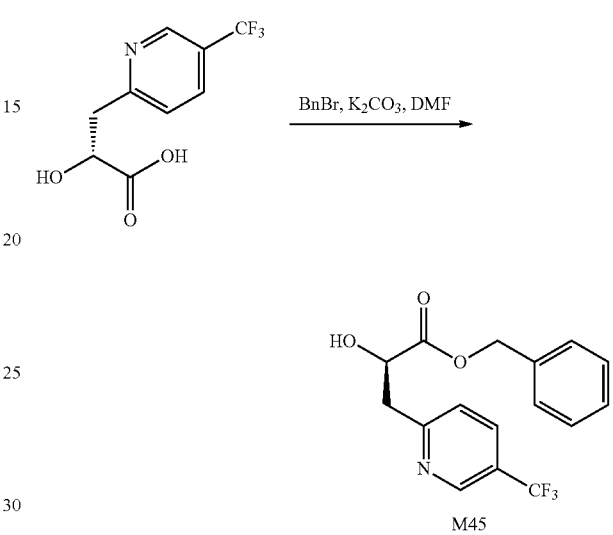

Benzyl-(2R)-2-hydroxy-3-[5-(trifluoromethyl)pyridin-2-yl]propanoate (M45)

Into a 250-mL round-bottom flask, was placed (2R)-2-hydroxy-3-[5-(trifluoromethyl)pyridin-2-yl]propanoic acid (2 g, 8.50 mmol, 1.00 equiv), N,N-dimethylformamide (100 mL), Cs$_2$CO$_3$ (13.87 g, 42.57 mmol, 5.01 equiv). This was followed by the addition of (bromomethyl)benzene (2.89 g, 16.90 mmol, 1.99 equiv) dropwise at 0° C. in 10 min. The resulting solution was stirred for 12 h at 25° C. The solids were filtered out. The resulting solution was diluted with 100 mL of H$_2$O. The resulting solution was extracted with 3×100 mL of ethyl acetate and the organic layers combined. The resulting mixture was washed with 6×100 mL of brine. The mixture was dried over anhydrous sodium sulfate and concentrated under vacuum. The residue was applied onto a silica gel column with ethyl acetate/petroleum ether (1:4). The collected fractions were combined and concentrated under vacuum. This resulted in 1.9 g (69%) of benzyl (2R)-2-hydroxy-3-[5-(trifluoromethyl)pyridin-2-yl]propanoate as light yellow oil. MS (ES, m/z): 326 (M+H); $^1$H NMR (DMSO, 300 MHz) δ: 8.85 (d, J=5.3 Hz, 1H), 8.10-8.07 (m, 1H), 7.54-7.50 (m, 1H), 7.38-7.29 (m, 5H), 5.74-5.65 (m, 1H), 5.12 (s, 2H), 4.61-4.54 (m, 1H), 3.25-3.11 (m, 2H).

Preparation Example 24: Preparation of Monomer M46

Monomer M46 was prepared by the process shown in Scheme 24 below.

Scheme 24

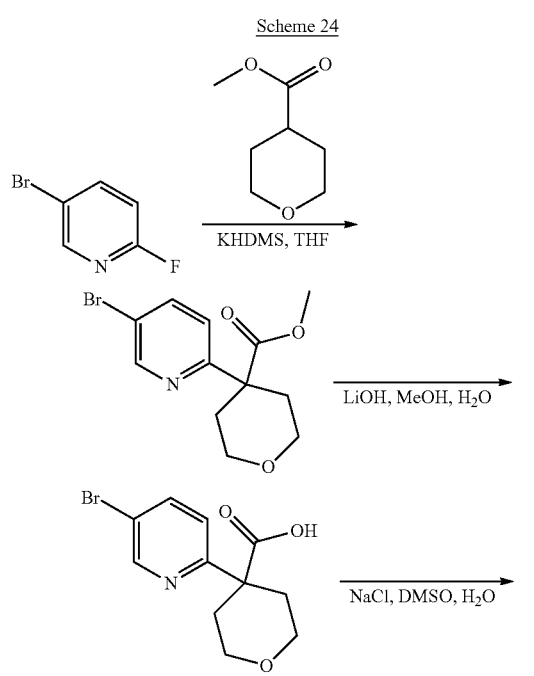

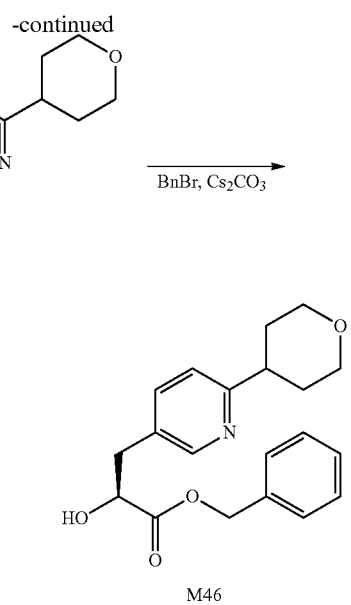

M46

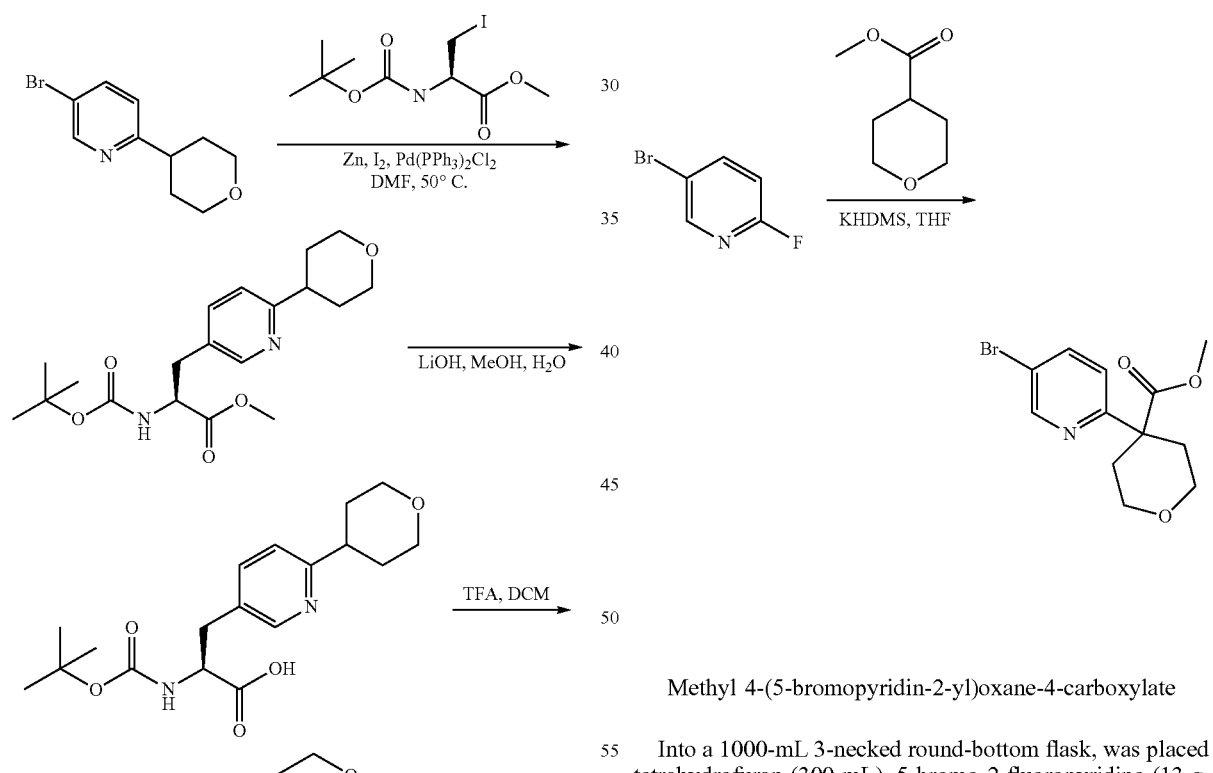

Experimental Details

Methyl 4-(5-bromopyridin-2-yl)oxane-4-carboxylate

Into a 1000-mL 3-necked round-bottom flask, was placed tetrahydrofuran (300 mL), 5-bromo-2-fluoropyridine (13 g, 73.87 mmol, 1.00 equiv), methyl oxane-4-carboxylate (17 g, 117.92 mmol, 1.60 equiv). This was followed by the addition of KHMDS (300 mL) dropwise with stirring at −30° C. The resulting solution was stirred for 3 h at room temperature. The reaction was then quenched by the addition of 100 mL of NH₄Cl. The resulting solution was extracted with 3×120 mL of ethyl acetate and the organic layers combined and dried over anhydrous sodium sulfate and concentrated under vacuum. This resulted in 22 g (99%) of methyl 4-(5-bromopyridin-2-yl)oxane-4-carboxylate as a solid. MS (ES, m/z): 301 (M+H).

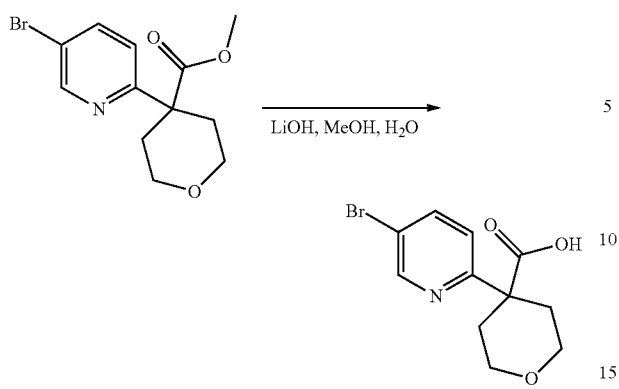

4-(5-bromopyridin-2-yl)oxane-4-carboxylic acid

Into a 50-mL round-bottom flask, was placed methanol (5 mL), water (1 mL), methyl 4-(5-bromopyridin-2-yl)oxane-4-carboxylate (500 mg, 1.67 mmol, 1.00 equiv), LiOH (80 mg, 3.34 mmol, 2.01 equiv). The resulting solution was stirred for 3 h at room temperature. The resulting mixture was concentrated under vacuum. This resulted in 420 mg (88%) of 4-(5-bromopyridin-2-yl)oxane-4-carboxylic acid as a yellow solid. MS (ES, m/z): 287 (M+H).

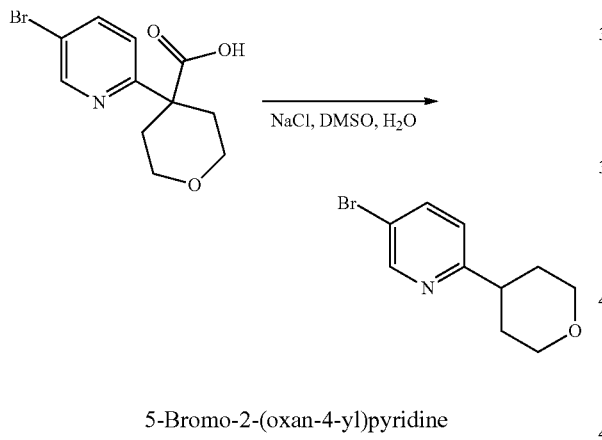

5-Bromo-2-(oxan-4-yl)pyridine

Into a 1000-mL round-bottom flask, was placed DMSO (200 mL), 4-(5-bromopyridin-2-yl)oxane-4-carboxylic acid (20 g, 69.90 mmol, 1.00 equiv), water (60 mL), sodium chloride (16 g). The resulting solution was stirred for 3 h at 150° C. The resulting solution was diluted with 500 mL of water/ice. The resulting solution was extracted with 3×300 mL of ethyl acetate and the organic layers combined and dried over anhydrous sodium sulfate and concentrated under vacuum. This resulted in 10 g (59%) of 5-bromo-2-(oxan-4-yl)pyridine as a yellow solid. MS (ES, m/z): 243 (M+H).

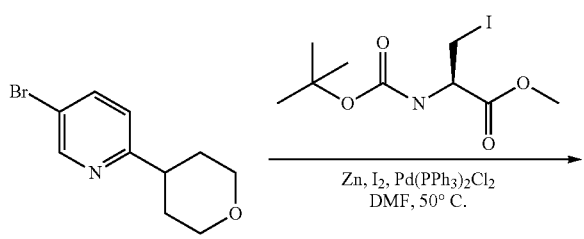

Methyl-(2S)-2-[[(tert-butoxy)carbonyl]amino]-3-[6-(oxan-4-yl)pyridin-3-yl]propanoate Into a 250-mL 3-necked round-bottom flask, was placed N,N-dimethylformamide (40 mL), Zn (26 g), I₂ (4 g), methyl (2S)-2-[[(tert-butoxy)carbonyl]amino]-3-iodopropanoate (10 g, 30.38 mmol, 1.00 equiv), Pd(PPh₃)₂Cl₂ (1.6 g, 2.28 mmol, 0.08 equiv), 5-bromo-2-(oxan-4-yl)pyridine (17 g, 70.22 mmol, 2.31 equiv). The resulting solution was stirred overnight at 50° C. The solids were filtered out. The resulting solution was extracted with 3×50 mL of ethyl acetate and the organic layers combined and dried over anhydrous sodium sulfate and concentrated under vacuum. The residue was applied onto a silica gel column with ethyl acetate/petroleum ether (3:1). This resulted in 4 g (36%) of methyl (2S)-2-[[(tert-butoxy)carbonyl]amino]-3-[6-(oxan-4-yl)pyridin-3-yl]propanoate as yellow oil. MS (ES, m/z): 365 (M+H).

(2S)-2-[[(tert-butoxy)carbonyl]amino]-3-[6-(oxan-4-yl)pyridin-3-yl]propanoic acid Into a 50-mL round-bottom flask, was placed water (2 mL), methanol (10 mL), LiOH (420 mg, 17.54 mmol, 3.20 equiv), methyl (2S)-2-[[(tert-butoxy)carbonyl]amino]-3-[6-(oxan-4-yl)pyridin-3-yl]propanoate (2 g, 5.49 mmol, 1.00 equiv). The resulting solution was stirred for 3 h at room temperature. The resulting mixture was concentrated under vacuum. This resulted in 1.5 g (78%) of (2S)-2-[[(tert-butoxy)carbonyl]amino]-3-[6-(oxan-4-yl)pyridin-3-yl]propanoic acid as a yellow crude solid. MS (ES, m/z): 351 (M+H).

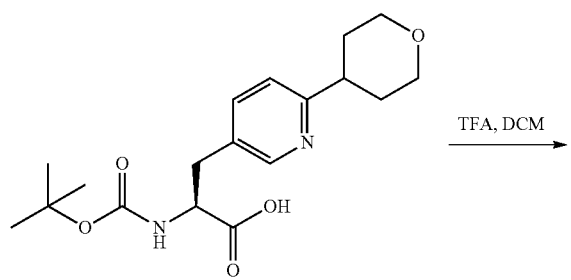

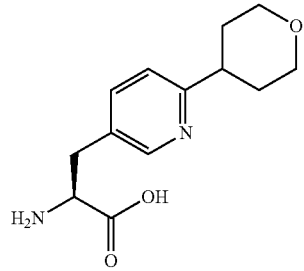

(2S)-2-amino-3-[6-(oxan-4-yl)pyridin-3-yl]propanoic acid

Into a 50-mL round-bottom flask, was placed dichloromethane (10 mL), (2S)-2-[[(tert-butoxy)carbonyl]amino]-3-[6-(oxan-4-yl)pyridin-3-yl]propanoic acid (900 mg, 2.57 mmol, 1.00 equiv), trifluoroacetic acid (3 mL). The resulting solution was stirred for 3 h at room temperature. The resulting mixture was concentrated under vacuum. This resulted in 700 mg (crude) of (2S)-2-amino-3-[6-(oxan-4-yl)pyridin-3-yl]propanoic acid. MS (ES, m/z): 251 (M+H).

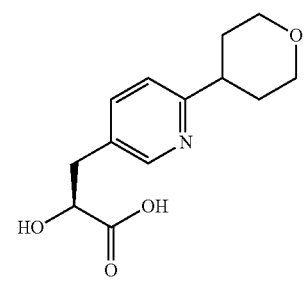

(2S)-2-hydroxy-3-[6-(oxan-4-yl)pyridin-3-yl]propanoic acid

Into a 100-mL round-bottom flask, was placed water (20 mg), trifluoroacetic acid (1.6 g, 14.15 mmol, 5.90 equiv), (2S)-2-amino-3-[6-(oxan-4-yl)pyridin-3-yl]propanoic acid (600 mg, 2.40 mmol, 1.00 equiv). This was followed by the addition of a solution of NaNO₂ (1 g, 14.49 mmol, 6.05 equiv) in water (10 mL) dropwise with stirring at 0° C. The resulting solution was stirred overnight at room temperature. The resulting mixture was concentrated under vacuum. The residue was diluted in DCM:MeOH (15:1, 50 mL). The solid was filtered out. The filtrate was concentrated under vacuum. This resulted in 300 mg (50%) of (2S)-2-hydroxy-3-[6-(oxan-4-yl)pyridin-3-yl]propanoic acid as yellow crude oil. MS (ES, m/z): 252 (M+H).

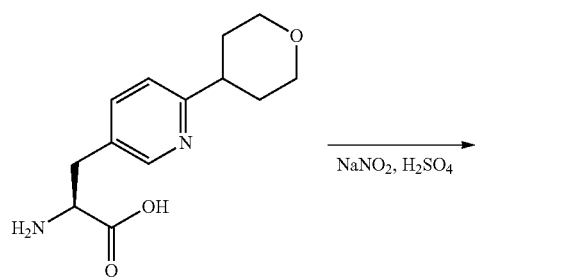

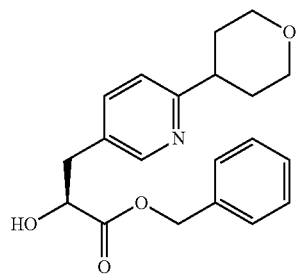

M46

Benzyl-(2S)-2-hydroxy-3-[6-(oxan-4-yl)pyridin-3-yl]propanoate (M46)

Into a 100-mL round-bottom flask, was placed N,N-dimethylformamide (15 mL), (2S)-2-hydroxy-3-[6-(oxan-4-yl)pyridin-3-yl]propanoic acid (2 g, 7.96 mmol, 1.00 equiv), Cs₂CO₃ (5 g, 15.35 mmol, 1.93 equiv), BnBr (2.6 g, 15.20 mmol, 1.91 equiv). The resulting solution was stirred for 2 h at room temperature. The solids were filtered out. The resulting solution was extracted with 3×30 mL of ethyl acetate and the organic layers combined and dried over anhydrous sodium sulfate and concentrated under vacuum. This resulted in 2.7 g (99%) of benzyl (2S)-2-hydroxy-3-[6-(oxan-4-yl)pyridin-3-yl]propanoate as yellow oil. MS (ES, m/z): 342 (M+H); ¹HNMR (300 MHz, CDCl₃): δ 8.37 (d, J=2.1 Hz, 1H), 7.48-7.45 (m, 1H), 7.41-7.33 (m, 5H), 7.06 (d, J=8.1 Hz, 1H), 5.21 (s, 2H), 4.50-4.46 (m, 1H), 4.12-4.07 (m, 2H), 3.59-3.51 (m, 2H), 3.14-2.89 (m, 3H), 1.89-1.82 (m, 4H).

Preparation Example 25: Preparation of Monomer M47

Monomer M47 was prepared by the process shown in Scheme 25 below.

Scheme 25

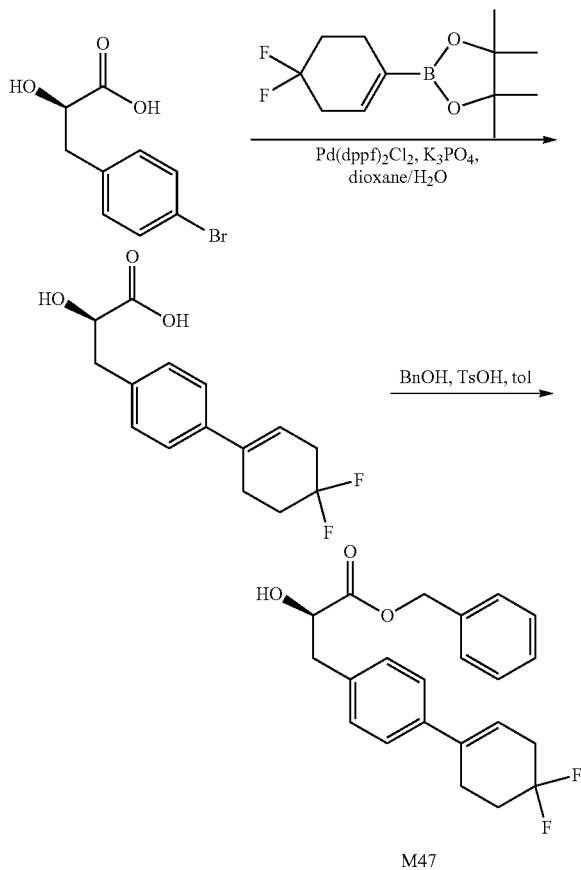

M47

Experimental Details

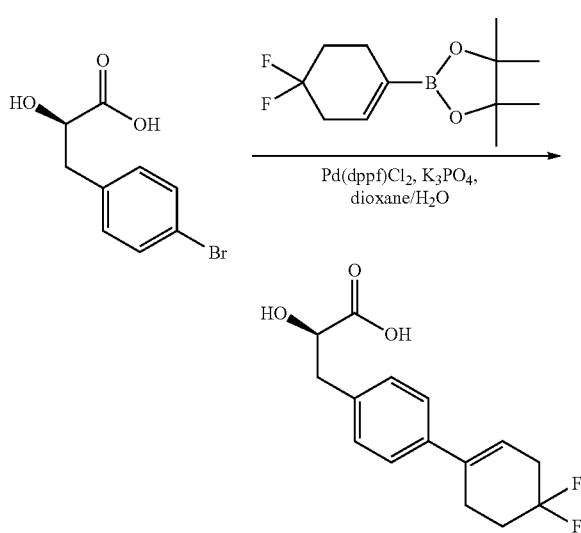

(2R)-3-[4-(4,4-difluorocyclohex-1-en-1-yl)phenyl]-2-hydroxypropanoic acid

Into a 250-mL round-bottom flask purged and maintained with an inert atmosphere of nitrogen, was placed dioxane/ H₂O (88 mL), (2R)-3-(4-bromophenyl)-2-hydroxypropanoic acid (4 g, 16.32 mmol, 1.00 equiv), 2-(4,4-difluorocyclohex-1-en-1-yl)-4,4,5,5-tetramethyl-1,3,2-dioxaborolane (4.0 g, 16.39 mmol, 1.00 equiv), Pd(dppf)Cl₂ (640 mg, 0.87 mmol, 0.05 equiv), K₃PO₄ (11 g, 51.82 mmol, 3.00 equiv). The resulting solution was stirred for 4 h at 80° C. in an oil bath. The reaction mixture was cooled. The resulting mixture was concentrated under vacuum. The residue was dissolved in 50 mL of ether. The solids were collected by filtration. The solids were dissolved in 50 mL of THF. The pH value of the solution was adjusted to 5 with hydrogen chloride (12 mol/L). The resulting solution was diluted with 200 mL of ethyl acetate. The solids were collected by filtration. The filtrate was dried over anhydrous sodium sulfate and concentrated under vacuum. This resulted in 4.5 g (98%) of (2R)-3-[4-(4,4-difluorocyclohex-1-en-1-yl)phenyl]-2-hydroxypropanoic acid as light yellow oil. MS (ES, m/z): 281 (M–H).

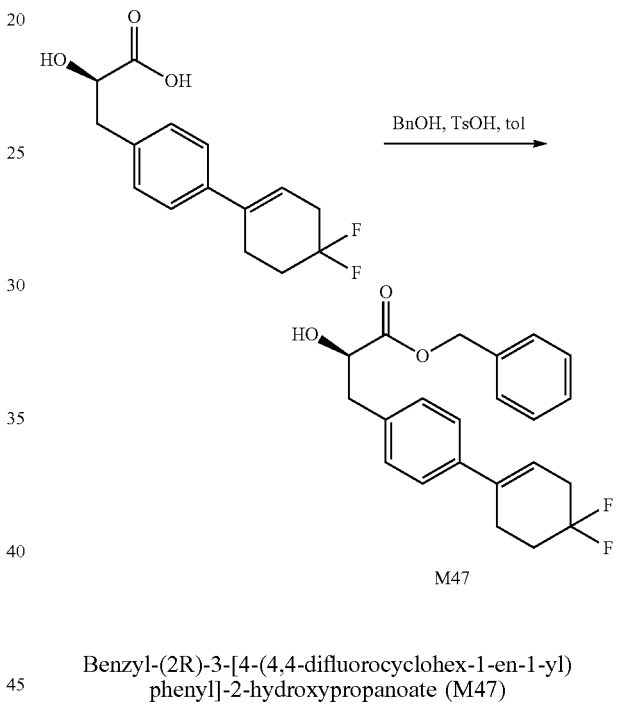

M47

Benzyl-(2R)-3-[4-(4,4-difluorocyclohex-1-en-1-yl) phenyl]-2-hydroxypropanoate (M47)

Into a 500-mL round-bottom flask, was placed toluene (200 mL), (2R)-3-[4-(4,4-difluorocyclohex-1-en-1-yl)phenyl]-2-hydroxypropanoic acid (4.5 g, 15.94 mmol, 1.00 equiv), BnOH (2.24 g, 1.30 equiv), TsOH (540 mg, 3.14 mmol, 0.20 equiv), 4A-MS (2 g). The resulting solution was stirred for 4 h at 110° C. in an oil bath. The reaction mixture was cooled. The solids were filtered out. The filtrate mixture was concentrated under vacuum. The residue was applied onto a silica gel column with ethyl acetate/petroleum ether (1:20-1:10). This resulted in 5 g (84%) of benzyl (2R)-3-[4-(4,4-difluorocyclohex-1-en-1-yl)phenyl]-2-hydroxypropanoate as a light yellow solid. ¹HNMR (300 MHz, CDCl₃): δ 7.62-7.30 (m, 7H), 7.11 (d, J=8.4 Hz, 2H), 5.89 (br, 1H), 5.21 (s, 2H), 4.52-4.48 (m, 1H), 3.16-2.95 (m, 2H), 2.71-2.67 (m, 4H), 2.25-2.12 (m, 2H).

Preparation Example 26: Preparation of Monomer M48

Monomer M48 was prepared by the process shown in Scheme 26 below.

Scheme 26

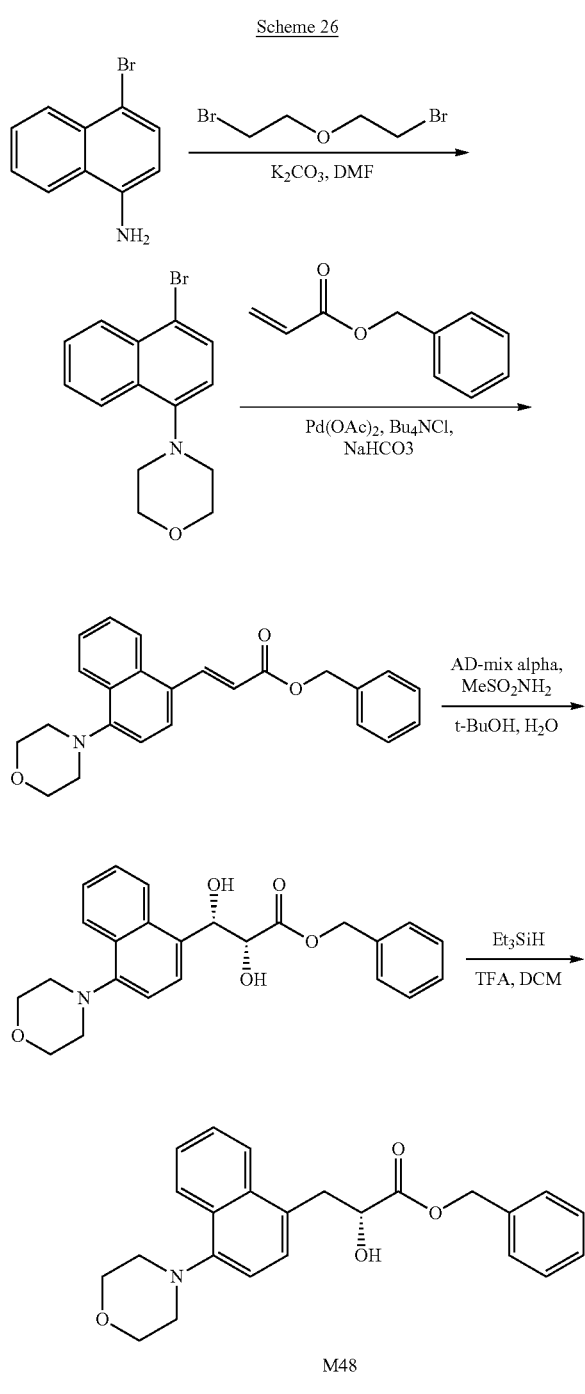

Experimental Details

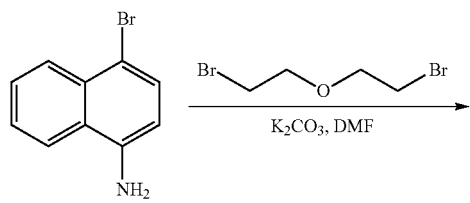

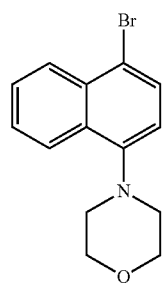

4-(4-Bromonaphthalen-1-yl)morpholine

Into a 250-mL round-bottom flask, was placed 4-bromonaphthalen-1-amine (5 g, 22.51 mmol, 1.00 equiv), 1-bromo-2-(2-bromoethoxy)ethane (8 g, 34.50 mmol, 1.53 equiv), N,N-dimethylformamide (100 mL), potassium carbonate (14 g, 101.30 mmol, 4.50 equiv). The resulting solution was stirred overnight at 110° C. The solids were filtered out. The resulting solution was quenched with 200 mL of water, extracted with 2×50 mL of ethyl acetate and the organic layers combined. The organic phase was washed with 2×20 mL of water. The organic phase was dried over anhydrous sodium sulfate and concentrated under vacuum. The residue was applied onto a silica gel column with ethyl acetate/petroleum ether (1:5). This resulted in 3.5 g (53%) of 4-(4-bromonaphthalen-1-yl)morpholine as brown oil. MS (ES, m/z): 292 (M+H); $^1$H NMR (CDCl$_3$, 300 MHz) δ: 8.29-8.25 (m, 2H), 7.73 (d, J=4.0 Hz, 1H), 7.64-7.59 (m, 2H), 6.98 (d, J=4.0 Hz, 1H), 4.00 (t, J=4.5 Hz, 4H), 3.11 (t, J=4.5 Hz, 4H).

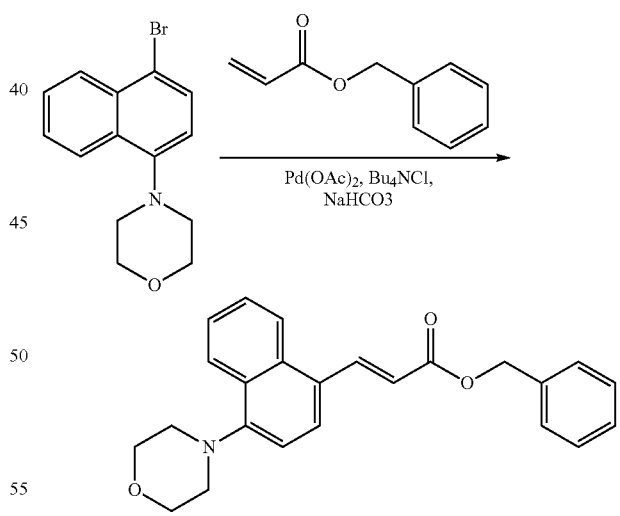

Benzyl (2E)-3-[4-(morpholin-4-yl)naphthalen-1-yl]prop-2-enoate

Into a 250-mL round-bottom flask purged and maintained with an inert atmosphere of nitrogen, was placed 4-(4-bromonaphthalen-1-yl)morpholine (3 g, 10.27 mmol, 1.00 equiv), benzyl prop-2-enoate (2.0 g, 12.33 mmol, 1.20 equiv), N,N-dimethylformamide (100 mL), Bu$_4$NCl (5.7 g, 20.51 mmol, 2.00 equiv), sodium bicarbonate (4.3 g, 51.18 mmol, 4.98 equiv), Pd(OAc)₂ (230 mg, 1.02 mmol, 0.10 equiv). The resulting solution was stirred overnight at 110° C. The solids were filtered out. The resulting solution was quenched with 200 mL of water, extracted with 2×50 mL of ethyl acetate and the organic layers combined. The organic phase was washed with 2×30 mL of water and 1×30 mL of brine. The organic phase was dried over anhydrous sodium sulfate and concentrated under vacuum. The residue was applied onto a silica gel column with ethyl acetate/petroleum ether (1:10). This resulted in 2.3 g (60%) of benzyl (2E)-3-[4-(morpholin-4-yl)naphthalen-1-yl]prop-2-enoate as yellow oil. MS (ES, m/z): 374 (M+H).

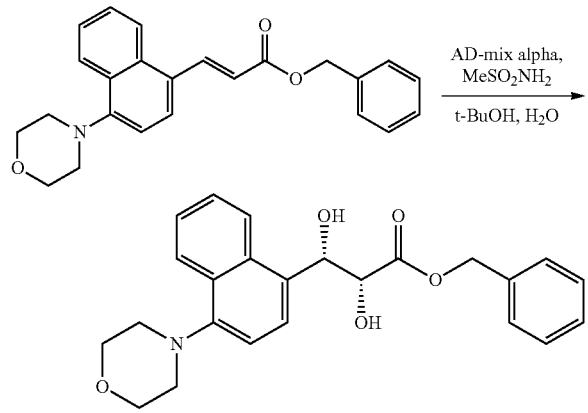

Benzyl (2R, 3S)-2,3-dihydroxy-3-[4-(morpholin-4-yl)naphthalen-1-yl]propanoate

Into a 250-mL round-bottom flask, was placed benzyl (2E)-3-[4-(morpholin-4-yl)naphthalen-1-yl]prop-2-enoate (2.1 g, 5.62 mmol, 1.00 equiv), tert-butanol (40 mL), water (40 mL), methane-sulfonamide (600 mg, 6.31 mmol, 1.12 equiv), AD-mix-α (8 g). The resulting solution was stirred overnight at room temperature. The reaction was then quenched by the addition of 11.5 g of Na₂SO₃. The solids were filtered out. The resulting solution was diluted with 200 mL of water, extracted with 2×50 mL of ethyl acetate and the organic layers combined. The organic phase was washed with 2×30 mL of water and 1×30 mL of brine. The organic phase was dried over anhydrous sodium sulfate and concentrated under vacuum. The residue was applied onto a silica gel column with ethyl acetate/petroleum ether (1:4). This resulted in 1.6 g (70%) of benzyl (2R, 3S)-2,3-dihydroxy-3-[4-(morpholin-4-yl)naphthalen-1-yl]propanoate as brown oil. MS (ES, m/z): 408 (M+H); ¹H NMR (CDCl₃, 300 MHz) δ: 8.34-8.31 (m, 1H), 8.06-8.03 (m, 1H), 7.66 (d, J=3.9 Hz, 1H), 7.58-7.52 (m, 2H), 7.41-7.31 (m, 5H), 7.13 (d, J=4.0 Hz, 1H), 5.84 (br s 1H), 5.34-5.21 (m, 2H), 4.73 (br s, 1H), 4.63-4.60 (m, 1H), 4.00 (t, J=4.5 Hz, 4H), 3.80-3.66 (m, 1H), 3.16-3.11 (m, 4H).

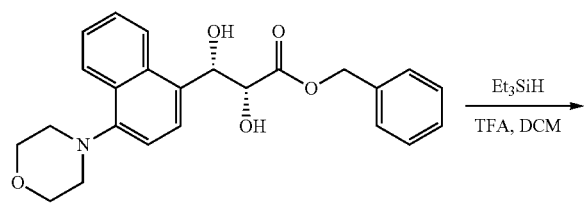

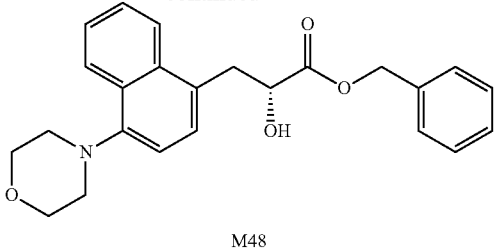

M48

Benzyl (2R)-2-hydroxy-3-[4-(morpholin-4-yl)naphthalen-1-yl]propanoate

Into a 250-mL round-bottom flask, was placed benzyl (2R, 3S)-2,3-dihydroxy-3-[4-(morpholin-4-yl)naphthalen-1-yl]propanoate (1.6 g, 3.93 mmol, 1.00 equiv), dichloromethane (100 mL), Et₃SiH (1.35 g, 11.61 mmol, 2.96 equiv), trifluoroacetic acid (1.3 g, 11.50 mmol, 2.93 equiv). The resulting solution was stirred overnight at room temperature. The reaction was then quenched by the addition of 40 mL of water. The resulting solution was extracted with 2×50 mL of dichloromethane and the organic layers combined. The organic phase was washed with 3×30 mL of brine. The organic phase was dried over anhydrous sodium sulfate and concentrated under vacuum. The residue was applied onto a silica gel column with ethyl acetate/petroleum ether (1:5). This resulted in 600 mg (39%) of benzyl (2R)-2-hydroxy-3-[4-(morpholin-4-yl)naphthalen-1-yl]propanoate as yellow oil. MS (ES, m/z): 392 (M+H); ¹H NMR (CDCl₃, 300 MHz) δ: 8.38-8.36 (m, 1H), 8.11-8.08 (m, 1H), 7.58-7.52 (m, 2H), 7.40-7.28 (m, 6H), 7.08 (d, J=3.8 Hz, 1H), 5.24-5.14 (m, 2H), 4.66-4.62 (m, 1H), 4.07 (t, J=4.5 Hz, 4H), 3.69-3.63 (m, 1H), 3.37-3.29 (m, 1H), 3.19-3.10 (m, 4H).

Preparation Example 27: Preparation of Monomer M49

Monomer M49 was prepared by the process shown in Scheme 27 below.

Scheme 27

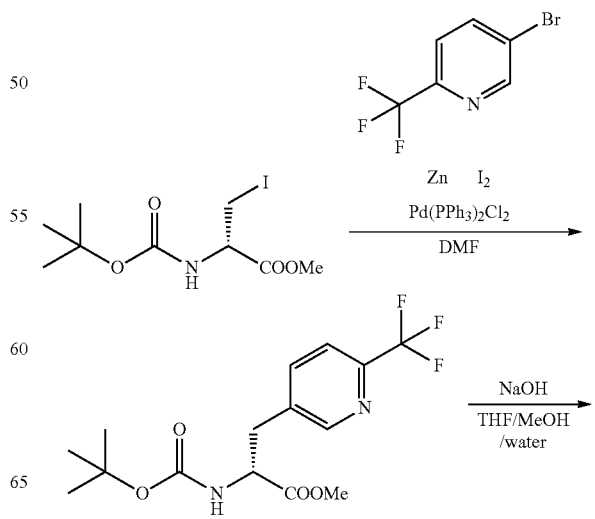

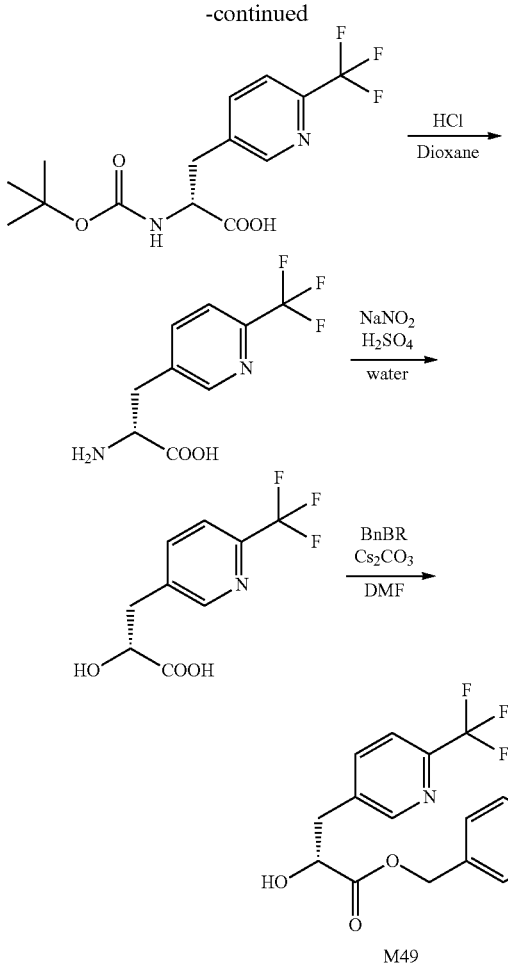

M49

Experimental Details

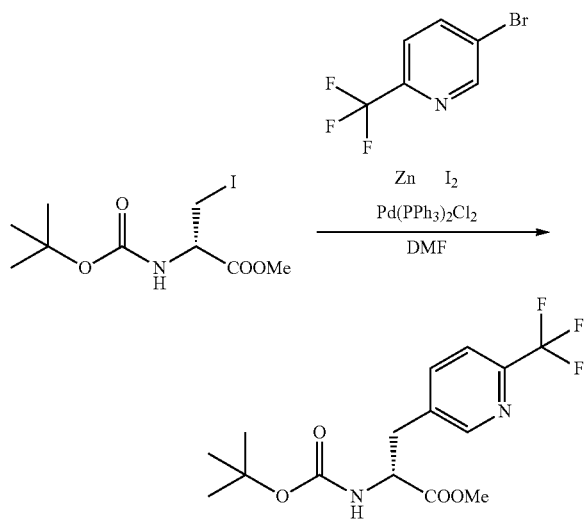

methyl (2R)-2-(tert-butoxycarbonylamino)-3-[6-(trifluoromethyl)-3-pyridyl]propanoate To a stirred mixture of zinc powder (0.7 g, 11 mmol) and iodine (0.1 g, 0.4 mmol) in 5 mL DMF under nitrogen atmosphere and cooled to 0° C. was added dropwise a solution of (S)—N-tert-butoxycarbonyl-beta-iodoalanine methyl ester (2.5 g, 7.6 mmol) in 10 mL DMF and the mixture stirred 30 min. The mixture was then treated with 5-bromo-2-trifluoromethylpyridine (1.7 g, 7.6 mmol) and bis-triphenylphosphine-palladium(II)chloride (0.26 g, 0.4 mmol) and heated 5 h at 50° C. The mixture was then cooled to room temperature, filtered through a celite plug, the filtrate diluted with 200 mL water and extracted into 200 mL ethyl acetate. The organic layer was washed with 100 mL 20% LiCl solution, washed with brine, dried over sodium sulfate, filtered, concentrated and the residue purified on silica gel column eluting with ethyl acetate/heptanes to obtain the target compound as a yellow oil. Yield: 1.4 g, 54%. MS (CI, m/z): 349 (M+H); $^1$H NMR (CDCl$_3$): δ 8.51 (s, 1H), 7.66 (m, 2H), 5.10 (m, 1H), 4.65 (m, 1H), 3.77 (s, 3H), 3.29 (m, 1H), 3.11 (m, 1H), 1.41 (s, 9H); $^{19}$F NMR (CDCl$_3$): δ 67.35 (s, 3F).

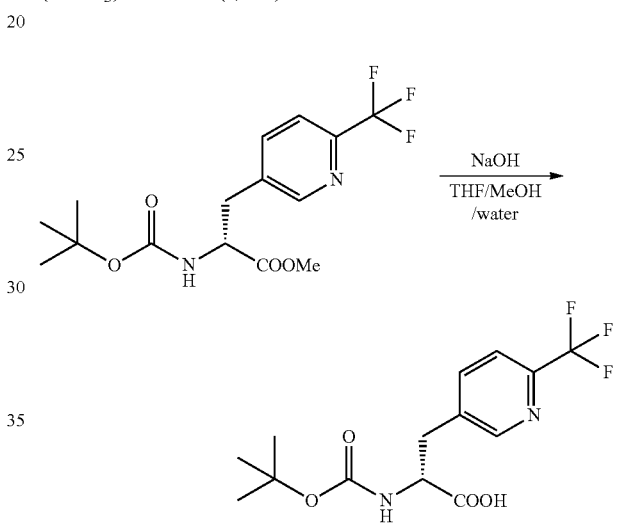

(2R)-2-(tert-butoxycarbonylamino)-3-[6-(trifluoromethyl)-3-pyridyl]propanoic acid To a stirred solution of methyl (2R)-2-(tert-butoxycarbonylamino)-3-[6-(trifluoromethyl)-3-pyridyl]propanoate (1.4 g, 4.0 mmol) in 15 mL 2:1 methanol:THF was added a solution of sodium hydroxide (0.32 g, 8.1 mmol) in 7 mL water and the mixture stirred 1 h. The mixture was diluted with 60 mL water, acidified to pH 2 with 1 M HCl and extracted into 75 mL ethyl acetate. The organic layer was washed with brine, dried over sodium sulfate, filtered and concentrated to obtain the target compound as a clear oil. Yield: 1.4 g (quantitative). MS (CI, m/z): 335 (M+H).

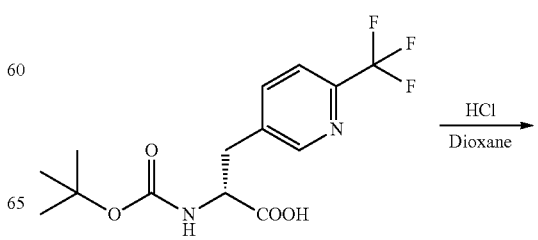

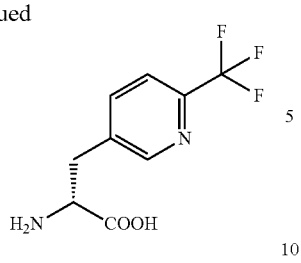

(2R)-2-amino-3-[6-(trifluoromethyl)-3-pyridyl]propanoic acid hydrochloride salt

To 10 mL of a 4 M solution of HCl in dioxane was added (2R)-2-(tert-butoxycarbonylamino)-3-[6-(trifluoromethyl)-3-pyridyl]propanoic acid (1.4 g, 4.0 mmol) and the mixture stirred 1 h. The mixture was concentrate and the residue dried under high vacuum to obtain the target compound as a clear oil. Yield: 1.1 g (quantitative). Mass spec (CI) m/z: (M+H)+ 235.

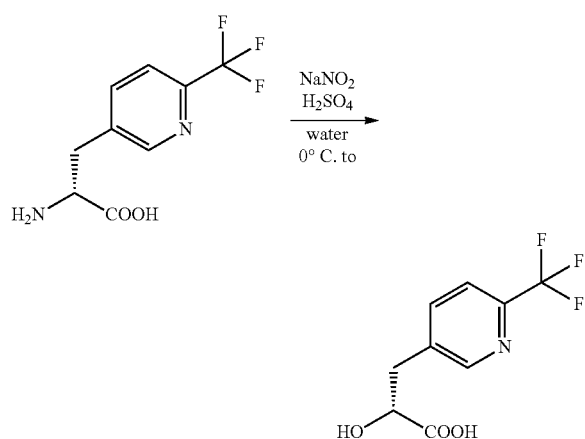

(2R)-2-hydroxy-3-[6-(trifluoromethyl)-3-pyridyl]propanoic acid

To a stirred mixture of (2R)-2-amino-3-[6-(trifluoromethyl)-3-pyridyl]propanoic acid hydrochloride salt (1.1 g, 4.0 mmol) in 16 mL 0.5 M sulfuric acid solution (8.0 mmoL) cooled to 0° C. was added dropwise a solution of sodium nitrite (1.7 g, 24 mmol) in 6 mL water and the mixture stirred 1 h. The mixture was diluted with 50 mL water and extracted into 75 mL ethyl acetate. The organic layer was washed with brine, dried over sodium sulfate, filtered and concentrated to obtain the target compound as a yellow solid. Yield (0.90 g, 94%). MS (CI, m/z): 236 (M+H); $^1$H NMR (CDCl$_3$): δ 8.67 (m, 1H), 7.92 (m, 1H), 7.71 (m, 1H), 4.61 (m, 1H), 3.45 (m, 1H), 3.25 (m, 1H); $^{19}$F NMR (CDCl$_3$): δ 67.35 (s, 3F).

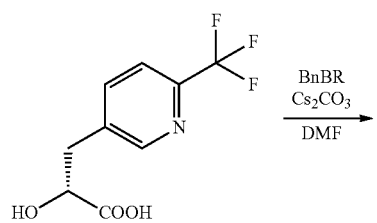

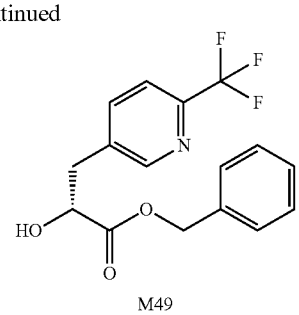

Benzyl (2R)-2-hydroxy-3-[6-(trifluoromethyl)-3-pyridyl]propanoate (M49)

To a stirred solution of (2R)-2-hydroxy-3-[6-(trifluoromethyl)-3-pyridyl]propanoic acid (0.90 g, 3.8 mmol) in 10 mL DMF was added cesium carbonate (1.2 g, 3.8 mmol) and the mixture stirred 30 min. The mixture was then treated with benzyl bromide (0.65 g, 3.8 mmol) and the mixture stirred overnight. The mixture was diluted with 60 mL water and extracted into 75 mL ethyl acetate. The organic layer was washed with 50 mL 20% LiCl solution, washed with brine, dried over sodium sulfate, filtered, concentrated and the residue purified on silica gel column eluting with ethyl acetate/heptanes to obtain the target compound as a clear oil. Yield: 0.57 g, 46%. MS (CI m/z): 326 (M+H); $^1$H NMR (CDCl$_3$): δ 8.55 (d, J=1.7 Hz, 1H), 7.64 (dd, J=1.7, 8.0 Hz, 1H), 7.64 (d, J=8.0 Hz, 1H), 7.40 (m, 3H), 7.34 (m, 2H), 5.22, (q, J=11.9 Hz, 2H), 4.52 (m, 1H), 3.21 (m, 1H), 3.05 (m, 1H), 2.93 (d, J=4.8 Hz, 1H); $^{19}$F NMR (CDCl$_3$): δ 67.87 (s, 3F).

Preparation Examples 28-82 below show how to prepare various dimer compounds from the certain of monomers M1 to M49 described above, which are used to prepare the compounds of the invention.

Preparation Example 28: Preparation of Dimer D1

Dimer D1 was prepared by the reaction shown below.

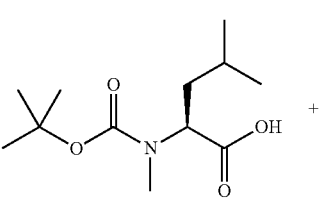

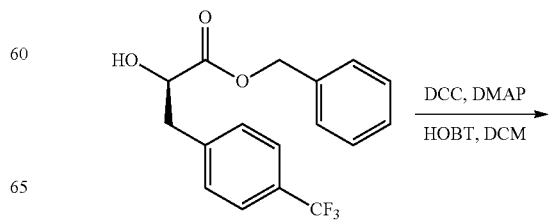

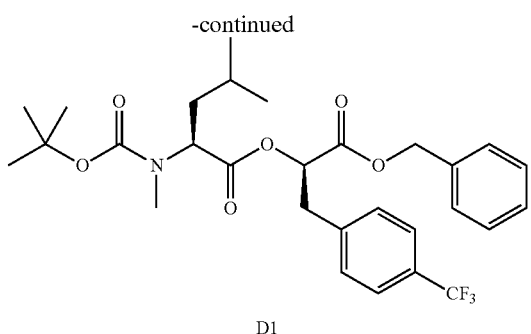

D1

(2R)-1-(benzyloxy)-1-oxo-3-[4-(trifluoromethyl) phenyl]propan-2-yl-(2S)-2-[[(tert-butoxy)carbonyl] (methyl)amino]-4-methylpentanoate (D1)

Into a 100-mL round-bottom flask, was placed (2S)-2-[[(tert-butoxy)carbonyl](methyl)amino]-4-methylpentanoic acid (200 mg, 0.82 mmol, 1.00 equiv), benzyl (2R)-2-hydroxy-3-[4-(trifluoromethyl)phenyl]propanoate (152 mg, 0.47 mmol, 1.00 equiv), dichloromethane (10 mL). This was followed by the addition of DCC (140 mg, 0.68 mmol, 1.10 equiv), 4-dimethylaminopyridine (83 mg, 0.68 mmol, 1.10 equiv) and HOBT (116 mg, 0.86 mmol, 1.10 equiv) respectively in portions with stirring at 0° C. The resulting solution was stirred overnight at room temperature. The solids were filtered out. The filtrate was concentrated under vacuum. The residue was applied onto a silica gel column with ethyl acetate/petroleum ether (1:20). This resulted in 159.3 mg (35%) of (2R)1-(benzyloxy)-1-oxo-3-[4-(trifluoromethyl) phenyl]propan-2-yl-(2S)-2-[[(tert-butoxy)carbonyl] (methyl)amino]-4-methylpentanoate as a light yellow solid. MS (ES, m/z): 552 (M+H); $^1$H NMR (300 MHz, CDCl$_3$): δ 7.52-7.47 (m, 2H), 7.36-7.34 (m, 3H), 7.26-7.24 (m, 4H), 5.32-5.28 (m, 1H), 4.18-4.99 (m, 2H), 4.97-4.67 (m, 1H), 3.26-3.13 (m, 2H), 2.62 (d, J=21.9 Hz, 3H), 1.60-1.14 (m, 12H), 0.93 (d, J=12.0 Hz, 6H).

Preparation Example 29: Preparation of Dimer D2

Dimer D2 was prepared by the reaction shown below.

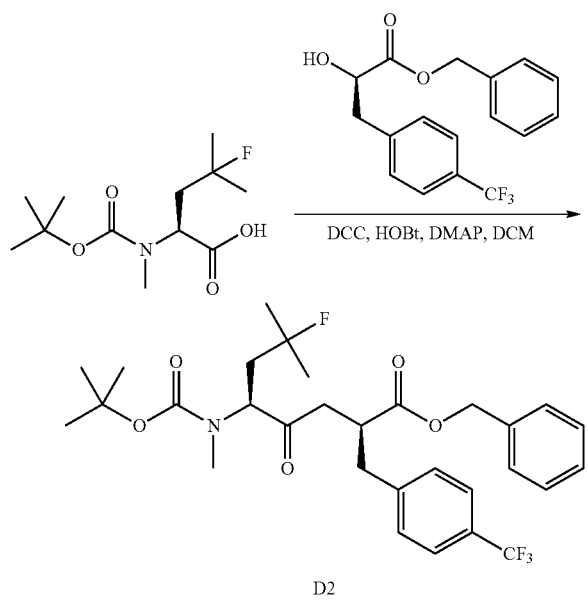

D2

(2R)-1-(benzyloxy)-1-oxo-3-[4-(trifluoromethyl) phenyl]propan-2-yl-(2S)-2-[[(tert-butoxy)carbonyl] (methyl)amino]-4-fluoro-4-methylpentanoate (D2)

Into a 1000-mL 3-necked round-bottom flask purged and maintained with an inert atmosphere of nitrogen, was placed a solution of (2S)-2-[[(tert-butoxy)carbonyl](methyl) amino]-4-fluoro-4-methylpentanoic acid (15 g, 56.97 mmol, 1.00 equiv) in dichloromethane (400 mL), benzyl (2R)2-hydroxy-3-[4-(trifluoromethyl)phenyl]propanoate (12 g, 37.00 mmol, 1.00 equiv). This was followed by the addition of HOBT (7.5 g, 55.51 mmol, 1.20 equiv), DCC (11 g, 53.31 mmol, 1.20 equiv) and 4-dimethylaminopyridine (6.8 g, 55.66 mmol, 1.20 equiv) respectively in portions with stirring at 0° C. The resulting solution was stirred overnight at room temperature. The resulting mixture was concentrated under vacuum. The residue was applied onto a silica gel column with ethyl acetate/petroleum ether (1:10). This resulted in 21 g (65%) of (2R)-1-(benzyloxy)-1-oxo-3-[4-(trifluoromethyl)phenyl]propan-2-yl (2S)-2-[[(tert-butoxy) carbonyl](methyl)amino]-4-fluoro-4-methylpentanoate as red oil. MS (ES, m/z): 570 (M+H).

Preparation Example 30: Preparation of Dimer D3

Dimer D3 was prepared by the reaction shown below.

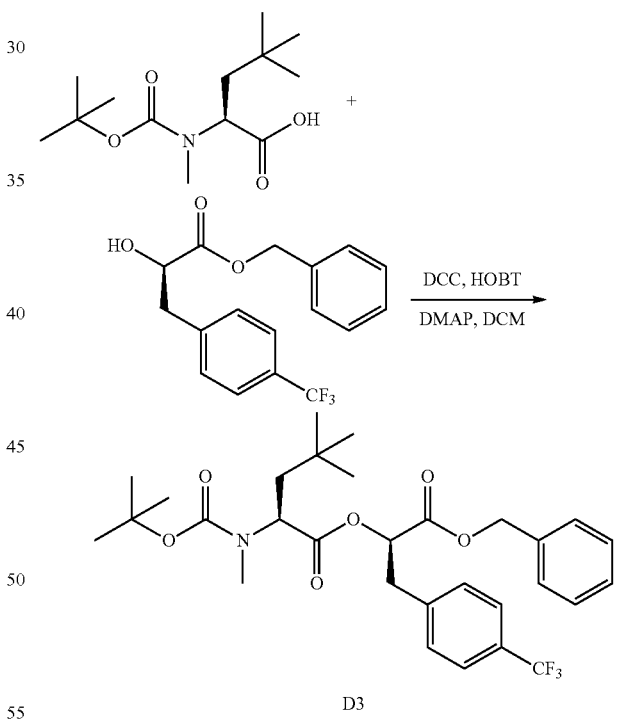

D3

(2R)-1-(benzyloxy)-1-oxo-3-[4-(trifluoromethyl) phenyl]propan-2-yl-(2S)-2-[[(tert-butoxy)carbonyl] (methyl)amino]-4,4-dimethylpentanoate (D3)

Into a 50-mL 3-necked round-bottom flask, was placed (2S)-2-[[(tert-butoxy)carbonyl](methyl)amino]-4,4-dimethylpentanoic acid (4 g, 15.42 mmol, 1.00 equiv), benzyl (2R)-2-hydroxy-3-[4-(trifluoromethyl)phenyl]propanoate (5 g, 15.42 mmol, 1.00 equiv), dichloromethane (40 mL). This was followed by the addition of DCC (4.1 g, 1.30 equiv), HOBT (2.7 g, 1.30 equiv) and 4-dimethylaminopyridine (2.5 g, 1.30 equiv) respectively in portions with stirring at 0° C. The resulting solution was stirred for 14 h at room temperature. The solids were filtered out. The filtrate was concentrated under vacuum. The residue was applied onto a silica gel column with ethyl acetate/petroleum ether (1:50). This resulted in 6 g (69%) of (2R)-1-(benzyloxy)-1-oxo-3-[4-(trifluoromethyl)phenyl]propan-2-yl-(2S)-2-[[(tert-butoxy)carbonyl](methyl)amino]-4,4-dimethylpentanoate as a white solid. MS (ES, m/z): 566 (M+H); $^1$H NMR (300 MHz, DMSO): δ 7.61-7.59 (m, 2H), 7.45-7.42 (m, 2H), 7.37-7.35 (m, 3H), 7.29 (br, 2H), 5.41-5.35 (m, 1H), 5.13 (s, 2H), 4.90-4.85 (m, 0.5H), 4.59 (br, 0.5H), 3.32-3.15 (m, 2H), 2.55-2.50 (m, 3H), 1.51-1.46 (m, 2H), 1.37 (d, J=21.0 Hz, 9H), 0.83 (s, 9H).

Preparation Example 31: Preparation of Dimer D4

Dimer D4 was prepared by the reaction shown below.

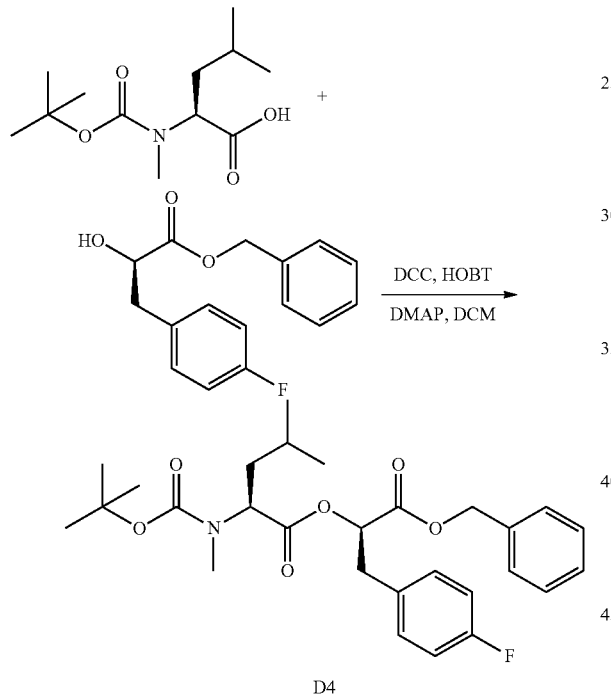

(2R)-1-(benzyloxy)-3-(4-fluorophenyl)-1-oxopropan-2-yl-(2S)-2-[[(tert-butoxy)carbonyl](methyl)amino]-4-methylpentanoate (D4)

Into a 250-mL 3-necked round-bottom flask, was placed benzyl (2R)3-(4-fluorophenyl)-2-hydroxypropanoate (1.5 g, 5.47 mmol, 1.00 equiv), (2S)-2-[[(tert-butoxy)carbonyl](methyl)amino]-4-methylpentanoic acid (1.5 g, 6.11 mmol, 1.10 equiv), dichloromethane (80 mL). This was followed by the addition of DCC (1.2 g, 5.82 mmol, 1.10 equiv), HOBT (0.8 g, 1.10 equiv) and 4-dimethylaminopyridine (0.7 g, 1.10 equiv) respectively in portions with stirring at 0° C. The resulting solution was stirred for 13 h at room temperature. The solids were filtered out. The filtrate was concentrated under vacuum. The residue was applied onto a silica gel column with ethyl acetate/petroleum ether (1:10). This resulted in 1.5 g (55%) of (2R)-1-(benzyloxy)-3-(4-fluorophenyl)-1-oxopropan-2-yl-(2S)-2-[[(tert-butoxy)carbonyl](methyl)amino]-4-methylpentanoate as a white solid. MS (ES, m/z): 502 (M+H); $^1$H NMR (300 MHz, DMSO): δ 7.41-7.21 (m, 7H), 7.09-7.03 (m, 2H), 5.31-5.29 (m, 1H), 5.13 (s, 2H), 4.82-4.78 (m, 0.5H), 4.58-4.54 (m, 0.5H), 3.19-3.05 (m, 2H), 2.56 (s, 3H), 1.52-1.23 (m, 12H), 0.90-0.79 (br, 6H).

Preparation Example 32: Preparation of Dimer D5

Dimer D5 was prepared by the reaction shown below.

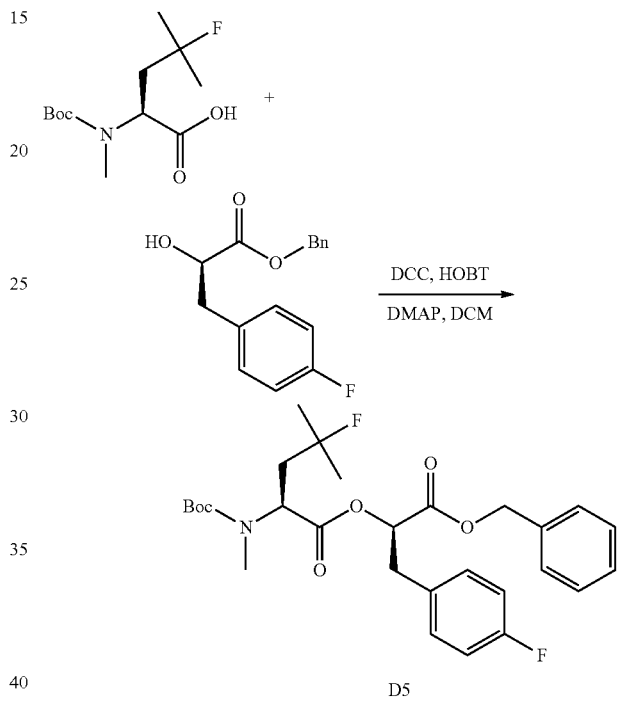

(2R)-1-(benzyloxy)-3-(4-fluorophenyl)-1-oxopropan-2-yl-(2S)-2-[[(tert-butoxy)carbonyl](methyl)amino]-4-fluoro-4-methylpentanoate (D5)

Into a 100-mL 3-necked round-bottom flask purged and maintained with an inert atmosphere of nitrogen, was placed dichloromethane (60 mL), (2S)-2-[[(tert-butoxy)carbonyl](methyl)amino]-4-fluoro-4-methylpentanoic acid (2.8 g, 10.63 mmol, 1.00 equiv), benzyl (2R)3-(4-fluorophenyl)-2-hydroxypropanoate (2.9 g, 10.57 mmol, 1.00 equiv). This was followed by the addition of DCC (2.4 g, 88.75 mmol, 1.10 equiv), 4-dimethylaminopyridine (1.4 g, 11.46 mmol, 1.10 equiv) and HOBT (1.58 g, 49.62 mmol, 1.10 equiv) respectively in portions at 0° C. The resulting solution was stirred overnight at room temperature. The residue was applied onto a silica gel column with ethyl acetate/petroleum ether (1:100-1:50). This resulted in 3.8 g (crude) of (2R)-1-(benzyloxy)-3-(4-fluorophenyl)-1-oxopropan-2-yl (2S)-2-[[(tert-butoxy)carbonyl](methyl)amino]-4-fluoro-4-methylpentanoate as a yellow solid. MS (ES, m/z): 520 (M+H).

Preparation Example 33: Preparation of Dimer D6

Dimer D6 was prepared by the reaction shown below.

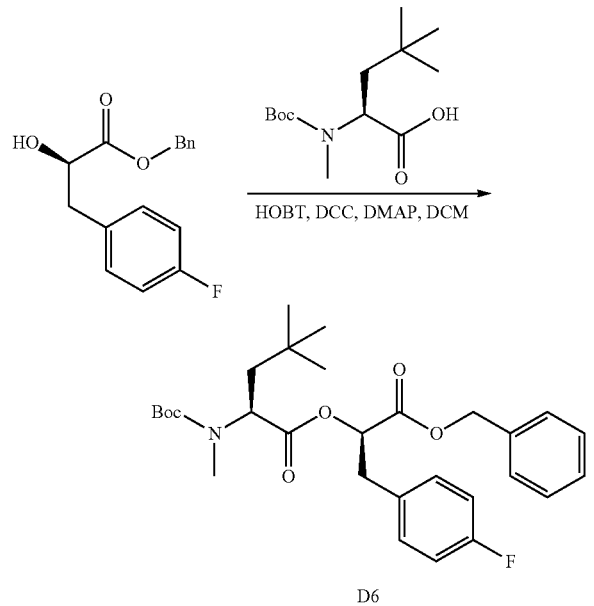

D6

(2R)-1-(benzyloxy)-3-(4-fluorophenyl)-1-oxopropan-2-yl-(2S)-2-[[(tert-butoxy)carbonyl](methyl)amino]-4,4-dimethylpentanoate (D6)

Into a 100-mL round-bottom flask, was placed dichloromethane (20 mL), benzyl (2R)3-(4-fluorophenyl)-2-hydroxypropanoate (2 g, 7.29 mmol, 1.00 equiv), (2S)-2-[[(tert-butoxy)carbonyl](methyl)amino]-4,4-dimethylpentanoic acid (2 g, 7.71 mmol, 1.06 equiv). This was followed by the addition of DCC (4.6 g, 22.29 mmol, 3.06 equiv), 4-dimethylaminopyridine (2.2 g, 18.01 mmol, 2.47 equiv) and HOBT (2.4 g, 17.76 mmol, 2.44 equiv) respectively in portions with stirring at 0° C. The resulting solution was stirred for 2 h at room temperature. The resulting mixture was concentrated under vacuum. The residue was applied onto a silica gel column with ethyl acetate/petroleum ether (1:5). This resulted in 2.6 g (69%) of (2R)-1-(benzyloxy)-3-(4-fluorophenyl)-1-oxopropan-2-yl-(2S)-2-[[(tert-butoxy)carbonyl](methyl)amino]-4,4-dimethylpentanoate as colorless oil. MS (ES, m/z): 416 (M+H-Boc).

Preparation Example 34: Preparation of Dimer D7

Dimer D7 was prepared by the reaction shown below.

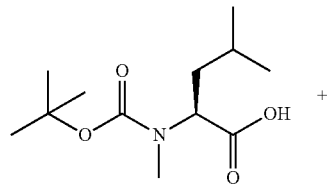

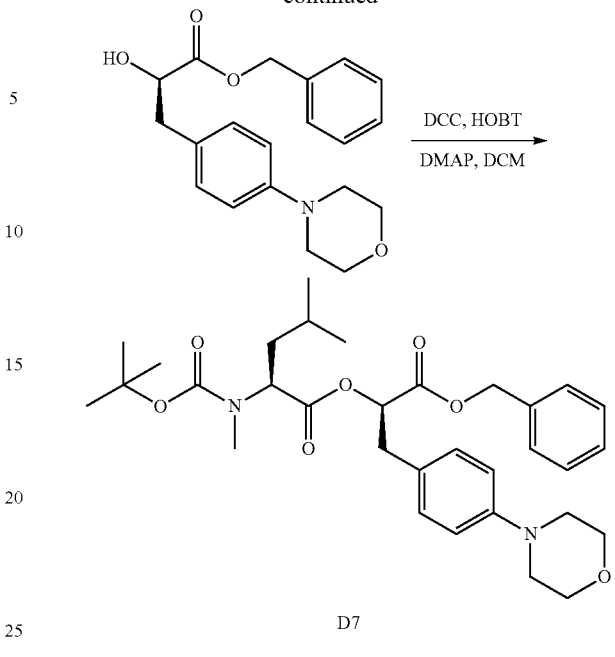

D7

(2R)-1-(benzyloxy)-3-[4-(morpholin-4-yl)phenyl]-1-oxopropan-2-yl-(2S)-2-[[(tert-butoxy) carbonyl](methyl)amino]-4-methylpentanoate (D7)

Into a 250-mL 3-necked round-bottom flask, was placed benzyl (2R)2-hydroxy-3-[4-(morpholin-4-yl)phenyl]propanoate (10 g, 29.29 mmol, 1.00 equiv), (2S)-2-[[(tert-butoxy)carbonyl](methyl)amino]-4-methylpentanoic acid (7.9 g, 32.20 mmol, 1.10 equiv), dichloromethane (180 mL). This was followed by the addition of DCC (6.6 g, 31.99 mmol, 1.10 equiv), 4-dimethylaminopyridine (3.9 g, 31.92 mmol, 1.10 equiv) and HOBT (4.3 g, 31.82 mmol, 11.10 equiv) respectively in portions with stirring at 0° C. The resulting solution was stirred overnight at room temperature. The solids were filtered out. The filtrate was concentrated under vacuum. The residue was applied onto a silica gel column with ethyl acetate/petroleum ether (1:10). This resulted in 14 g (84%) of (2R)1-(benzyloxy)-3-[4-(morpholin-4-yl)phenyl]-1-oxopropan-2-yl-(2S)-2-[[(tert-butoxy) carbonyl](methyl)amino]-4-methylpentanoate as a white solid. MS (ES, m/z): 569 (M+H); 1H NMR (300 MHz, CDCl$_3$): δ 7.41-7.36 (m, 3H), 7.33-7.29 (m, 2H), 7.10 (d, J=8.1 Hz, 2H), 6.85 (br, 2H), 5.26-5.23 (m, 1H), 5.19-5.11 (m, 2H), 5.08-4.99 (m, 0.5H), 4.77-4.72 (m, 0.5H), 3.89 (br, 4H), 3.16-3.03 (m, 6H), 2.67 (d, J=8.4 Hz, 3H), 1.65-1.56 (m, 3H), 1.49 (d, J=15.9 Hz, 9H), 0.92 (d, J=6.0 Hz, 6H).

Preparation Example 35: Preparation of Dimer D8

Dimer D8 was prepared by the reaction shown below.

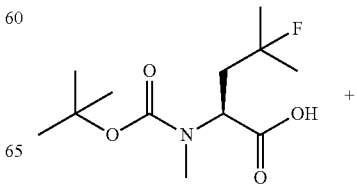

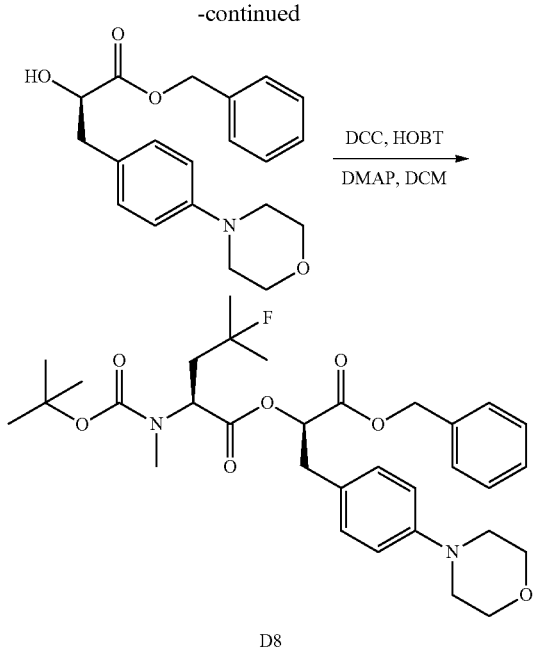

(2R)-1-(benzyloxy)-3-[4-(morpholin-4-yl)phenyl]-1-oxopropan-2-yl-(2S)-2-[[(tert-butoxy) carbonyl](methyl)amino]-4-fluoro-4-methylpentanoate (D8)

Into a 100-mL 3-necked round-bottom flask purged and maintained with an inert atmosphere of nitrogen, was placed dichloromethane (10 mL, 1.10 equiv), benzyl (2R)-2-hydroxy-3-[4-(morpholin-4-yl)phenyl]propanoate (130 mg, 0.38 mmol, 1.00 equiv), (2S)-2-[(tert-butoxy)carbonyl](methyl)amino-4-fluoro-4-methylpentanoic acid (100 mg, 0.38 mmol, 1.00 equiv). This was followed by the addition of HOBT (57 mg, 0.42 mmol, 1.10 equiv), DCC (86 mg, 0.42 mmol, 1.10 equiv) and 4-dimethylaminopyridine (51 mg, 0.42 mmol, 1.10 equiv) respectively in portions with stirring at 0° C. The resulting solution was stirred overnight at room temperature. The solids were filtered out. The filtrate was concentrated under vacuum. The residue was applied onto a silica gel column with ethyl acetate/petroleum ether (1:10). This resulted in 180 mg (80.5%) of (2R)-1-(benzyloxy)-3-[4-(morpholin-4-yl)phenyl]-1-oxopropan-2-yl (2S)-2-[[(tert-butoxy)carbonyl](methyl)amino]-4-fluoro-4-methylpentanoate as a light yellow solid. MS (ES, m/z): 587 (M+H); $^1$H NMR (300 MHz, CDCl$_3$): δ 7.38-7.36 (m, 4H), 7.29-7.25 (m, 1H), 7.20-6.99 (m, 4H), 5.27-5.18 (m, 1H), 5.18-5.09 (m, 2H), 5.08-4.83 (m, 1H), 4.01 (br, 4H), 3.23 (br, 4H), 3.15-3.05 (m, 2H), 2.68 (s, 3H), 2.28-1.91 (m, 2H), 1.51-1.28 (m, 15H).

Preparation Example 36: Preparation of Dimer D9

Dimer D9 was prepared by the reaction shown below.

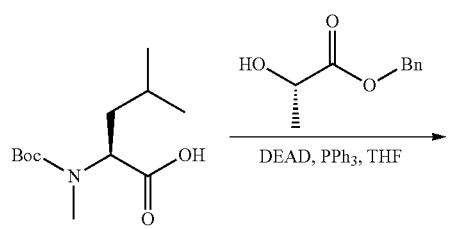

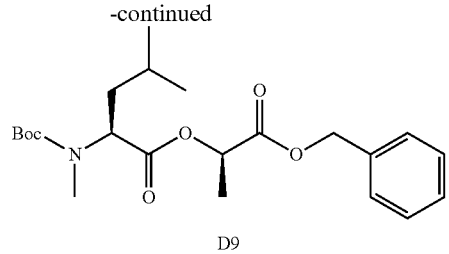

(2R)-1-(benzyloxy)-1-oxopropan-2-yl-(2S)-2-[[(tert-butoxy)carbonyl](methyl)amino]-4-methylpentanoate (D9)

Into a 2-L round-bottom flask purged and maintained with an inert atmosphere of nitrogen, was placed tetrahydrofuran (1.5 L), (2S)-2-[[(tert-butoxy)carbonyl](methyl)amino]-4-methylpentanoic acid (50 g, 203.82 mmol, 1.00 equiv), benzyl (2S)-2-hydroxypropanoate (36.7 g, 203.66 mmol, 1.00 equiv), triphenylphosphane (85 g, 324.07 mmol, 1.50 equiv). This was followed by the addition of DEAD (56.5 g, 324.43 mmol, 1.20 equiv) dropwise with stirring at 0° C. The resulting solution was stirred overnight at room temperature. The resulting mixture was concentrated under vacuum. The residue was applied onto a silica gel column with ethyl acetate/petroleum ether (1:50-1:10). This resulted in 82 g (99%) of (2R)1-(benzyloxy)-1-oxopropan-2-yl-(2S)-2-[[(tert-butoxy)carbonyl](methyl)amino]-4-methylpentanoate as pink oil. MS (ES, m/z): 408 (M+H); $^1$HNMR (300 MHz, CDCl$_3$): δ7.41-7.31 (m, 5H), 5.31-5.10 (m, 3H), 5.01-4.73 (m, 1H), 2.77-2.74 (m, 3H), 1.72-1.65 (m, 2H), 1.60-1.58 (m, 1H), 1.52-1.50 (m, 3H), 1.47 (s, 9H), 0.96-0.94 (m, 6H).

Preparation Example 37: Preparation of Dimer D10

Dimer D10 was prepared by the reaction shown below.

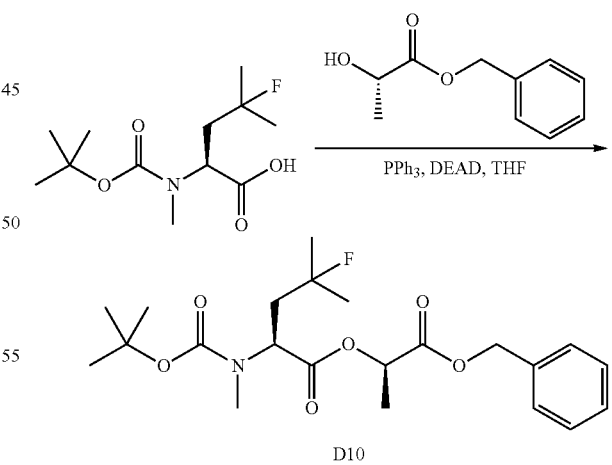

(2R)-1-(benzyloxy)-1-oxopropan-2-yl-(2S)-2-[[(tert-butoxy)carbonyl](methyl)amino]-4-fluoro-4-methylpentanoate (D10)

Into a 50-mL 3-necked round-bottom flask purged and maintained with an inert atmosphere of nitrogen, was placed tetrahydrofuran (10 mL), (2S)-2-[[(tert-butoxy)carbonyl](methyl)amino]-4-fluoro-4-methylpentanoic acid (100 mg, 0.38 mmol, 1.00 equiv), benzyl (2S)-2-hydroxypropanoate (69 mg, 0.38 mmol, 1.00 equiv), triphenylphosphane (150 mg, 0.57 mmol, 1.50 equiv). This was followed by the addition of DEAD (99 mg, 0.57 mmol, 1.50 equiv). The resulting solution was stirred overnight at room temperature. The resulting mixture was concentrated under vacuum. The residue was applied onto a silica gel column with ethyl acetate/petroleum ether (1:100-1:50). This resulted in 106 mg (66%) of (2R)1-(benzyloxy)-1-oxopropan-2-yl (2S)-2-[[(tert-butoxy)carbonyl](methyl)amino]-4-fluoro-4-methylpentanoate as off-white oil. MS (ES, m/z): 426 (M+H); $^1$H NMR (300 MHz, CDCl$_3$): δ 7.41-7.32 (m, 5H), 5.23-5.10 (m, 3H), 5.09-4.82 (m, 1H), 2.80-2.77 (m, 3H), 2.31-2.06 (m, 2H), 1.54-1.27 (m, 18H).

Preparation Example 38: Preparation of Dimer D11

Dimer D11 was prepared by the reaction shown below.

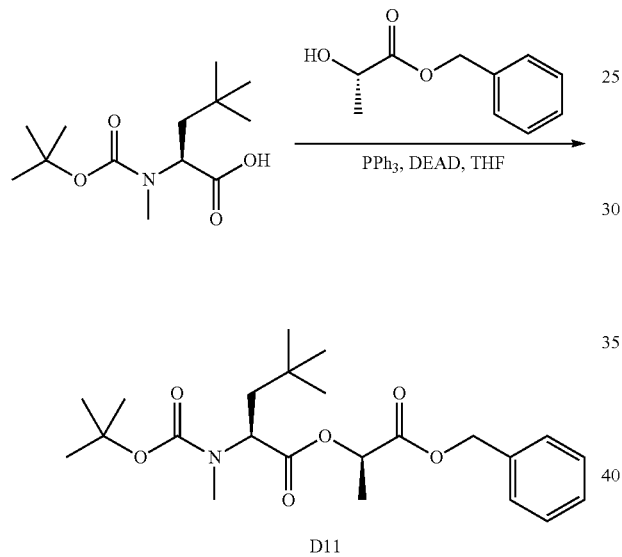

(2R)-1-(benzyloxy)-1-oxopropan-2-yl-(2S)-2-[[(tert-butoxy)carbonyl](methyl)amino]-4,4-dimethylpentanoate (D11)

Into a 1000-mL 3-necked round-bottom flask purged and maintained with an inert atmosphere of nitrogen, was placed a solution of (2S)-2-[[(tert-butoxy)carbonyl](methyl)amino]-4,4-dimethylpentanoic acid (18 g, 69.41 mmol, 1.00 equiv) in tetrahydrofuran (500 mL), benzyl (2S)-2-hydroxypropanoate (12.5 g, 69.37 mmol, 1.00 equiv), PPh$_3$ (22 g, 83.88 mmol, 1.20 equiv). This was followed by the addition of DEAD (14.5 g, 83.26 mmol, 1.20 equiv) dropwise with stirring at 0° C. The resulting solution was stirred for 2 h at room temperature in an ice/salt bath. The resulting mixture was concentrated under vacuum. The resulting solution was diluted with 1000 mL of EA. The resulting mixture was washed with 2×1000 mL of brine. The organic layer was collected and dried over anhydrous sodium sulfate. The solids were filtered out. The filtrate was concentrated under vacuum. The residue was applied onto a silica gel column with ethyl acetate/petroleum ether (1:20-1:10). This resulted in 25.3 g (86%) of (2R)-1-(benzyloxy)-1-oxopropan-2-yl-(2S)-2-[[(tert-butoxy)carbonyl](methyl)amino]-4,4-dimethylpentanoate as yellow oil. MS (ES, m/z): 422 (M+H); $^1$H NMR (300 MHz, CDCl$_3$): δ 7.40-7.33 (m, 5H), 5.23-4.79 (m, 4H), 2.75 (d, J=8.4 Hz, 3H), 1.85-1.61 (m, 2H), 1.59-1.52 (m, 3H), 1.47 (s, 9H), 0.95 (s, 9H).

Preparation Example 39: Preparation of Dimer D12

Dimer D12 was prepared by the reaction shown below.

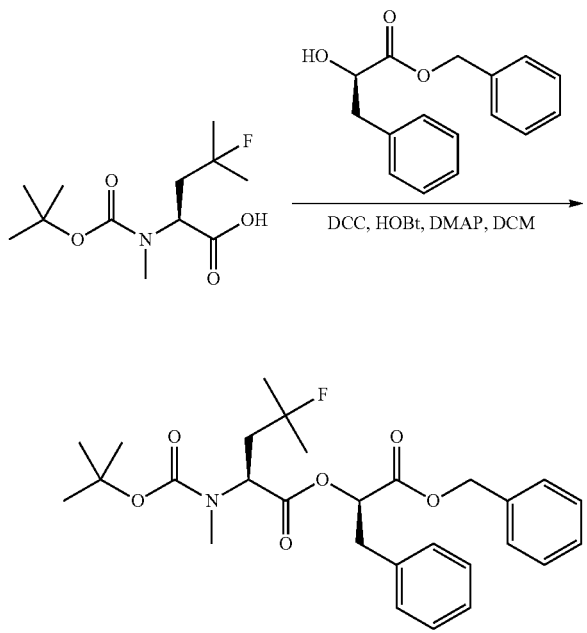

(2R)-1-(benzyloxy)-1-oxo-3-phenylpropan-2-yl-(2S)-2-[[(tert-butoxy)carbonyl](methyl) amino]-4-fluoro-4-methylpentanoate (D12)

Into a 250-mL 3-necked round-bottom flask purged and maintained with an inert atmosphere of nitrogen, was placed a solution of (2S)-2-[[(tert-butoxy)carbonyl](methyl)amino]-4-fluoro-4-methylpentanoic acid (1.2 g, 4.56 mmol, 1.00 equiv) in dichloromethane (100 mL), benzyl (2R)-2-hydroxy-3-phenylpropanoate (1.17 g, 4.57 mmol, 1.00 equiv). This was followed by the addition of DCC (1.13 g, 5.48 mmol, 1.20 equiv), HOBT (740 mg, 5.48 mmol, 1.20 equiv) and 4-dimethylaminopyridine (670 mg, 5.48 mmol, 1.20 equiv) respectively in portions with stirring at 0° C. The resulting solution was stirred for 2 h at room temperature. The resulting mixture was concentrated under vacuum. The residue was applied onto a silica gel column with ethyl acetate/petroleum ether (1:10). This resulted in 1.52 g (66%) of (2R) 1-(benzyloxy)-1-oxo-3-phenylpropan-2-yl-(2S)-2-[[(tert-butoxy)carbonyl](methyl)amino]-4-fluoro-4-methylpentanoate as colorless oil. MS (ES, m/z): 502 (M+H).

Preparation Example 40: Preparation of Dimer D13

Dimer D13 was prepared by the reaction shown below.

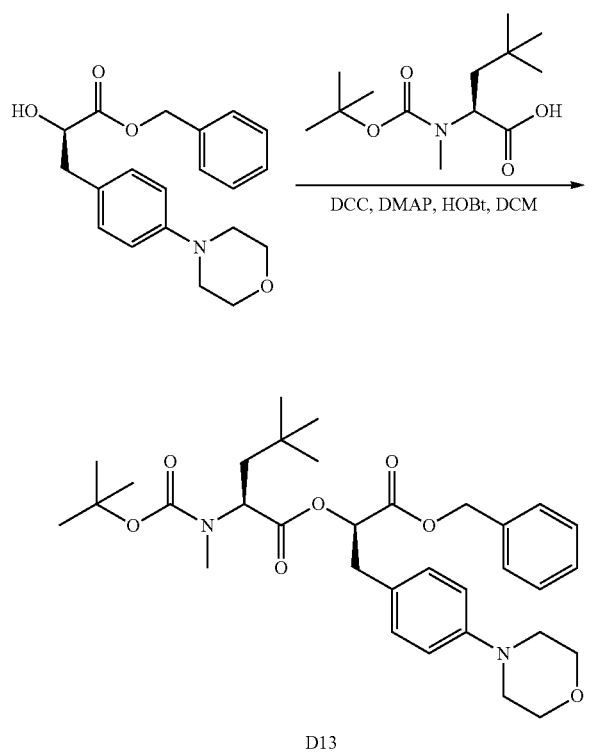

D13

(2R)-1-(benzyloxy)-3-[4-(morpholin-4-yl)phenyl]-1-oxopropan-2-yl-(2S)-2-[[(tert-butoxy)carbonyl](methyl)amino]-4,4-dimethylpentanoate (D13)

Into a 250-mL 3-necked round-bottom flask, was placed (2S)-2-[[(tert-butoxy)carbonyl](methyl)amino]-4,4-dimethylpentanoic acid (3.8 g, 14.65 mmol, 1.00 equiv), benzyl (2R)2-hydroxy-3-[4-(morpholin-4-yl)phenyl]propanoate (5 g, 14.65 mmol, 1.00 equiv), dichloromethane (20 mL). This was followed by the addition of DCC (3.3 g, 1.10 equiv), HOBT (2 g, 1.10 equiv), and 4-dimethylaminopyridine (2.2 g, 1.10 equiv) respectively in portions with stirring at 0° C. The resulting solution was stirred for 14 h at room temperature. The solids were filtered out. The filtrate was concentrated under vacuum. The residue was applied onto a silica gel column with ethyl acetate/petroleum ether (1:10). This resulted in 6.5 g (76%) of (2R)1-(benzyloxy)-3-[4-(morpholin-4-yl)phenyl]-1-oxopropan-2-yl (2S)-2-[[(tert-butoxy)carbonyl](methyl)amino]-4,4-dimethylpentanoate as a white solid. MS (ES, m/z): 583 (M+H).

Preparation Example 41: Preparation of Dimer D14

Dimer D14 was prepared by the reaction shown below.

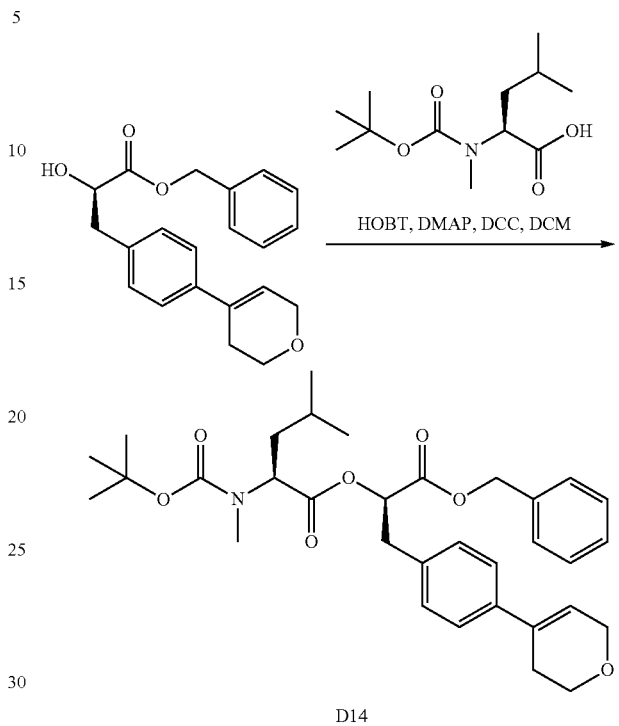

D14

(2R)-1-(benzyloxy)-3-[4-(3,6-dihydro-2H-pyran-4-yl)phenyl]-1-oxopropan-2-yl-(2S)-2-[[(tert-butoxy)carbonyl](methyl)amino]-4-methylpentanoate (D14)

Into a 1000-mL round-bottom flask, was placed dichloromethane (200 mL), benzyl (2R)-3-[4-(3,6-dihydro-2H-pyran-4-yl)phenyl]-2-hydroxypropanoate (12 g, 35.46 mmol, 1.00 equiv), (2S)-2-[[(tert-butoxy)carbonyl](methyl)amino]-4-methylpentanoic acid (10.6 g, 43.21 mmol, 1.22 equiv), HOBT (6 g, 44.40 mmol, 1.25 equiv), DCC (9 g, 43.62 mmol, 1.23 equiv), 4-dimethylaminopyridine (6 g, 49.11 mmol, 1.38 equiv). The resulting solution was stirred for 2 h at room temperature. The solids were filtered out. The filtrate concentrated under vacuum. The filtrate was applied onto a silica gel column with ethyl acetate/petroleum ether (1:5). This resulted in 18.0 g (90%) of (2R)-1-(benzyloxy)-3-[4-(3,6-dihydro-2H-pyran-4-yl)phenyl]-1-oxopropan-2-yl-(2S)-2-[[(tert-butoxy)carbonyl](methyl)amino]-4-methylpentanoate as light yellow oil. MS (ES, m/z): 566 (M+H)

Preparation Example 42: Preparation of Dimer D15

Dimer D15 was prepared by the reaction shown below.

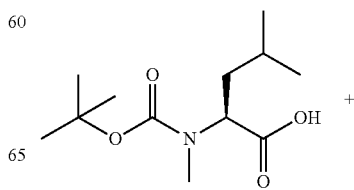

-continued

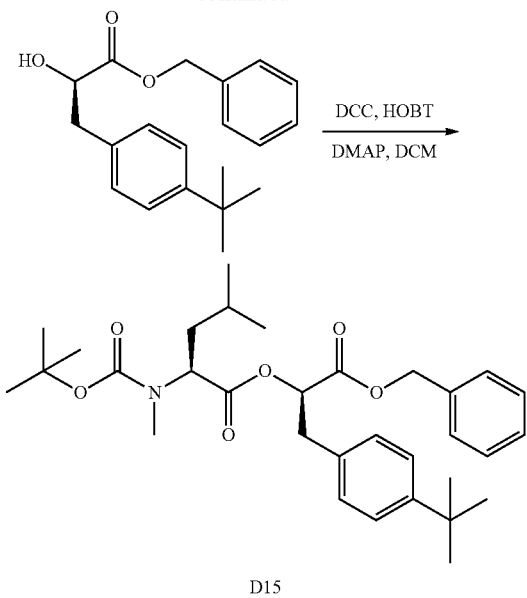

D15

(2R)-1-(benzyloxy)-3-(4-tert-butylphenyl)-1-oxopropan-2-yl-(2S)-2-[[(tert-butoxy)carbonyl](methyl)amino]-4-methylpentanoate (D15)

Into a 250-mL round-bottom flask, was placed a solution of benzyl (2R)-3-(4-tert-butylphenyl)-2-hydroxypropanoate (5.3 g, 16.97 mmol, 1.00 equiv) in dichloromethane (90 mL), (2S)-2-[[(tert-butoxy)carbonyl](methyl)amino]-4-methylpentanoic acid (4.2 g, 17.12 mmol, 1.00 equiv). This was followed by the addition of DCC (3.85 g, 18.66 mmol, 1.10 equiv), HOBT (2.52 g, 18.65 mmol, 1.10 equiv) and 4-dimethylaminopyridine (2.28 g, 18.66 mmol, 1.10 equiv) respectively in portions with stirring at 0° C. The resulting solution was stirred overnight at room temperature. The solids were filtered out. The filtrate was concentrated under vacuum. The residue was applied onto a silica gel column with ethyl acetate/petroleum ether (1:8). This resulted in 10 g (crude) of (2R)1-(benzyloxy)-3-(4-tert-butylphenyl)-1-oxopropan-2-yl-(2S)-2-[[(tert-butoxy)carbonyl](methyl)amino]-4-methylpentanoate as light yellow oil. MS (ES, m/z): 562 (M+Na).

Preparation Example 43: Preparation of Dimer D16

Dimer D16 was prepared by the reaction shown below.

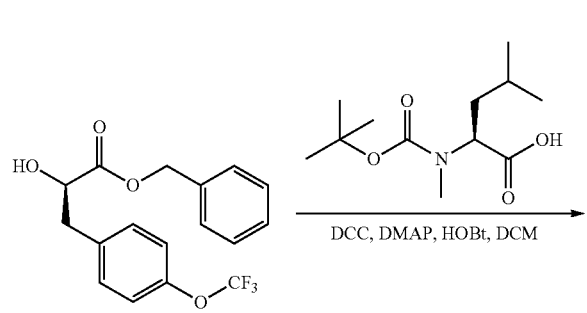

-continued

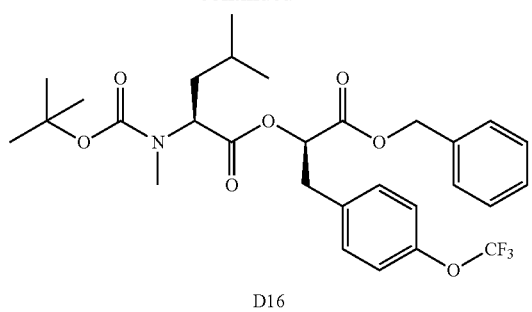

D16

(2R)-1-(benzyloxy)-1-oxo-3-[4-(trifluoromethoxy)phenyl]propan-2-yl-(2S)-2-[[(tert-butoxy)carbonyl](methyl)amino]-4-methylpentanoate (D16)

Into a 250-mL 3-necked round-bottom flask, was placed benzyl (2R)-2-hydroxy-3-[4-(trifluoromethoxy)phenyl]propanoate (4.0 g, 11.75 mmol, 1.00 equiv), (2S)-2-[[(tert-butoxy)carbonyl](methyl)amino]-4-methylpentanoic acid (2.94 g, 11.98 mmol, 1.00 equiv), dichloromethane (100 mL). This was followed by the addition of DCC (2.72 g, 13.18 mmol, 1.10 equiv), 4-dimethylaminopyridine (1.61 g, 13.18 mmol, 1.10 equiv) and HOBt (1.78 g, 13.17 mmol, 1.10 equiv) respectively in portions with stirring at 0° C. The resulting solution was stirred overnight at room temperature. The solids were filtered out. The filtrate was concentrated under vacuum. The residue was applied onto a silica gel column with ethyl acetate/petroleum ether (1:30). This resulted in 4.5 g (67%) of (2R)-1-(benzyloxy)-1-oxo-3-[4-(trifluoromethoxy)phenyl]propan-2-yl-(2S)-2-[[(tert-butoxy)carbonyl](methyl)amino]-4-methylpentanoate as yellow oil. MS (ES, m/z): 568 (M+H).

Preparation Example 44: Preparation of Dimer D17

Dimer D17 was prepared by the reaction shown below.

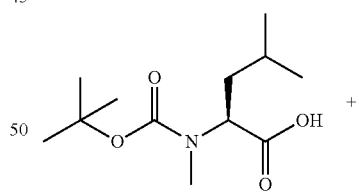

+

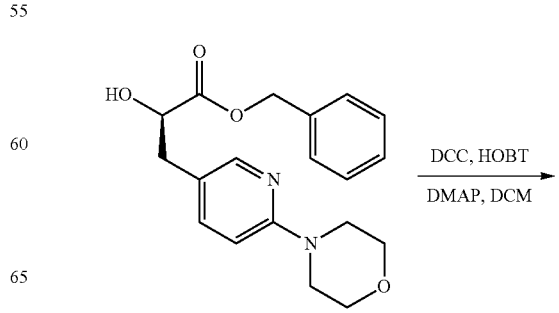

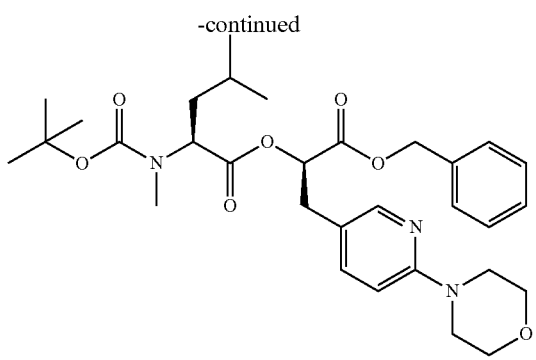

D17

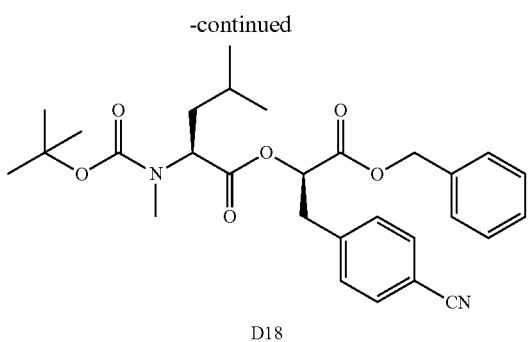

D18

(2R)-1-(benzyloxy)-3-[6-(morpholin-4-yl)pyridin-3-yl]-1-oxopropan-2-yl-(2S)-2-[[(tert-butoxy)carbonyl](methyl)amino]-4-methylpentanoate (D17)

Into a 100-mL round-bottom flask, was placed a solution of benzyl (2R)-2-hydroxy-3-[6-(morpholin-4-yl)pyridin-3-yl]propanoate (1.36 g, 3.97 mmol, 1.00 equiv), (2S)-2-[(tert-butoxy)carbonyl](methyl)amino-4-methylpentanoic acid (980 mg, 3.99 mmol, 1.00 equiv) in dichloromethane (40 mL). This was followed by the addition of DCC (900 mg, 4.36 mmol, 1.10 equiv), 4-dimethylaminopyridine (540 mg, 4.42 mmol, 1.10 equiv) and HOBT (740 mg, 5.48 mmol, 1.10 equiv) respectively in portions with stirring at 0° C. The resulting solution was stirred overnight at room temperature. The solids were filtered out. The filtrate was concentrated under vacuum. The residue was applied onto a silica gel column with ethyl acetate/petroleum ether (1:5). This resulted in 1.2572 g (56%) of (2R)-1-(benzyloxy)-3-[6-(morpholin-4-yl)pyridin-3-yl]-1-oxopropan-2-yl-(2S)-2-[[(tert-butoxy)carbonyl](methyl)amino]-4-methylpentanoate as a off-white solid. MS (ES, m/z): 570 (M+H); $^1$H NMR (300 MHz, CDCl$_3$): δ 8.01 (s, 1H), 7.39-7.33 (m, 4H), 7.30-7.28 (m, 2H), 6.59-6.56 (m, 1H), 5.23-5.19 (m, 1H), 5.14 (s, 2H), 5.05-4.99 (m, 0.5H), 4.78-4.73 (m, 0.5H), 3.85-3.82 (m, 4H), 3.49 (br, 4H), 3.10-2.95 (m, 2H), 2.68 (d, J=10.8 Hz, 3H), 1.64-1.57 (m, 3H), 1.48 (d, J=12.9 Hz, 9H), 0.97-0.91 (m, 6H).

Preparation Example 45: Preparation of Dimer D18

Dimer D18 was prepared by the reaction shown below.

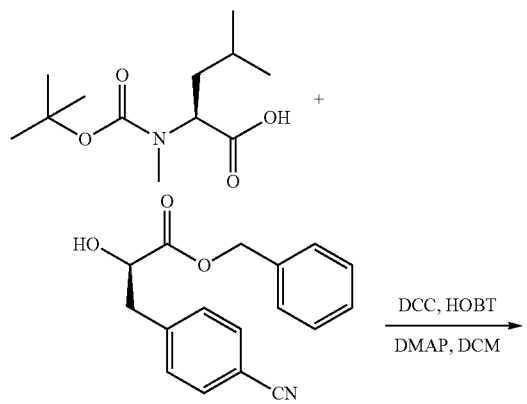

(2R)-1-(benzyloxy)-3-(4-cyanophenyl)-1-oxopropan-2-yl-(2S)-2-[[(tert-butoxy)carbonyl](methyl)amino]-4-methylpentanoate (D18)

Into a 100-mL 3-necked round-bottom flask, was placed benzyl (2R)-3-(4-cyanophenyl)-2-hydroxypropanoate (2 g, 7.11 mmol, 1.00 equiv), (2S)-2-[[(tert-butoxy)carbonyl](methyl)amino]-4-methylpentanoic acid (2.3 g, 9.38 mmol, 1.30 equiv), dichloromethane (40 mL). This was followed by the addition of DCC (1.6 g, 7.75 mmol, 1.10 equiv), 4-dimethylaminopyridine (960 mg, 7.86 mmol, 1.10 equiv) and HOBT (1.1 g, 8.14 mmol, 1.10 equiv) respectively in portions with stirring at 0° C. The resulting solution was stirred for 17 h at room temperature. The solids were filtered out. The filtrate was concentrated under vacuum. The residue was applied onto a silica gel column with ethyl acetate/petroleum ether (1:10). This resulted in 3.3 g (91%) of (2R)-1-(benzyloxy)-3-(4-cyanophenyl)-1-oxopropan-2-yl (2S)-2-[[(tert-butoxy)carbonyl](methyl)amino]-4-methylpentanoate as a white solid. MS (ES, m/z): 509 (M+H).

Preparation Example 46: Preparation of Dimer D19

Dimer D19 was prepared by the reaction shown below.

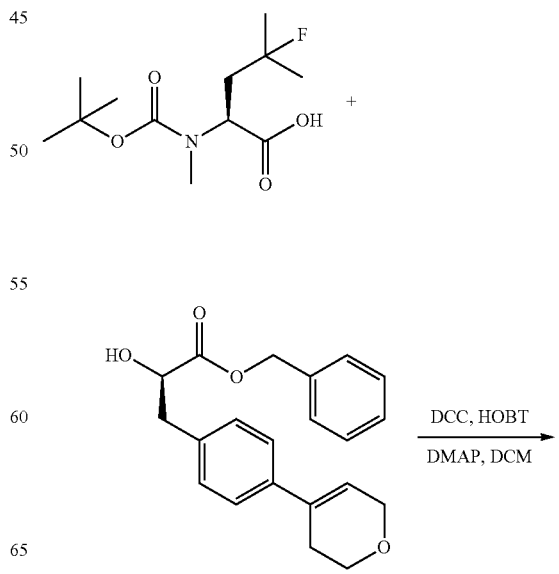

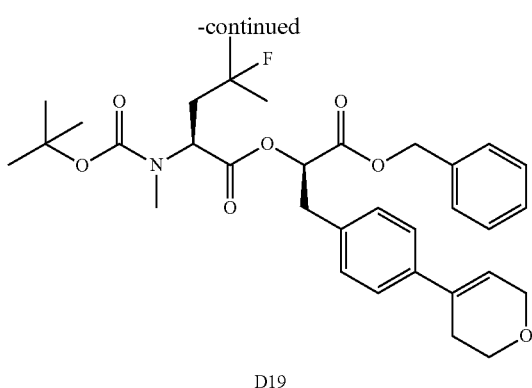

D19

(2R)-1-(benzyloxy)-3-[4-(3,6-dihydro-2H-pyran-4-yl)phenyl]-1-oxopropan-2-yl-(2S)-2-[[(tert-butoxy)carbonyl](methyl)amino]-4-fluoro-4-methylpentanoate (D19)

Into a 500-mL round-bottom flask, was placed dichloromethane (400 mL), (2S)-2-[[(tert-butoxy)carbonyl](methyl)amino]-4-fluoro-4-methylpentanoic acid (20 g, 75.96 mmol, 1.00 equiv), benzyl (2R)-3-[4-(3,6-dihydro-2H-pyran-4-yl)phenyl]-2-hydroxypropanoate (25.8 g, 76.24 mmol, 1.00 equiv). This was followed by the addition of HOBT (12 g, 88.81 mmol, 1.15 equiv), DCC (18 g, 87.24 mmol, 1.15 equiv) and 4-dimethylaminopyridine (10.7 g, 87.58 mmol, 1.15 equiv) respectively in portions with stirring at 0° C. The resulting solution was stirred for 4 h at room temperature. The solids were filtered out. The filtrate was concentrated under vacuum. The residue was applied onto a silica gel column with ethyl acetate/petroleum ether (1:10-1:5). This resulted in 80 g (90%) of (2R)-1-(benzyloxy)-3-[4-(3,6-dihydro-2H-pyran-4-yl)phenyl]-1-oxopropan-2-yl (2S)-2-[[(tert-butoxy)carbonyl](methyl)amino]-4-fluoro-4-methylpentanoate as colorless oil. MS (ES, m/z): 584 (M+H); $^1$H NMR (300 MHz, CDCl$_3$): δ 7.37-7.16 (m, 7H), 7.14 (d, J=8.4 Hz, 2H), 6.12 (s, 1H), 5.28-5.25 (m, 1H), 5.15-5.13 (m, 2H), 5.12-4.81 (m, 1H), 4.35-4.33 (m, 2H), 3.95 (t, J=8.7 Hz, 2H), 3.18-3.14 (m, 2H), 2.68 (d, J=12.9 Hz, 3H), 2.53-2.49 (m, 2H), 2.22-2.10 (m, 1H), 2.06-1.85 (m, 1H), 1.48 (d, J=16.8 Hz, 9H), 1.39 (s, 3H), 1.32 (s, 3H).

Preparation Example 47: Preparation of Dimer D20

Dimer D20 was prepared by the process shown in Scheme 28 below.

Scheme 28

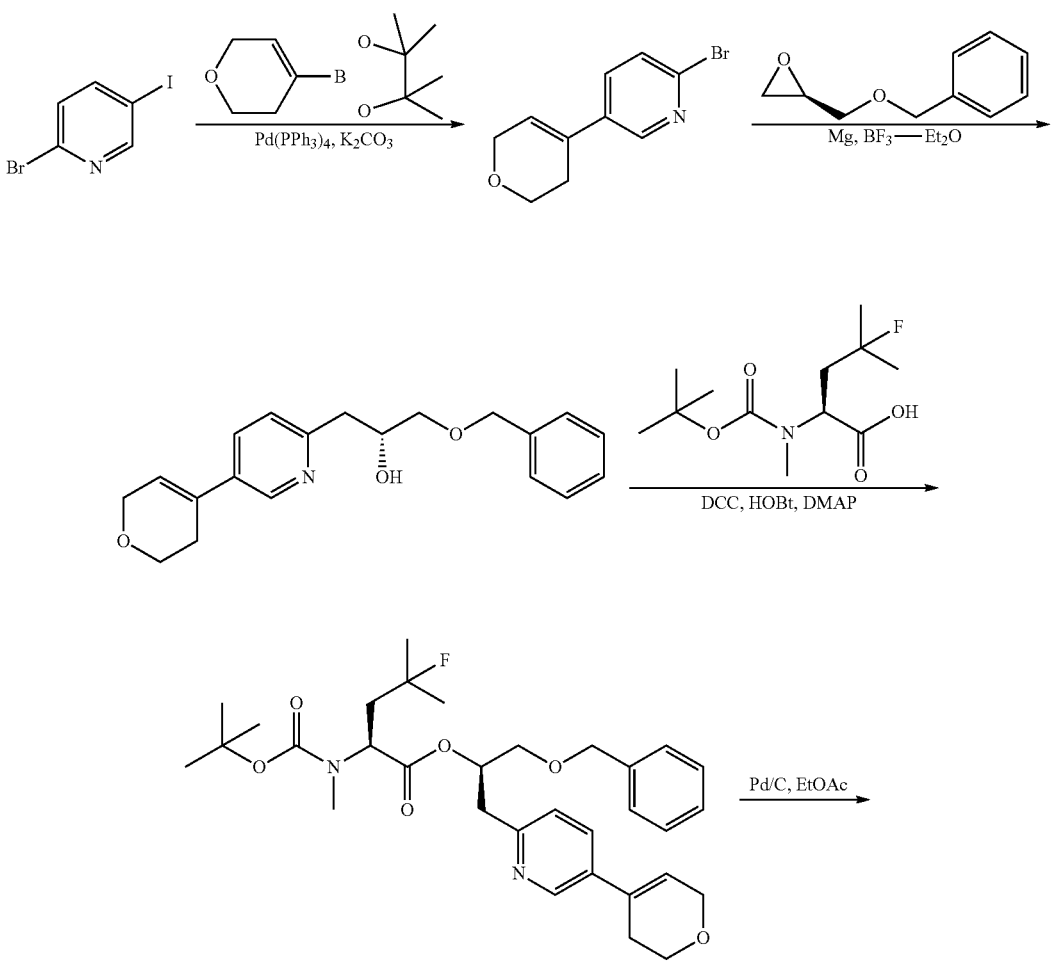

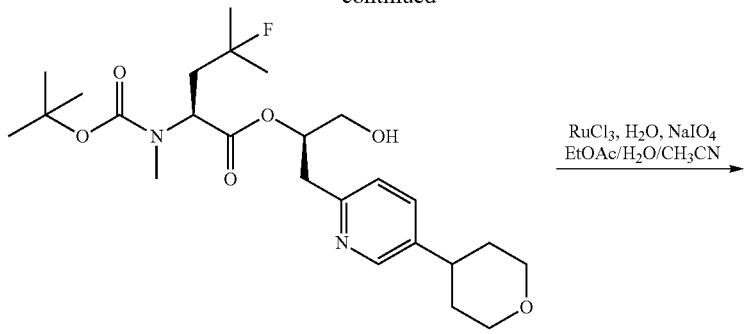

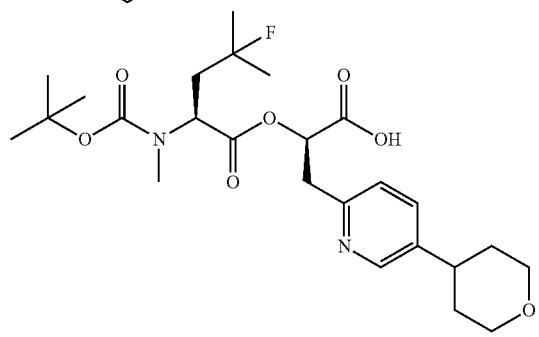

D20

Experimental Details

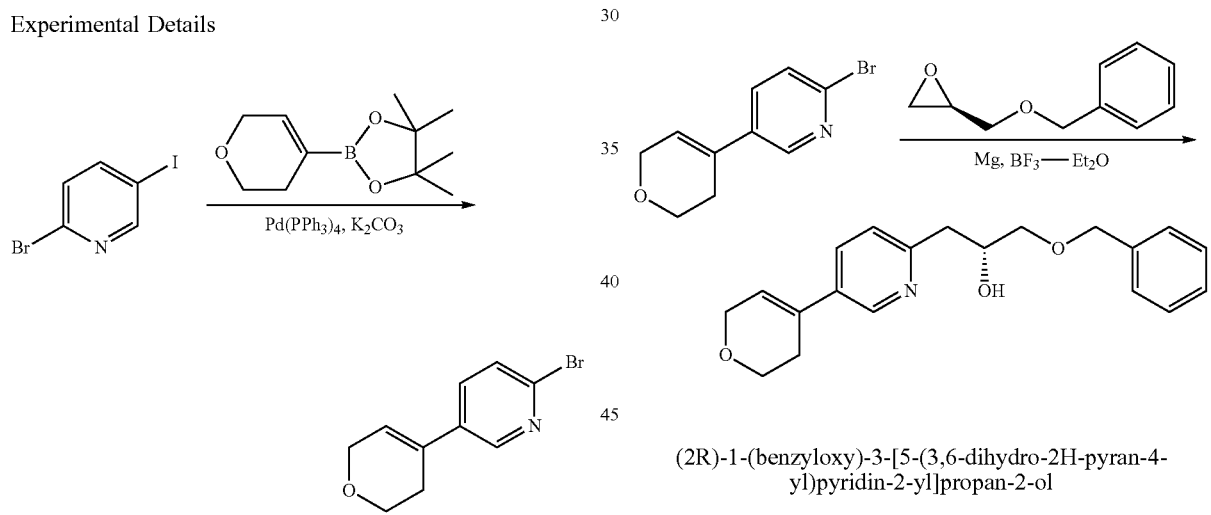

2-bromo-5-(3,6-dihydro-2H-pyran-4-yl)pyridine

Into a 50-mL round-bottom flask purged and maintained with an inert atmosphere of nitrogen, was placed dioxane (2 mL), water (1 mL), 2-bromo-5-iodopyridine (100 mg, 0.35 mmol, 1.00 equiv), 2-(3,6-dihydro-2H-pyran-4-yl)-4,4,5,5-tetramethyl-1,3,2-dioxaborolane (104 mg, 0.50 mmol, 1.30 equiv), potassium carbonate (120 mg, 0.86 mmol, 3.00 equiv), Pd(PPh$_3$)$_4$ (40 mg, 0.03 mmol, 0.10 equiv). The resulting solution was stirred overnight at 80° C. in an oil bath. The reaction mixture was cooled and concentrated under vacuum. The residue was purified by preparative TLC (EtOAc:PE=1:1). This resulted in 50 mg (59%) of 2-bromo-5-(3,6-dihydro-2H-pyran-4-yl)pyridine as colorless oil. MS (ES, m/z): 240 (M+H).

(2R)-1-(benzyloxy)-3-[5-(3,6-dihydro-2H-pyran-4-yl)pyridin-2-yl]propan-2-ol

Into a 250-mL 3-necked round-bottom flask, was placed tetrahydrofuran (200 mL), 2-bromo-5-(3,6-dihydro-2H-pyran-4-yl)pyridine (4 g, 16.66 mmol, 1.00 equiv). This was followed by the addition of butyllithium (8.7 mL, 1.30 equiv) dropwise with stirring at −78° C. To this was added BF$_3$.Et$_2$O (2.8 mL, 1.00 equiv) at −78° C. To the mixture was added a solution of (2R)-2-[(benzyloxy)methyl]oxirane (3.6 g, 21.92 mmol, 1.30 equiv) in tetrahydrofuran (10 mL) at −78° C. The resulting solution was stirred for 1.5 h at −78° C. The reaction was then quenched by the addition of 100 mL of NH$_4$Cl(aq). The resulting solution was extracted with 3×100 mL of ethyl acetate and the organic layers combined. The organic layer was washed with 3×50 mL of brine. The organic layer was collected and dried over anhydrous sodium sulfate and concentrated under vacuum. The residue was applied onto a silica gel column with ethyl acetate/petroleum ether (1:1). This resulted in 2 g (37%) of (2R)-1-(benzyloxy)-3-[5-(3,6-dihydro-2H-pyran-4-yl)pyridin-2-yl]propan-2-ol as a yellow solid. MS (ES, m/z): 326 (M+H).

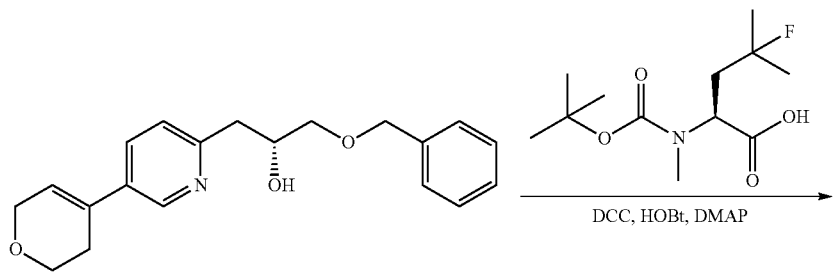

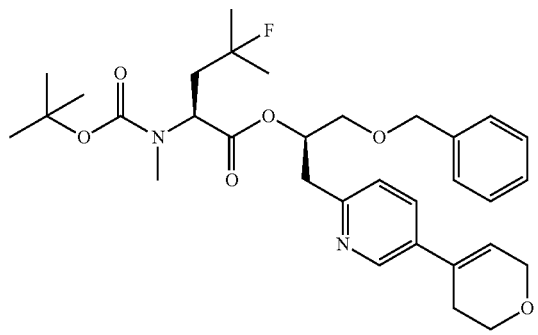

(2R)-1-(benzyloxy)-3-[5-(3,6-dihydro-2H-pyran-4-yl)pyridin-2-yl]propan-2-yl-(2S)-2-[[(tert-butoxy)carbonyl](methyl)amino]-4-fluoro-4-methylpentanoate Into a 100-mL round-bottom flask purged and maintained with an inert atmosphere of nitrogen, was placed dichloromethane (50 mL), (2R)-1-(benzyloxy)-3-[5-(3,6-dihydro-2H-pyran-4-yl)pyridin-2-yl]propan-2-ol (1.84 g, 5.65 mmol, 1.00 equiv), (2S)-2-[(tert-butoxy)carbonyl](methyl)amino]-4-fluoro-4-methylpentanoic acid (3.4 g, 12.91 mmol, 2.50 equiv). This was followed by the addition of 4-dimethylaminopyridine (1.4 g, 11.46 mmol, 2.00 equiv), HOBT (1.5 g, 47.11 mmol, 2.00 equiv) and DCC (2.3 g, 85.05 mmol, 2.00 equiv) respectively in portions with stirring at 0° C. The resulting solution was stirred overnight at room temperature. The resulting mixture was concentrated under vacuum. The residue was applied onto a silica gel column with ethyl acetate/petroleum ether (1:1). This resulted in 4.0 g of (2R)-1-(benzyloxy)-3-[5-(3,6-dihydro-2H-pyran-4-yl)pyridin-2-yl]propan-2-yl (2S)-2-[[(tert-butoxy)carbonyl](methyl)amino]-4-fluoro-4-methylpentanoate as a yellow solid. MS (ES, m/z): 571 (M+H).

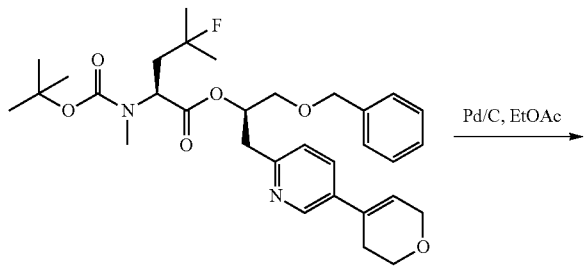

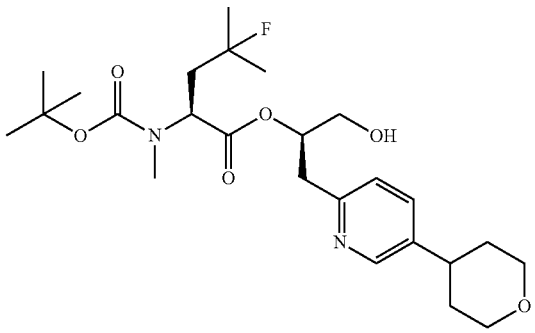

(2R)-1-hydroxy-3-[5-(oxan-4-yl)pyridin-2-yl]propan-2-yl-(2S)-2-[[(tert-butoxy)carbonyl](methyl)amino]-4-fluoro-4-methylpentanoate Into a 250-mL round-bottom flask, was placed Pd(OH)$_2$/C (4 g), (2R)-1-(benzyloxy)-3-[5-(3,6-dihydro-2H-pyran-4-yl)pyridin-2-yl]propan-2-yl (2S)-2-[[(tert-butoxy)carbonyl](methyl)amino]-4-fluoro-4-methylpentanoate (4 g, 7.01 mmol, 1.00 equiv). This was followed by the addition of ethyl acetate (100 mL). To the above hydrogen was introduced. The resulting solution was stirred for 8 h at room temperature. The solid was filtered out. The filtrate was concentrated under vacuum. The residue was applied onto a silica gel column with ethyl acetate/petroleum ether (1:1). This resulted in 800 mg of (2R)-1-hydroxy-3-[5-(oxan-4-yl)pyridin-2-yl]propan-2-yl-(2S)-2-[[(tert-butoxy)carbonyl](methyl)amino]-4-fluoro-4-methylpentanoate as a brown solid. MS (ES, m/z): 483 (M+H).

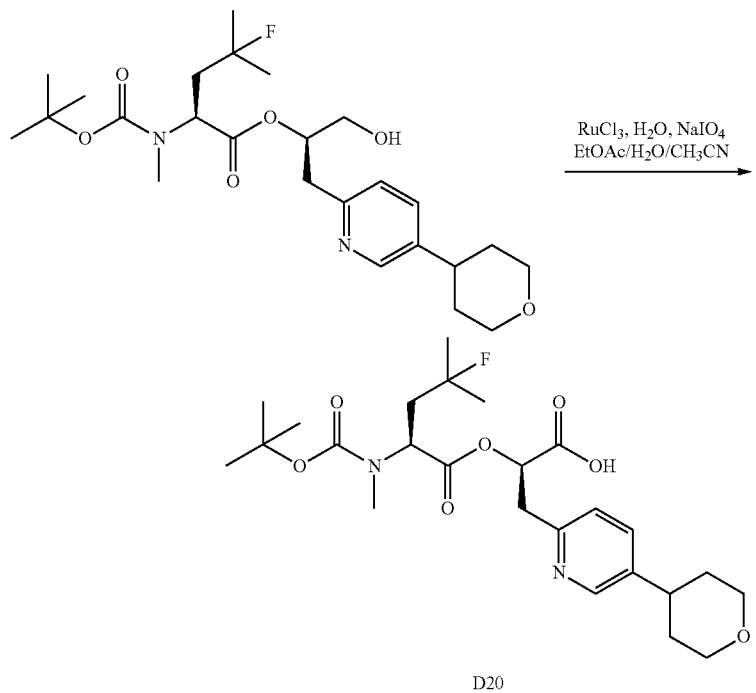

D20

(2R)-2-[(2S)-2-[tert-butoxycarbonyl(methyl)amino]-4-fluoro-4-methyl-pentanoyl]oxy-3-(5-tetrahydropyran-4-yl-2-pyridyl)propanoic acid Into a 8-mL vial, was placed (2R)-1-hydroxy-3-[5-(oxan-4-yl)pyridin-2-yl]propan-2-yl-(2S)-2-[[(tert-butoxy)carbonyl](methyl) amino]-4-fluoro-4-methylpentanoate (20 mg, 0.04 mmol, 1.00 equiv), CH$_3$CN (1 mL), chloroform (1 mL), water (2 mL), sodium periodate (44 mg, 0.21 mmol, 5.00 equiv), trichlororuthenium (1 mg, 0.10 equiv). The resulting solution was stirred for 2 h at room temperature. MS (ES, m/z): 497 (M+H).

Preparation Example 48: Preparation of Dimer D21

Dimer D21 was prepared by the reaction shown below.

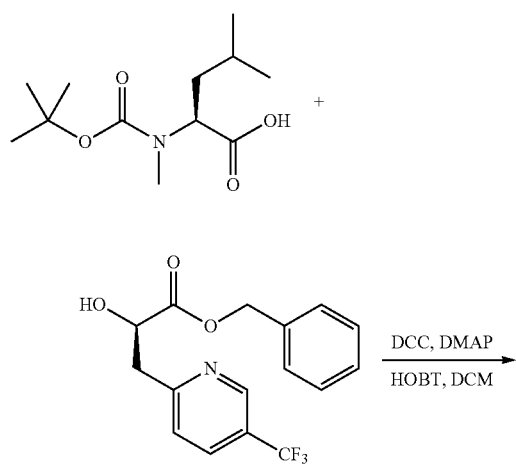

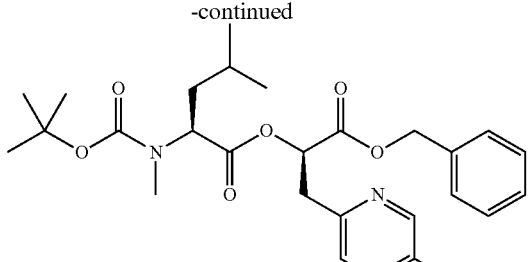

D21

(2R)-1-(benzyloxy)-1-oxo-3-[5-(trifluoromethyl)pyridin-2-yl]propan-2-yl-(2S)-2-[[(tert-butoxy)carbonyl](methyl)amino]-4-methylpentanoate (D21)

Into a 50-mL round-bottom flask, was placed benzyl (2R)-2-hydroxy-3-[5-(trifluoromethyl)pyridin-2-yl]propanoate (500 mg, 1.54 mmol, 1.00 equiv), (2S)-2-[[(tert-butoxy)carbonyl](methyl)amino]-4-methylpentanoic acid (489.9 mg, 2.00 mmol, 1.30 equiv), 4-dimethylaminopyridine (206.4 mg, 1.69 mmol, 1.10 equiv), HOBT (230.1 mg, 1.70 mmol, 1.11 equiv), dichloromethane (10 mL). This was followed by the addition of DCC (348.5 mg, 1.69 mmol, 1.10 equiv) in portions at 0° C. The resulting solution was stirred for 12 h at 0-25° C. The solids were filtered out. The filtrate was concentrated under vacuum. The residue was applied onto a silica gel column with ethyl acetate/petroleum ether (1:5). The collected fractions were combined and concentrated under vacuum. This resulted in 281.2 mg (33%) of (2R)-1-(benzyloxy)-1-oxo-3-[5-(trifluoromethyl)pyridin-2-yl]propan-2-yl (2S)-2-[[(tert-butoxy)carbonyl](methyl)amino]-4-methylpentanoate as light yellow oil. MS (ES, m/z): 553 (M+H).

Preparation Example 49: Preparation of Dimer D22

Dimer D22 was prepared by the reaction shown below.

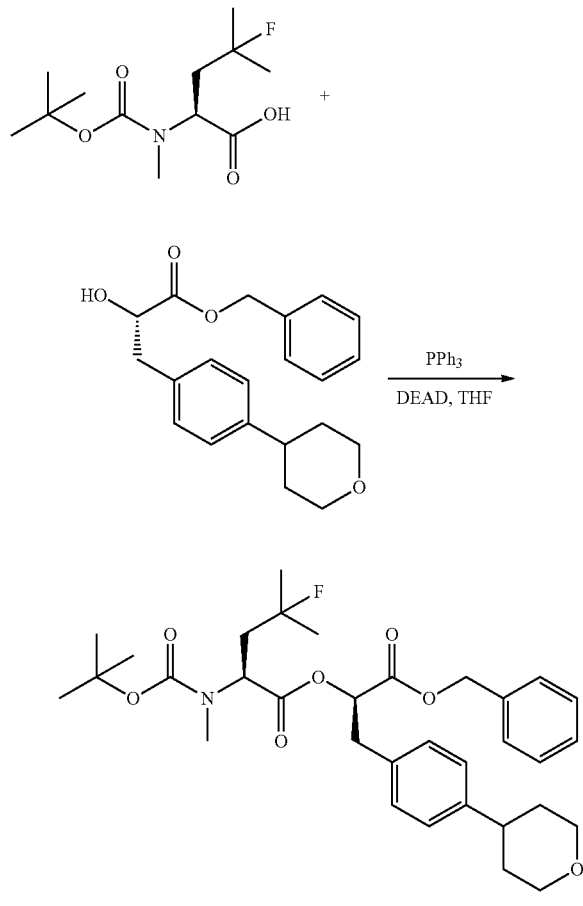

D22

(2R)-1-(benzyloxy)-3-[6-(oxan-4-yl)pyridin-3-yl]-1-oxopropan-2-yl (2S)-2-[[(tert-butoxy)carbonyl](methyl)amino]-4-fluoro-4-methylpentanoate (D22)

Into a 50-mL round-bottom flask, was placed tetrahydrofuran (5 mL), benzyl (2S)-2-hydroxy-3-[6-(oxan-4-yl)pyridin-3-yl]propanoate (900 mg, 2.64 mmol, 1.00 equiv), (2S)-2-[(tert-butoxy)carbonyl](methyl)amino-4-fluoro-4-methylpentanoic acid (1.1 g, 4.18 mmol, 1.58 equiv), PPh3 (1.7 g, 6.48 mmol, 2.46 equiv), DEAD (1.3 g, 7.46 mmol, 2.83 equiv). The resulting solution was stirred for 3 h at room temperature. The resulting mixture was concentrated under vacuum. The residue was applied onto a silica gel column with ethyl acetate/petroleum ether (1:1). This resulted in 1.7 g of (2R)-1-(benzyloxy)-3-[6-(oxan-4-yl)pyridin-3-yl]-1-oxopropan-2-yl-(2S)-2-[[(tert-butoxy)carbonyl](methyl)amino]-4-fluoro-4-methylpentanoate as a white solid. MS (ES, m/z): 587 (M+H); $^1$HNMR (300 MHz, CDCl$_3$): δ 8.38 (s, 1H), 7.50-7.49 (br, 1H), 7.37-7.31 (m, 5H), 7.12 (br, 1H), 5.32-5.12 (m, 3H), 4.92-4.63 (m, 1H), 4.13-4.09 (m, 2H), 3.61-3.56 (m, 2H), 3.17-3.16 (m, 2H), 2.98 (br, 1H), 2.74-2.66 (m, 3H), 2.29-1.96 (m, 2H), 1.87-1.85 (4H), 1.51-1.27 (m, 15)

Preparation Example 50: Preparation of Dimer D23

Dimer D23 was prepared by the reaction shown below.

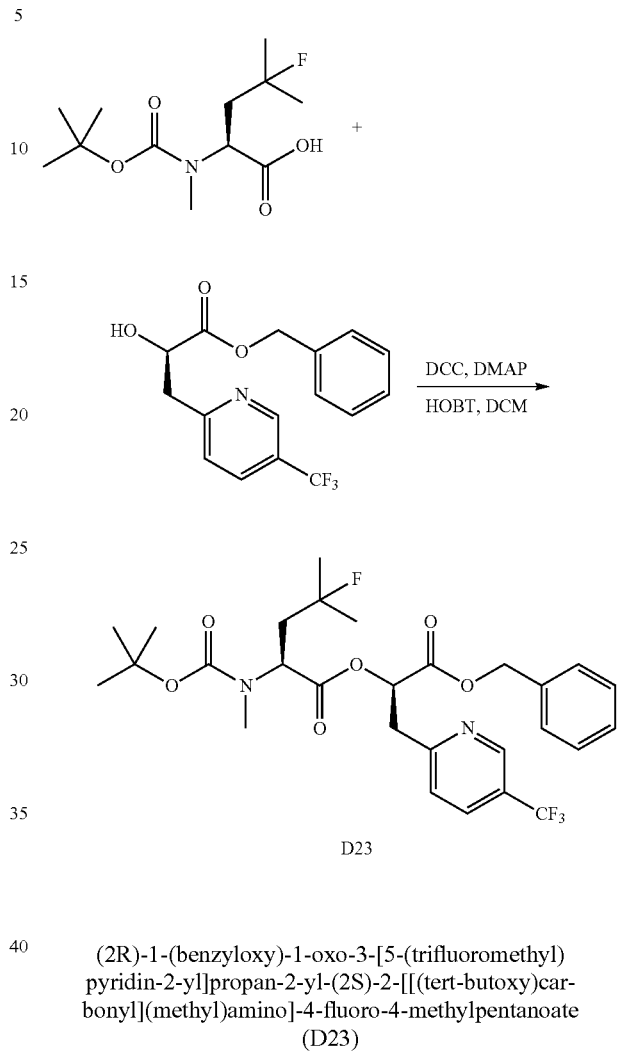

D23

(2R)-1-(benzyloxy)-1-oxo-3-[5-(trifluoromethyl)pyridin-2-yl]propan-2-yl-(2S)-2-[[(tert-butoxy)carbonyl](methyl)amino]-4-fluoro-4-methylpentanoate (D23)

Into a 50-mL round-bottom flask, was placed (2S)-2-[[(tert-butoxy)carbonyl](methyl)amino]-4-fluoro-4-methylpentanoic acid (526 mg, 2.00 mmol, 1.30 equiv), benzyl (2R)-2-hydroxy-3-[5-(trifluoromethyl)pyridin-2-yl]propanoate (500 mg, 1.54 mmol, 1.00 equiv), dichloromethane (10 mL). This was followed by addition of 4-dimethylaminopyridine (206.4 mg, 1.69 mmol, 1.10 equiv), HOBT (230.1 mg, 1.70 mmol, 1.10 equiv) and DCC (348.6 mg, 1.69 mmol, 1.10 equiv) respectively in several batches at 0° C. The resulting solution was stirred for 12 h at 25° C. The solids were filtered out. The filtrate was concentrated under vacuum. The residue was applied onto a silica gel column with ethyl acetate/petroleum ether (1:5). The collected fractions were combined and concentrated under vacuum. This resulted in 305 mg (27%) of (2R)-1-(benzyloxy)-1-oxo-3-[5-(trifluoromethyl)pyridin-2-yl]propan-2-yl-(2S)-2-[[(tert-butoxy) carbonyl](methyl)amino]-4-fluoro-4-methylpentanoate as light yellow oil. MS (ES, m/z): 571 (M+H); $^1$H NMR (300 MHz, CDCl$_3$): δ 8.75 (s, 1H), 7.86-7.82 (m, 1H), 7.38-7.28 (m, 6H), 5.63-5.58 (m, 1H), 5.31-5.17 (m, 2H), 5.12-4.71 (m, 1H), 3.48-3.45 (m, 2H), 2.69 (d, J=11.7 Hz, 2H), 2.29-1.83 (m, 2H), 1.45-1.27 (m, 15H).

Preparation Example 51: Preparation of Dimer D24

Dimer D24 was prepared by the reaction shown below.

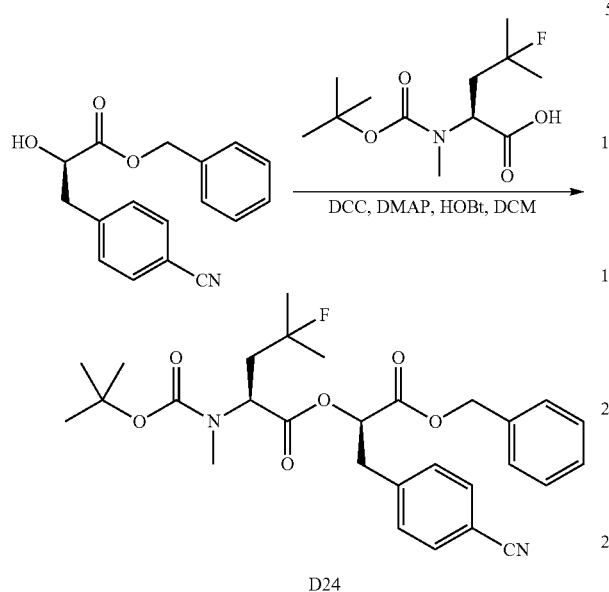

(2R)-1-(benzyloxy)-1-oxo-3-[5-(trifluoromethyl) pyridin-2-yl]propan-2-yl (2S)-2-[[(tert-(2R)-1-(benzyloxy)-3-(4-cyanophenyl)-1-oxopropan-2-yl-(2S)-2-[[(tert-butoxy)carbonyl](methyl) amino]-4-fluoro-4-methylpentanoate (D24)

Into a 100-mL 3-necked round-bottom flask, was placed (2S)-2-[[(tert-butoxy)carbonyl](methyl)amino]-4-fluoro-4-methylpentanoic acid (5.2 g, 19.75 mmol, 1.00 equiv), benzyl (2R)-3-(4-cyanophenyl)-2-hydroxypropanoate (4.25 g, 15.11 mmol, 1.30 equiv), dichloromethane (40 mL). This was followed by the addition of DCC (3.4 g, 16.48 mmol, 1.10 equiv), 4-dimethylaminopyridine (2 g, 16.37 mmol, 1.10 equiv) and HOBt (2.2 g, 16.28 mmol, 1.10 equiv) respectively in portions with stirring at 0° C. The resulting solution was stirred for 17 h at room temperature. The solids were filtered out. The filtrate was concentrated under vacuum. The residue was applied onto a silica gel column with ethyl acetate/petroleum ether (1:10). This resulted in 3.2 g (31%) of (2R)-1-(benzyloxy)-3-(4-cyanophenyl)-1-oxopropan-2-yl-(2S)-2-[[(tert-butoxy)carbonyl](methyl) amino]-4-fluoro-4-methylpentanoate as a white solid. MS (ES, m/z): 527 (M+H).

Preparation Example 52: Preparation of Dimer D25

Dimer D25 was prepared by the reaction shown below.

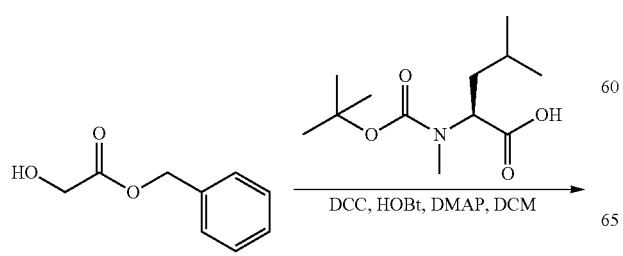

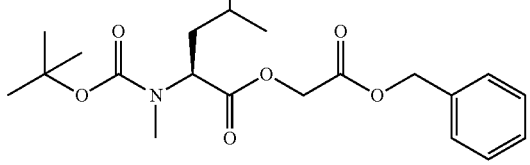

2-(Benzyloxy)-2-oxoethyl-(2S)-2-[[(tert-butoxy) carbonyl](methyl)amino]-4-methyl pentanoate (D25)

Into a 250-mL 3-necked round-bottom flask purged and maintained with an inert atmosphere of nitrogen, was placed a solution of benzyl 2-hydroxyacetate (3.5 g, 21.06 mmol, 1.00 equiv), dichloromethane (100 mL), (2S)-2-[(tert-butoxy)carbonyl](methyl)amino-4-methylpentanoic acid (5.2 g, 21.20 mmol, 1.00 equiv). This was followed by the addition of DCC (5.21 g, 25.25 mmol, 1.20 equiv), HOBT (3.42 g, 25.31 mmol, 1.20 equiv) and 4-dimethylaminopyridine (3.1 g, 25.37 mmol, 1.20 equiv) respectively in portions with stirring at 0° C. The resulting solution was stirred for 2 h at room temperature. The resulting mixture was concentrated under vacuum. The residue was applied onto a silica gel column with ethyl acetate/petroleum ether (1:20-1:5). This resulted in 5.3 g (64%) of 2-(benzyloxy)-2-oxoethyl (2S)-2-[[(tert-butoxy)carbonyl](methyl)amino]-4-methylpentanoate as colorless oil. MS (ES, m/z): 394 (M+H).

Preparation Example 53: Preparation of Dimer D26

Dimer D26 was prepared by the reaction shown below.

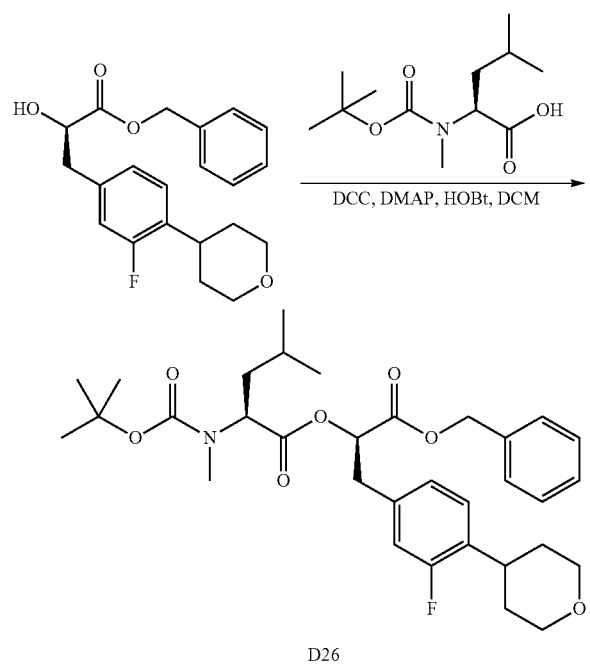

(2R)-1-(benzyloxy)-3-[3-fluoro-4-(oxan-4-yl)phenyl]-1-oxopropan-2-yl-(2S)-2-[[(tert-butoxy)carbonyl](methyl)amino]-4-methylpentanoate (D26)

Into a 250-mL round-bottom flask, was placed (2S)-2-[[(tert-butoxy)carbonyl](methyl)amino]-4-methylpentanoic acid (900 mg, 3.67 mmol, 1.00 equiv), dichloromethane (30 mL), benzyl (2S)-3-[3-fluoro-4-(oxan-4-yl)phenyl]-2-hydroxypropanoate (620 mg, 1.73 mmol, 1.00 equiv). This was followed by the addition of DCC (570 mg, 2.76 mmol, 1.10 equiv), HOBT (373 mg, 2.76 mmol, 1.10 equiv) and 4-dimethylaminopyridine (340 mg, 2.78 mmol, 1.10 equiv) respectively in portions with stirring at 0° C. The resulting solution was stirred overnight at room temperature. The resulting mixture was concentrated under vacuum. The residue was applied onto a silica gel column with ethyl acetate/petroleum ether (1:5). This resulted in 1.2 g (56%) of (2R)1-(benzyloxy)-3-[3-fluoro-4-(oxan-4-yl)phenyl]-1-oxopropan-2-yl-(2S)-2-[[(tert-butoxy)carbonyl](methyl)amino]-4-methylpentanoate as colorless oil. MS (ES, m/z): 586 (M+H).

Preparation Example 54: Preparation of Dimer D27

Dimer D27 was prepared by the reaction shown below.

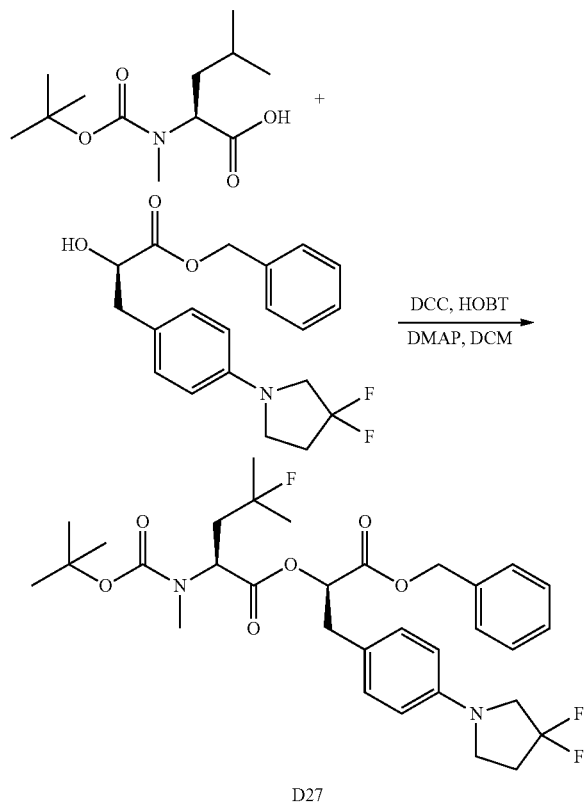

D27

(2R)-1-(benzyloxy)-3-[4-(3,3-difluoropyrrolidin-1-yl)phenyl]-1-oxopropan-2-yl-(2S)-2-[[(tert-butoxy)carbonyl](methyl)amino]-4-methylpentanoate Into a 250-mL 3-necked round-bottom flask, was placed benzyl (2R)-3-[4-(3,3-difluoropyrrolidin-1-yl)phenyl]-2-hydroxypropanoate (1.5 g, 4.15 mmol, 1.00 equiv), (2S)-2-[[(tert-butoxy)carbonyl](methyl)amino]-4-methylpentanoic acid (1 g, 4.08 mmol, 1.00 equiv), dichloromethane (80 mL). This was followed by the addition of DCC (1.1 g, 5.33 mmol, 1.20 equiv), 4-dimethylaminopyridine (600 mg, 4.91 mmol, 1.20 equiv) and HOBT (700 mg, 5.18 mmol, 1.20 equiv) respectively in portions with stirring at 0° C. The resulting solution was stirred overnight at room temperature. The resulting mixture was concentrated under vacuum. The residue was applied onto a silica gel column with ethyl acetate/petroleum ether (1:15). This resulted in 1.7 g (70%) of (2R)-1-(benzyloxy)-3-[4-(3,3-difluoropyrrolidin-1-yl)phenyl]-1-oxopropan-2-yl-(2S)-2-[[(tert-butoxy)carbonyl](methyl)amino]-4-methylpentanoate as yellow oil. MS (ES, m/z): 589 (M+H).

Preparation Example 55: Preparation of Dimer D28

Dimer D28 was prepared by the reaction shown below.

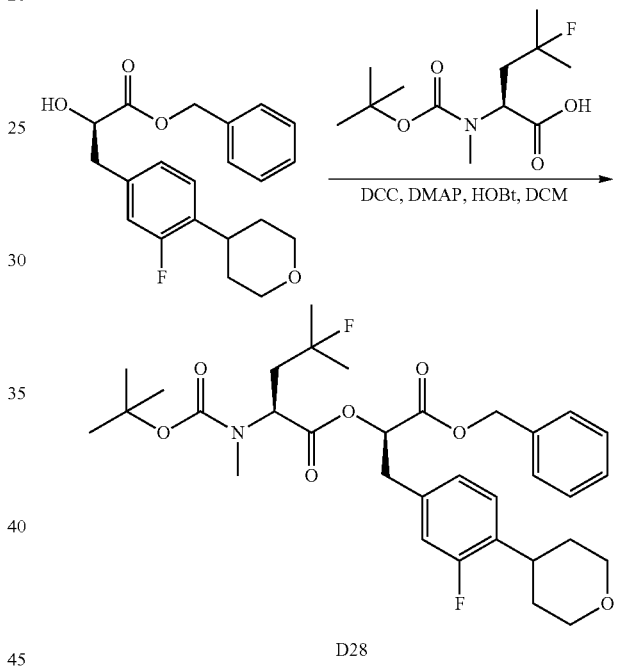

D28

(2R)-1-(benzyloxy)-3-[3-fluoro-4-(oxan-4-yl)phenyl]-1-oxopropan-2-yl-(2S)-2-[[(tert-butoxy)carbonyl](methyl)amino]-4-fluoro-4-methylpentanoate (D28)

Into a 100-mL round-bottom flask, was placed (2S)-2-[[(tert-butoxy)carbonyl](methyl)amino]-4-fluoro-4-methylpentanoic acid (700 mg, 2.66 mmol, 1.00 equiv), DCM (30 mL), benzyl (2S)-3-[3-fluoro-4-(oxan-4-yl)phenyl]-2-hydroxypropanoate (513 mg, 1.43 mmol, 1.00 equiv). This was followed by the addition of HOBT (262 mg, 1.94 mmol, 1.10 equiv), DCC (442 mg, 2.14 mmol, 1.10 equiv) and 4-dimethylaminopyridine (290 mg, 2.37 mmol, 1.10 equiv) respectively in portions with stirring at 0° C. The resulting solution was stirred overnight at room temperature. The solids were filtered out. The filtrate was concentrated under vacuum. The residue was applied onto a silica gel column with ethyl acetate/petroleum ether (1:5). This resulted in 850 mg (53%) of (2R)-1-(benzyloxy)-3-[3-fluoro-4-(oxan-4-yl)phenyl]-1-oxopropan-2-yl-(2S)-2-[[(tert-butoxy) carbonyl]

(methyl)amino]-4-fluoro-4-methylpentanoate as colorless oil. MS (ES, m/z): 604 (M+H).

Preparation Example 56: Preparation of Dimer D29

Dimer D29 was prepared by the reaction shown below.

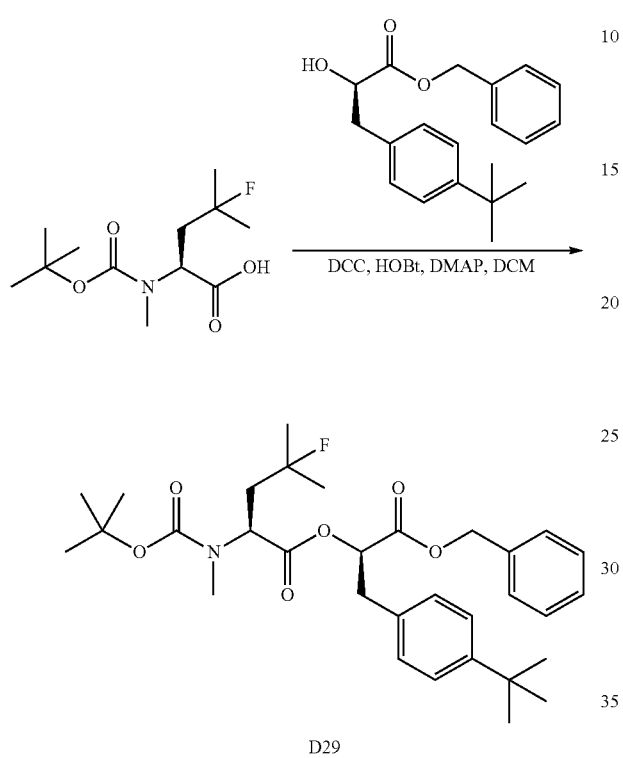

(2R)-1-(benzyloxy)-3-(4-tert-butylphenyl)-1-oxopropan-2-yl-(2S)-2-[[(tert-butoxy)carbonyl](methyl)amino]-4-fluoro-4-methylpentanoate (D29)

Into a 1000-mL 3-necked round-bottom flask, was placed a solution of (2S)-2-[[(tert-butoxy)carbonyl](methyl)amino]-4-fluoro-4-methylpentanoic acid (25 g, 94.95 mmol, 1.00 equiv) in dichloromethane (1000 mL), benzyl (2R)-3-(4-tert-butylphenyl)-2-hydroxypropanoate (30 g, 96.03 mmol, 1.00 equiv), DCC (40 g, 193.86 mmol, 2.00 equiv), HOBT (26 g, 192.42 mmol, 2.00 equiv), 4-dimethylaminopyridine (23.5 g, 192.35 mmol, 2.00 equiv). The resulting solution was stirred for 2 h at room temperature in an ice/salt bath. The resulting mixture was concentrated under vacuum. The residue was applied onto a silica gel column with ethyl acetate/petroleum ether (1:50~1:10). This resulted in 50 g (94%) of (2R)-1-(benzyloxy)-3-(4-tert-butylphenyl)-1-oxopropan-2-yl-(2S)-2-[[(tert-butoxy)carbonyl](methyl)amino]-4-fluoro-4-methylpentanoate as colorless oil. MS (ES, m/z): 558 (M+H); $^1$H NMR (300 MHz, CDCl$_3$): δ 7.35-7.27 (m, 7H), 7.12-7.09 (m, 2H), 5.27-4.62 (m, 4H), 3.15-3.09 (m, 2H), 2.69-2.61 (m, 3H), 2.20-1.82 (m, 2H), 1.61-1.31 (m, 24H).

Preparation Example 57: Preparation of Dimer D30

Dimer D30 was prepared by the reaction shown below.

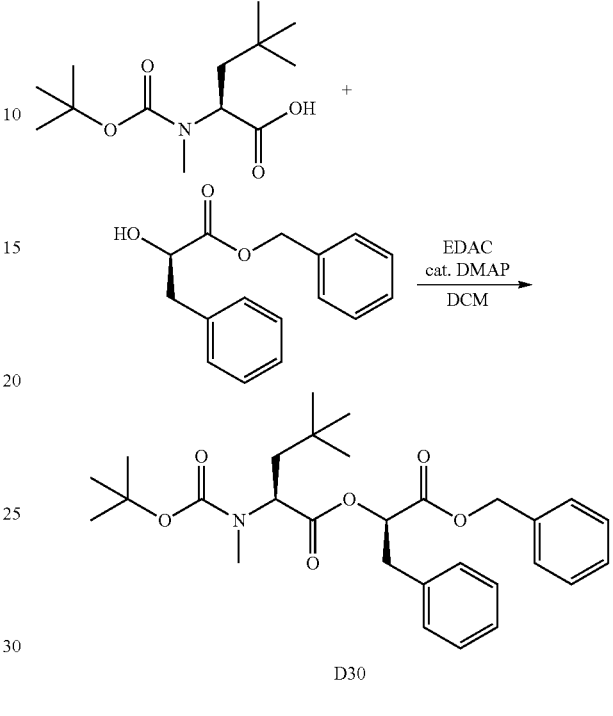

[(1R)-1-benzyl-2-benzyloxy-2-oxo-ethyl]-(2S)-2-[tert-butoxycarbonyl(methyl)amino]-4,4-dimethyl-pentanoate (D30)

To a stirred solution of N-tert-butoxycarbonyl-N-methyl-gamma-methyl-L-leucine (0.8 g, 3.1 mmol), benzyl R-2-hydroxy-3-phenylpropionate (0.8 g, 3.1 mmol) and DMAP (cat.) in 8 mL DCM cooled to 0° C. was added EDAC (1.0 g, 4.6 mmol) and the mixture stirred overnight allowing it to warm to room temperature. The mixture was diluted with 70 ml DCM, washed with 70 mL water, dried over sodium sulfate, filtered, concentrated and the residue purified on silica gel column eluting with ethyl acetate/heptanes to obtain the target compound as a white solid. Yield: 1.46 g, 95%. $^1$H NMR (DMSO-d$_6$): δ 7.28 (m, 10H), 5.28 (m, 1H), 5.12 (d, J=6.1 Hz, 2H), 4.89 (m, 0.5H), 4.63 (m, 0.5H), 3.17 (m, 1H), 3.07 (m, 1H), 2.54 (m, 3H), 1.50 (m, 2H), 1.41 (s, 5H), 1.35 (s, 4H).

Preparation Example 58: Preparation of Dimer D31

Dimer D31 was prepared by the reaction shown below.

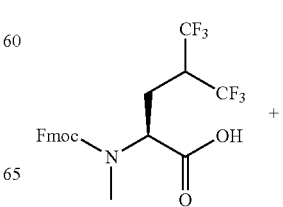

-continued

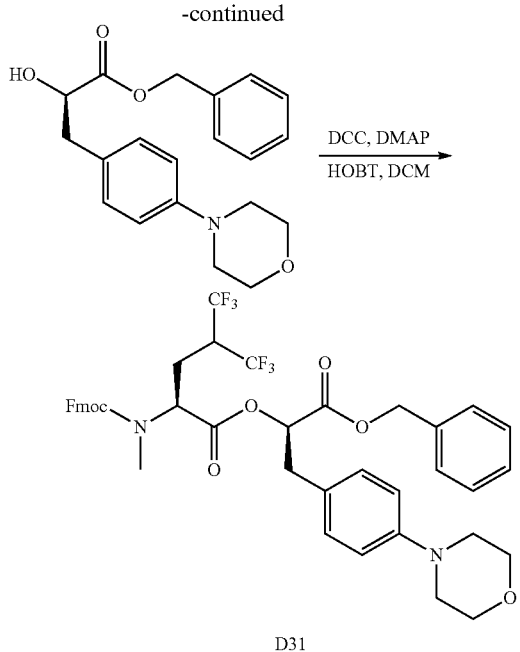

D31

(2R)-1-(benzyloxy)-3-[4-(morpholin-4-yl)phenyl]-1-oxopropan-2-yl-(2S)-2-[[(9H-fluoren-9-ylmethoxy)carbonyl](methyl)amino]-5,5,5-trifluoro-4-(trifluoromethyl)pentanoate (D31)

Into a 8-mL round-bottom flask, was placed dichloromethane (4 mL), (2S)-2-[[(9H-fluoren-9-ylmethoxy)carbonyl](methyl)amino]-5,5,5-trifluoro-4-(trifluoromethyl)pentanoic acid (200 mg, 0.42 mmol, 1.00 equiv), benzyl (2R)-2-hydroxy-3-[4-(morpholin-4-yl)phenyl]propanoate (173 mg, 0.51 mmol, 1.20 equiv). This was followed by the addition of HOBT (70 mg, 0.52 mmol, 1.20 equiv), DCC (104 mg, 0.50 mmol, 1.20 equiv) and 4-dimethylaminopyridine (62 mg, 0.51 mmol, 1.20 equiv) respectively in portions with stirring at 0° C. The resulting solution was stirred for 2 h at room temperature. The resulting mixture was concentrated under vacuum. The residue was purified by preparative TLC (EtOAc:PE=1:3). This resulted in 177 mg (53%) of (2R)-1-(benzyloxy)-3-[4-(morpholin-4-yl)phenyl]-1-oxopropan-2-yl-(2S)-2-[[(9H-fluoren-9-ylmethoxy)carbonyl](methyl)amino]-5,5,5-trifluoro-4-(trifluoromethyl)pentanoate as a off-white solid. MS (ES, m/z): 799 (M+H); $^1$H NMR (300 MHz, CDCl$_3$): δ 7.81-7.78 (m, 2H), 7.65-7.60 (m, 2H), 7.48-7.28 (m, 11H), 7.10-7.00 (m, 2H), 5.29-5.26 (m, 1H), 5.21-5.17 (m, 2H), 5.13-4.94 (m, 1H), 4.60-4.50 (m, 3H), 4.32-4.18 (m, 1H), 4.01 (br, 4H), 3.20-3.07 (m, 6H), 2.70 (s, 3H), 2.45-2.33 (m, 1H), 2.14-1.96 (m, 1H).

Preparation Example 59: Preparation of Dimer D32

Dimer D32 was prepared by the reaction shown below.

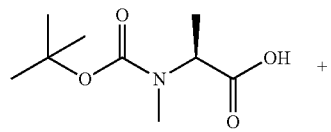

-continued

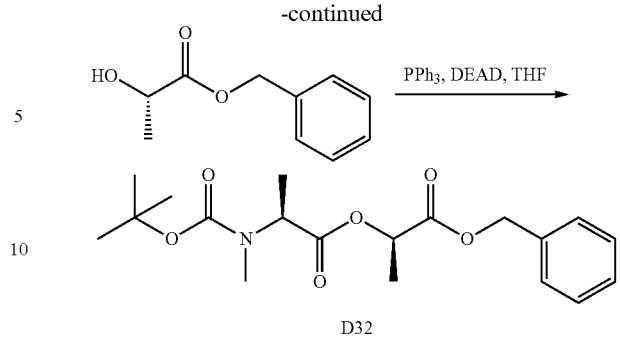

D32

(2R)-1-(benzyloxy)-1-oxopropan-2-yl-(2S)-2-[[(tert-butoxy)carbonyl](methyl)amino]propanoate (D32)

Into a 250-mL round-bottom flask purged and maintained with an inert atmosphere of nitrogen, was placed tetrahydrofuran (100 mL), (2S)-2-[[(tert-butoxy)carbonyl](methyl)amino]propanoic acid (5 g, 24.60 mmol, 1.00 equiv), benzyl (2S)-2-hydroxypropanoate (4.43 g, 24.58 mmol, 1.00 equiv), PPh$_3$ (8.4 g, 32.03 mmol, 1.30 equiv). This was followed by the addition of DEAD (5.6 g, 32.16 mmol, 1.30 equiv) dropwise with stirring at 0° C. The resulting solution was stirred overnight at room temperature. The resulting mixture was concentrated under vacuum. The residue was applied onto a silica gel column with ethyl acetate/petroleum ether (1:30-1:15). This resulted in 9 g (100%) of (2R)-1-(benzyloxy)-1-oxopropan-2-yl (2S)-2-[[(tert-butoxy)carbonyl](methyl)amino]propanoate as colorless oil. MS (ES, m/z): 366 (M+H); $^1$H NMR (300 MHz, CDCl$_3$): δ 7.42-7.32 (m, 5H), 5.24-5.12 (m, 3H), 5.03-4.69 (m, 1H), 2.83-2.79 (m, 3H), 1.53-1.39 (m, 15H).

Preparation Example 60: Preparation of Dimer D33

Dimer D33 was prepared by the reaction shown below.

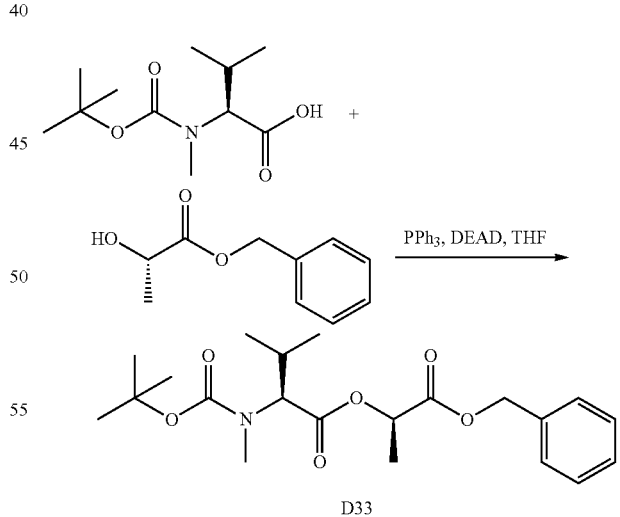

D33

(2R)-1-(benzyloxy)-1-oxopropan-2-yl-(2S)-2-[[(tert-butoxy)carbonyl](methyl)amino]-3-methylbutanoate (D33)

Into a 250-mL 3-necked round-bottom flask purged and maintained with an inert atmosphere of nitrogen, was placed (2S)-2-[[(tert-butoxy)carbonyl](methyl)amino]-3-methylbutanoic acid (2 g, 8.65 mmol, 1.00 equiv), tetrahydrofuran (80 mL), benzyl (2S)-2-hydroxypropanoate (1.6 g, 8.88 mmol, 1.00 equiv), PPh₃ (4.6 g, 17.54 mmol, 2.00 equiv). This was followed by the addition of DEAD (3 g, 17.23 mmol, 2.00 equiv) dropwise with stirring at 0° C. The resulting solution was stirred for 2 h at room temperature. The resulting mixture was concentrated under vacuum. The residue was applied onto a silica gel column with ethyl acetate/petroleum ether (1/9). This resulted in 3.3 g (97%) of (2R)-1-(benzyloxy)-1-oxopropan-2-yl-(2S)-2-[[(tert-butoxy)carbonyl](methyl)amino]-3-methylbutanoate as a pink liquid. MS (ES, m/z): 394 (M+H).

Preparation Example 61: Preparation of Dimer D34

Dimer D34 was prepared by the reaction shown below.

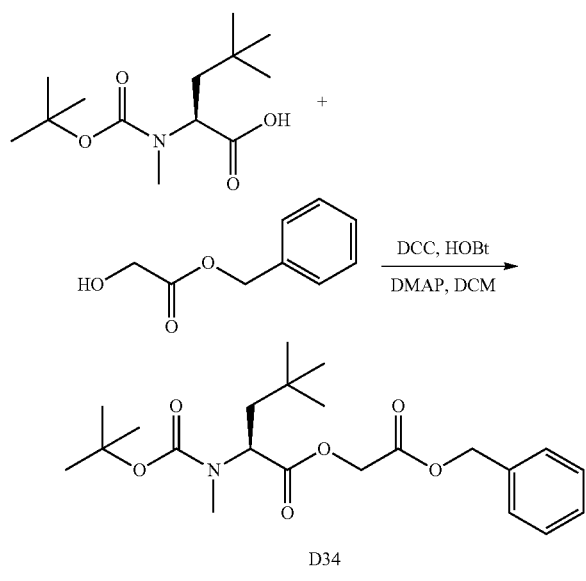

2-(Benzyloxy)-2-oxoethyl-(2S)-2-[[(tert-butoxy)carbonyl](methyl)amino]-4,4-dimethyl pentanoate (D34)

Into a 100-mL round-bottom flask, was placed (2S)-2-[[(tert-butoxy)carbonyl](methyl)amino]-4,4-dimethylpentanoic acid (1 g, 3.86 mmol, 1.00 equiv), benzyl 2-hydroxyacetate (770 mg, 4.63 mmol, 1.20 equiv), dichloromethane (25 mL). This was followed by the addition of DCC (950 mg, 4.60 mmol, 1.20 equiv), HOBt (630 mg, 4.66 mmol, 1.20 equiv) and 4-dimethylaminopyridine (570 mg, 4.67 mmol, 1.20 equiv) respectively in portions with stirring at 0° C. The resulting solution was stirred for 2 h at room temperature. The solids were filtered out. The filtrate was concentrated under vacuum. The residue was applied onto a silica gel column with ethyl acetate/petroleum ether (1:9). This resulted in 1.15 g (73%) of 2-(benzyloxy)-2-oxoethyl-(2S)-2-[[(tert-butoxy)carbonyl](methyl)amino]-4,4-dimethyl pentanoate as colorless oil. MS (ES, m/z): 408 (M+H); ¹HNMR (300 MHz, CDCl₃): δ 7.40-7.34 (m, 5H), 5.20 (s, 2H), 5.09-4.71 (m, 1H), 4.70-4.68 (m, 2H), 2.81-2.79 (m, 3H), 1.93-1.88 (m, 1H), 1.71-1.66 (m, 1H), 1.47 (s, 9H), 0.94 (s, 9H).

Preparation Example 62: Preparation of Dimer D36

Dimer D36 was prepared by the reaction shown below.

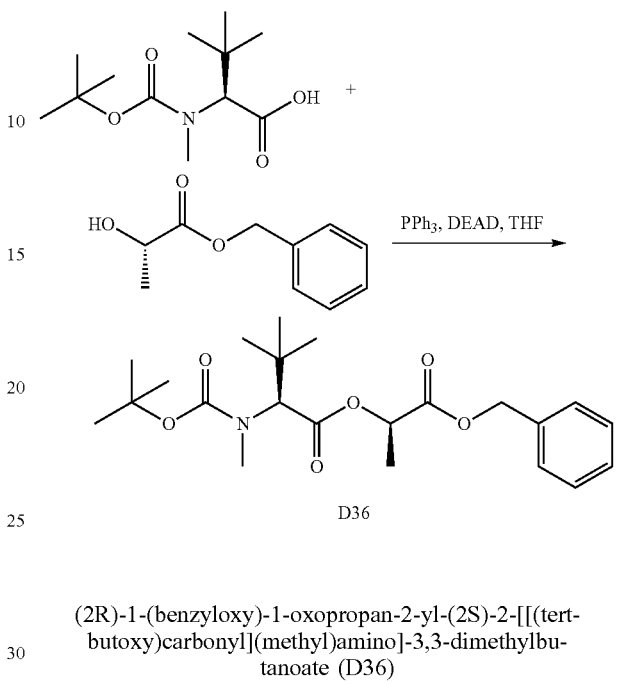

(2R)-1-(benzyloxy)-1-oxopropan-2-yl-(2S)-2-[[(tert-butoxy)carbonyl](methyl)amino]-3,3-dimethylbutanoate (D36)

Into a 100-mL round-bottom flask purged and maintained with an inert atmosphere of nitrogen, was placed (2S)-2-[[(tert-butoxy)carbonyl](methyl)amino]-3,3-dimethylbutanoic acid (1.5 g, 6.11 mmol, 1.00 equiv), tetrahydrofuran (40 mL), benzyl (2S)-2-hydroxypropanoate (1.1 g, 6.10 mmol, 1.00 equiv), PPh₃ (1.92 g, 7.32 mmol, 1.20 equiv). This was followed by the addition of DEAD (1.27 g, 7.29 mmol, 1.20 equiv) dropwise with stirring at 0° C. The resulting solution was stirred overnight at room temperature. The resulting mixture was concentrated under vacuum. The residue was applied onto a silica gel column with ethyl acetate/petroleum ether (1:10). This resulted in 2 g (80%) of (2R)-1-(benzyloxy)-1-oxopropan-2-yl (2S)-2-[[(tert-butoxy)carbonyl](methyl)amino]-3,3-dimethylbutanoate as light yellow oil. MS (ES, m/z): 408 (M+H).

Preparation Example 63: Preparation of Dimer D37

Dimer D37 was prepared by the reaction shown below.

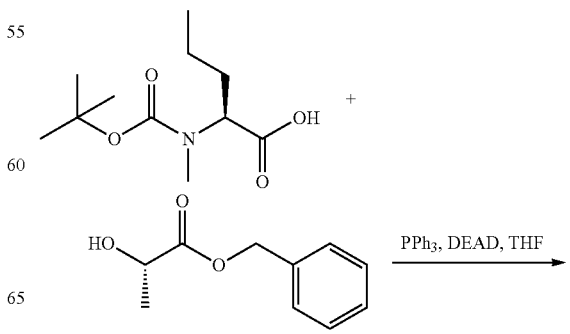

-continued

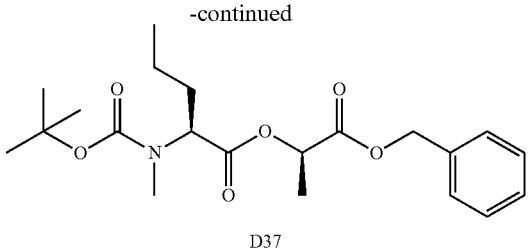

D37

(2R)-1-(benzyloxy)-1-oxopropan-2-yl-(2S)-2-[[(tert-butoxy)carbonyl](methyl)amino]pentanoate (D37)

Into a 100-mL 3-necked round-bottom flask purged and maintained with an inert atmosphere of nitrogen, was placed (2S)-2-[[(tert-butoxy)carbonyl](methyl) amino]pentanoic acid (800 mg, 3.46 mmol, 1.00 equiv), tetrahydrofuran (60 mL), benzyl (2S)-2-hydroxypropanoate (623 mg, 3.46 mmol, 1.00 equiv), PPh$_3$ (1.8 g, 6.86 mmol, 1.99 equiv). This was followed by the addition of DEAD (1.20 g, 6.89 mmol, 2.00 equiv) dropwise with stirring at 0° C. The resulting solution was stirred for 2 h at room temperature. The resulting mixture was concentrated under vacuum. The residue was applied onto a silica gel column with ethyl acetate/petroleum ether (1/9). This resulted in 1.05 g (77%) of (2R)-1-(benzyloxy)-1-oxopropan-2-yl-(2S)-2-[[(tert-butoxy)carbonyl](methyl)amino]pentanoate as a colorless liquid. MS (ES, m/z): 394 (M+H).

Preparation Example 64: Preparation of Dimer D38

Dimer D38 was prepared by the reaction shown below.

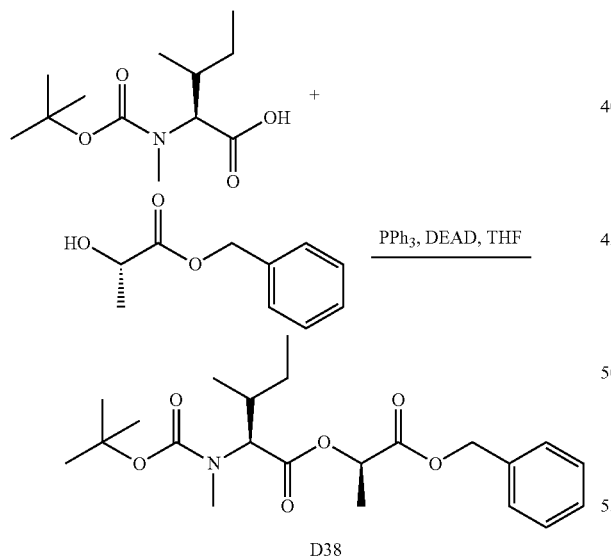

D38

(2R)-1-(benzyloxy)-1-oxopropan-2-yl-(2S)-2-[[(tert-butoxy)carbonyl](methyl)amino]-3-methylpentanoate (D38)

Into a 250-mL 3-necked round-bottom flask purged and maintained with an inert atmosphere of nitrogen, was placed (2S)-2-[[(tert-butoxy)carbonyl](methyl)amino]-3-methylpentanoic acid (4 g, 16.31 mmol, 1.00 equiv), benzyl (2S)-2-hydroxypropanoate (3.2 g, 17.76 mmol, 1.09 equiv), tetrahydrofuran (100 mL), PPh$_3$ (5.3 g, 20.21 mmol, 1.24 equiv). This was followed by the addition of DEAD (4.1 g, 23.54 mmol, 1.44 equiv) dropwise with stirring at 0° C. The resulting solution was stirred for 4 h at room temperature. The resulting mixture was concentrated under vacuum. The residue was applied onto a silica gel column with ethyl acetate/petroleum ether (1:5). This resulted in 4.2 g (63%) of (2R)-1-(benzyloxy)-1-oxopropan-2-yl-(2S)-2-[[(tert-butoxy)carbonyl](methyl)amino]-3-methylpentanoate as yellow oil. MS (ES, m/z): 408 (M+H).

Preparation Example 65: Preparation of Dimer D40

Dimer D40 was prepared by the reaction shown below.

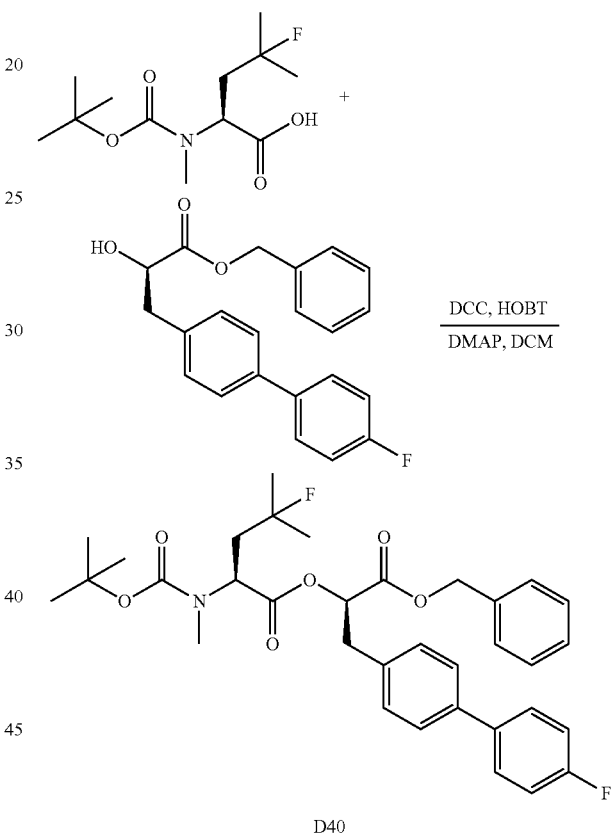

D40

(2R)-1-(benzyloxy)-3-[4-(4-fluorophenyl)phenyl]-1-oxopropan-2-yl-(2S)-2-[[(tert-butoxy) carbonyl](methyl)amino]-4-fluoro-4-methylpentanoate (D40)

Into a 100-mL round-bottom flask, was placed a solution of (2S)-2-[[(tert-butoxy)carbonyl](methyl)amino]-4-fluoro-4-methylpentanoic acid (1.2 g, 4.56 mmol, 1.00 equiv), dichloromethane (30 mL), benzyl (2R)3-[4-(4-fluorophenyl)phenyl]-2-hydroxypropanoate (900 mg, 2.57 mmol, 1.00 equiv). This was followed by the addition of 4-dimethylaminopyridine (500 mg, 4.09 mmol, 1.10 equiv), DCC (780 mg, 3.78 mmol, 1.10 equiv) and HOBT (510 mg, 3.77 mmol, 1.10 equiv) respectively in portions at 0° C. The resulting solution was stirred overnight at room temperature. The resulting mixture was concentrated under vacuum. The residue was applied onto a silica gel column with ethyl acetate/petroleum ether (1:10). This resulted in 2 g (74%) of (2R)-1-(benzyloxy)-3-[4-(4-fluorophenyl)phenyl]-1-oxopropan-2-yl-(2S)-2-[[(tert-butoxy)carbonyl](methyl)amino]-4-fluoro-4-methylpentanoate as colorless oil. MS (ES, m/z): 596 (M+H).

Preparation Example 66: Preparation of Dimer D41

Dimer D41 was prepared by the reaction shown below.

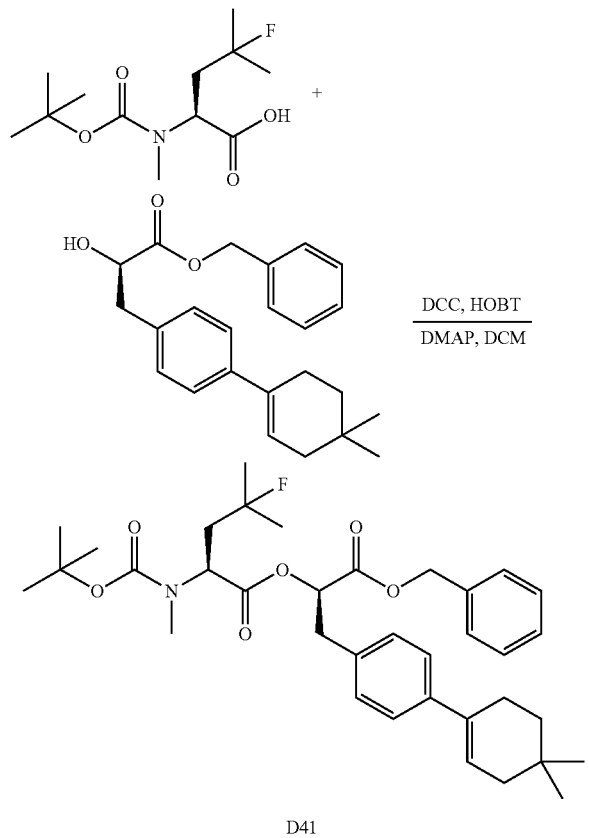

D41

(2R)-1-(benzyloxy)-3-[4-(4,4-dimethylcyclohex-1-en-1-yl)phenyl]-1-oxopropan-2-yl-(2S)-2-[[(tert-butoxy)carbonyl](methyl)amino]-4-fluoro-4-methylpentanoate (D41)

Into a 100-mL 3-necked round-bottom flask, was placed (2S)-2-[[(tert-butoxy)carbonyl](methyl)amino]-4-fluoro-4-methylpentanoic acid (542 mg, 2.06 mmol, 1.00 equiv), benzyl (2R)3-[4-(4,4-dimethylcyclohex-1-en-1-yl)phenyl]-2-hydroxypropanoate (750 mg, 2.06 mmol, 1.00 equiv), dichloromethane (60 mL). This was followed by the addition of DCC (467 mg, 2.26 mmol, 1.10 equiv), 4-dimethylaminopyridine (276 mg, 2.26 mmol, 1.10 equiv) and HOBt (306 mg, 2.26 mmol, 1.10 equiv) respectively in portions at 0° C. The resulting solution was stirred overnight at room temperature. The resulting mixture was concentrated under vacuum. The residue was applied onto a silica gel column with ethyl acetate/petroleum ether (1:20). This resulted in 850 mg (68%) of (2R)-1-(benzyloxy)-3-[4-(4,4-dimethylcyclohex-1-en-1-yl)phenyl]-1-oxopropan-2-yl-(2S)-2-[[(tert-butoxy)carbonyl](methyl)amino]-4-fluoro-4-methylpentanoate as yellow oil. MS (ES, m/z): 610 (M+H).

Preparation Example 67: Preparation of Dimer D42

Dimer D42 was prepared by the reaction shown below.

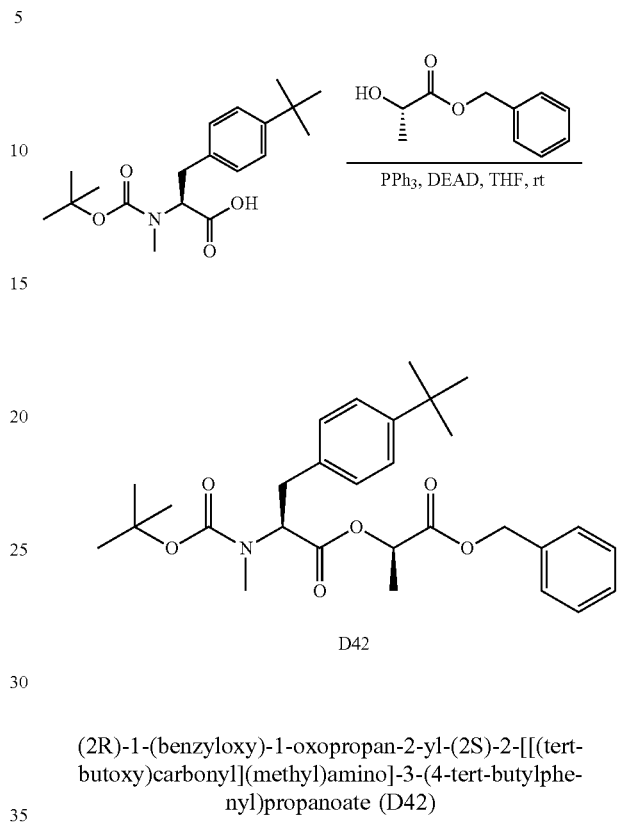

D42

(2R)-1-(benzyloxy)-1-oxopropan-2-yl-(2S)-2-[[(tert-butoxy)carbonyl](methyl)amino]-3-(4-tert-butylphenyl)propanoate (D42)

Into a 50-mL round-bottom flask, was placed tetrahydrofuran (20 mL), (2S)-2-[[(tert-butoxy)carbonyl](methyl)amino]-3-(4-tert-butylphenyl)propanoic acid (1 g, 2.98 mmol, 1.00 equiv), benzyl (2S)-2-hydroxypropanoate (530 mg, 2.94 mmol, 1.00 equiv), PPh₃ (1 g, 3.81 mmol, 1.30 equiv). This was followed by the addition of DEAD (670 mg, 3.85 mmol, 1.30 equiv) dropwise with stirring at 0° C. The resulting solution was stirred overnight at room temperature. The resulting mixture was concentrated under vacuum. The residue was applied onto a silica gel column with ethyl acetate/petroleum ether (1:5). This resulted in 1.4 g (94%) of (2R)-1-(benzyloxy)-1-oxopropan-2-yl-(2S)-2-[[(tert-butoxy)carbonyl](methyl)amino]-3-(4-tert-butylphenyl)propanoate as colorless oil. MS (ES, m/z): 498 (M+H).

Preparation Example 68: Preparation of Dimer D43

Dimer D43 was prepared by the reaction shown below.

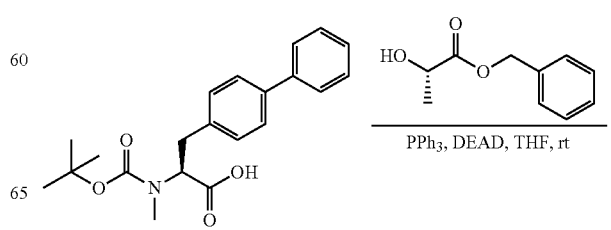

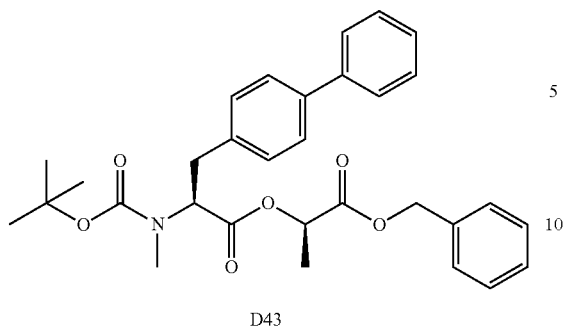

D43

(2R)-1-(benzyloxy)-1-oxopropan-2-yl-(2S)-2-[[(tert-butoxy)carbonyl](methyl)amino]-3-(4-phenylphenyl)propanoate (D43)

Into a 50-mL round-bottom flask, was placed tetrahydrofuran (10 mL), benzyl (2S)-2-[[(tert-butoxy)carbonyl](methyl)amino]-3-(4-phenylphenyl)propanoate (1 g, 2.24 mmol, 1.00 equiv), benzyl-(2S)-2-hydroxypropanoate (760 mg, 4.22 mmol, 1.88 equiv), PPh$_3$ (1.5 g, 5.72 mmol, 2.55 equiv). This was followed by the addition of DEAD (960 mg, 5.51 mmol, 2.46 equiv) dropwise with stirring at 0° C. The resulting solution was stirred for 2 h at room temperature. The resulting mixture was concentrated under vacuum. The residue was applied onto a silica gel column with ethyl acetate/petroleum ether (1:5). This resulted in 1.1 g (91%) of (2R)-1-(benzyloxy)-1-oxopropan-2-yl-(2S)-2-[[(tert-butoxy)carbonyl](methyl)amino]-3-(4-phenylphenyl)propanoate as colorless oil. MS (ES, m/z): 518 (M+H); $^1$H NMR (300 MHz, CDCl$_3$): δ 7.58-7.30 (m, 14H), 5.27-5.15 (m, 3H), 4.96-4.91 (m, 1H), 3.36-3.30 (m, 1H), 3.06-2.82 (m, 1H), 2.78-2.71 (m, 3H), 1.55-1.52 (m, 3H), 1.46-1.22 (m, 12H).

Preparation Example 69: Preparation of Dimer D44

Dimer D44 was prepared by the reaction shown below.

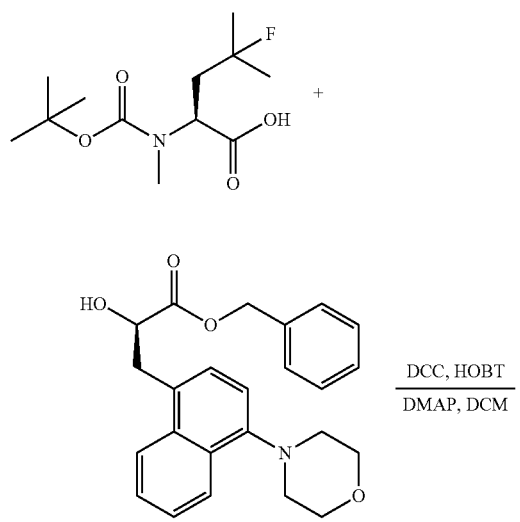

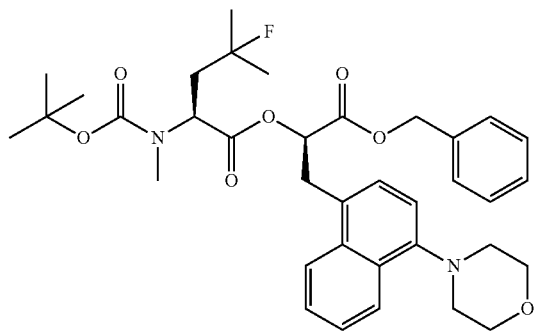

D44

(2R)-1-(benzyloxy)-3-[4-(morpholin-4-yl)naphthalen-1-yl]-1-oxopropan-2-yl-(2S)-2-[[(tert-butoxy)carbonyl](methyl)amino]-4-fluoro-4-methylpentanoate (D44)

Into a 100-mL round-bottom flask, was placed benzyl (2R)-2-hydroxy-3-[4-(morpholin-4-yl)naphthalen-1-yl]propanoate (600 mg, 1.53 mmol, 1.00 equiv), (2S)-2-[[(tert-butoxy)carbonyl](methyl)amino]-4-fluoro-4-methylpentanoic acid (600 mg, 2.28 mmol, 1.49 equiv), dichloromethane (20 mL). This was followed by the addition of HOBt (410 mg, 3.03 mmol, 1.98 equiv), 4-dimethylaminopyridine (370 mg, 3.03 mmol, 1.98 equiv) and DCC (470 mg, 2.28 mmol, 1.49 equiv) respectively in portions with stirring at 0° C. The resulting solution was stirred overnight at room temperature. The solids were filtered out. The filtrate was concentrated under vacuum. The residue was applied onto a silica gel column with ethyl acetate/petroleum ether (1:10). This resulted in 600 mg (61%) of (2R)-1-(benzyloxy)-3-[4-(morpholin-4-yl)naphthalen-1-yl]-1-oxopropan-2-yl (2S)-2-[[(tert-butoxy)carbonyl](methyl)amino]-4-fluoro-4-methylpentanoate as colorless oil. MS (ES, m/z): 637 (M+H).

Preparation Example 70: Preparation of Dimer D45

Dimer D45 was prepared by the reaction shown below.

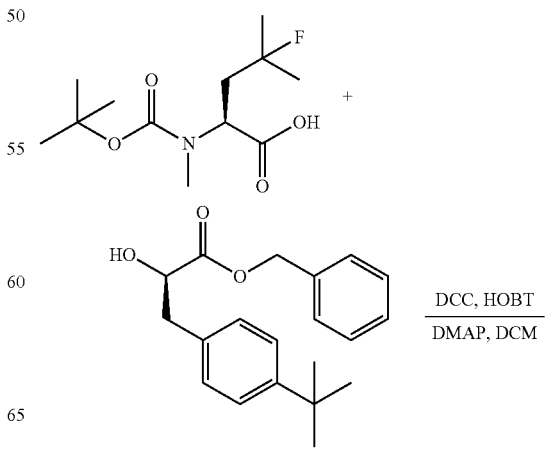

-continued

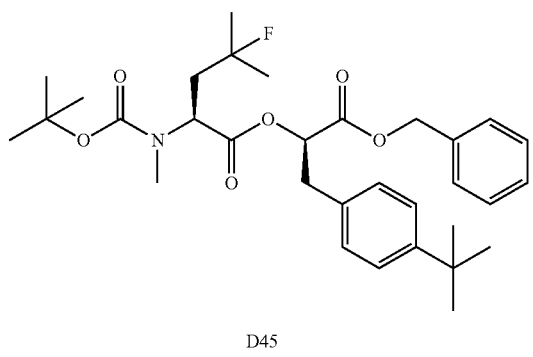

D45

(2R)-1-(benzyloxy)-3-[4-(cyclohex-1-en-1-yl)-3-fluorophenyl]-1-oxopropan-2-yl-(2S)-2-[[(tert-butoxy)carbonyl](methyl)amino]-4-fluoro-4-methylpentanoate (D45)

Into a 100-mL 3-necked round-bottom flask purged and maintained with an inert atmosphere of nitrogen, was placed tetrahydrofuran (25 mL), benzyl (2S)-3-[4-(cyclohex-1-en-1-yl)-3-fluorophenyl]-2-hydroxypropanoate (710 mg, 2.00 mmol, 1.00 equiv), (2S)-2-[(tert-butoxy)carbonyl](methyl)amino-4-fluoro-4-methylpentanoic acid (527 mg, 2.00 mmol, 1.00 equiv), PPh₃ (790 mg, 3.01 mmol, 1.50 equiv). This was followed by the addition of DEAD (517 mg, 2.97 mmol, 1.50 equiv) dropwise with stirring at 0° C. The resulting solution was stirred for 2 h at room temperature. The resulting mixture was concentrated under vacuum. The residue was purified by thin layer chromatography developed with ethyl acetate/PE (1/5). This resulted in 710 mg (59%) of (2R)-1-(benzyloxy)-3-[4-(cyclohex-1-en-1-yl)-3-fluorophenyl]-1-oxopropan-2-yl (2S)-2-[[(tert-butoxy)carbonyl](methyl)amino]-4-fluoro-4-methylpentanoate as colorless oil. MS (ES, m/z): 600 (M+H).

Preparation Example 71: Preparation of Dimer D46

Dimer D46 was prepared by the reaction shown below.

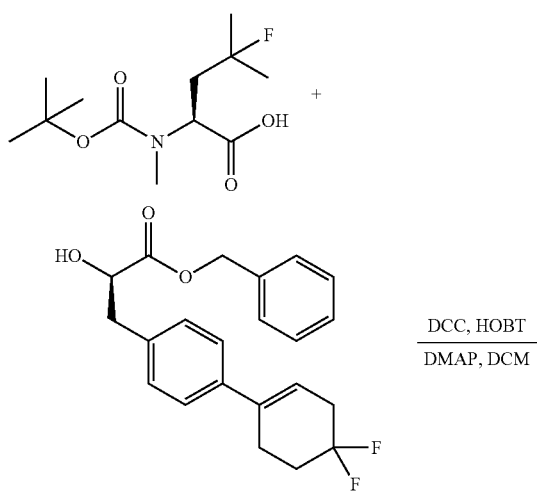

DCC, HOBT
DMAP, DCM

-continued

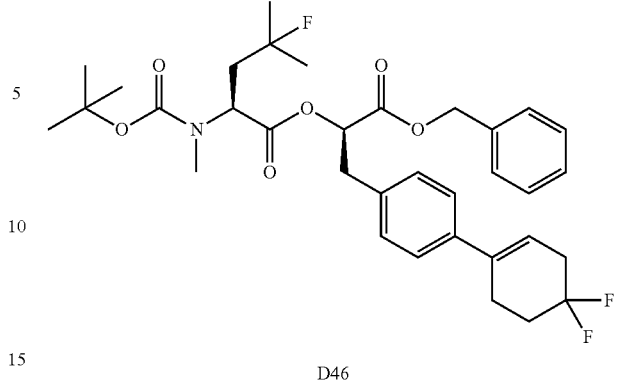

D46

(2R)-1-(benzyloxy)-3-[4-(4,4-difluorocyclohex-1-en-1-yl)phenyl]-1-oxopropan-2-yl-(2S)-2-[[(tert-butoxy)carbonyl](methyl)amino]-4-fluoro-4-methylpentanoate (D46)

Into a 100-mL round-bottom flask, was placed dichloromethane (50 mL), benzyl (2R)-3-[4-(4,4-difluorocyclohex-1-en-1-yl)phenyl]-2-hydroxypropanoate (2 g, 5.37 mmol, 1.00 equiv), (2S)-2-[(tert-butoxy)carbonyl](methyl)amino-4-fluoro-4-methylpentanoic acid (1.42 g, 5.39 mmol, 1.10 equiv). This was followed by the addition of HOBT (870 mg, 6.44 mmol, 1.20 equiv), in portions. To this was added DCC (1.33 g, 6.45 mmol, 1.20 equiv), in portions. To the mixture was added 4-dimethylaminopyridine (780 mg, 6.38 mmol, 1.20 equiv), in portions. The resulting solution was stirred for 2 h at room temperature. The resulting mixture was concentrated under vacuum. The residue was applied onto a silica gel column with ethyl acetate/petroleum ether (1:20-1:15). This resulted in 3.2 g (96%) of (2R)-1-(benzyloxy)-3-[4-(4,4-difluorocyclohex-1-en-1-yl)phenyl]-1-oxopropan-2-yl-(2S)-2-[[(tert-butoxy)carbonyl](methyl)amino]-4-fluoro-4-methylpentanoate as colorless oil. MS (ES, m/z): 618 (M+H); ¹HNMR (300 MHz, CDCl₃): δ 7.36-7.34 (m, 5H), 7.26-7.25 (m, 2H), 7.14-7.11 (m, 2H), 5.89 (br, 1H), 5.29-5.23 (m, 1H), 5.18-5.06 (m, 2H), 4.89-4.78 (m, 1H), 3.17-3.10 (m, 2H), 2.77-2.65 (m, 7H), 2.23-1.97 (m, 2H), 1.59-1.15 (m, 17H).

Preparation Example 72: Preparation of Dimer D47

Dimer D47 was prepared by the reaction shown below.

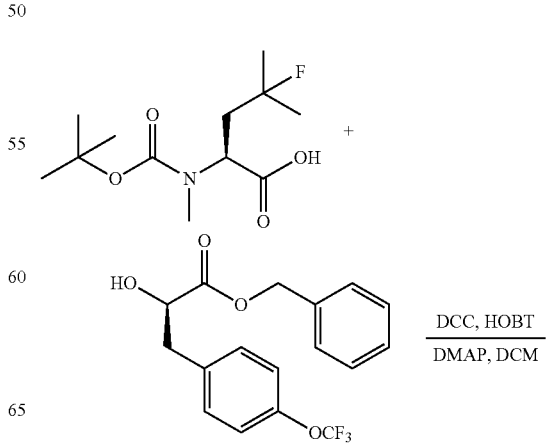

DCC, HOBT
DMAP, DCM

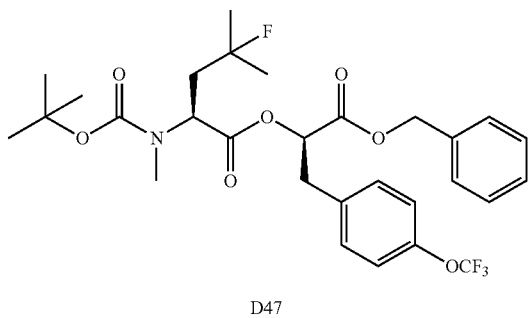

D47

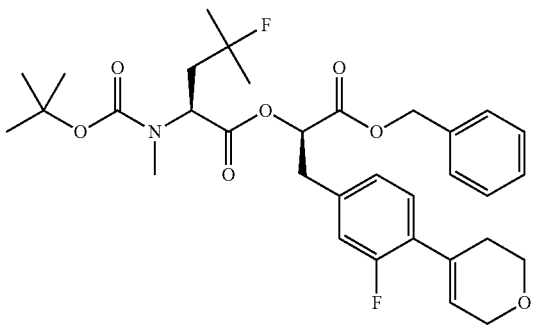

D48

(2R)-1-(benzyloxy)-1-oxo-3-[4-(trifluoromethoxy)phenyl]propan-2-yl-(2S)-2-[[(tert-butoxy)carbonyl](methyl)amino]-4-fluoro-4-methylpentanoate (D47)

Into a 250-mL 3-necked round-bottom flask, was placed (2S)-2-[[(tert-butoxy)carbonyl](methyl)amino]-4-fluoro-4-methylpentanoic acid (3.1 g, 11.77 mmol, 1.00 equiv), benzyl (2R)-2-hydroxy-3-[4-(trifluoromethoxy)phenyl]propanoate (4 g, 11.75 mmol, 1.00 equiv), dichloromethane (120 mL). This was followed by the addition of DCC (2.7 g, 13.09 mmol, 1.10 equiv), 4-dimethylaminopyridine (1.6 g, 13.10 mmol, 1.10 equiv) and HOBt (1.7 g, 12.58 mmol, 1.10 equiv) respectively in portions with stirring at 0° C. The resulting solution was stirred overnight at room temperature. The resulting mixture was concentrated under vacuum. The residue was applied onto a silica gel column with ethyl acetate/petroleum ether (1:10). This resulted in 3.5 g (51%) of (2R)-1-(benzyloxy)-1-oxo-3-[4-(trifluoromethoxy)phenyl]propan-2-yl-(2S)-2-[[(tert-butoxy)carbonyl](methyl)amino]-4-fluoro-4-methylpentanoate as yellow oil. MS (ES, m/z): 586 (M+H); $^1$H NMR (300 MHz, CDCl$_3$): δ 7.39-7.37 (m, 4H), 7.28-7.26 (m, 1H), 7.19-7.08 (m, 4H), 5.30-5.27 (m, 1H), 5.22-5.10 (m, 2H), 5.05-4.82 (m, 1H), 3.19-3.16 (m, 2H), 2.66 (d, J=22.5 Hz, 3H), 2.28-2.16 (m, 1H), 2.07-1.92 (m, 1H), 1.51-1.33 (m, 15H).

Preparation Example 73: Preparation of Dimer D48

Dimer D48 was prepared by the reaction shown below.

(2R)-1-(benzyloxy)-3-[4-(3,6-dihydro-2H-pyran-4-yl)-3-fluoropheny]-1-oxopropan-2-yl-(2S)-2-[[(tert-butoxy)carbonyl](methyl)amino]-4-fluoro-4-methylpentanoate (D48)

Into a 250-mL round-bottom flask purged and maintained with an inert atmosphere of nitrogen, was placed benzyl (2S)-3-[4-(3,6-dihydro-2H-pyran-4-yl)-3-fluorophenyl]-2-hydroxypropanoate (700 mg, 1.96 mmol, 1.00 equiv), (2S)-2-[[(tert-butoxy)carbonyl](methyl)amino]-4-fluoro-4-methylpentanoic acid (776 mg, 2.95 mmol, 1.50 equiv), PPh$_3$ (1.03 g, 3.93 mmol, 2.00 equiv), tetrahydrofuran (50 mL). This was followed by the addition of DEAD (684 mg, 3.93 mmol, 2.00 equiv) dropwise with stirring at 0° C. The resulting solution was stirred for 2 h at room temperature. The resulting mixture was concentrated under vacuum. The residue was applied onto a silica gel column with ethyl acetate/petroleum ether (1/4). This resulted in 950 mg (80%) of (2R)-1-(benzyloxy)-3-[4-(3,6-dihydro-2H-pyran-4-yl)-3-fluorophenyl]-1-oxopropan-2-yl (2S)-2-[[(tert-butoxy)carbonyl](methyl)amino]-4-fluoro-4-methylpentanoate as light yellow oil. MS (ES, m/z): 602 (M+H); $^1$H NMR (300 MHz, CD$_3$OD): δ 7.36-7.28 (m, 5H), 7.14-7.12 (m, 1H), 6.97-6.93 (m, 2H), 6.03 (br, 1H), 5.33-5.31 (m, 1H), 5.17-5.12 (m, 2H), 4.93-4.90 (m, 0.5H), 4.73-4.56 (m, 0.5H), 4.34-4.23 (m, 2H), 3.88-3.83 (m, 2H), 3.15-3.12 (m, 2H), 2.75-2.71 (m, 3H), 2.50 (br, 2H), 2.31-1.97 (m, 2H), 1.47-1.23 (m, 15H).

Preparation Example 74: Preparation of Dimer D49

Dimer D49 was prepared by the reaction shown below.

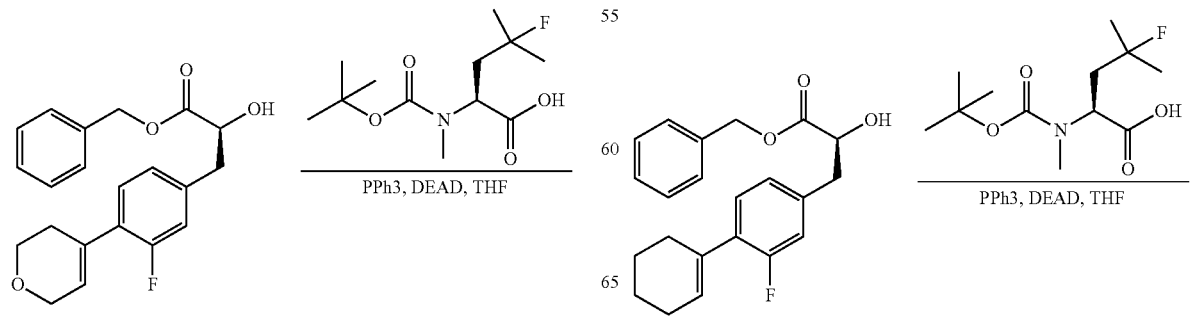

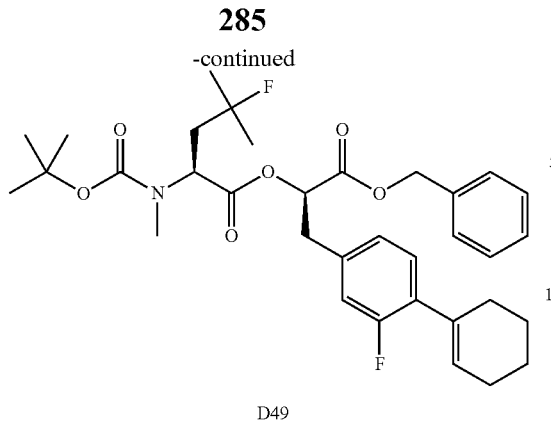

D49

(2R)-1-(benzyloxy)-3-[4-(cyclohex-1-en-1-yl)-3-fluorophenyl]-1-oxopropan-2-yl-(2S)-2-[[(tert-butoxy)carbonyl](methyl)amino]-4-fluoro-4-methylpentanoate (D49)

Into a 100-mL 3-necked round-bottom flask purged and maintained with an inert atmosphere of nitrogen, was placed tetrahydrofuran (25 mL), benzyl (2S)-3-[4-(cyclohex-1-en-1-yl)-3-fluorophenyl]-2-hydroxypropanoate (710 mg, 2.00 mmol, 1.00 equiv), (2S)-2-[(tert-butoxy)carbonyl](methyl)amino-4-fluoro-4-methylpentanoic acid (527 mg, 2.00 mmol, 1.00 equiv), PPh$_3$ (790 mg, 3.01 mmol, 1.50 equiv). This was followed by the addition of DEAD (517 mg, 2.97 mmol, 1.50 equiv) dropwise with stirring at 0° C. The resulting solution was stirred for 2 h at room temperature. The resulting mixture was concentrated under vacuum. The residue was purified by thin layer chromatography developed with ethyl acetate/PE (1/5). This resulted in 710 mg (59%) of (2R)-1-(benzyloxy)-3-[4-(cyclohex-1-en-1-yl)-3-fluorophenyl]-1-oxopropan-2-yl-(2S)-2-[[(tert-butoxy)carbonyl](methyl)amino]-4-fluoro-4-methylpentanoate as colorless oil. MS (ES, m/z): 600 (M+H); $^1$HNMR (300 MHz, CDCl$_3$): δ 7.35-7.27 (m, 5H), 7.15-7.11 (m, 1H), 6.87-6.82 (m, 2H), 5.91 (br, 1H), 5.30-5.06 (m, 3H), 4.94-4.65 (m, 1H), 3.14-3.10 (m, 2H), 2.74-2.68 (m, 3H), 2.22-1.96 (m, 2H), 1.80-1.70 (m, 4H), 1.69-1.25 (m, 19H).

Preparation Example 75: Preparation of Dimer D50

Dimer D50 was prepared by the process shown in Scheme 29 below.

Scheme 29

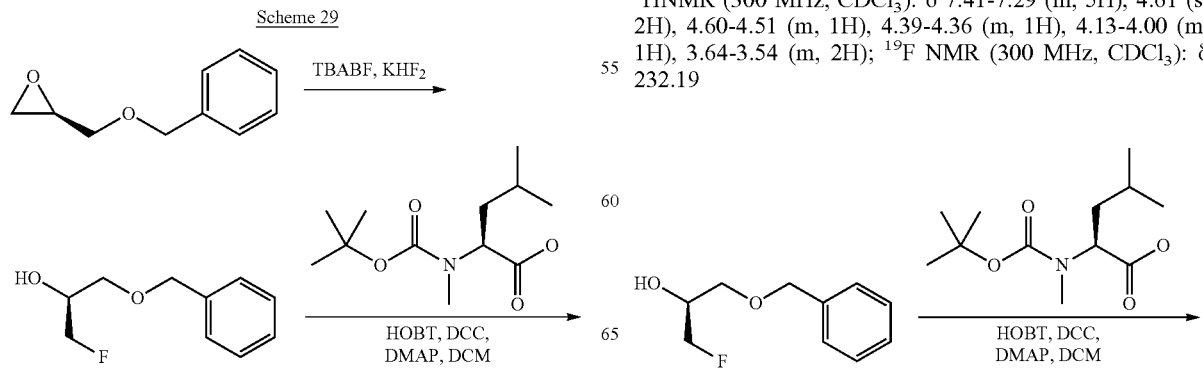

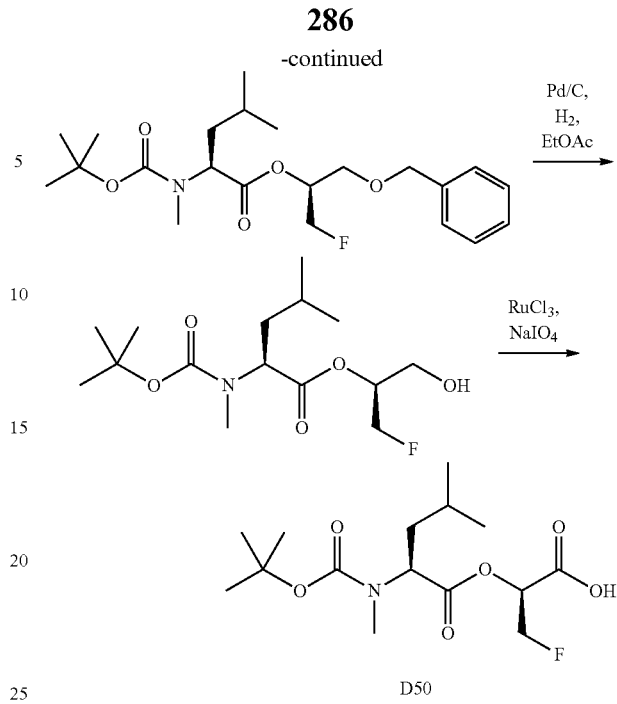

D50

Experimental Details

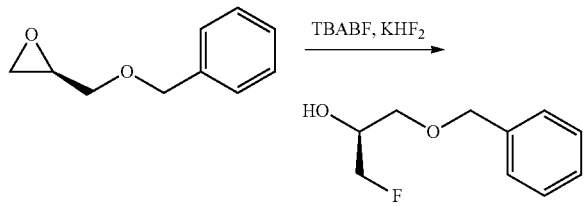

(2S)-1-(benzyloxy)-3-fluoropropan-2-ol

Into a 250-mL round-bottom flask, was placed a solution of (2R)-2-[(benzyloxy)methyl]oxirane (3 g, 18.27 mmol, 1.00 equiv) in heptane (50 mL), TBABF (15 g, 3.00 equiv), KHF$_2$ (3.2 g, 3.00 equiv). The resulting solution was stirred for 5 h at 130° C. The reaction was then quenched by the addition of 200 mL of water/ice. The resulting solution was extracted with 3×50 mL of ethyl acetate and the organic layers combined and dried over anhydrous sodium sulfate and concentrated under vacuum. This resulted in 3.1 g (92%) of (2S)-1-(benzyloxy)-3-fluoropropan-2-ol as colorless oil. $^1$HNMR (300 MHz, CDCl$_3$): δ 7.41-7.29 (m, 5H), 4.61 (s, 2H), 4.60-4.51 (m, 1H), 4.39-4.36 (m, 1H), 4.13-4.00 (m, 1H), 3.64-3.54 (m, 2H); $^{19}$F NMR (300 MHz, CDCl$_3$): δ 232.19

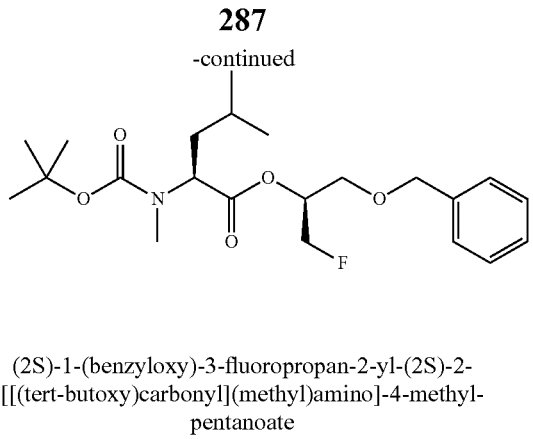

(2S)-1-(benzyloxy)-3-fluoropropan-2-yl-(2S)-2-[[(tert-butoxy)carbonyl](methyl)amino]-4-methylpentanoate Into a 500-mL round-bottom flask, was placed dichloromethane (200 mL), (2S)-2-[[(tert-butoxy)carbonyl](methyl)amino]-4-methylpentanoic acid (14.6 g, 59.52 mmol, 1.10 equiv), (2S)-1-(benzyloxy)-3-fluoropropan-2-ol (10 g, 54.29 mmol, 1.00 equiv), DCC (14 g, 67.85 mmol, 1.25 equiv), 4-dimethylaminopyridine (8 g, 65.48 mmol, 1.21 equiv), HOBT (8.8 g, 65.13 mmol, 1.20 equiv). The resulting solution was stirred for 2 h at room temperature. The solids were filtered out. The filtrate was concentrated under vacuum. The residue was applied onto a silica gel column with ethyl acetate/petroleum ether (1:10). This resulted in 16 g (72%) of (2S)-1-(benzyloxy)-3-fluoropropan-2-yl-(2S)-2-[[(tert-butoxy)carbonyl](methyl)amino]-4-methylpentanoate as colorless oil. MS (ES, m/z): 412 (M+H).

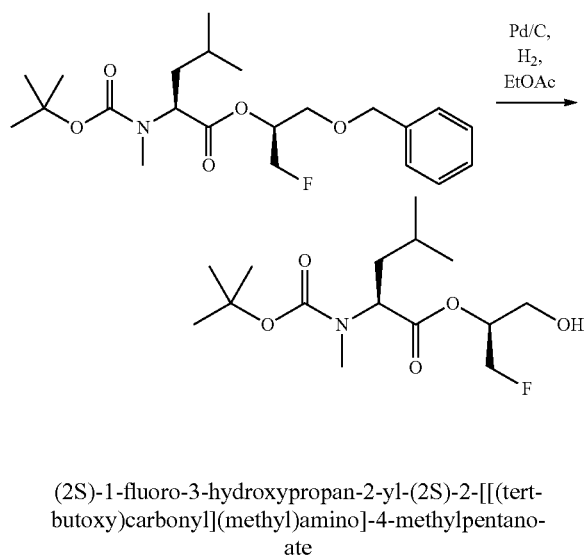

(2S)-1-fluoro-3-hydroxypropan-2-yl-(2S)-2-[[(tert-butoxy)carbonyl](methyl)amino]-4-methylpentanoate Into a 100-mL round-bottom flask, was placed methanol (30 mL), (2S)-1-(benzyloxy)-3-fluoropropan-2-yl-(2S)-2-[[(tert-butoxy)carbonyl](methyl)amino]-4-methyl pentanoate (7 g, 17.01 mmol, 1.00 equiv), and Palladium on carbon (2 g). To the above mixture hydrogen was introduced. The resulting solution was stirred overnight at room temperature. The solids were filtered out. The filtrate was concentrated under vacuum. This resulted in 5.3 g (97%) of (2S)-1-fluoro-3-hydroxypropan-2-yl-(2S)-2-[[(tert-butoxy)carbonyl](methyl)amino]-4-methylpentanoate as light yellow oil. MS (ES, m/z): 322 (M+H).

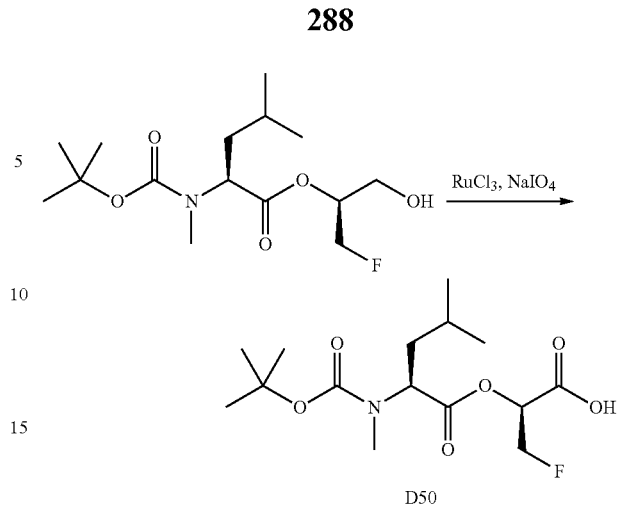

(2S)-2-[[(2S)-2-[[(tert-butoxy)carbonyl](methyl)amino]-4-methylpentanoyl]oxy]-3-fluoropropanoic acid (D50)

Into a 1000-mL round-bottom flask, was placed water (100 mL), chloroform (150 mL), ACN (150 mL), (2S)-1-fluoro-3-hydroxypropan-2-yl (2S)-2-[[(tert-butoxy)carbonyl](methyl)amino]-4-methylpentanoate (6 g, 18.67 mmol, 1.00 equiv), RuCl₃ (2.1 g), NaIO₄ (20 g). The resulting solution was stirred for 3 h at room temperature. The solids were filtered out. The resulting solution was extracted with 3×50 mL of ethyl acetate and the organic layers combined. The resulting mixture was washed with 3×60 mL of brine. The mixture was dried over anhydrous sodium sulfate and concentrated under vacuum. This resulted in 4.2 g (67%) of (2S)-2-[[(2S)-2-[[(tert-butoxy)carbonyl](methyl)amino]-4-methylpentanoyl]oxy]-3-fluoropropanoic acid as yellow oil. MS (ES, m/z): 236 (M+H-Boc); ¹H NMR (300 MHz, CDCl₃): δ 5.42 (br, 1H), 4.92-4.63 (m, 3H), 2.85-2.82 (m, 3H), 1.83-1.53 (m, 3H), 1.46 (s, 9H), 1.02-0.86 (m, 6H).

Preparation Example 76: Preparation of Dimer D51

Dimer D51 was prepared by the reaction shown below.

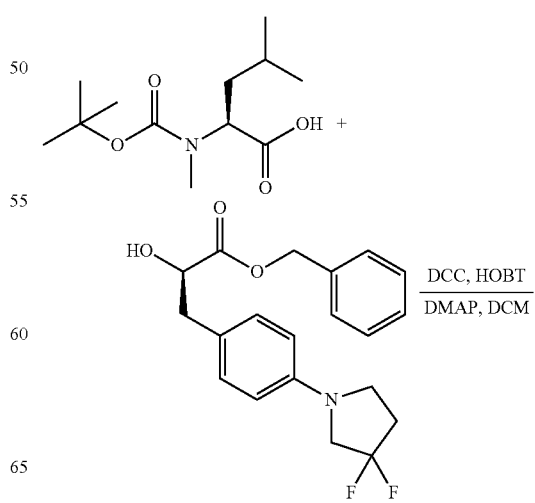

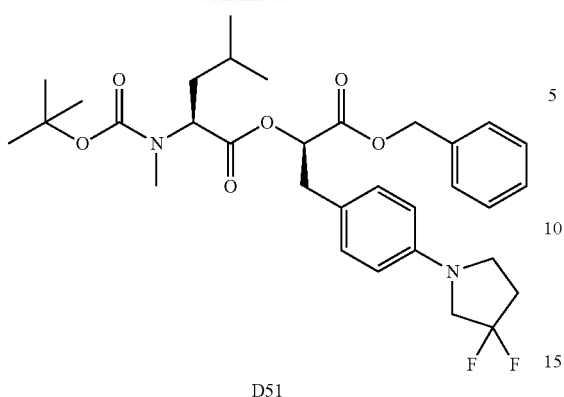

D51

(2R)-1-(benzyloxy)-3-[4-(3,3-difluoropyrrolidin-1-yl)phenyl]-1-oxopropan-2-yl-(2S)-2-[[(tert-butoxy)carbonyl](methyl)amino]-4-methylpentanoate (D51)

Into a 250-mL 3-necked round-bottom flask, was placed benzyl (2R)-3-[4-(3,3-difluoropyrrolidin-1-yl)phenyl]-2-hydroxypropanoate (1.5 g, 4.15 mmol, 1.00 equiv), (2S)-2-[[(tert-butoxy)carbonyl](methyl)amino]-4-methylpentanoic acid (1 g, 4.08 mmol, 1.00 equiv), dichloromethane (80 mL). This was followed by the addition of DCC (1.1 g, 5.33 mmol, 1.20 equiv), 4-dimethylaminopyridine (600 mg, 4.91 mmol, 1.20 equiv) and HOBT (700 mg, 5.18 mmol, 1.20 equiv) respectively in portions with stirring at 0° C. The resulting solution was stirred overnight at room temperature. The resulting mixture was concentrated under vacuum. The residue was applied onto a silica gel column with ethyl acetate/petroleum ether (1:15). This resulted in 1.7 g (70%) of (2R)-1-(benzyloxy)-3-[4-(3,3-difluoropyrrolidin-1-yl)phenyl]-1-oxopropan-2-yl (2S)-2-[[(tert-butoxy)carbonyl](methyl)amino]-4-methylpentanoate as yellow oil. MS (ES, m/z): 589 (M+H).

Preparation Example 77: Preparation of Dimer D52

Dimer D52 was prepared by the reaction shown below.

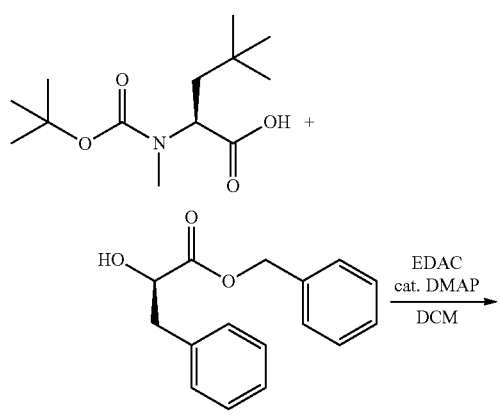

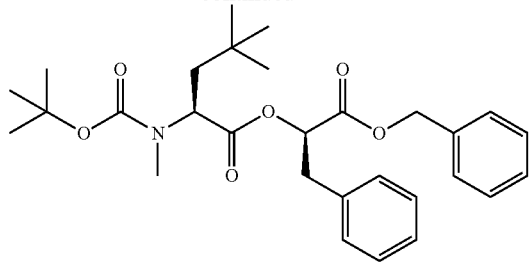

D52

[(1R)-1-benzyl-2-benzyloxy-2-oxo-ethyl]-(2S)-2-[tert-butoxycarbonyl(methyl)amino]-4,4-dimethyl-pentanoate (D52)

To a stirred solution of N-tert-butoxycarbonyl-N-methyl-gamma-methyl-L-leucine (0.8 g, 3.1 mmol), benzyl R-2-hydroxy-3-phenylpropionate (0.8 g, 3.1 mmol) and DMAP (cat.) in 8 mL DCM cooled to 0° C. was added EDAC (1.0 g, 4.6 mmol) and the mixture stirred overnight allowing it to warm to room temperature. The mixture was diluted with 70 ml DCM, washed with 70 mL water, dried over sodium sulfate, filtered, concentrated and the residue purified on silica gel column eluting with ethyl acetate/heptanes to obtain the target compound as a white solid. Yield: 1.46 g, 95%. $^1$H NMR (DMSO-d$_6$): δ 7.28 (m, 10H), 5.28 (m, 1H), 5.12 (d, J=6.1 Hz, 2H), 4.89 (m, 0.5H), 4.63 (m, 0.5H), 3.17 (m, 1H), 3.07 (m, 1H), 2.54 (m, 3H), 1.50 (m, 2H), 1.41 (s, 5H), 1.35 (s, 4H).

Preparation Example 78: Preparation of Dimer D53

Dimer D53 was prepared by the reaction shown below.

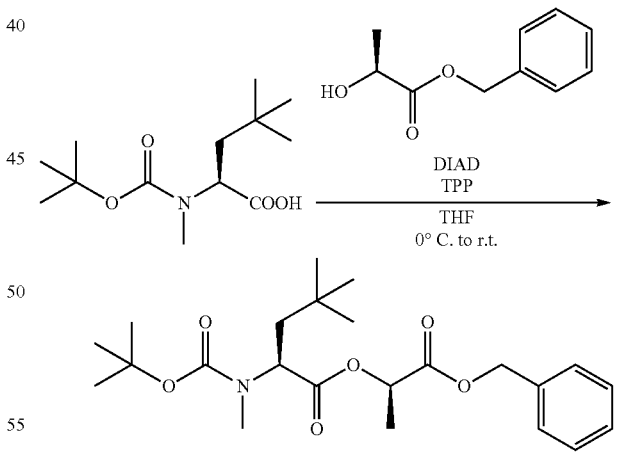

[(1R)-2-benzyloxy-1-methyl-2-oxo-ethyl]-(2S)-2-[tert-butoxycarbonyl(methyl)amino]-4,4-dimethyl-pentanoate (D53)

To a stirred solution of N-tert-butoxycarbonyl-N-methyl-gamma-methyl-L-leucine (0.8 g, 3.1 mmol), benzyl L-lactate (0.56 g, 3.1 mmol) and triphenylphosphine (1.0 g, 3.7 mmol) in 8 mL THF cooled to 0° C. was added dropwise a solution of diisobutylazodicarboxylate (0.76 g, 3.7 mmol) in 2 mL THF and the mixture stirred overnight allowing it to warm to room temperature. The mixture was diluted with 100 mL ethyl acetate, washed with 100 mL water, washed with brine, dried over sodium sulfate and concentrated. The residue was purified on silica gel column eluting with ethyl acetate and heptanes to obtain the target compound as a clear oil. Yield: 1.3 g (quantitative). ¹H NMR (DMSO-d₆): δ 7.36 (m, 5H), 5.16 (s, 2H), 5.09 (m, 1H), 4.90 (m, 0.5H), 4.69 (m, 0.5), 2.65 (s, 3H), 1.66 (m, 2H), 1.40 (m, 12H), 0.89 (m, 9H).

Preparation Example 79: Preparation of Dimer D54

Dimer D54 was prepared by the reaction shown below.

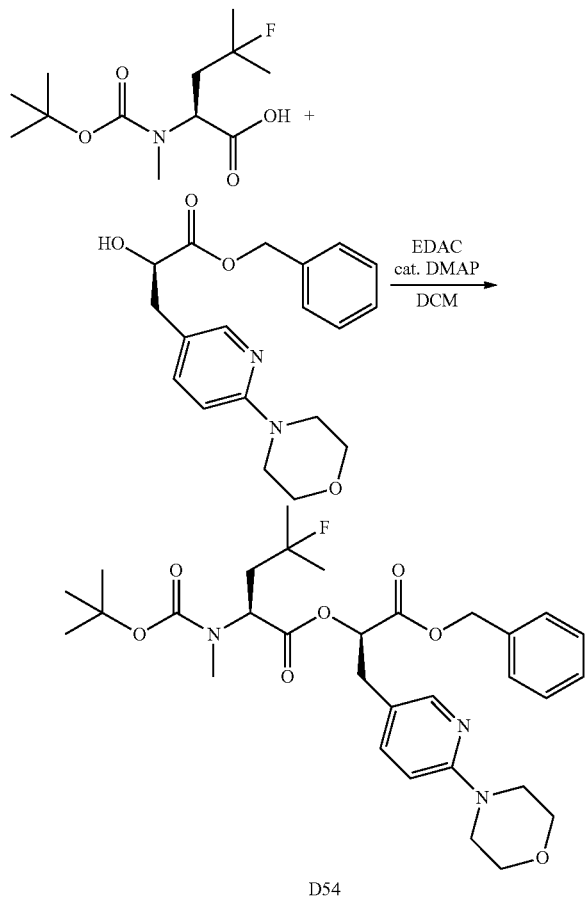

[(1R)-2-benzyloxy-1-[(6-morpholino-3-pyridyl) methyl]-2-oxo-ethyl]-(2S)-2-[tert-butoxy-carbonyl (methyl)amino]-4-fluoro-4-methyl-pentanoate (D54)

To a stirred solution of N-tert-butoxycarbonyl-N-methyl-gamma-fluoro-L-leucine (0.31 g, 1.2 mmol), benzyl R-2-hydroxy-3-[2-(4-morpholino)-5-pyridyl]propionate (0.4 g, 1.2 mmol) and DMAP (cat.) in 5 mL DCM cooled to 0° C. was added EDAC (0.34 g, 1.8 mmol) and the mixture stirred overnight allowing it to warm to room temperature. The mixture was diluted with 50 ml DCM, washed with 50 mL water, dried over sodium sulfate, filtered, concentrated and the residue purified on silica gel column eluting with ethyl acetate and heptanes to obtain the target compound as a clear oil. Yield: 0.56 g, 82%. MS (CI, m/z): 588 (M+H).

Preparation Example 80: Preparation of Dimer D55

Dimer D55 was prepared by the reaction shown below.

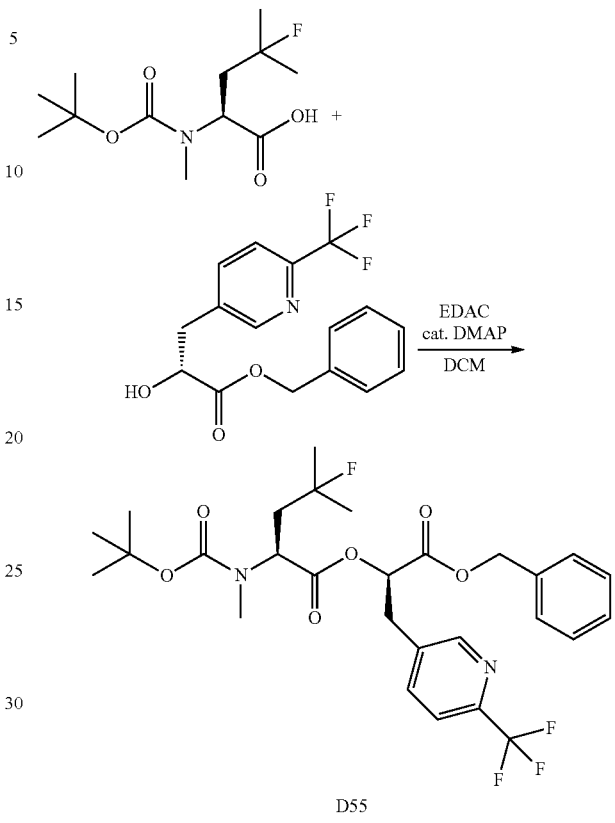

[(1R)-2-benzyloxy-2-oxo-1-[[6-(trifluoromethyl)-3-pyridyl]methyl]ethyl]-(2S)-2-[tert-butoxy-carbonyl (methyl)amino]-4-fluoro-4-methyl-pentanoate (D55)

To a stirred solution of N-tert-butoxy-carbonyl-N-methyl-gamma-fluoro-L-leucine (0.46 g, 1.7 mmol), benzyl R-2-hydroxy-3-[2-(trifluoro-methyl)-5-pyridyl]propanoate (0.56 g, 1.7 mmol) and DMAP (cat.) in 6 mL DCM cooled to 0° C. was added EDAC (0.51 g, 2.6 mmol) and the mixture stirred overnight allowing it to warm to room temperature. The mixture was diluted with 50 ml DCM, washed with 50 mL water, dried over sodium sulfate, filtered, concentrated and the residue purified on silica gel column eluting with ethyl acetate and heptanes to obtain the target compound as a clear oil. Yield: 0.80 g, 81%. MS (CI, m/z): 571 (M+H); ¹H NMR (CDCl₃): δ 8.52 (s, 1H), 7.59 (m, 2H), 7.37 (m, 3H), 7.26 (m, 3H), 5.33 (m, 1H), 5.12 (m, 2.5H), 4.87 (m, 0.5H), 3.26 (m, 2H), 2.66 (m, 3H), 2.22 (m, 1H), 1.96 (m, 1H), 1.58 (s, 2H), 1.49 (s, 4H), 1.38 (m 9H).

Preparation Example 81: Preparation of Dimer D56

Dimer D56 was prepared by the reaction shown below.

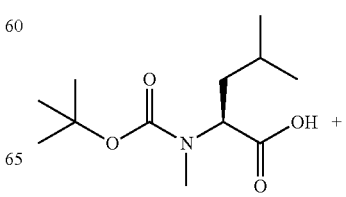

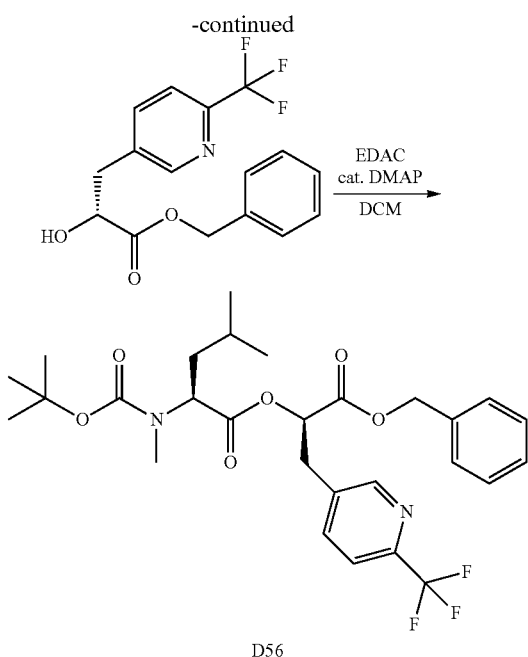

D56

[(1R)-2-benzyloxy-2-oxo-1-[[6-(trifluoromethyl)-3-pyridyl]methyl]ethyl]-(2S)-2-[tert-butoxy-carbonyl(methyl)amino]-4-methyl-pentanoate (D56)

To a stirred solution of N-tert-butoxycarbonyl-N-methyl-gamma-fluoro-L-leucine (0.46 g, 1.7 mmol), benzyl R-2-hydroxy-3-[2-(trifluoromethyl)-5-pyridyl]propanoate (0.56 g, 1.7 mmol) and DMAP (cat.) in 6 mL DCM cooled to 0° C. was added EDAC (0.51 g, 2.6 mmol) and the mixture stirred overnight allowing it to warm to room temperature. The mixture was diluted with 50 ml DCM, washed with 50 mL water, dried over sodium sulfate, filtered, concentrated and the residue purified on silica gel column eluting with ethyl acetate and heptanes to obtain the target compound as a clear oil. Yield: 0.80 g, 81%. MS (CI, m/z): 553 (M+H).

Preparation Example 82: Preparation of Dimer D57

Dimer D57 was prepared by the process shown in Scheme 30 below.

Experimental Details

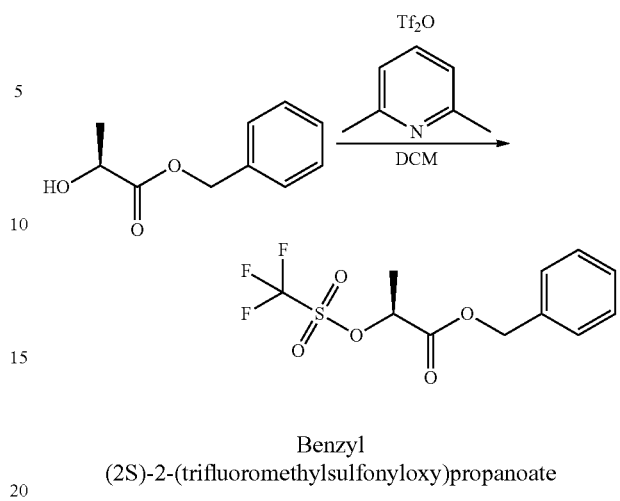

Benzyl (2S)-2-(trifluoromethylsulfonyloxy)propanoate

To a solution of benzyl (S)-lactate (3.5 g, 17.5 mmol) and 2,6-lutidine (2.0 g, 18.4 mmol) in 100 mL DCM cooled to 0° C. was added triflic anhydride (5.3 g, 18.4 mmol) and the mixture was stirred 1 h. The mixture was concentrated and the residue purified on silica gel column eluting with ethyl acetate and heptanes to obtain the target compound as a light pink oil. Yield: 3.8 g, 70%. $^1$H NMR (CD$_2$Cl$_2$): δ 7.38 (m, 5H), 5.29 (d, J=7.0 Hz, 1H), 5.26 (s, 2H), 1.71 (d, J=7.0 Hz, 3H); $^{19}$F NMR (CD$_2$Cl$_2$): δ 75.70 (s, 3F).

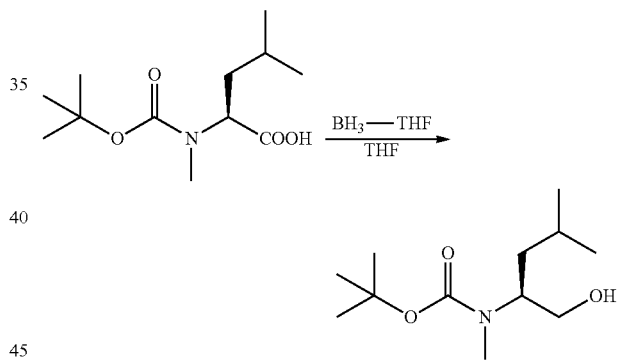

Scheme 30

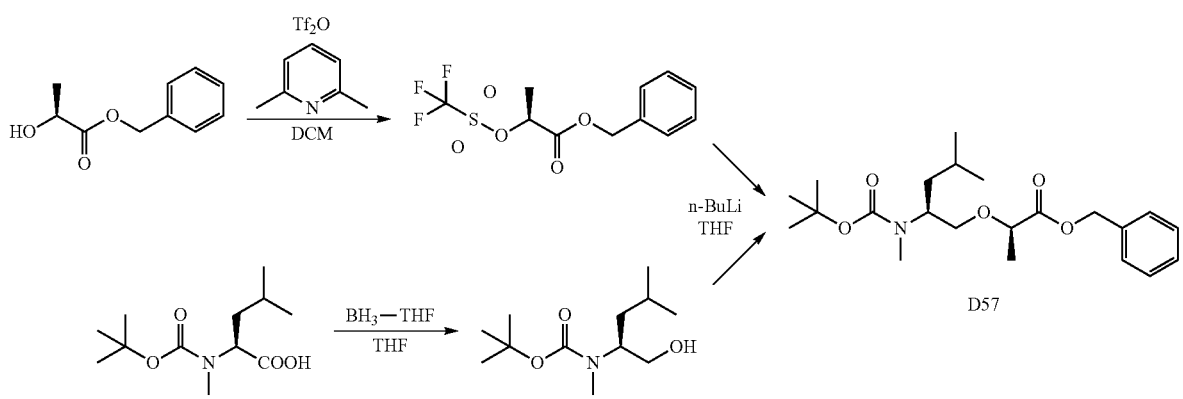

D57 tert-butyl N-[(1S)-1-(hydroxymethyl)-3-methyl-butyl]-N-methyl-carbamate

To a solution of N-boc-N-methyl-(L) leucine (4.0 g, 16 mmol) in 20 mL THF was added 18 mL of 1M borane-THF complex in THF and the mixture stirred 30 min. The mixture was quenched with 10 mL methanol and concentrated. The residue was dissolved in 150 mL ethyl acetate, washed with 100 mL water, washed with brine, dried over sodium sulfate, filtered and concentrated to obtain the target compound as a clear oil. Yield: 3.5 g, 93%. $^1$H NMR (CD$_2$Cl$_2$): δ 4.19 (m, 1H), 3.50 (d, J=6.9 Hz, 2H), 2.68 (s, 3H), 1.86 (m, 1H), 1.51 (m, 1H), 1.44 (s, 9H), 1.39 (m, 1H), 1.1 (m, 1H), 0.92 (s, 3H), 0.91 (s, 3H).

mL THF under nitrogen atmosphere cooled to −78° C. was added dropwise 7.6 mL of 1.6 M solution of butyllithium in THF and the mixture stirred 30 min. allowing it to warm to −20° C. The mixture was cooled back down to −78 OC and treated dropwise with a solution of benzyl (2S)-2-(trifluoromethyl-sulfonyloxy)propanoate (3.8 g, 12 mmol) in 10 mL THF and stirred overnight allowing it to warm to room temperature. The mixture was diluted with 100 mL water and extracted into 100 mL ethyl acetate. The organic layer was separated, washed with brine, dried over sodium sulfate, filtered and concentrated. The residue was purified on silica gel column eluting with ethyl acetate and heptanes to obtain the target compound as a clear oil. Yield: 0.35 g, 7.8%. MS (CI, m/z): 294 (M+H-Boc); $^1$H NMR (CD$_2$Cl$_2$): δ 7.33 (m, 5H), 5.16 (m, 1H), 4.73 (m, 3H), 4.07 (m, 1H), 3.57 (m, 1H), 2.69 (m, 3H), 1.44 (m, 15H), 0.91 (m, 6H).

Preparation Example 83

Preparation of Compound 4-18

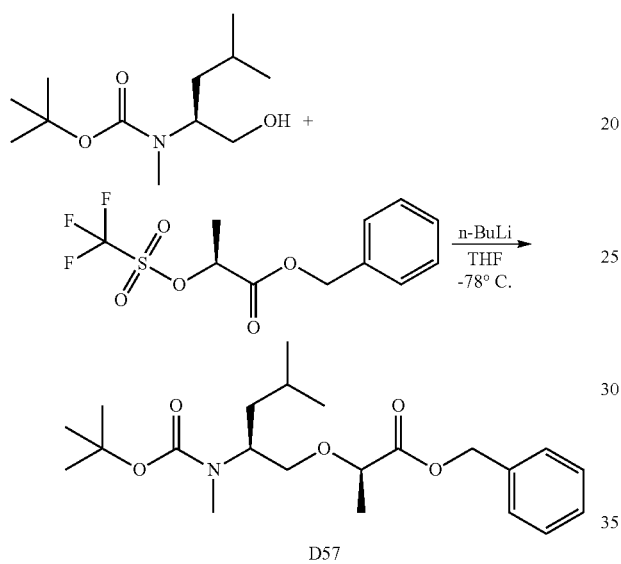

Benzyl (2R)-2-[(2S)-2-[tert-butoxycarbonyl(methyl)amino]-4-methyl-pentoxy]propanoate (D57)

To a solution of tert-butyl N-[(1S)-1-(hydroxymethyl)-3-methyl-butyl]-N-methyl-carbamate (2.8 g, 12 mmol) in 35

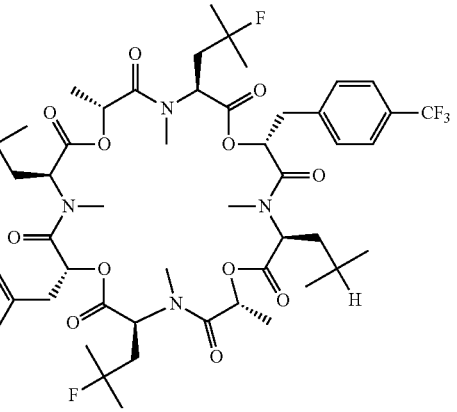

Compound 4-18 was prepared according to Schemes 31 to 33 shown below.

Scheme 31

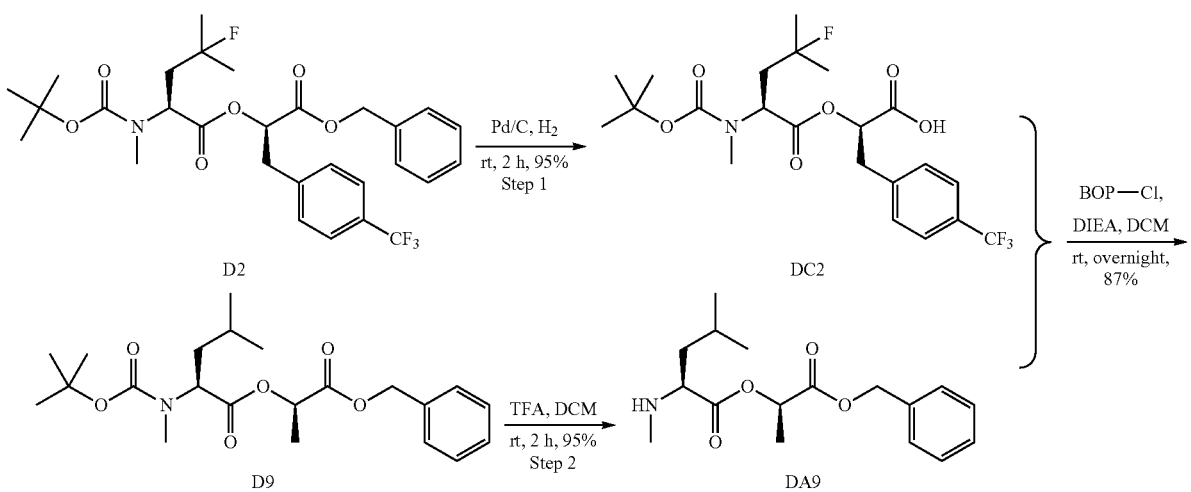

-continued
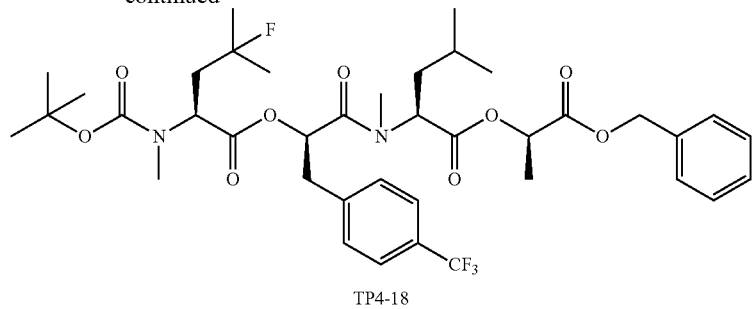
TP4-18
15
Scheme 32
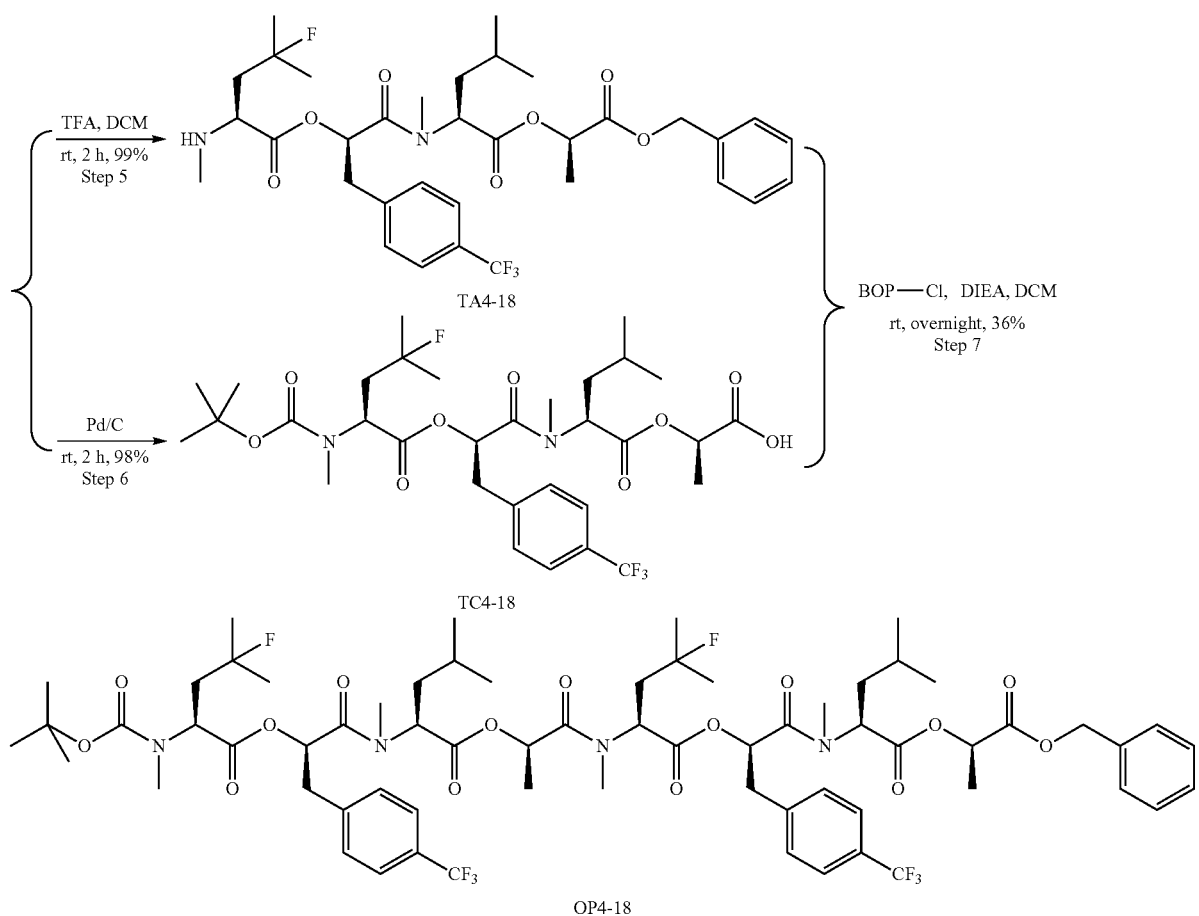
Scheme 33
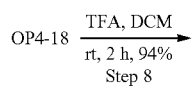

-continued
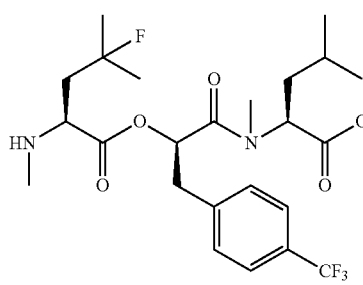
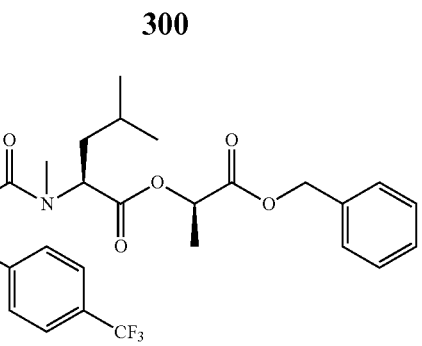
OA4-18
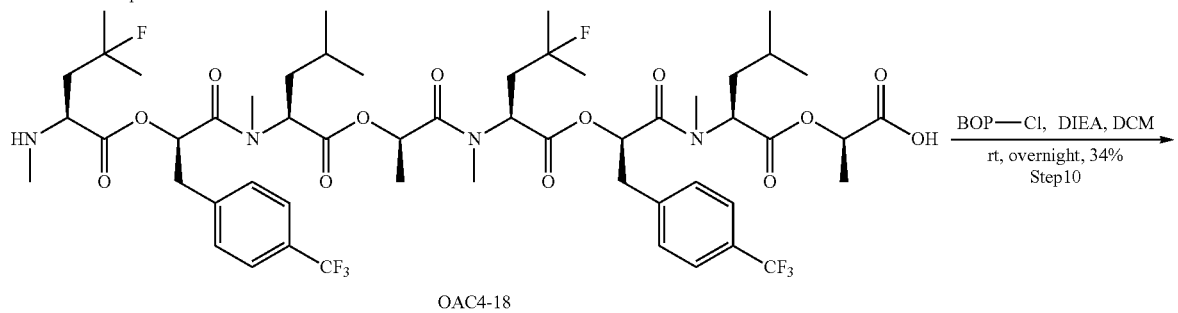
OAC4-18
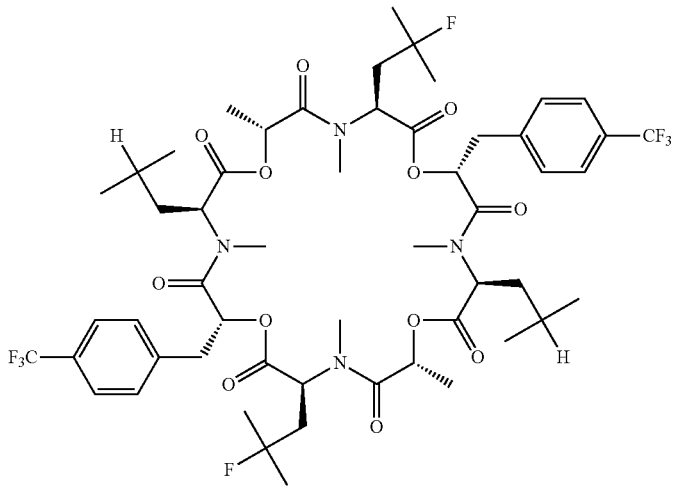
4-18
1. Preparation of Intermediate DC2
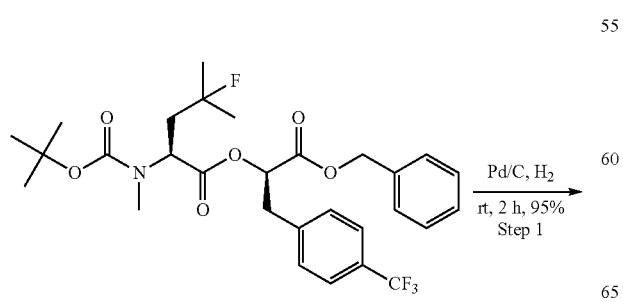
-continued
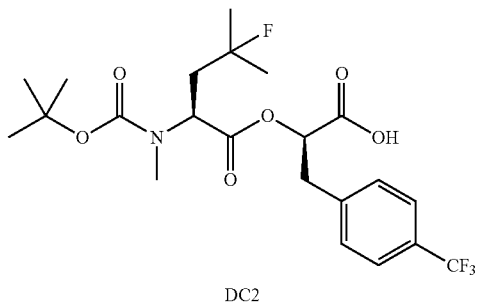
DC2

301

(2R)-2-[[(2S)-2-[[(tert-butoxy)carbonyl](methyl)amino]-4-fluoro-4-methylpentanoyl]oxy]-3-[4-(trifluoromethyl)phenyl]propanoic acid Into a 100-mL round-bottom flask purged and maintained with hydrogen, was placed methanol (10 mL), 2R)-1-(benzyloxy)-1-oxo-3-[4-(trifluoromethyl)phenyl]propan-2-yl (2S)-2-[[(tert-butoxy)carbonyl](methyl)amino]-4-fluoro-4-methylpentanoate (3.5 g, 6.14 mmol, 1.00 equiv), Pd/C (500 mg, 0.40 equiv). The resulting solution was stirred for 1 h at room temperature. The solids were filtered out. The resulting mixture was concentrated under vacuum. This resulted in 2.8 g (95%) of (2R)-2-[[(2S)-2-[[(tert-butoxy)carbonyl](methyl)amino]-4-fluoro-4-methylpentanoyl]oxy]-3-[4-(trifluoromethyl) phenyl]propanoic acid (DC2) as light yellow oil. MS (ES, m/z): 480 (M+H).

2. Preparation of Intermediate DA9

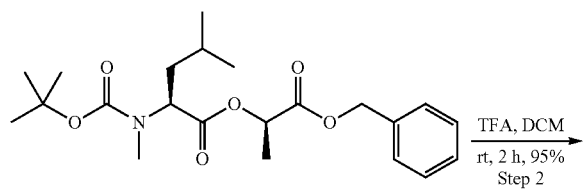

TFA, DCM
rt, 2 h, 95%
Step 2

302

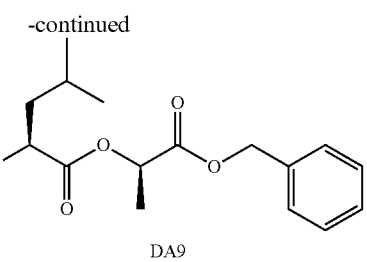

DA9

(2R)-1-(benzyloxy)-1-oxopropan-2-yl-(2S)-4-methyl-2-(methylamino)pentanoate

Into a 100-mL round-bottom flask, was placed dichloromethane (15 mL), (2R)-1-(benzyloxy)-1-oxopropan-2-yl-(2S)-2-[[(tert-butoxy)carbonyl](methyl)amino]-4-methyl-pentanoate (2.5 g, 6.13 mmol, 1.00 equiv), trifluoroacetic acid (4 mL, 20.00 equiv). The resulting solution was stirred for 2 h at room temperature. The pH value of the solution was adjusted to 9 with sodium bicarbonate (2 mol/L). The resulting solution was extracted with 3×20 mL of ethyl acetate and the organic layers combined and dried over anhydrous sodium sulfate and concentrated under vacuum. This resulted in 2 g (95%) of (2R)-1-(benzyloxy)-1-oxopropan-2-yl (2S)-4-methyl-2-(methylamino)pentanoate as colorless oil.

3. Preparation of Intermediate TP4-18

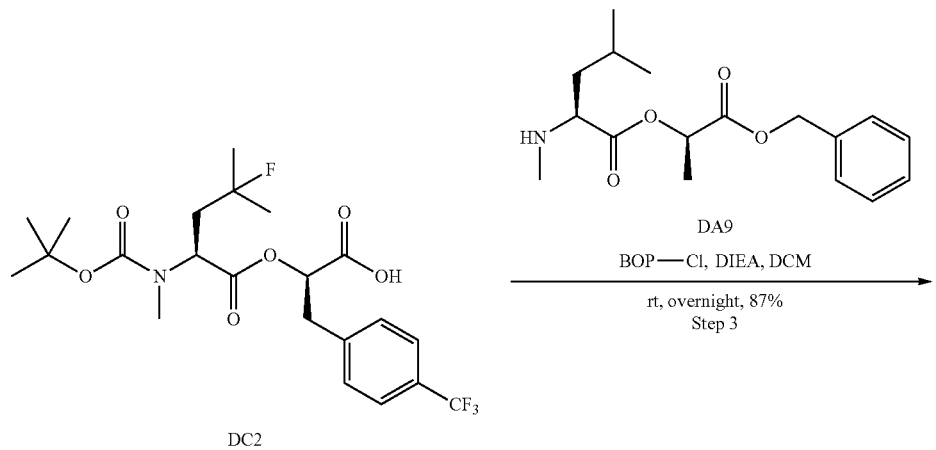

DC2

DA9

BOP—Cl, DIEA, DCM
rt, overnight, 87%
Step 3

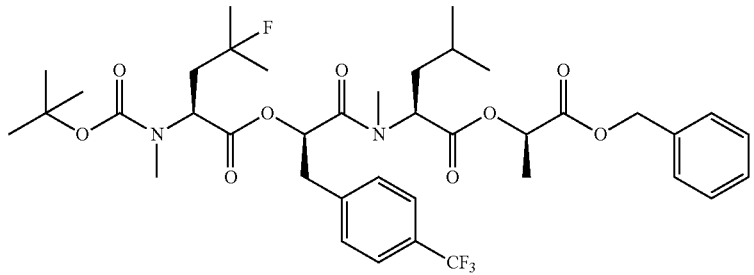

TP4-18

TA4-18:

Into a 250-mL round-bottom flask, was placed dichloromethane (30 mL), (2R)-2-[[(2S)-2-[[(tert-butoxy)carbonyl](methyl)amino]-4-fluoro-4-methylpentanoyl]oxy]-3-[4-(trifluoromethyl)phenyl]propanoic acid (2 g, 4.17 mmol, 1.00 equiv), (2R)-1-(benzyloxy)-1-oxopropan-2-yl (2S)-4-methyl-2-(methylamino)pentanoate (2 g, 6.51 mmol, 1.56 equiv), BOP-Cl (2.2 g, 8.64 mmol, 2.00 equiv), DIEA (1.1 g, 8.51 mmol, 2.04 equiv) at 0° C. The resulting solution was stirred overnight at room temperature. The solids were filtered out. The residue was applied onto a silica gel column with ethyl acetate/petroleum ether (1:10). This resulted in 2.8 g (87%) of TP4-18 as yellow oil.

4. Synthesis of Intermediate TA4-18

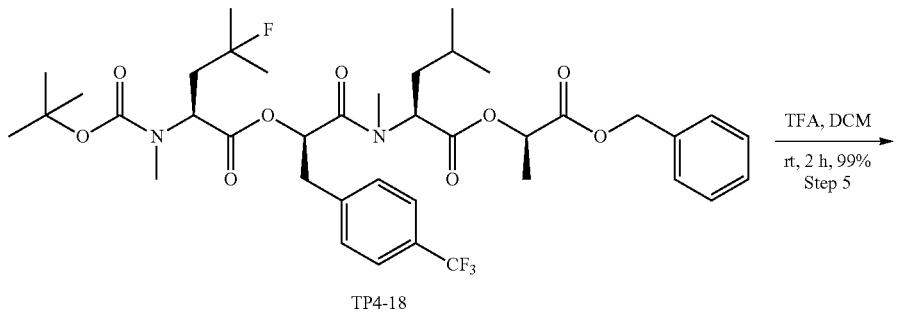

TP4-18

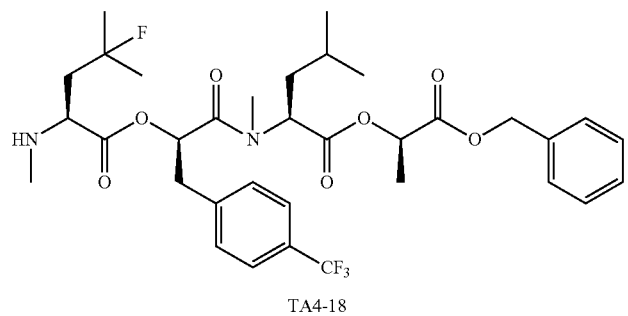

TA4-18

TA4-18:

Into a 100-mL round-bottom flask, was placed dichloromethane (15 mL), TP4-18 (700 mg, 0.91 mmol, 1.00 eq.), trifluoroacetic acid (4 mL, 20.00 eq.). The resulting solution was stirred for 2 h at room temperature. The pH value of the solution was adjusted to 9 with sodium bicarbonate (2 mol/L). The resulting solution was extracted with 3×30 mL of ethyl acetate and the organic layers combined and dried over anhydrous sodium sulfate. This resulted in 600 mg (99%) of TA4-18 as yellow oil.

5. Synthesis of Intermediate TC4-18

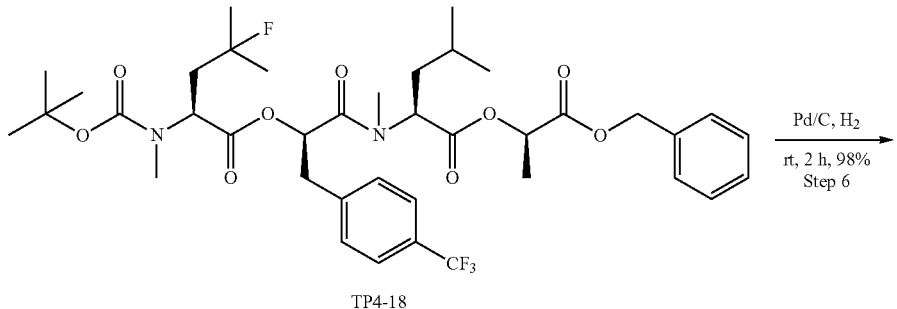

TP4-18

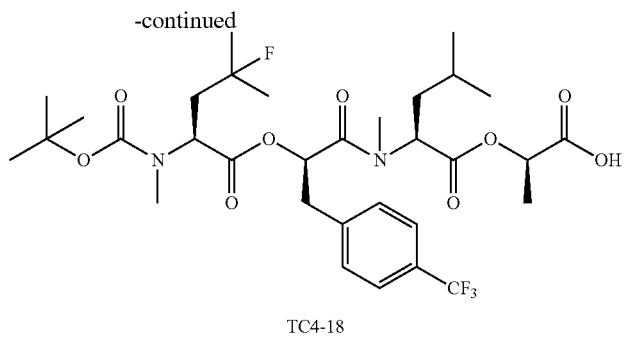

TC4-18

TC4-18:

Into a 50-mL round-bottom flask purged and maintained with hydrogen, was placed methanol (10 mL), TP4-18 (700 mg, 0.91 mmol, 1.00 equiv), Palladium on carbon (70 mg, 0.40 equiv). The resulting solution was stirred for 1 h at room temperature. The solids were filtered out. The resulting mixture was concentrated under vacuum to afford TC4-18 (610 mg, 98%) as a white solid.

6. Synthesis of OP4-18

OP4-18:

Into a 100-mL round-bottom flask, was placed dichloromethane (20 mL), TC4-18 (700 mg, 1.03 mmol, 1.00 equiv), TA4-18 (700 mg, 1.05 mmol, 1.00 equiv), BOP-Cl (530 mg, 2.08 mmol, 2.02 equiv), DIEA (270 mg, 2.09 mmol, 2.03 equiv) at 0° C. The resulting solution was stirred overnight at room temperature. The solids were filtered out. The residue was concentrated under vacuum and applied onto a silica gel column with ethyl acetate/petroleum ether (1:2) to afford OP4-18 (500 mg, 36%) as light yellow oil.

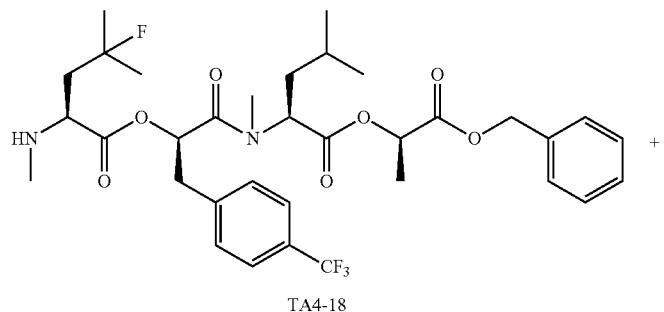

TA4-18

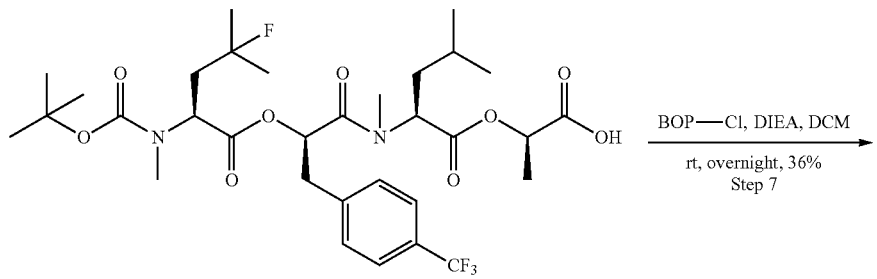

TC4-18

BOP—Cl, DIEA, DCM
rt, overnight, 36%
Step 7

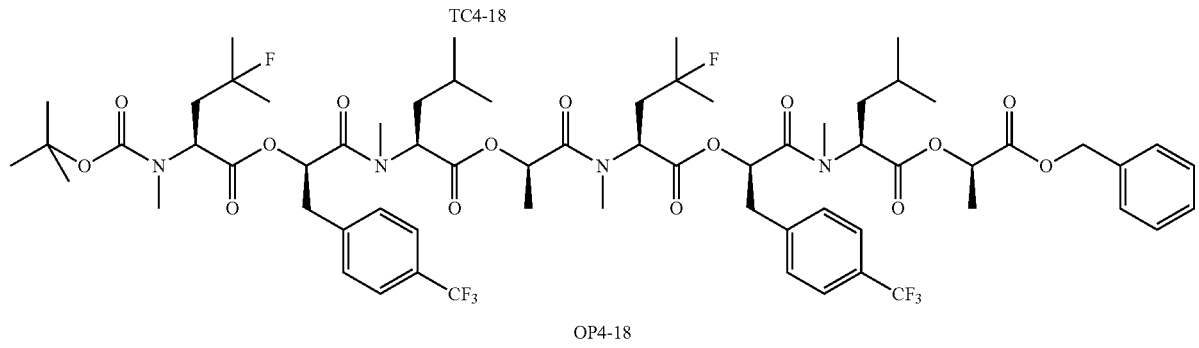

OP4-18

7. Synthesis of Intermediate OA4-18

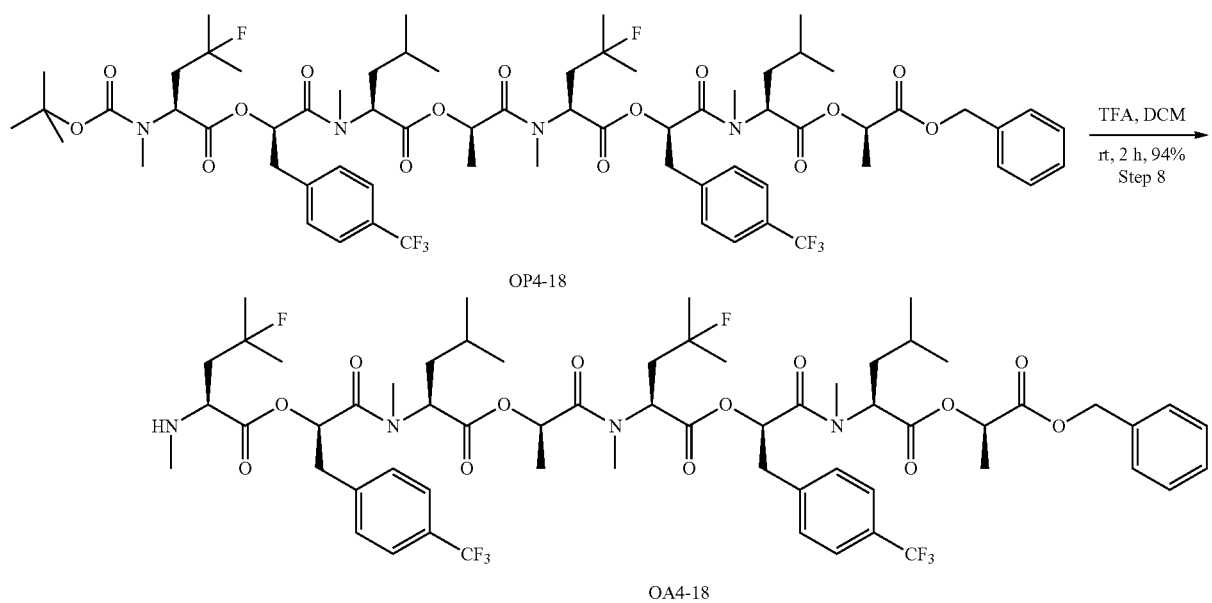

OA4-18:
Into a 50-mL round-bottom flask, was placed dichloromethane (10 mL), intermediate OP4-18 (600 mg, 0.45 mmol, 1.00 equiv), trifluoroacetic acid (4 mg, 0.04 mmol, 20.00 equiv). The resulting solution was stirred for 2 h at room temperature. The pH value of the solution was adjusted to 9 with sodium bicarbonate (2 mol/L). The resulting solution was extracted with 3×30 mL of ethyl acetate. The organic layers combined and dried over anhydrous sodium sulfate and concentrated under vacuum. This resulted in 520 mg (94%) of OA4-18 as light yellow oil.
Synthesis of Intermediate OAC4-18

OAC4-18:
Into a 50-mL round-bottom flask purged and maintained with hydrogen, was placed methanol (15 mL), intermediate 4-18-9 (400 mg, 0.33 mmol, 1.00 equiv), Palladium on carbon (100 mg, 0.60 equiv). The resulting solution was stirred for 1 h at room temperature. The solids were filtered out. The resulting mixture was concentrated under vacuum. This resulted in 340 mg (92%) of OAC4-18 as a colorless solid.

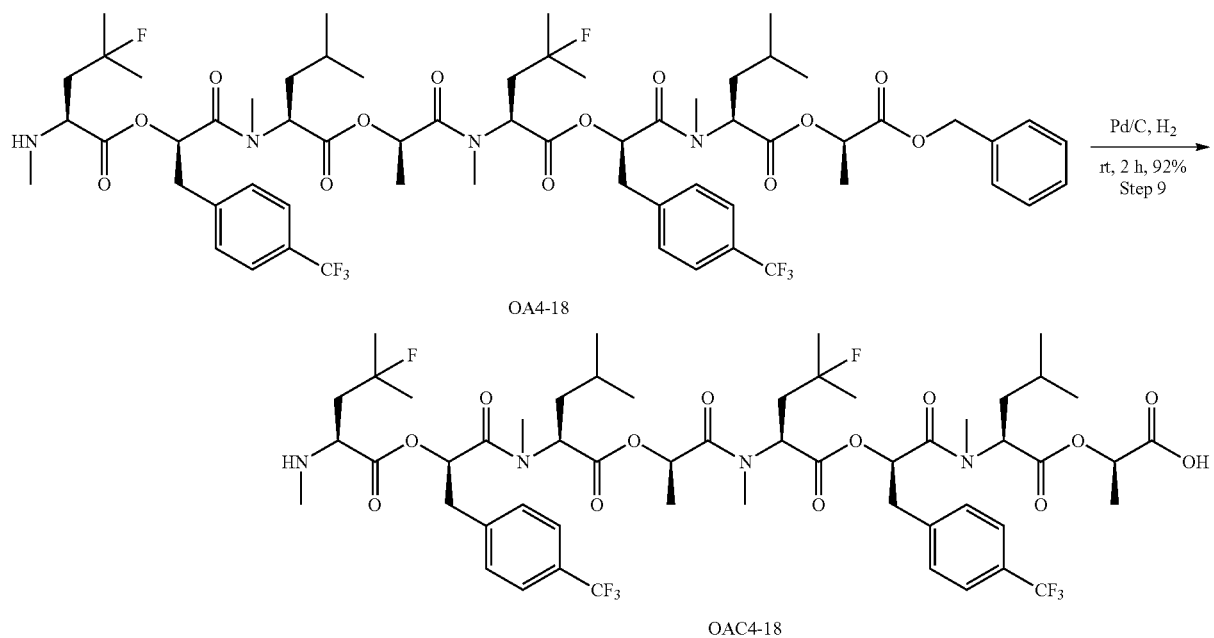

9. Preparation of Compound 4-18

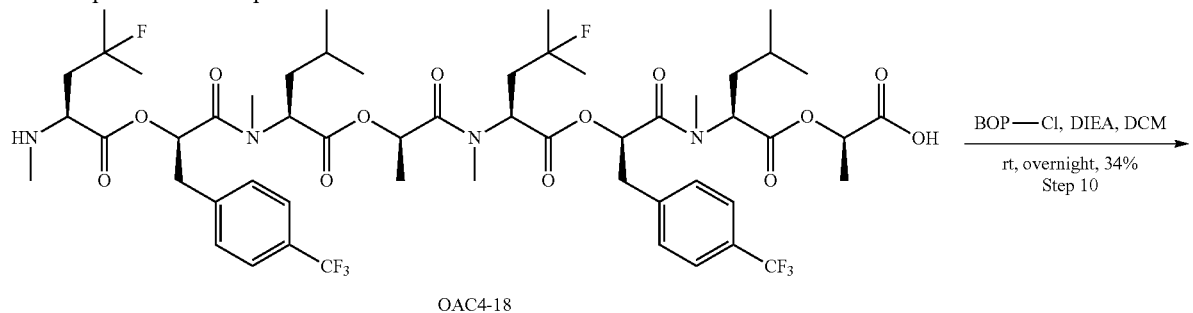

OAC4-18

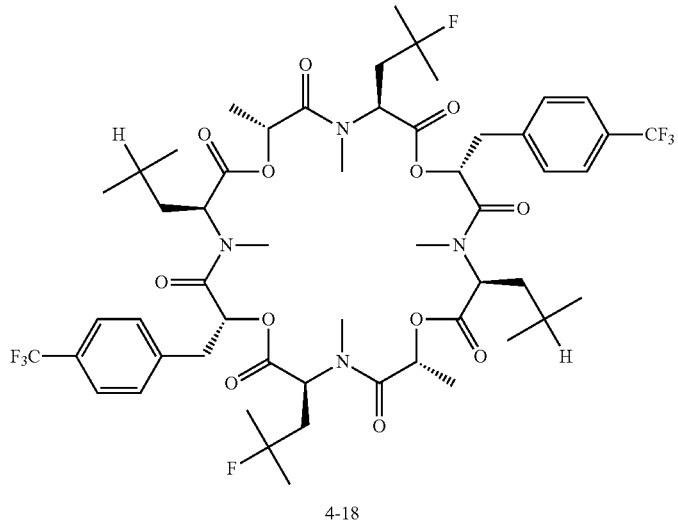

4-18

4-18:

Into a 500-mL round-bottom flask, was placed OAC4-18 (300 mg, 0.26 mmol, 1.00 equiv), dichloromethane (50 mL), BOP-Cl (168 mg, 0.66 mmol, 2.00 equiv), DIEA (85 mg, 0.66 mmol, 2.50 equiv) at 0° C. The resulting solution was stirred overnight at room temperature. The resulting mixture was concentrated under vacuum. The crude product was purified by Prep-HPLC with the following conditions: Column, SunFire Prep C18 5 um 19*150 mm; mobile phase, water (it contains 0.05% Trifluoroacetic acid) and $CH_3CN$; Gradient: 75% to 88% in 8 min; Detector, 254 nm. This resulted in 101.1 mg (34%) of 4-18 as a white solid. (ES, m/z): 1120.5 (calculated, M), 1121.5 (found, M+H).

$^1H$ NMR (300 MHz, $CDCl_3$): δ 7.58-7.56 (m, 4H), 7.39-7.28 (m, 4H), 5.76-5.70 (m, 2H), 5.42-5.15 (m, 5H), 4.51 (m, 1H), 3.2-3.07 (m, 4H), 3.01 (m, 2H), 2.88-2.76 (m, 10H), 2.21-1.91 (m, 4H), 1.70-1.66 (m, 2H), 1.52-1.27 (m, 19H), 1.17-0.80 (m, 15H). [c]=−50.08° (T=27.2° C., c 0.86 g/100 mL in MeOH).

Preparation Example 84: Preparation of Compound 6-18

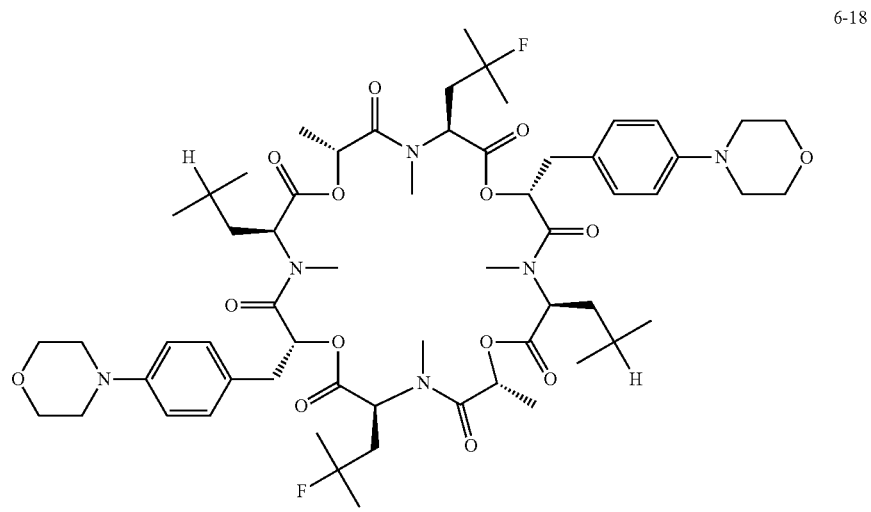 [SMILES: CC(C)C[C@H]1C(=O)O[C@H](C)C(=O)N(C)[C@@H](CC(C)(C)F)C(=O)O[C@H](Cc2ccc(N3CCOCC3)cc2)C(=O)N(C)[C@@H](CC(C)C)C(=O)O[C@H](C)C(=O)N(C)[C@@H](CC(C)(C)F)C(=O)O[C@H](Cc2ccc(N3CCOCC3)cc2)C(=O)N1C]

6-18

Compound 6-18 was prepared in a similar way to compound 4-18 according to Schemes 34 to 36 shown below.
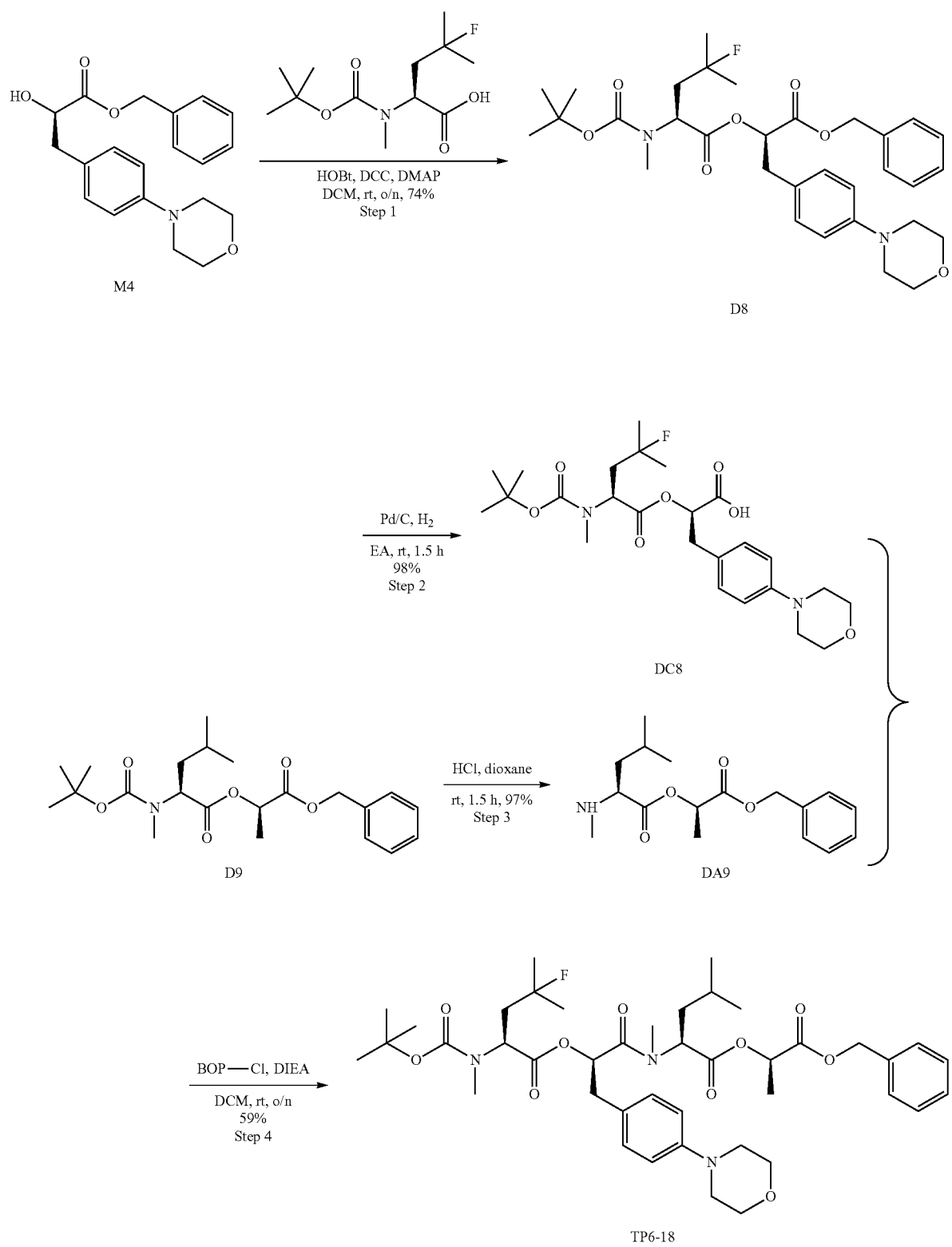

Scheme 35
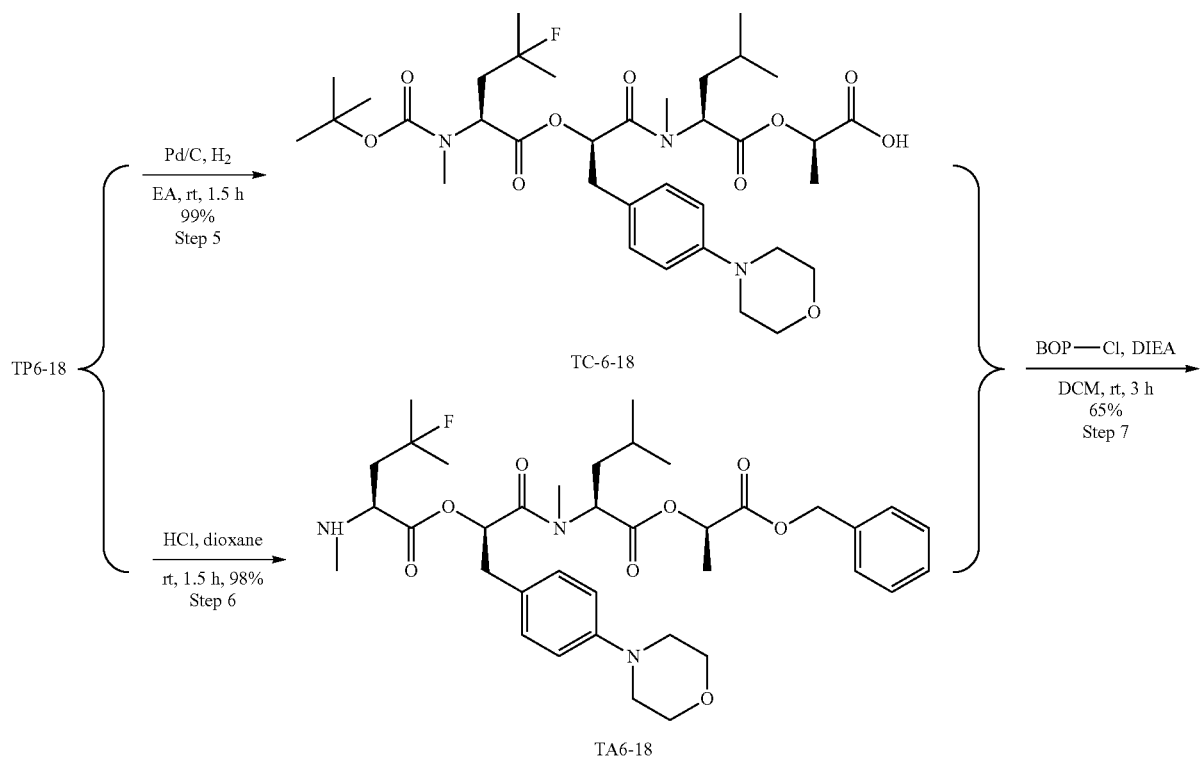
Scheme 36
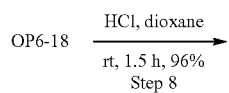 $\xrightarrow{\text{HCl, dioxane}}_{\substack{\text{rt, 1.5 h, 96\%} \\ \text{Step 8}}}$

315
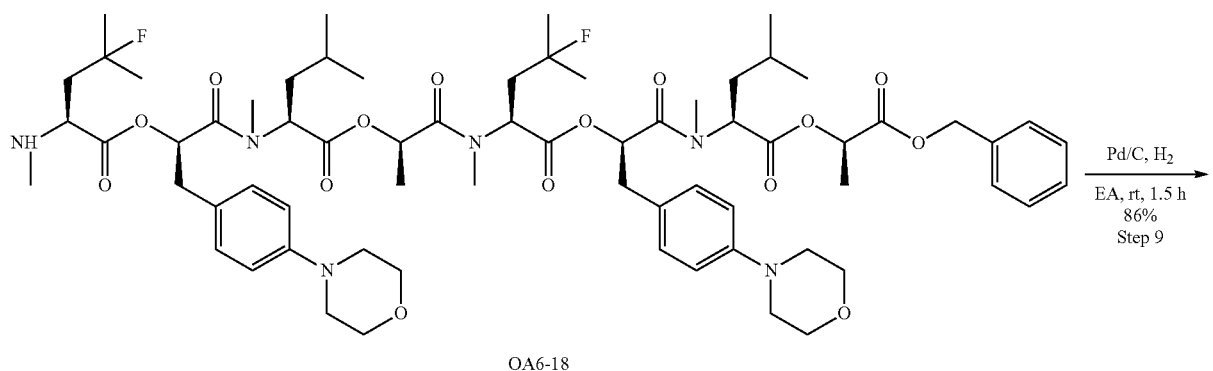
OA6-18
Pd/C, H₂
EA, rt, 1.5 h
86%
Step 9
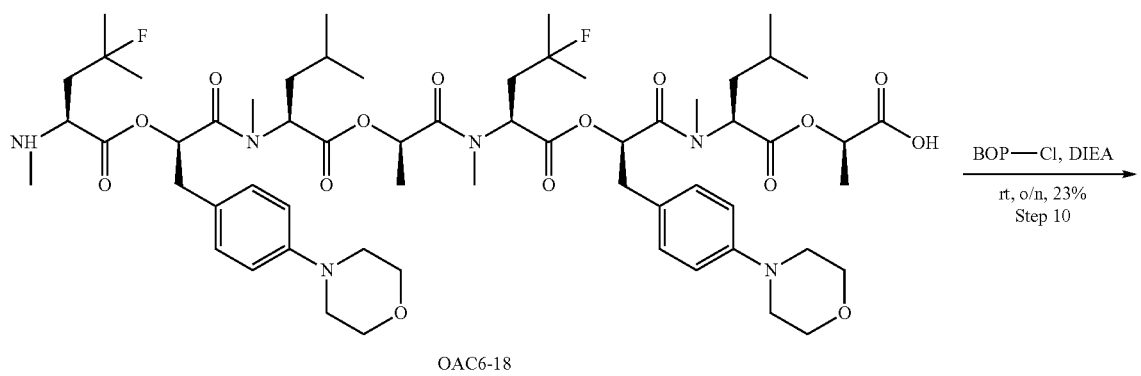
OAC6-18
BOP—Cl, DIEA
rt, o/n, 23%
Step 10
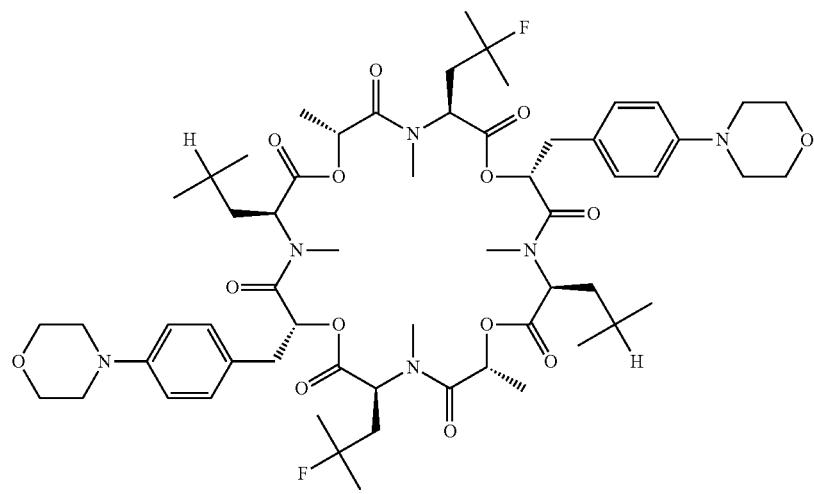
6-18

1. Synthesis of D8

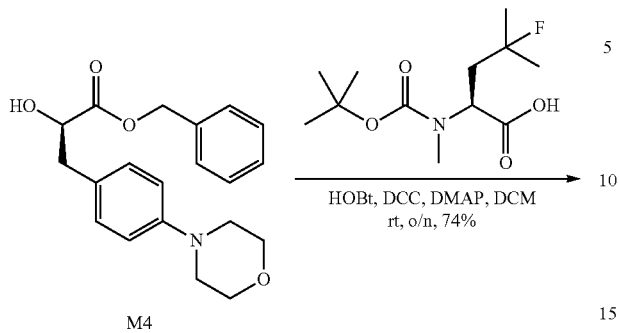

M4

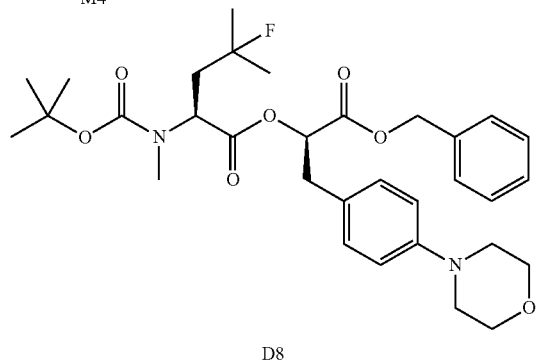

D8

(2R)-1-(benzyloxy)-3-[4-(morpholin-4-yl)phenyl]-1-oxopropan-2-yl-(2S)-2-[[(tert-butoxy) carbonyl](methyl)amino]-4-fluoro-4-methylpentanoate Into a 250-mL round-bottom flask purged and maintained with an inert atmosphere of nitrogen, 0° C., was placed dichloromethane (50 mL), benzyl (2R)-2-hydroxy-3-[4-(morpholin-4-yl)phenyl]propanoate (2.72 g, 7.97 mmol, 1.00 equiv), (2S)-2-[(tert-butoxy)carbonyl](methyl)amino-4-fluoro-4-methylpentanoic acid (2.1 g, 7.98 mmol, 1.00 equiv), HOBT (1.2 g, 8.89 mmol, 1.10 equiv), DCC (1.8 g, 8.74 mmol, 1.10 equiv), 4-dimethylaminopyridine (1.1 g, 9.00 mmol, 1.10 equiv). The resulting solution was stirred overnight at room temperature. The residue was applied onto a silica gel column with ethyl acetate/petroleum ether (1:10-1:5). This resulted in 3.5 g (75%) of (2R)-1-(benzyloxy)-3-[4-(morpholin-4-yl)phenyl]-1-oxopropan-2-yl (2S)-2-[[(tert-butoxy)carbonyl](methyl)amino]-4-fluoro-4-methylpentanoate as a colorless oil.

2. Synthesis of DC8

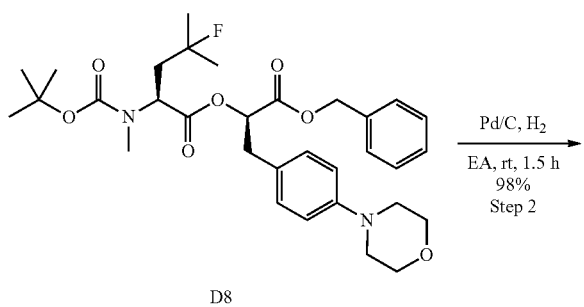

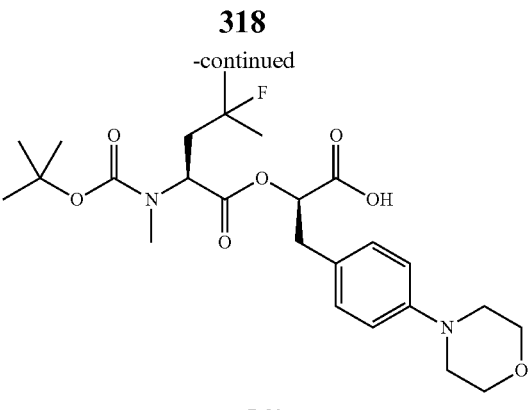

DC8

(2R)-2-[[(2S)-2-[[(tert-butoxy)carbonyl](methyl)amino]-4-fluoro-4-methylpentanoyl]oxy]-3-[4-(morpholin-4-yl)phenyl]propanoic acid Into a 50-mL round-bottom flask purged and maintained with hydrogen, was placed ethyl acetate (10 mL), Pd/C (130 mg), (2R)-1-(benzyloxy)-3-[4-(morpholin-4-yl)phenyl]-1-oxopropan-2-yl-(2S)-2-[[(tert-butoxy)carbonyl](methyl)amino]-4-fluoro-4-methylpentanoate (650 mg, 1.11 mmol, 1.00 equiv). The resulting solution was stirred for 1.5 h at room temperature. The solids were filtered out. The resulting mixture was concentrated under vacuum. This resulted in 540 mg (98%) of (2R)-2-[[(2S)-2-[[(tert-butoxy)carbonyl](methyl)amino]-4-fluoro-4-methylpentanoyl]oxy]-3-[4-(morpholin-4-yl)phenyl]propanoic acid as a white solid.

3. Synthesis of DA9

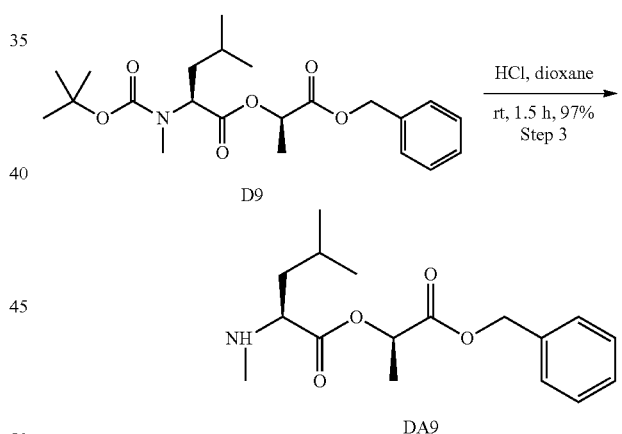

(2R)-1-(benzyloxy)-1-oxopropan-2-yl-(2S)-4-methyl-2-(methylamino)pentanoate

Into a 50-mL round-bottom flask, was placed dioxane/HCl (10 mL), (2R)-1-(benzyloxy)-1-oxopropan-2-yl-(2S)-2-[[(tert-butoxy)carbonyl](methyl)amino]-4-methylpentanoate (460 mg, 1.13 mmol, 1.00 equiv). The resulting solution was stirred for 1.5 h at room temperature. The reaction was then quenched by the addition of 10 mL of NaHCO$_3$ (aq). The resulting solution was extracted with 3×20 mL of dichloromethane and the organic layers combined. The resulting mixture was washed with 3×5 mL of brine. The mixture was dried over anhydrous sodium sulfate and concentrated under vacuum. This resulted in 340 mg (98%) of (2R)-1-(benzyloxy)-1-oxopropan-2-yl-(2S)-4-methyl-2-(methylamino)pentanoate (DA9) as a colorless oil.

4. Synthesis of TP6-18

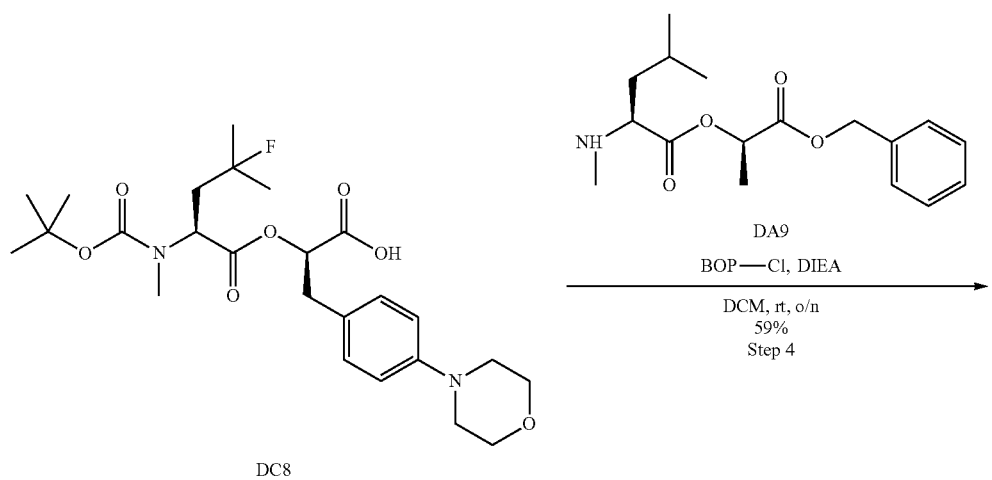

DC8

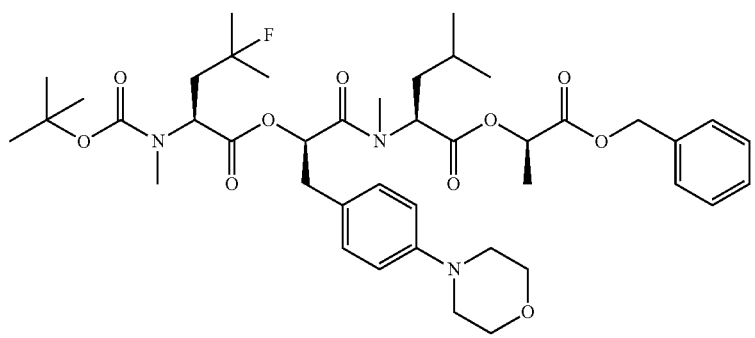

TP6-18

TP6-18:

Into a 50-mL round-bottom flask, was placed dichloromethane (10 mL), (2R)-2-[[(2S)-2-[[(tert-butoxy)carbonyl](methyl) amino]-4-fluoro-4-methylpentanoyl]oxy]-3-[4-(morpholin-4-yl)phenyl]propanoic acid (540 mg, 1.09 mmol, 1.00 equiv), (2R)-1-(benzyloxy)-1-oxopropan-2-yl-(2S)-4-methyl-2-(methylamino)pentanoate (DC8, 340 mg, 1.11 mmol, 1.00 equiv), BOP-Cl (554 mg, 2.18 mmol, 2.00 equiv). This was followed by the addition of DIEA (280 mg, 2.17 mmol, 2.00 equiv) dropwise with stirring at 0° C. The resulting solution was stirred overnight at room temperature. The resulting mixture was concentrated under vacuum. The residue was purified by preparative TLC (EA:PE=1:2). This resulted in 510 mg (60%) of TP6-18 as a colorless oil.

5. Synthesis of TC6-18

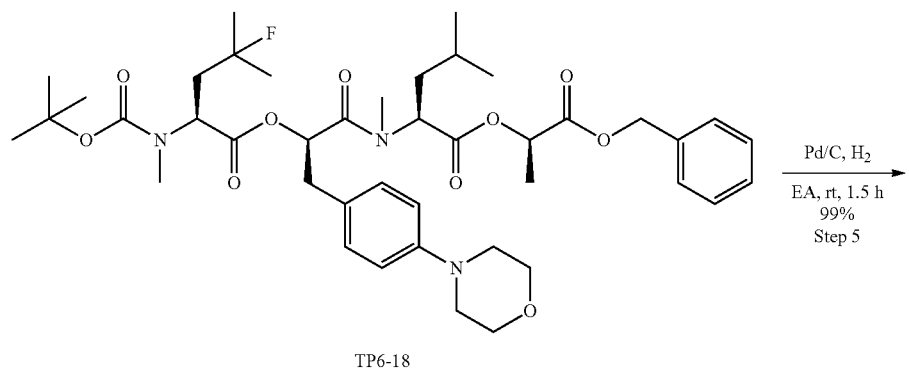

TP6-18

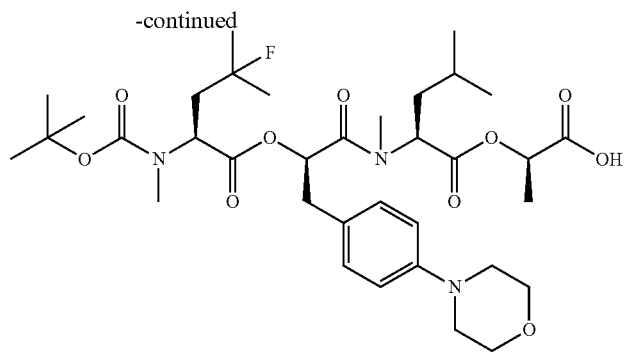

TC6-18

TC6-18:

Into a 50-mL round-bottom flask purged and maintained with hydrogen, was placed ethyl acetate (10 mL), Pd/C (52 mg), TP6-18 (260 mg, 0.33 mmol, 1.00 equiv). The resulting solution was stirred for 1.5 h at room temperature. The solids were filtered out. The resulting mixture was concentrated under vacuum. This resulted in 230 mg (100%) of TC6-18 as a white solid.

6. Synthesis of TA6-18

TA6-18:

Into a 50-mL round-bottom flask, was placed dioxane/HCl (10 mL), TP6-18 (250 mg, 0.32 mmol, 1.00 equiv). The resulting solution was stirred for 1.5 h at room temperature. The reaction was then quenched by the addition of 10 mL of NaHCO$_3$ (aq). The resulting solution was extracted with 3×20 mL of dichloromethane and the organic layers combined. The resulting mixture was washed with 3×5 mL of brine. The mixture was dried over anhydrous sodium sulfate and concentrated under vacuum. This resulted in 215 mg (99%) of TA6-18 as a colorless oil.

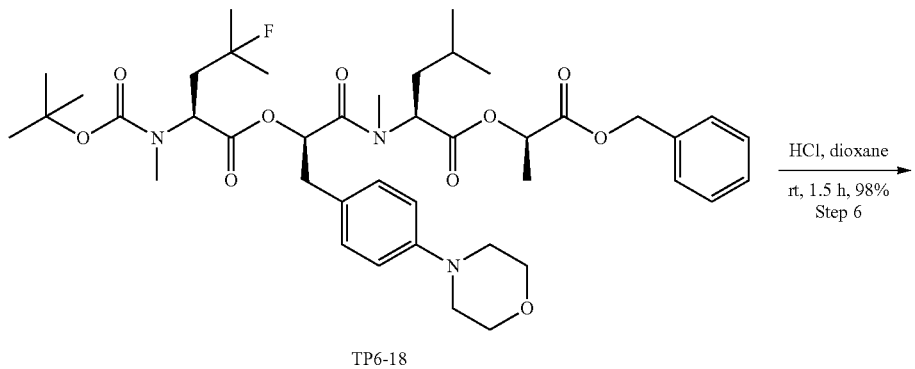

TP6-18

HCl, dioxane
rt, 1.5 h, 98%
Step 6

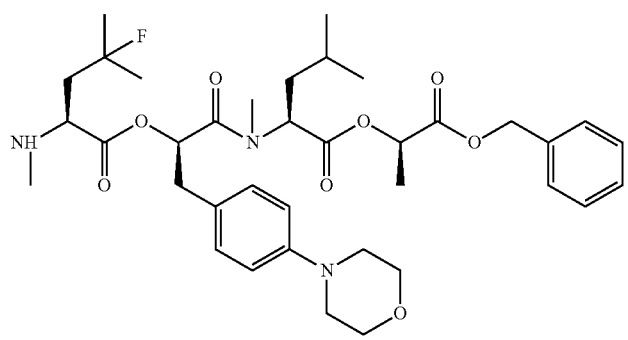

TA6-18

7. Synthesis of OP6-18

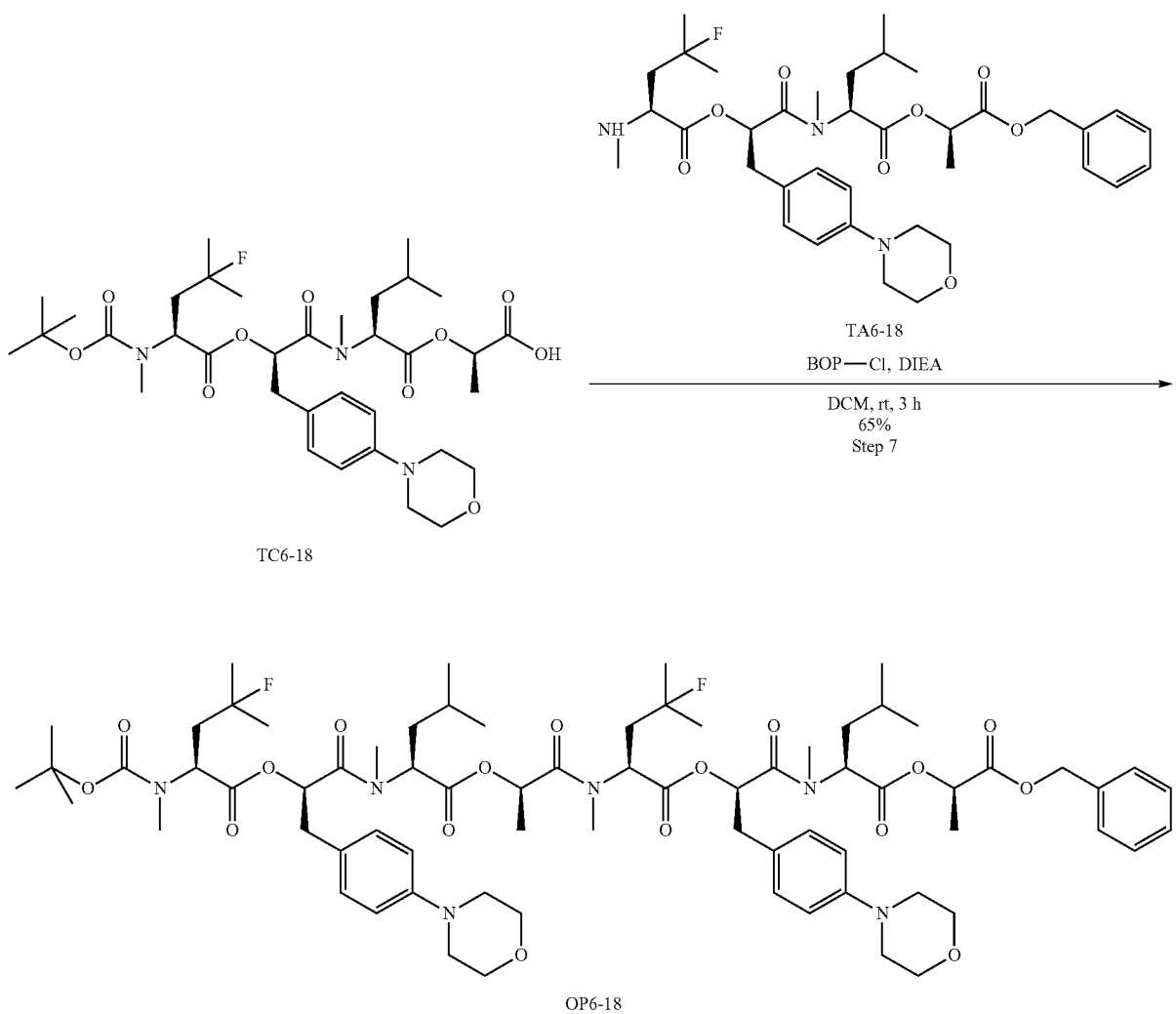

OP6-18:
Into a 50-mL round-bottom flask, was placed dichloromethane (10 mL), TC6-18 (218 mg, 0.31 mmol, 1.00 equiv), TA6-18 (215 mg, 0.31 mmol, 1.00 equiv), BOP-Cl (159 mg, 0.62 mmol, 2.00 equiv). This was followed by the addition of DIEA (80 mg, 0.62 mmol, 2.00 equiv) dropwise with stirring at 0° C. The resulting solution was stirred for 3 h at room temperature. The resulting mixture was concentrated under vacuum. The residue was purified by preparative TLC (EA:PE=1:1). This resulted in 280 mg (66%) of OP6-18 as a white solid.

8. Synthesis of OA6-18

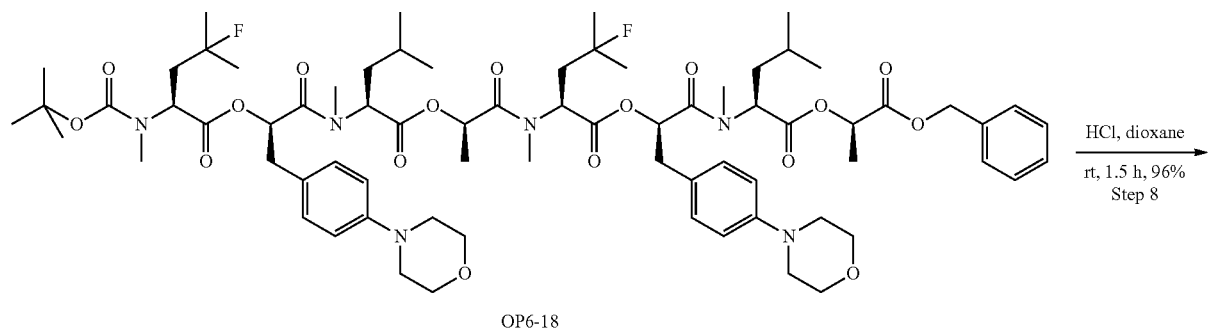

-continued

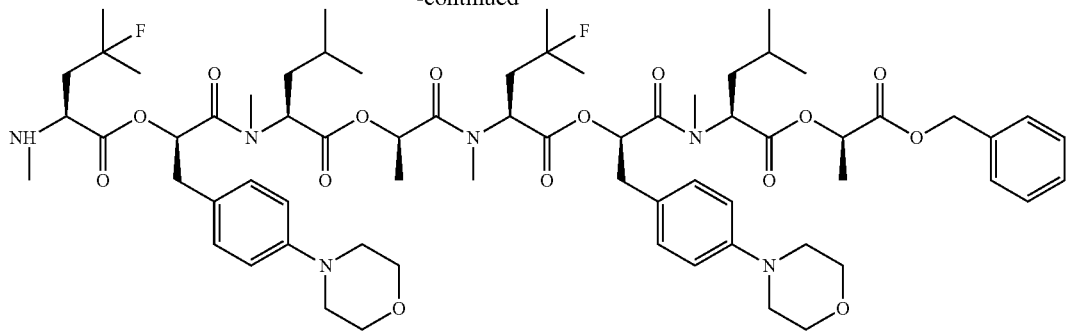

OA6-18

OA6-18:
Into a 50-mL round-bottom flask, was placed dioxane/HCl (10 mL), OP6-18 (280 mg, 0.21 mmol, 1.00 equiv). The resulting solution was stirred for 1 h at room temperature. The reaction was then quenched by the addition of 10 mL of NaHCO$_3$ (aq). The resulting solution was extracted with 3×20 mL of dichloromethane and the organic layers combined. The resulting mixture was washed with 3×5 mL of brine. The DCM phase was dried over anhydrous sodium sulfate and concentrated under vacuum. This resulted in 250 mg (96%) of OA6-18 as a colorless oil.

9. Synthesis of OAC6-18

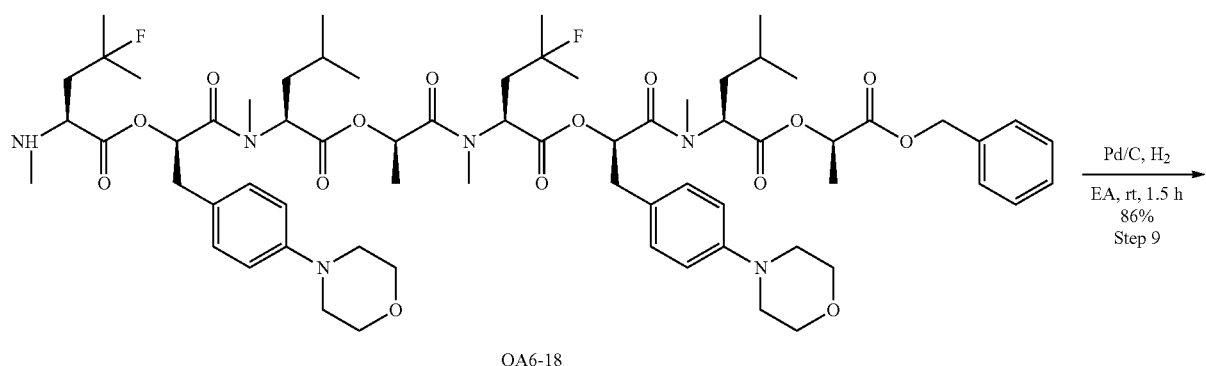

OA6-18

Pd/C, H$_2$
EA, rt, 1.5 h
86%
Step 9

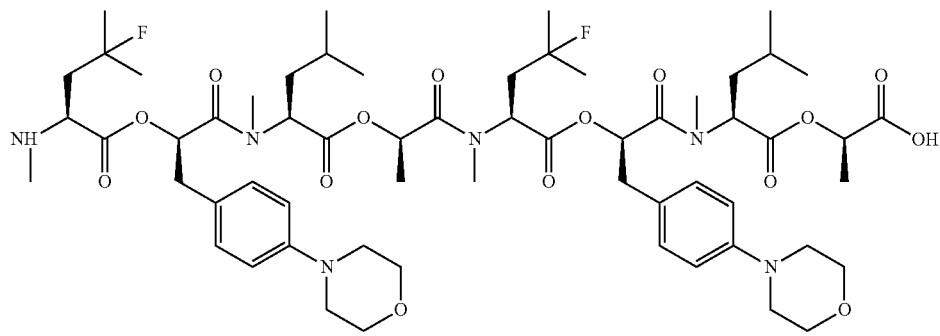

OAC6-18

OAC6-18:
Into a 50-mL round-bottom flask, was placed ethyl acetate hydrogen (10 mL), Pd/C (50 mg), OA6-18 (250 mg, 0.20 mmol, 1.00 equiv), The flask was evacuated and flushed three times with hydrogen, followed by flushing with hydrogen. The resulting solution was stirred for 1.5 h at room temperature under an atmosphere of hydrogen. The solids were filtered out. The resulting mixture was concentrated under vacuum. This resulted in 200 mg (86%) of OAC6-18 as a white solid.

10. Synthesis of 6-18

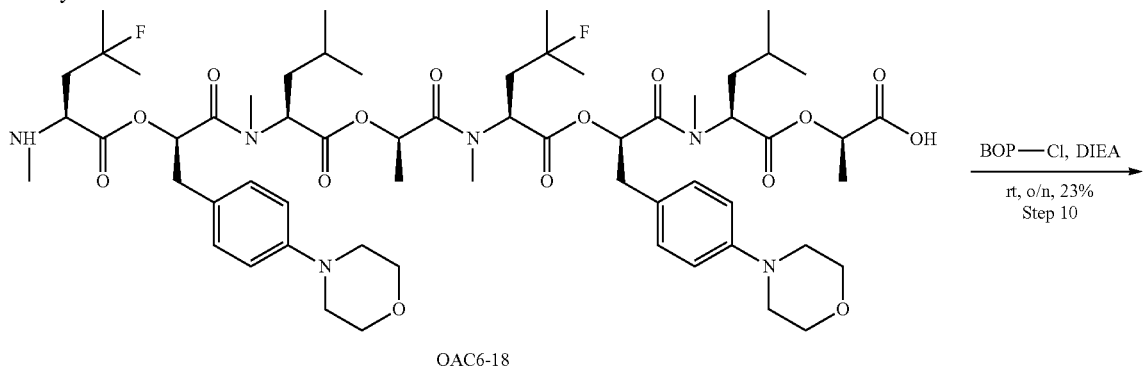

OAC6-18

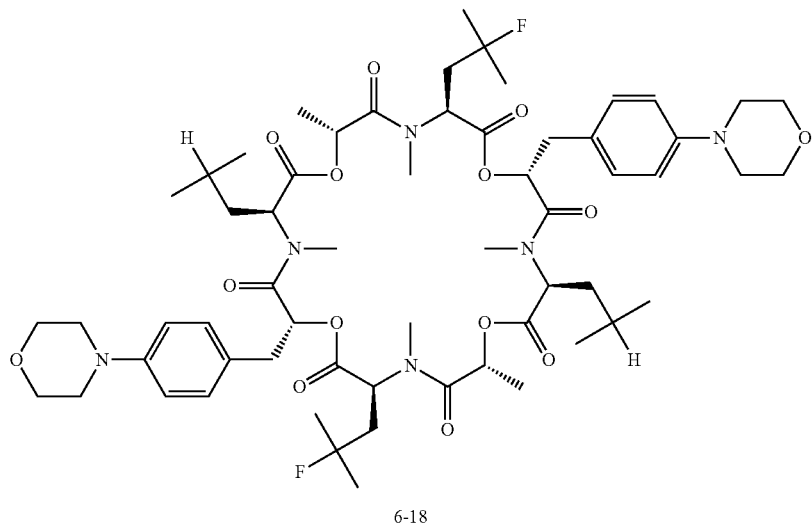 [SMILES: CC(C)C[C@H]1C(=O)O[C@H](Cc2ccc(N3CCOCC3)cc2)C(=O)N(C)[C@@H](CC(C)C)C(=O)O[C@H](C)C(=O)N(C)[C@@H](CC(C)C)C(=O)O[C@H](Cc2ccc(N3CCOCC3)cc2)C(=O)N(C)[C@@H](CC(C)C)C(=O)O[C@H](C)C(=O)N1C]

6-18

6-18:

Into a 250-mL round-bottom flask, was placed dichloromethane (100 mL), OAC6-18 (200 mg, 0.17 mmol, 1.00 equiv), BOP-Cl (86 mg, 0.34 mmol, 2.00 equiv). This was followed by the addition of DIEA (44 mg, 0.34 mmol, 2.00 equiv) dropwise with stirring at 0° C. The resulting solution was stirred overnight at room temperature. The resulting mixture was concentrated under vacuum. The crude product was purified by Prep-HPLC with the following conditions Column: SunFire Prep C18 5 um 19*150 mm; mobile phase: water (it contains 0.1% formic acid and $CH_3CN$; Gradient: 15% to 25% in 4 min, 25% to 60% in 6 min; Flow rate: 15 mL/min; Detector UV wavelength: 254 nm. This resulted in 45.6 mg (23%) of 6-18 as a white solid. (ES, m/z): 1154.6 (calculated, M), 1156.0 (found, M+H). $^1$H NMR: (300 MHz, $CD_3OD$): δ7.21-7.16 (m, 4H), 6.95-6.91 (m, 4H), 5.83-5.10 (m, 7H), 4.97-4.90 (m, 1H), 3.91-9.79 (m, 8H), 3.18-2.81 (m, 24H), 2.41-2.02 (m, 4H), 1.83-1.31 (m, 21H), 1.2-0.75 (m, 15H), [α]=−62° (T=27.2° C., c 0.528 g/100 mL in MeOH).

Preparation Example 85: Preparation of Compound 7-27

7-27

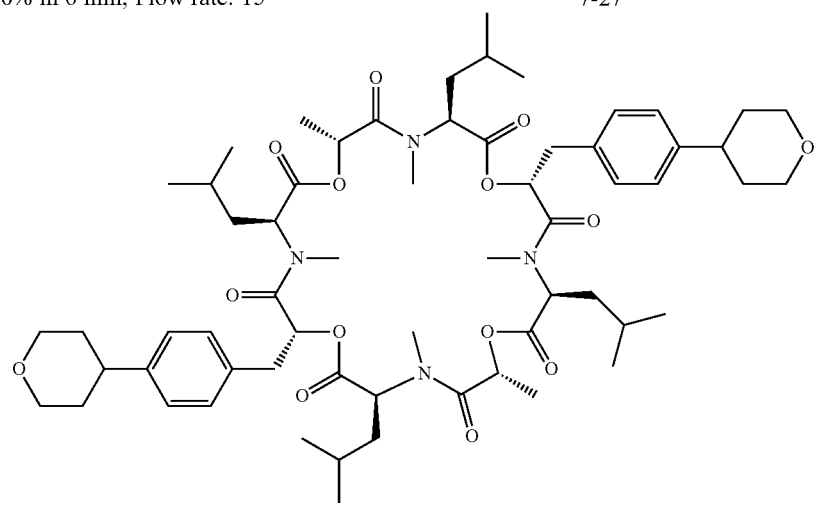

Compound 7-27 was prepared according to Schemes 37-39 below:
Scheme 37
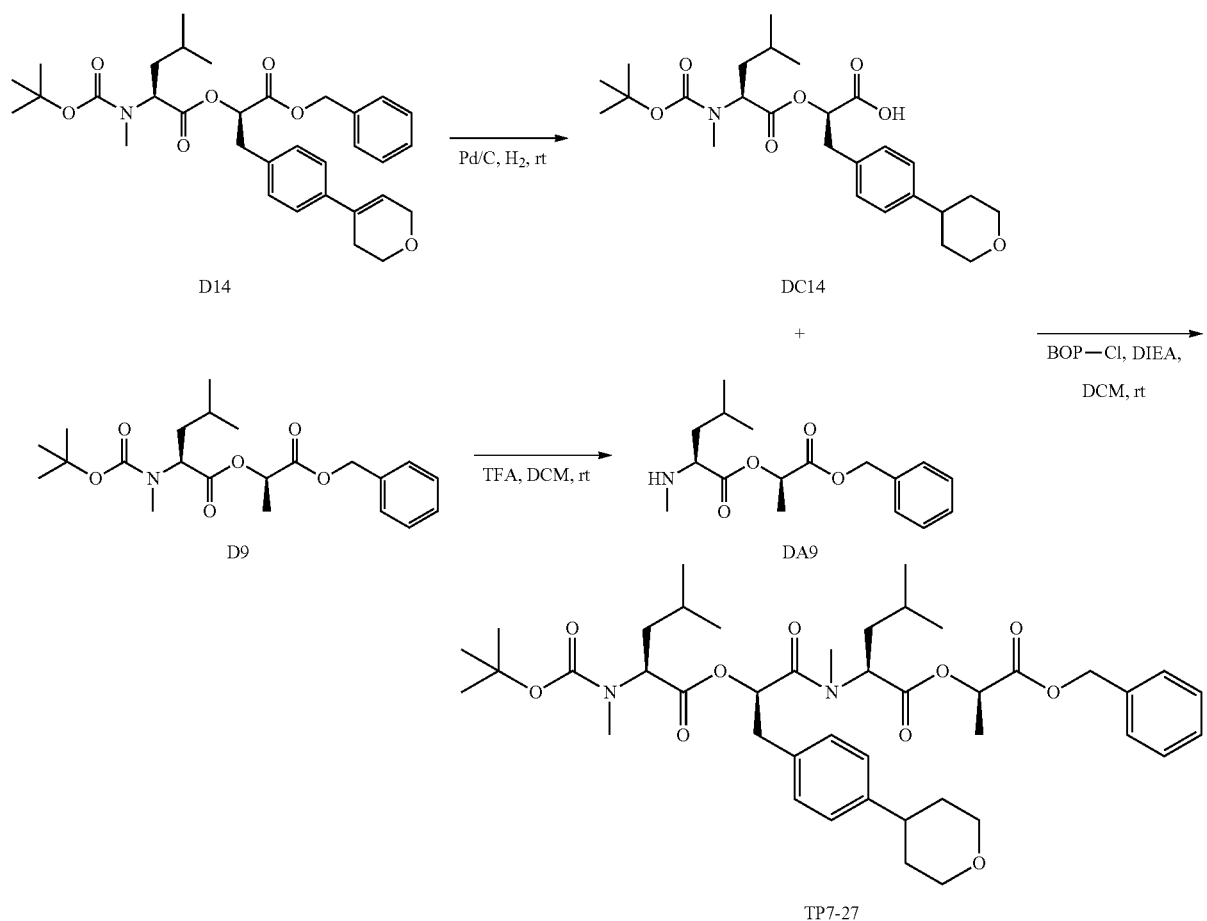

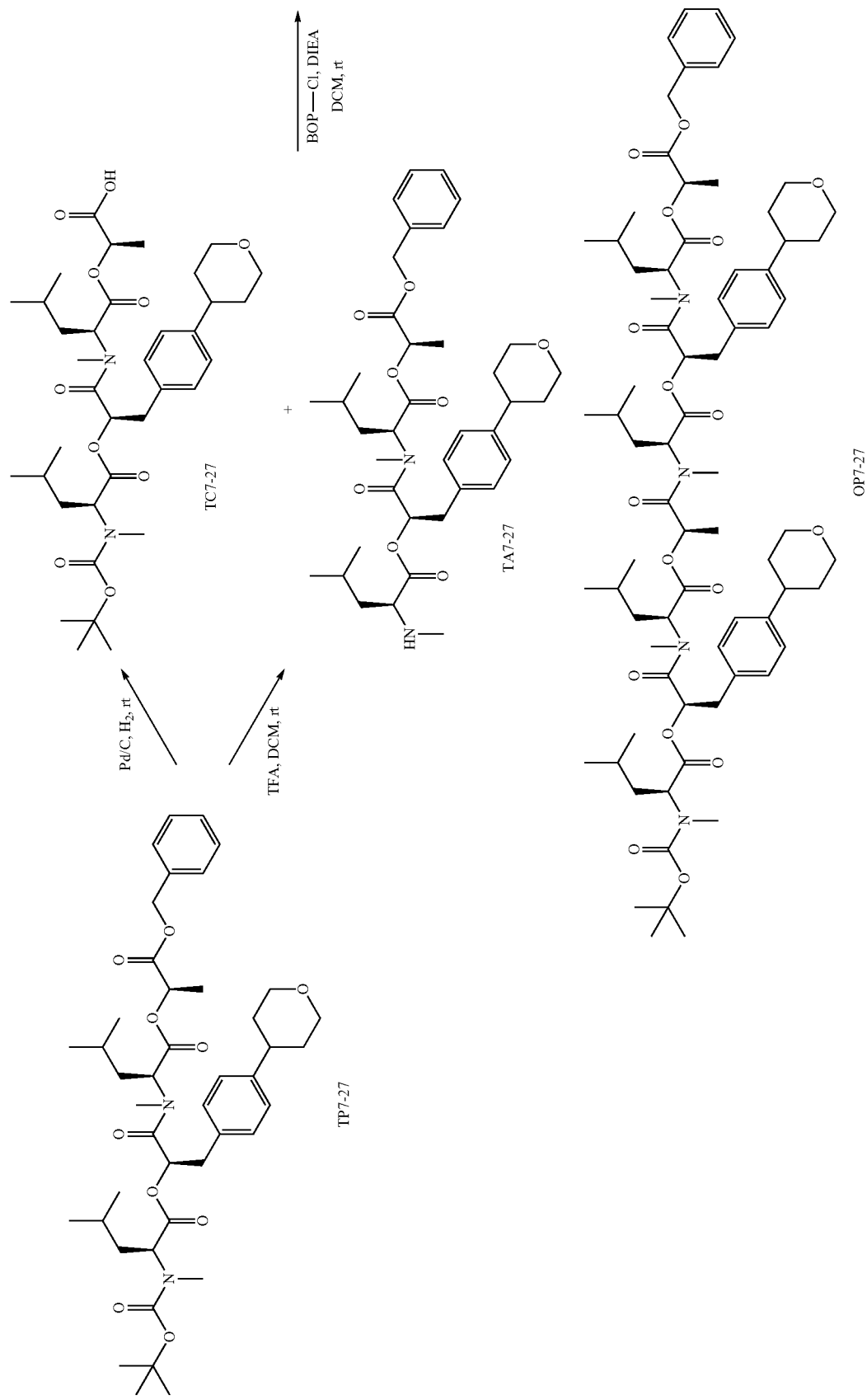

Scheme 39
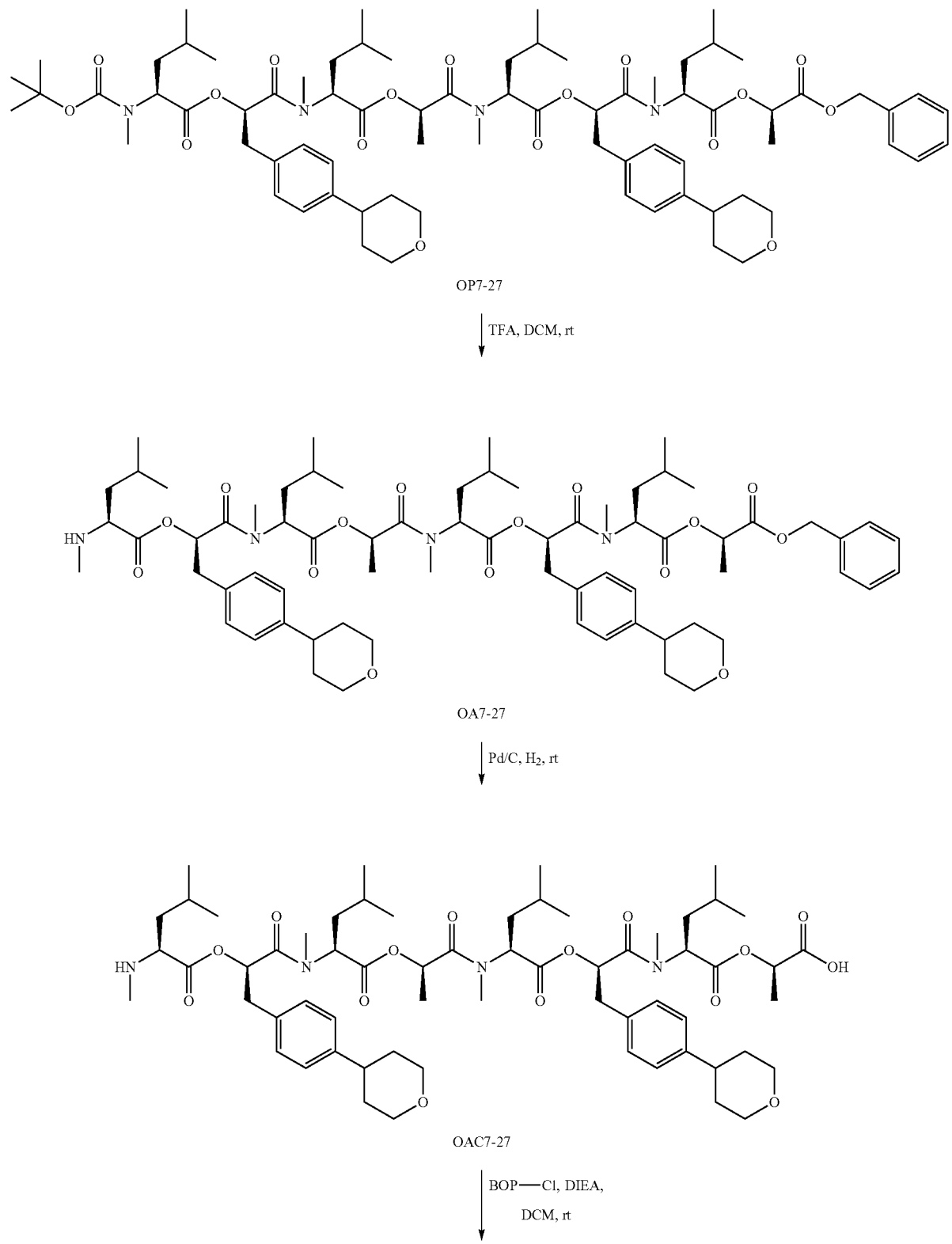

-continued

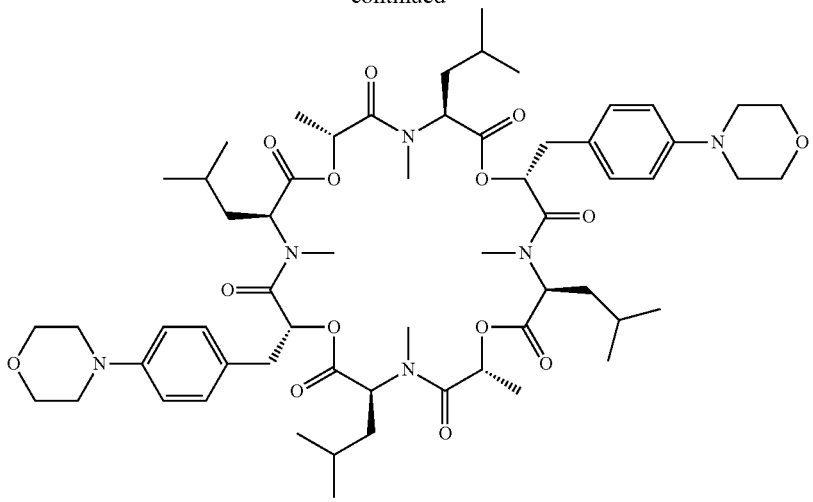

7-27

Experimental Details

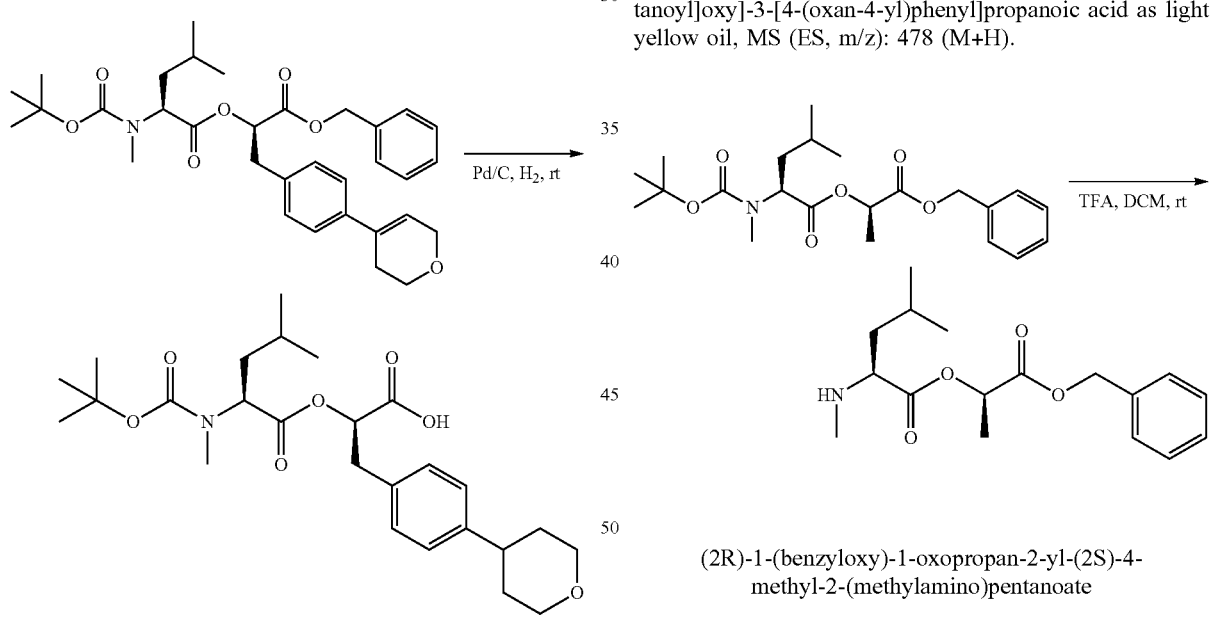

(2R)-2-[[(2S)-2-[[(tert-butoxy)carbonyl](methyl)amino]-4-methylpentanoyl]oxy]-3-[4-(oxan-4-yl)phenyl]propanoic acid Into a 500-mL round-bottom flask purged and maintained with hydrogen, was placed methanol (50 mL), (2R)-1-(benzyloxy)-3-[4-(3,6-dihydro-2H-pyran-4-yl)phenyl]-1-oxopropan-2-yl-(2S)-2-[[(tert-butoxy)carbonyl](methyl)amino]-4-methyl pentanoate (7 g, 12.37 mmol, 1.00 equiv), Palladium on carbon (2 g, 0.60 equiv). The resulting solution was stirred for 1 h at room temperature. The solids were filtered out. The resulting mixture was concentrated under vacuum. This resulted in 5 g (85%) of (2R)-2-[[(2S)-2-[[(tert-butoxy)carbonyl](methyl)amino]-4-methylpentanoyl]oxy]-3-[4-(oxan-4-yl)phenyl]propanoic acid as light yellow oil, MS (ES, m/z): 478 (M+H).

(2R)-1-(benzyloxy)-1-oxopropan-2-yl-(2S)-4-methyl-2-(methylamino)pentanoate

Into a 250-mL round-bottom flask, was placed dichloromethane (25 mL), (2R)-1-(benzyloxy)-1-oxopropan-2-yl (2S)-2-[[(tert-butoxy)carbonyl](methyl)amino]-4-methylpentanoate (5.0 g, 12.27 mmol, 1.00 equiv), trifluoroacetic acid (6 mL, 20.00 equiv). The resulting solution was stirred for 2 h at room temperature. The pH value of the solution was adjusted to 9 with sodium bicarbonate (2 mol/L). The resulting solution was extracted with 3×20 mL of dichloromethane and the organic layers combined and dried over anhydrous sodium sulfate and concentrated under vacuum. This resulted in 3.6 g (95%) of (2R)-1-(benzyloxy)-1-oxopropan-2-yl (2S)-4-methyl-2-(methylamino)pentanoate as yellow oil, MS (ES, m/z): 308 (M+H).

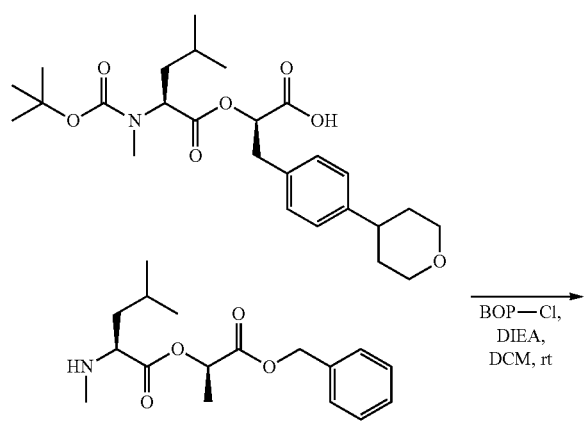

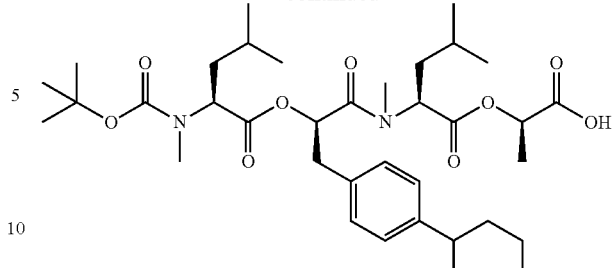

TC7-27:

Into a 100-mL round-bottom flask purged and maintained with hydrogen, was placed TP7-27 (4.6 g, 6.00 mmol, 1.00 equiv), Palladium on carbon (2 g, 0.50 equiv). The resulting solution was stirred for 1 h at room temperature. The solids were filtered out. The resulting mixture was concentrated under vacuum. This resulted in 4.0 g (99%) of TC7-27 as a solid, MS (ES, m/z): 677 (M+H).

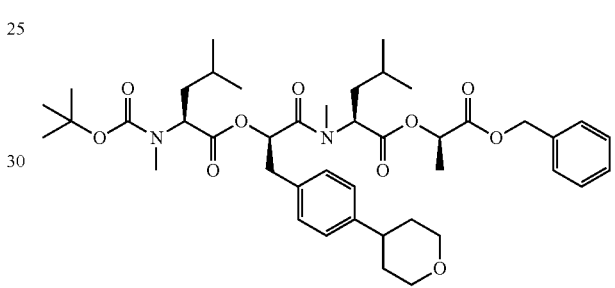

| TFA, DCM, rt

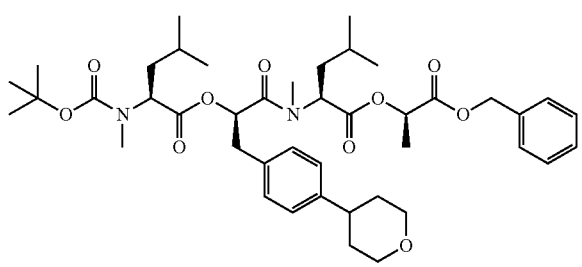

TP7-27:

Into a 250-mL round-bottom flask, was placed (2R)-2-[[(2S)-2-[[(tert-butoxy) carbonyl](methyl)amino]-4-methyl-pentanoyl]oxy]-3-[4-(oxan-4-yl)phenyl]propanoic acid (6 g, 12.56 mmol, 1.00 equiv), (2R)-1-(benzyloxy)-1-oxopropan-2-yl-(2S)-4-methyl-2-(methylamino) pentanoate (5 g, 16.27 mmol, 1.00 equiv), BOP-Cl (6.4 g, 25.14 mmol, 2.00 equiv), DIEA (3.2 g, 24.76 mmol, 1.97 equiv). The resulting solution was stirred overnight at room temperature. The solids were filtered out. The residue was applied onto a silica gel column with ethyl acetate/petroleum ether (1:10). This resulted in 4.5 g (47%) of TP7-27 as yellow oil, MS (ES, m/z): 767 (M+H).

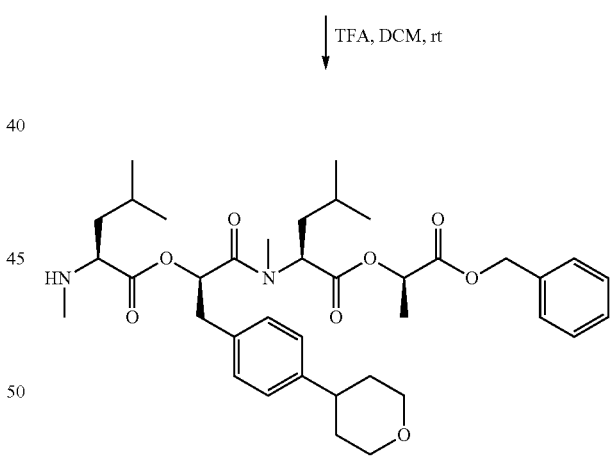

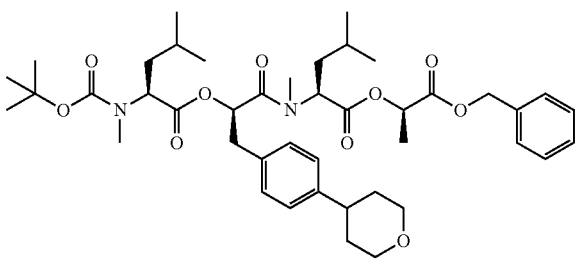

| Pd/C, H₂, rt

TA7-27:

Into a 100-mL round-bottom flask, was placed TP7-27 (4.8 g, 6.26 mmol, 1.00 equiv), trifluoroacetic acid (5 mL, 20.00 equiv). The resulting solution was stirred for 1 h at room temperature. The pH value of the solution was adjusted to 9 with sodium bicarbonate (2 mol/L). The resulting solution was extracted with 3×30 mL of dichloromethane and the organic layers combined and dried over anhydrous sodium sulfate and concentrated under vacuum. This resulted in 4.0 g (96%) of TA7-27 as light yellow oil, MS (ES, m/z): 677 (M+H).

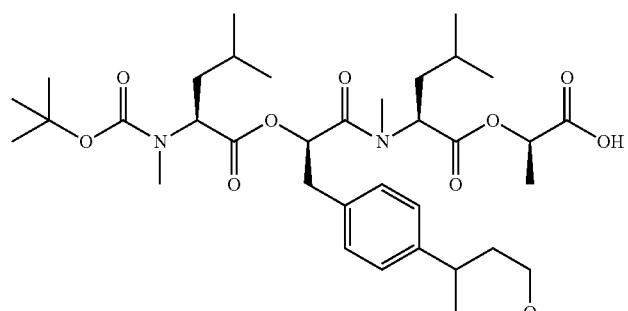
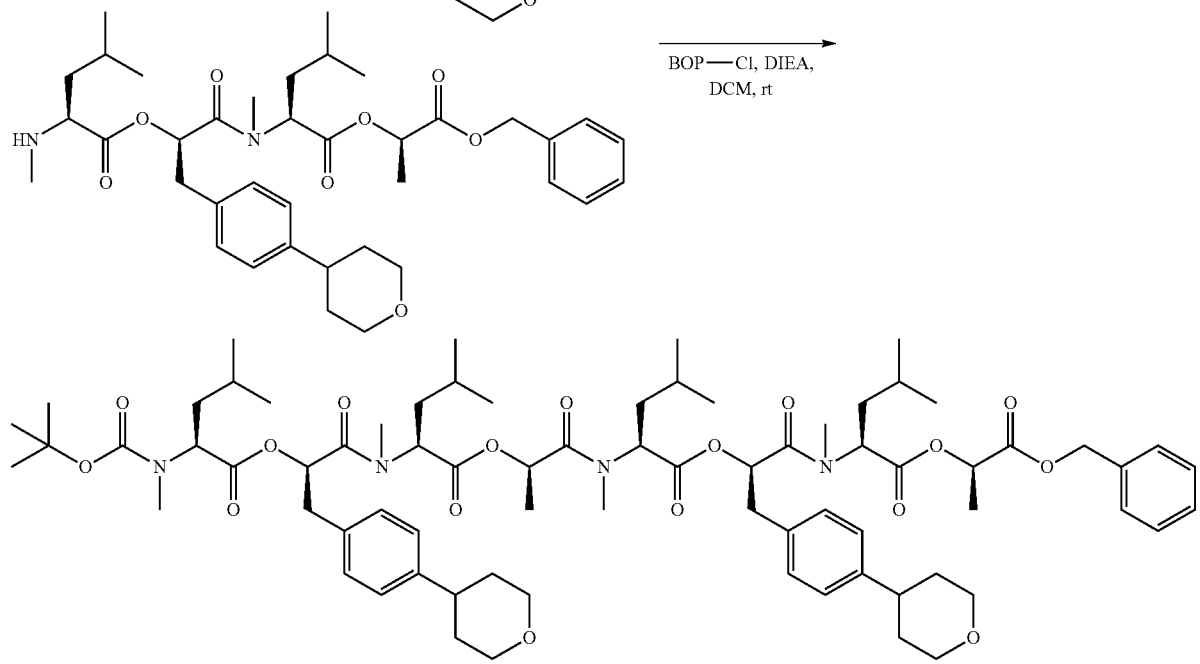
OP7-27:
Into a 100-mL round-bottom flask, was placed TA7-27 (4.2 g, 6.30 mmol, 1.00 equiv), TC7-27 (4.0 g, 5.91 mmol, 1.00 equiv), BOP-Cl (3.1 g, 12.18 mmol, 1.93 equiv), DIEA (1.7 g, 13.15 mmol, 2.09 equiv). The resulting solution was stirred for 3 h at room temperature. The solids were filtered out. The residue was applied onto a silica gel column with ethyl acetate/petroleum ether (1:10). This resulted in 3.5 g (42%) of OP7-27 as a white solid, MS (ES, m/z): 1326 (M+H).
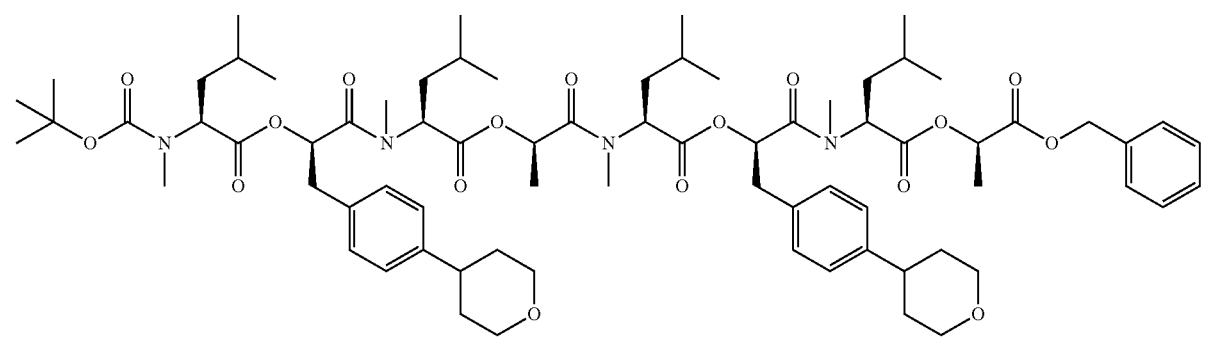

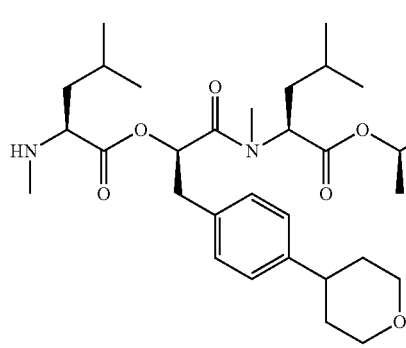
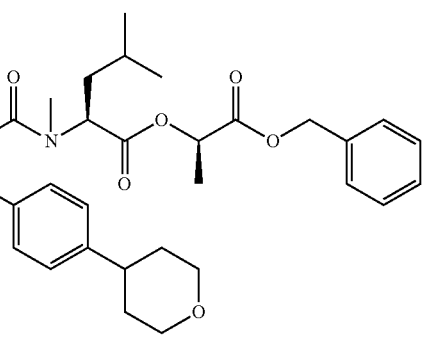

-continued

OA7-27:
Into a 100-mL round-bottom flask, was placed OP7-27 (3.5 g, 2.64 mmol, 1.00 equiv), trifluoroacetic acid (5 mL, 20.00 equiv). The resulting solution was stirred for 2 h at room temperature. The pH value of the solution was adjusted to 9 with sodium bicarbonate (2 mol/L). The resulting mixture was washed with 3×30 mL of DCM. The mixture was dried over anhydrous sodium sulfate and concentrated under vacuum. This resulted in 3.1 g (96%) of OA7-27 as a white solid, MS (ES, m/z): 1226 (M+H).

OAC7-27:
Into a 100-mL round-bottom flask purged and maintained with hydrogen, was placed OC7-27 (3.1 g, 2.53 mmol, 1.00 equiv), Palladium on carbon (1.5 g, 0.50 equiv). The resulting solution was stirred for 1 h at room temperature. The solids were filtered out. The resulting mixture was concentrated under vacuum. This resulted in 2.7 g (94%) of OAC7-27 as a white solid, MS (ES, m/z): 1136 (M+H).

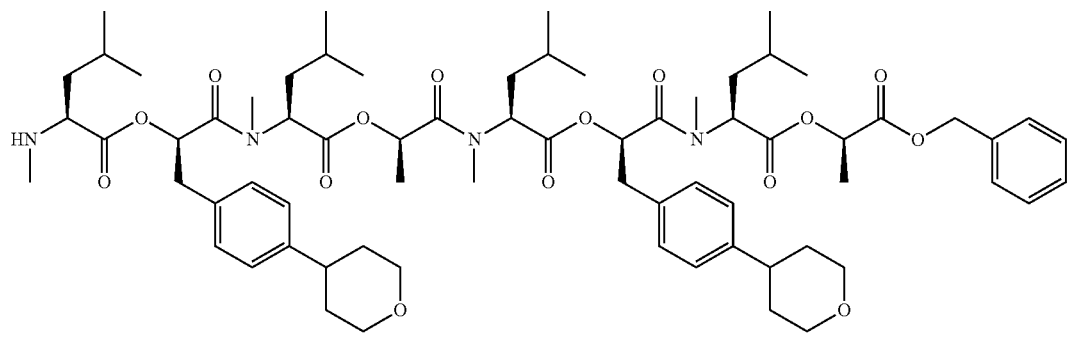

OA7-27

↓ Pd/C, H₂, rt

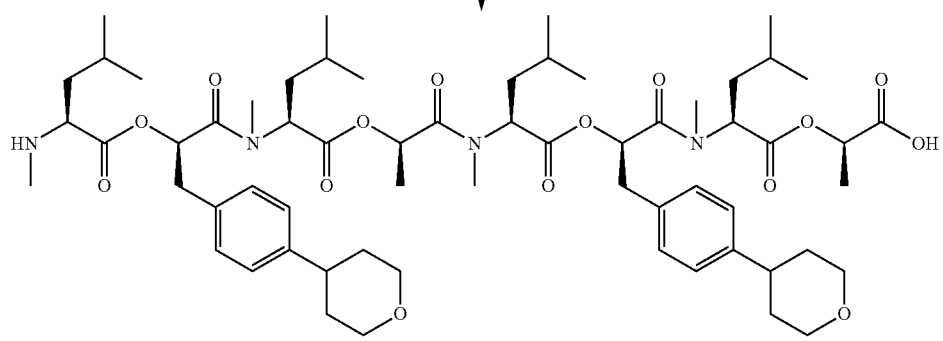

OAC7-27

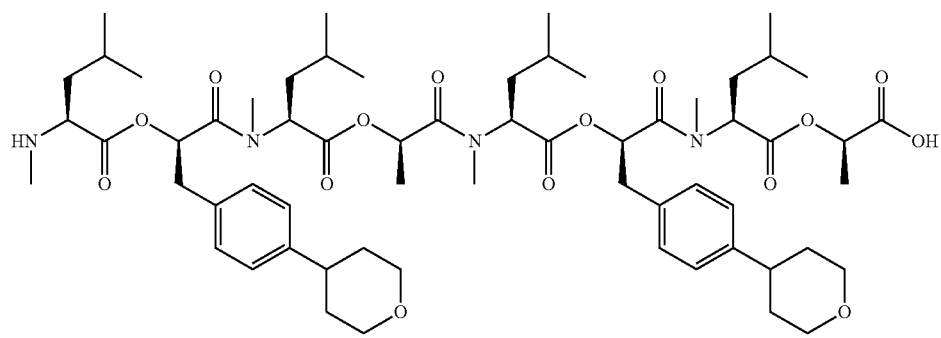

OAC7-27

| BOP—Cl, DIEA,
| DCM, rt

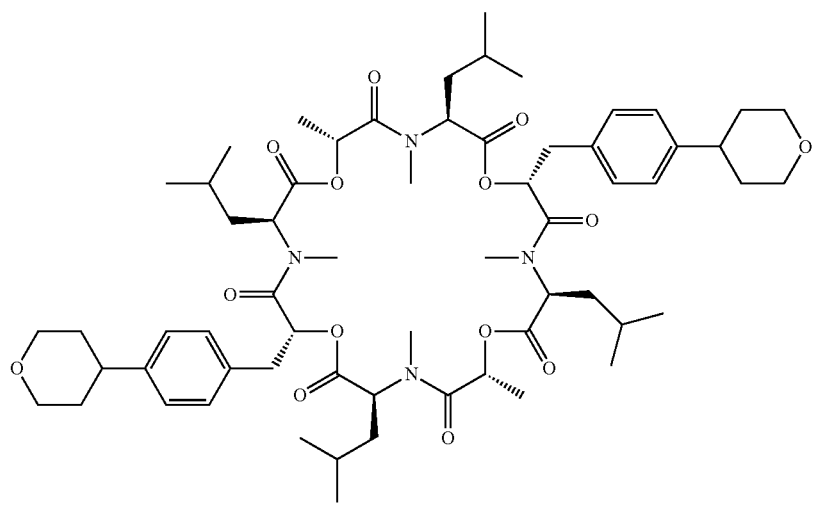

7-27

7-27:

Into a 500-mL round-bottom flask, was placed OAC7-27 (2.7 g, 2.38 mmol, 1.00 equiv), BOP-Cl (2 g, 7.86 mmol, 2.00 equiv), DIEA (1 g, 7.74 mmol, 3.25 equiv). The resulting solution was stirred for 3 h at room temperature. The solids were filtered out. The crude product was purified by Prep-HPLC with the following conditions: SunFire Prep C18 5 um 19*150 mm; mobile phase, water (it contains 0.05% Trifluoroacetic acid) and $CH_3CN$; Gradient:87% to 90% in 8 min; Flow rate: 20 mL/min; Detector UV wavelength: 254 nm. This resulted in 350.1 mg (13%) of 7-27 as a white solid. MS (ES, m/z): 1116.7 (calculated, M), 1118.0 (found, M+H). $^1$HNMR (300 MHz, $CD_3OD$): δ 7.26-7.24 (m, 8H), 5.81-5.73 (m, 2H), 5.55-5.43 (m, 5H), 4.88 (m, 1H), 4.06-4.03 (m, 4H), 3.56-3.53 (m, 4H), 3.35-3.08 (m, 4H), 2.95-2.93 (m, 7H), 2.87-2.80 (m, 7H), 1.81-1.37 (m, 22H), 1.07-0.81 (m, 28H).

Preparation Example 86: Preparation of Compound 18-19

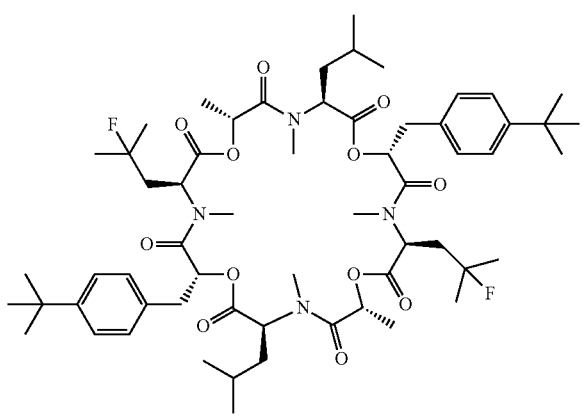

18-19

Compound 18-19 was prepared according to Schemes 40-42
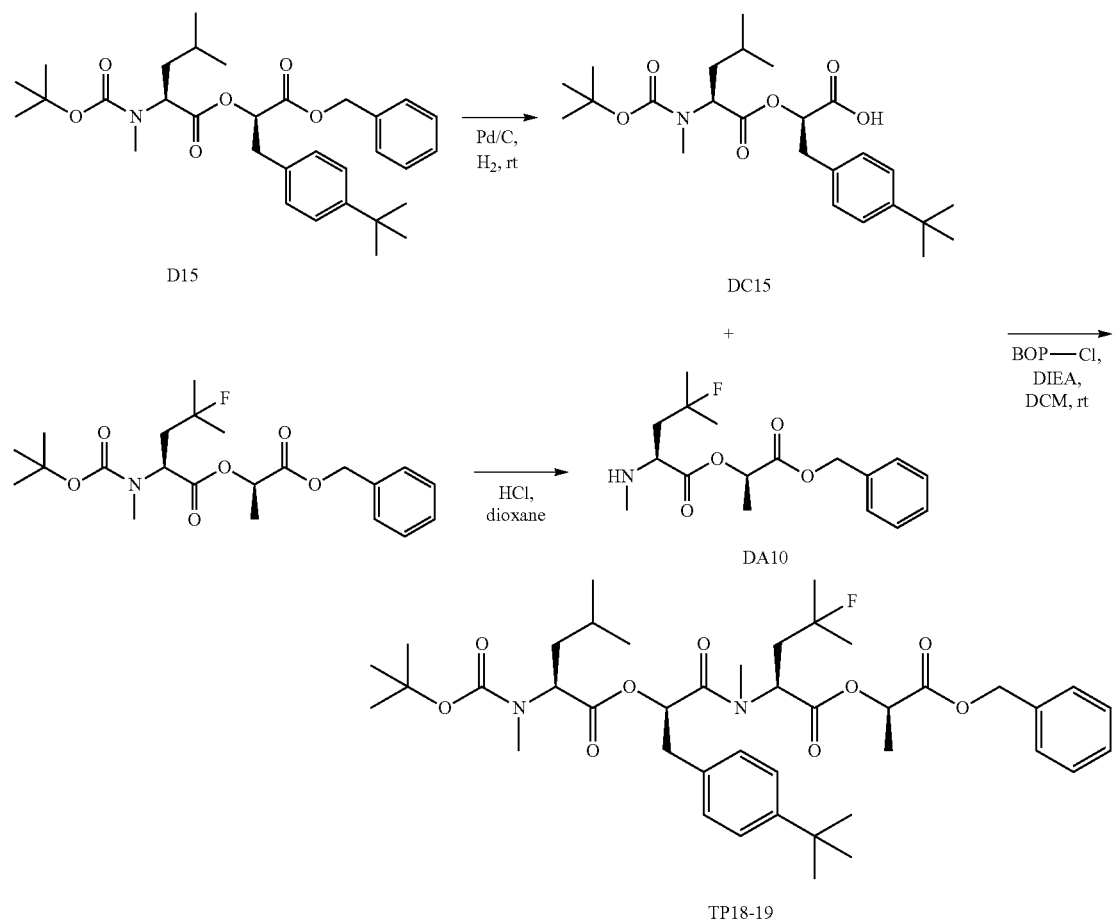
Scheme 40
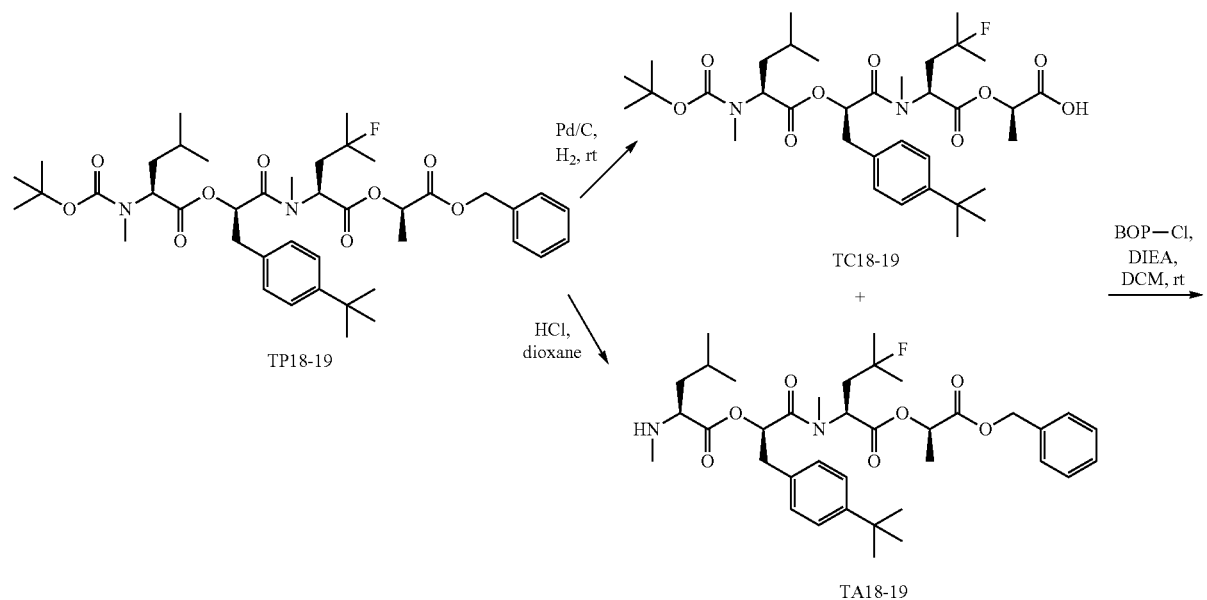
Scheme 41

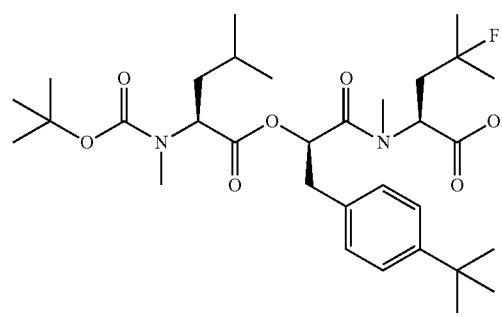
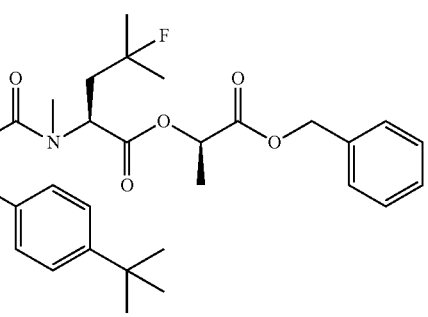
-continued
OP18-19
Scheme 42
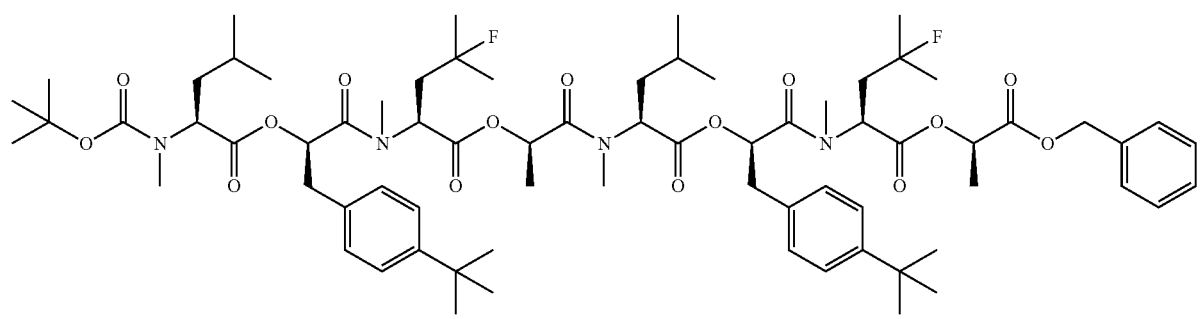
OP18-19
↓ HCl, dioxane
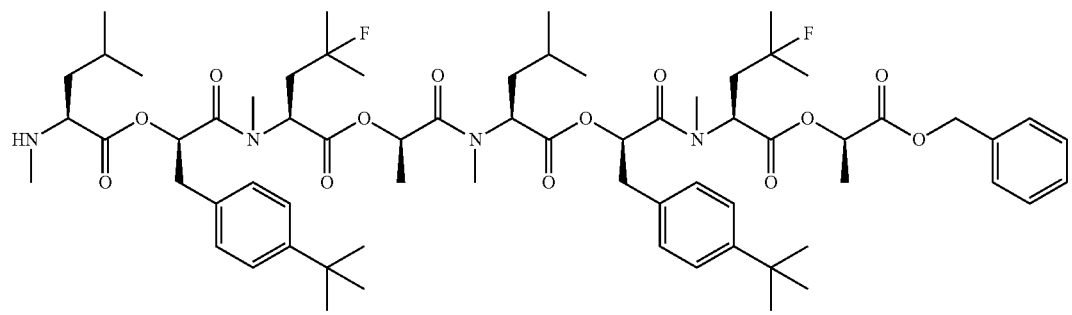
OA18-19
↓ Pd/C, H₂, rt

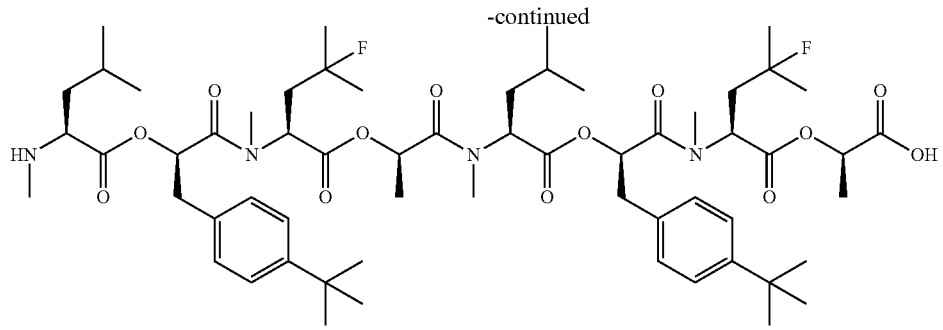

OAC18-19

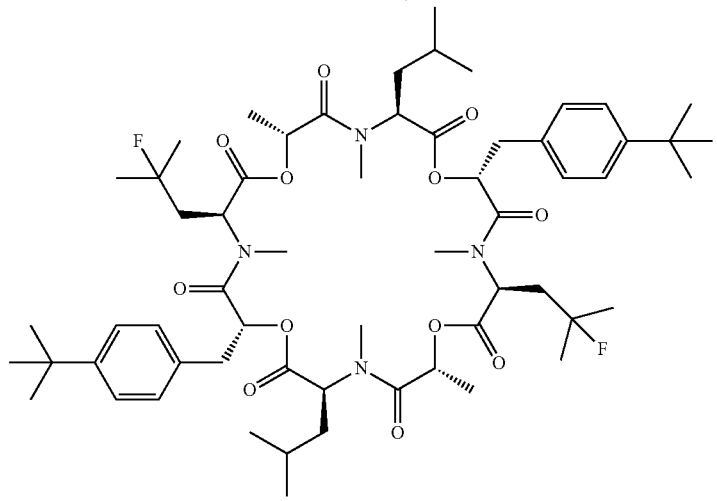

18-19

Experimental Details

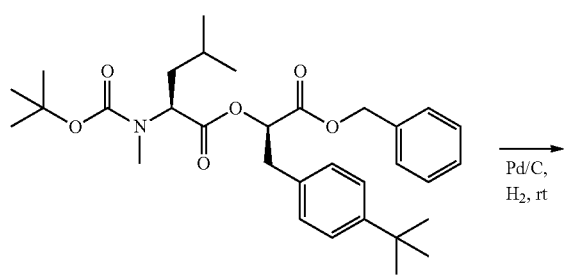

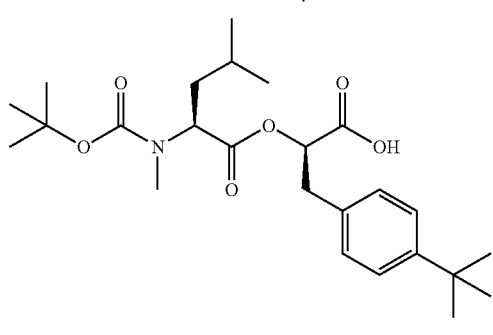

(2R)-2-[[(2S)-2-[[(tert-butoxy)carbonyl](methyl)amino]-4-methylpentanoyl]oxy]-3-(4-tert-butylphenyl)propanoic acid Into a 100-mL round-bottom flask, was placed (2R)-1-(benzyloxy)-3-(4-tert-butylphenyl)-1-oxopropan-2-yl-(2S)-2-[[(tert-butoxy)carbonyl](methyl) amino]-4-methylpentanoate (1 g, 1.85 mmol, 1.00 equiv), Palladium on carbon (200 mg), methanol (30 mL). To the above hydrogen gas was introduced. The resulting mixture was stirred for 1 h at room temperature. The solids were filtered out. The filtrate was concentrated under vacuum. This resulted in 830 mg (100%) of (2R)-2-[[(2S)-2-[[(tert-butoxy) carbonyl](methyl)amino]-4-methylpentanoyl]oxy]-3-(4-tert-butylphenyl)propanoic acid as a white solid. MS (ES, m/z): 450 (M+H).

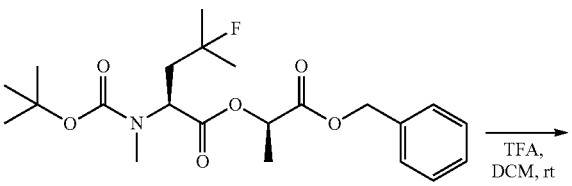

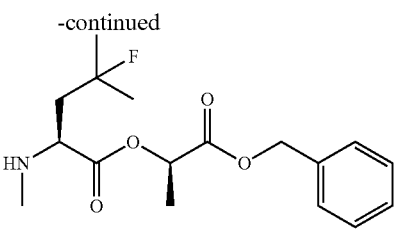

(2R)-2-[[(2S)-2-[[(tert-butoxy)carbonyl](methyl)amino]-4-methylpentanoyl]oxy]-3-(4-tert-butylphenyl)propanoic acid Into a 100-mL round-bottom flask, was placed (2R)-1-(benzyloxy)-3-(4-tert-butylphenyl)-1-oxopropan-2-yl (2S)-2-[[(tert-butoxy)carbonyl](methyl) amino]-4-methylpentanoate (1 g, 1.85 mmol, 1.00 equiv), Palladium on carbon (200 mg), methanol (30 mL). To the above hydrogen gas was introduced. The resulting mixture was stirred for 1 h at room temperature. The solids were filtered out. The filtrate was concentrated under vacuum. This resulted in 830 mg (100%) of (2R)-2-[[(2S)-2-[[(tert-butoxy) carbonyl](methyl)amino]-4-methylpentanoyl]oxy]-3-(4-tert-butylphenyl)propanoic acid as a white solid. MS (ES, m/z): 450 (M+H).

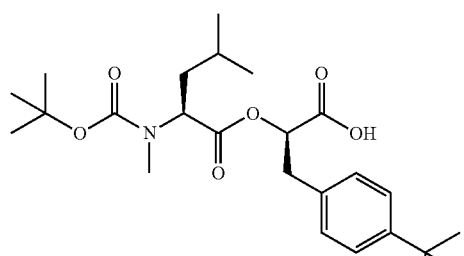

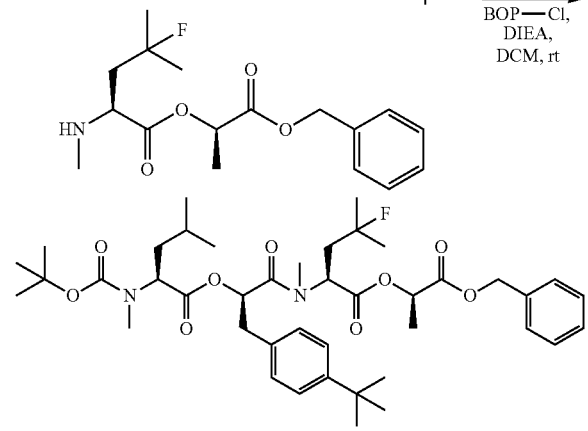

TP18-19:
Into a 250-mL 3-necked round-bottom flask, was placed (2R)2-[[(2S)-2-[[(tert-butoxy)carbonyl](methyl)amino]-4-methylpentanoyl]oxy]-3-(4-tert-butylphenyl)propanoic acid (1 g, 2.22 mmol, 1.00 equiv), (2R)1-(benzyloxy)-1-oxopropan-2-yl (2S)-4-fluoro-4-methyl-2-(methylamino)pentanoate (760 mg, 2.34 mmol, 1.00 equiv), dichloromethane (100 mL). This was followed by the addition of BOP-Cl (1.2 g, 4.71 mmol, 2.00 equiv) in portions and DIEA (603 mg, 4.67 mmol, 2.00 equiv) dropwise with stirring at 0° C. The resulting solution was stirred overnight at room temperature. The solids were filtered out. The filtrate was concentrated under vacuum. The residue mixture was applied onto a silica gel column with ethyl acetate/petroleum ether (1:5). This resulted in 900 mg (53%) of TP18-19 as yellow oil. MS (ES, m/z): 757 (M+H).

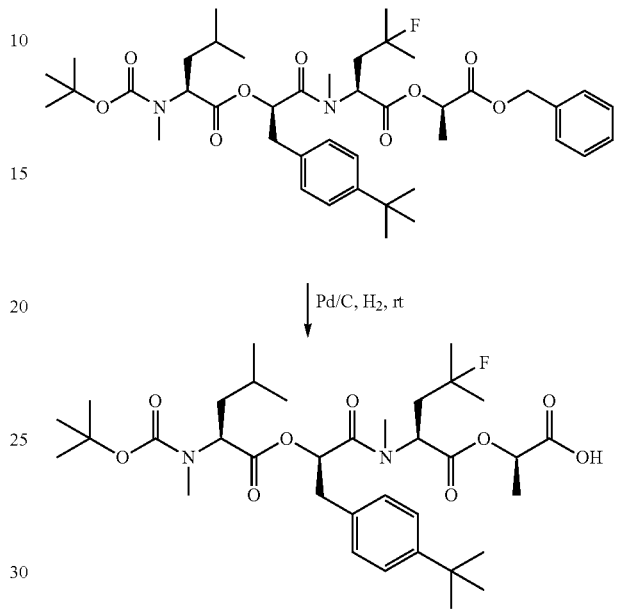

TC18-19:
Into a 100-mL round-bottom flask, was placed TP18-19 (450 mg, 0.59 mmol, 1.00 equiv), Palladium on carbon (200 mg), and methanol (40 mL). To the above Hydrogen gas was introduced. The resulting mixture was stirred for 1 h at room temperature. The solids were filtered out. The filtrate was concentrated under vacuum. This resulted in 420 mg (crude) of TC18-19 as a white solid. MS (ES, m/z): 667 (M+H).

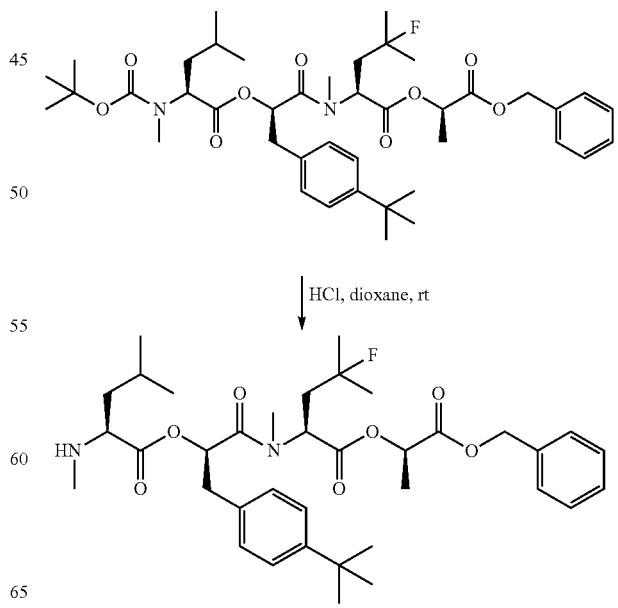

TA18-19:

Into a 100-mL 3-necked round-bottom flask, was placed TP18-19 (450 mg, 0.59 mmol, 1.00 equiv), dioxane (16 mL), to the above HCl$_{(g)}$ was introduced. The resulting solution was stirred for 1 h at room temperature. The pH value of the solution was adjusted to 8 with sodium bicarbonate (Sat.). The resulting solution was extracted with 3×15 mL of dichloromethane and the organic layers combined and washed with 3×20 mL of brine. The organic phase was collected and dried over anhydrous sodium sulfate and concentrated under vacuum. This resulted in 400 mg (crude) of TA18-19 as yellow oil. MS (ES, m/z): 657 (M+H).

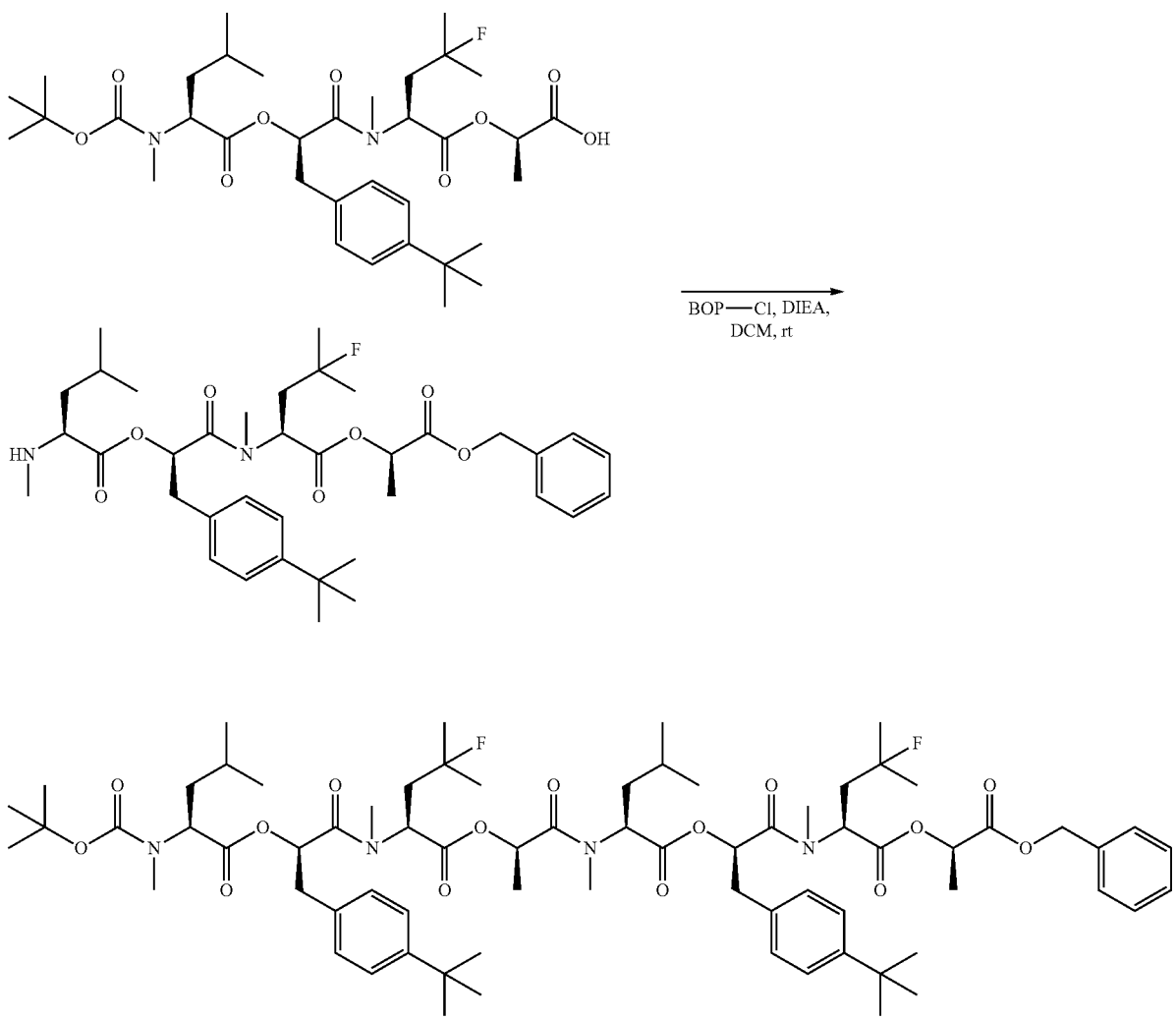

OP18-19:

Into a 100-mL 3-necked round-bottom flask, was placed TC18-19 (406 mg, 0.61 mmol, 1.00 equiv), TA18-19 (400 mg, 0.61 mmol, 1.00 equiv), dichloromethane (25 mL). This was followed by the addition of BOP-Cl (311 mg, 2.00 equiv) in portions and DIEA (157.4 mg, 1.22 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:3). This resulted in 460 mg (58%) of OP18-19 as yellow oil. MS (ES, m/z): 1306 (M+H).

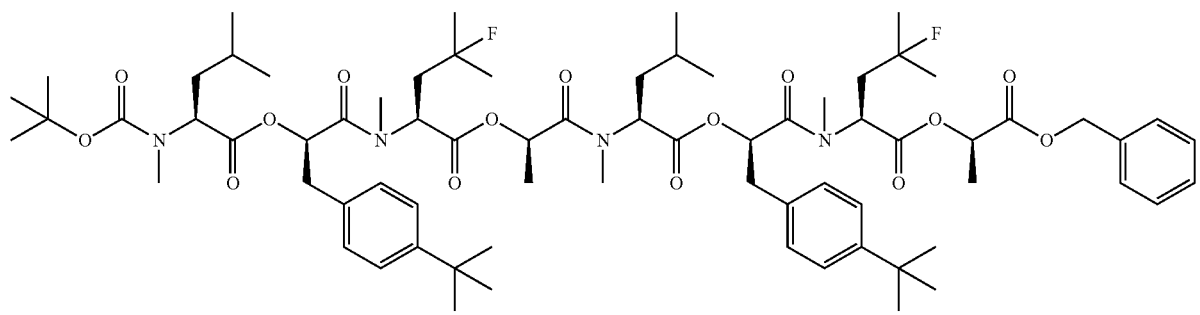

↓ HCl, dioxane

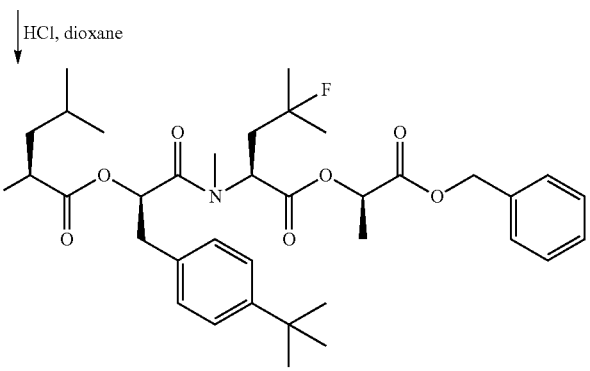

OA18-19:

Into a 100-mL 3-necked round-bottom flask, was placed OP18-19 (460 mg, 0.35 mmol, 1.00 equiv), dioxane (15 mL). To the above HCl$_{(g)}$ was introduced. The resulting solution was stirred for 1 h at room temperature. The pH value of the solution was adjusted to 8 with sodium bicarbonate (Sat.). The resulting solution was extracted with 3×20 mL of dichloromethane and the organic layers combined and washed with 3×30 mL of brine. The organic phase was collected and dried over anhydrous sodium sulfate and concentrated under vacuum. This resulted in 350 mg (82%) of OA18-19 as yellow oil. MS (ES, m/z): 1206 (M+H).

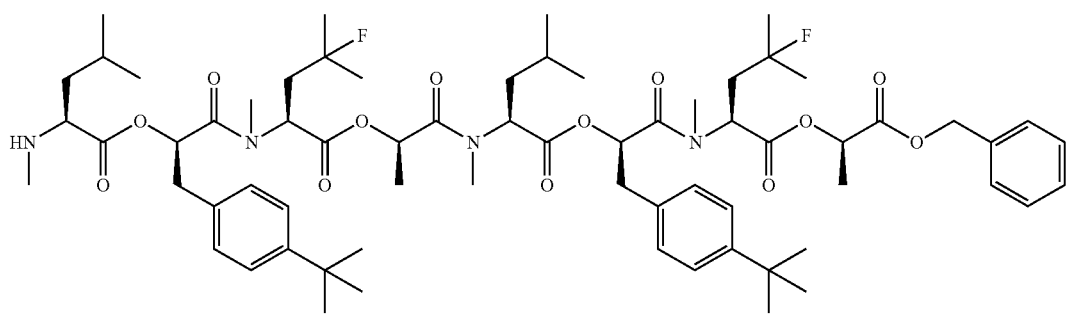

↓ Pd/C, H$_2$, rt

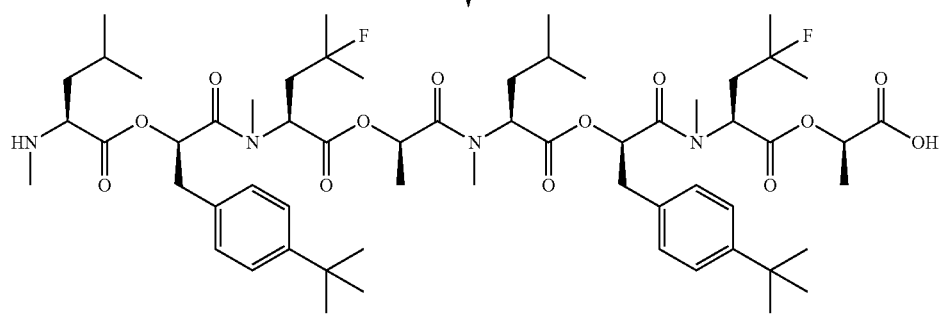

OAC18-19:

Into a 100-mL round-bottom flask, was placed OC18-19 (350 mg, 0.29 mmol, 1.00 equiv), Palladium on carbon (300 mg), and methanol (30 mL). To the above, hydrogen gas was introduced. The resulting solution was stirred for 1 h at room temperature. The solids were filtered out. The filtrate was concentrated under vacuum. This resulted in 300 mg (93%) of OAC18-19 as a white solid. MS (ES, m/z): 1116 (M+H).

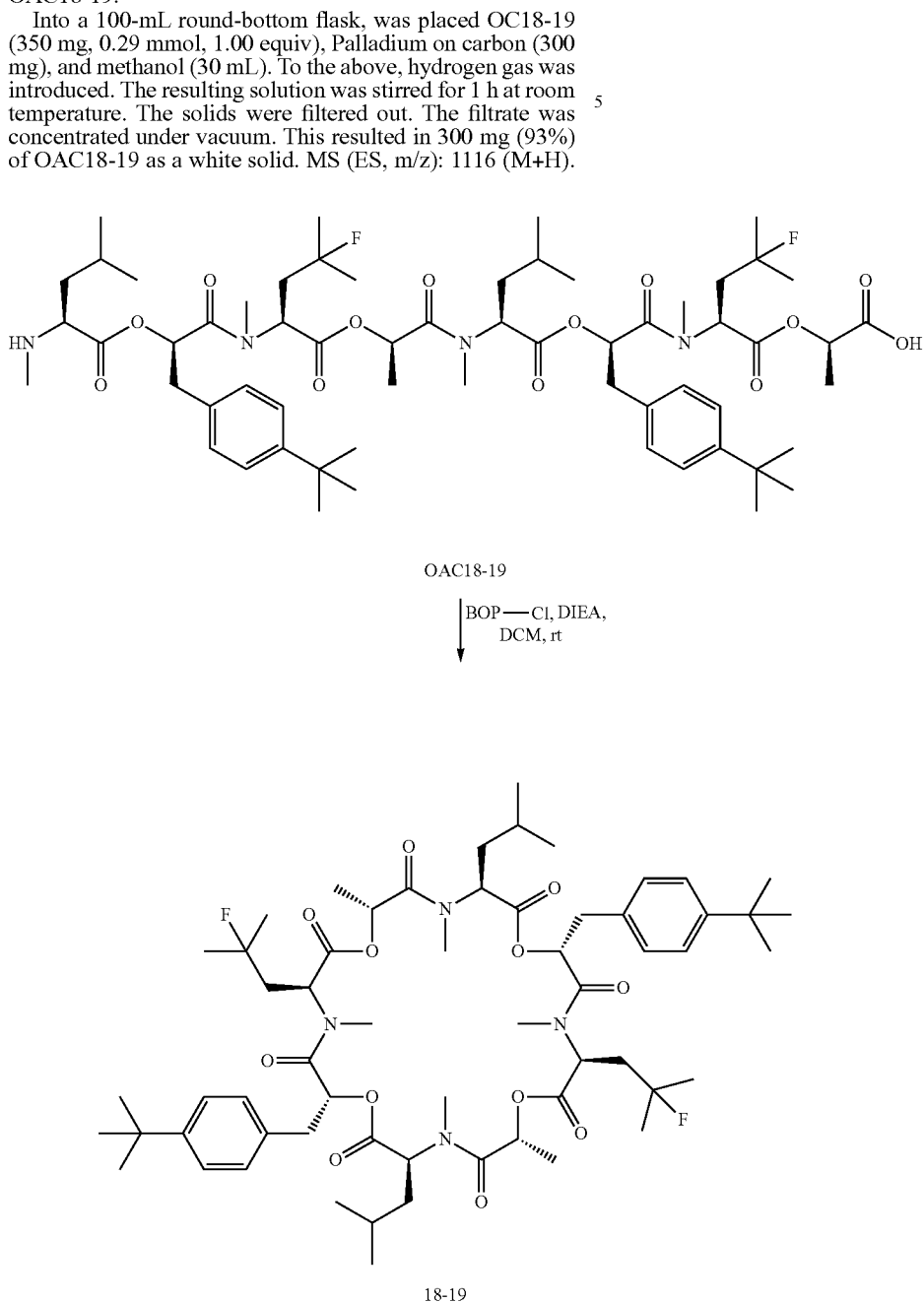

18-19:

Into a 500-mL 3-necked round-bottom flask, was placed OAC18-19 (300 mg, 0.27 mmol, 1.00 equiv), dichloromethane (300 mL). This was followed by addition of BOP-Cl (137.2 mg, 0.54 mmol, 2.00 equiv) in portions and DIEA (69.4 mg, 0.54 mmol, 3.00 equiv) dropwise with stirring at 0° C. The resulting solution was stirred overnight at room temperature. The solids were filtered out. The filtrate was concentrated under vacuum. The crude product was purified by Prep-HPLC with the following conditions: Column, SunFire Prep C18 5 um 19*150 mm; mobile phase, water and $CH_3CN$; Gradient: 90% to 95% in 20 min; Detector, 220 nm. This resulted in 37.4 mg (13%) of 18-19 as a white solid. MS (ES, m/z): 1096.7 (calculated, M), 1098.0 (found, M+H). $^1$H-NMR ($CD_3OD$, 300 MHz) δ: 7.50-7.30 (m, 4H), 7.30-7.21 (m, 4H), 5.90-5.10 (m, 7H), 4.87-4.70 (m, 1H), 3.34-2.80 (m, 16H), 2.50-1.92 (m, 4H), 1.71-1.20 (m, 40H), 1.10-0.80 (m, 14H); [α]=−45.82° (T=27.2° C., C=0.625 g/100 mL in MeOH).

Preparation Example 87: Preparation of Compound 7-18
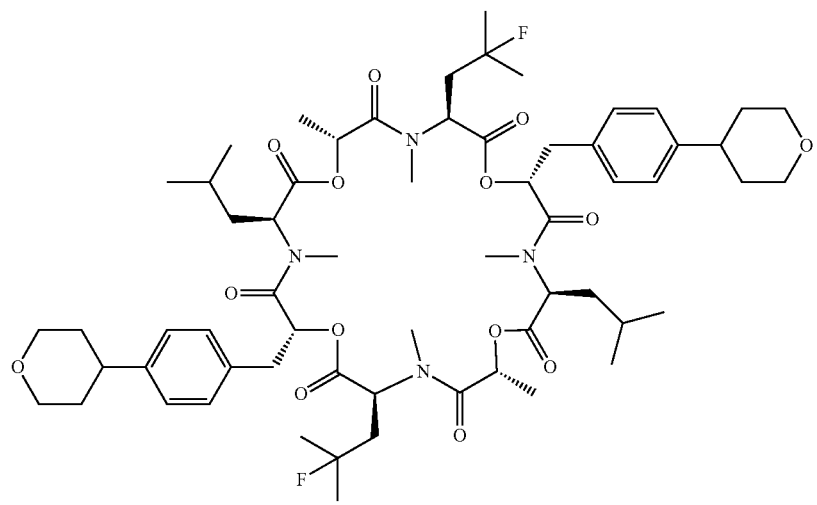
Compound 7-18 was prepared according to Schemes 43-45 below:
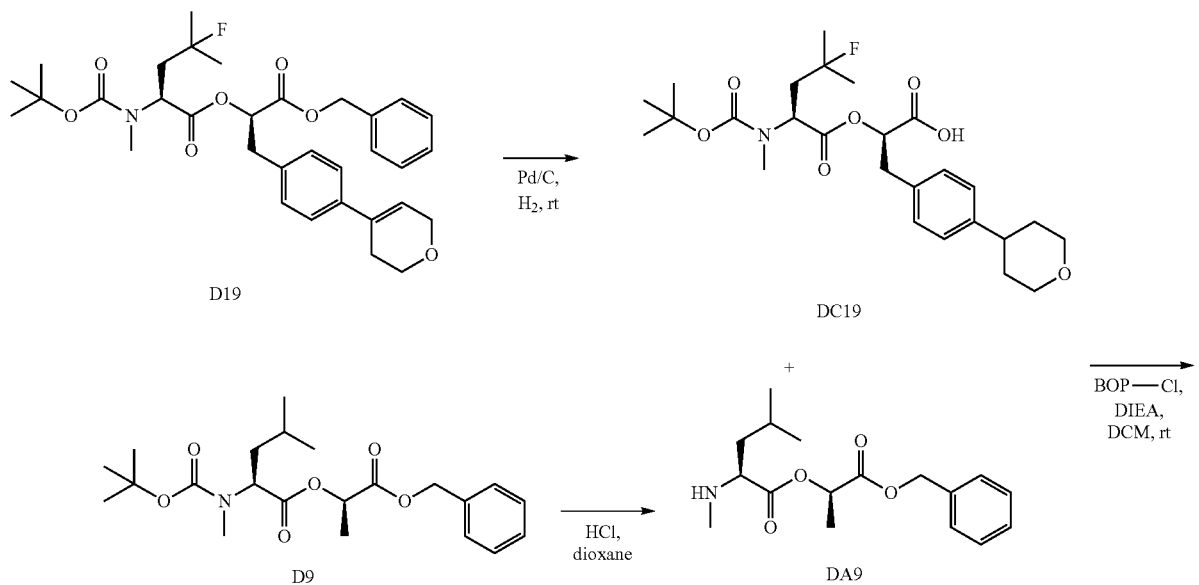

-continued
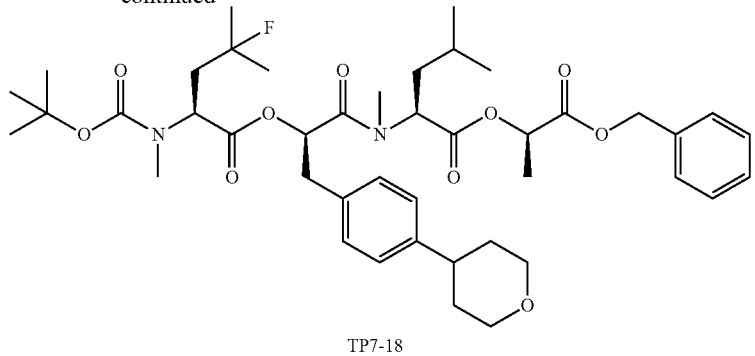
TP7-18
Scheme 44
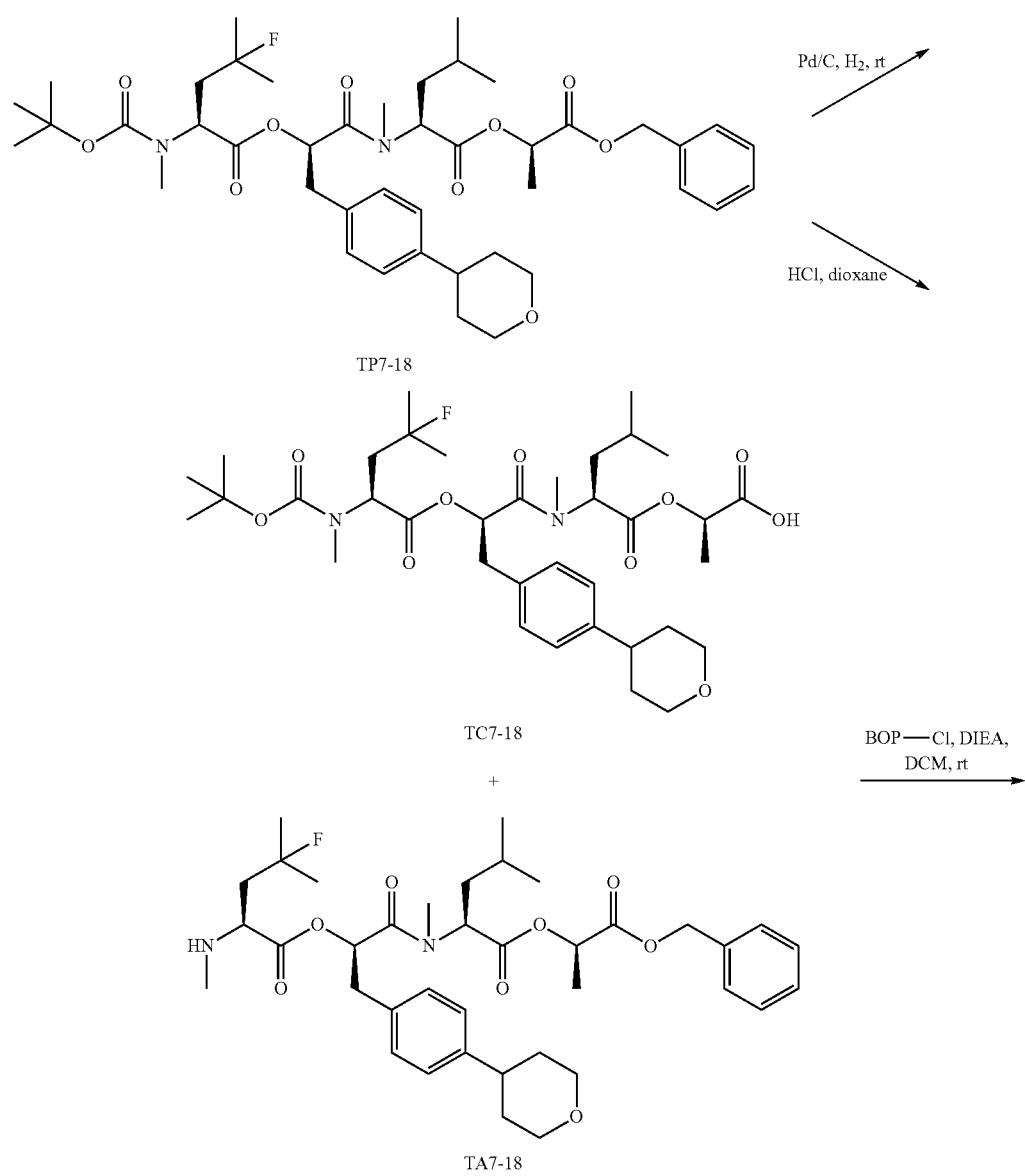

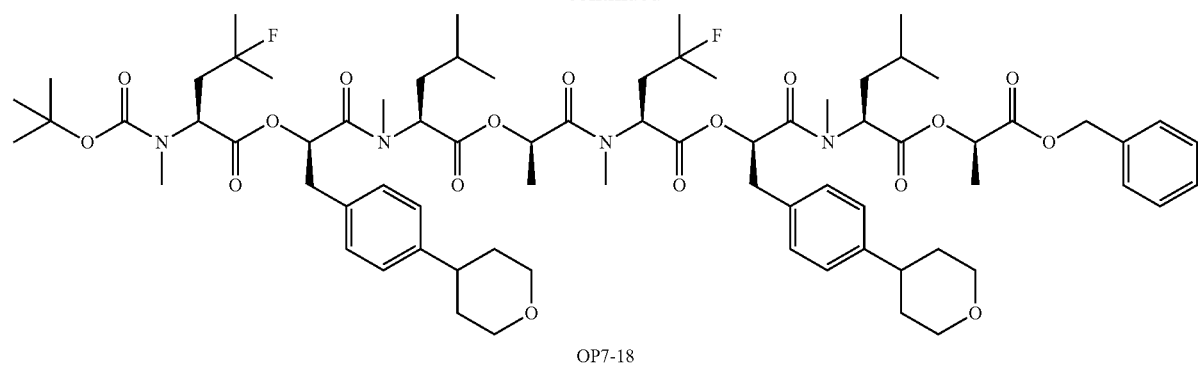
OP7-18
Scheme 45
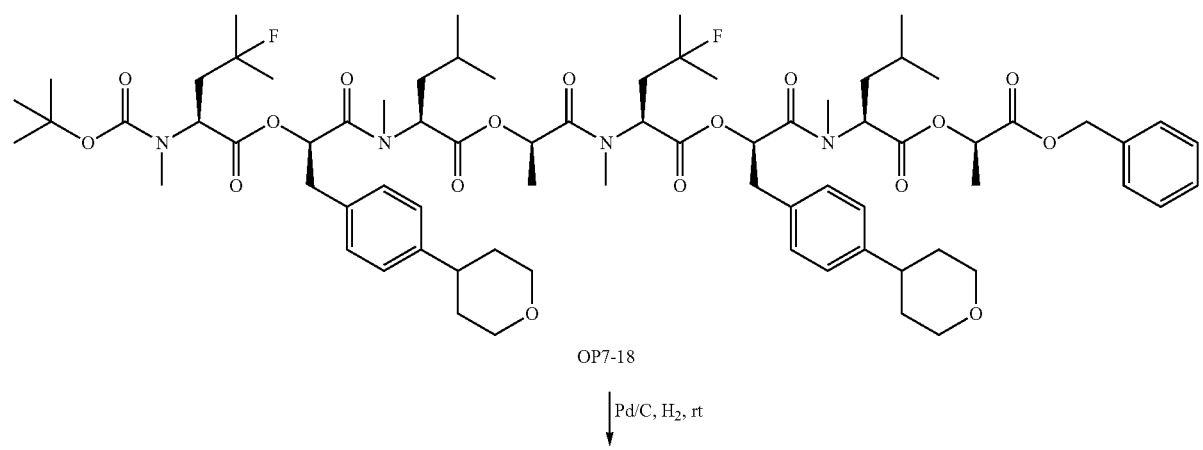
OP7-18
↓ Pd/C, H₂, rt
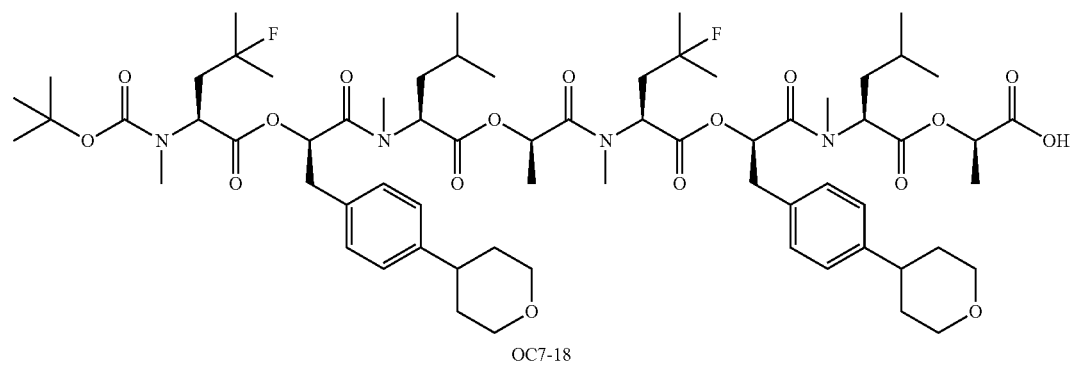
OC7-18
↓ HCl, dioxane -continued

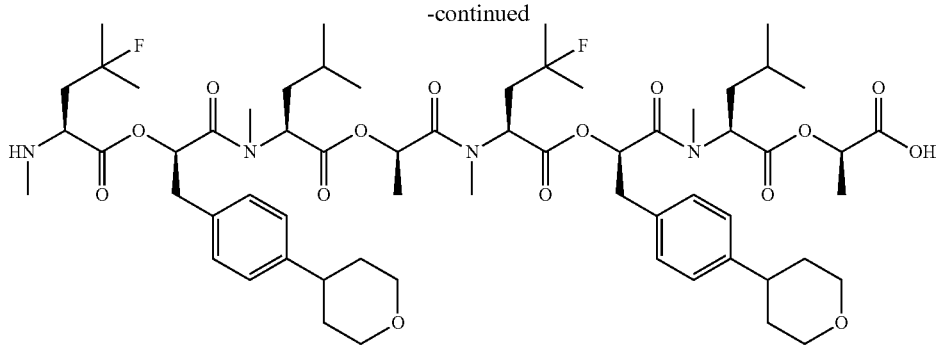

OAC7-18

BOP—Cl, DIEA, DCM, rt

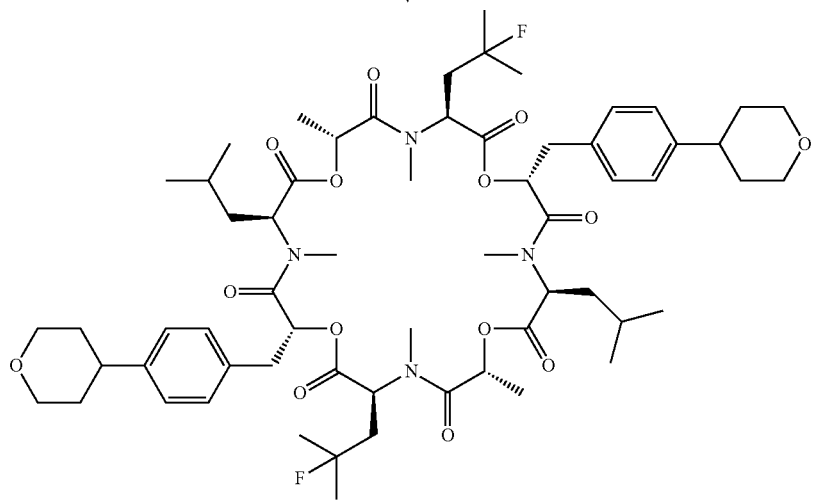

7-18

Experimental Details

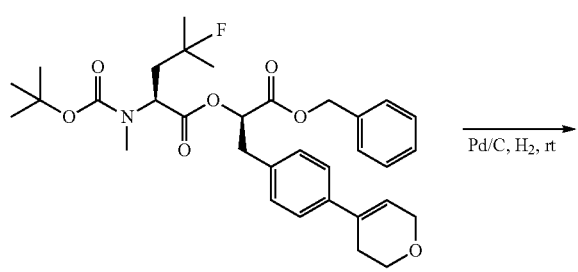

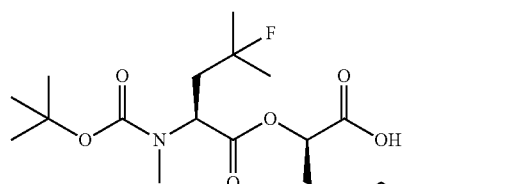

(2R)-2-[[(2S)-2-[[(tert-butoxy)carbonyl](methyl)amino]-4-fluoro-4-methylpentanoyl]oxy]-3-[4-(oxan-4-yl)phenyl]propanoic acid Into a 250-mL round-bottom flask, was placed Palladium on carbon (1.8 g), ethyl acetate (150 mL), (2R)-1-(benzyloxy)-3-[4-(3,6-dihydro-2H-pyran-4-yl)phenyl]-1-oxopropan-2-yl-(2S)-2-[[(tert-butoxy)carbonyl](methyl)amino]-4-fluoro-4-methylpentanoate (8.8 g, 15.08 mmol, 1.00 equiv). The flask was evacuated and flushed three times with nitrogen, followed by flushing with hydrogen. The mixture was stirred 2 h at room temperature under an atmosphere of hydrogen at room temperature. The solids were filtered out. The resulting mixture was concentrated under vacuum. This resulted in 7 g (crude) of (2R)-2-[[(2S)-2-[[(tert-butoxy)carbonyl](methyl)amino]-4-fluoro-4-methylpentanoyl]oxy]-3-[4-(oxan-4-yl)phenyl]propanoic acid as a white solid. MS (ES, m/z): 496 (M+H).

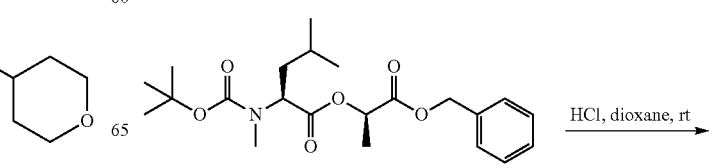

HCl, dioxane, rt

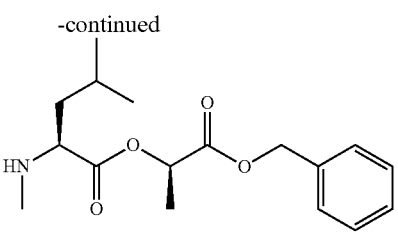

(2R)-1-(benzyloxy)-1-oxopropan-2-yl-(2S)-4-methyl-2-(methylamino)pentanoate

Into a 50-mL round-bottom flask, was placed dioxane/HCl (10 mL), (2R)-1-(benzyloxy)-1-oxopropan-2-yl (2S)-2-[[(tert-butoxy)carbonyl](methyl)amino]-4-methylpentanoate (460 mg, 1.13 mmol, 1.00 equiv). The resulting solution was stirred for 1.5 h at room temperature. The reaction was then quenched by the addition of 10 mL of NaHCO₃ (aq). The resulting solution was extracted with 3×20 mL of dichloromethane and the organic layers combined. The resulting mixture was washed with 3×5 mL of brine. The mixture was dried over anhydrous sodium sulfate and concentrated under vacuum. This resulted in 340 mg (98%) of (2R)-1-(benzyloxy)-1-oxopropan-2-yl (2S)-4-methyl-2-(methylamino)pentanoate as a colorless oil. MS (ES, m/z): 308 (M+H).

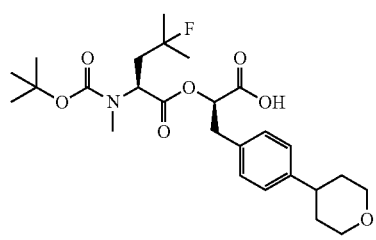

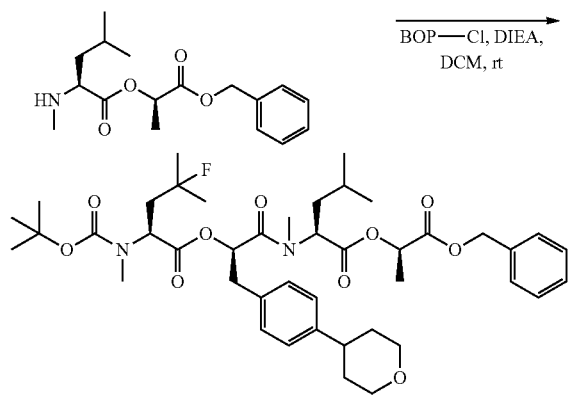

TP7-18:

Into a 8-mL round-bottom flask, was placed dichloromethane (80 mL), (2R)-2-[[(2S)-2-[[(tert-butoxy)carbonyl](methyl)amino]-4-fluoro-4-methylpentanoyl]oxy]-3-[4-(oxan-4-yl)phenyl]propanoic acid (3.8 g, 7.67 mmol, 1.00 equiv), (2R)-1-(benzyloxy)-1-oxopropan-2-yl (2S)-4-methyl-2-(methylamino)pentanoate (2.8 g, 9.11 mmol, 1.20 equiv). This was followed by the addition of BOP-Cl (3.9 g, 15.32 mmol, 2.00 equiv) in portions at 0° C. To this was added DIEA (3 g, 23.22 mmol, 3.00 equiv) dropwise with stirring at 0° C. The resulting solution was stirred overnight at room temperature. The resulting solution was diluted in 200 mL DCM and wash with brine 50 mL×3. The organic layers combined and dried over anhydrous sodium sulfate. The solids were filtered out. The filtrate was concentrated under vacuum. The residue was applied onto a silica gel column with ethyl acetate/petroleum ether (1:10-1:3). This resulted in 4.5 g (75%) of TP7-18 as a white solid. MS (ES, m/z): 785 (M+H).

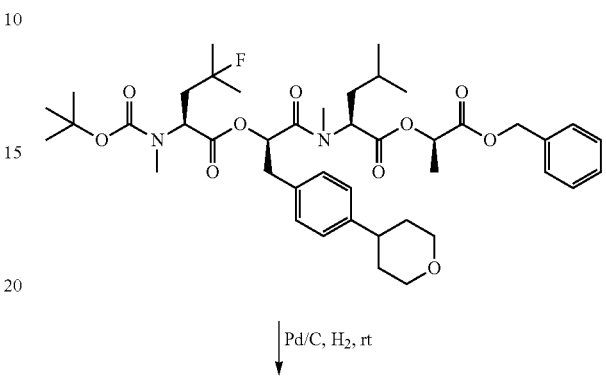

TC7-18:

To a solution of TP7-18 (1 g, 1.27 mmol, 1.00 equiv) in ethyl acetate (10 mL) was placed Palladium on carbon (200 mg). The flask was evacuated and flushed three times with nitrogen, followed by flushing with hydrogen. The mixture was stirred 1.5 h at room temperature under an atmosphere of hydrogen. The solids were filtered out. The resulting mixture was concentrated under vacuum. This resulted in 880 mg (crude) of TC7-18 as a white solid. MS (ES, m/z): 695 (M+H).

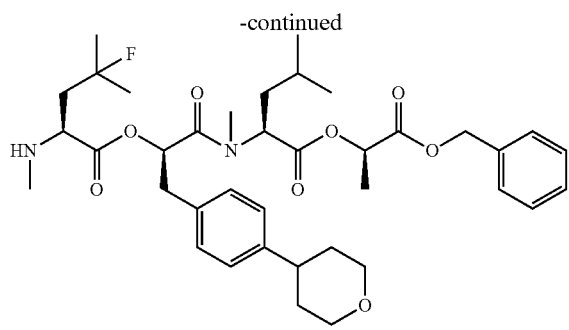

TA7-18:
Into a 50-mL round-bottom flask, was placed hydrogen chloride in dioxane (10 mL), TP7-18 (500 mg, 0.64 mmol, 1.00 equiv). The resulting solution was stirred for 1.5 h at room temperature. The resulting mixture was concentrated under vacuum. This resulted in 470 mg (crude) of TA7-18 as colorless oil. MS (ES, m/z): 685 (M+H).

OP7-18:
To a solution of TC7-18 (440 mg, 0.63 mmol, 1.00 equiv), TA7-18 (433 mg, 0.63 mmol, 1.00 equiv) in dichloromethane (8 mL) was placed BOP-Cl (403 mg, 1.58 mmol, 2.00 equiv) in portions at 0° C. This was followed by the addition of DIEA (408 mg, 3.16 mmol, 4.00 equiv) dropwise with stirring at 0° C. The resulting solution was stirred for 2 h at room temperature. The resulting solution was diluted in 50 mL DCM and wash with brine 10 mL×3. The organic layers combined and dried over anhydrous sodium sulfate. The solids were filtered out. The filtrate was concentrated under vacuum. The residue was applied onto a silica gel column with ethyl acetate/petroleum ether (1:5-1:1). This resulted in 760 mg (88%) of OP7-18 as a white solid. MS (ES, m/z): 1384 (M+Na).

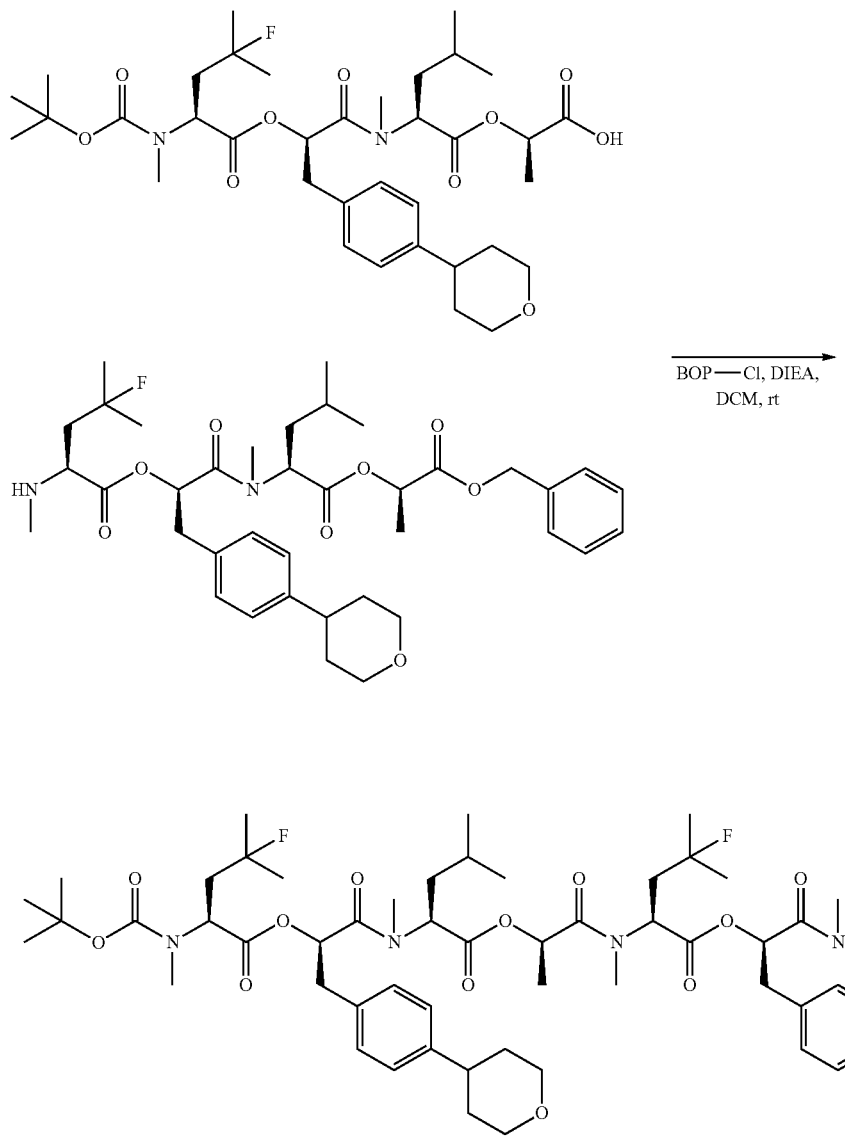

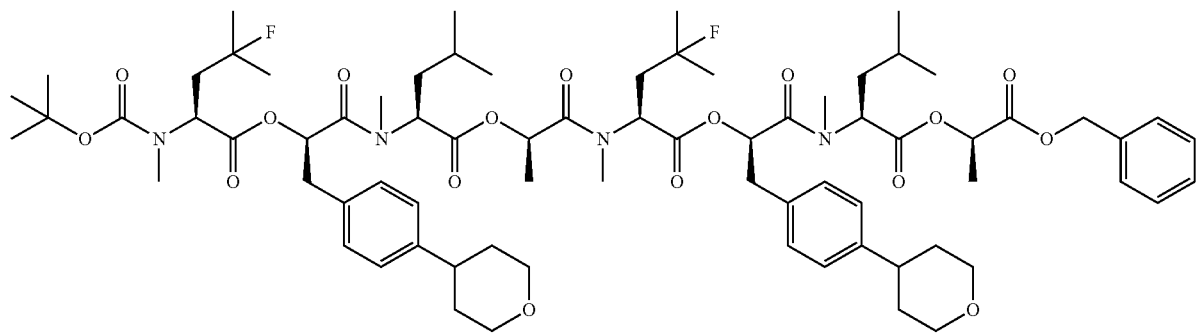

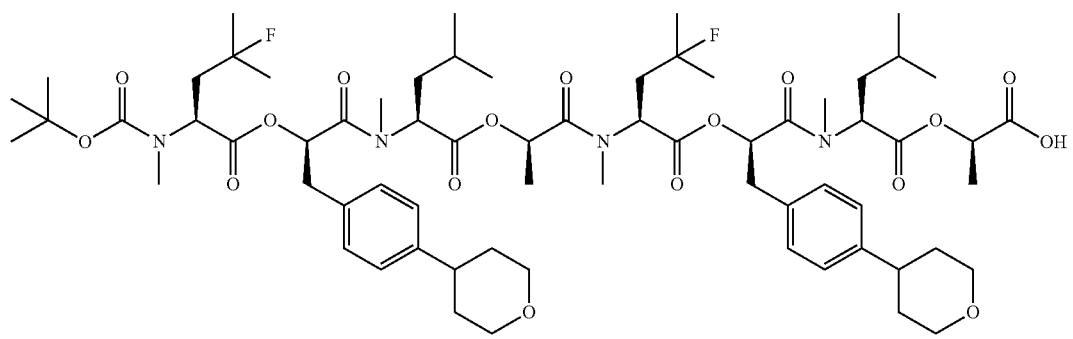

OC7-18:

To a solution of OP7-18 (760 mg, 0.56 mmol, 1.00 equiv) in ethyl acetate (10 mL) was placed Palladium on carbon (150 mg). The flask was evacuated and flushed three times with nitrogen, followed by flushing with hydrogen. The mixture was stirred 1.5 h at room temperature under an atmosphere of hydrogen. The solids were filtered out. The filtrate was concentrated under vacuum. This resulted in 710 mg (100%) of OC7-18 as a white solid. MS (ES, m/z): 1262 (Ms+H-Boc).

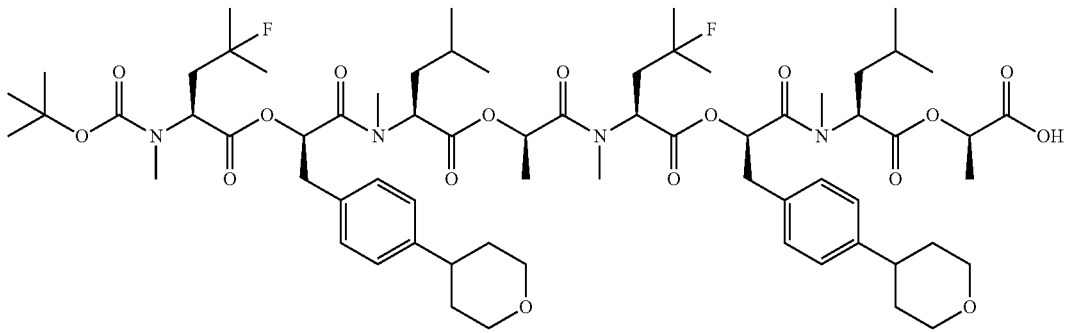

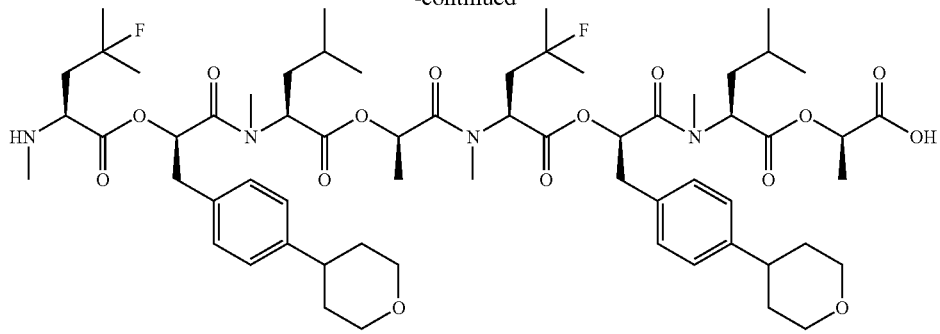

OAC7-18:

Into a 50-mL round-bottom flask, was placed hydrogen chloride/dioxane (10 mL), OC7-18 (710 mg, 0.56 mmol, 1.00 equiv). The resulting solution was stirred for 1.5 h at room temperature. The resulting mixture was concentrated under vacuum. This resulted in 678 mg (crude) of OAC7-18 as a white solid. MS (ES, m/z): 1172 (M+H).

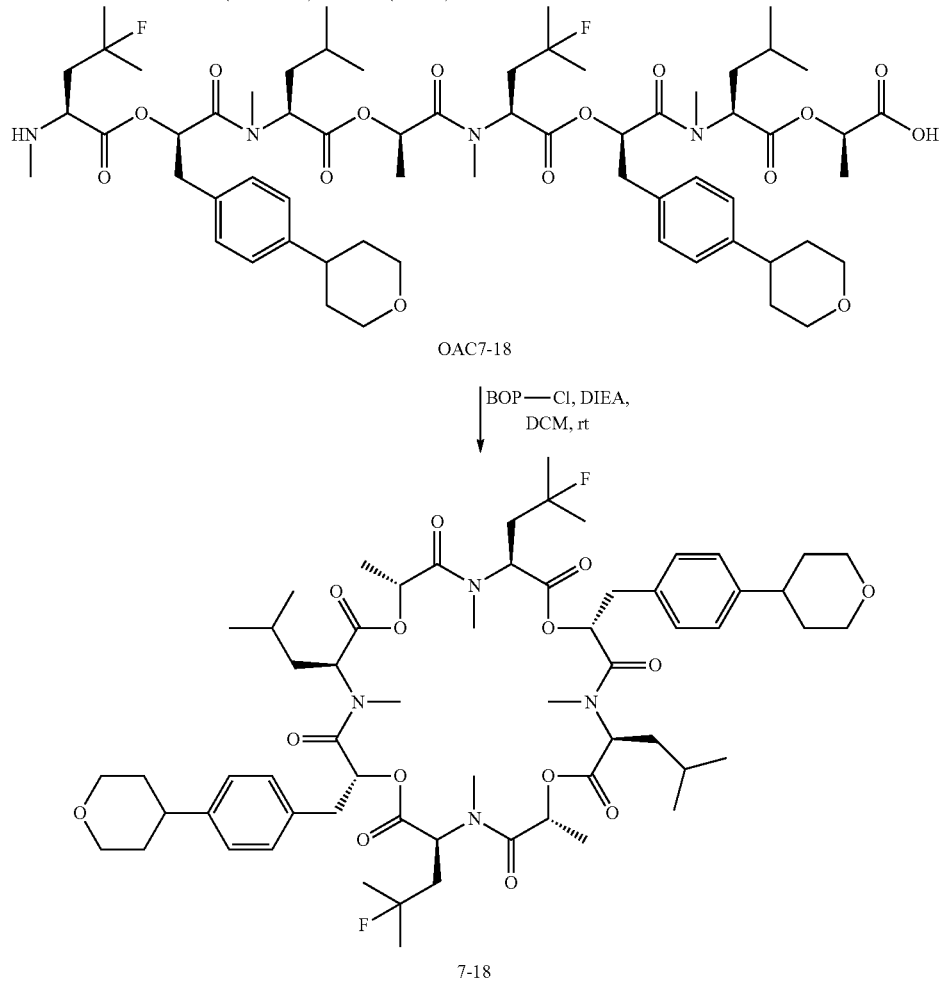

7-18:

To a solution of OAC7-18 (500 mg, 0.43 mmol, 1.00 equiv) in dichloromethane (40 mL) was added BOP-Cl (217 mg, 0.85 mmol, 2.00 equiv) in portions at 0° C. This was followed by the addition of DIEA (275 mg, 2.125 mmol, 5.00 equiv) dropwise with stirring at 0° C. The resulting solution was diluted in 50 mL DCM and wash with brine 10 mL×3. The organic layers combined and dried over anhydrous sodium sulfate. The solids were filtered out. The filtrate was concentrated under vacuum. The crude product was purified by Flash-Prep-HPLC with the following conditions (IntelFlash-1): Column, C18; mobile phase, $CH_3CN/H_2O$=50% increasing to $CH_3CN/H_2O$=80% within 20 min; Detector, UV 254 nm. This resulted in 294 mg (60%) of 7-18 as a white solid. MS (ES, m/z): 1152.6 (calculated, M), 1154.0 (found, M+H). $^1$HNMR (300 MHz, $CD_3OD_3$): δ 7.28-7.22 (m, 8H), 5.73-5.24 (m, 7H), 4.88 (m, 1H), 4.06-4.02 (d, J=11.1 Hz, 4H), 3.60-3.52 (m, 4H), 3.33-3.31 (m, 4H), 3.11-2.80 (m, 14H), 2.30-1.91 (m, 4H), 1.80-1.63 (m, 12H), 1.51-1.29 (m, 17H), 0.97-0.82 (m, 15H); [α]=−61.3° (T=24.7° C., c=0.82 g/100 mL in MeOH).

Preparation Example 88: Preparation of Compound 7-32
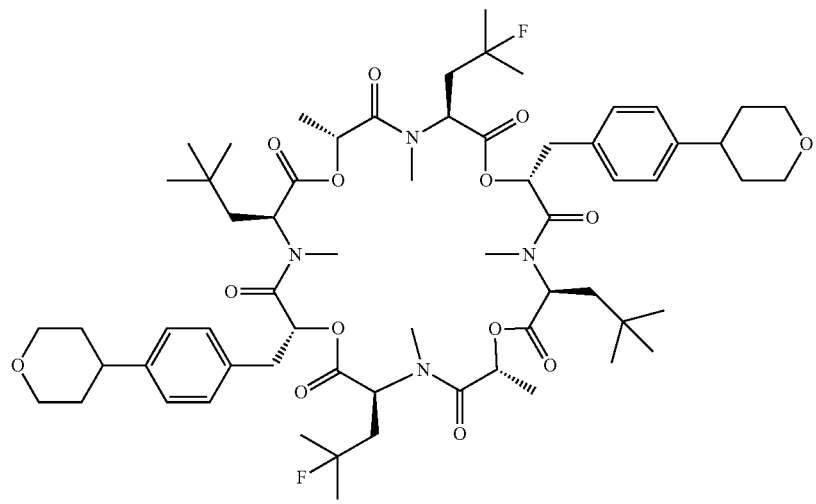
7-32
Compound 7-32 was prepared according to Schemes 46-48 below.
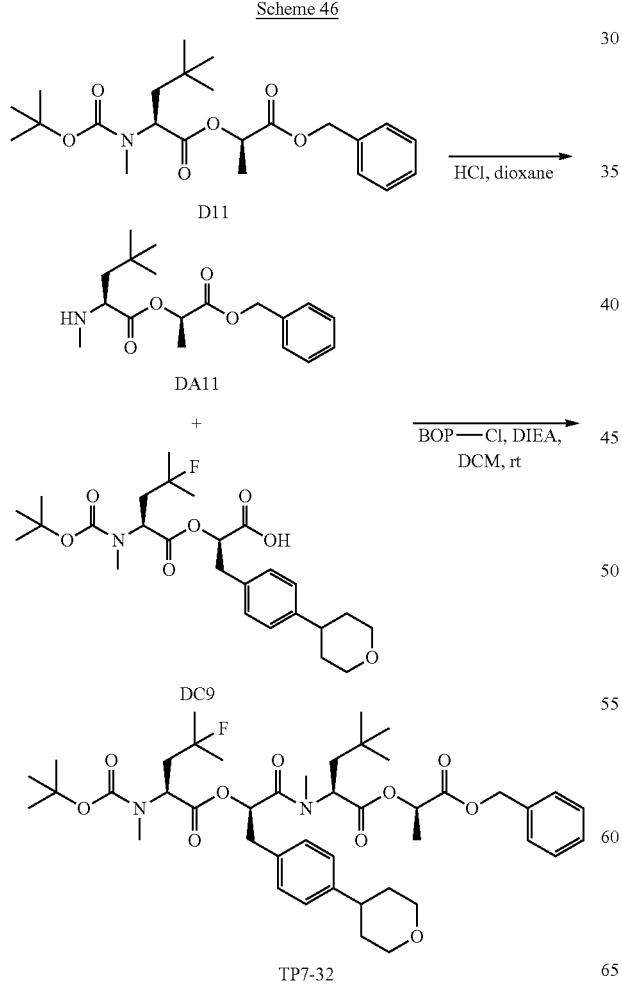

Scheme 47
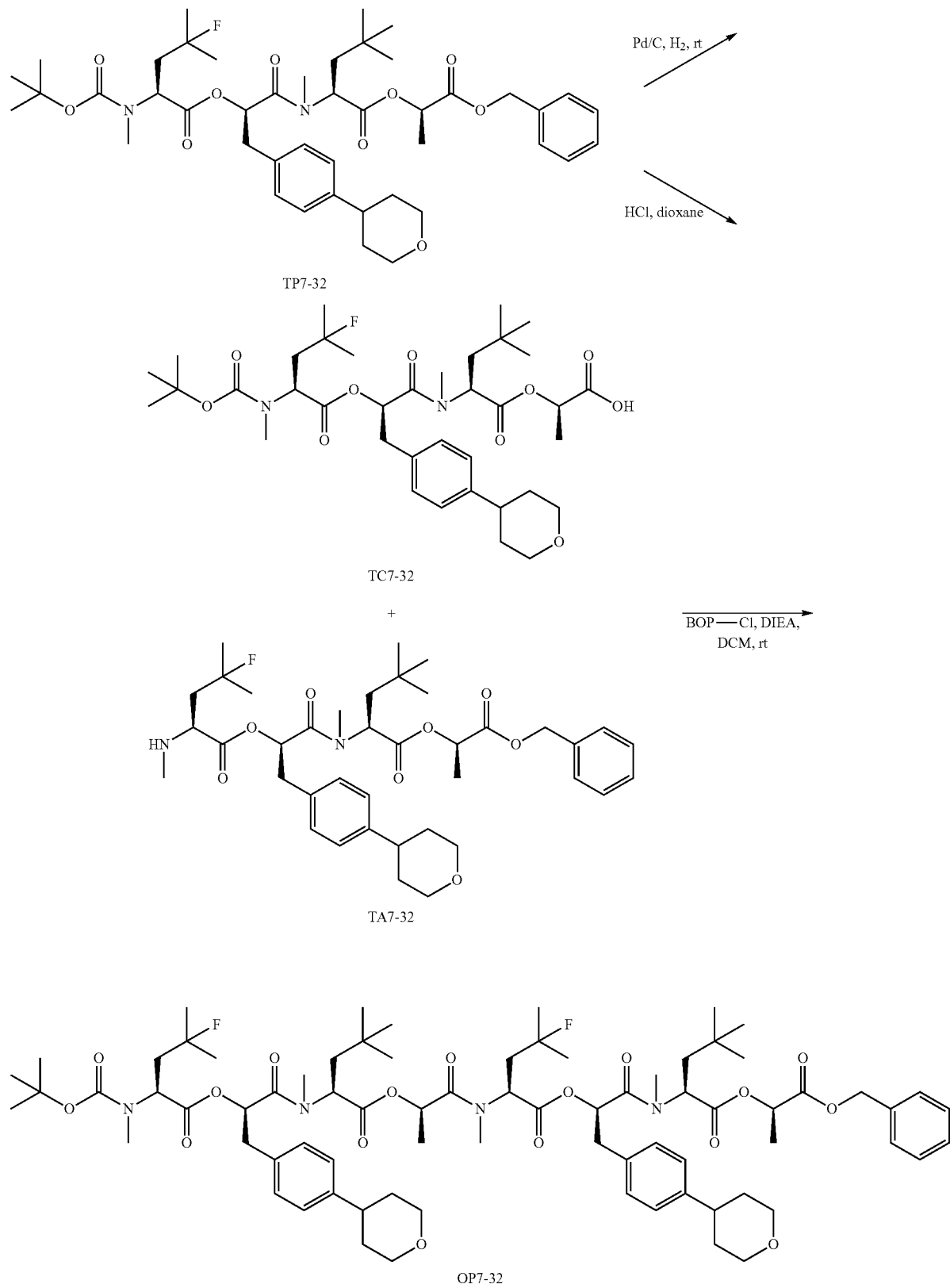

Scheme 48
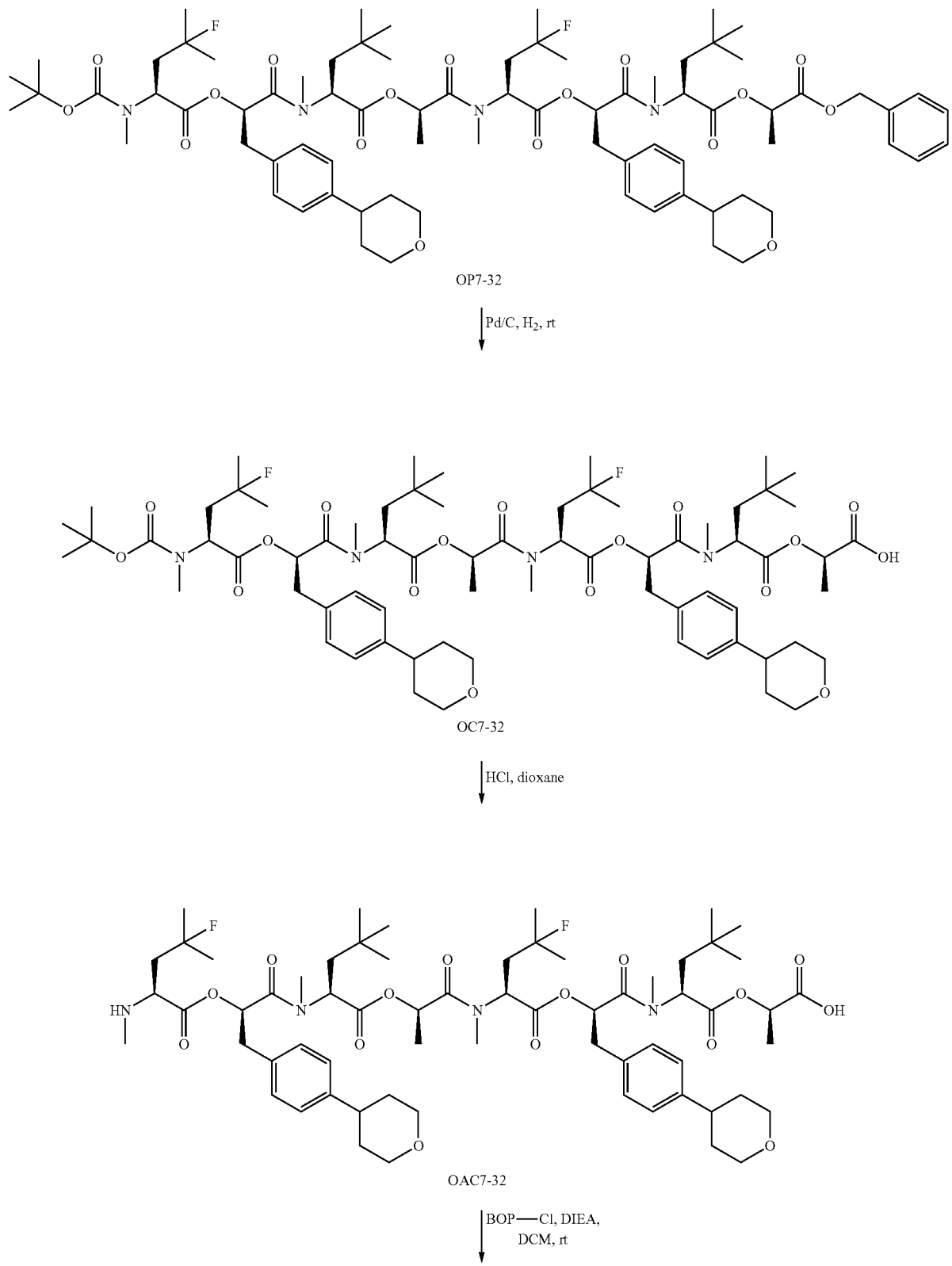

-continued

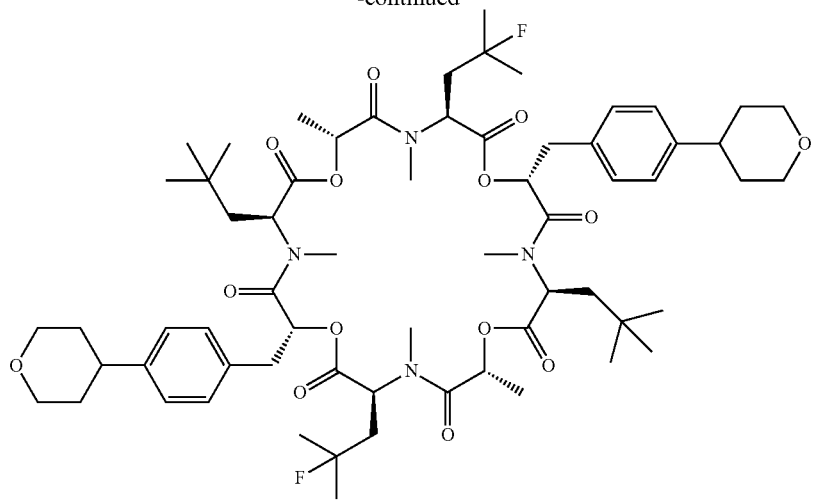

7-32

Experimental Details

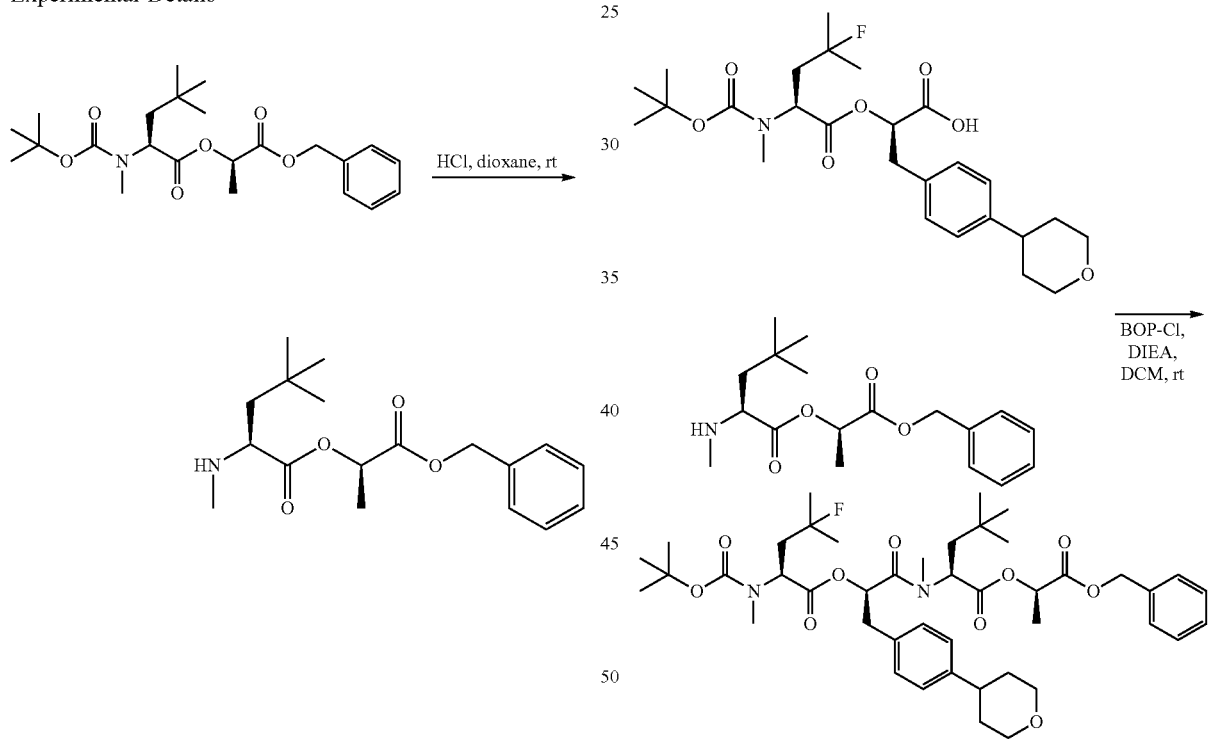

(2R)-1-(benzyloxy)-1-oxopropan-2-yl (2S)-4,4-dimethyl-2-(methylamino)pentanoate Into a 500-mL round-bottom flask, was placed hydrogen chloride(gas) in dioxane (200 mL), (2R)-1-(benzyloxy)-1-oxopropan-2-yl (2S)-2-[[(tert-butoxy)carbonyl](methyl)amino]-4,4-dimethyl pentanoate (23 g, 54.56 mmol, 1.00 equiv). The resulting solution was stirred for 3 h at room temperature. The resulting mixture was concentrated under vacuum. This resulted in 26 g (crude) of (2R)-1-(benzyloxy)-1-oxopropan-2-yl (2S)-4,4-dimethyl-2-(methylamino)pentanoate as a white solid. MS (ES, m/z): 322 (M+H).

TP7-32:

Into a 500-mL 3-necked round-bottom flask, was placed dichloromethane (400 mL), (2R)-1-(benzyloxy)-1-oxopropan-2-yl-(2S)-4,4-dimethyl-2-(methylamino)pentanoate (14 g, 43.56 mmol, 1.00 equiv), (2R)-2-[[(2S)-2-[[(tert-butoxy)carbonyl](methyl)amino]-4-fluoro-4-methylpentanoyl]oxy]-3-[4-(oxan-4-yl)phenyl]propanoic acid (21.58 g, 43.54 mmol, 1.00 equiv). This was followed by the addition of BOP-Cl (22 g, 86.42 mmol, 2.00 equiv) in portions at 0° C. To this was added DIEA (22 g, 170.23 mmol, 4.00 equiv) dropwise with stirring at 0° C. The resulting solution was stirred overnight at room temperature. The resulting mixture was concentrated under vacuum. The residue was applied onto a silica gel column with ethyl acetate/petroleum ether (1:10-1:5). This resulted in 32 g (92%) of TP7-32 as colorless oil. MS (ES, m/z): 799 (M+H).

concentrated under vacuum. This resulted in 14 g (99%) of TC7-32 as a white solid. MS (ES, m/z): 709 (M+H).

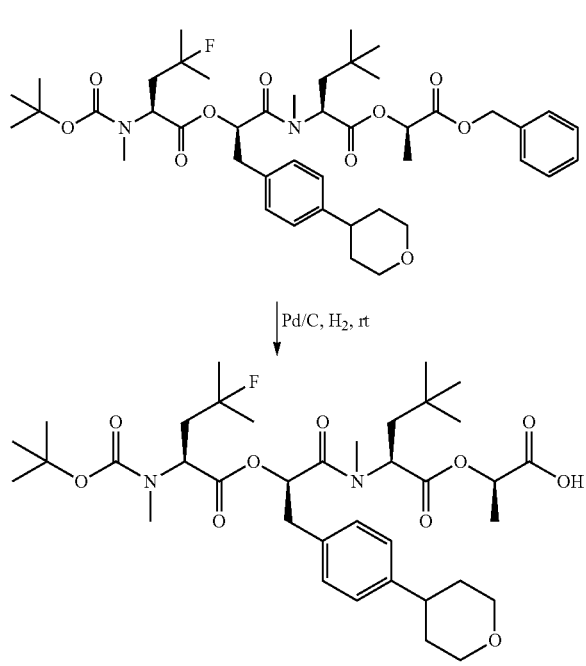

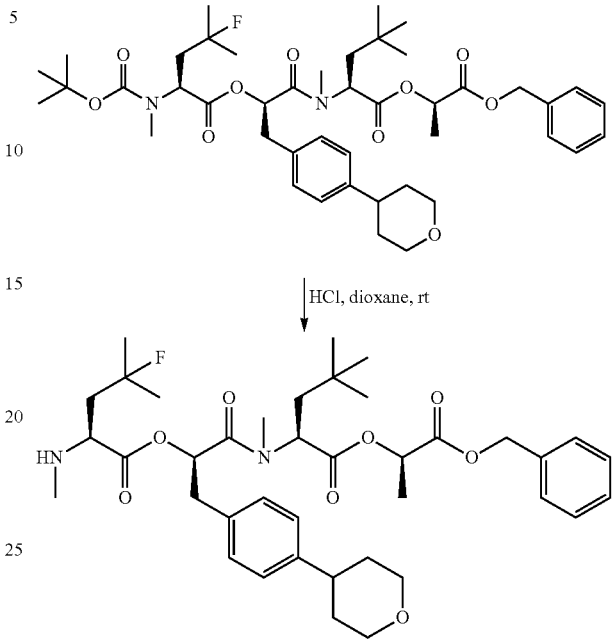

TC7-32:

Into a 500-mL round-bottom flask, was placed Palladium on carbon (3.2 g), ethyl acetate (300 mL), TP7-32 (16 g, 20.03 mmol, 1.00 equiv). The flask was evacuated and flushed three times with nitrogen, followed by flushing with hydrogen. The resulting solution was stirred for 2 h at room temperature. The solids were filtered out. The filtrate was

TA7-32:

Into a 500-mL round-bottom flask, was placed hydrogen chloride in dioxane (300 mL), TP7-32 (16 g, 20.03 mmol, 1.00 equiv). The resulting solution was stirred for 2 h at room temperature. The resulting mixture was concentrated under vacuum. This resulted in 15 g (crude) of TA7-32 as a white solid. MS (ES, m/z): 699 (M+H).

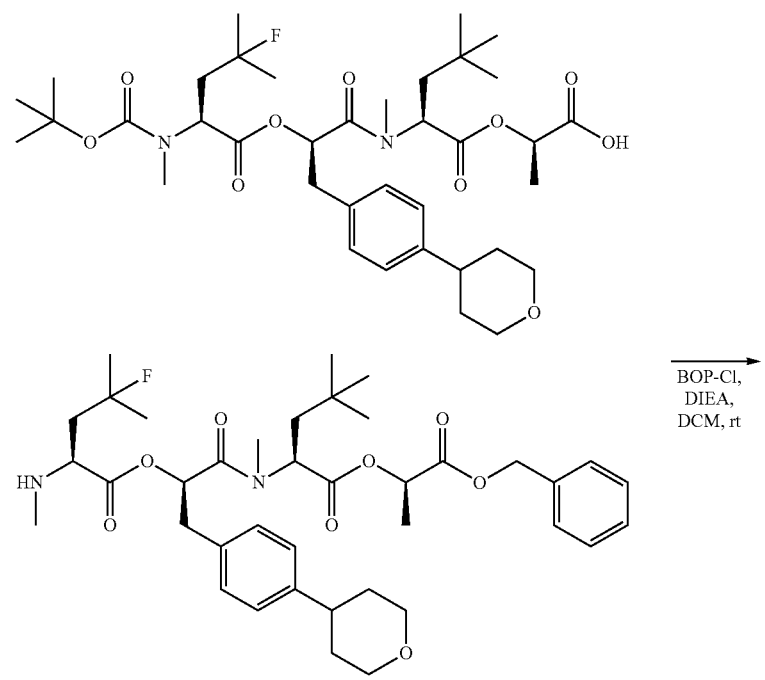

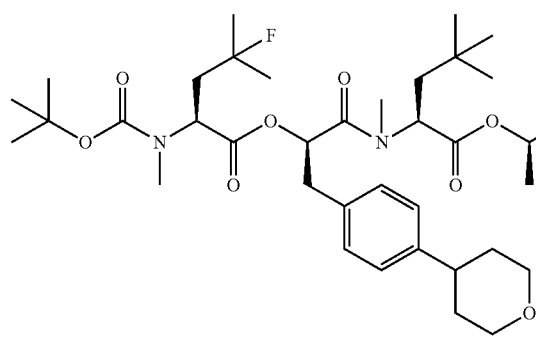

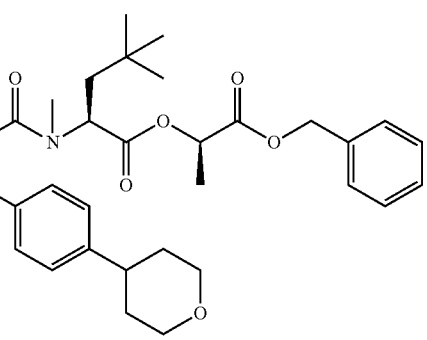

OP7-32:

Into a 500-mL round-bottom flask, was placed dichloromethane (400 mL), TA7-32 (14 g, 20.03 mmol, 1.00 equiv), TC7-32 (13.8 g, 19.47 mmol, 1.00 equiv). This was followed by the addition of BOP-Cl (10 g, 39.28 mmol, 2.00 equiv) in portions at 0° C. To this was added DIEA (10 g, 77.38 mmol, 4.00 equiv) dropwise with stirring at 0° C. The resulting solution was stirred for 3 h at room temperature. The resulting mixture was concentrated under vacuum. The residue was applied onto a silica gel column with ethyl acetate/petroleum ether (1:10-1:2). This resulted in 26.7 g (96%) of OP7-32 as off-white oil. MS (ES, m/z): 1412 (M+Na).

OC7-32:

Into a 1-L round-bottom flask, was placed Palladium on carbon (5 g), ethyl acetate (500 mL), OP7-32 (26.7 g, 19.22 mmol, 1.00 equiv). The flask was evacuated and flushed three times with nitrogen, followed by flushing with hydrogen. The resulting solution was stirred for 2 h at room temperature. The solids were filtered out. The resulting mixture was concentrated under vacuum. This resulted in 24.8 g (99%) of OC7-32 as a white solid. MS (ES, m/z): 1300 (M+H).

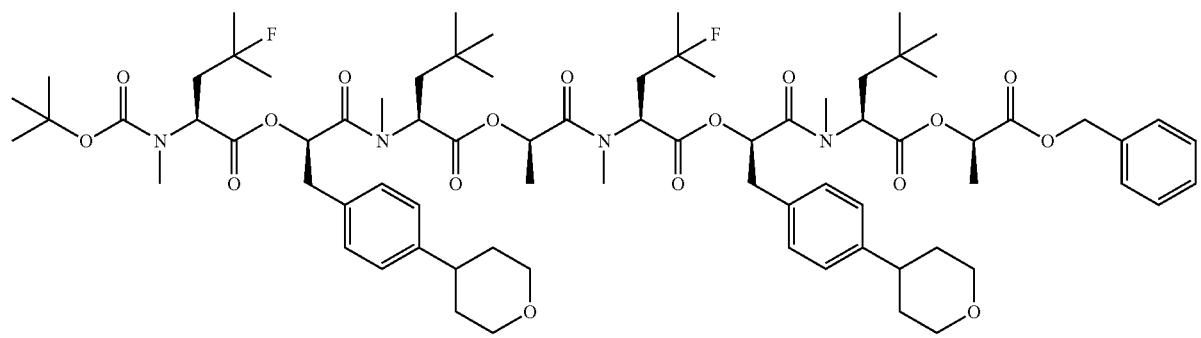

Pd/C, H₂, EtOAc

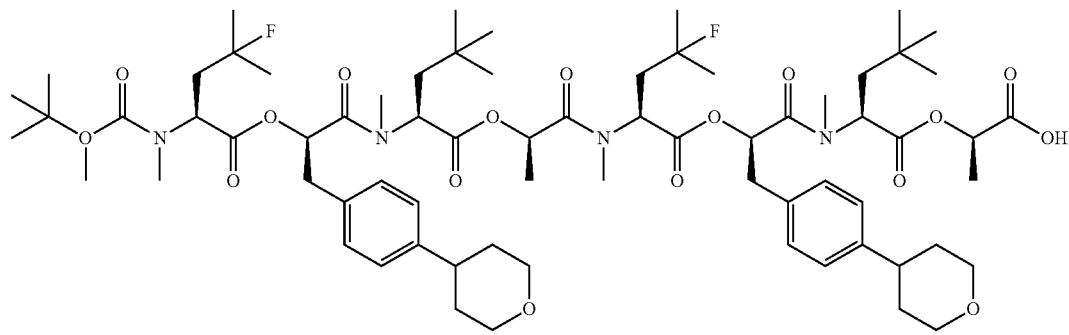

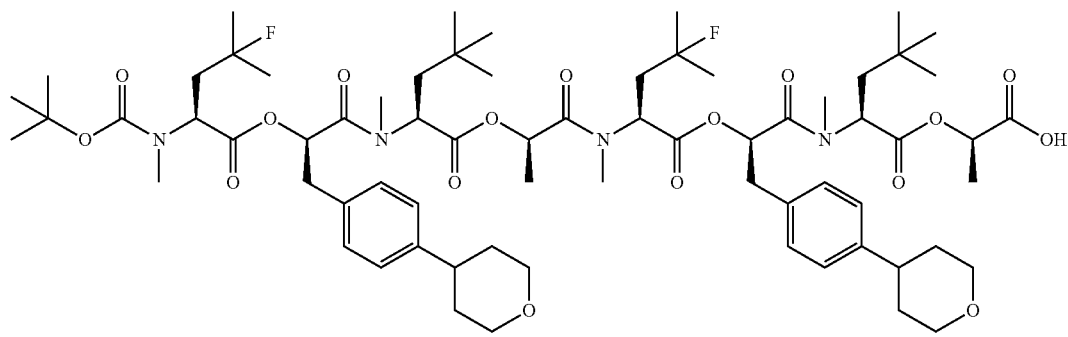
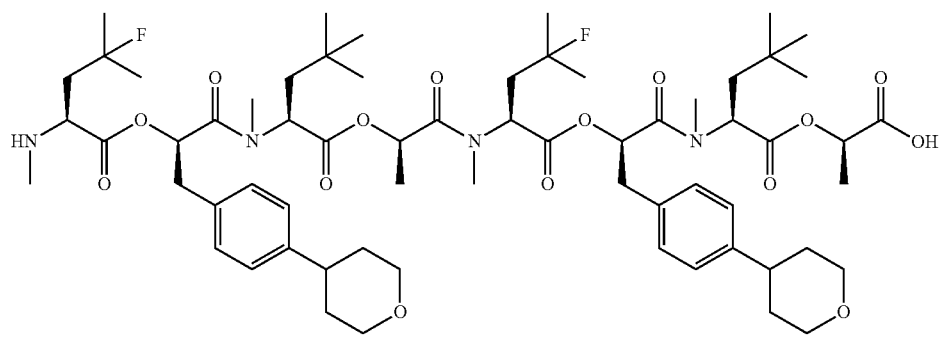
OAC7-32:
Into a 1-L round-bottom flask, was placed hydrogen chloride/dioxane (500 mL), OC7-32 (24.8 g, 19.09 mmol, 1.00 equiv). The resulting solution was stirred for 2 h at room temperature. The resulting mixture was concentrated under vacuum. This resulted in 24 g (crude) of OAC7-32 as a white solid. MS (ES, m/z): 1200 (M+H).
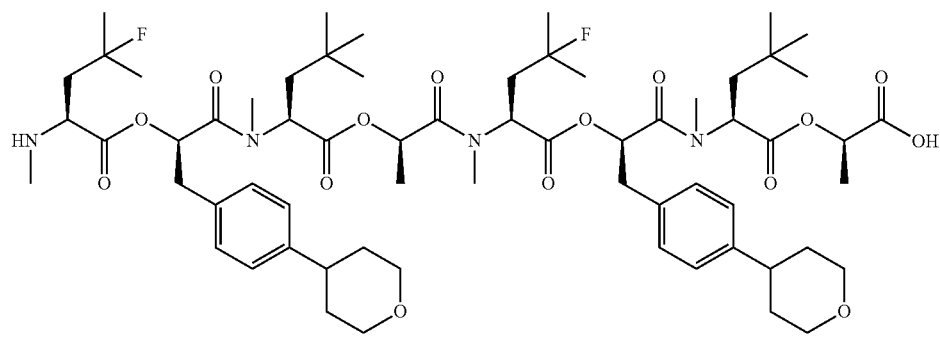
OAC7-32
BOP-Cl, DIEA,
DCM, rt

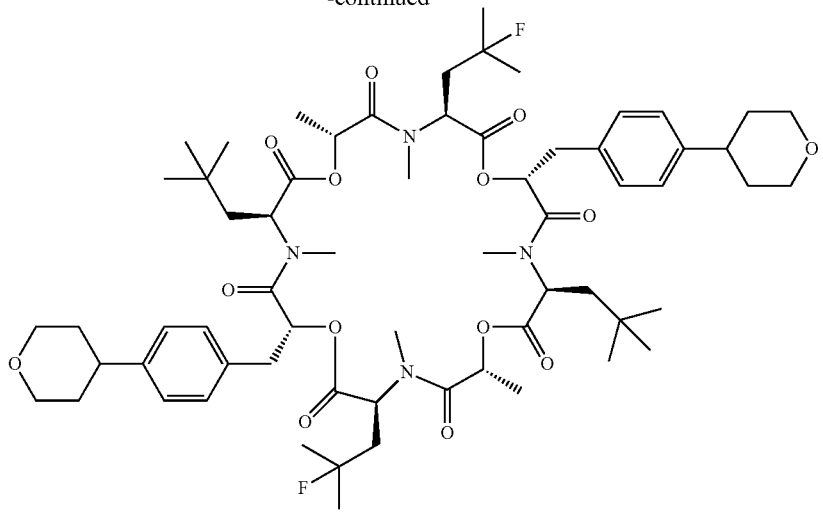

7-32

7-32:

Into a 1-L round-bottom flask, was placed dichloromethane (800 mL), OAC7-32 (24 g, 20.02 mmol, 1.00 equiv). This was followed by the addition of BOP-Cl (10 g, 39.28 mmol, 2.00 equiv) in portions at 0° C. To this was added DIEA (10 g, 77.38 mmol, 4.00 equiv) dropwise with stirring at 0° C. The resulting solution was stirred overnight at room temperature. The resulting mixture was concentrated under vacuum. The crude product was purified by Flash-Prep-HPLC with the following conditions (IntelFlash-1): Column, C18 silica gel; mobile phase, $CH_3CN/H_2O=60\%$ increasing to $CH_3CN/H_2O=90\%$ within 20 min; Detector, UV 220 nm. This resulted in 14.5 g (61%) of 7-32 as a white solid. MS (ES, m/z): 1180.7 (calculated, M), 1182.0 (found, M+H). $^1H$ NMR: (300 MHz, $CDCl_3$, ppm): δ 7.22-7.09 (m, 8H), 5.77-5.31 (m, 8H), 4.75-4.65 (m, 1H), 4.11-4.07 (m, 4H), 3.57-3.50 (m, 4H), 3.18-3.0 (m, 6H), 2.83-2.72 (m, 12H), 2.4-1.7 (m, 15H), 1.52-0.78 (m, 40H); [α]=−53.26° (T=27.2° C., c=0.52 g/100 mL in MeOH).

Preparation Example 89: Preparation of Compound 5-32

Compound 5-32 was prepared according to the process shown in Schemes 49-51 below.

Scheme 49

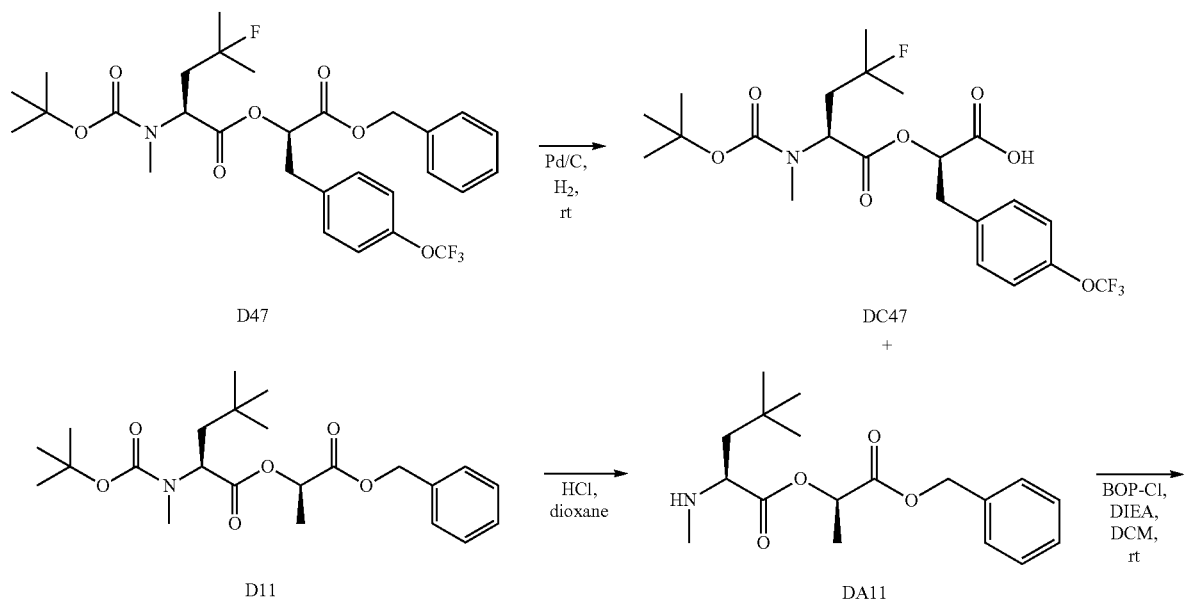

-continued
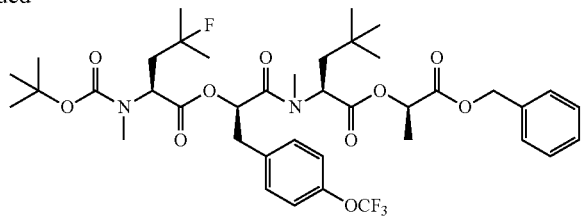
TP5-32
Scheme 50
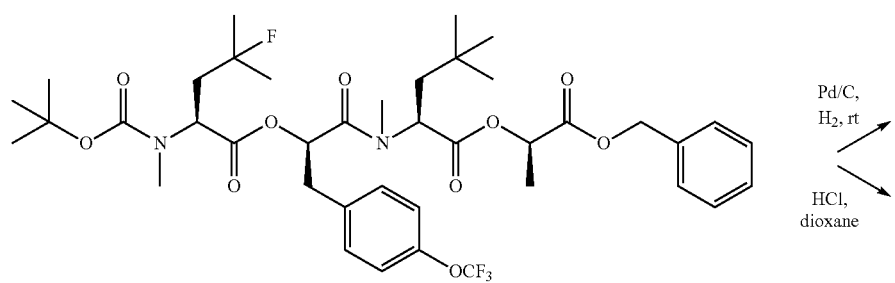
TP5-32
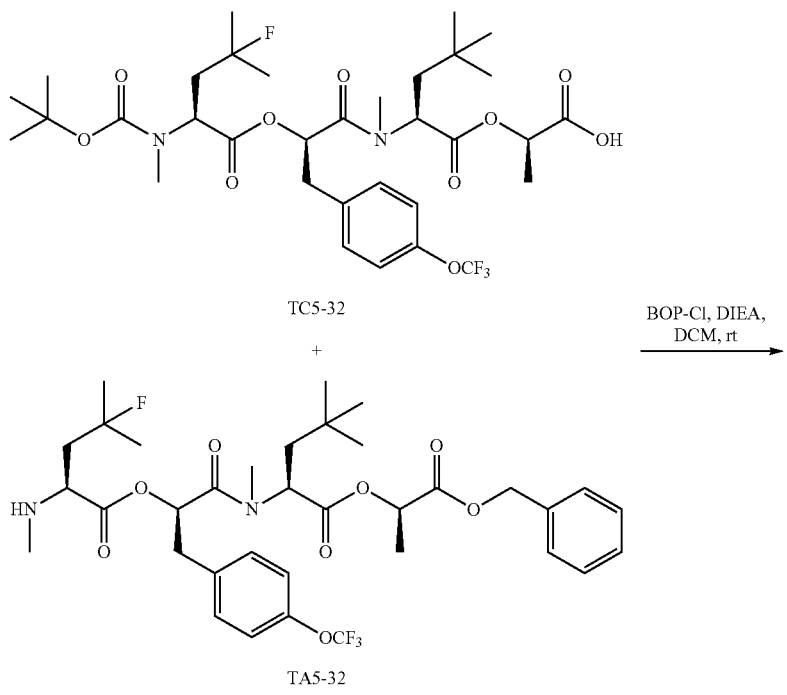
TC5-32
+
TA5-32

393    394
-continued
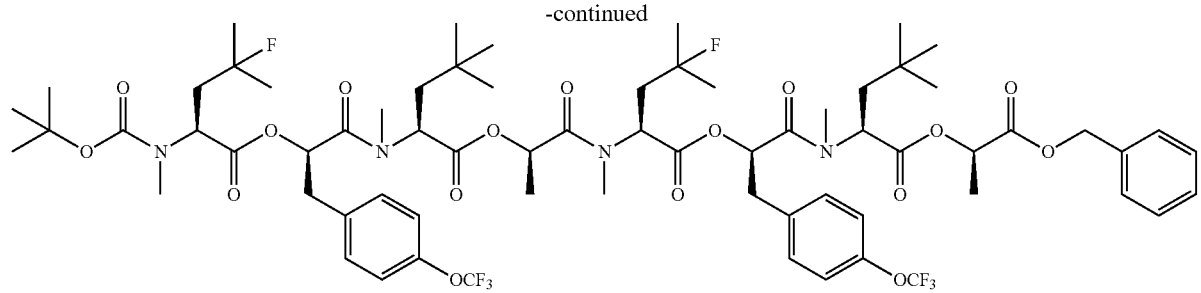
OP5-32
Scheme 51
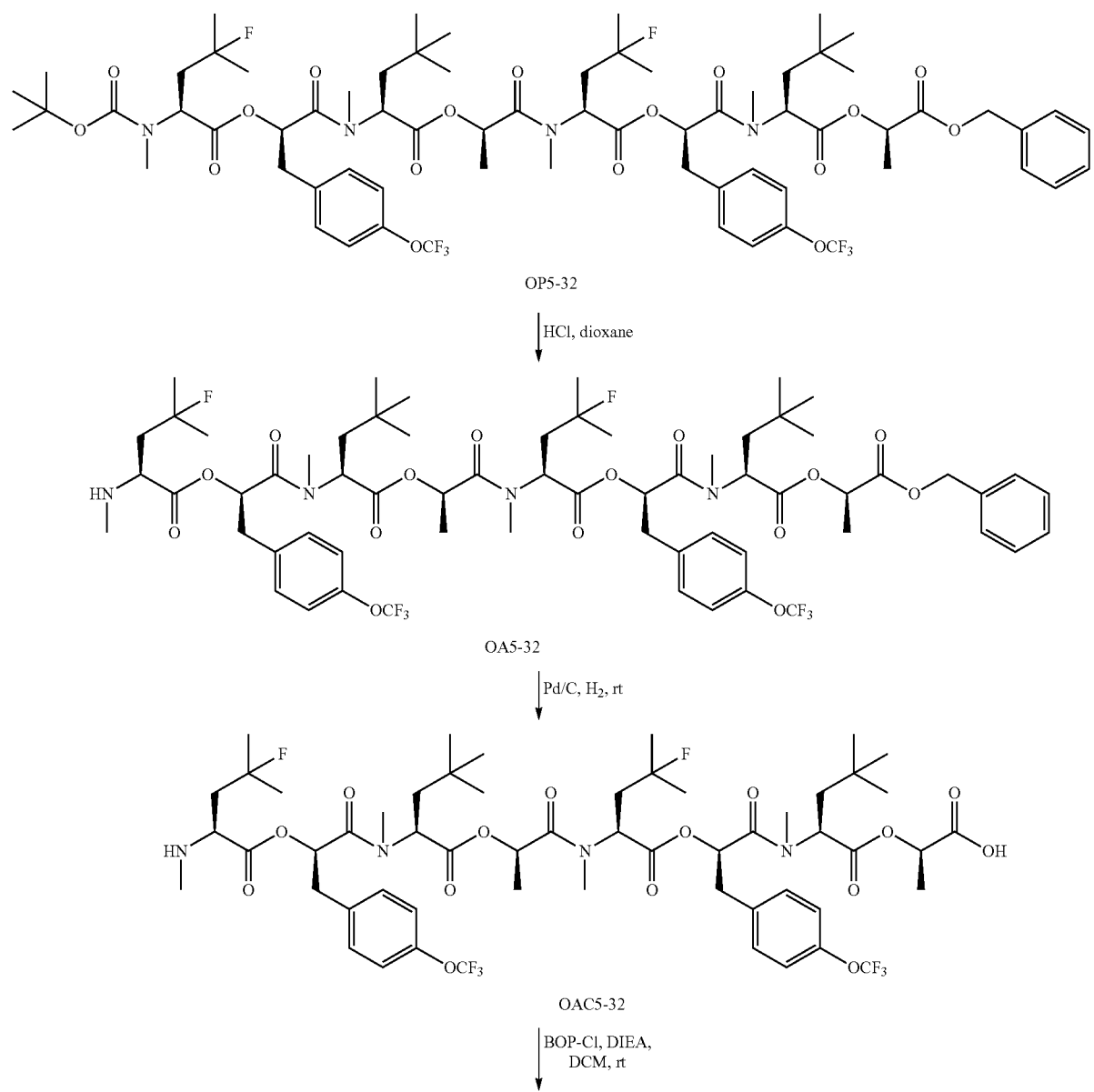

-continued

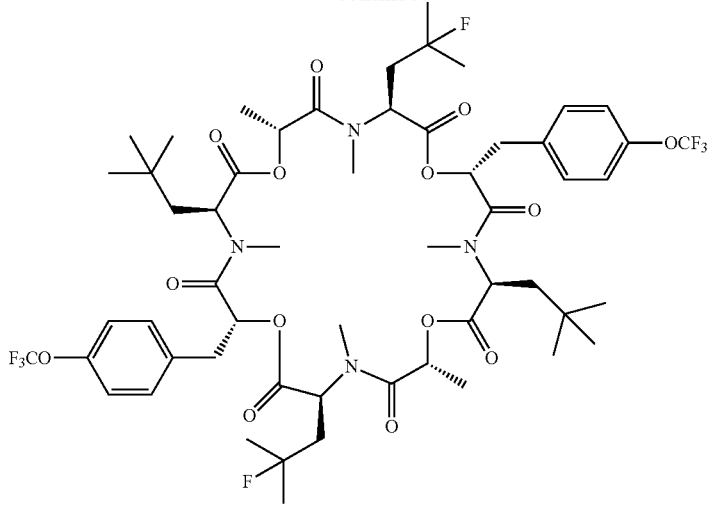

5-32

Experimental Details

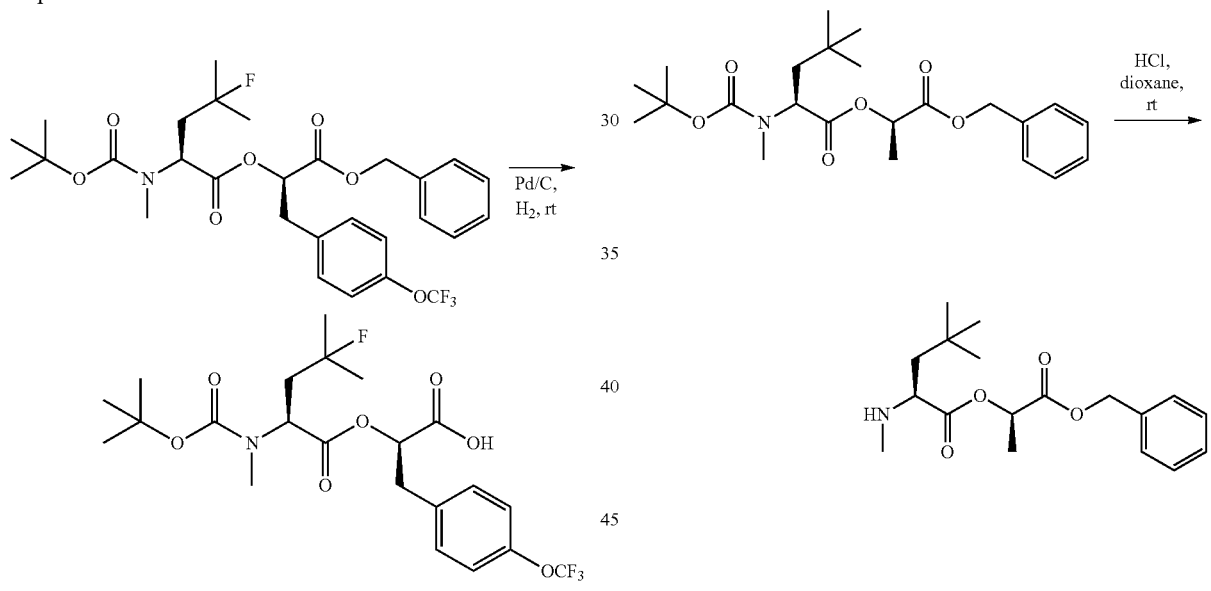

(2R)-2-[[(2S)-2-[[(tert-butoxy)carbonyl](methyl)amino]-4-fluoro-4-methylpentanoyl]oxy]-3-[4-(trifluoromethoxy)phenyl]propanoic acid Into a 250-mL round-bottom flask, was placed (2R)-1-(benzyloxy)-3-[4-(trifluoromethoxy)phenyl]propan-2-yl-(2S)-2-[[(tert-butoxy)carbonyl](methyl)amino]-4-fluoro-4-methylpentanoate (3 g, 5.25 mmol, 1.00 equiv), Pd/C (500 mg), methanol (80 mL). To the above Hydrogen gas was introduced. The resulting solution was stirred for 1.5 h at room temperature. The solids were filtered out. The filtrate was concentrated under vacuum. This resulted in 2 g (77%) of (2R)-2-[[(2S)-2-[[(tert-butoxy) carbonyl](methyl)amino]-4-fluoro-4-methylpentanoyl]oxy]-3-[4-(trifluoromethoxy)phenyl]propanoic acid as a white solid. MS (ES, m/z): 496 (M+H).

(2R)-1-(benzyloxy)-1-oxopropan-2-yl-(2S)-4,4-dimethyl-2-(methylamino)pentanoate

Into a 250-mL round-bottom flask, was placed (2R)-1-(benzyloxy)-1-oxopropan-2-yl-(2S)-2-[[(tert-butoxy)carbonyl](methyl)amino]-4,4-dimethylpentanoate (3 g, 7.12 mmol, 1.00 equiv), dichloromethane (80 mL). To the above HCl (gas) was introduced. The resulting solution was stirred for 1.5 h at room temperature. The pH value of the solution was adjusted to 8 with sodium bicarbonate (Sat.). The resulting solution was extracted with 3×70 mL of dichloromethane and the organic layers combined and washed with 3×100 mL of brine. The organic phase was collected and dried over anhydrous sodium sulfate and concentrated under vacuum. This resulted in 2.1 g (92%) of (2R)-1-(benzyloxy)-1-oxopropan-2-yl-(2S)-4,4-dimethyl-2-(methylamino)pentanoate as yellow oil. MS (ES, m/z): 322 (M+H).

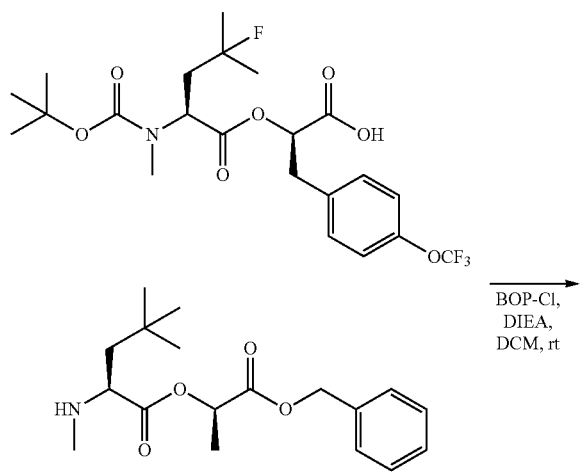

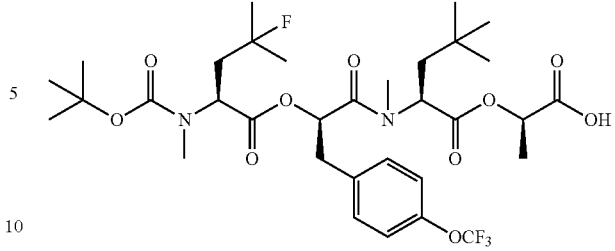

TC5-32:

Into a 100-mL round-bottom flask, was placed TP5-32 (700 mg, 0.88 mmol, 1.00 equiv), Palladium on carbon (120 mg), methanol (30 mL). To the above Hydrogen gas was introduced. The resulting solution was stirred for 1.5 h at room temperature. The solids were filtered out. The filtrate was concentrated under vacuum. The resulting mixture was concentrated under vacuum. This resulted in 610 mg (98%) of TC5-32 as a white solid. MS (ES, m/z): 709 (M+H).

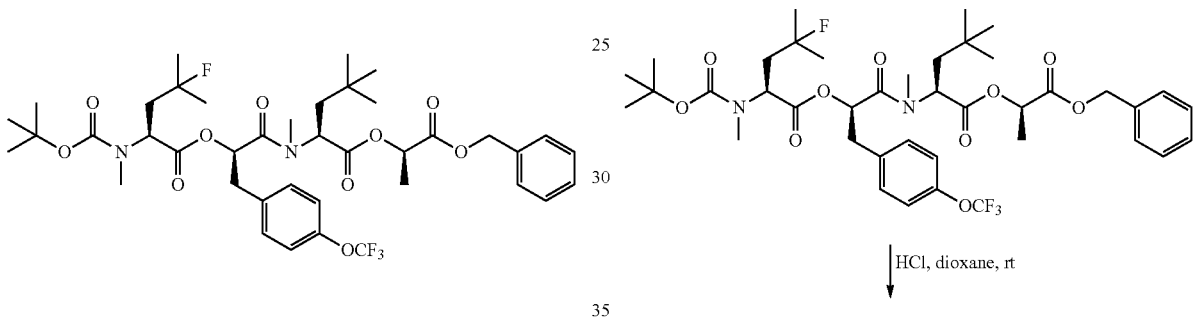

TP5-32:

Into a 250-mL 3-necked round-bottom flask, was placed (2R)-2-[[(2S)-2-[[(tert-butoxy)carbonyl](methyl)amino]-4-fluoro-4-methylpentanoyl]oxy]-3-[4-(trifluoromethoxy)phenyl]propanoic acid (2 g, 4.04 mmol, 1.00 equiv), (2R)-1-(benzyloxy)-1-oxopropan-2-yl (2S)-4,4-dimethyl-2-(methylamino)pentanoate (1.3 g, 4.04 mmol, 1.00 equiv), dichloromethane (100 mL). This was followed by the addition of BOP-Cl (2.1 g, 8.25 mmol, 2.00 equiv) with stirring at 0° C. in portions. To this was added DIEA (1.1 g, 8.51 mmol, 2.00 equiv) dropwise with stirring at 0° C. The resulting solution was stirred overnight at room temperature. The solids were filtered out. The filtrate was concentrated under vacuum. The residue mixture was applied onto a silica gel column with ethyl acetate/petroleum ether (1:5). This resulted in 1.4 g (43%) of TP5-32 as yellow oil. MS (ES, m/z): 799 (M+H).

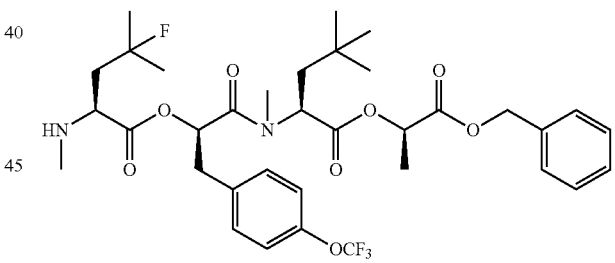

TA5-32:

Into a 100-mL round-bottom flask, was placed TP5-32 (700 mg, 0.88 mmol, 1.00 equiv), dichloromethane (35 mL). To the above HCl (gas) was introduced. The resulting solution was stirred for 1.5 h at room temperature. The pH value of the solution was adjusted to 8 with sodium bicarbonate (Sat.). The resulting solution was extracted with 3×30 mL of dichloromethane and the organic layers combined and washed with 3×30 mL of brine. The organic phase was collected and dried over anhydrous sodium sulfate and concentrated under vacuum. This resulted in 600 mg (98%) of TA5-32 as yellow oil. MS (ES, m/z): 699 (M+H).

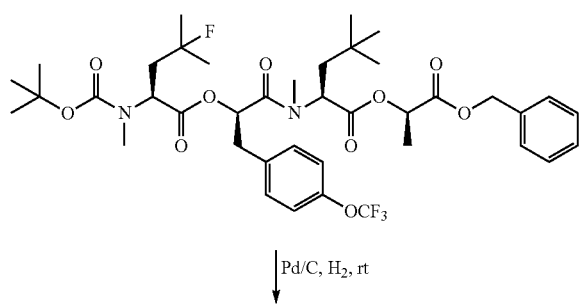

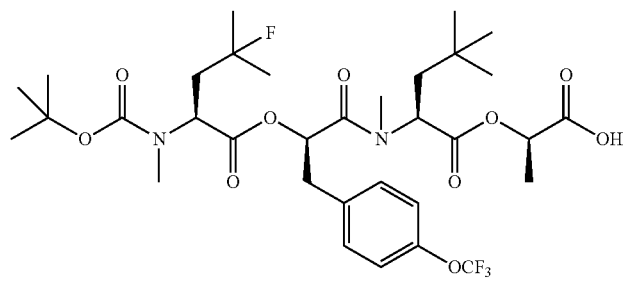

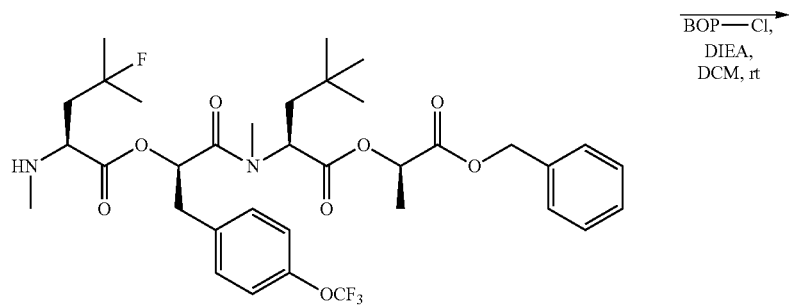

BOP—Cl,
DIEA,
DCM, rt

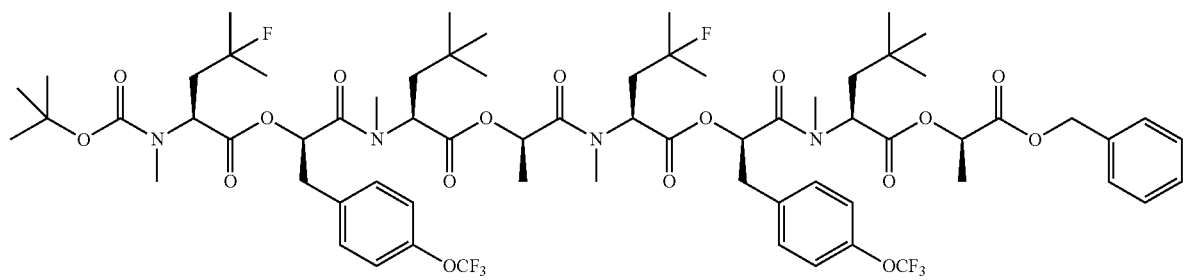

OP5-32:

Into a 250-mL 3-necked round-bottom flask, was placed TA5-32 (600 mg, 0.86 mmol, 1.00 equiv), TC5-32 (609 mg, 0.86 mmol, 1.00 equiv), dichloromethane (80 mL). This was followed by the addition of BOP-Cl (439 mg, 1.72 mmol, 2.00 equiv) with stirring at 0° C. in portions. To this was added DIEA (222 mg, 1.72 mmol, 2.00 equiv) dropwise with stirring at 0° C. The resulting solution was stirred overnight at room temperature. The solids were filtered out. The filtrate was concentrated under vacuum. The residue was applied onto a silica gel column with ethyl acetate/petroleum ether (1:2). This resulted in 830 mg (70%) of OP5-32 as yellow oil. MS (ES, m/z): 1390 (M+H).

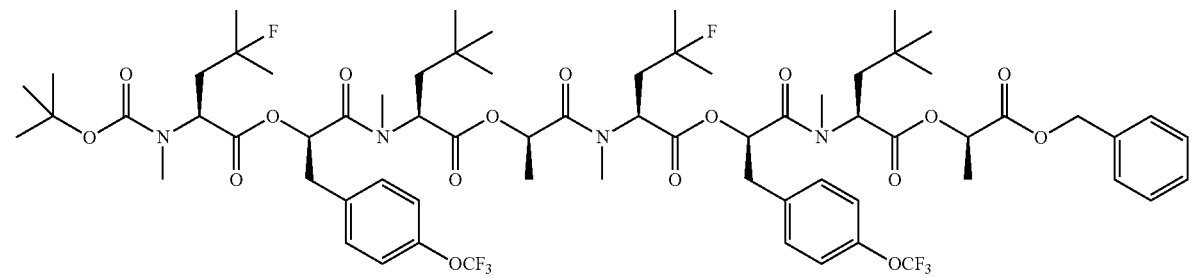

HCl, dioxane, rt

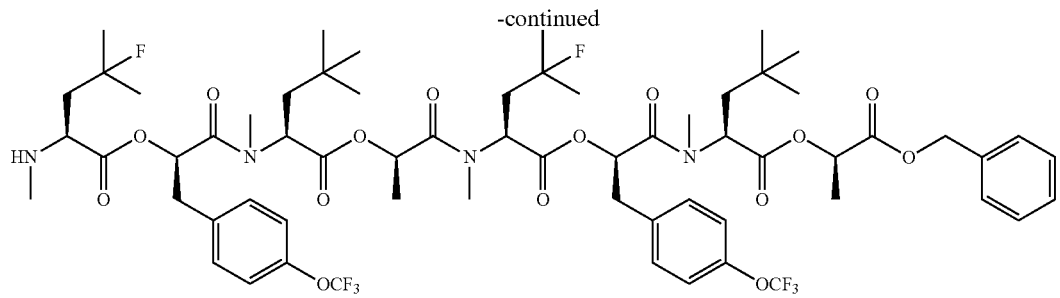

OA5-32:

Into a 100-mL round-bottom flask, was placed OP5-32 (830 mg, 0.60 mmol, 1.00 equiv), dichloromethane (50 mL). To the above H₂ (gas) was introduced. The resulting solution was stirred for 1.5 h at room temperature. The pH value of the solution was adjusted to 8 with sodium bicarbonate (Sat.). The resulting solution was extracted with 3×30 mL of dichloromethane and the organic layers combined. The organic phase was washed with 3×30 mL of brine and dried over anhydrous sodium sulfate and concentrated under vacuum. This resulted in 700 mg (91%) of OA5-32 as yellow oil. MS (ES, m/z): 1290 (M+H).

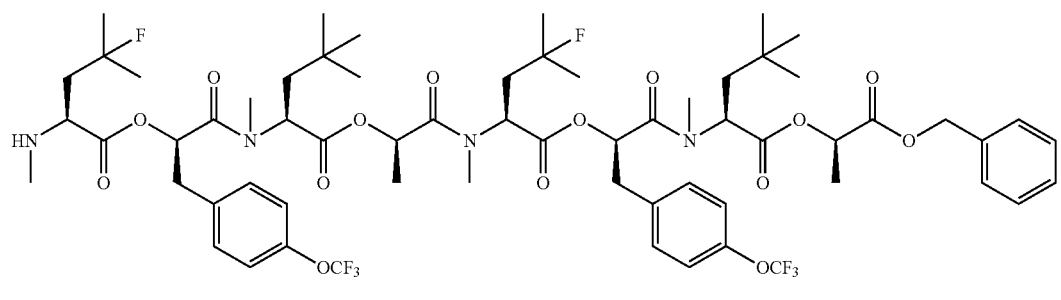

Pd/C, H₂, rt

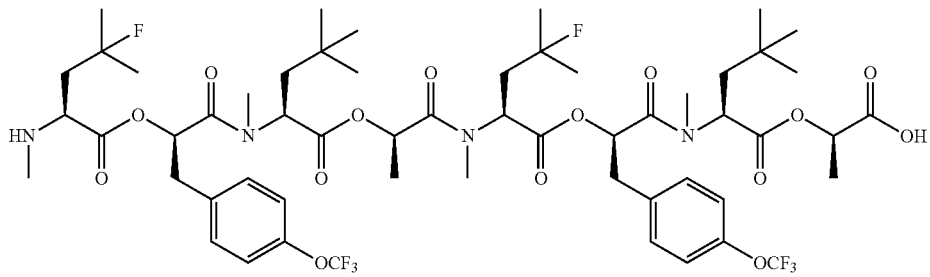

OAC5-32:

Into a 100-mL round-bottom flask, was placed OA5-32 (700 mg, 0.54 mmol, 1.00 equiv), Palladium on carbon (150 mg), methanol (40 mL). To the above H₂ (gas) was introduced. The resulting solution was stirred for 1.5 h at room temperature. The solids were filtered out. The filtrate was concentrated under vacuum. This resulted in 600 mg (92%) of OAC5-32 as a white solid. MS (ES, m/z): 1200 (M+H).

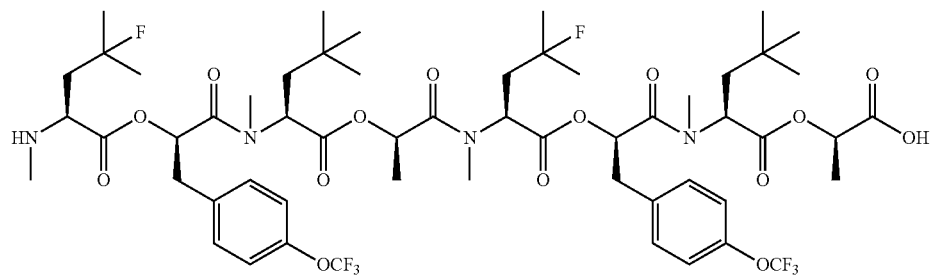

OAC5-32

| BOP—Cl,
| DIEA,
| DCM, rt

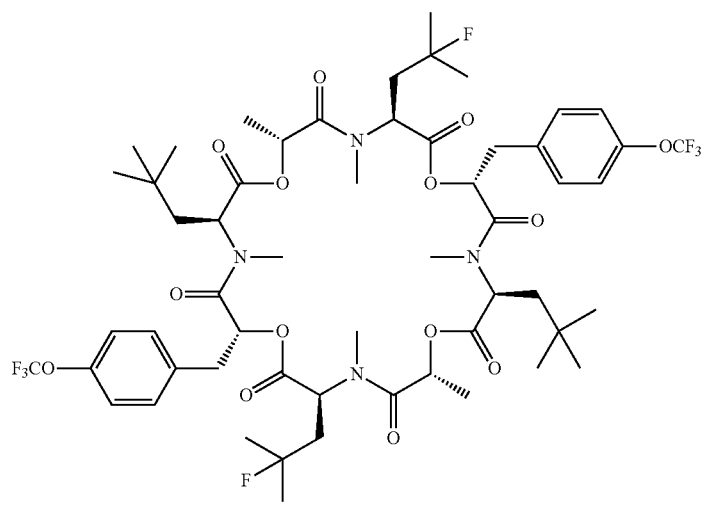

5-32

5-32:

Into a 250-mL 3-necked round-bottom flask, was placed product OAC5-32 (600 mg, 0.50 mmol, 1.00 equiv), dichloromethane (120 mL). This was followed by the addition of BOP-Cl (255 mg, 1.00 mmol, 2.00 equiv) with stirring at 0° C. in portions. To this was added DIEA (129 mg, 1.00 mmol, 2.00 equiv) dropwise with stirring at 0° C. The resulting solution was stirred overnight at room temperature. The solids were filtered out. The filtrate was concentrated under vacuum. The crude product was purified by Prep-HPLC with the following conditions: Column, SunFire Prep C18 5 um 19*150 mm; mobile phase, water and $CH_3CN$; Gradient: 90% to 95% in 20 min; Detector, 220 nm. This resulted in 350 mg (59%) of 5-32 as a white solid. MS (ES, m/z): 1180.5 (calculated, M), 1181.5 (found, M+H). $^1$HNMR (300 MHz, $CD_3OD$): δ 7.48-7.40 (m, 4H), 7.29-7.22 (m, 4H), 5.68-4.89 (m, 8H), 3.34-2.82 (m, 16H), 2.30-1.70 (m, 8H), 1.60-1.10 (m, 18H), 1.05-1.02 (m, 2H), 0.99-0.80 (m, 16H); [α]=−34.64°, T=27.2° C., c=1.085 g/100 mL in MeOH.

Preparation Example 90: Compound 18-32

Compound 18-32 was prepared according to the process described in Schemes 52-54 below.

Scheme 52

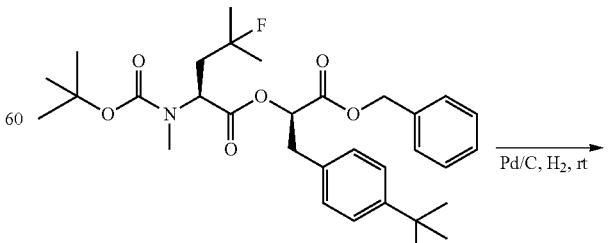

D29

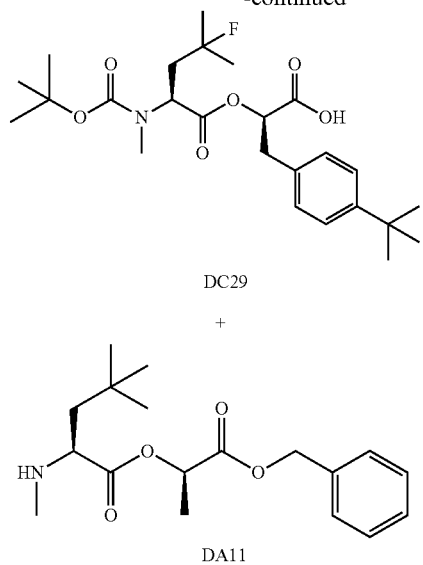
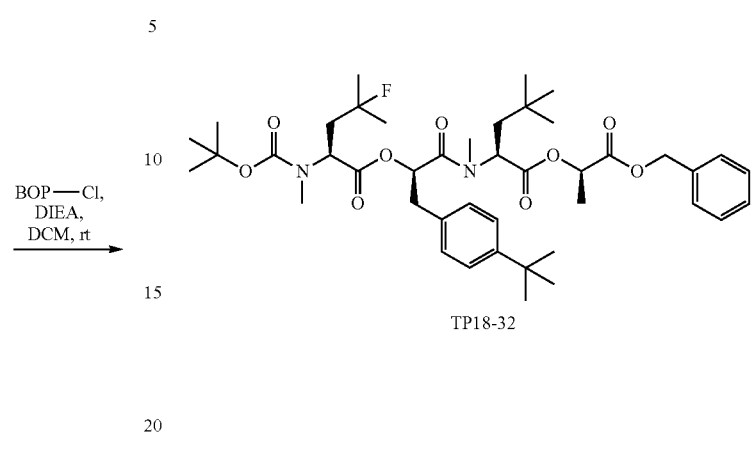
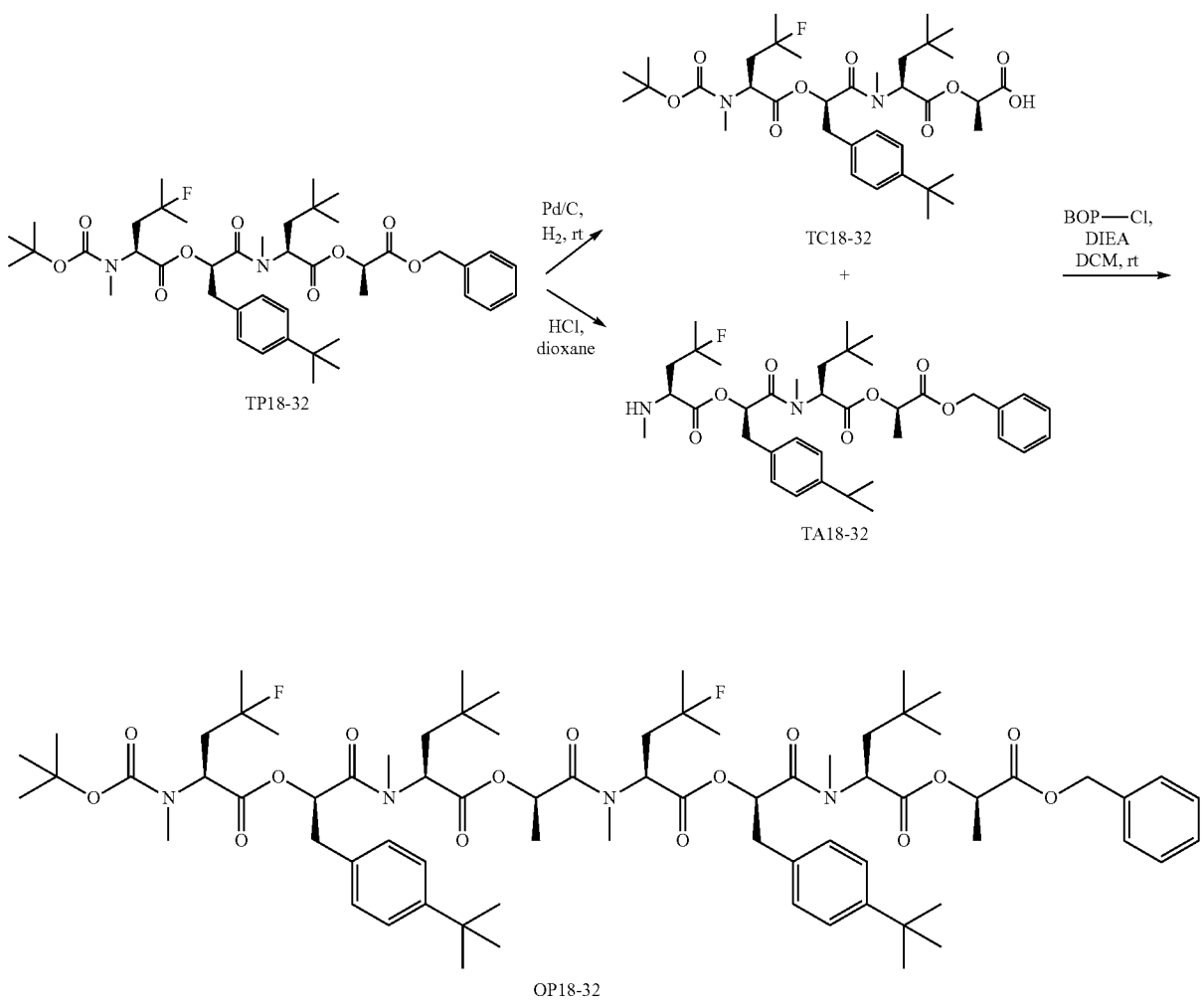

Scheme 54
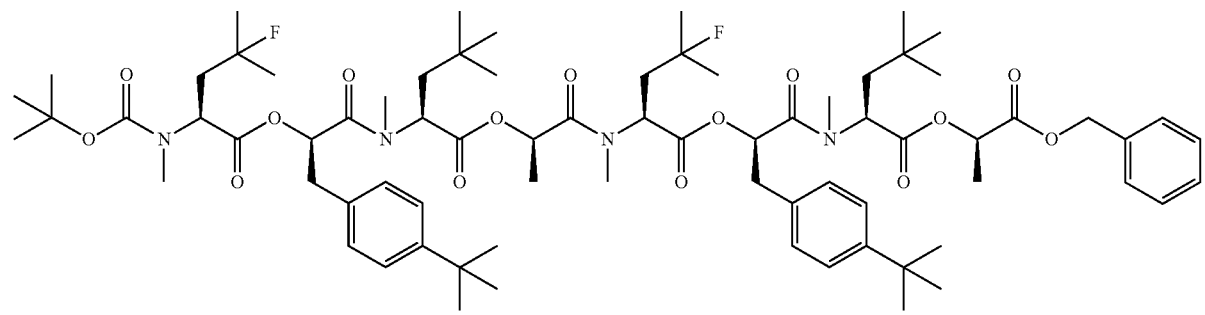
OP18-32
↓ Pd/C, H₂, rt
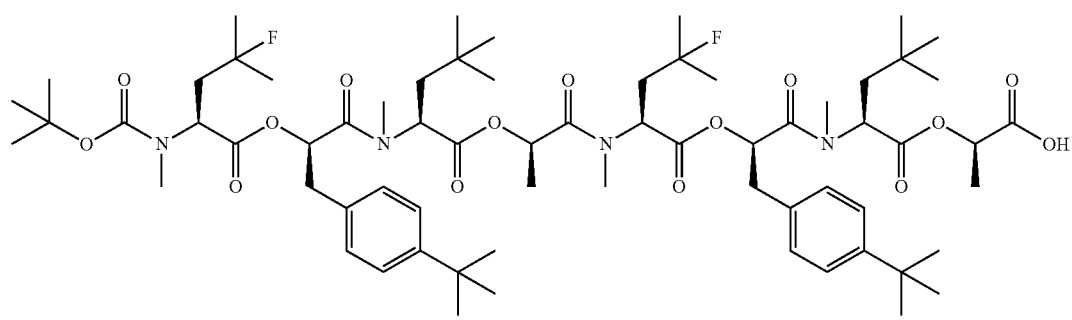
OC18-32
↓ HCl, dioxane
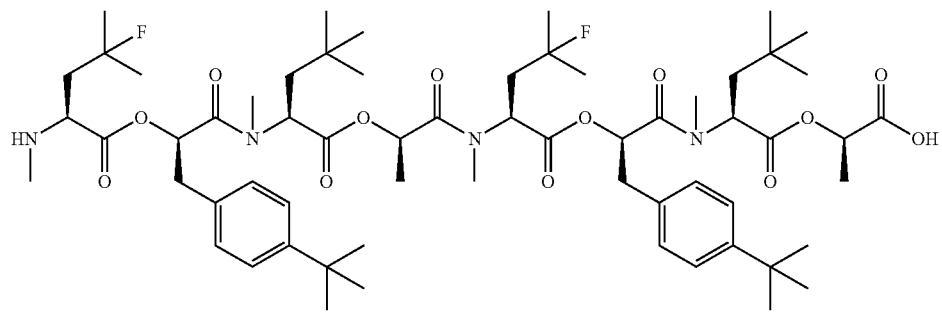
OAC18-32
↓ BOP—Cl, DIEA, DCM, rt -continued

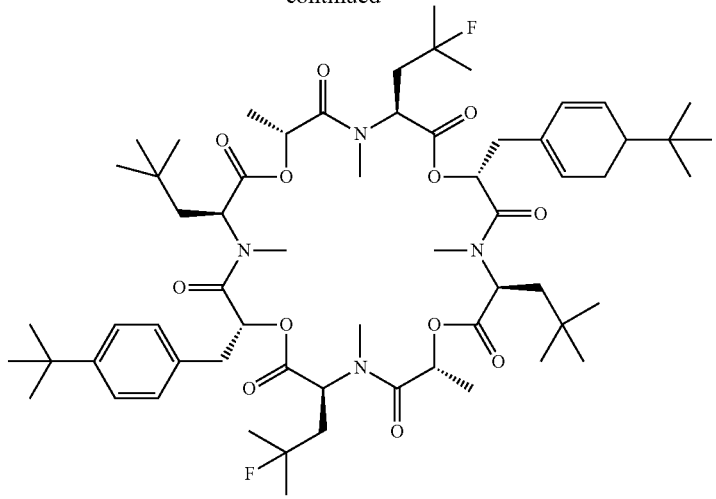

18-32

Experimental Details

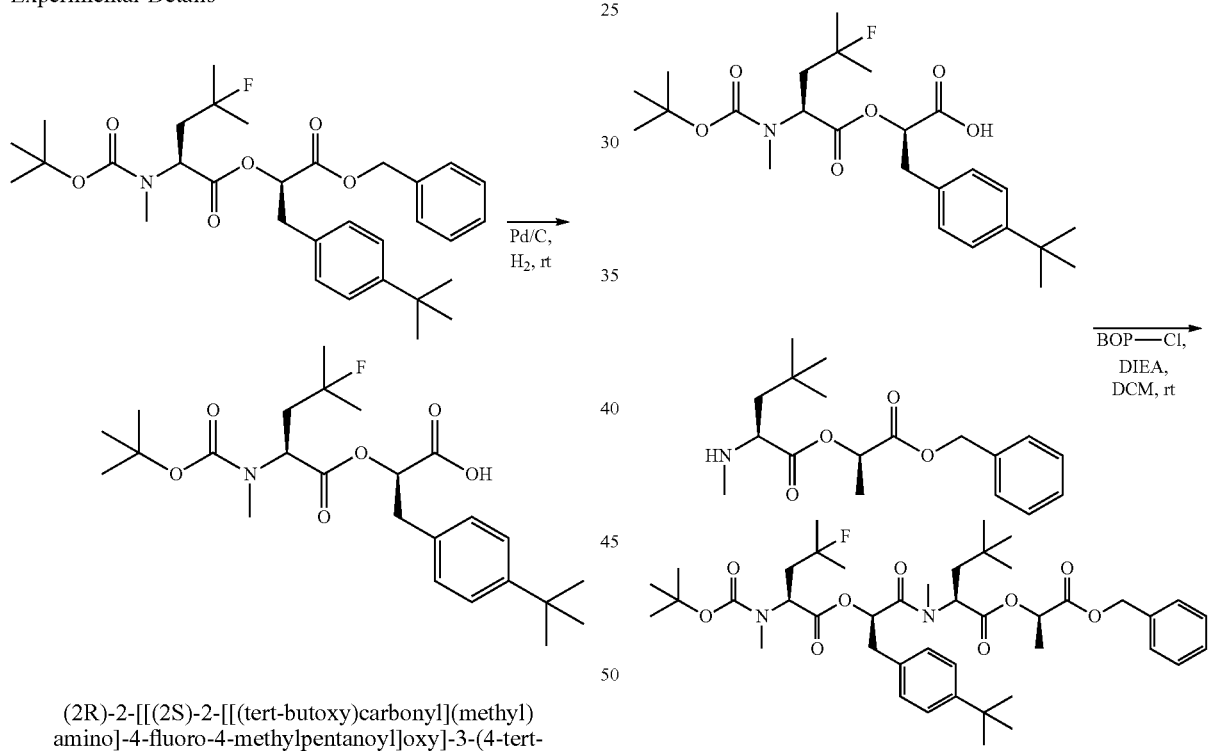

(2R)-2-[[(2S)-2-[[(tert-butoxy)carbonyl](methyl)amino]-4-fluoro-4-methylpentanoyl]oxy]-3-(4-tert-butylphenyl)propanoic acid To a solution of (2R)-1-(benzyloxy)-3-(4-tert-butylphenyl)-1-oxopropan-2-yl (2S)-2-[[(tert-butoxy)carbonyl](methyl)amino]-4-fluoro-4-methylpentanoate (15 g, 26.90 mmol, 1.00 equiv) in methanol (150 mL) was added Palladium on carbon (1.5 g, 0.10 equiv). The flask was evacuated and flushed three times with nitrogen, followed by flushing with hydrogen. The resulting solution was stirred for 2 h at room temperature. The solids were filtered out. The filtrate was concentrated under vacuum. This resulted in 12.0 g (95%) of (2R)-2-[[(2S)-2-[[(tert-butoxy)carbonyl](methyl)amino]-4-fluoro-4-methylpentanoyl]oxy]-3-(4-tert-butylphenyl)propanoic acid as a white solid. MS (ES, m/z): 488 (M+H).

TP18-32:

Into a 500-mL 3-necked round-bottom flask purged and maintained with an inert atmosphere of nitrogen, was placed a solution of (2R)-2-[[(2S)-2-[[(tert-butoxy)carbonyl](methyl)amino]-4-fluoro-4-methylpentanoyl]oxy]-3-(4-tert-butylphenyl) propanoic acid (12 g, 25.66 mmol, 1.00 equiv) in dichloromethane (150 mL), (2R)-1-(benzyloxy)-1-oxopropan-2-yl (2S)-4,4-dimethyl-2-(methylamino)pentanoate hydrochloride (9.13 g, 25.51 mmol, 1.00 equiv), BOP-Cl (13.0 g, 51.07 mmol, 2.00 equiv), DIEA (6.6 g, 51.07 mmol, 2.00 equiv) at 0° C. The resulting solution was stirred for 2 h at room temperature. The resulting mixture was concentrated under vacuum. The residue was applied onto a silica gel column with ethyl acetate/petroleum ether (1:100~1:10). This resulted in 17.14 g (87%) of TP18-32 as a white solid. MS (ES, m/z): 771 (M+H).

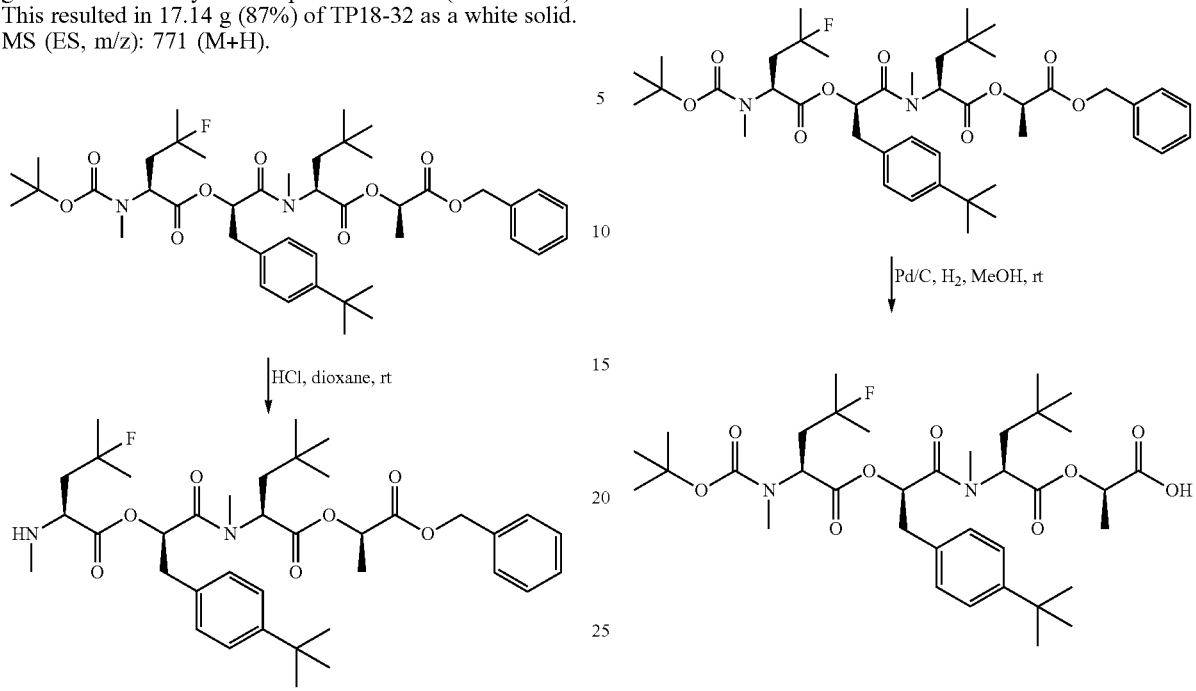

TA18-32:
Into a 500-mL 3-necked round-bottom flask, was placed a solution of TP18-32 (9.57 g, 12.41 mmol, 1.00 equiv) in hydrogen chloride(gas) dioxane (200 mL). The resulting solution was stirred for 30 min at room temperature. The resulting mixture was concentrated under vacuum. This resulted in 9.22 g (crude) of TA18-32 as a white solid. MS (ES, m/z): 671 (M+H).

TC18-32:
To a solution of TP18-32 (9.57 g, 12.41 mmol, 1.00 equiv) in methanol (100 mL) was added Palladium on carbon (957 mg, 0.10 equiv). The flask was evacuated and flushed three times with nitrogen, followed by flushing with hydrogen. The resulting solution was stirred for 2 h at room temperature. The solids were filtered out. The filtrate was concentrated under vacuum. This resulted in 8.33 g (99%) of TC18-32 as a white solid. MS (ES, m/z): 681 (M+H).

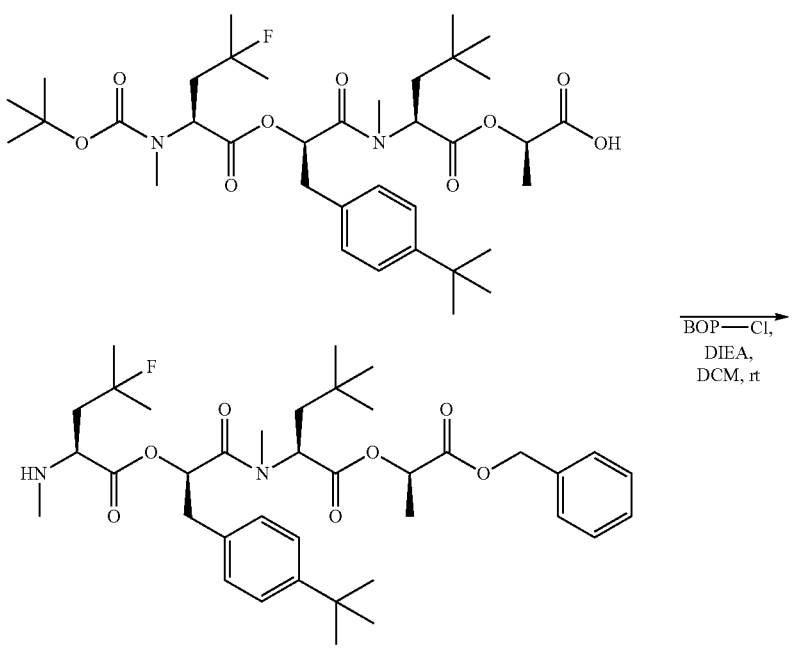

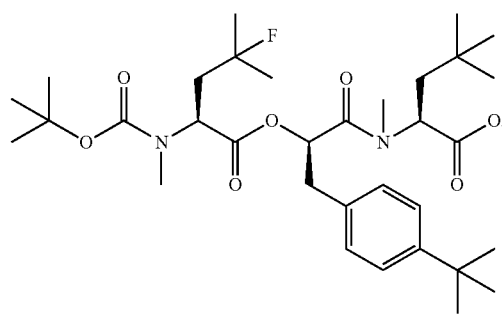
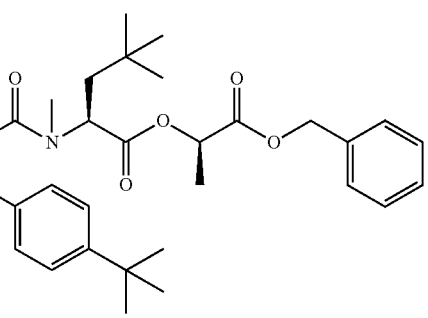

OP18-32:
Into a 500-mL 3-necked round-bottom flask purged and maintained with an inert atmosphere of nitrogen, was placed a solution of TA18-32 (8.54 g, 12.07 mmol, 1.00 equiv) in dichloromethane (150 mL), TC18-32 (8.23 g, 12.09 mmol, 1.00 equiv), BOP-Cl (6.15 g, 24.16 mmol, 2.00 equiv), DIEA (3.12 g, 24.14 mmol, 2.00 equiv) at 0° C. The resulting solution was stirred for 2 h at room temperature. The resulting mixture was concentrated under vacuum. The residue was applied onto a silica gel column with ethyl acetate/petroleum ether (1:50~1:10). This resulted in 13.0 g (81%) of OP18-32 as a white solid. MS (ES, m/z): 1356 (M+Na).

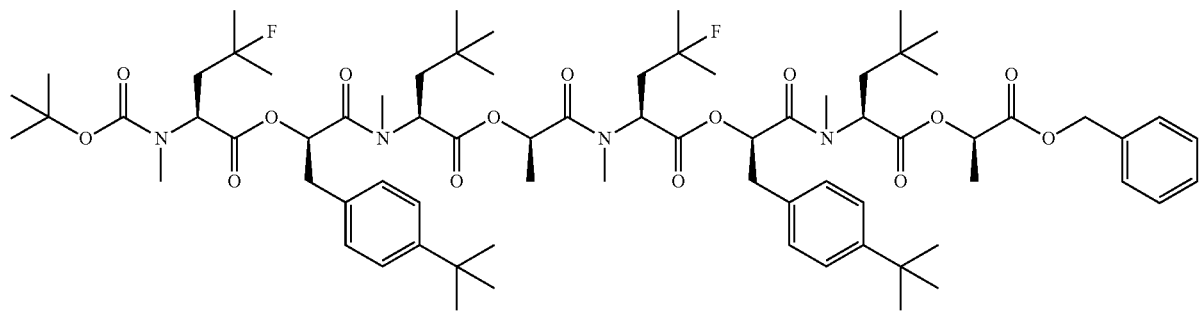

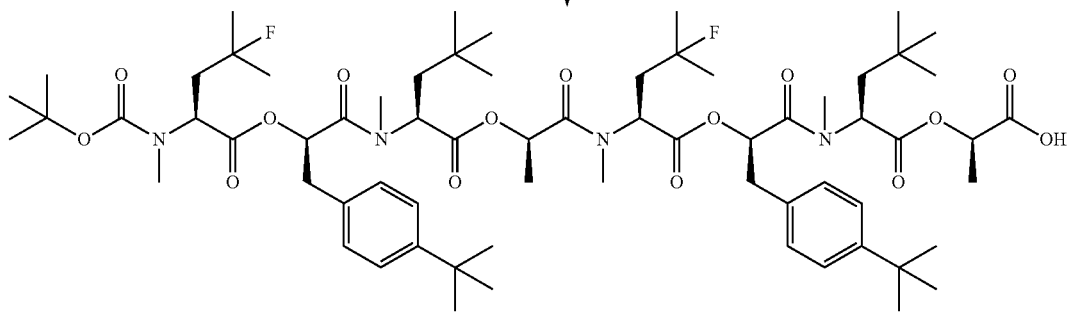

OC18-32:
To a solution of OP18-32 (13 g, 9.75 mmol, 1.00 equiv) in methanol (150 mL) was added Palladium on carbon (1.3 g, 0.10 equiv). The flask was evacuated and flushed three times with nitrogen, followed by flushing with hydrogen. The resulting solution was stirred for 2 h at room temperature. The solids were collected by filtration. The resulting mixture was concentrated under vacuum. This resulted in 11.52 g (95%) of OC18-32 as a white solid. MS (ES, m/z): 1266 (M+Na).

415
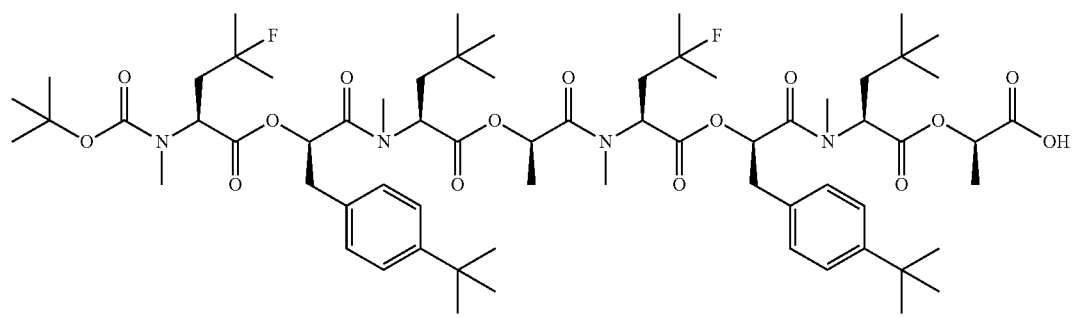
HCl, dioxane, rt
416
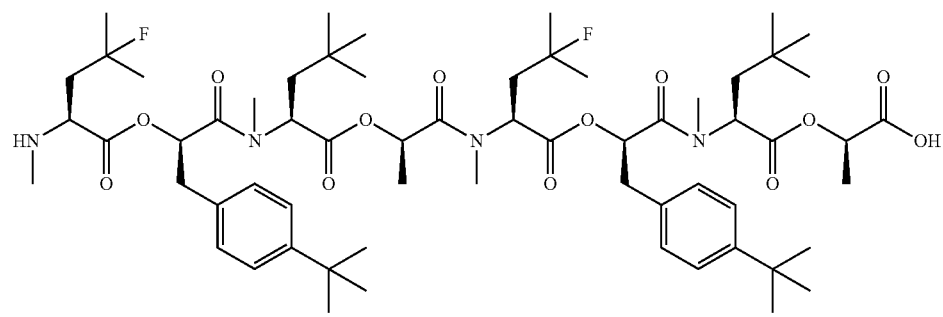
OAC18-32:
To a solution of OC18-32 (11.52 g, 9.27 mmol, 1.00 equiv) in dichloromethane (150 mL) was added hydrogen chloride (gas) in dioxane. The resulting solution was stirred for 30 min at room temperature. The resulting mixture was concentrated under vacuum. This resulted in 10.1 g (95%) of OAC18-32 as a white solid. MS (ES, m/z): 1144 (M+H).
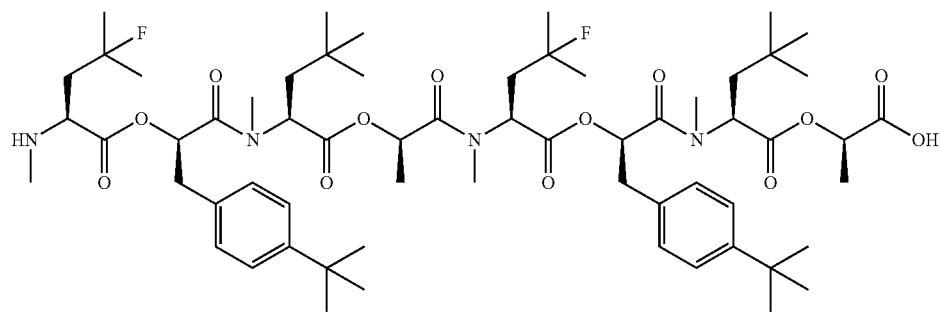
BOP—Cl,
DIEA,
DCM, rt

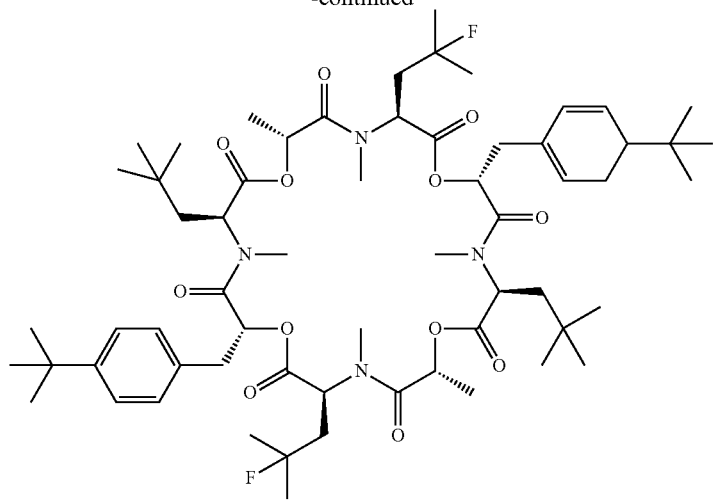

18-32

18-32:

Into a 500-mL 3-necked round-bottom flask purged and maintained with an inert atmosphere of nitrogen, was placed a solution of OAC18-32 (10.1 g, 8.84 mmol, 1.00 equiv) in dichloromethane (150 mL), BOP-Cl (4.5 g, 17.68 mmol, 2.00 equiv), DIEA (2.3 g, 17.80 mmol, 2.00 equiv) at 0° C. The resulting solution was stirred for 2 h at room temperature. The resulting mixture was concentrated under vacuum. The residue was applied onto a silica gel column with ethyl acetate/petroleum ether (1:100~1:20). This resulted in 5.452 g (55%) of 18-32 as a white solid. MS (ES, m/z): 1124.7 (calculated, M), 1126.0 (found, M+H). $^1$H NMR (300 MHz, CDCl$_3$): δ 7.33-7.27 (m, 4H), 7.18-7.14 (m, 4H), 5.80-5.75 (m, 1H), 5.70-5.55 (m, 1H), 5.49-5.29 (m, 5H), 5.20-5.10 (m, 1H), 4.72-4.60 (m, 1H), 3.16-3.03 (m, 6H), 2.98-2.60 (m, 10H), 2.26-2.15 (m, 2H), 1.95-1.87 (m, 4H), 1.51-0.70 (m, 56H); [α]=−37° (T=27.2° C., c=1.0 g/100 mL in MeOH).

In addition to depsipeptide compounds of the invention described in Examples 83-90, the additional numbered compounds shown in Table 113 below (which are described in Tables 2 to 112 above, wherein R', R", R'" and R"" are each methyl), were prepared in accordance with the synthetic procedures described in the examples with the exception that different dimer compounds (e.g. from dimers D1 to D57) having the desired functionality were selected as to prepare the desired depsipeptide compounds. The selected dimers are prepared in turn from the required monomer compounds (e.g. from monomer compounds M1 to M49). It will be apparent to the skilled person that using this methodology additional depsipeptide compounds of the invention may be prepared using other monomer and dimer components.

TABLE 113

Additional Compounds of Formula (I) Prepared

| Compound # | Observed Mass | Mass Comment |
|---|---|---|
| 2-1 | 1005.2 | M + H |
| 2-3 | 963.2 | M + H |
| 2-4 | 963.2 | M + H |
| 2-6 | 977.2 | M + H |
| 2-8 | 977.2 | M + H |

TABLE 113-continued

Additional Compounds of Formula (I) Prepared

| Compound # | Observed Mass | Mass Comment |
|---|---|---|
| 2-10 | 991.2 | M + H |
| 2-15 | 967.6 | M + H |
| 2-16 | 967.6 | M + H |
| 2-18 | 986 | M + H |
| 2-20 | 985.2 | M + H |
| 3-6 | 1014 | M + H |
| 3-7 | 1014 | M + H |
| 3-8 | 1013.6 | M + H |
| 3-18 | 1021.6 | M + H |
| 3-19 | 1021.6 | M + H |
| 3-20 | 1022 | M + H |
| 3-26 | 1057.6 | M + H |
| 3-27 | 985.5 | M + H |
| 3-31 | 1021.6 | M + H |
| 4-6 | 1113.6 | M + H |
| 4-7 | 1114 | M + H |
| 4-8 | 1114 | M + H |
| 4-18 | 1121.5 | M + H |
| 4-19 | 1121.6 | M + H |
| 4-20 | 1121.4 | M + H |
| 4-26 | 1157.5 | M + H |
| 4-27 | 1085.6 | M + H |
| 4-32 | 1150 | M + H |
| 4-31 | 1122 | M + H |
| 5-6 | 1146 | M + H |
| 5-27 | 1117.6 | M + H |
| 5-32 | 1181.5 | M + H |
| 6-33 | 1164 | M + H |
| 6-34 | 1172 | M + H |
| 6-35 | 1336 | M + H |
| 6-49 | 1072 | M + H |
| 6-37 | 1150 | M + Na |
| 6-43 | 1128 | M + H |
| 6-44 | 1128 | M + H |
| 6-24 | 1156 | M + H |
| 6-42 | 1156 | M + H |
| 6-45 | 1156 | M + H |
| 6-46 | 1156 | M + H |
| 6-18 | 1156 | M + H |
| 6-38 | 1184 | M + H |
| 6-32 | 1205.7 | M + Na |
| 6-36 | 1192 | M + H |
| 6-26 | 1213.2 | M + Na |
| 6-3 | 567.4 | (M + 2H)/2 |
| 6-40 | 1114 | M + Na |
| 6-27 | 1120.1 | M + H |

TABLE 113-continued

Additional Compounds of Formula (I) Prepared

| Compound # | Observed Mass | Mass Comment |
|---|---|---|
| 6-16 | 1138 | M + H |
| 6-41 | 1148 | M + H |
| 6-8 | 1148 | M + H |
| 6-6 | 1147.8 | M + H |
| 6-20 | 1177 | M + Na |
| 6-39 | 1156 | M + H |
| 6-19 | 1178 | M + Na |
| 6-7 | 1148 | M + H |
| 6-1 | 588.8 | (M + 2H)/2 |
| 7-34 | 1170 | M + H |
| 7-49 | 1070 | M + H |
| 7-37 | 1126 | M + H |
| 7-50 | 1126 | M + H |
| 7-44 | 1126 | M + H |
| 7-18 | 1154 | M + H |
| 7-42 | 1154 | M + H |
| 7-45 | 1154 | M + H |
| 7-46 | 1154 | M + H |
| 7-38 | 1182 | M + H |
| 7-32 | 1182 | M + H |
| 7-48 | 1334 | M + H |
| 7-47 | 1374 | M + H |
| 7-40 | 1090 | M + H |
| 7-27 | 1118 | M + H |
| 7-41 | 1146 | M + H |
| 7-31 | 1153.7 | M + H |
| 7-51 | 1209.8 | M + H |
| 7-52 | 1181.8 | M + H |
| 9-18 | 579.3 | (M + 2H)/2 |
| 9-19 | 579.3 | (M + 2H)/2 |
| 9-27 | 1122 | M + H |
| 9-6 | 1150 | M + H |
| 10-18 | 1124 | M + H |
| 10-27 | 543 | (M + 2H)/2 |
| 11-18 | 1123 | M + H |
| 11-27 | 1087.2 | M + H |
| 13-18 | 1155.4 | M + H |
| 14-27 | | |
| 15-27 | 1177.5 | M + H |
| 16-27 | | |
| 17-27 | | |
| 18-18 | 1119.7 | M + Na |
| 18-32 | 1126 | M + H |
| 18-6 | 1111.8 | M + Na |
| 18-19 | 1098 | M + H |
| 19-18 | 1180 | M + H |
| 19-27 | 1144 | M + H |
| 20-27 | 1057 | M + H |
| 21-27 | | |
| 22-27 | | |
| 23-27 | 1105.3 | M + H |
| 24-18 | 1036 | M + H |
| 24-27 | 999.45 | M + H |
| 24-6 | 1027.5 | M + H |
| 25-8 | 532 | (M + 2H)/2 |
| 25-6 | 532 | (M + 2H)/2 |
| 26-27 | 1189.4 | M + H |
| 27-27 | 1063.5 | M + H |
| 28-27 | 1039.2 | M + H |
| 29-18 | 1186 | M + H |
| 30-18 | 1192 | M + H |
| 30-32 | 1242.1 | M + Na |
| 30-27 | 1156 | M + H |
| 31-18 | 1190 | M + H |
| 31-27 | 1154 | M + H |
| 32-18 | 1222 | M + H |
| 32-32 | 1250 | M + H |
| 32-27 | 1186 | M + H |
| 33-18 | 1228 | M + Na |
| 34-18 | 1235.6 | M + H |
| 34-27 | 1199.6 | M + H |
| 35-18 | 1223.7 | M + H |
| 35-32 | 1252 | M + H |
| 35-27 | 1187.8 | M + H |
| 36-18 | 1196 | M + H |
| 37-18 | 1174 | M + H |
| 38-18 | 1256 | M + H |

The LCMS data shown above in table 113 was acquired on multiple instruments and differing software was used for analysis. Therefore, some of the data points have been automatically rounded/truncated to display the monisotope and some are showing the mass defect.

Biological Activity Examples

Method A: Screening Method to Test Activity of Compounds Against *Haemonchus contortus*

Twenty L1 *Haemonchus contortus* larvae were added to wells of a microtitre plate containing a nutrient medium and the test compound in DMSO. An analysis was conducted at 4 days to determine the extent of development of the larvae. Larvae exposed to DMSO alone served as controls. The potencies of the compounds were evaluated in an $MIC_{90}$ and/or $EC_{50}$ format. Compounds 2-3, 2-4, 2-15, 3-20, 3-26, 3-27, 3-31, 4-20, 4-27, 6-3, 6-7, 6-24, 6-26, 6-33, 6-39, 7-38, 7-49, 7-50, 10-18, 11-18, 15-27, 16-27, 18-19, and 23-27 exhibited median $MIC_{90}$ values of between 1.0 and 10 µM, compounds 2-16, 2-20, 33-18, 4-26, 4-31, 5-27, 6-20, 6-32, 7-42, 26-27, 27-27, 35-27, and 36-18 exhibited median $MIC_{90}$ values of between 0.1 µM and 1.0 µM, and compounds 2-18, 30-18, and 30-27 exhibited median $MIC_{90}$ values of less than 0.1 µM when assessed at the 4 day time point. As a comparison, PF1022A and emodepside exhibit median $MIC_{90}$ values of between 1 µM and 0.1 µM in this assay. Compounds 6-16, 6-42, 6-45, 7-18, 7-27, 7-40, 7-45, 18-18, 18-32, 32-27, 35-32, and 37-18 exhibited median $EC_{50}$ values of between 1.0 and 10 µM, compounds 3-18, 4-18, 5-32, 6-18, 6-44, 7-31, 7-37, and 30-32 exhibited median $EC_{50}$ values of between 0.1 µM and 1.0 µM, and compounds 7-32, 7-44, 31-18, 31-27, and 35-18 exhibited median $EC_{50}$ values of less than 0.1 µM when assessed at the 4 day time point. As a comparison, emodepside exhibited a median $EC_{50}$ value of between 1 µM and 0.1 µM in this assay.

Method B: Screening Method to Test Activity of Compounds Against Microfilaria of *Dirofilaria immitis*

Microfilaria of *Dirofilaria immitis* were added to the wells of a microtitre plate containing buffer and the test compounds in DMSO. An assessment was conducted at 72 hours to determine survival of the microfilaria. Microfilaria exposed to DMSO alone served as controls. Compounds 3-6, 3-7, 3-19, 3-26, 6-18, 6-19, 6-26, 6-36, 6-37, 6-38, 6-40, 6-41, 6-43, 6-45, 6-46, 7-41, -19, 9-27, 10-27, 13-18, 14-27, 18-6, 19-18, 19-27, 21-27, 24-18, 24-27, and 32-32 exhibited median $EC_{50}$ values of between 1 µM and 10 µM, compounds 2-10, 3-8, 4-19, 4-32, 5-32, 6-3, 6-6, 6-7, 6-8, 6-20, 6-24, 6-33, 6-39, 6-42, 7-38, 7-46, 7-49, 7-50, 9-6, 9-18, 10-18, 11-27, 20-27, 22-27, 25-8, 28-27, 32-27, 35-32, 37-18, and 38-18 exhibited median $EC_{50}$ values of between 0.1 µM and 1.0 µM, and compounds 2-3, 2-4, 2-6, 2-8, 2-15, 2-16, 2-18, 2-20, 3-18, 3-20, 3-27, 3-31, 4-18, 4-20, 4-26, 4-27, 4-31, 5-27, 6-16, 6-18, 6-32, 6-44 7-18, 7-27, 7-31, 7-32, 7-37, 7-40, 7-42, 7-44, 7-45, 11-18, 15-27, 16-27, 18-18, 18-19, 18-32, 23-27, 25-6, 26-27, 27-27, 30-18, 30-27, 30-32, 31-18, 31-27, 32-18, 35-18, and 36-18 exhibited median $EC_{50}$ values of less than 0.1 μM. As a comparison, emodepside exhibited a median $ECC_{50}$ value of between 1 μM and 0.1 μM in this assay and PF1022A exhibited a median $EC_{50}$ value of less than 0.1 μM.

Method C: Screening Method to Test Activity of Compounds Against Fleas Following Ingestion A cylindrical test container was filled with 10 adult *Ctenocephalides felis*. A cylindrical well was closed on one end with a self-sealing flexible film and placed on top of the test container in such a position that the fleas could pierce the film and feed on the contents of the cylinder. The test compound solution was then pipetted into bovine blood and added to the well. The container part with the *Ctenocephalides felis* was held at 20-22° C. and 40-60% relative humidity while the well part containing the treated blood was held at 37° C. and 40-60% relative humidity. Assessment was performed at 72 hours after application in comparison with untreated controls. Compounds 6-7, 6-8, 6-16, 6-19, 6-20, 7-27, 7-32, & 7-42 all exhibited mean $EC_{50}$ values of 10-50 ppm. Compounds 3-18, 4-26, 5-27, 6-32, 6-39, 6-41, 27-27, 30-27, & 36-18 all exhibited mean $EC_{50}$ values of 50-200 ppm. As a comparison Emodepside exhibited a mean $EC_{50}$ value of 10-50 ppm.

Method D: Screening Method to Evaluate the Efficacy of Compounds Against *Dirofilaria immits* In Vivo Beagle dogs were tested for microfilaria and heartworm antigen and received a full physical examination prior to inclusion in the study. Each dog was inoculated with 50 infective third-stage *D. immitis* larvae on Day −30 or Day −29 (using isolates with either reduced sensitivity to macrocyclic lactones including ivermectin (R) or those which are sensitive to macrocyclic lactones at standard doses (S) in studies 1 or 2 respectively). Antigen testing performed on blood collected on Day 90 confirmed that animals had not been exposed to *D. immitis* prior to the induced infection.

In study 1, five blocks of four dogs each were formed based on descending Day −14 to Day −7 body weights. Within blocks, dogs were randomly allocated to one of five treatment groups by lottery and treated orally five times at monthly intervals with an oral solution of ivermectin and a compound of this invention at monthly dosing intervals according to the following table 114.

In study 2, two blocks of four dogs each were formed based on descending Day −3 to Day 0 body weights. Within blocks, dogs were randomly allocated to one of two treatment groups by lottery and treated with an oral solution of a compound of this invention at two doses and two different dosing intervals: either using 3 monthly doses plus one dose 1 day prior to necropsy or using 5 monthly dosing intervals as is described in the following table 41.

TABLE 114

Efficacy against *D. immitis* in beagles.

| Study | Trt. Group | HW Isolate | Investigational Material | Dose | Dosing Days | Efficacy |
|---|---|---|---|---|---|---|
| 1 | 1 | R | (—) control | n/a | n/a | n/a |
| 1 | 2 | R | emodepside + ivermectin | 2.5 mg/kg + 6 μg/kg | 0, 32, 60, 90, & 119 | 98.8% |
| 1 | 3 | R | cmpd 4-18 + ivermectin | 2.5 mg/kg + 6 μg/kg | 0, 32, 60, 90, & 119 | 100% |
| 1 | 4 | R | cmpd 7-27 + ivermectin | 2.5 mg/kg + 6 μg/kg | 0, 32, 60, 90, & 119 | 100% |
| 1 | 5 | R | cmpd 6-18 + ivermectin | 2.5 mg/kg + 6 μg/kg | 0, 32, 60, 90, & 119 | 100% |
| 1 | 6 | R | cmpd 7-18 + ivermectin | 1.0 mg/kg + 6 μg/kg | 0, 32, 60, 90, & 119 | 100% |
| 2 | 1 | S | (—) control | n/a | n/a | n/a |
| 2 | 2 | S | cmpd 7-18 | 2.5 mg/kg | 0, 30, 60, & 154 | 100% |
| 2 | 3 | S | cmpd 7-18 | 0.5 mg/kg | 0, 30, 60, 90, & 120 | 100% |

All animals were humanely euthanized on Day 150 or Day 155 (studies 1 and 2 respectively) and a necropsy was performed for parasite recovery and live *D. immitis* counts for individual dogs. The percent efficacies by treatment group are listed in Table 114.

In study #1, compounds from this invention (@ 1.0 or 2.5 mg/kg) administered orally (in solution) in combination with ivermectin (@ 6 μg/kg) for five monthly doses, provided 100% efficacy against induced infections of the R isolate of *Dirofilaria immitis*. Emodepside provided a 98.8% efficacy when administered in the same fashion (in solution @ 2.5 mg/kg w/ 6 μg/kg ivermectin).

In study #2, compound 7-18 from this invention (@ 2.5 or 0.5 mg/kg) administered orally (in solution) for four or five doses respectively, provided 100% efficacy against induced infections of the S isolate of *Dirofilaria immitis*.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

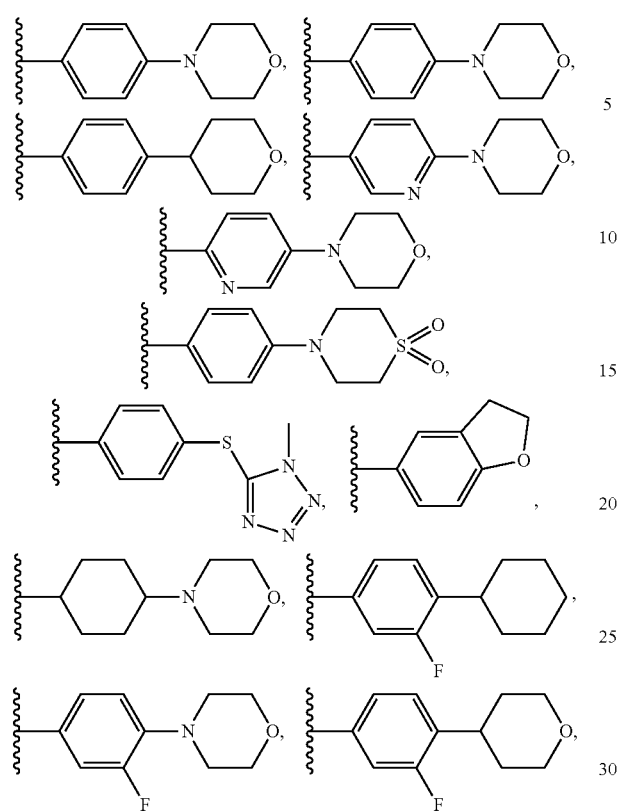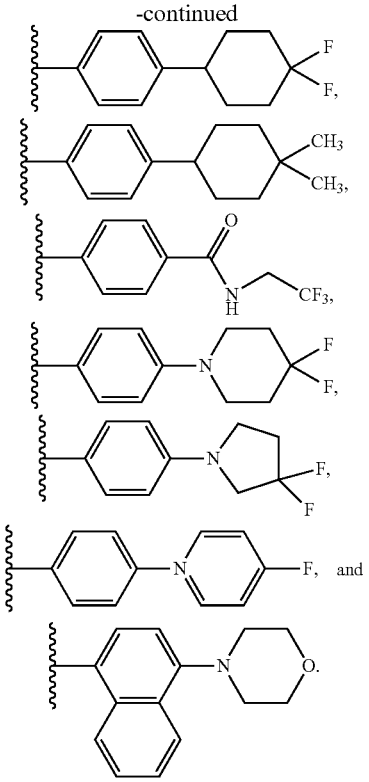

What is claimed is:

1. An anthelmintic cyclic depsipeptide compound of formula (I), or a pharmaceutically or veterinarily acceptable salt thereof:

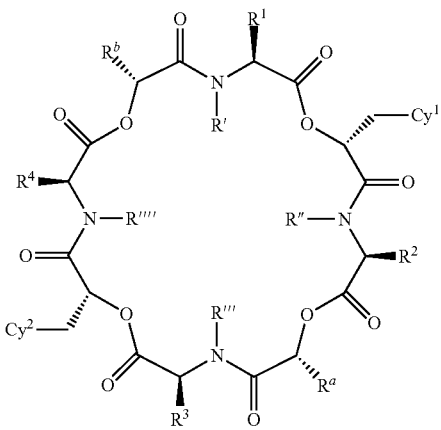

(I)

wherein:
- Cy$^1$ and Cy$^2$ are independently aryl, carbocyclic, heteroaryl or heterocyclic optionally substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN, —NO$_2$, cycloalkyl, heteroalkyl, heterocyclyl, aryl, heteroaryl, —O-heteroaryl, —S-heteroaryl, —O— heterocyclyl or —S-heterocyclyl, wherein each cycloalkyl, heterocyclyl, aryl or heteroaryl is optionally further substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$OC(O)—, R$^5$C(O)O—, R$^5$C(O)NR$^6$—, —CN and —NO$_2$;
- R$^5$ and R$^6$ are independently hydrogen, alkyl, haloalkyl, thioalkyl, alkylthioalkyl, hydroxyalkyl, alkoxyalkyl, alkenyl, haloalkenyl, alkynyl, haloalkynyl, or the group —CH$_2$C(O)NHCH$_2$CF$_3$; or R$^5$ and R$^6$ together with the atom(s) to which they are bonded form a C$_3$-C$_6$ cyclic group;
- R', R'', R''' and R'''' are each independently hydrogen or C$_1$-C$_3$alkyl;
- R$^a$ and R$^b$ are independently hydrogen, C$_1$-C$_3$alkyl or C$_1$-C$_3$haloalkyl; and
- (a) R$^1$ and R$^2$ are each independently C$_1$-C$_8$ alkyl substituted by one or more halogen; and
  R$^3$ and R$^4$ are each independently C$_1$-C$_8$ alkyl; or
- (b) R$^1$ and R$^3$ are each independently C$_1$-C$_8$ alkyl substituted by one or more halogen; and
  R$^2$ and R$^4$ are each independently C$_1$-C$_8$ alkyl; or
- (c) R$^1$ and R$^4$ are each independently C$_1$-C$_8$ alkyl substituted by one or more halogen; and
  R$^2$ and R$^3$ are each independently C$_1$-C$_8$ alkyl; or
- (d) R$^2$ and R$^4$ are each independently C$_1$-C$_8$ alkyl substituted by one or more halogen; and
  R$^1$ and R$^3$ are each independently C$_1$-C$_8$ alkyl; or
- (e) R$^2$ and R$^3$ are each independently C$_1$-C$_8$ alkyl substituted by one or more halogen; and R$^1$ and R$^4$ are each independently C$_1$-C$_8$ alkyl; or
- (f) R$^3$ and R$^4$ are each independently C$_1$-C$_8$ alkyl substituted by one or more halogen; and
  R$^1$ and R$^2$ are each independently C$_1$-C$_8$ alkyl.

2. The anthelmintic cyclic depsipeptide compound of claim 1, wherein R$^1$ and R$^3$ are C$_1$-C$_8$ alkyl substituted by halogen.

3. The anthelmintic cyclic depsipeptide compound of claim 1, wherein R$^2$ and R$^4$ are C$_1$-C$_8$ alkyl substituted by halogen.

4. The anthelmintic cyclic depsipeptide compound of claim 2 or 3, wherein halogen is fluoro.

5. The anthelmintic cyclic depsipeptide compound of claim 1, wherein two of R$^1$, R$^2$, R$^3$ and R$^4$ are G-1:

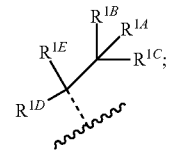

G-1 wherein R$^{1A}$, R$^{1B}$, R$^{1C}$, R$^{1D}$ and R$^{1E}$ are independently hydrogen, halogen, C$_{1-3}$alkyl or C$_{1-3}$haloalkyl.

6. The anthelmintic cyclic depsipeptide compound of claim 5, wherein:
R$^{1A}$ is fluoro or trifluoromethyl; R$^{1B}$ and R$^{1C}$ are independently hydrogen or methyl; and
R$^{1D}$ and R$^{1E}$ are independently hydrogen or methyl.

7. The anthelmintic cyclic depsipeptide compound of claim 6, wherein R$^{1A}$ is fluoro; and R$^{1D}$ and R$^{1E}$ are hydrogen.

8. The anthelmintic cyclic depsipeptide compound of claim 6, wherein:
R$^{1A}$ is fluoro; R$^{1B}$ and R$^{1C}$ are methyl; and
R$^{1D}$ and R$^{1E}$ are independently hydrogen or fluoro.

9. The anthelmintic cyclic depsipeptide compound of claim 1, wherein two of R$^1$, R$^2$, R$^3$ and R$^4$ are independently CH$_2$F, CHF$_2$ or CF$_3$.

10. The anthelmintic cyclic depsipeptide compound of any one of claims 1, 2-3 and 5-9, wherein Cy$^1$ and Cy$^2$ are independently phenyl, a 5-membered heteroaryl or a 6-membered heteroaryl, wherein said phenyl, 5-membered heteroaryl or 6-membered heteroaryl is optionally substituted with halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN, —NO$_2$, cycloalkyl, heteroalkyl, heterocyclyl, aryl, heteroaryl, —O-heteroaryl, —S-heteroaryl, —O-heterocyclyl or —S-heterocyclyl, and wherein each cycloalkyl, heteroalkyl, aryl or heteroaryl substituent is optionally further substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, SF$_5$, R$^5$S(O)—, R$^5$S(O)$_2$—, R$^5$C(O)—, R$^5$R$^6$NC(O)—, R$^5$R$^6$NC(O)NR$^5$—, R$^5$OC(O)—, R$^5$C(O)O—, R$^5$C(O)NR$^6$—, —CN and —NO$_2$.

11. The anthelmintic cyclic depsipeptide compound of claim 10, wherein Cy$^1$ and Cy$^2$ are independently phenyl, a 5-membered heteroaryl or a 6-membered heteroaryl; wherein said phenyl, 5-membered heteroaryl or 6-membered heteroaryl is independently substituted with halogen, —CN, alkyl, cycloalkyl, haloalkyl, alkoxy, haloalkoxy, alkylthio, haloalkylthio, $R^5R^6NC(O)$— or heterocyclyl.

12. The anthelmintic cyclic depsipeptide compound of claim 11, wherein $Cy^1$ and $Cy^2$ are independently phenyl, a 5-membered heteroaryl or a 6-membered heteroaryl substituted with t-butyl, cyclohexyl, heterocyclyl, fluoro, trifluoromethyl, trifluoromethoxy or cyano.

13. The anthelmintic cyclic depsipeptide compound of claim 12, wherein $Cy^1$ and $Cy^2$ are independently phenyl, a 5-membered heteroaryl or pyridinyl substituted with pyrrolidinyl, morpholinyl, tetrahydropyranyl, tetrazolyl or —S-tetrazolyl.

14. The anthelmintic cyclic depsipeptide compound of claim 11, wherein $Cy^1$ and $Cy^2$ are independently phenyl, thienyl, oxazolyl, isothiazolyl, 1,3-4-thiadazolyl, pyrazolyl, furyl, imidazolyl, pyrrolyl, pyridinyl, pyridazinyl, pyrimidinyl, pyrazinyl or tetrazinyl, each independently optionally substituted with $R^5R^6NC(O)$—, wherein $R^5$ and $R^6$ are independently hydrogen or —$CH_2C(O)NHCH_2CF_3$; or $R^5$ and $R^6$ together with the nitrogen atom to which they are bonded together form a $C_3$-$C_6$ cyclic amine.

15. The anthelmintic cyclic depsipeptide compound of claim 1, wherein $Cy^1$ and $Cy^2$ are independently R1 to R8:

R1

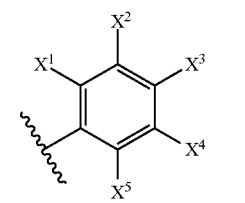

R2

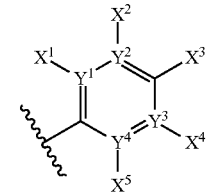

R3

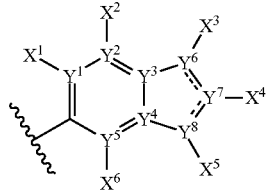

R4

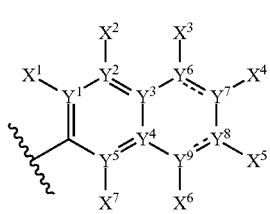

R5

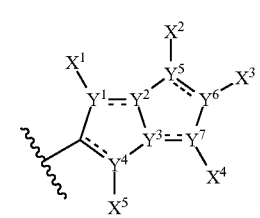

R6

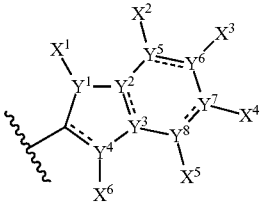

R7

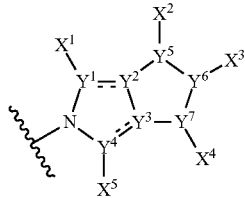

R8

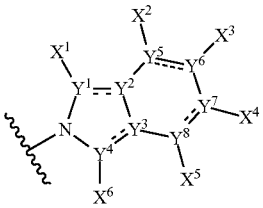

wherein $Y^1$, $Y^2$, $Y^3$, $Y^4$, $Y^5$, $Y^6$, $Y^7$, $Y^8$ and $Y^9$ are each independently C, CH or N; and $X^1$, $X^2$, $X^3$, $X^4$, $X^5$, $X^6$ and $X^7$ are independently hydrogen, halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN, —$NO_2$, cycloalkyl, heteroalkyl, heterocyclyl, aryl or heteroaryl, wherein each cycloalkyl, heteroalkyl, heterocyclyl, aryl or heteroaryl is optionally further independently substituted with one or more substituents selected from the group consisting of halogen, hydroxy, alkoxy, haloalkoxy, alkylthio, haloalkylthio, thioamido, amino, alkylamino, dialkylamino, alkyl, haloalkyl, alkenyl, haloalkenyl, alkynyl, haloalkynyl, $SF_5$, $R^5S(O)$—, $R^5S(O)_2$—, $R^5C(O)$—, $R^5R^6NC(O)$—, $R^5R^6NC(O)NR^5$—, $R^5OC(O)$—, $R^5C(O)O$—, $R^5C(O)NR^6$—, —CN and —$NO_2$.

16. The anthelmintic cyclic depsipeptide compound of claim 15, wherein $X^1$, $X^2$, $X^3$, $X^4$, $X^5$, $X^6$ and $X^7$ are independently hydrogen, halogen, hydroxy, alkoxy, haloalkoxy, alkylthio, haloalkylthio, $R^5R^6NC(O)$—, $R^5R^6NC(O)NR^5$—, thioamido, amino, alkylamino or dialkylamino.

17. The anthelmintic cyclic depsipeptide compound of claim 15, wherein $X^1$, $X^2$, $X^3$, $X^4$, $X^5$, $X^6$ and $X^7$ are independently hydrogen, alkyl, haloalkyl, alkenyl, haloalkenyl, alkynyl or haloalkynyl.

18. The anthelmintic cyclic depsipeptide compound of claim 15, wherein $X^1$, $X^2$, $X^3$, $X^4$, $X^5$, $X^6$ and $X^7$ are independently hydrogen, methyl, ethyl, propyl, isopropyl, butyl, isobutyl, tert-butyl, $CF_3$, —$CH_2CF_3$, —$CHFCF_3$ or $CF_2CF_3$.

19. The anthelmintic cyclic depsipeptide compound of claim 15, wherein $X^1$, $X^2$, $X^3$, $X^4$, $X^5$, $X^6$ and $X^7$ are independently hydrogen, hydroxy, methoxy, trifluoromethoxy, —$OCH_2CF_3$, —$OCHFCF_3$, —$OCF_2CF_3$, methylthio, trifluoromethylthio, —$SCH_2CF_3$, —$SCHFCF_3$ or —$SCF_2CF_3$.

20. An anthelmintic veterinary composition comprising the anthelmintic cyclic depsipeptide compound of claim 1, or a pharmaceutically or veterinarily acceptable salt thereof, in combination with a veterinarily acceptable carrier.

21. An anthelmintic veterinary composition comprising the anthelmintic cyclic depsipeptide compound of claim 1, or a pharmaceutically or veterinarily acceptable salt thereof, in combination with a second parasiticidal active agent and a veterinarily acceptable carrier.

22. The anthelmintic cyclic depsipeptide compound of claim 1, wherein $R^a$ and $R^b$ are independently hydrogen or $C_1$-$C_3$alkyl.

23. The anthelmintic cyclic depsipeptide compound of claim 22, wherein $R^a$ and $R^b$ are methyl.

24. The anthelmintic cyclic depsipeptide compound of claim 1, wherein R', R'', R''' and R'''' are independently $C_1$-$C_3$alkyl.

25. The anthelmintic cyclic depsipeptide compound of claim 24, wherein R', R'', R''' and R'''' are methyl.

26. The anthelmintic cyclic depsipeptide compound of claim 11, wherein:
$Cy^1$ and $Cy^2$ are independently phenyl substituted with alkyl, cycloalkyl, heterocyclyl, halogen, haloalkyl, haloalkoxy, haloalkylthio or cyano;
$R^a$ and $R^b$ are independently hydrogen or $C_1$-$C_3$alkyl;
R', R'', R''' and R'''' are independently $C_1$-$C_3$alkyl; and
(a) $R^1$ and $R^2$ are each independently $C_1$-$C_8$ alkyl substituted by one or more fluoro; and
$R^3$ and $R^4$ are each independently $C_1$-$C_8$ alkyl; or
(b) $R^1$ and $R^3$ are each independently $C_1$-$C_8$ alkyl substituted by one or more fluoro; and
$R^2$ and $R^4$ are each independently $C_1$-$C_8$ alkyl; or
(c) $R^1$ and $R^4$ are each independently $C_1$-$C_8$ alkyl substituted by one or more fluoro; and
$R^2$ and $R^3$ are each independently $C_1$-$C_8$ alkyl; or
(d) $R^2$ and $R^4$ are each independently $C_1$-$C_8$ alkyl substituted by one or more fluoro; and
$R^1$ and $R^3$ are each independently $C_1$-$C_8$ alkyl; or
(e) $R^2$ and $R^3$ are each independently $C_1$-$C_8$ alkyl substituted by one or more fluoro; and
$R^1$ and $R^4$ are each independently $C_1$-$C_8$ alkyl; or
(f) $R^3$ and $R^4$ are each independently $C_1$-$C_8$ alkyl substituted by one or more fluoro; and
$R^1$ and $R^2$ are each independently $C_1$-$C_8$ alkyl.

27. The anthelmintic cyclic depsipeptide compound of claim 26, wherein
(b) $R^1$ and $R^3$ are each independently $C_1$-$C_8$ alkyl substituted by one or more fluoro; and
$R^2$ and $R^4$ are each independently $C_1$-$C_8$ alkyl.

28. The anthelmintic cyclic depsipeptide compound of claim 26, wherein
(a) $R^2$ and $R^4$ are each independently $C_1$-$C_8$ alkyl substituted by one or more fluoro; and
$R^1$ and $R^3$ are each independently $C_1$-$C_8$ alkyl.

29. The anthelmintic cyclic depsipeptide compound of claim 27, wherein $R^1$ and $R^3$ are each —CH$_2$CF(CH$_3$)$_2$; and $R^2$ and $R^4$ are independently 2-methylpropyl or 2,2-dimethylpropyl.

30. The anthelmintic cyclic depsipeptide compound of claim 28, wherein $R^2$ and $R^4$ are each —CH$_2$CF(CH$_3$)$_2$; and $R^1$ and $R^3$ are independently 2-methylpropyl or 2,2-dimethylpropyl.

31. The anthelmintic cyclic depsipeptide compound of claim 27, wherein $Cy^1$ and $Cy^2$ are independently phenyl substituted by t-butyl, fluoro, trifluoromethyl, trifluoromethoxy, cyano, morpholinyl or tetrahydropyranyl.

32. The anthelmintic cyclic depsipeptide compound of claim 28, wherein $Cy^1$ and $Cy^2$ are independently phenyl substituted by t-butyl, fluoro, trifluoromethyl, trifluoromethoxy, cyano, morpholinyl or tetrahydropyranyl.

33. The anthelmintic cyclic depsipeptide compound of claim 29, wherein $Cy^1$ and $Cy^2$ are independently phenyl substituted by t-butyl, fluoro, trifluoromethyl, trifluoromethoxy, cyano, morpholinyl or tetrahydropyranyl.

34. The anthelmintic cyclic depsipeptide compound of claim 30, wherein $Cy^1$ and $Cy^2$ are independently phenyl substituted by t-butyl, fluoro, trifluoromethyl, trifluoromethoxy, cyano, morpholinyl or tetrahydropyranyl.

35. The anthelmintic cyclic depsipeptide compound of claim 31, wherein:
$R^a$ and $R^b$ are each methyl; and
R', R'', R''' and R'''' are methyl.

36. The anthelmintic cyclic depsipeptide compound of claim 32, wherein:
$R^a$ and $R^b$ are reach methyl; and
R', R'', R''' and R'''' are each methyl.

37. The anthelmintic cyclic depsipeptide compound of claim 33, wherein:
$R^a$ and $R^b$ are each methyl; and
R', R'', R''' and R'''' are methyl.

38. The anthelmintic cyclic depsipeptide compound of claim 34, wherein:
$R^a$ and $R^b$ are reach methyl; and
R', R'', R''' and R'''' are each methyl.

39. An anthelmintic cyclic depsipeptide compound of formula (I), or a pharmaceutically or veterinarily acceptable salt thereof:

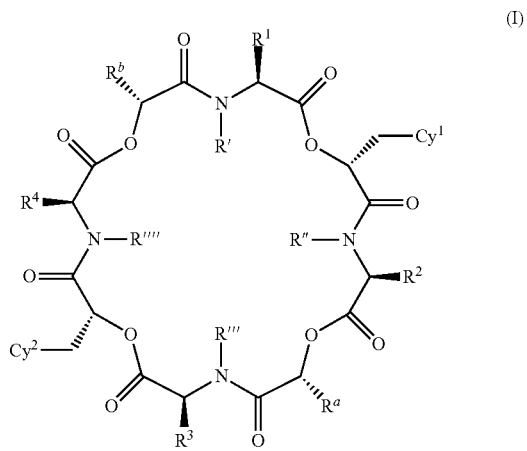

wherein:
$R^1$ and $R^3$ are each —CH$_2$CF(CH$_3$)$_2$; and $R^2$ and $R^4$ are independently 2-methylpropyl or 2,2-dimethylpropyl; or
$R^2$ and $R^4$ are each —CH$_2$CF(CH$_3$)$_2$; and $R^1$ and $R^3$ are independently 2-methylpropyl or 2,2-dimethylpropyl;
$R^a$ and $R^b$ are each methyl;
R', R'', R''' and R'''' are each methyl; and
$Cy^1$ and $Cy^2$ are independently selected from the group consisting of:
para-fluorophenyl, para-trifluoromethoxyphenyl, para-trifluoromethylphenyl, 3,4,5-trifluorophenyl, para-iodophenyl, para-bromophenyl, p-nitrophenyl, p-tert-butylphenyl, para-SF$_5$-phenyl, para-aminophenyl,